(12) United States Patent
Haketa et al.

(10) Patent No.: US 10,941,144 B2
(45) Date of Patent: Mar. 9, 2021

(54) ORGANIC ELECTROLUMINESCENCE DEVICE AND ELECTRONIC DEVICE

(71) Applicant: IDEMITSU KOSAN CO., LTD., Chiyoda-ku (JP)

(72) Inventors: Tasuku Haketa, Chiba (JP); Hirokatsu Ito, Ichihara (JP); Yu Kudo, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 392 days.

(21) Appl. No.: 15/850,109

(22) Filed: Dec. 21, 2017

(65) Prior Publication Data

US 2018/0179206 A1 Jun. 28, 2018

(30) Foreign Application Priority Data

Dec. 28, 2016 (JP) .............................. JP2016-256114

(51) Int. Cl.
*H01L 51/50* (2006.01)
*C07D 471/10* (2006.01)
(Continued)

(52) U.S. Cl.
CPC ............ *C07D 471/10* (2013.01); *C09K 11/06* (2013.01); *H01L 51/006* (2013.01);
(Continued)

(58) Field of Classification Search
None
See application file for complete search history.

(56) References Cited

U.S. PATENT DOCUMENTS

2018/0069180 A1* 3/2018 Cha ..................... C09K 11/025

FOREIGN PATENT DOCUMENTS

KR 10-2016-0111778 9/2016
KR 2018027230 * 3/2018 ............. H01L 51/50
(Continued)

*Primary Examiner* — Gregory D Clark
(74) *Attorney, Agent, or Firm* — Oblon, McClelland, Maier & Neustadt, L.L.P.

(57) ABSTRACT

A compound represented by formula (1):

(Continued)

-continued

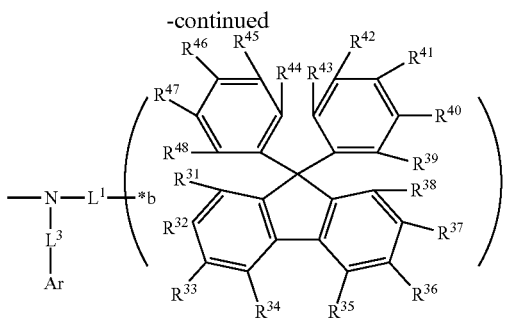

wherein $R^1$ to $R^8$, $R^{12}$ to $R^{18}$, $R^{21}$ to $R^{25}$, $R^{31}$ to $R^{48}$, $L^1$ to $L^3$, and Ar are as defined in the specification,
provides a high performance organic electroluminescence device which comprises a cathode, an anode and an organic layer between the cathode and the anode,
wherein the organic layer comprises a light emitting layer and at least one layer of the organic layer comprises the compound.

21 Claims, 1 Drawing Sheet

(51) Int. Cl.
  *H01L 51/00* (2006.01)
  *C09K 11/06* (2006.01)
(52) U.S. Cl.
  CPC ...... *H01L 51/0061* (2013.01); *H01L 51/0072* (2013.01); *H01L 51/0074* (2013.01); *H01L 51/5012* (2013.01); *C09K 2211/1022* (2013.01); *C09K 2211/1033* (2013.01); *C09K 2211/1037* (2013.01); *H01L 51/0051* (2013.01); *H01L 51/0054* (2013.01); *H01L 51/0059* (2013.01); *H01L 51/0073* (2013.01); *H01L 51/5064* (2013.01)

(56) References Cited

FOREIGN PATENT DOCUMENTS

| WO | WO 2006/080640 A1 | 8/2006 |
| WO | WO 2016/027989 A1 | 2/2016 |
| WO | WO 2016/204453 A1 | 12/2016 |

* cited by examiner

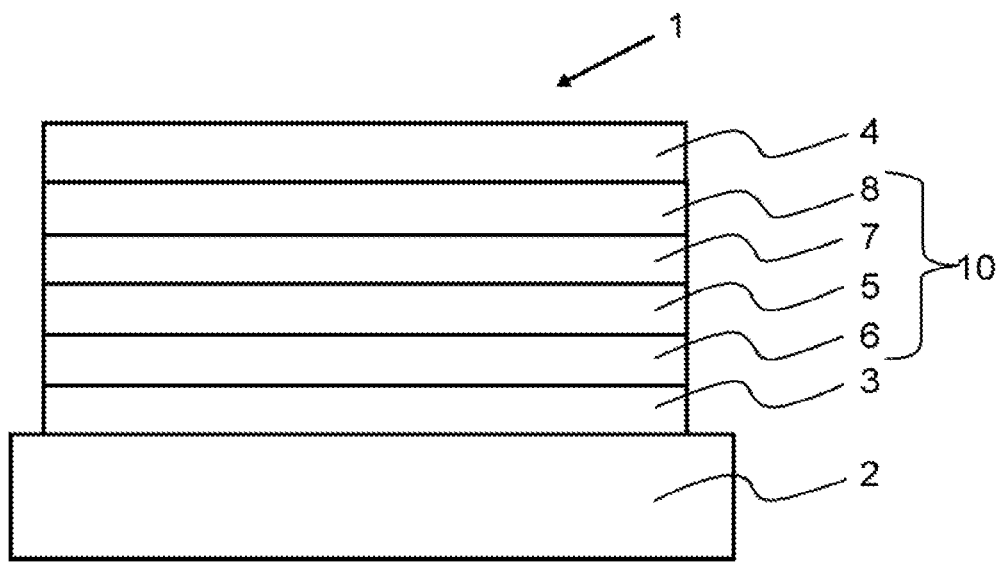

ORGANIC ELECTROLUMINESCENCE DEVICE AND ELECTRONIC DEVICE

CROSS-REFERENCE TO RELATED APPLICATION

This application is based upon and claims the benefit of priority from the prior Japanese Patent Application No. 2016-256114, filed on Dec. 28, 2016; the entire contents of which are incorporated herein by reference.

TECHNICAL FIELD

The present invention relates to organic electroluminescence devices and electronic devices.

BACKGROUND ART

An organic electroluminescence ("EL") device generally comprises an anode, a cathode, and an organic thin film layer comprising one or more layers between the anode and the cathode. When a voltage is applied between the electrodes, electrons are injected from the cathode and holes are injected from the anode into a light emitting region. The injected electrons recombine with the injected holes in the light emitting region to form excited states. When the excited state returns to the ground state, the energy is released as light.

Many researches have been made on the applications of organic EL device to display, etc. because of its possibility of wide selection of emission colors by using various emitting materials in a light emitting layer. Particularly, the research on the emitting materials which emit three primary red, green, and blue colors has been made most actively, and the intensive research has been made to improve their properties.

The recent research is directed to the development of a hole transporting layer material as one of methods for improving the performance of organic EL devices.

Patent Literature 1 describes that the compound of the following formula is usable as a material for organic EL device.

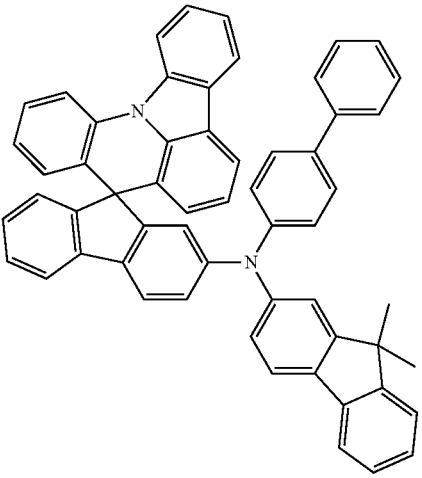

For example, the performance of an organic EL device comprising the compound of formula 2-11 in the hole transporting layer is measured in the working example.

Formula 2-11

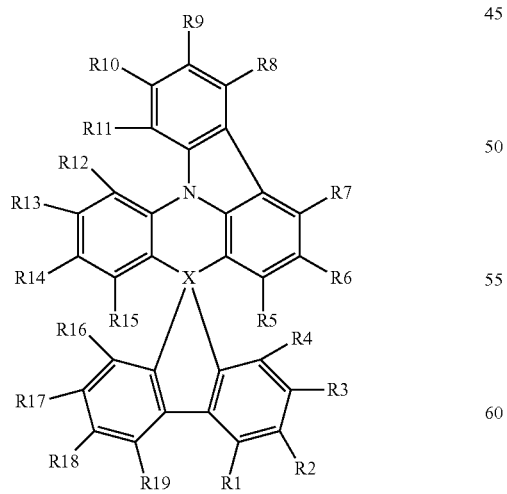

Patent Literature 2 describes that the compound of the following formula is usable in a hole transporting layer of organic EL device.

Patent Literature 3 describes that the compound of the following formula is usable as a material for organic EL device.

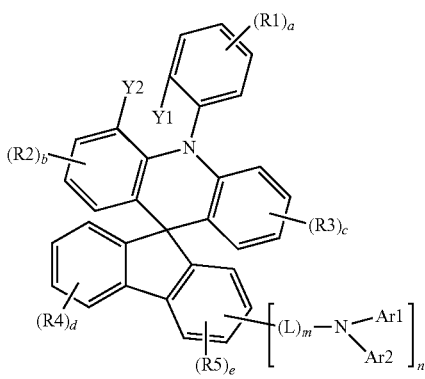

CITATION LIST

Patent Literature

Patent Literature 1: WO 2006/080640 A1
Patent Literature 2: WO 2016/027989 A1
Patent Literature 3: KR10-2016-0111778

SUMMARY OF INVENTION

Technical Problem

The present invention has been made to solve the above problem and an object thereof is to provide organic EL devices having good performance.

Solution to Problem

As a result of extensive research, the inventors have found that the emission efficiency of the organic EL device is improved by using a compound represented by formula (1) as a material for an organic EL device.

In an aspect, the invention provides a compound represented by formula (1):

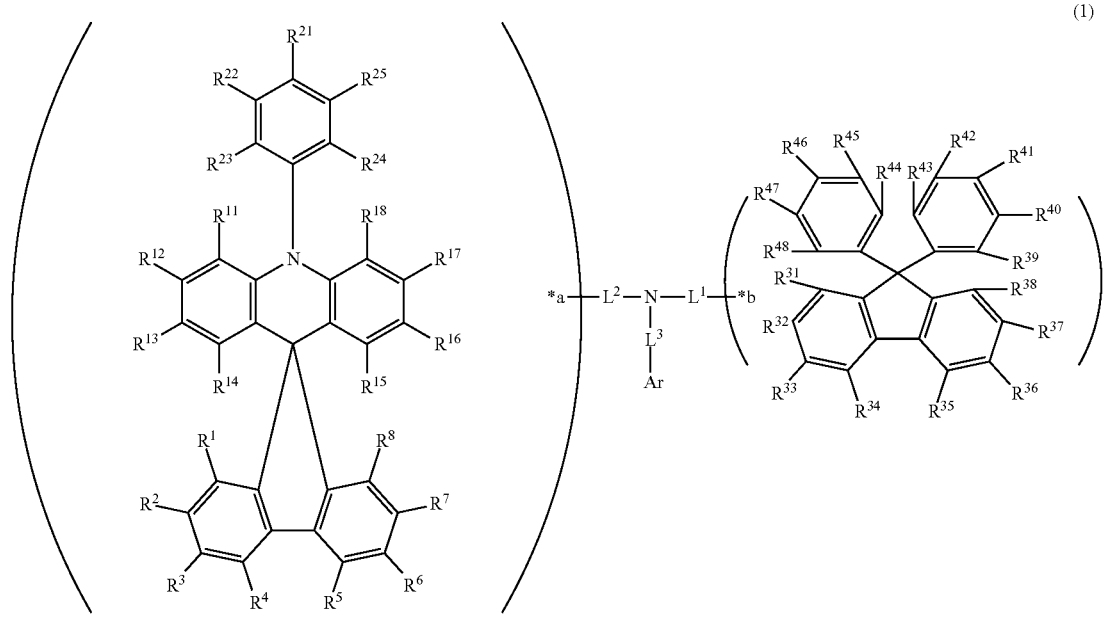

wherein,
one selected from $R^1$ to $R^8$, $R^{11}$ to $R^{18}$, and $R^{21}$ to $R^{25}$ is a single bond bonded to *a;
each of $R^1$ to $R^8$, $R^{11}$ to $R^{18}$, and $R^{21}$ to $R^{25}$ which is not the single bond bonded to *a is a hydrogen atom or a substituent;
$R^{11}$ and $R^{23}$, or $R^{18}$ and $R^{24}$ may be bonded to each other to form a single bond;
one selected from $R^{31}$ to $R^{48}$ is a single bond bonded to *b;
each of $R^{31}$ to $R^{38}$ and $R^{39}$ to $R^{48}$ which is not the single bond bonded to *b is a hydrogen atom or a substituent;
$R^{43}$ and $R^{44}$ may be bonded to each other to form a single bond;
adjacent two selected from $R^{31}$ to $R^{34}$ may be bonded to each other to form a ring structure;
adjacent two selected from $R^{35}$ to $R^{38}$ may be bonded to each other to form a ring structure;
adjacent two selected from $R^{39}$ to $R^{43}$ may be bonded to each other to form a ring structure;
adjacent two selected from $R^{44}$ to $R^{48}$ may be bonded to each other to form a ring structure;
each of $L^1$, $L^2$, and $L^3$ is independently a single bond or a substituted or unsubstituted arylene group having 6 to 30 ring carbon atoms; and
Ar is a substituted or unsubstituted aryl group having 6 to 30 ring carbon atoms or a substituted or unsubstituted heteroaryl group having 5 to 30 ring atoms.

In another aspect, the invention provides a material for organic electroluminescence devices comprising the above compound.

In still another aspect, the invention provides an organic electroluminescence device comprising a cathode, an anode and an organic layer between the cathode and the anode, wherein the organic layer comprises a light emitting layer and at least one layer of the organic layer comprises the above compound.

Advantageous Effects of Invention

The present invention provides organic EL devises having their emission efficiency improved.

BRIEF DESCRIPTION OF DRAWINGS

FIG. 1 is a schematic view showing the structure of an organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The terms of "a heteroaryl group," "a heteroarylene group," and "a heterocyclic group" used herein means a group comprising at least one ring hetero atom. The ring hetero atom is preferably at least one selected from a nitrogen atom, an oxygen atom, a sulfur atom, a silicon atom, and a selenium atom.

A "substituted or unsubstituted carbazolyl group" referred to herein includes the following carbazolyl groups:

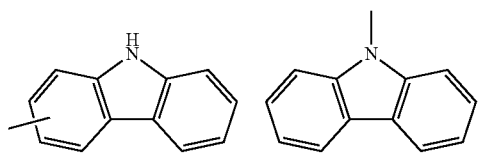

and a substituted carbazolyl group, wherein each of the carbazolyl groups has an optional substituent.

The optional substituents may be bonded to each other to form a fused ring structure which may comprise a hetero atom, such as a nitrogen atom, an oxygen atom, a sulfur atom, a silicon atom, and selenium atom, and the optional substituent may be bonded to any of 1- to 9-positions. Examples of such substituted carbazolyl groups are shown below.

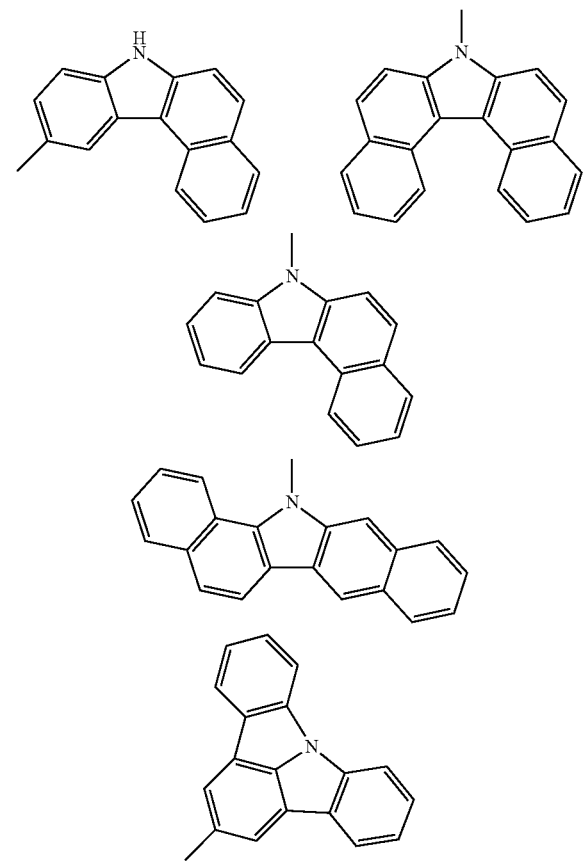

A "substituted or unsubstituted dibenzofuranyl group" and a "substituted or unsubstituted dibenzothiophenyl group" referred to herein include the following dibenzofuranyl group and the following dibenzothiophenyl group:

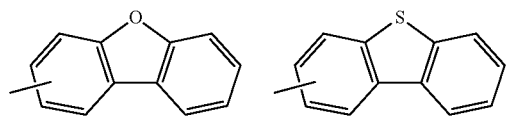

and a substituted dibenzofuranyl group and a substituted dibenzothiophenyl group, wherein each of the dibenzofuranyl group and the dibenzothiophenyl group has an optional substituent.

The optional substituents may be bonded to each other to form a fused ring structure which may comprise a hetero atom, such as a nitrogen atom, an oxygen atom, a sulfur atom, a silicon atom, and selenium atom, and the optional substituent may be bonded to any of 1- to 8-positions. Examples of such substituted dibenzofuranyl groups and substituted dibenzothiophenyl groups are shown below:

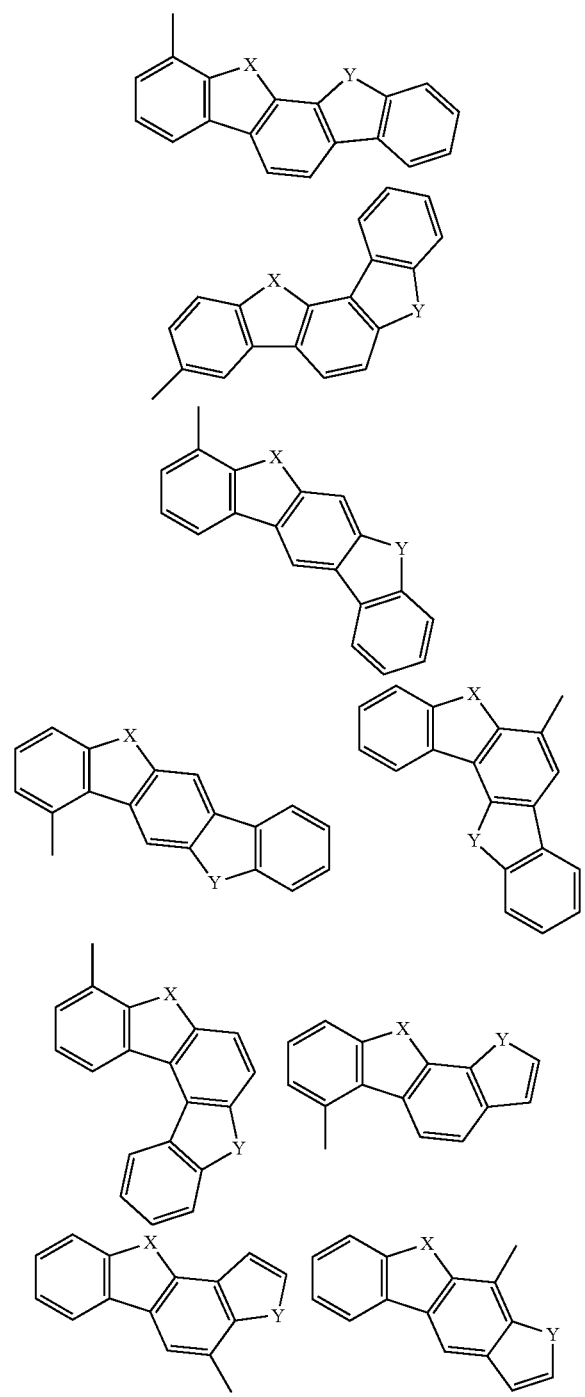

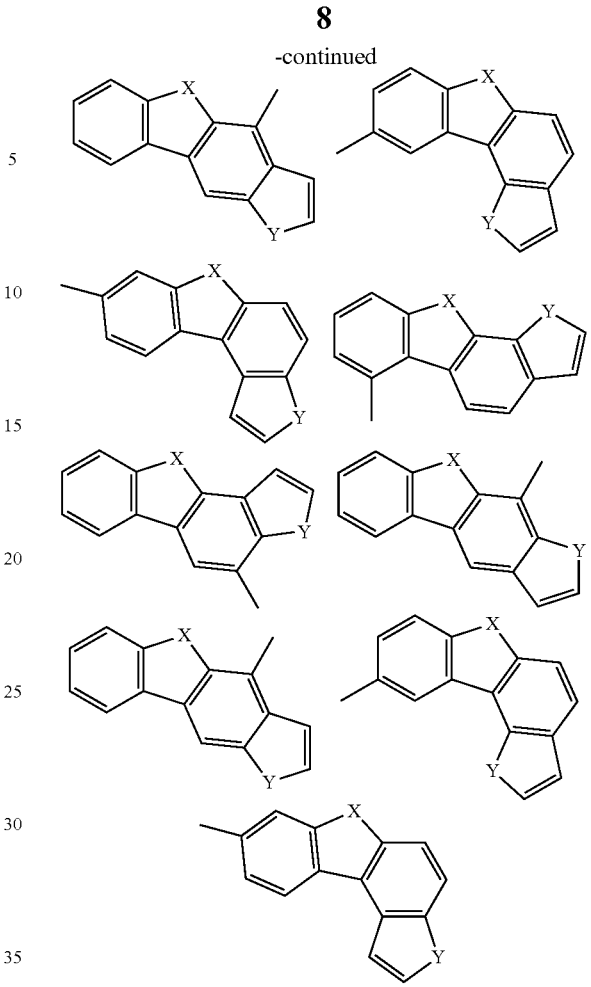

wherein X is an oxygen atom or a sulfur atom and Y is an oxygen atom, a sulfur atom, NH, $NR^a$ wherein $R^a$ is an alkyl group or an aryl group, $CH_2$, or $CR^b{}_2$ wherein $R^b$ is an alkyl group or an aryl group.

The substituent referred to herein simply by "a substituent" and the optional substituent referred to herein by "a substituted or unsubstituted" is, unless otherwise noted, selected from an alkyl group having 1 to 30, preferably 1 to 18, and more preferably 1 to 8 carbon atoms; a cycloalkyl group having 3 to 30, preferably 3 to 10, more preferably 3 to 8, and still more preferably 5 or 6 ring carbon atoms; an aryl group (inclusive of a non-fused aryl group, a fused aryl group, and an aromatic ring assembly) having 6 to 30, preferably 6 to 25, more preferably 6 to 18 carbon atoms; an aralkyl group having 7 to 31, preferably 7 to 26, and more preferably 7 to 20 calcium atoms which includes an aryl group having 6 to 30, preferably 6 to 25, and more preferably 6 to 18 ring carbon atoms; an amino group; a mono- or di-substituted amino group having a substituent selected from an alkyl group having 1 to 30, preferably 1 to 18, and more preferably 1 to 8 carbon atoms and an aryl group having 6 to 30, preferably 6 to 25, and more preferably 6 to 18 ring carbon atoms; an alkoxy group having an alkyl group having 1 to 30, preferably 1 to 18, and more preferably 1 to 8 carbon atoms; an aryloxy group having an aryl group (inclusive of a non-fused aryl group, a fused aryl group, and an aromatic ring assembly) having 6 to 30, preferably 6 to 25, and more preferably 6 to 18 ring carbon atoms; an alkylthio group having an alkyl group having 1 to 30, preferably 1 to 18, and more preferably 1 to 8 carbon atoms; an arylthio group having an aryl group (inclusive of a non-fused aryl group, a fused aryl group, and an aromatic ring assembly) having 6 to 30, preferably 6 to 25, and more preferably 6 to 18 ring carbon atoms; a mono-, di- or tri-substituted silyl group having a substituent selected from an alkyl group having 1 to 30, preferably 1 to 18, and more preferably 1 to 8 carbon atoms and an aryl group (inclusive of a non-fused aryl group, a fused aryl group, and an aromatic ring assembly) having 6 to 30, preferably 6 to 25, and more preferably 6 to 18 ring calcium atoms; a haloalkyl group having 1 to 30, preferably 1 to 18, and more preferably 1 to 8 carbon atoms; a haloalkoxy group having a haloalkyl group having 1 to 30, preferably 1 to 18, and more preferably 1 to 8 carbon atoms; an aromatic or non-aromatic heterocyclic group (inclusive of a non-fused heterocyclic group, a fuse heterocyclic group, and a heterocyclic ring assembly) having 5 to 30, preferably 5 to 24, and more preferably 5 to 13 ring atoms (hereinafter also referred to as "heteroaryl group"); a halogen atom; a cyano group; and a nitro group.

The substituent and the optional substituent is more preferably selected from an alkyl group having 1 to 30, preferably 1 to 18, and more preferably 1 to 8 carbon atoms; a cycloalkyl group having 3 to 30, preferably 3 to 10, more preferably 3 to 8, and still more preferably 5 or 6 ring carbon atoms; an aryl group (inclusive of a non-fused aryl group, a fused aryl group, and an aromatic ring assembly) having 6 to 30, preferably 6 to 25, more preferably 6 to 18 carbon atoms; a mono- or di-substituted amino group having a substituent selected from an alkyl group having 1 to 30, preferably 1 to 18, and more preferably 1 to 8 carbon atoms and an aryl group (inclusive of a non-fused aryl group, a fused aryl group, and an aromatic ring assembly) having 6 to 30, preferably 6 to 25, and more preferably 6 to 18 ring carbon atoms; an aromatic heterocyclic group (inclusive of a non-fused aromatic heterocyclic group, a fuse aromatic heterocyclic group, and an aromatic heterocyclic ring assembly) having 5 to 30, preferably 5 to 24, and more preferably 5 to 13 ring atoms; a halogen atom; and a cyano group.

Examples of the alkyl group having 1 to 30 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the cycloalkyl group having 3 to 30 ring carbon atoms include a cyclopropyl group, a cyclobutyl group, a cyclopentyl group, a cyclohexyl group, and a cycloheptyl group.

Examples of the aryl group (inclusive of a non-fused aryl group, a fused aryl group, and an aromatic ring assembly) having 6 to 30 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group. Preferred are a phenyl group, a biphenylyl group, a terphenylyl group, and a naphthyl group, with a phenyl group, a biphenylyl group, and a naphthyl group being more preferred, and a phenyl group being still more preferred.

Preferred examples of the substituted aryl group having 6 to 50 ring carbon atoms include a 9,9-dimethylfluorenyl group and a 9,9-diphenylfluorenyl group.

The details of the aryl group having 6 to 30 ring carbon atoms of the aralkyl group having 7 to 31 carbon atoms are the same as those of the aryl group having 6 to 30 ring carbon atoms mentioned above. The alkyl portion of the aralkyl group is selected from the alkyl group mentioned above so as to allow the aralkyl group to have 7 to 31 carbon atoms. Preferred examples of the aralkyl group having 7 to 31 carbon atoms are a benzyl group, a phenethyl group, and a phenylpropyl group, with a benzyl group being preferred.

The details of the alkyl group having 1 to 30 carbon atoms and the aryl group (inclusive of a non-fused aryl group, a fused aryl group, and an aromatic ring assembly) having 6 to 30 ring carbon atoms for the mono- or di-substituted amino group are the same as those of the alkyl group having 1 to 30 carbon atoms mentioned above and the aryl group having 6 to 30 ring carbon atoms mentioned above. Examples of the mono- or di-substituted amino group include a dialkylamino group, a diarylamino group, and an alkylarylamino group.

The details of the alkyl group having 1 to 30 carbon atoms for the alkoxy group are the same as those of the alkyl group having 1 to 30 carbon atoms mentioned above. Examples of the alkoxy group include a t-butoxy group, a propoxy group, an ethoxy group, and a methoxy group, with an ethoxy group and a methoxy group being more preferred, and a methoxy group being still more preferred.

The details of the aryl group (inclusive of a non-fused aryl group, a fused aryl group, and an aromatic ring assembly) having 6 to 30 ring carbon atoms for the aryloxy group are the same as those of the aryl group having 6 to 30 ring carbon atoms mentioned above. Preferred examples of the aryloxy group include a terphenyloxy group, a biphenyloxy group, and a phenoxy group, with a biphenyloxy group, and a phenoxy group, and a phenoxy group being more preferred, and a phenoxy group being still more preferred.

The details of the alkyl group having 1 to 30 carbon atoms for the alkylthio group are the same as those of the alkyl group having 1 to 30 carbon atoms mentioned above. Examples of the alkylthio group include a methylthio group and an ethylthio group.

The details of the aryl group (inclusive of a non-fused aryl group, a fused aryl group, and an aromatic ring assembly) having 6 to 30 ring carbon atoms for the arylthio group are the same as those of the aryl group having 6 to 30 ring carbon atoms mentioned above. Example of the arylthio group include a phenylthio group.

The details of the alkyl group having 1 to 30 carbon atoms and the aryl group (inclusive of a non-fused aryl group, a fused aryl group, and an aromatic ring assembly) having 6 to 30 ring carbon atoms for the mono-, di- or tri-substituted silyl group are the same as those of the alkyl group having 1 to 30 carbon atoms mentioned above and the aryl group having 6 to 30 ring carbon atoms mentioned above. Preferred is a tri-substituted silyl group, for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

The haloalkyl group having 1 to 30 carbon atoms is a group derived from the alkyl group having 1 to 30 carbon atoms mentioned above by replacing at least one, preferably 1 to 7 hydrogen atoms or all the hydrogen atoms with a halogen atom, such as a fluorine atom, a chlorine atom, a bromine atom, and an iodine atom, preferably a fluorine atom. Preferred example thereof is a fluoroalkyl group having 1 to 30, preferably 1 to 18, and more preferably 1 to 8 carbon atoms, with a heptafluoropropyl group (inclusive of isomeric groups), a pentafluoroethyl group, a 2,2,2-trifluoroethyl group, and a trifluoromethyl group being more preferred, a pentafluoroethyl group, a 2,2,2-trifluoroethyl group, and a trifluoromethyl group being still more preferred, and a trifluoromethyl group being particularly preferred.

The details of the haloalkyl group having 1 to 30 carbon atoms for the haloalkoxy group are the same as those of the haloalkyl group having 1 to 30 carbon atoms mentioned above. Preferred example thereof is a fluoroalkoxy group having 1 to 30, preferably 1 to 18, and more preferably 1 to 8 carbon atoms, with a heptafluoropropoxy group (inclusive of isomeric groups), a pentafluoroethoxy group, a 2,2,2-trifluoroethoxy group, and trifluoromethoxy group being more preferred, a pentafluoroethoxy group, a 2,2,2-trifluoroethoxy group, and trifluoromethoxy group being still more preferred, and a trifluoromethoxy group being particularly preferred.

The aromatic or non-aromatic heterocyclic group having 5 to 30 ring atoms comprises 1 to 5, preferably 1 to 3, more preferably 1 to 2 ring heteroatoms, for example, a nitrogen atom, a sulfur atom, and a oxygen atom.

Examples of the aromatic heterocyclic group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group (a benzothienyl group, the same applies below), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group (a dibenzothienyl group, the same applies below), a naphthobenzothiophenyl group (a naphthobenzothienyl group), a carbazolyl group (a N-carbazolyl group and a C-carbazolyl group), a benzocarbazolyl group (a benzo-N-carbazolyl group and a benzo-C-carbazolyl group), a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group, with a thienyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group being more preferred. Preferred examples of the substituted aromatic heterocyclic group include a N-phenylcarbazolyl group, a N-biphenylylcarbazolyl group, a N-phenylphenylcarbazolyl group, a N-naphthylcarbazolyl group, phenyldibenzofuranyl group, and a phenyldibenzothiophenyl group (a phenyldibenzothienyl group).

Examples of the non-aromatic heterocyclic group include the group derived from the aromatic heterocyclic group mentioned above by hydrogenating its aromatic ring partially or wholly into an aliphatic ring.

The halogen atom is a fluorine atom, a chlorine atom, a bromine atom, or an iodine atom, with a fluorine atom being preferred.

Compound

The compound in an aspect of the invention is represented by formula (1) (also referred to as "compound (1)"):

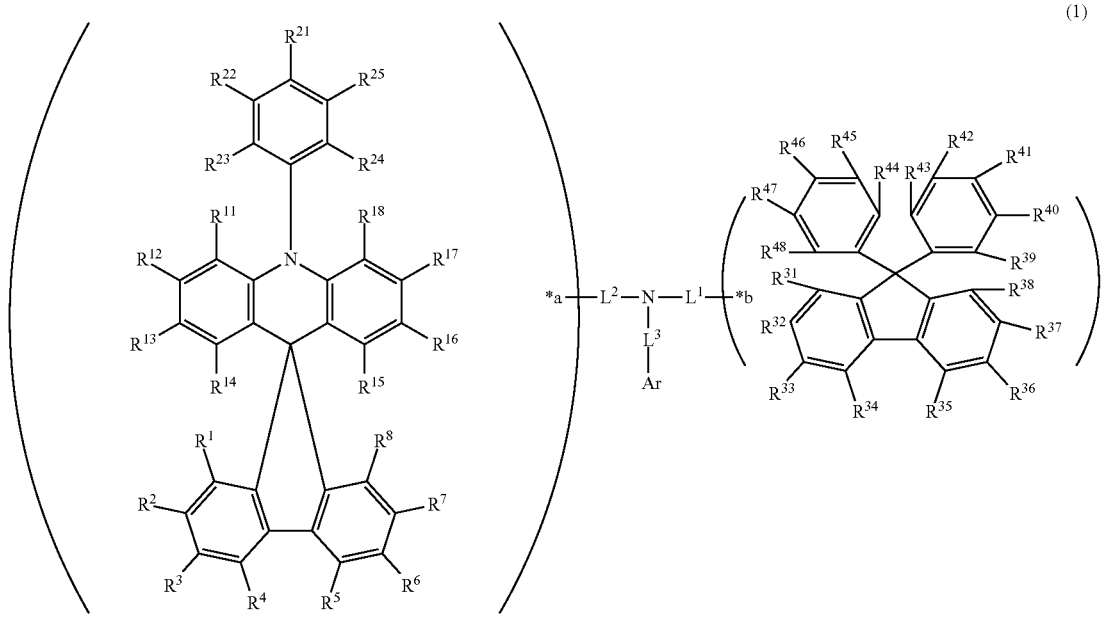

(1)

wherein, one selected from $R^1$ to $R^8$, $R^{11}$ to $R^{18}$, and $R^{21}$ to $R^{25}$ is a single bond bonded to *a;

each of $R^1$ to $R^8$, $R^{11}$ to $R^{18}$, and $R^{21}$ to $R^{25}$ which is not the single bond bonded to *a is a hydrogen atom or a substituent;

$R^{11}$ and $R^{23}$, or $R^{18}$ and $R^{24}$ may be bonded to each other to form a single bond, wherein, in an embodiment of the invention, one of a pair of $R^{11}$ and $R^{23}$ and a pair of $R^{18}$ and $R^{24}$ form the single bond, for example, when $R^{11}$ and $R^{23}$ form the single bond, one selected from $R^1$ to $R^8$, $R^{12}$ to $R^{18}$, $R^{21}$, $R^{22}$, $R^{24}$, and $R^{25}$, preferably one selected from $R^2$ to $R^7$, $R^{13}$, $R^{16}$, and $R^{17}$, more preferably one selected from $R^2$ to $R^7$ and $R^{17}$, and still more preferably one selected from $R^2$, $R^4$, $R^5$, and $R^7$ is the single bond bonded to *a;

one selected from $R^{31}$ to $R^{48}$ is a single bond bonded to *b;

each of $R^{31}$ to $R^{38}$ and $R^{39}$ to $R^{48}$ which is not the single bond bonded to *b is a hydrogen atom or a substituent;

$R^{43}$ and $R^{44}$ may be bonded to each other to form a single bond;

adjacent two selected from $R^{31}$ to $R^{34}$ may be bonded to each other to form a ring structure; adjacent two selected from $R^{35}$ to $R^{38}$ may be bonded to each other to form a ring structure; adjacent two selected from $R^{39}$ to $R^{43}$ may be bonded to each other to form a ring structure; adjacent two selected from $R^{44}$ to $R^{48}$ may be bonded to each other to form a ring structure;

each of $L^1$, $L^2$, and $L^3$ is independently a single bond or a substituted or unsubstituted arylene group having 6 to 30 ring carbon atoms; and Ar is a substituted or unsubstituted aryl group having 6 to 30 ring carbon atoms or a substituted or unsubstituted heteroaryl group having 5 to 30 ring atoms.

Examples of the aryl group having 6 to 30, preferably 6 to 25, and more preferably 6 to 18 ring carbon atoms for Ar include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group, with a phenyl group, a biphenylyl group, a terphenylyl group, a naphthyl group, a phenanthryl group, and a triphenylenyl group being preferred.

Examples of the heteroaryl group having 5 to 30, preferably 5 to 24, and more preferably 5 to 13 ring atoms for Ar include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group (a benzothienyl group, the same applies below), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group (a dibenzothienyl group, the same applies below), a naphthobenzothiophenyl group (a naphthobenzo-thienyl group), a carbazolyl group (a N-carbazolyl group and a C-carbazolyl group), a benzocarbazolyl group (a benzo-N-carbazolyl group and a benzo-C-carbazolyl group), a phenanthridinyl group, an acridinyl group, a phenanthrolinyl group, a phenazinyl group, a phenothiazinyl group, a phenoxazinyl group, and a xanthenyl group, with a carbazolyl group, a dibenzothiophenyl group, and a dibenzofuranyl group being preferred.

Examples of the substituted or unsubstituted arylene group having 6 to 30 ring carbon atoms for $L^1$, $L^2$, and $L^3$ include the divalent group derived from the aryl group mentioned with respect to Ar, with a phenylene group, a biphenylene group, a terphenylene group, and a naphthylene group being particularly preferred. The preferred range of the carbon number is also the same.

$L^1$ and $L^2$ are preferably both single bonds, and $L^3$ is preferably a substituted or unsubstituted arylene group having 6 to 30 ring carbon atoms.

Each of the substituent represented by $R^1$ to $R^8$, $R^{11}$ to $R^{18}$, $R^{21}$ to $R^{25}$, and $R^{31}$ to $R^{48}$ and the substituent referred to by "substituted or unsubstituted" is preferably at least one selected from the group consisting of an alkyl group having 1 to 30 carbon atoms; a cycloalkyl group having 3 to 30 ring carbon atoms; an aryl group (inclusive of a non-fused aryl group, a fused aryl group, and an aromatic ring assembly) having 6 to 30 ring carbon atoms; an aralkyl group having 7 to 31 carbon atoms which includes an aryl group having 6 to 30 ring carbon atoms; an alkoxy group having an alkyl group having 1 to 30 carbon atoms; an aryloxy group having an aryl group (inclusive of a non-fused aryl group, a fused aryl group, and an aromatic ring assembly) having 6 to 30 ring carbon atoms; a mono-, di- or tri-substituted silyl group having a substituent selected from an alkyl group having 1 to 30 carbon atoms and an aryl group (inclusive of a non-fused aryl group, a fused aryl group, and an aromatic ring assembly) having 6 to 30 ring carbon atoms; a haloalkyl group having 1 to 30 carbon atoms; a haloalkoxy group having a haloalkyl group having 1 to 30 carbon atoms; a halogen atom; a cyano group; and a nitro group. Preferred are a methyl group, an ethyl group, a butyl group, a phenyl group, a biphenyl group, a terphenyl group, a naphthyl group, a phenanthryl group, a triphenyl group, a benzofuranyl group, a benzothienyl group, a dibenzofuranyl group, a dibenzothienyl group, a carbazolyl group, and a fluorenyl group.

In formula (1), examples of the partial structure represented by formula (A):

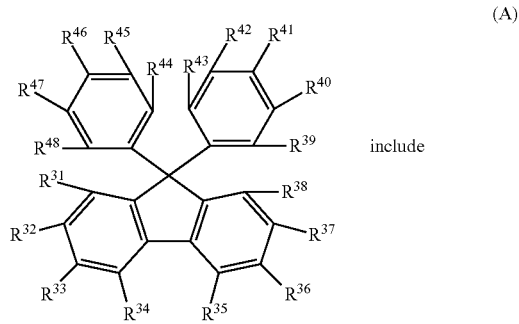

include

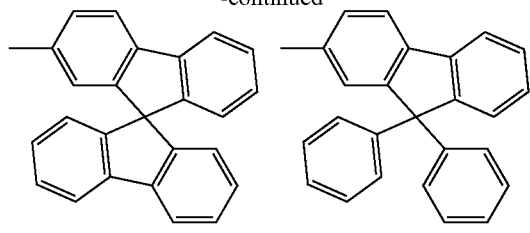
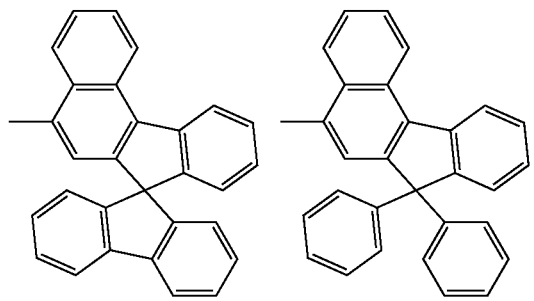
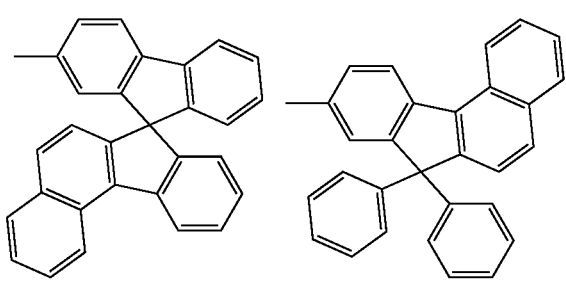
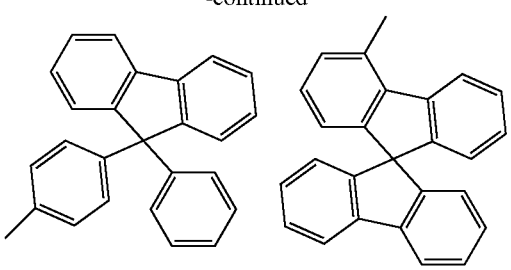
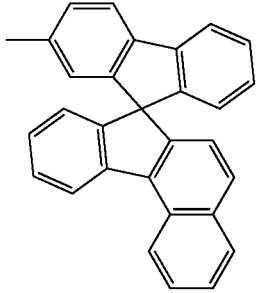 [SMILES: Cc1ccc2c(c1)C1(c3ccccc3-2)c2ccccc2-c2c1ccc1ccccc21]
wherein - is a bonding site to *b and $R^{31}$ to $R^{48}$ are omitted for conciseness.
Formula (1) is preferably represented by formula (2) or (3):
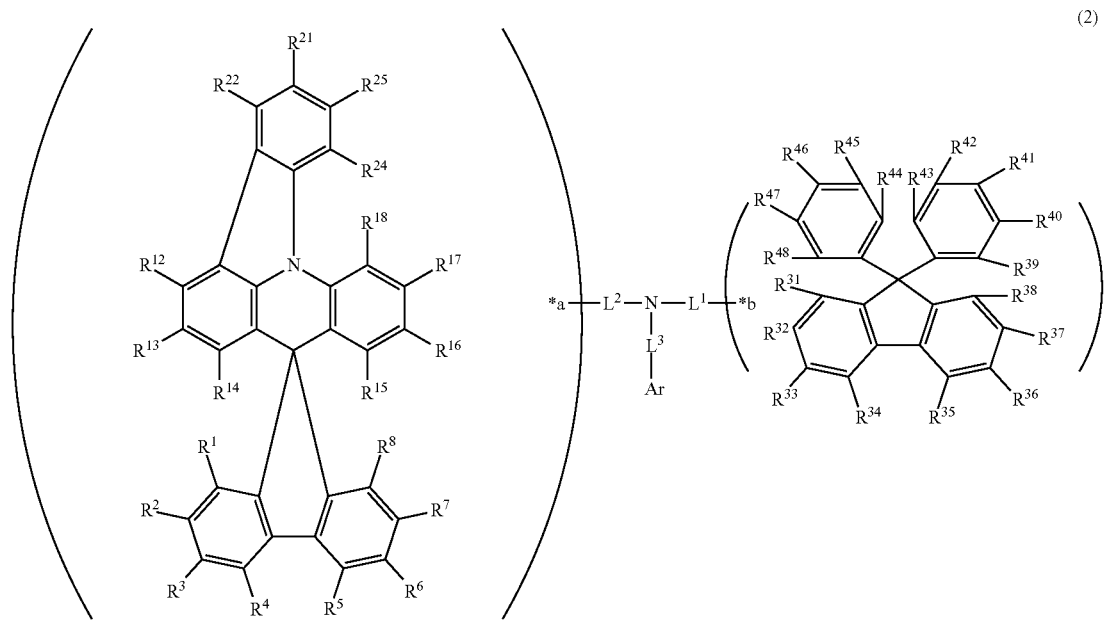

wherein $R^1$ to $R^8$, $R^{12}$ to $R^{18}$, $R^{21}$ to $R^{22}$, $R^{24}$ to $R^{25}$, $R^{31}$ to $R^{48}$, $L^1$ to $L^3$, and Ar are as defined above, and examples thereof and preferred ranges for the number of carbon atoms and the number of atoms are as described above.

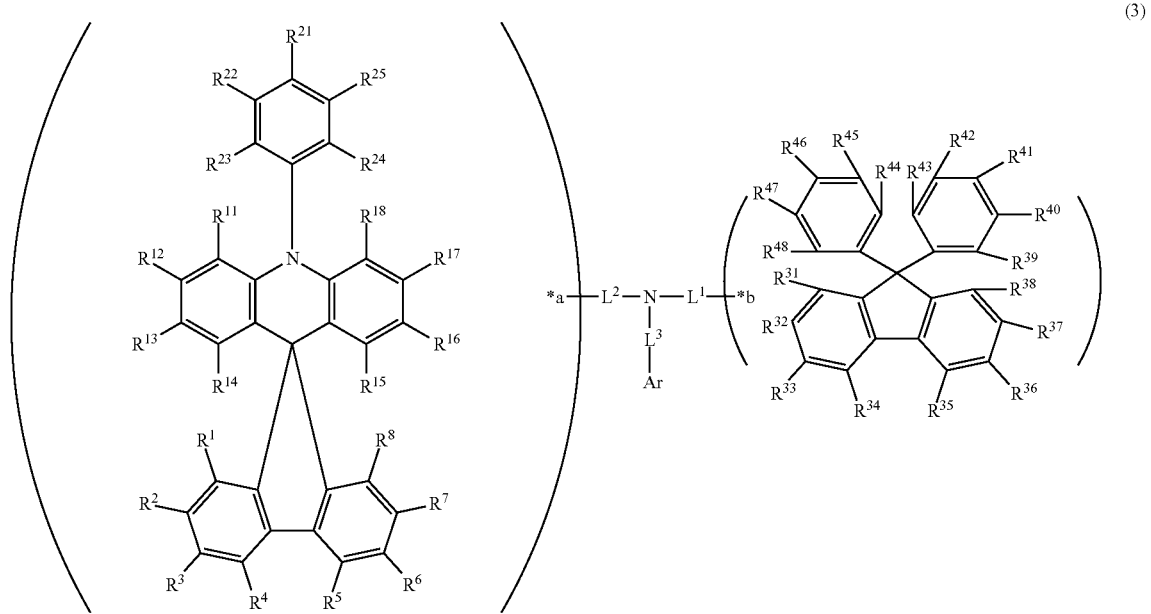

(3)

wherein $R^1$, to $R^8$, $R^{12}$ to $R^{18}$, $R^{21}$ to $R^{25}$, $R^{31}$ to $R^{48}$, $L^1$ to $L^3$, and Ar are as defined above, and examples thereof and preferred ranges for the number of carbon atoms and the number of atoms are as described above, provided that $R^{11}$ and $R^{23}$ are not bonded to each other.

Formula (1) may be represented by formula (4):

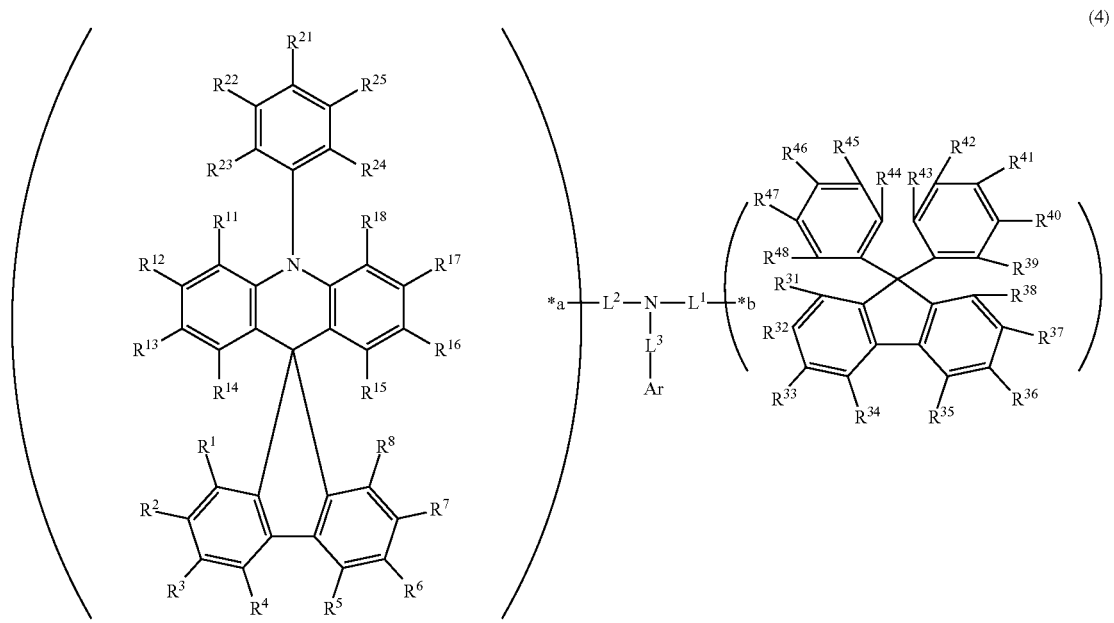

(4)

wherein $R^1$ to $R^8$, $R^{12}$ to $R^{18}$, $R^{21}$ to $R^{25}$, $R^{31}$ to $R^{48}$, $L^1$ to $L^3$, and Ar are as defined above, provided that $R^{18}$ and $R^{24}$ are not bonded to each other.

In formula (1), $R^2$, $R^4$, $R^5$, or $R^7$ is preferably the single bond bonded to *a.

Formula (1) is preferably represented by formula (2a) or (3a) and more preferably represented by formula (2b) or (3b):

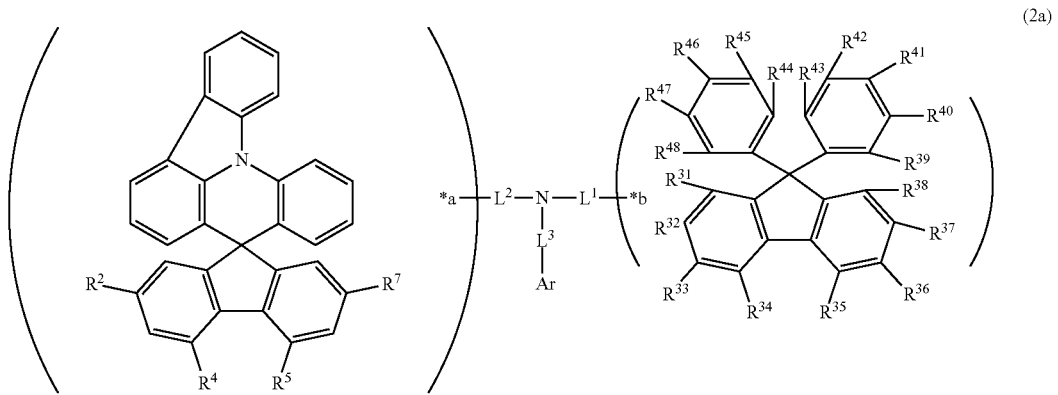

(2a)

wherein $R^2$, $R^4$, $R^5$, $R^7$, $R^{31}$ to $R^{48}$, $L^1$ to $L^3$, and Ar are as defined above, and examples thereof and preferred ranges for the number of carbon atoms and the number of atoms are as described above, provided that $R^{43}$ and $R^{44}$ are not bonded to each other;

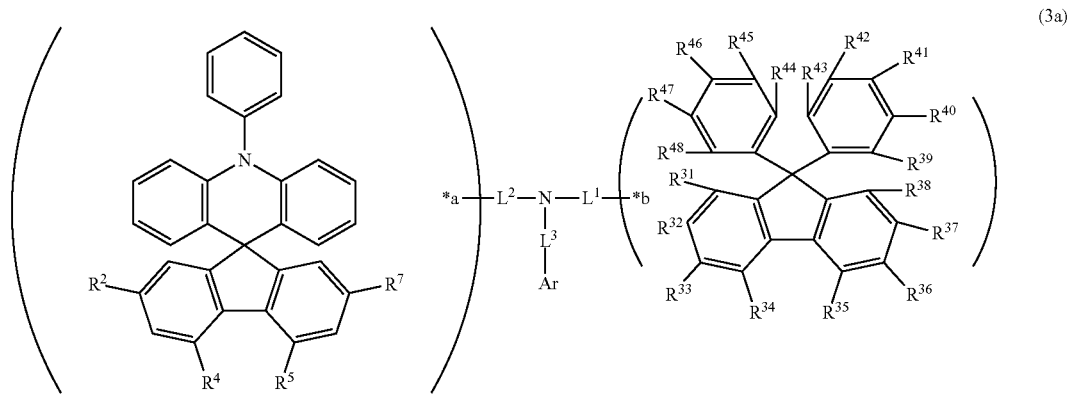

(3a)

wherein $R^2$, $R^4$, $R^5$, $R^7$, $R^{31}$ to $R^{48}$, $L^1$ to $L^3$, and Ar are as defined above, and examples thereof and preferred ranges for the number of carbon atoms and the number of atoms are as described above, provided that $R^{43}$ and $R^{44}$ are not bonded to each other;

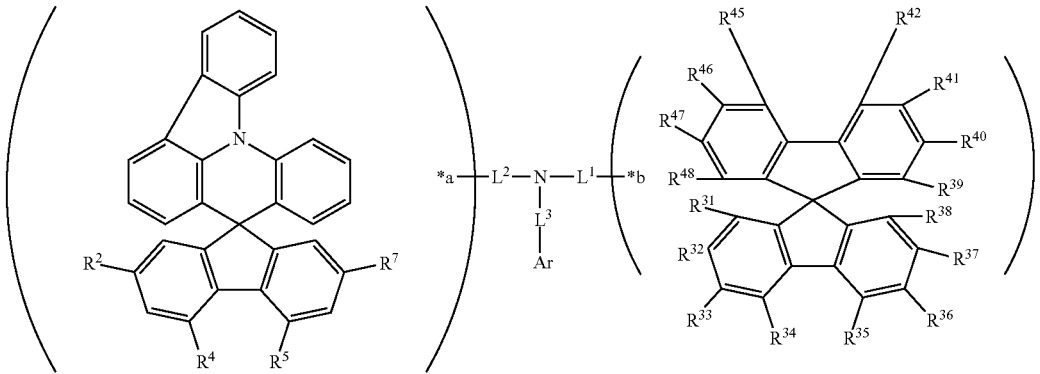

(2b)

wherein $R^2$, $R^4$, $R^5$, $R^7$, $R^{31}$ to $R^{42}$, $R^{45}$ to $R^{48}$, $L^1$ to $L^3$, and Ar are as defined above, and examples thereof and preferred ranges for the number of carbon atoms and the number of atoms are as described above; and

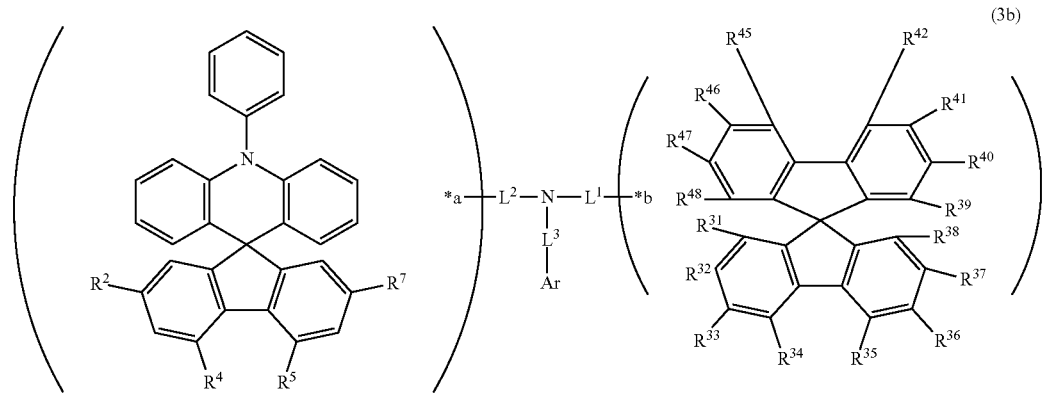

(3b)

wherein $R^2$, $R^4$, $R^5$, $R^7$, $R^{31}$ to $R^{42}$, $R^{45}$ to $R^{48}$, $L^1$ to $L^3$, and Ar are as defined above, and examples thereof and preferred ranges for the number of carbon atoms and the number of atoms are as described above.

Formula (1) may be represented by formula (4a) or (5a):

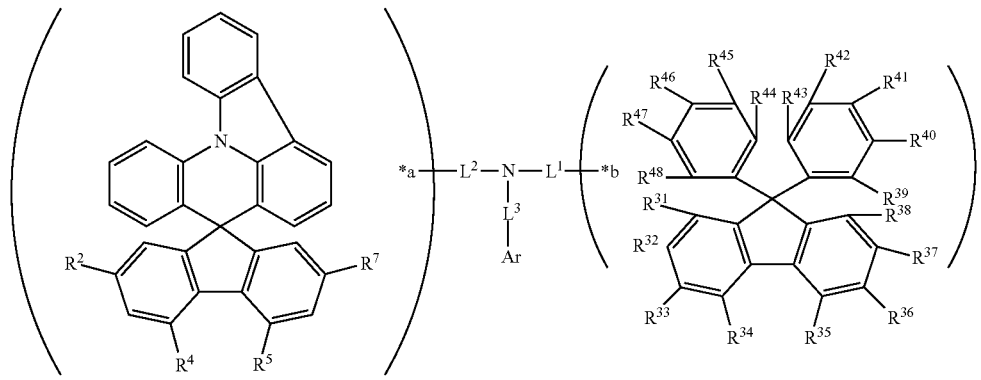

(4a)

wherein $R^2$, $R^4$, $R^5$, $R^7$, $R^{31}$ to $R^{48}$, $L^1$ to $L^3$, and Ar are as defined above, and examples thereof and preferred ranges for the number of carbon atoms and the number of atoms are as described above, provided that $R^{43}$ and $R^{44}$ are not bonded to each other; and

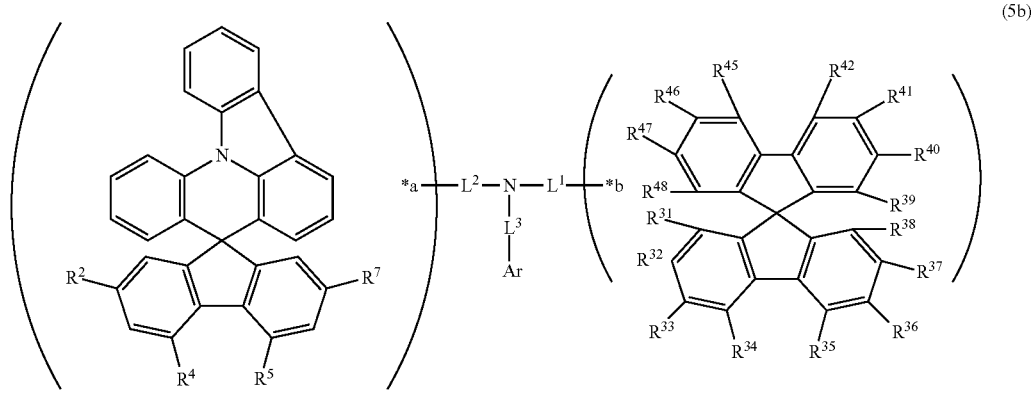

(5b)

wherein $R^2$, $R^4$, $R^5$, $R^7$, $R^{31}$ to $R^{42}$, $R^{45}$ to $R^{48}$, $L^1$ to $L^3$, and Ar are as defined above, and examples thereof and preferred ranges for the number of carbon atoms and the number of atoms are as described above.

In formulae (1), (2), (3), (2a), (2b), (3a), (3b), (4a), and (5a), $R^{32}$, $R^{34}$, $R^{35}$, or $R^{37}$ is preferably the single bond bonded to *b, and $R^2$, $R^4$, $R^5$, or $R^7$ is preferably the single bond bonded to *a when $R^{32}$, $R^{34}$, $R^{35}$, or $R^{37}$ is the single bond bonded to *b.

The Spiro carbon atom in formula (1) can be an asymmetric carbon atom. When the spiro carbon atoms is asymmetric, the compound (1) of the invention may be any of a single optical isomer, a racemic mixture, and a mixture of two optical isomers in an arbitrary ratio.

Examples of the compound represented by formula (1) are shown below, although not limited thereto.

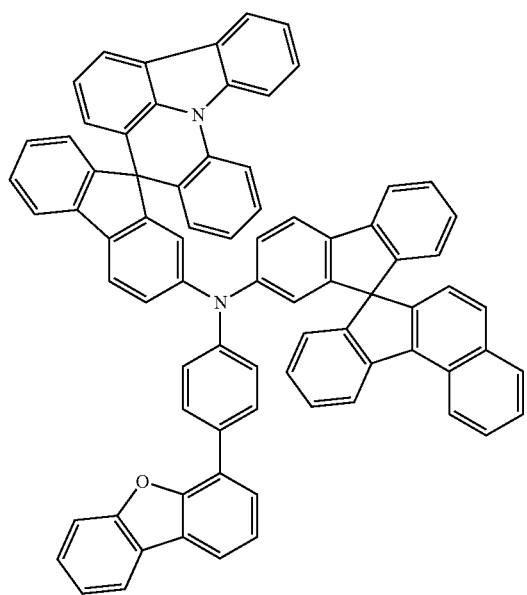

-continued

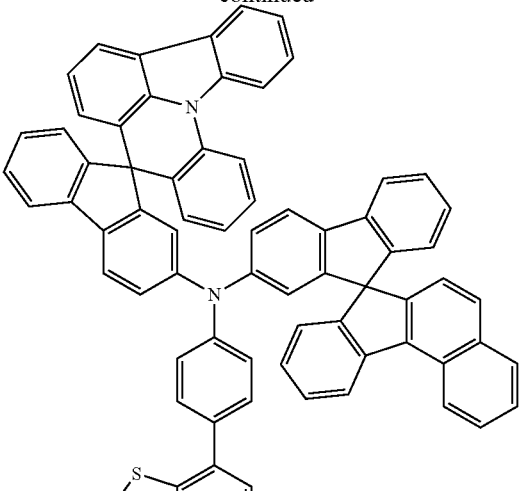

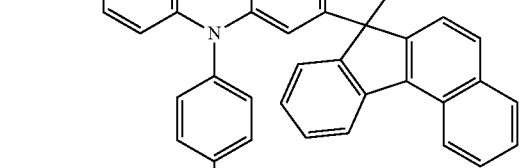

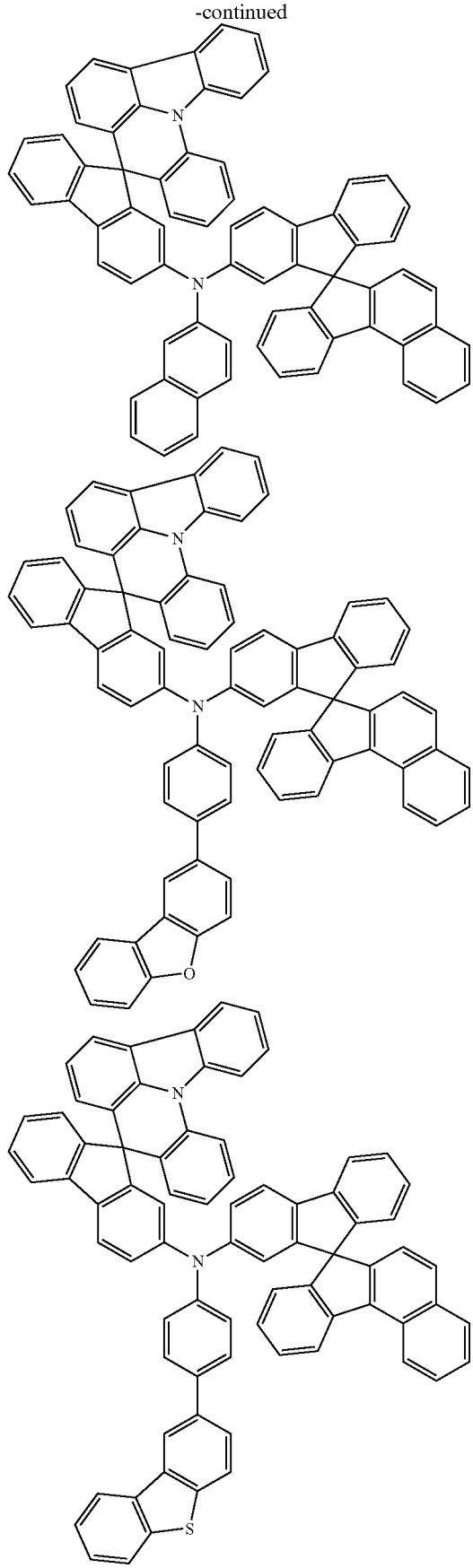
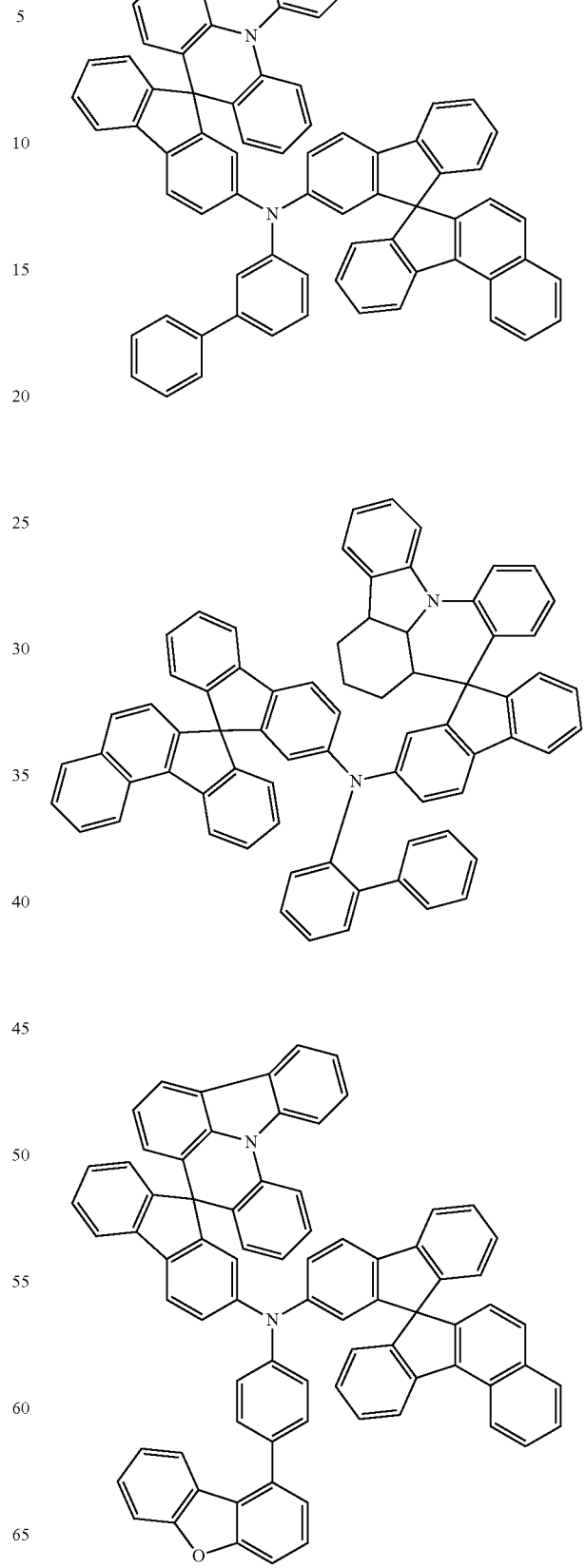

27
-continued
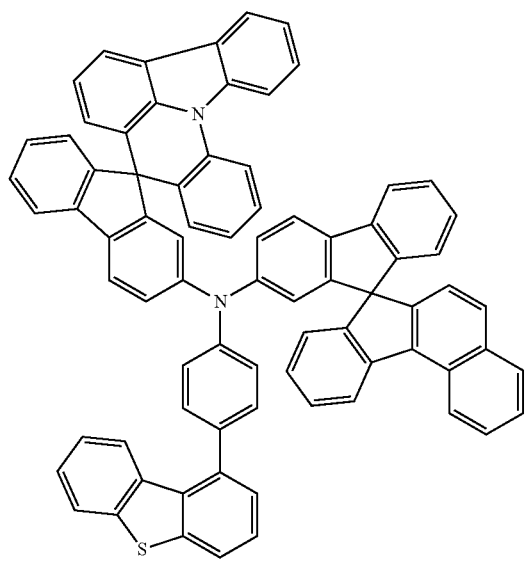
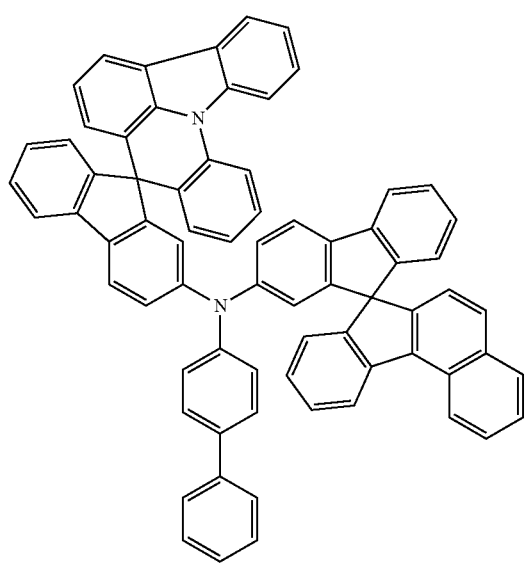
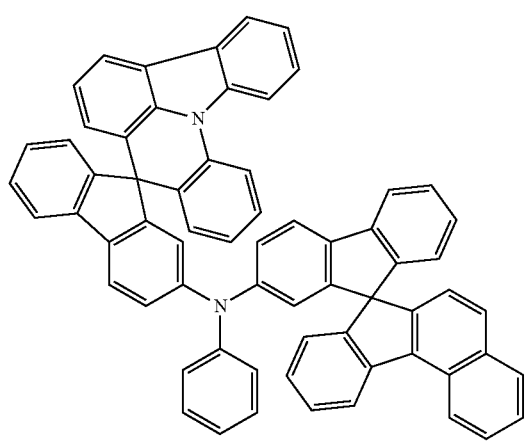
28
-continued
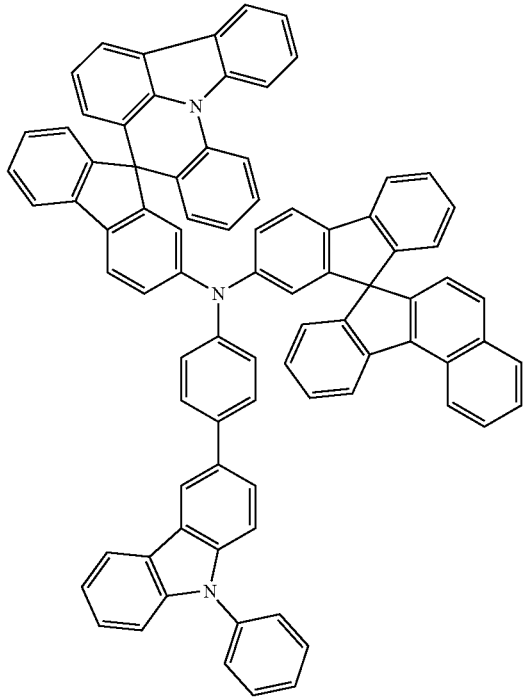
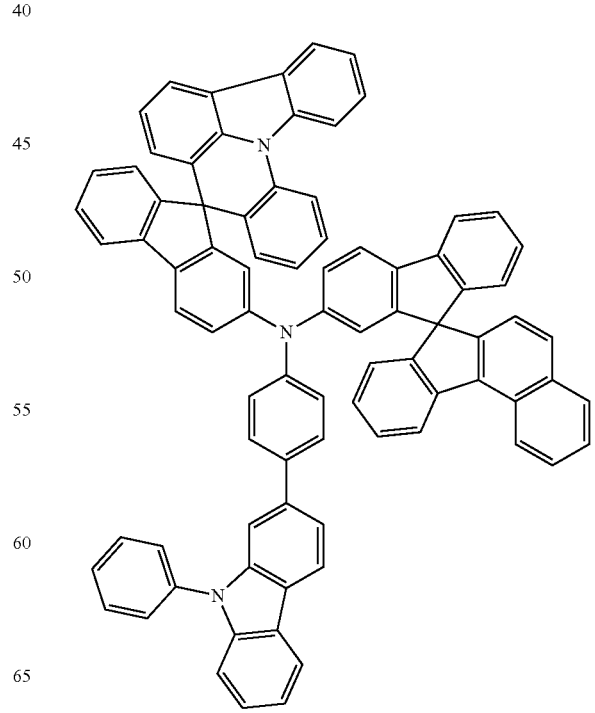

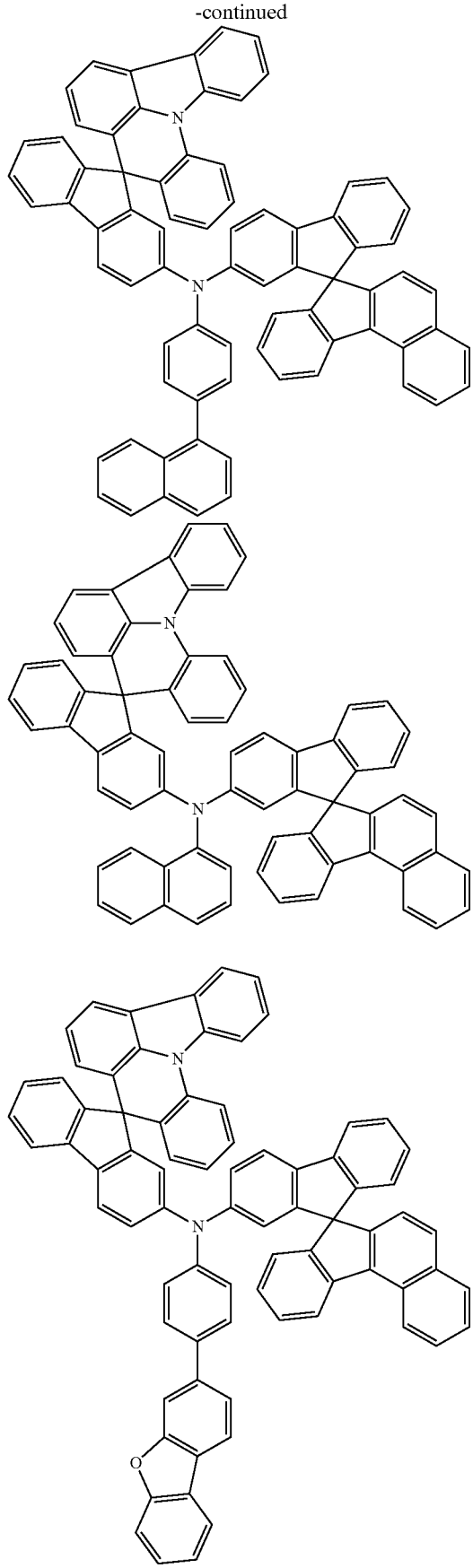
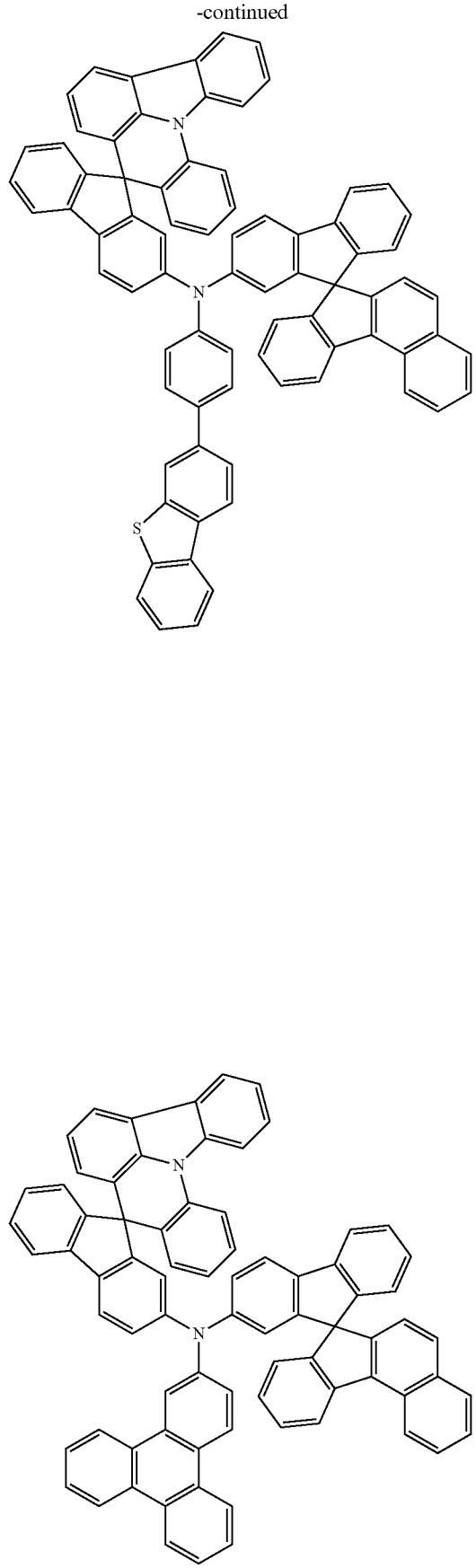

31
-continued
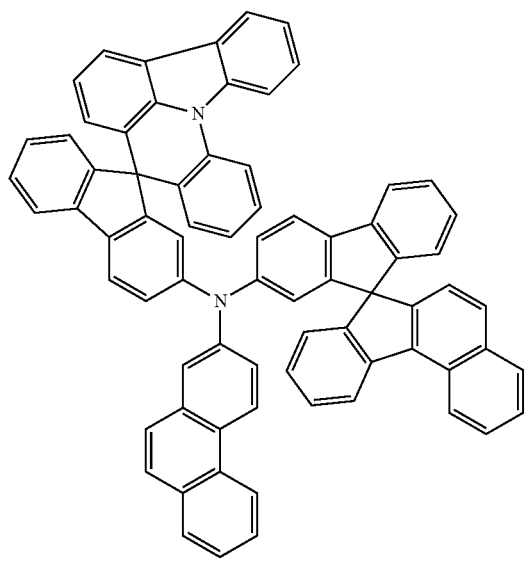
32
-continued
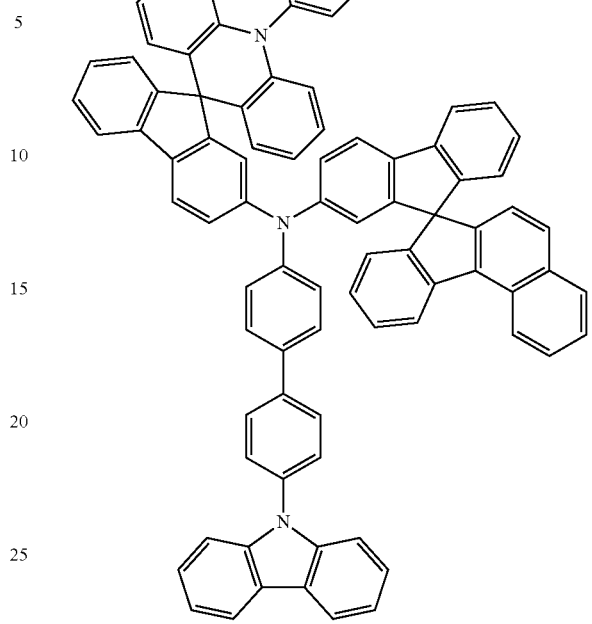
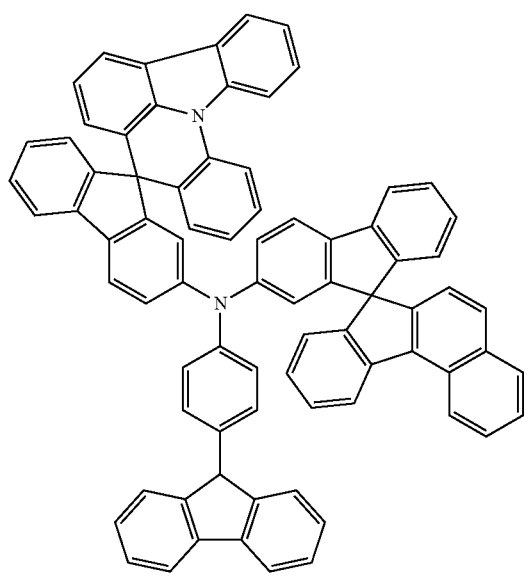
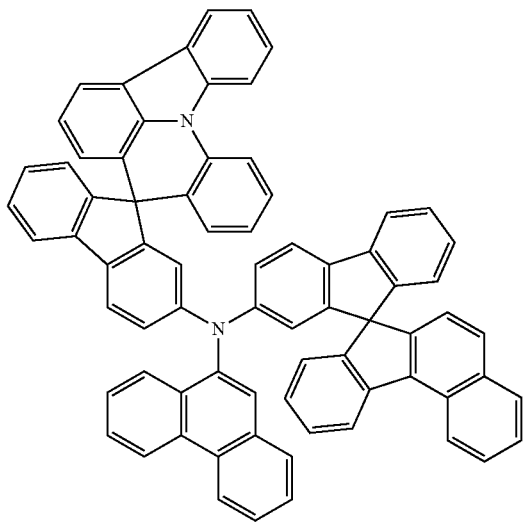

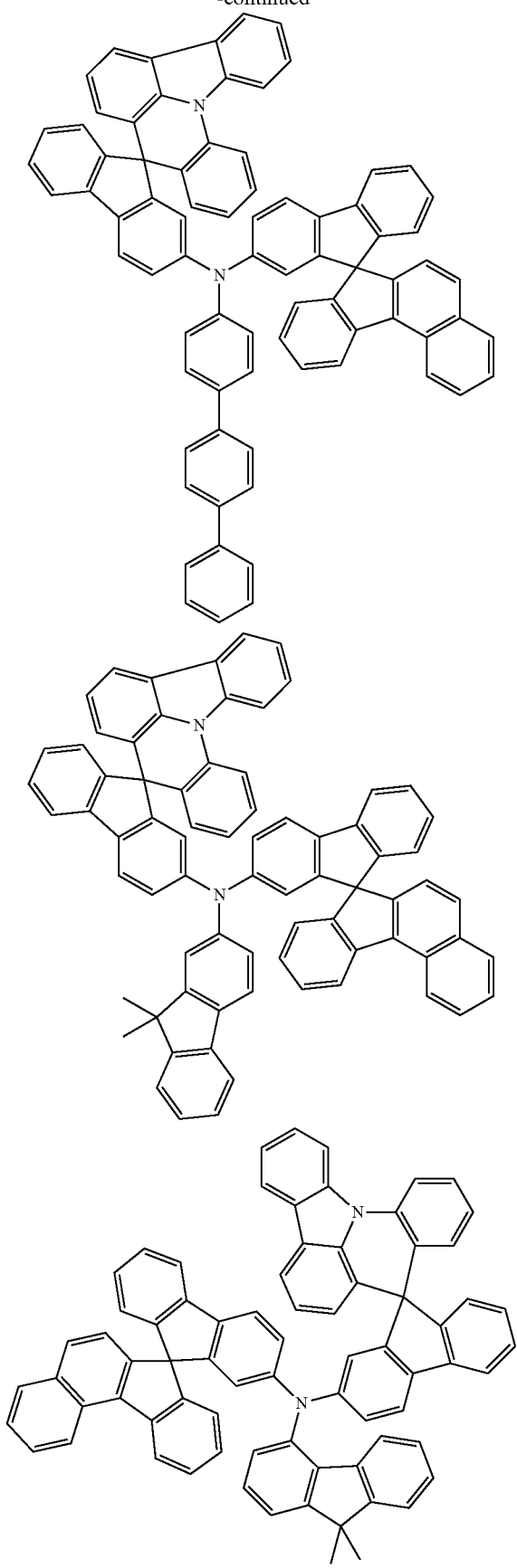

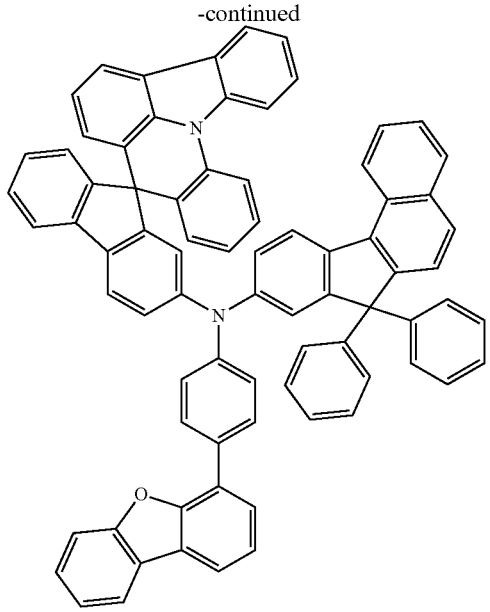
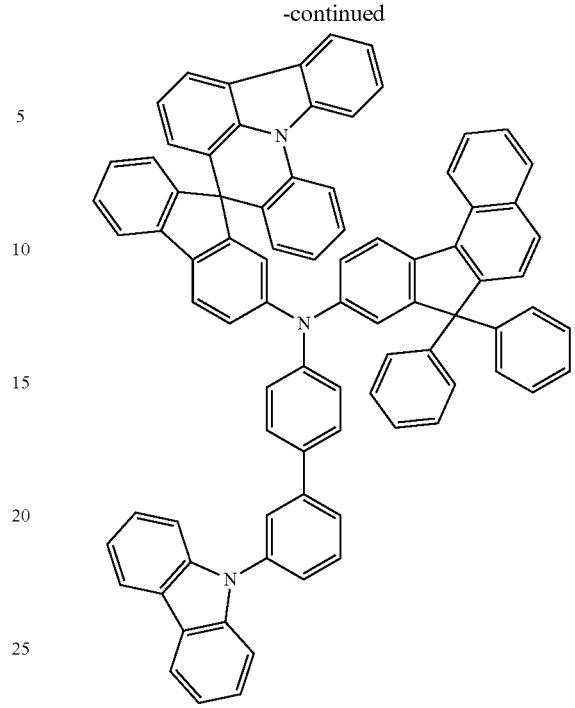
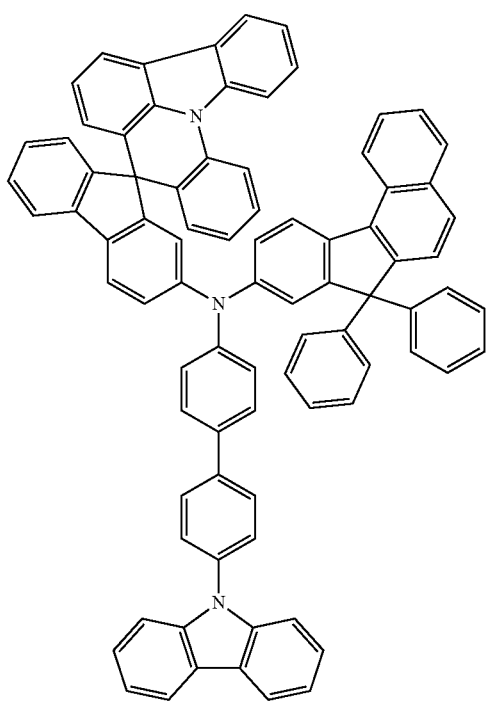
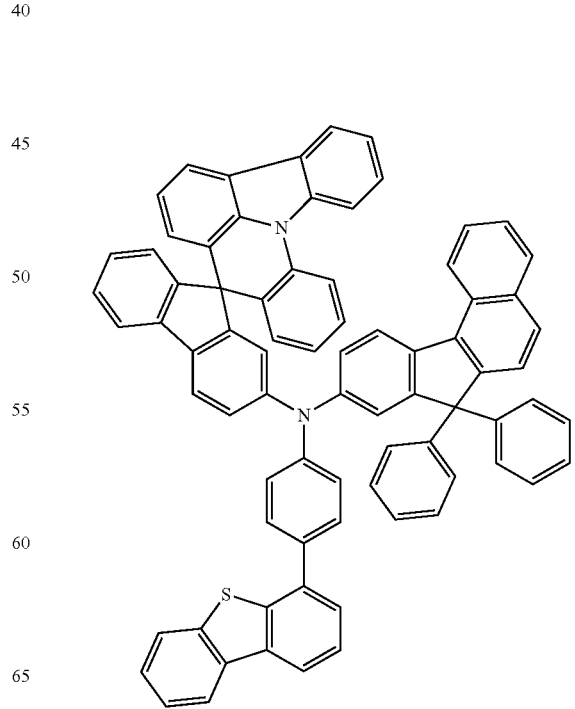

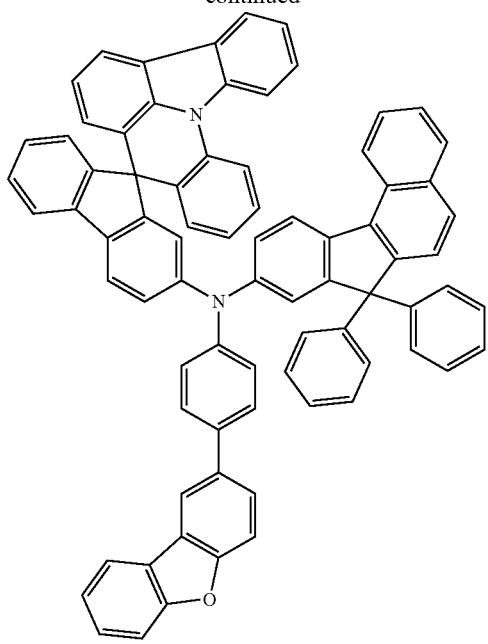
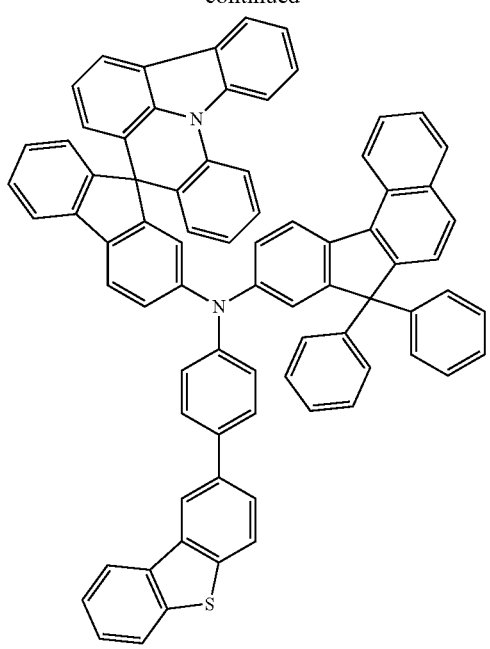
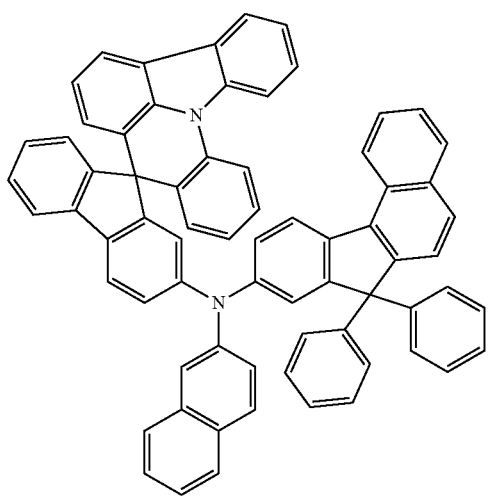
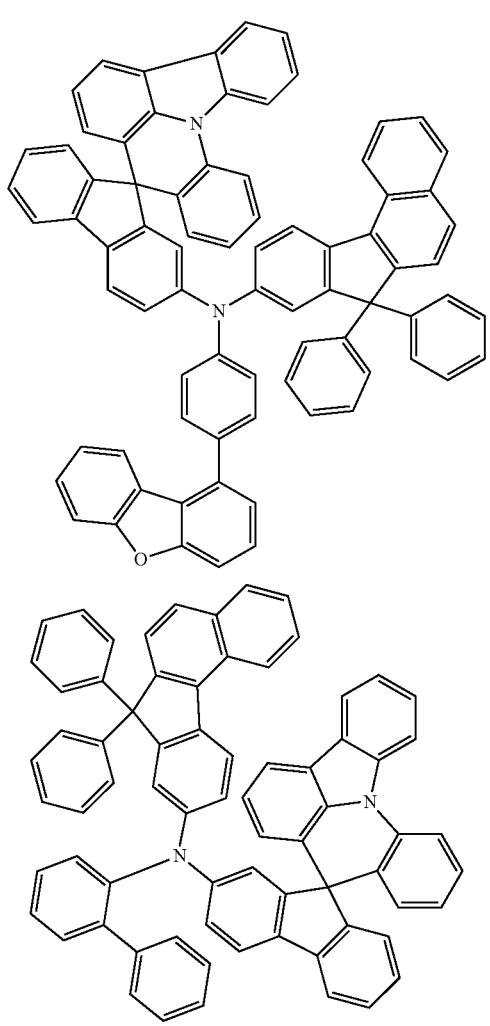

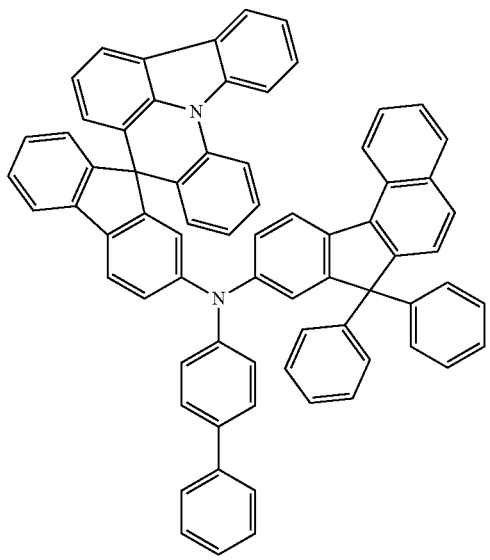
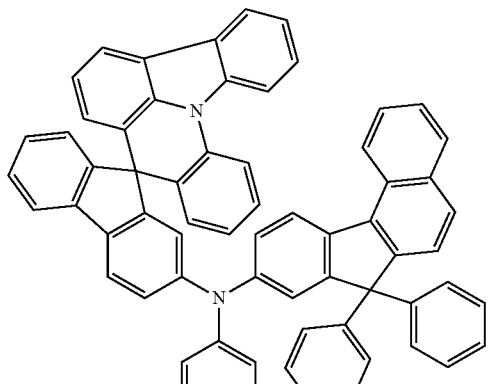
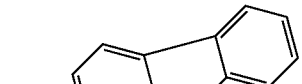
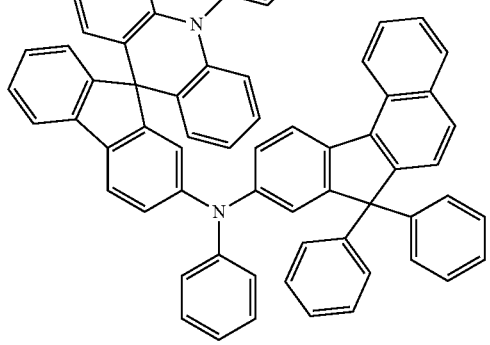
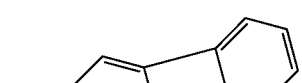
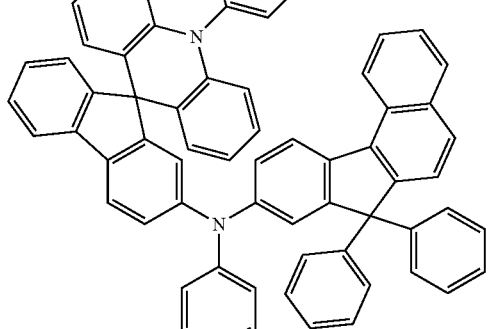
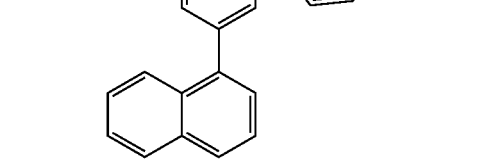
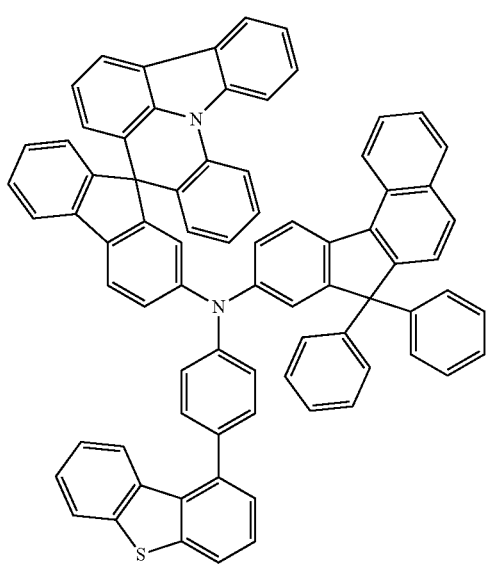

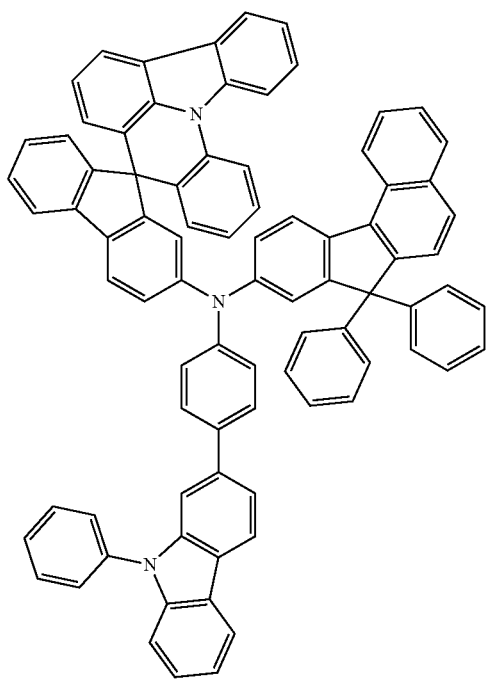
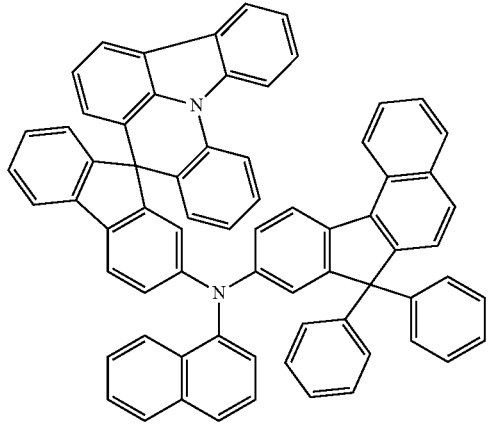
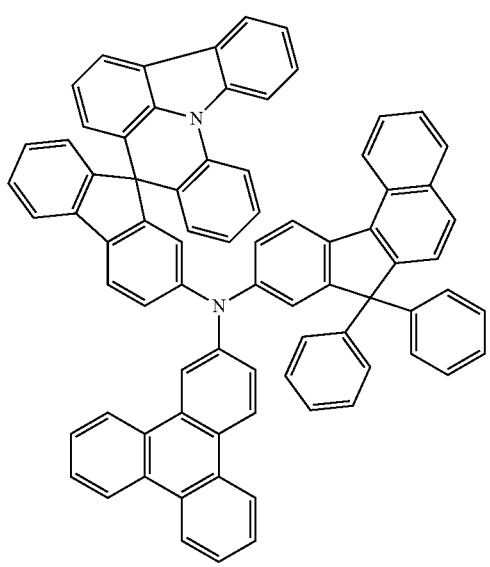
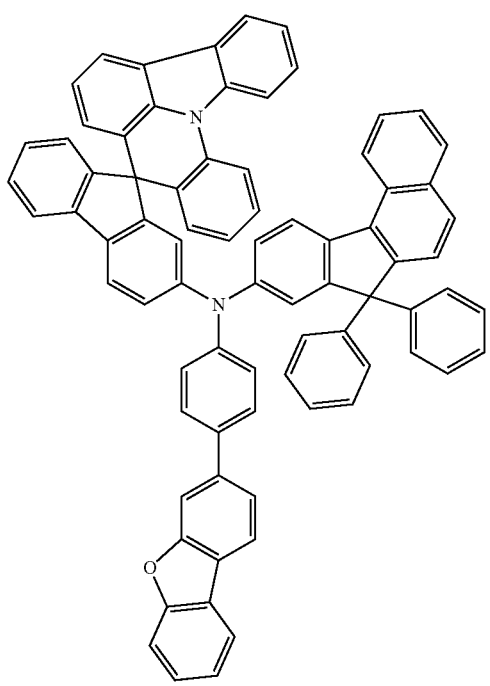
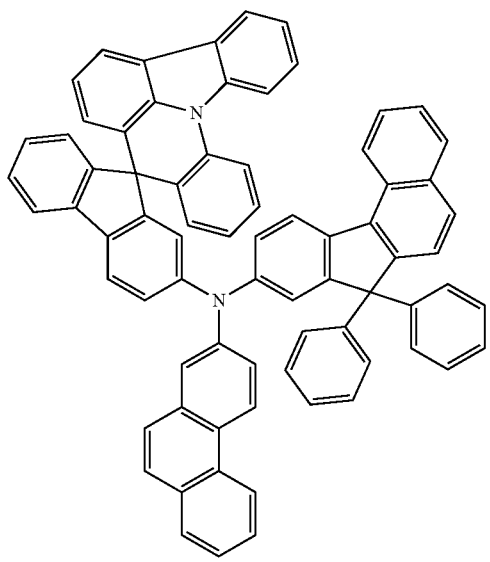

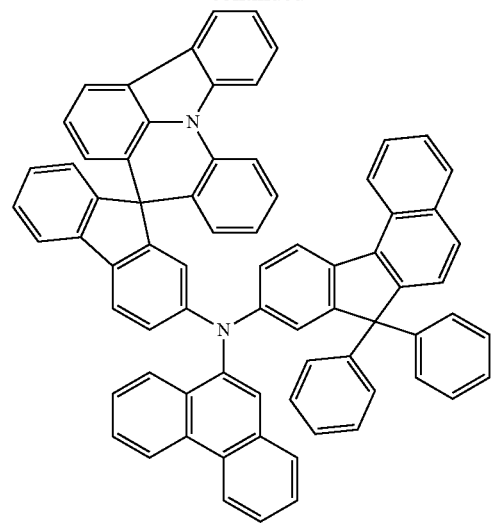
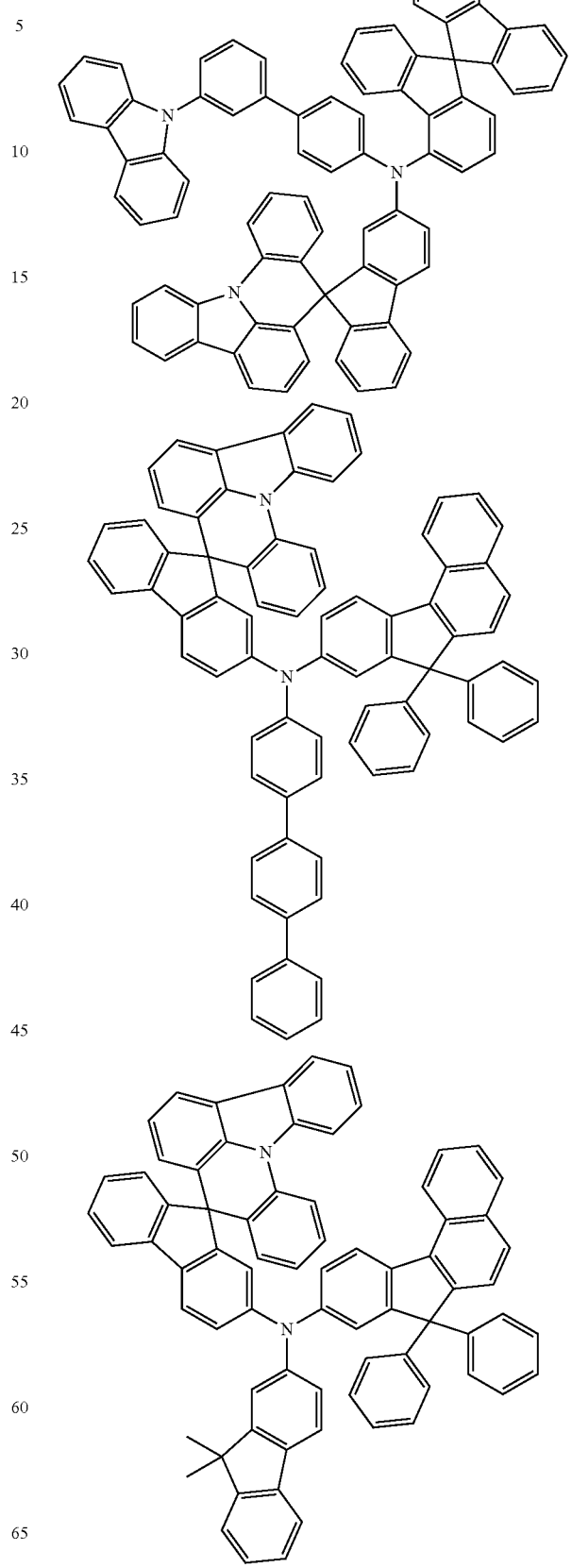

45
-continued
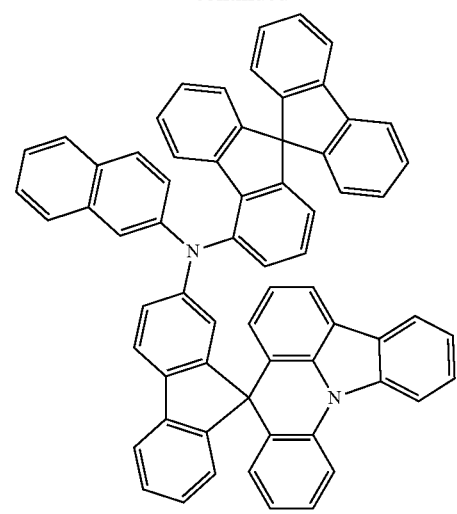
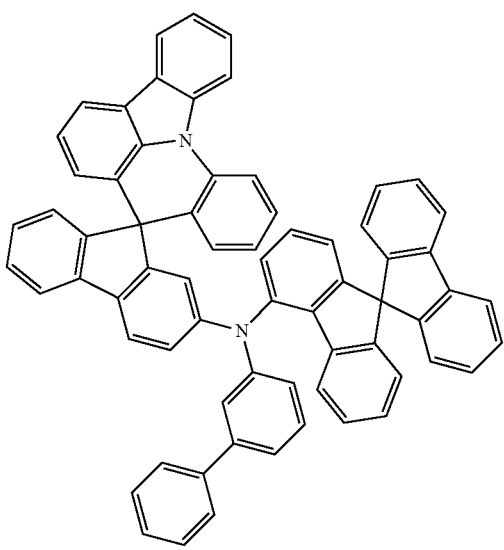
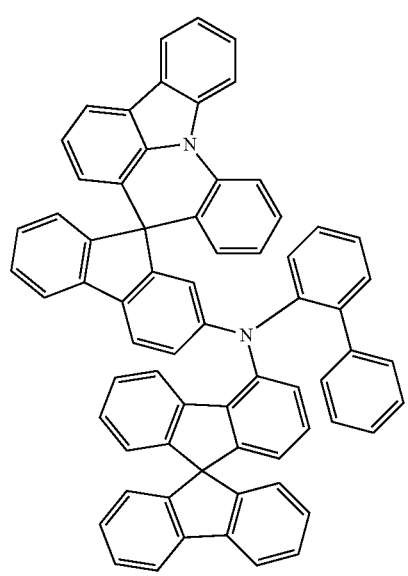
46
-continued
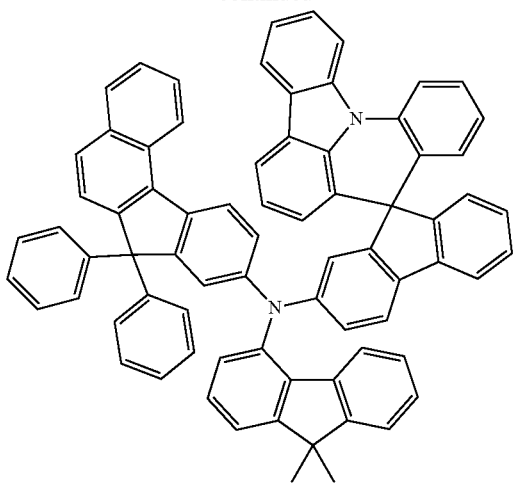
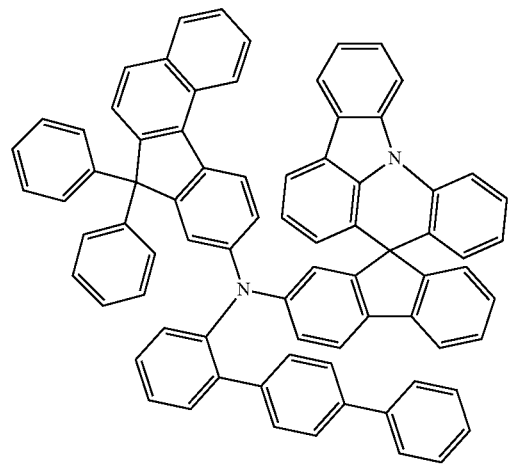
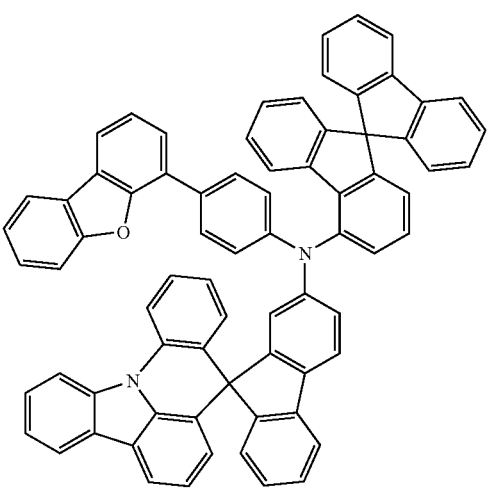

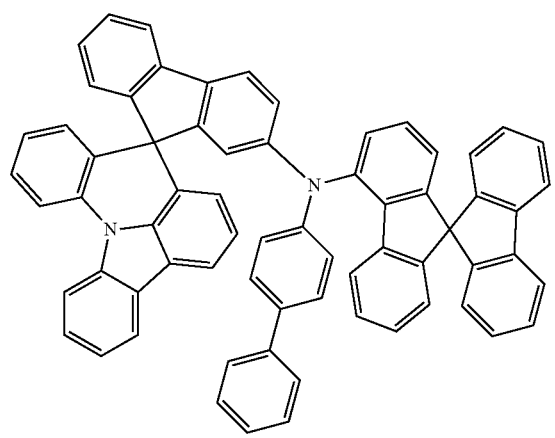
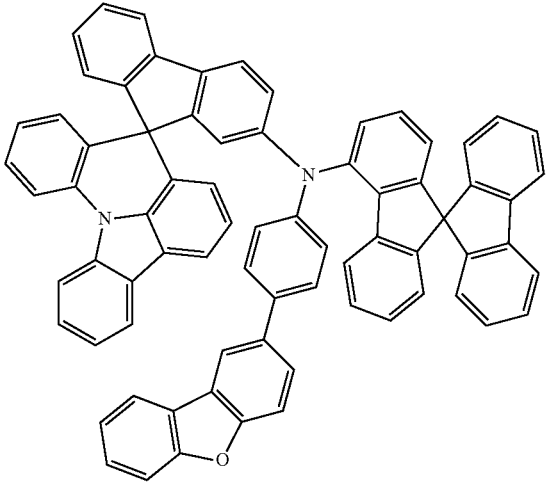
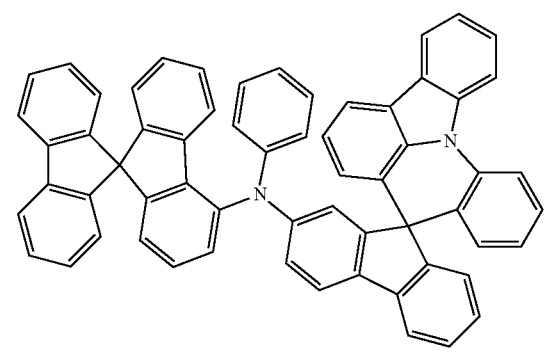
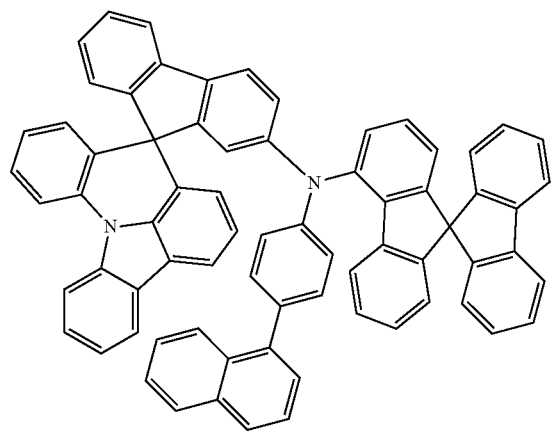
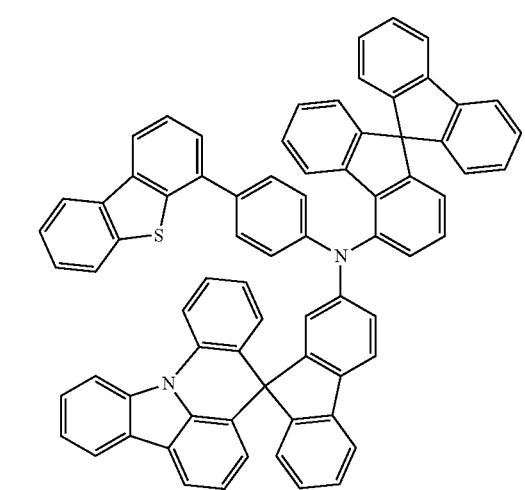
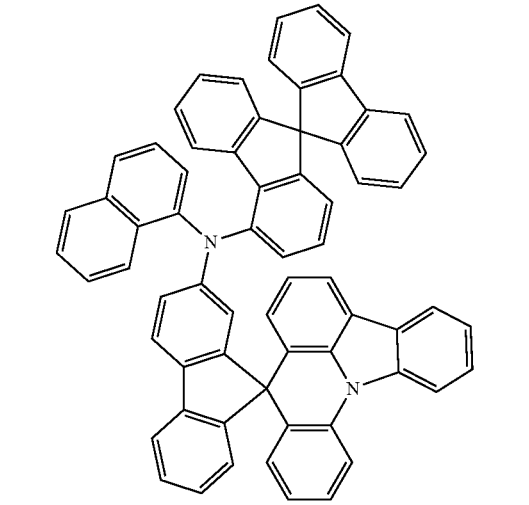

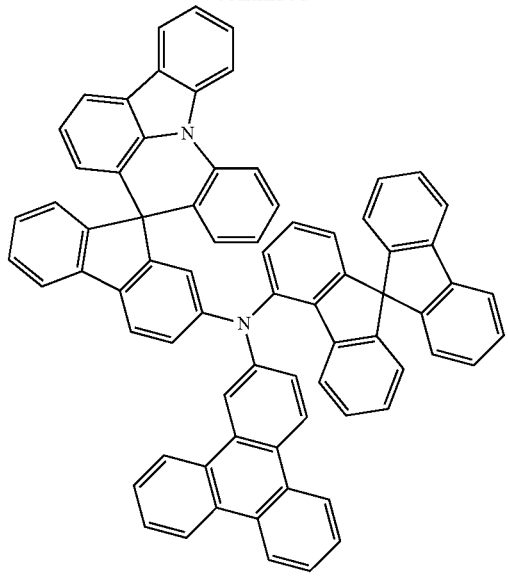
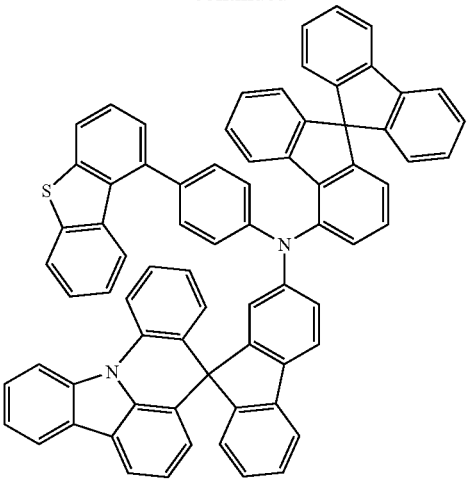
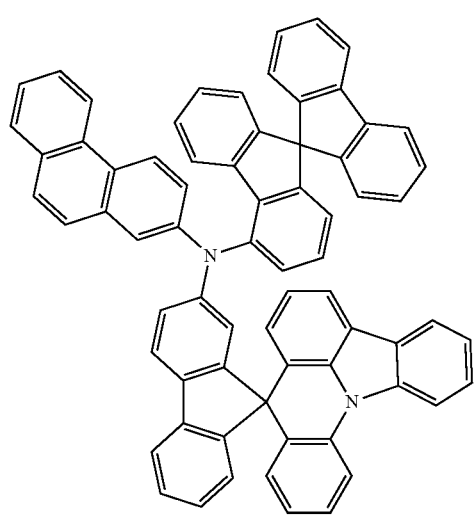
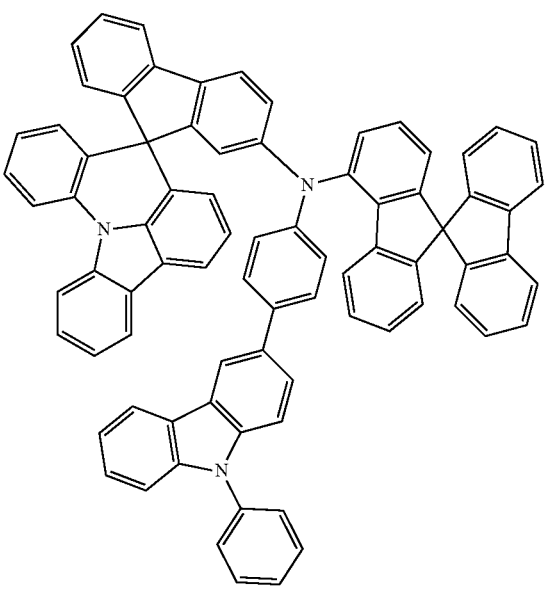
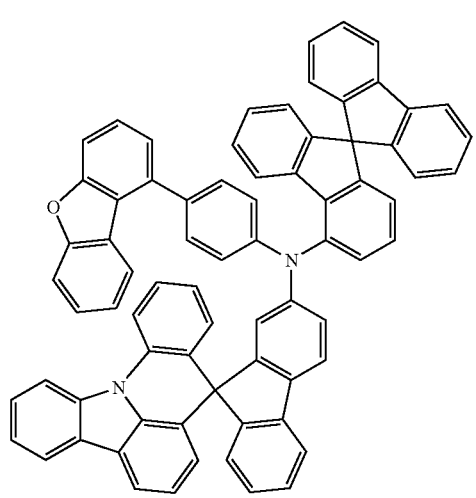
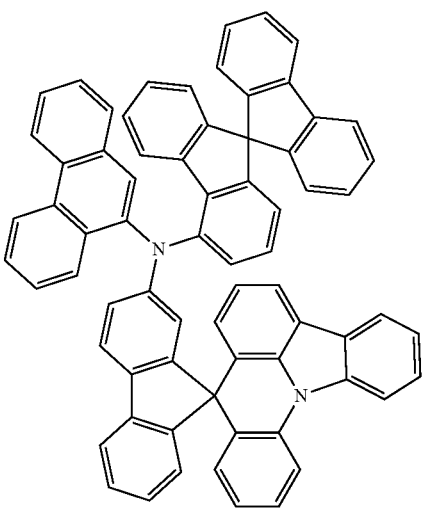

51
-continued
52
-continued
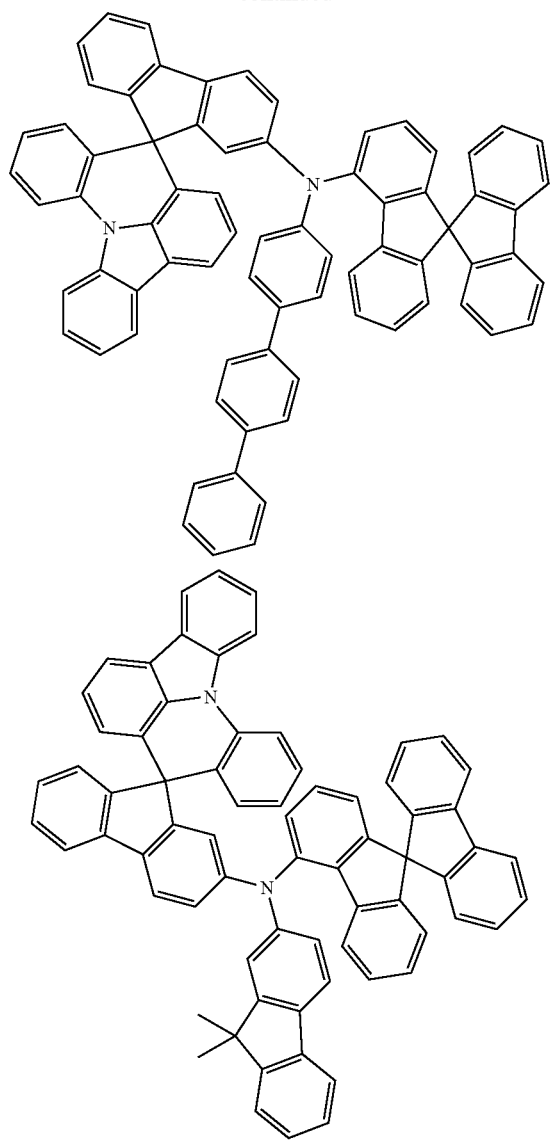
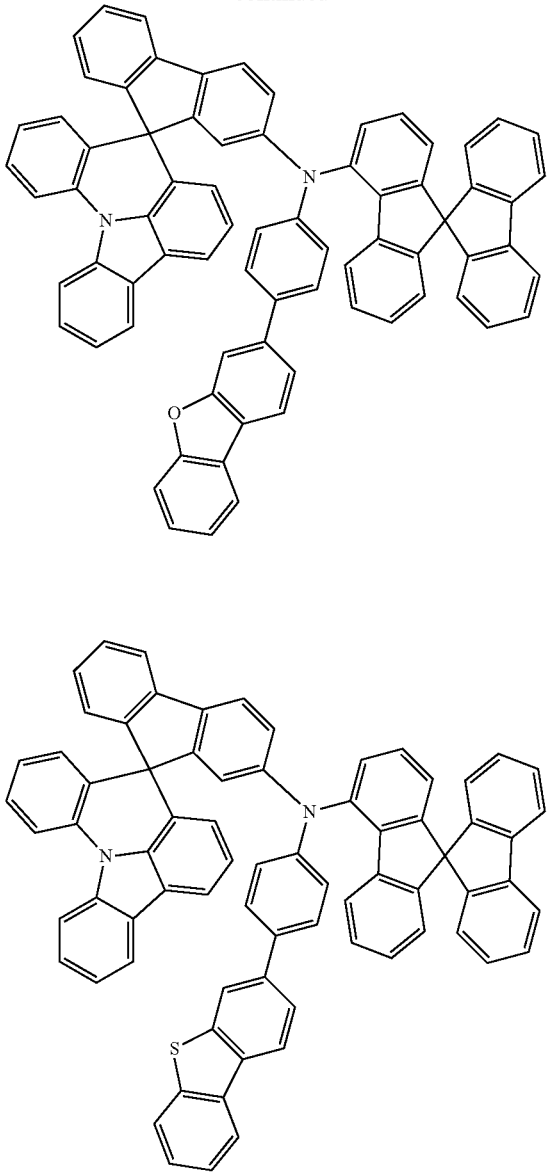
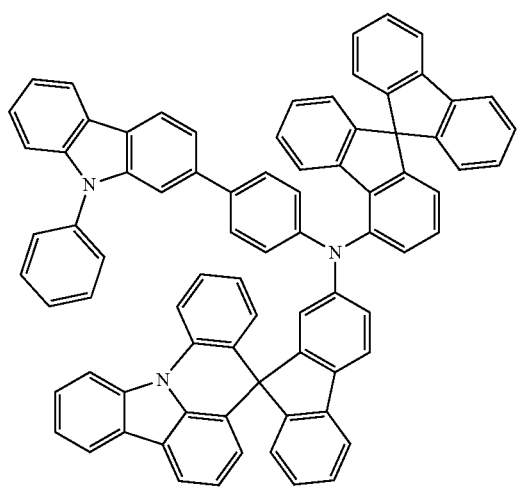

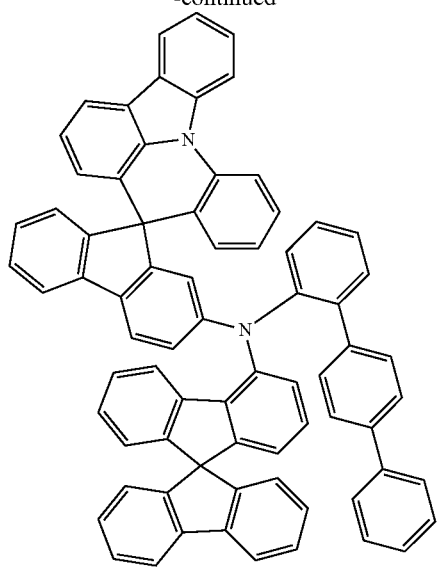
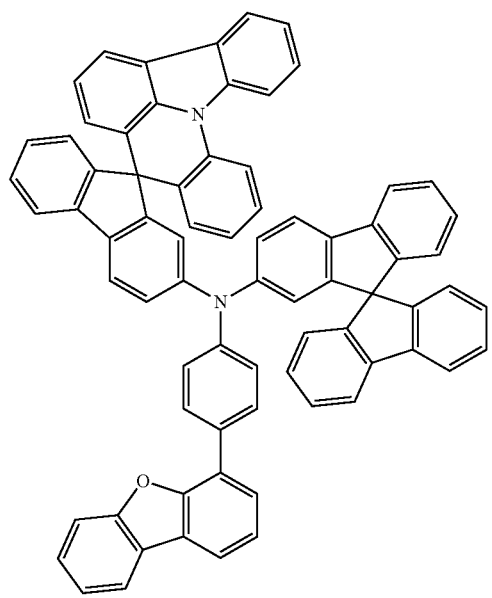
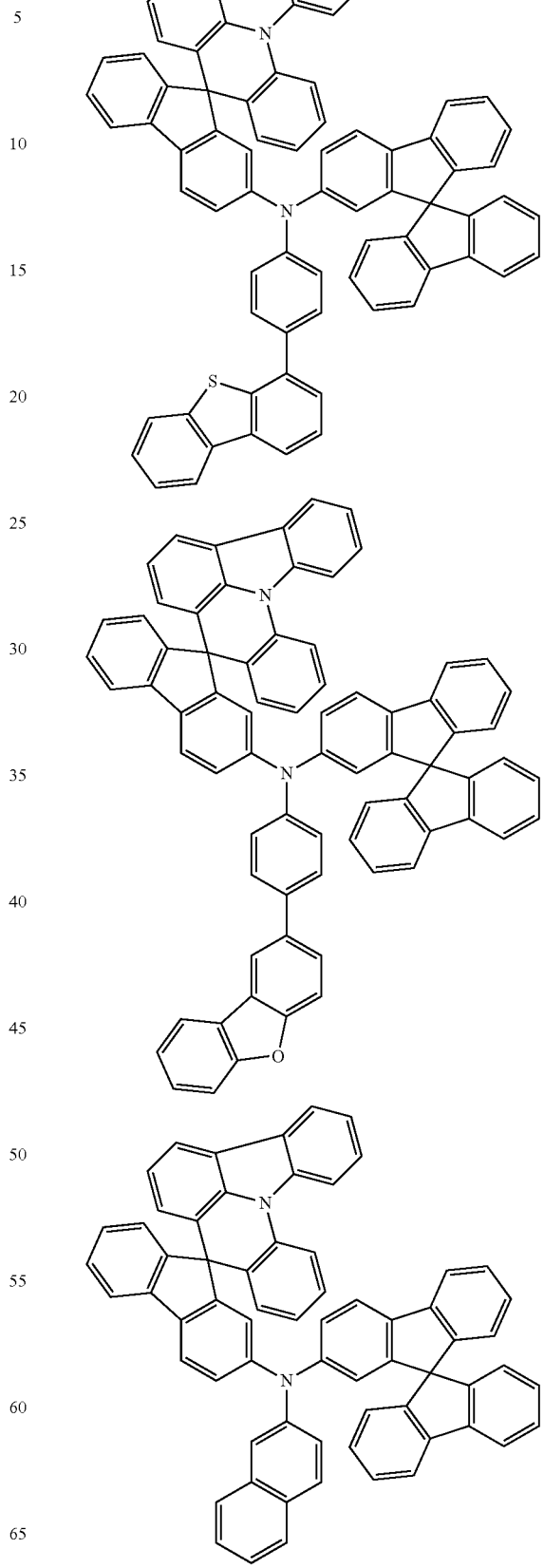

-continued
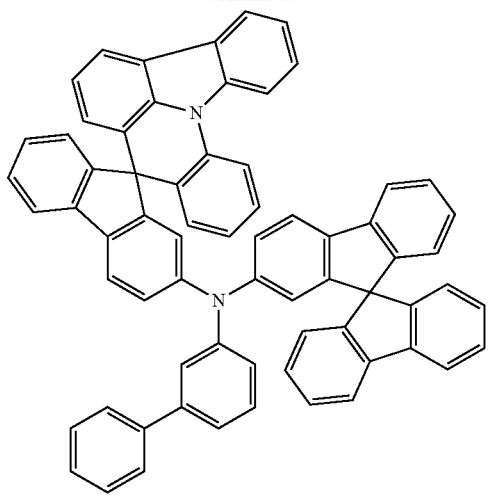
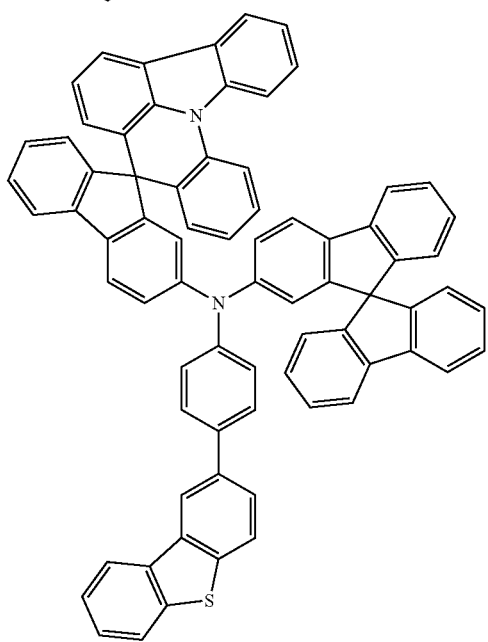
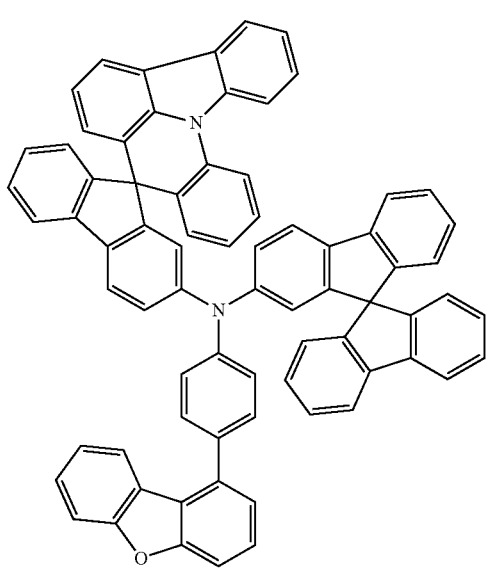
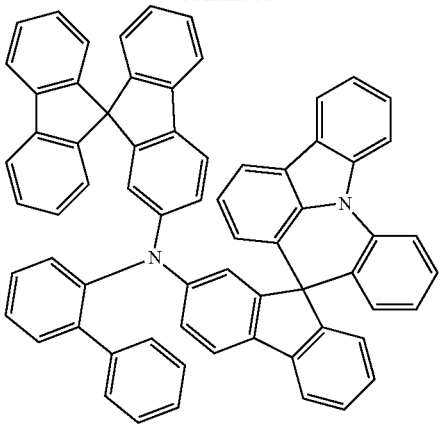
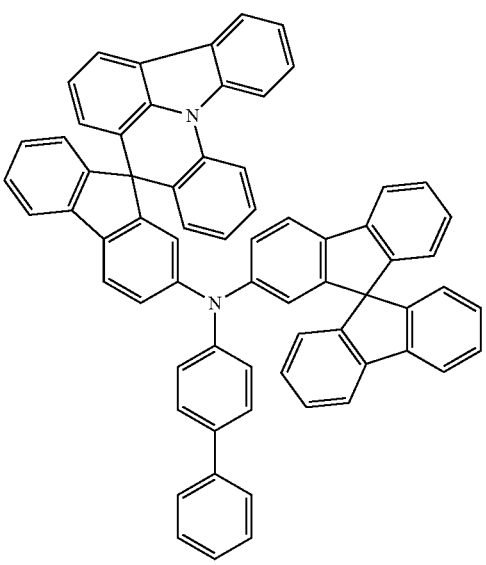
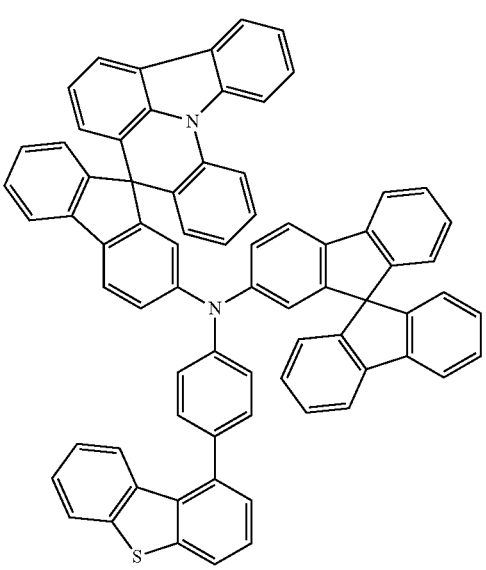

57
-continued
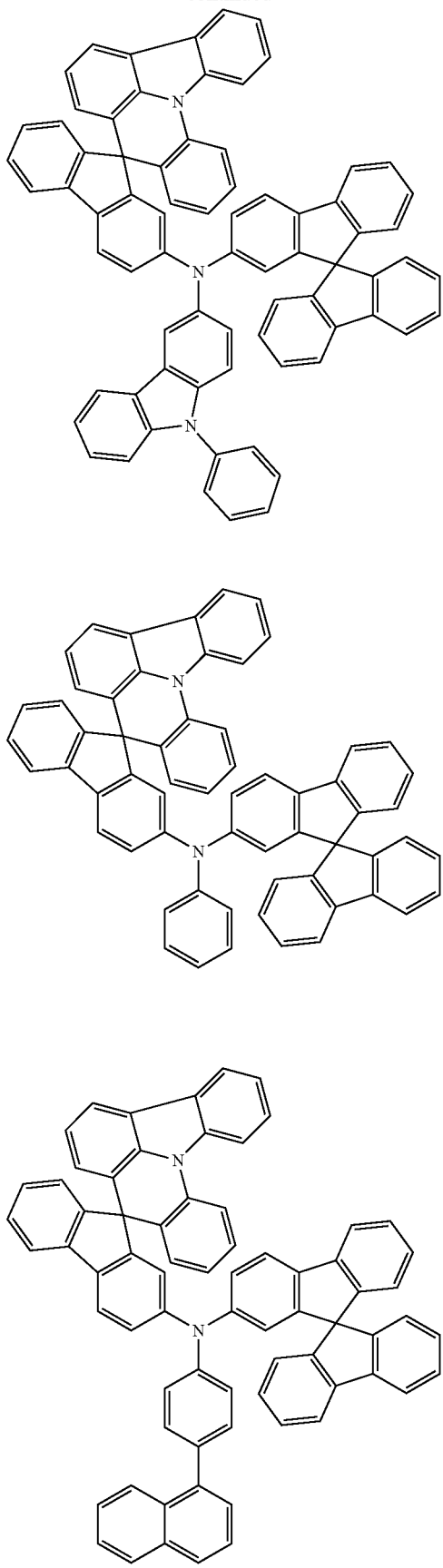 [SMILES: c1ccc(-n2c3ccccc3c3cc(N(c4ccc5c(c4)C4(c6ccccc6-c6ccccc64)c4ccccc4-5)c4ccc5c(c4)C4(c6ccccc6-5)c5ccccc5-n5c6ccccc6c6cccc4c65)ccc32)cc1 ; c1ccc(N(c2ccc3c(c2)C2(c4ccccc4-c4ccccc42)c2ccccc2-3)c2ccc3c(c2)C2(c4ccccc4-3)c3ccccc3-n3c4ccccc4c4cccc2c43)cc1 ; c1ccc2c(c1)-c1ccccc1C21c2ccccc2-c2ccc(N(c3ccc(-c4cccc5ccccc45)cc3)c3ccc4c(c3)C3(c5ccccc5-4)c4ccccc4-n4c5ccccc5c5cccc3c54)cc21]
58
-continued
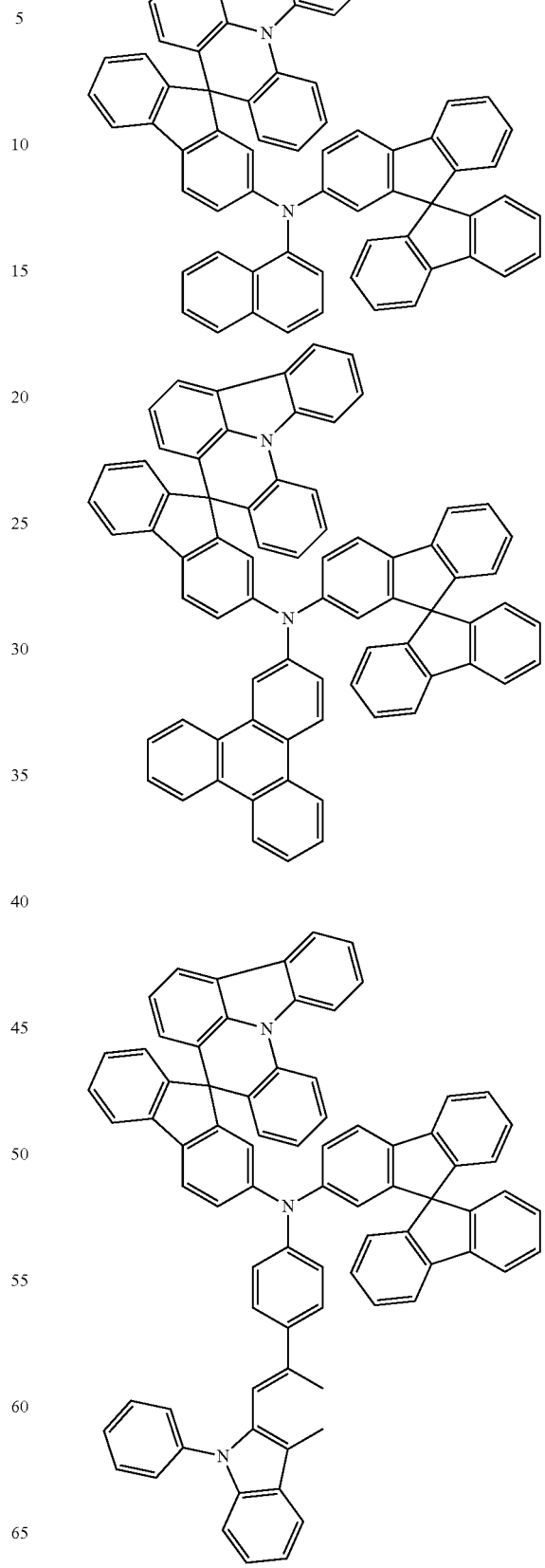

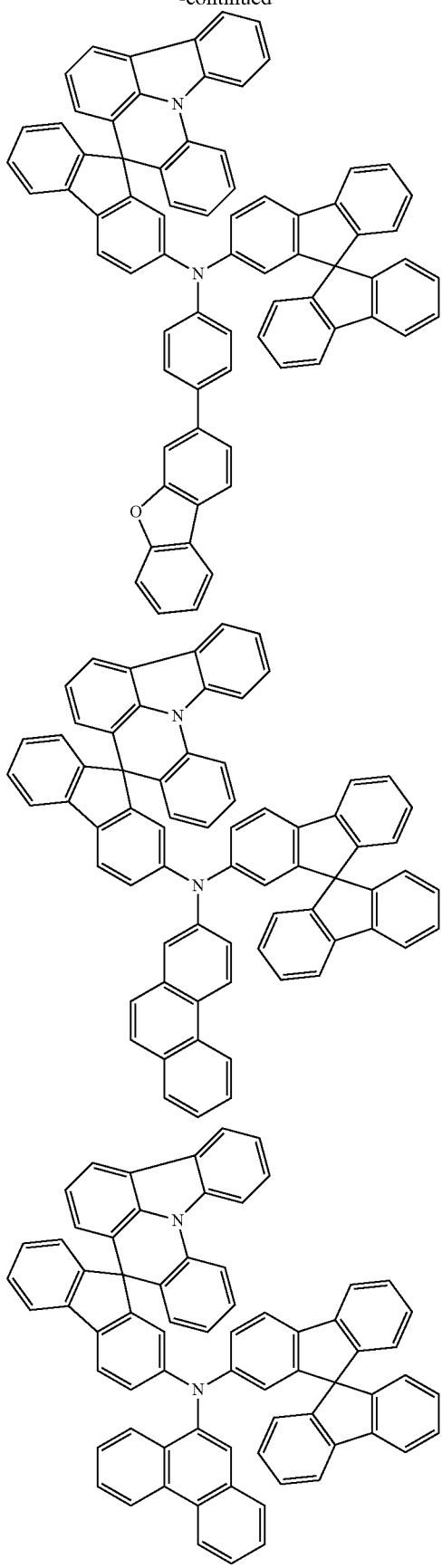
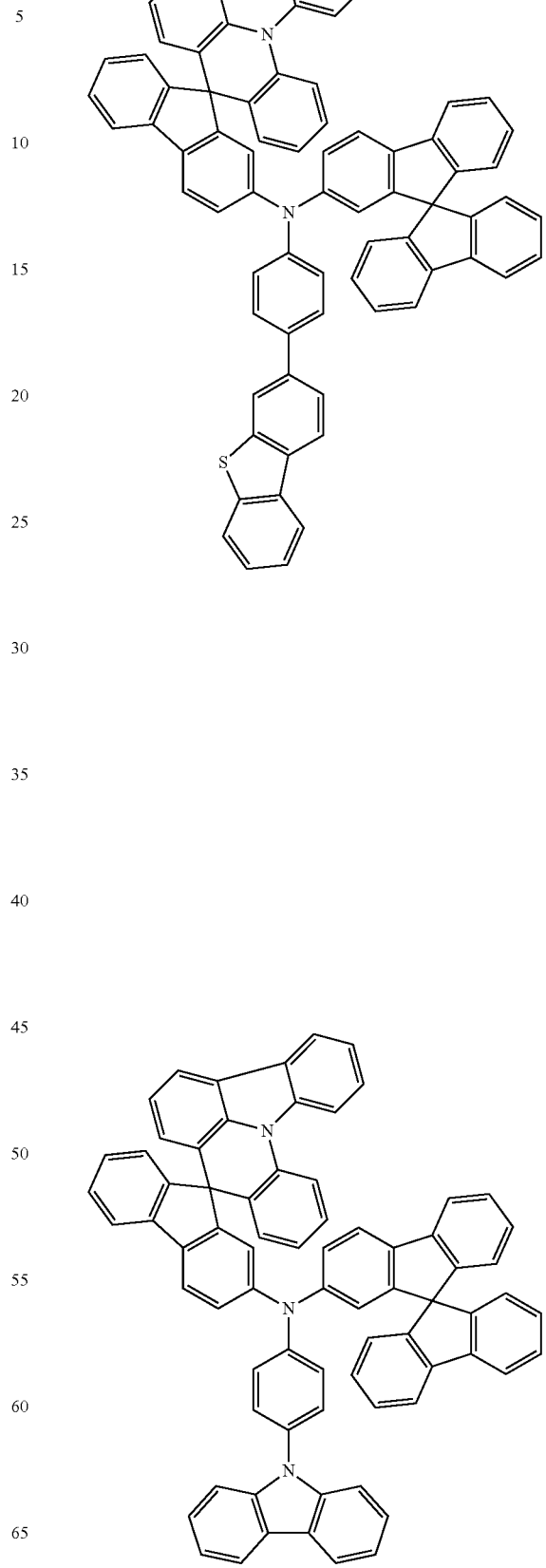

61
-continued
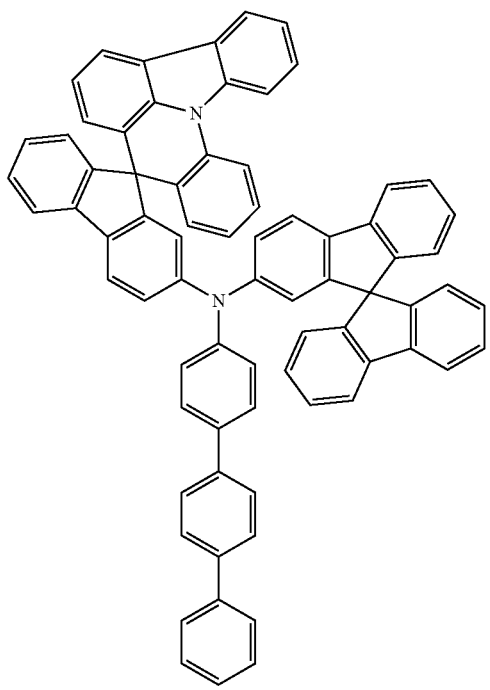
62
-continued
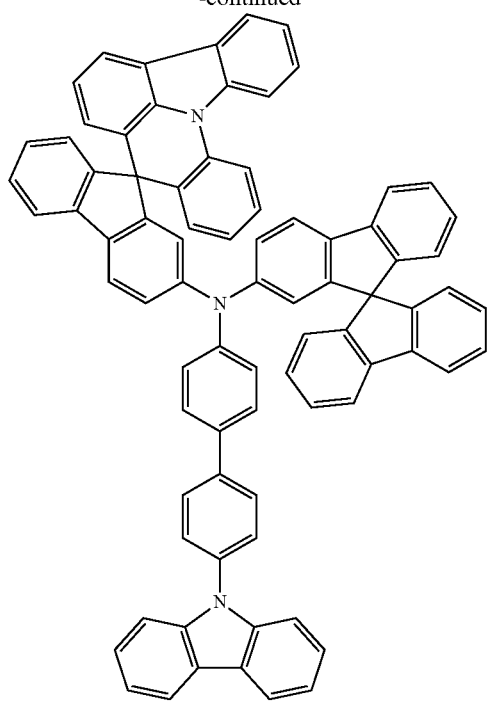
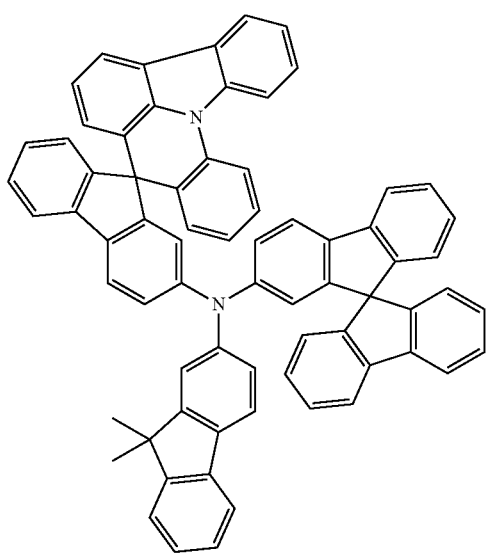
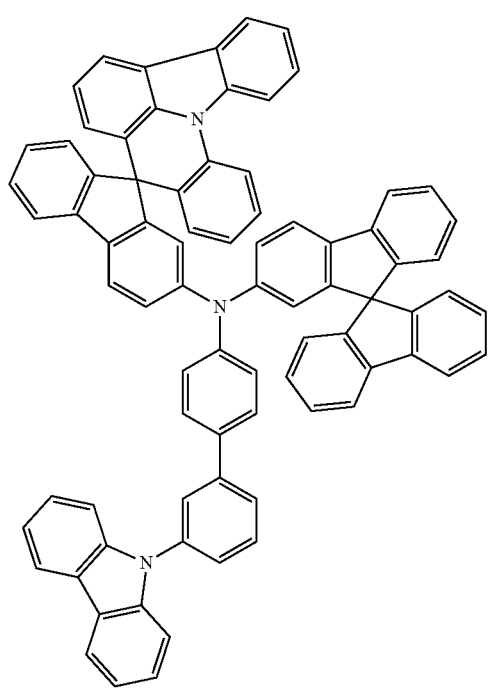

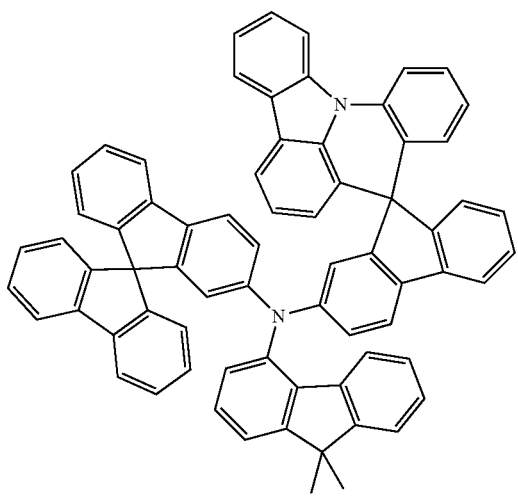
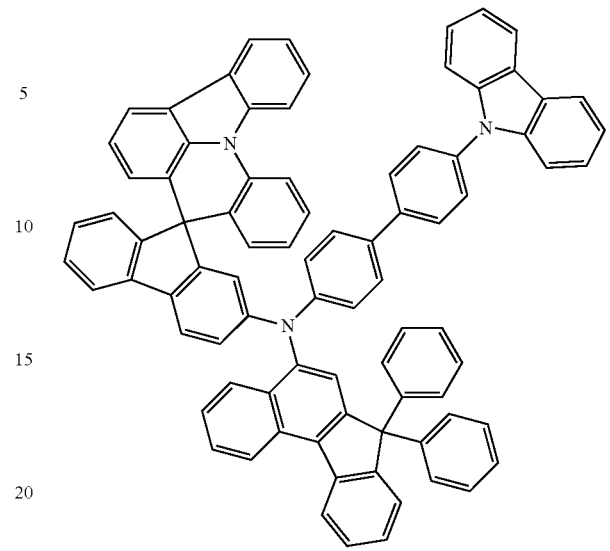
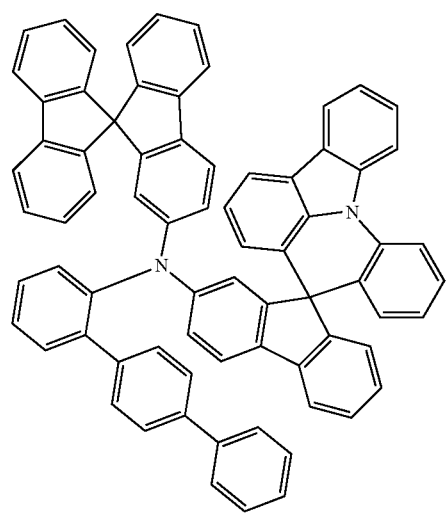
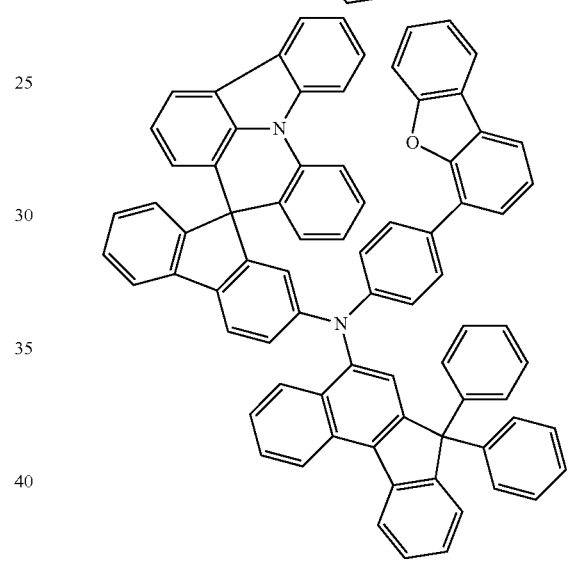
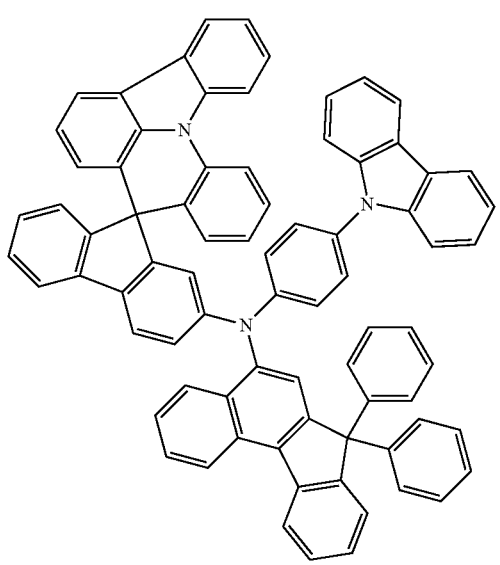
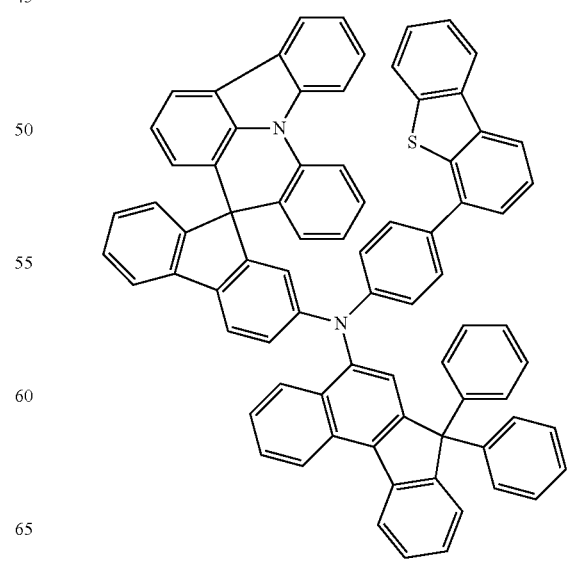

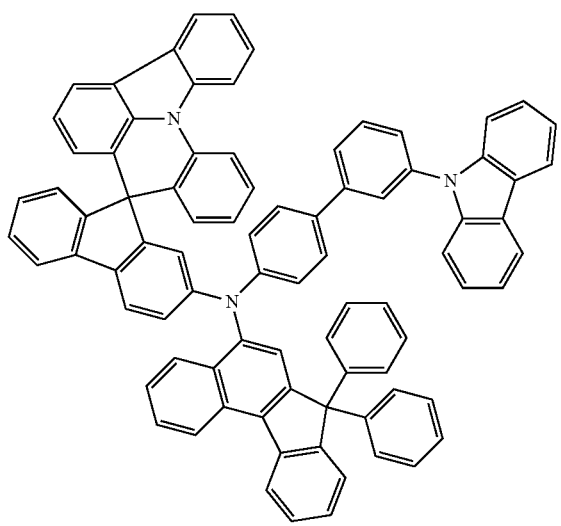
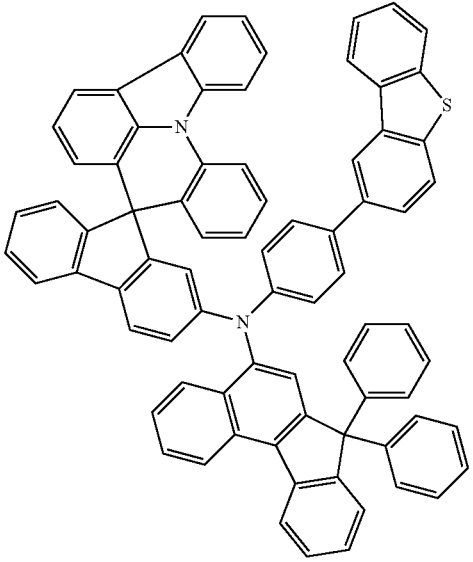
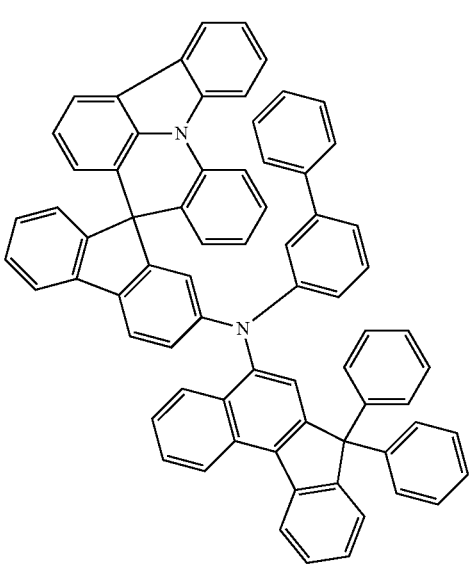
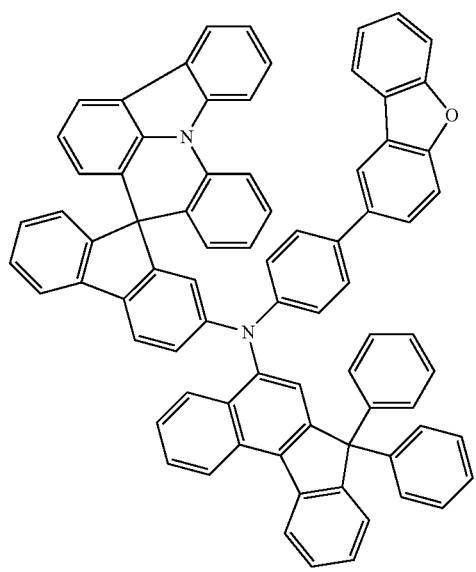
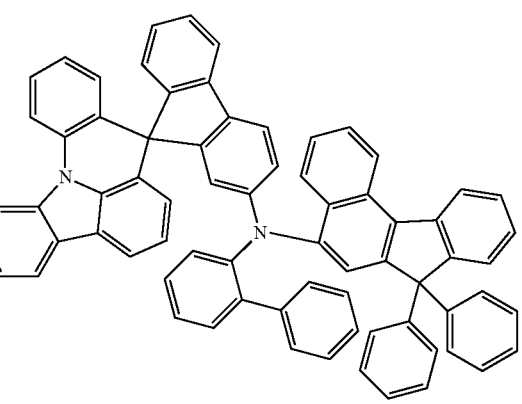

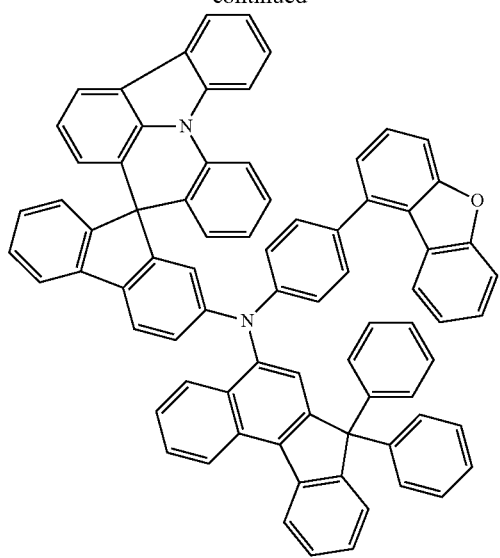
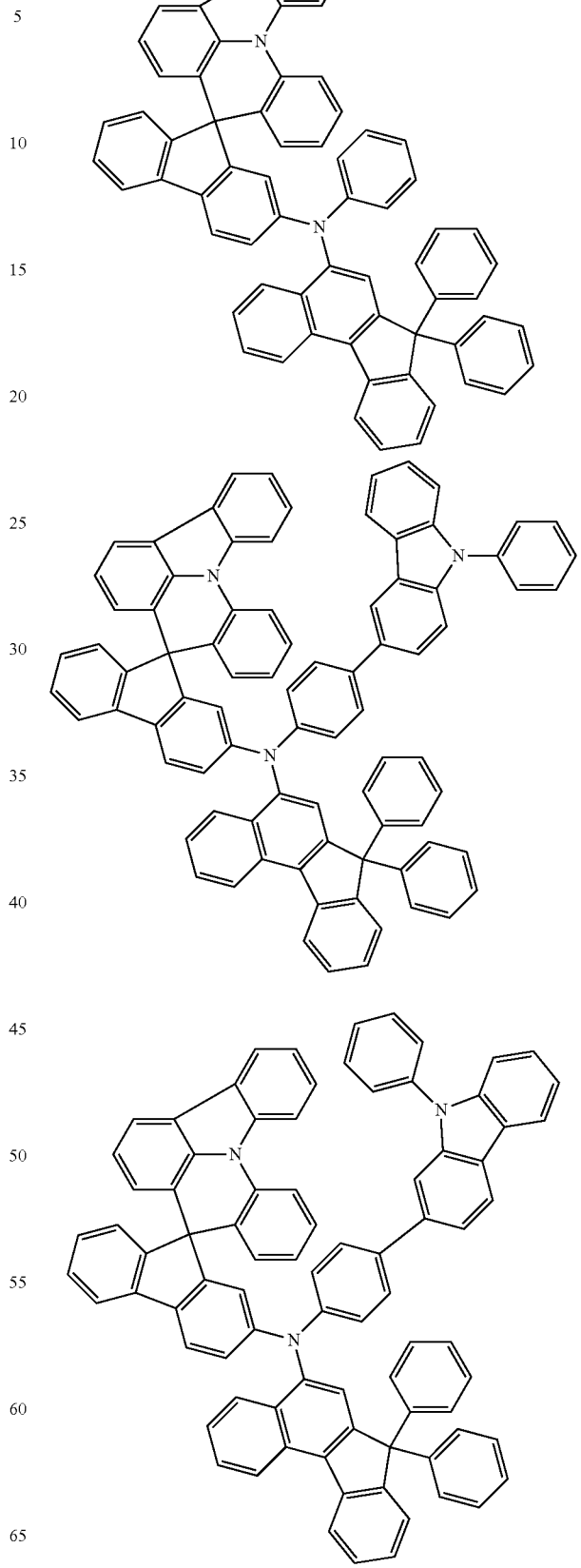

69
-continued
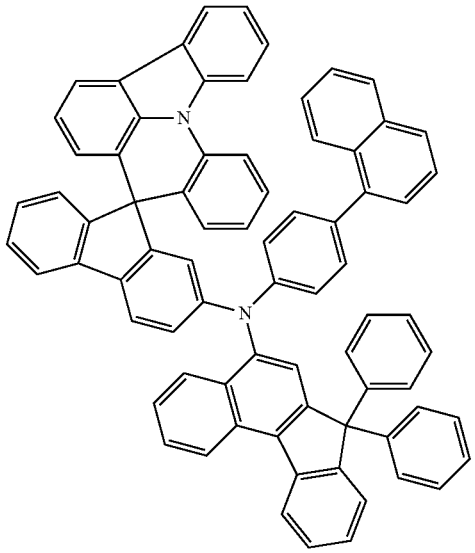
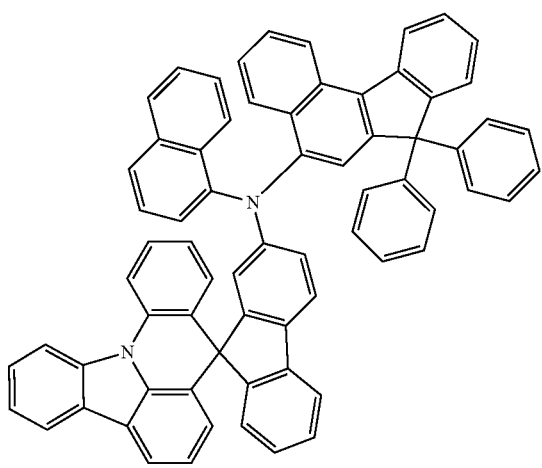
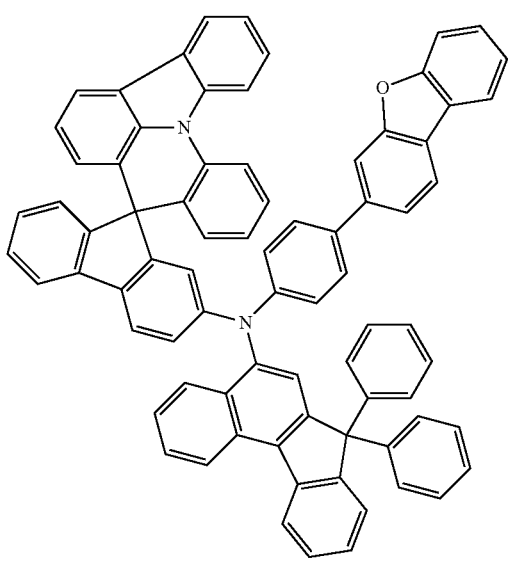
70
-continued
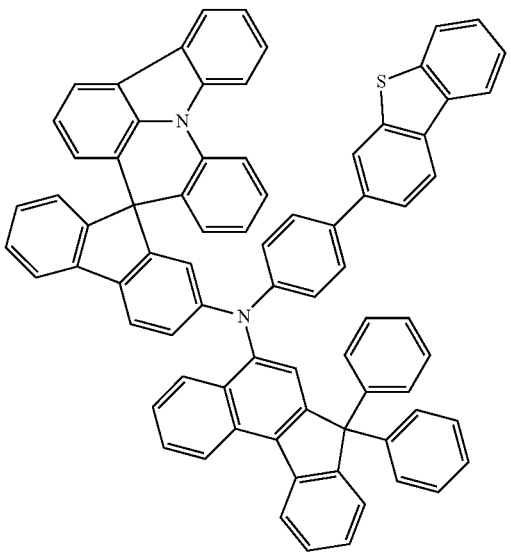
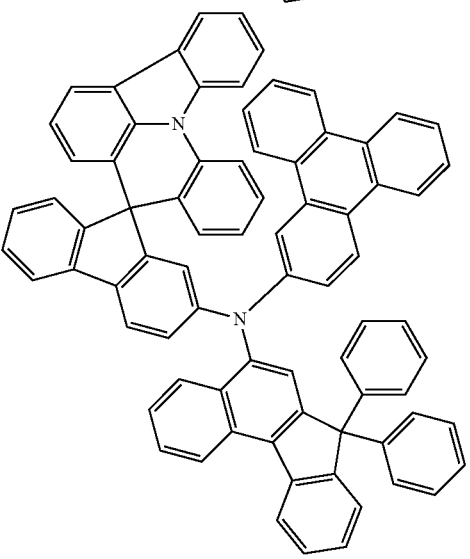
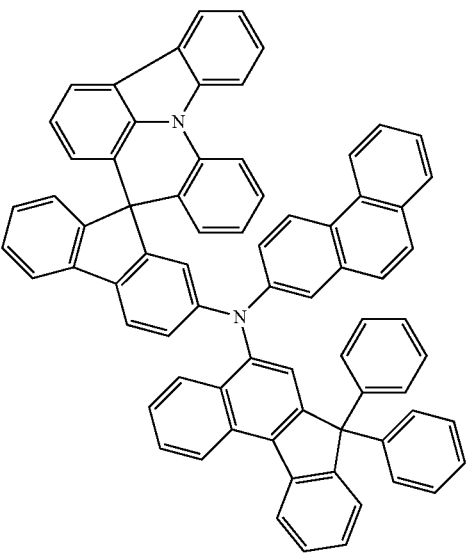

71
-continued
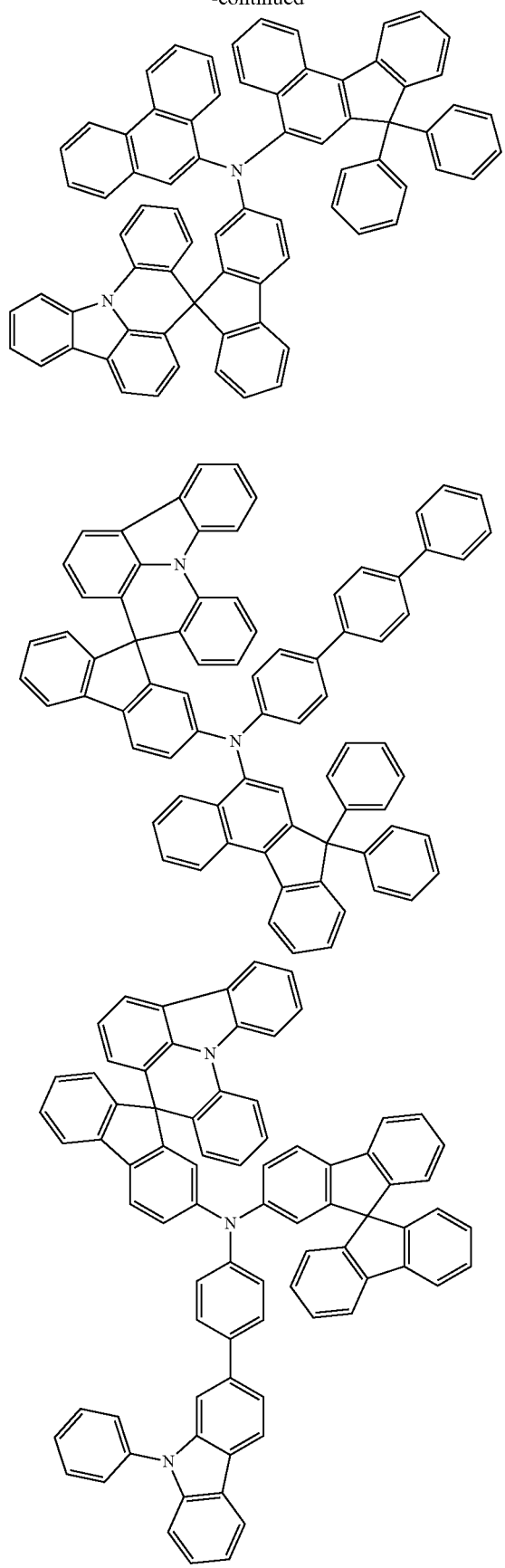
72
-continued
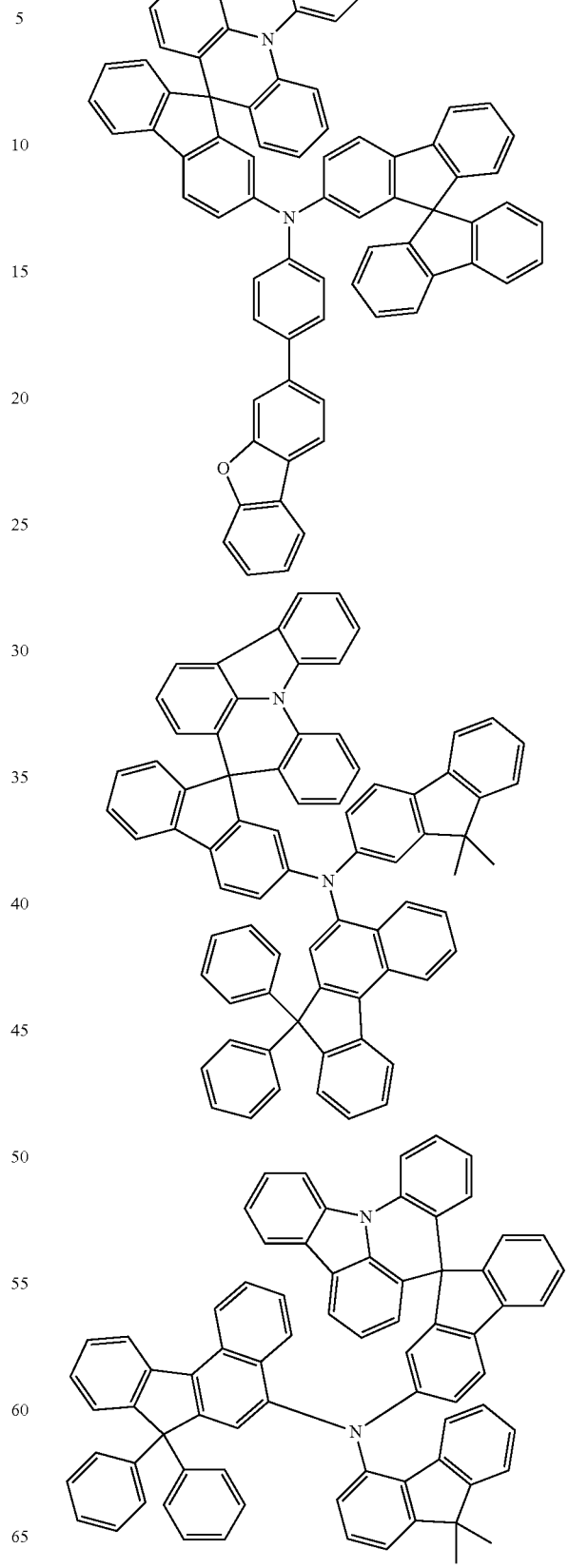

73
-continued
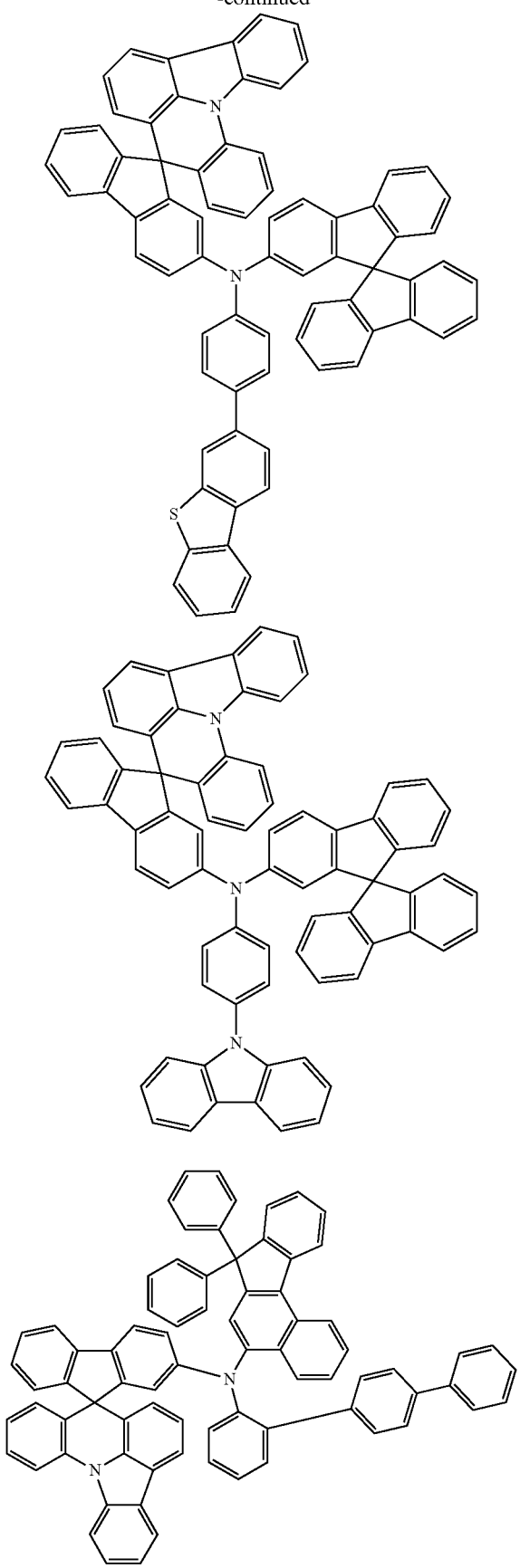
74
-continued
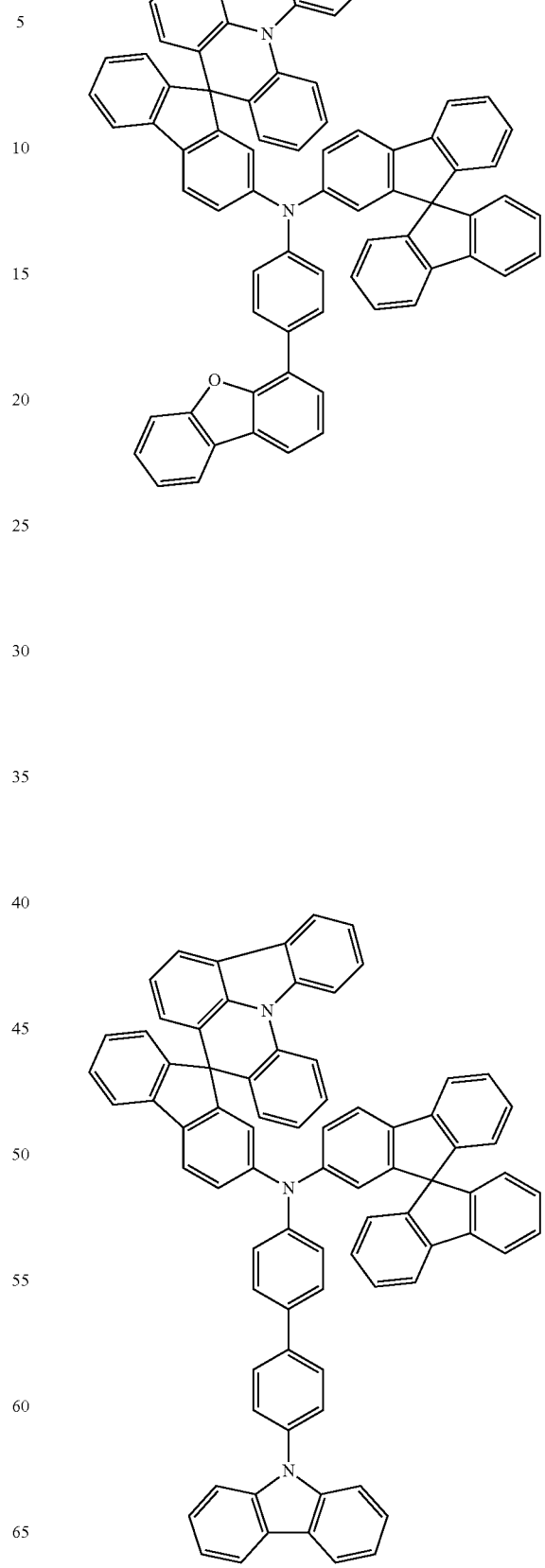

75
-continued
76
-continued
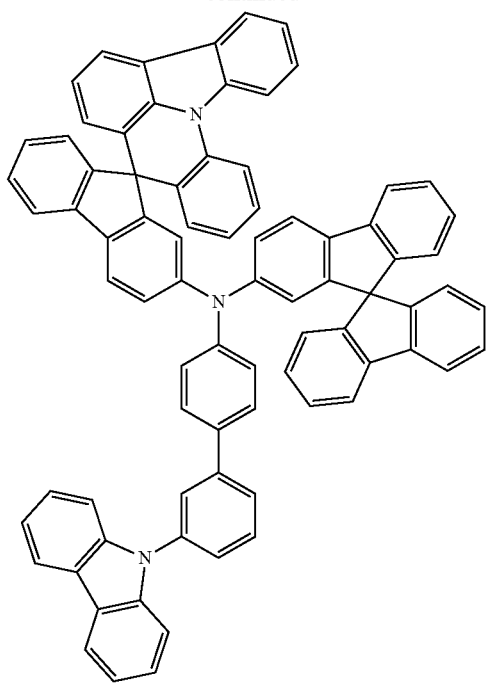
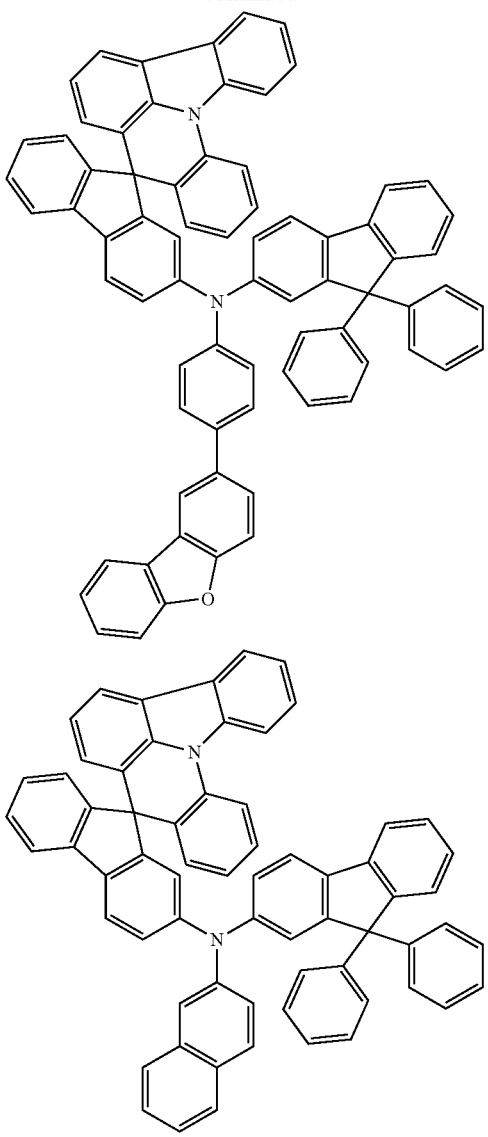
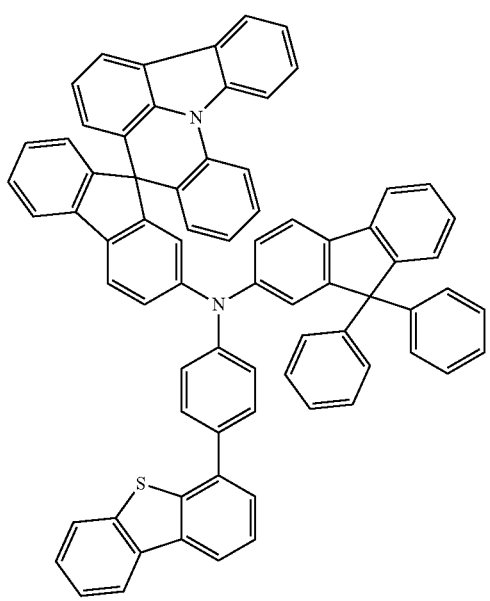
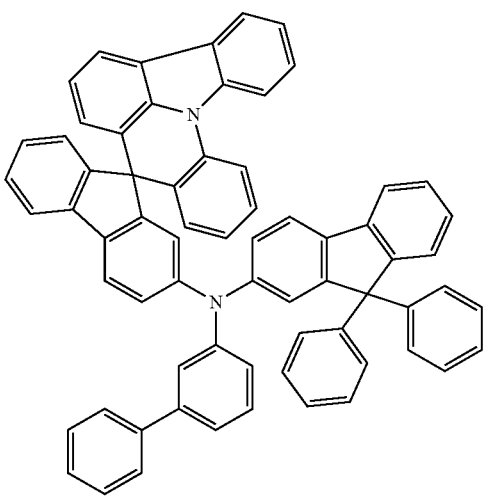

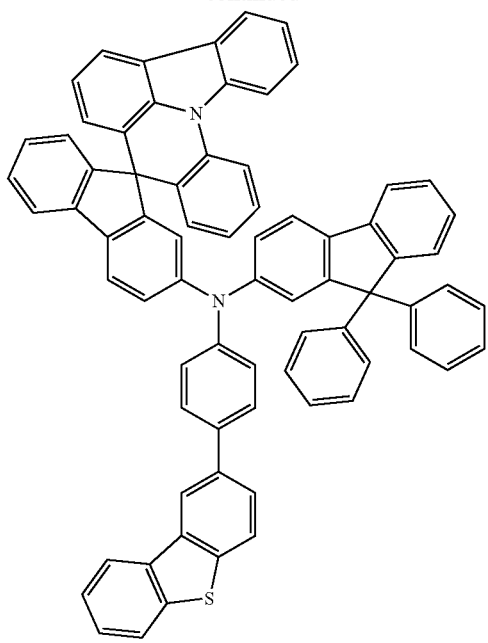
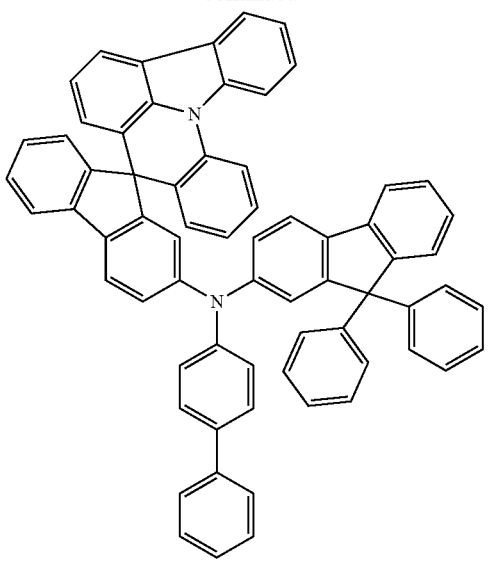
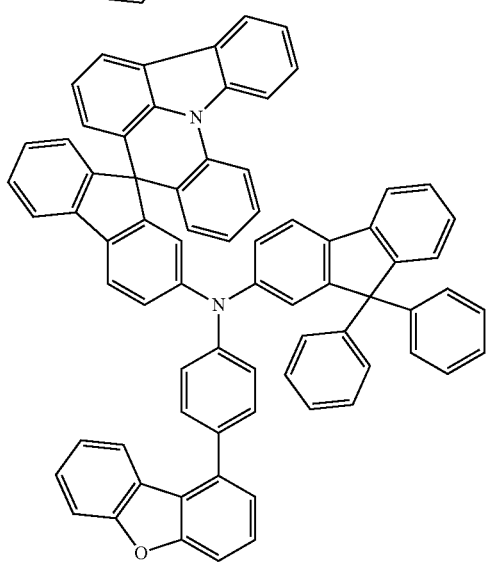
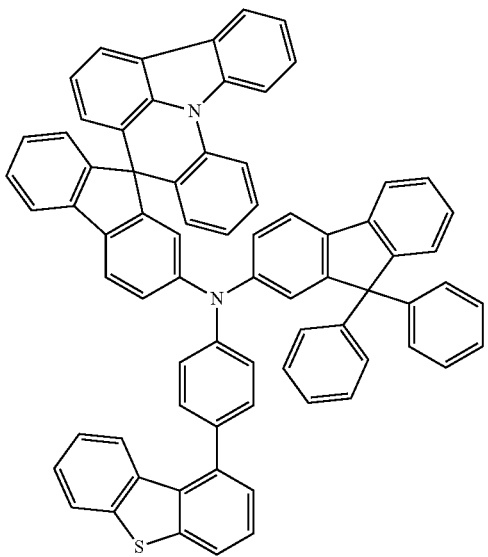
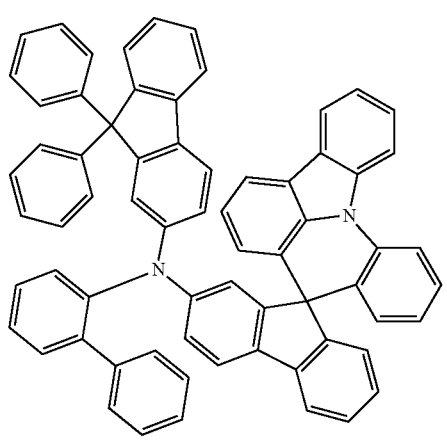

79
-continued
80
-continued
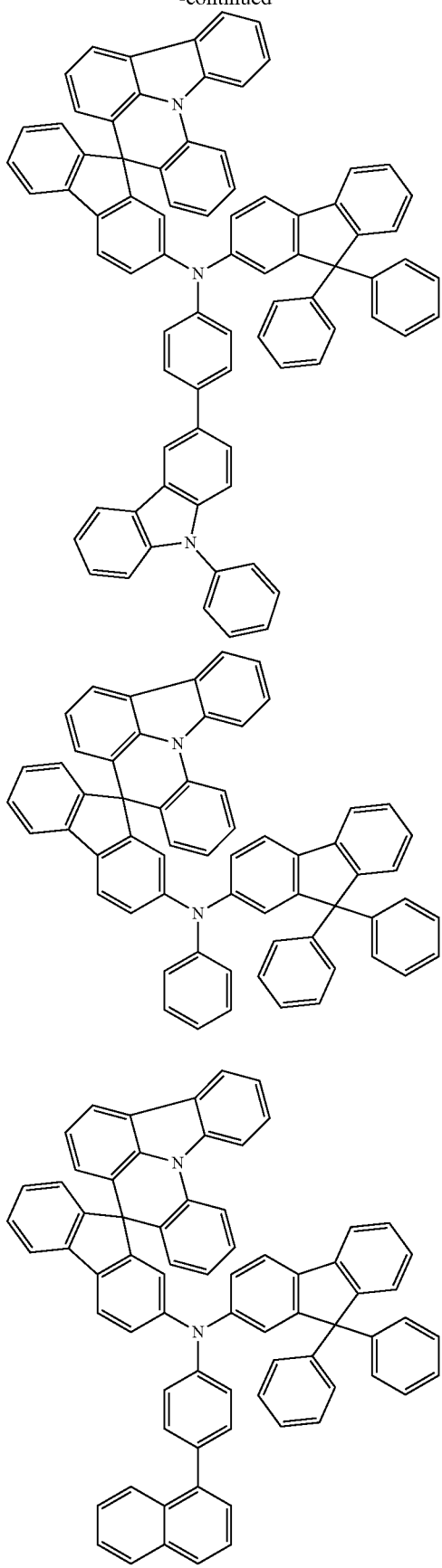
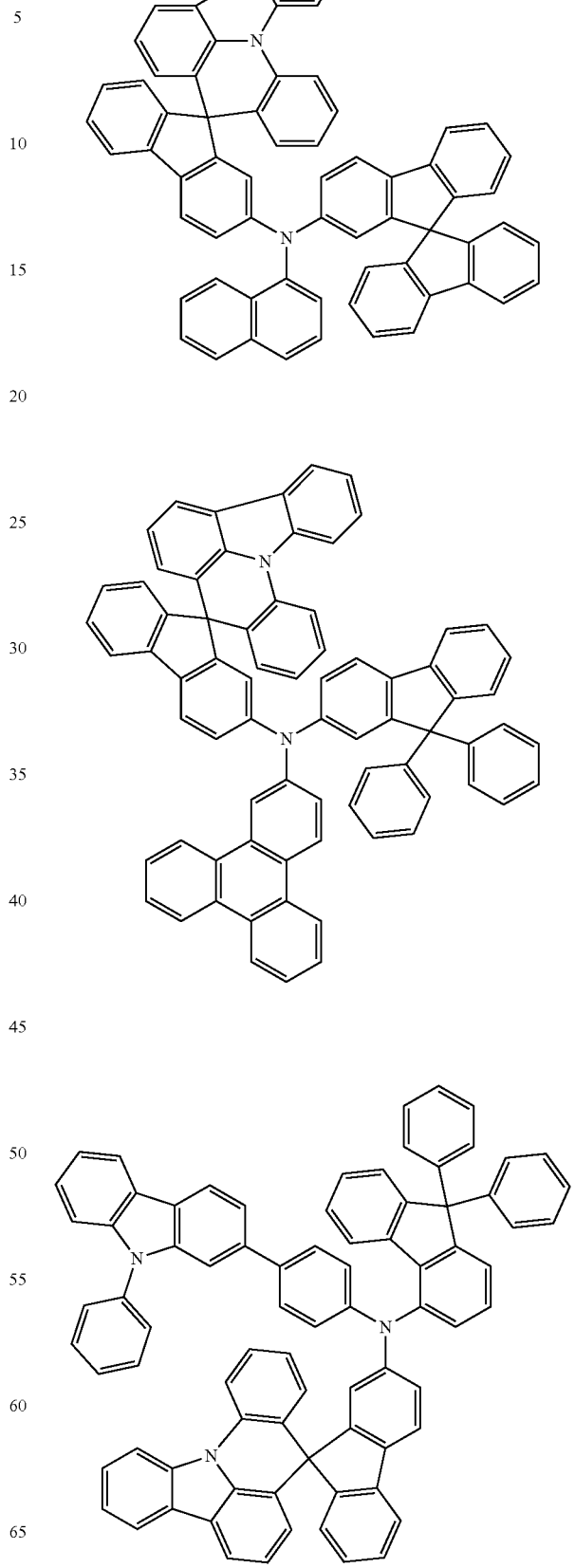

81
-continued
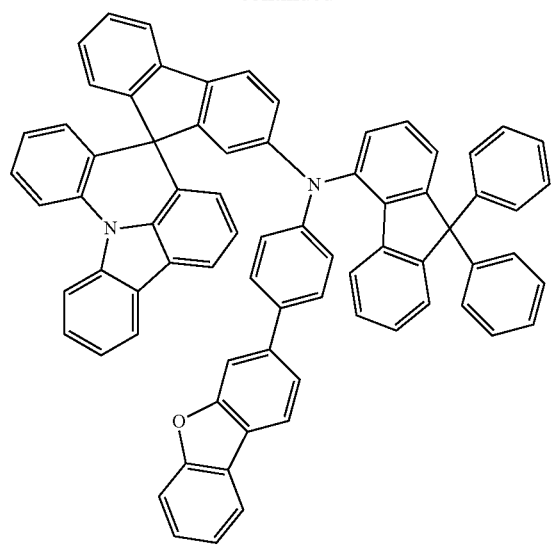
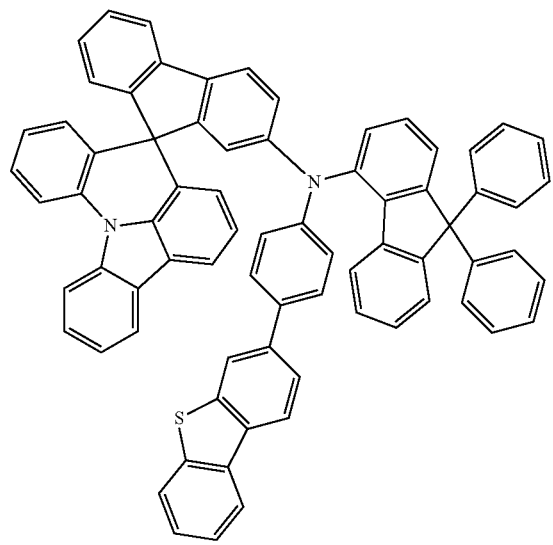
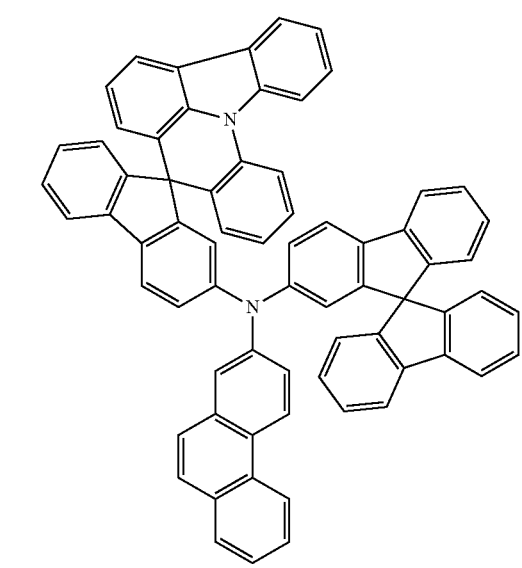
82
-continued
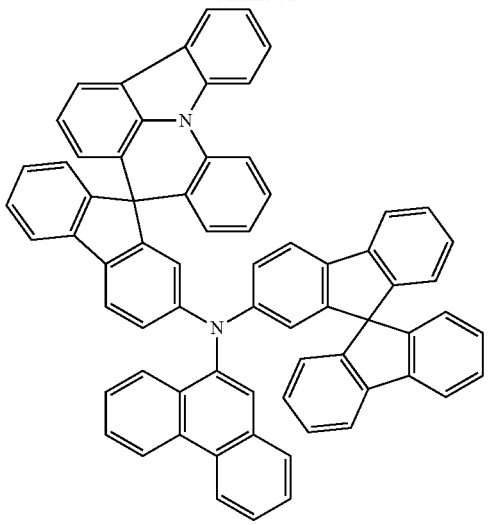
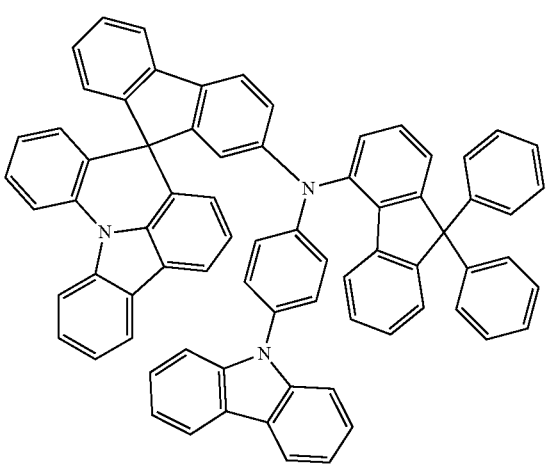
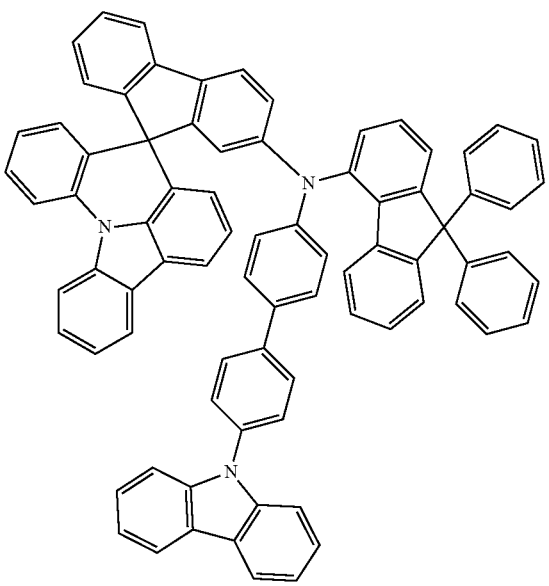

83
-continued
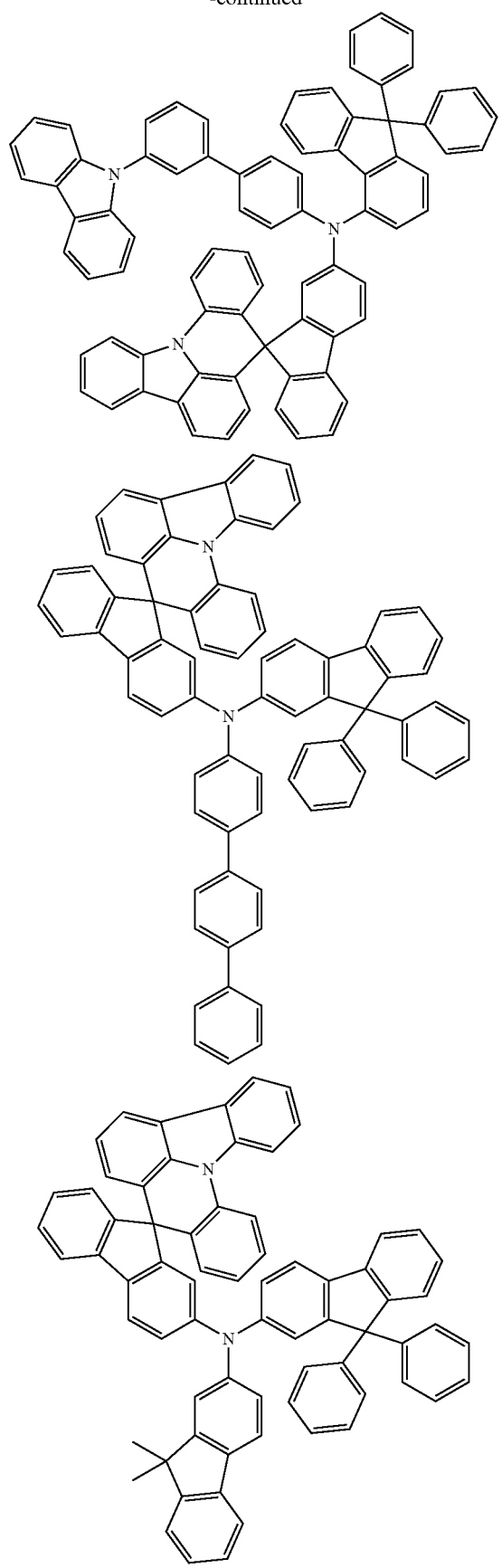
84
-continued
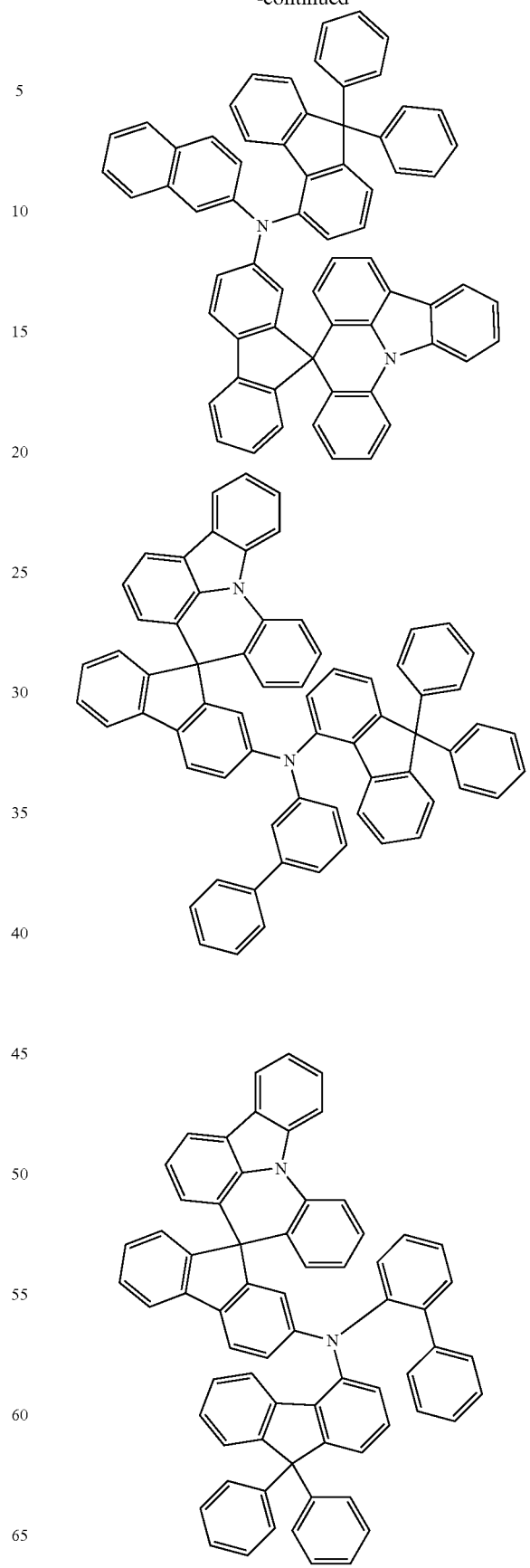

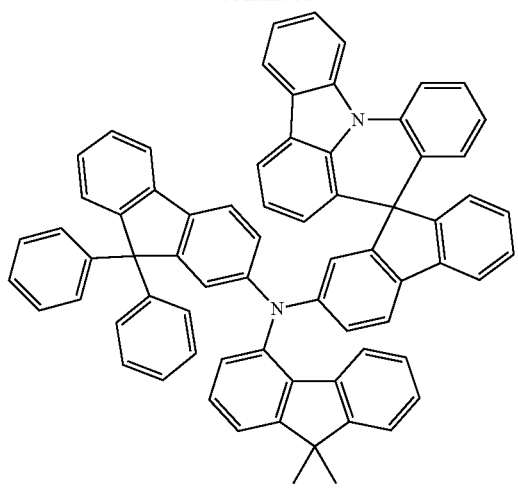
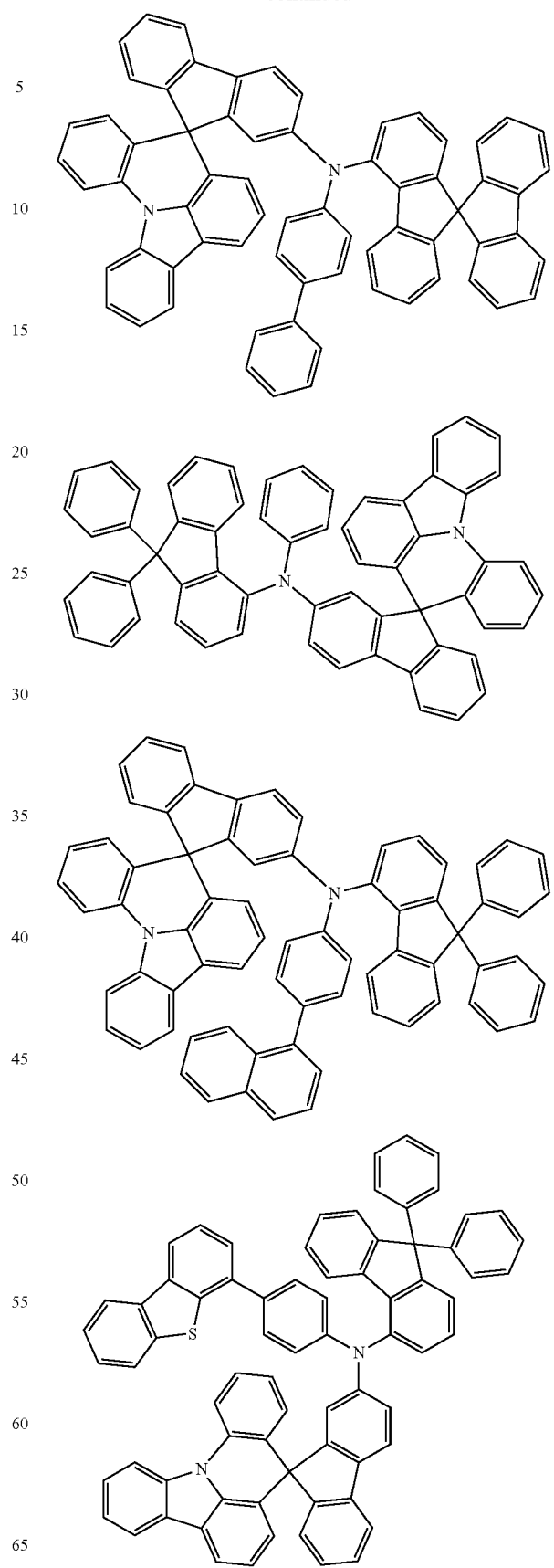

87
-continued
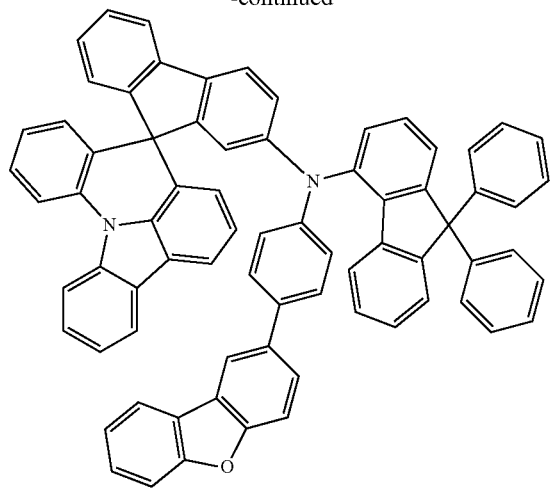
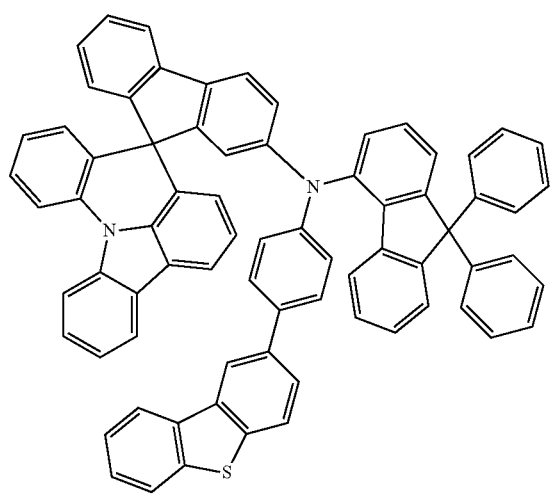
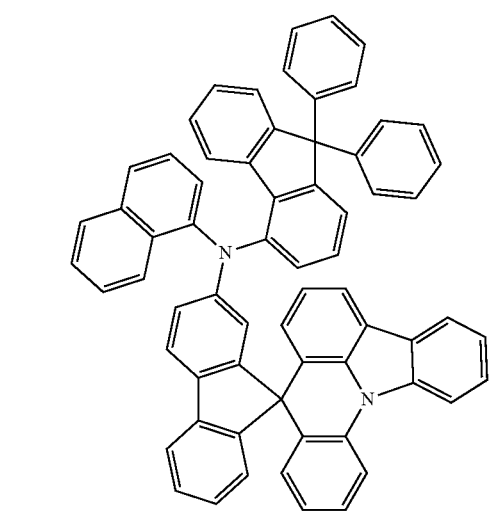
88
-continued
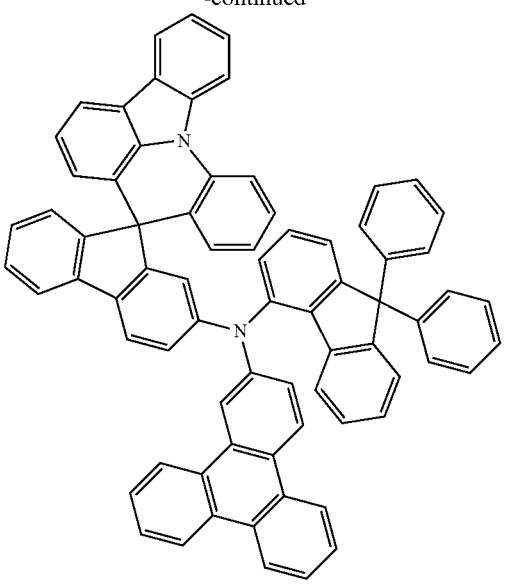
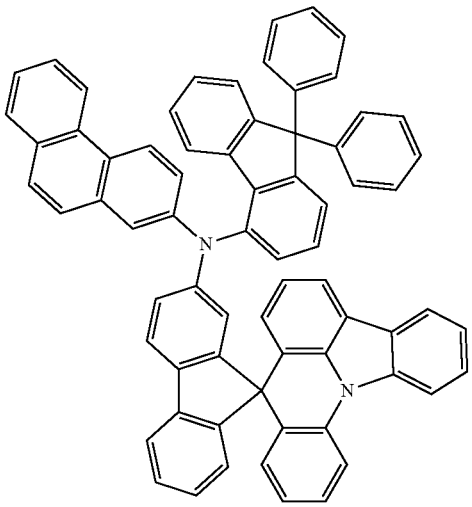
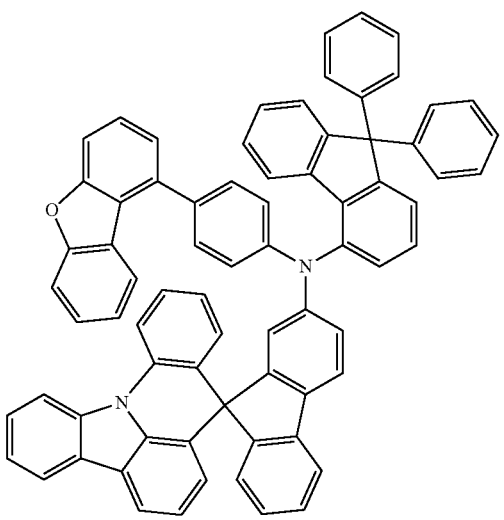

89
-continued
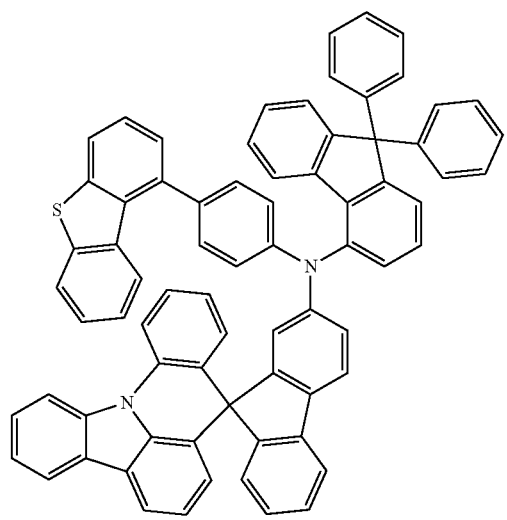
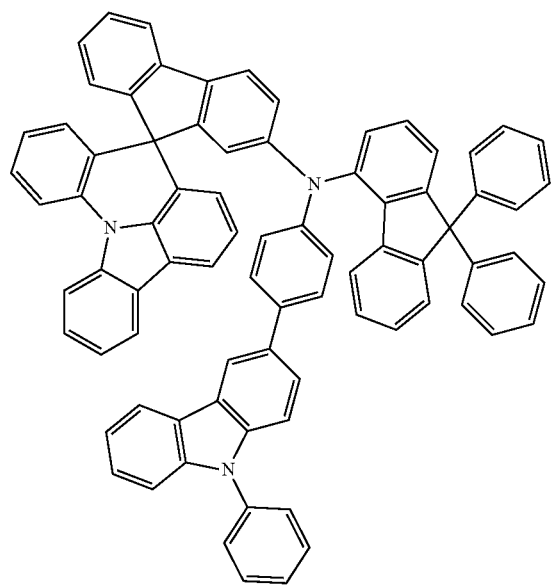
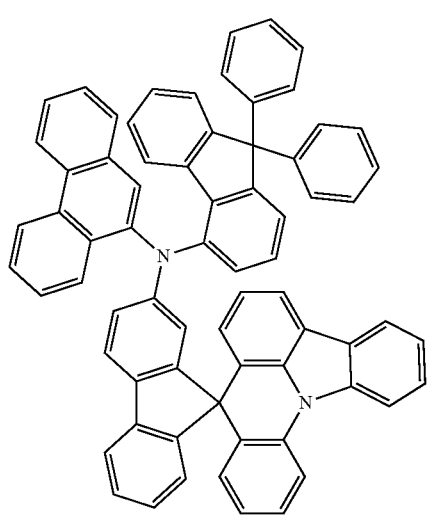
90
-continued
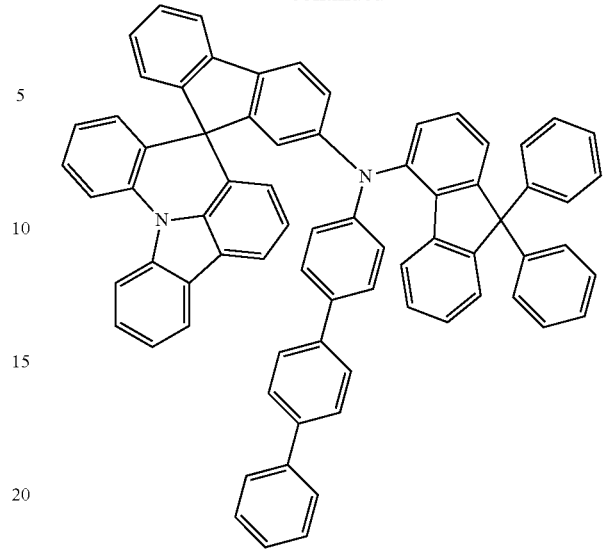
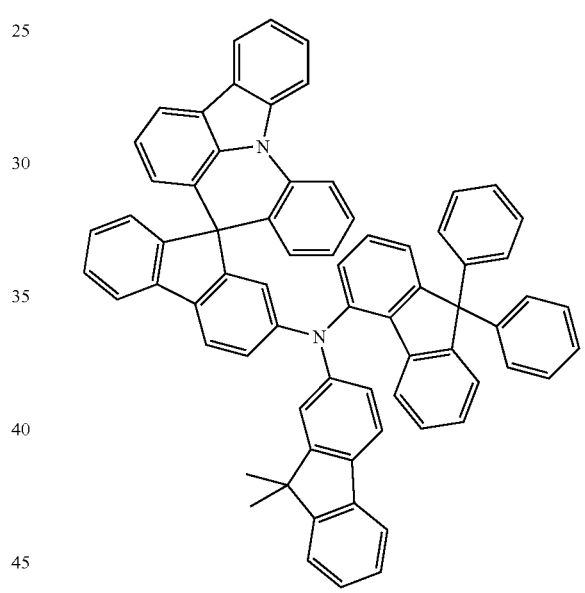
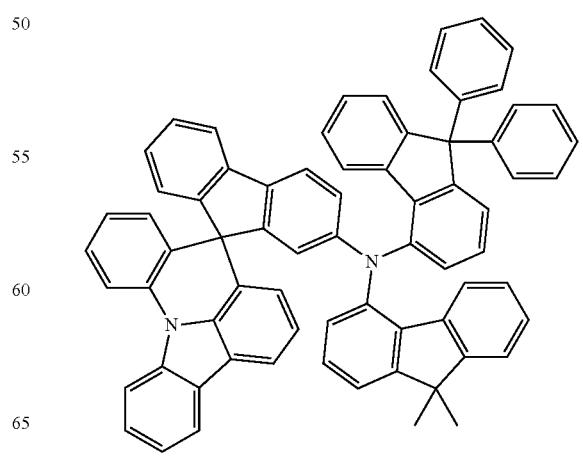

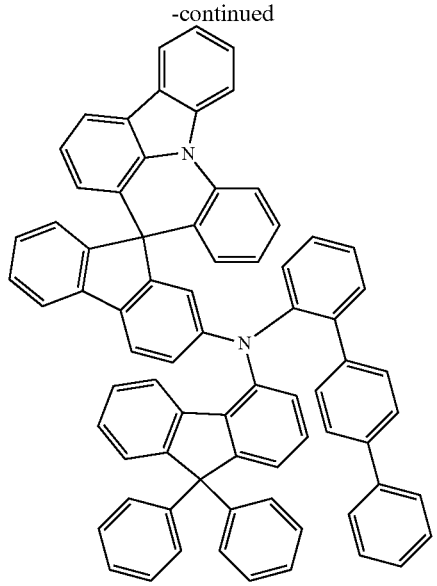
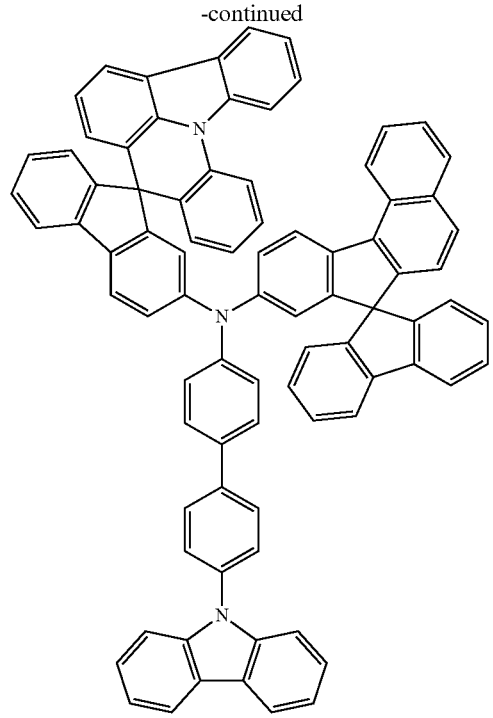
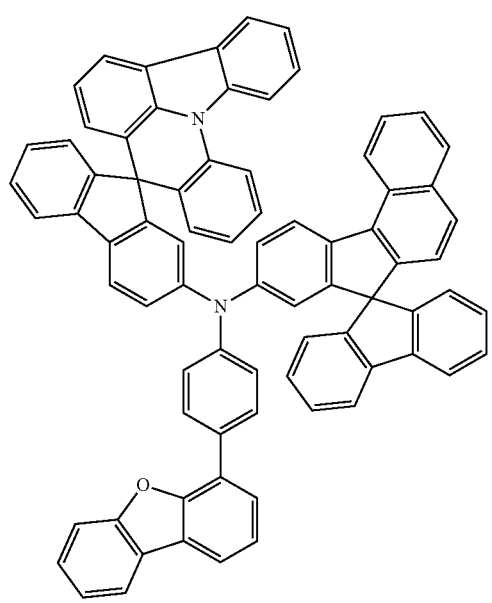
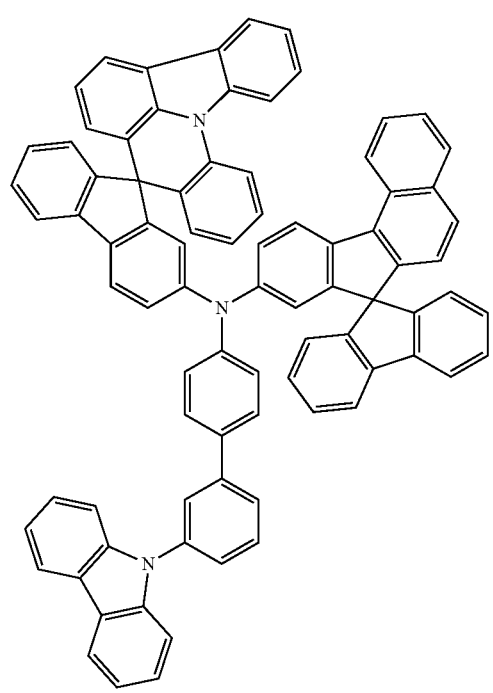

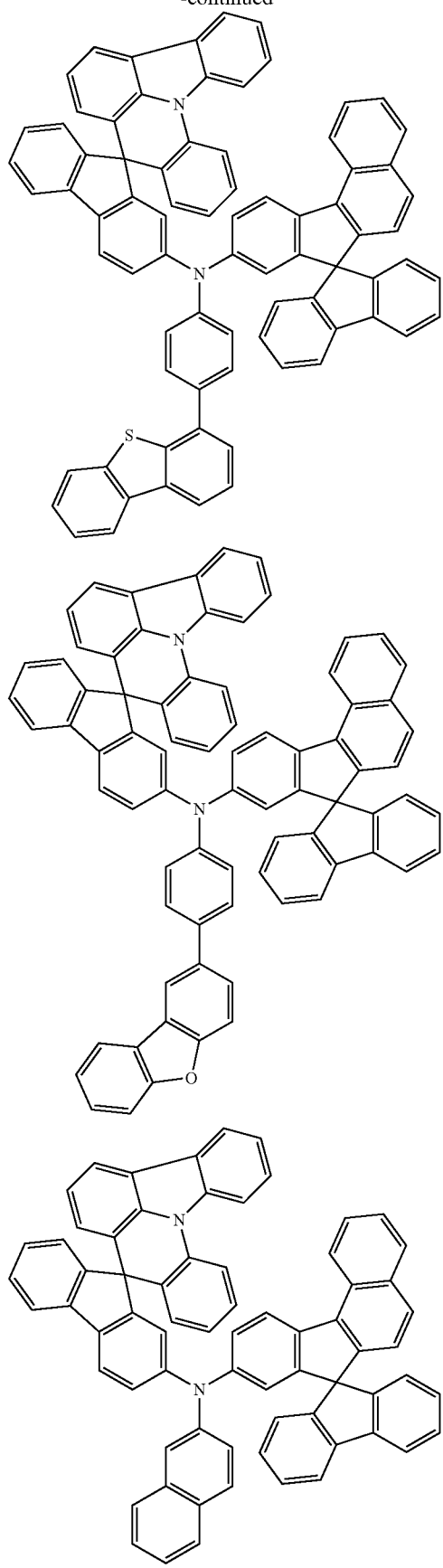
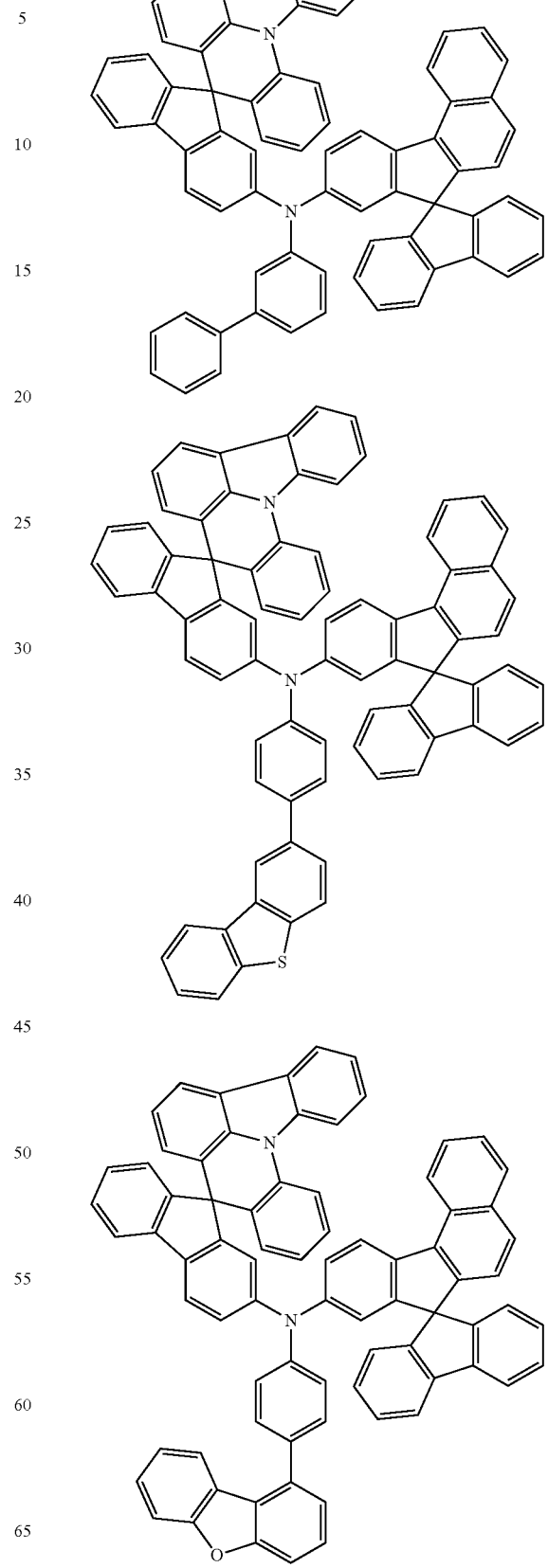

95
-continued
96
-continued
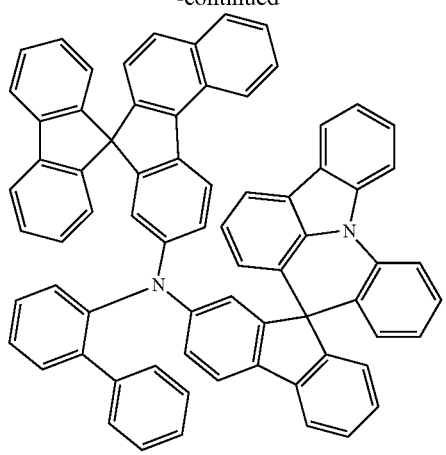
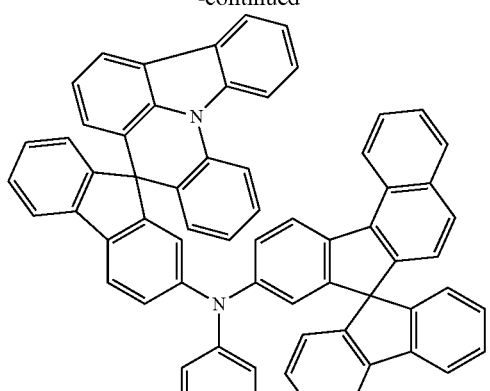
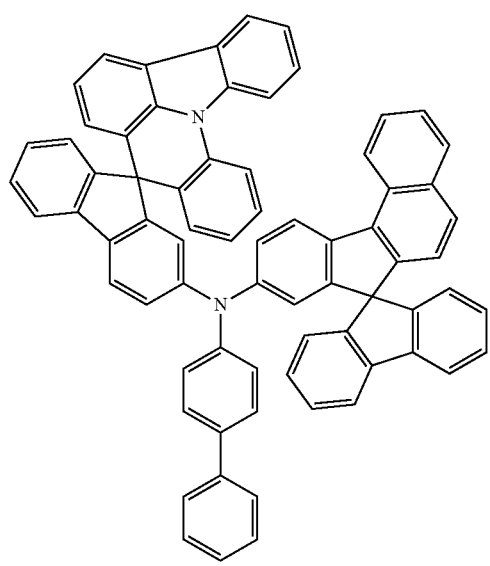
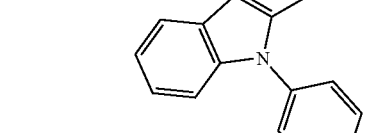
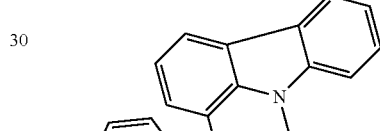
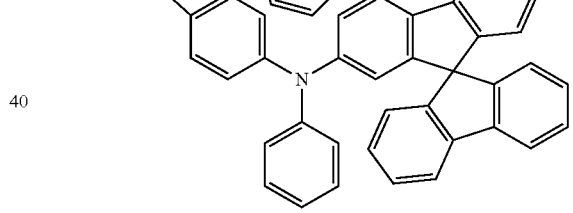
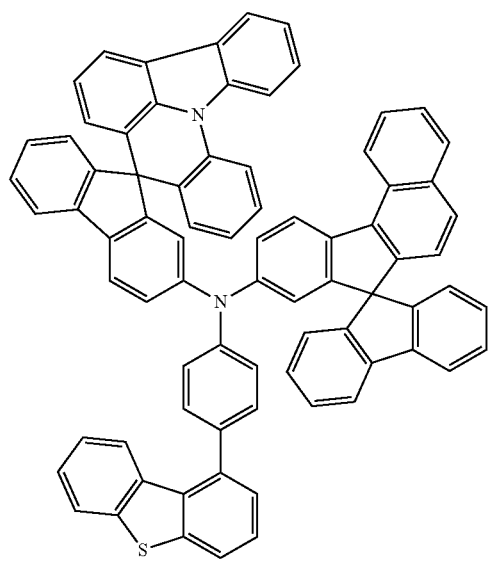
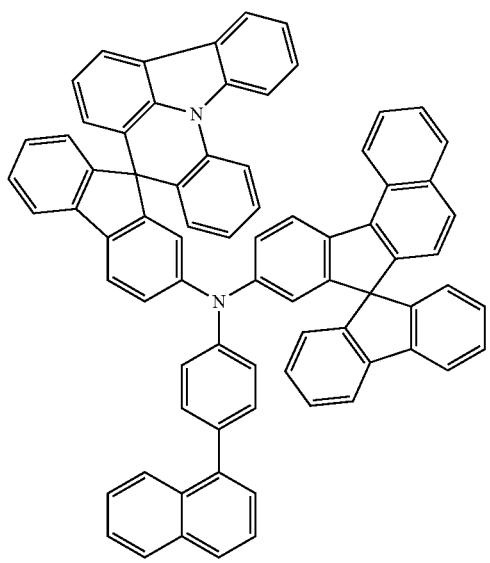

97
-continued
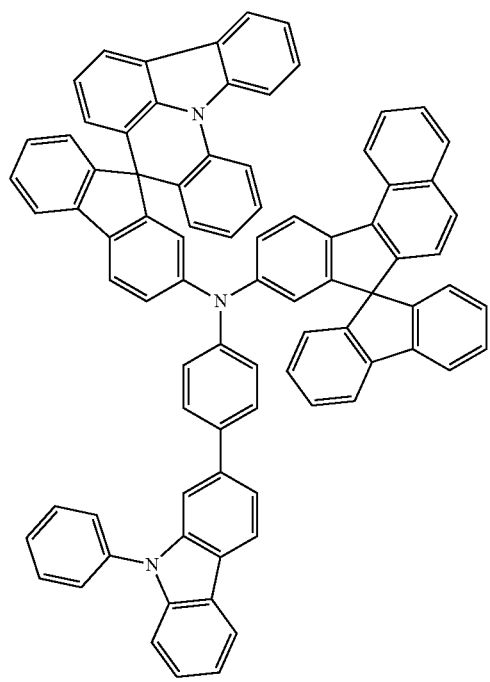
98
-continued
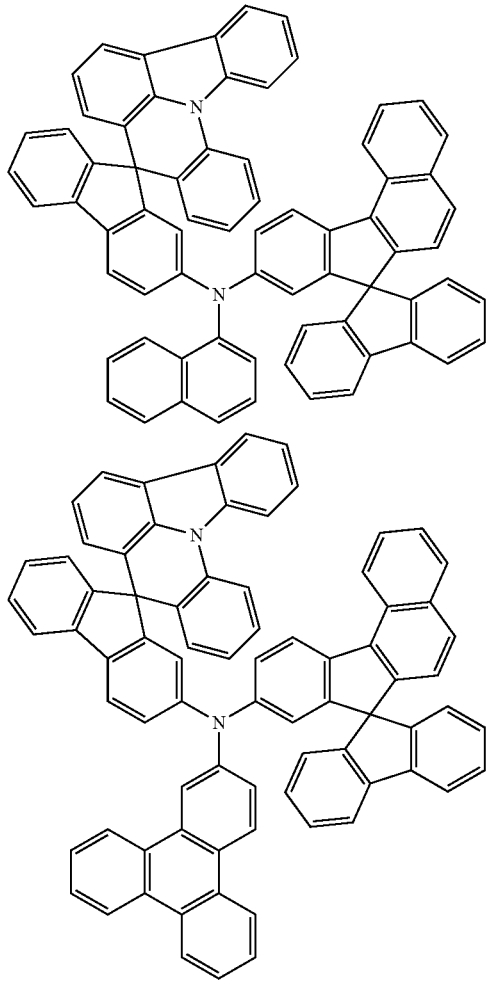
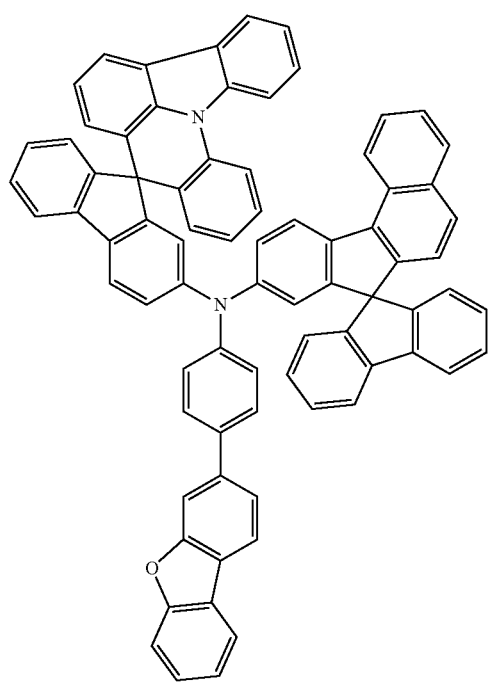
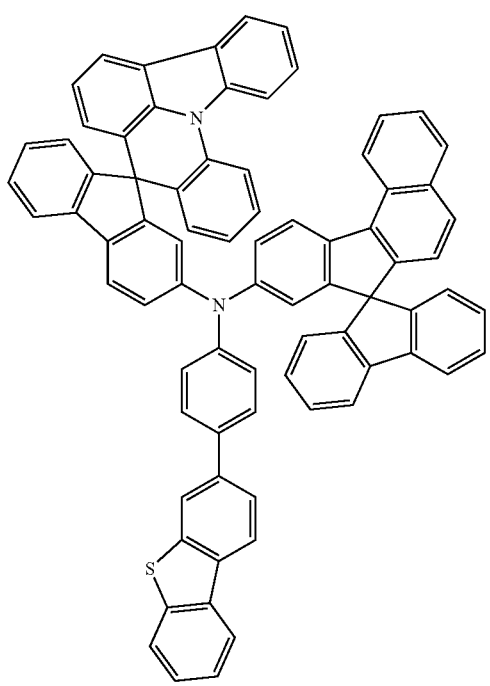

99
-continued
100
-continued
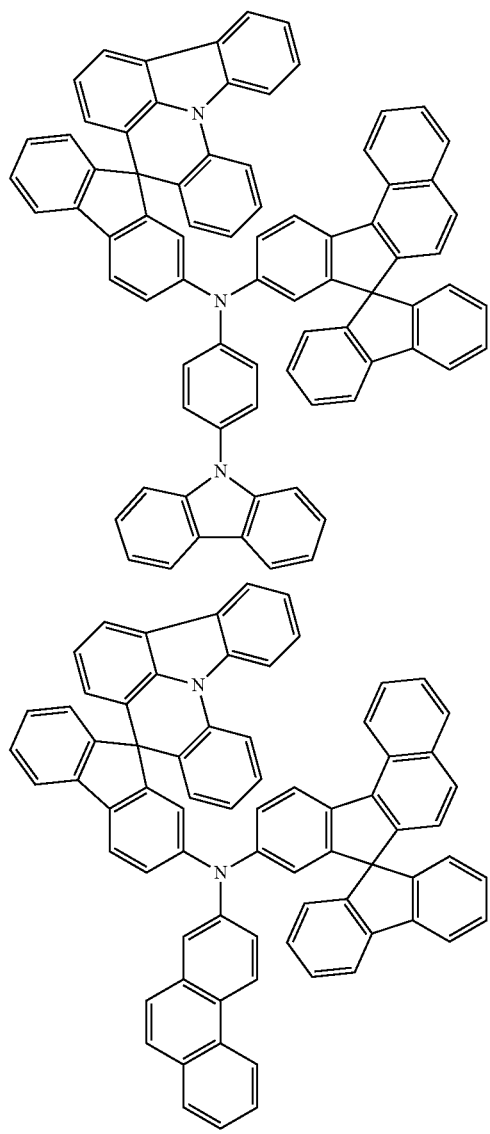
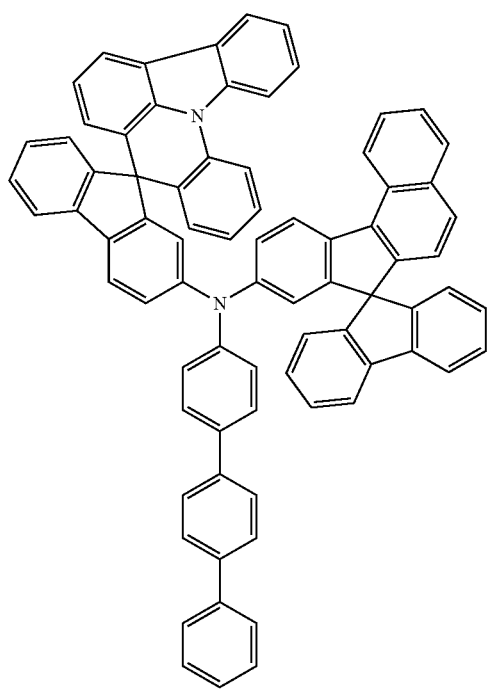
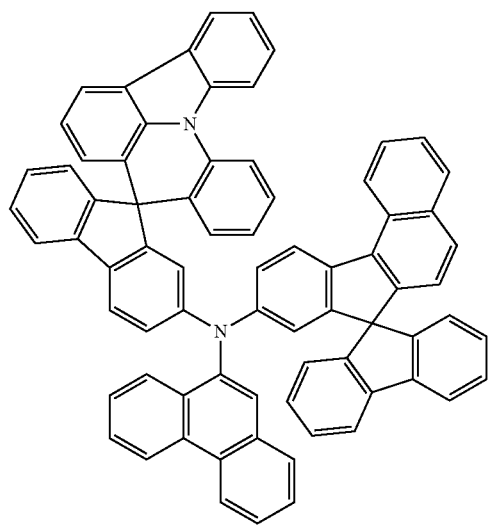
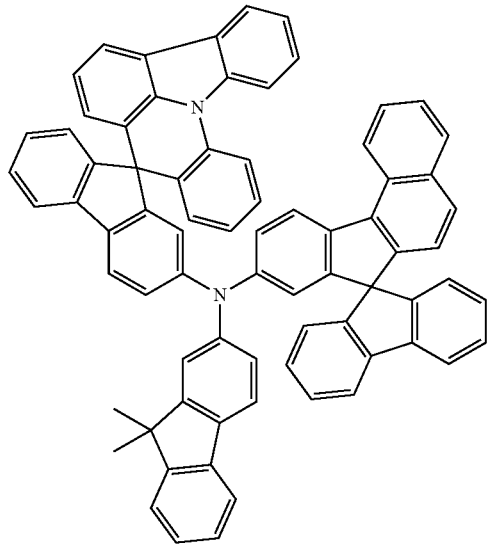

101
-continued
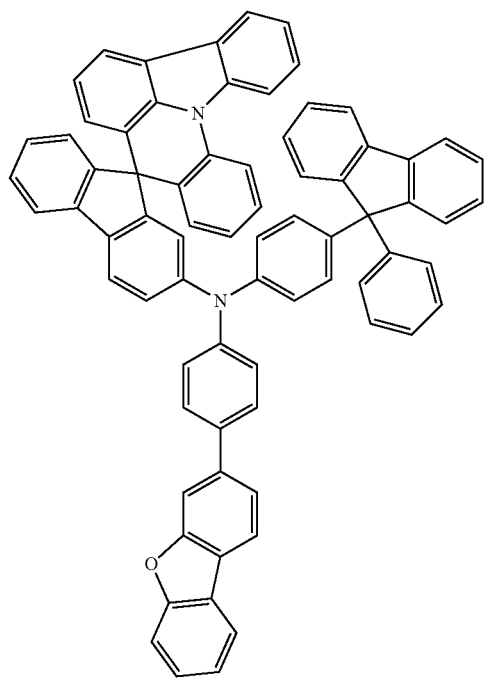
102
-continued
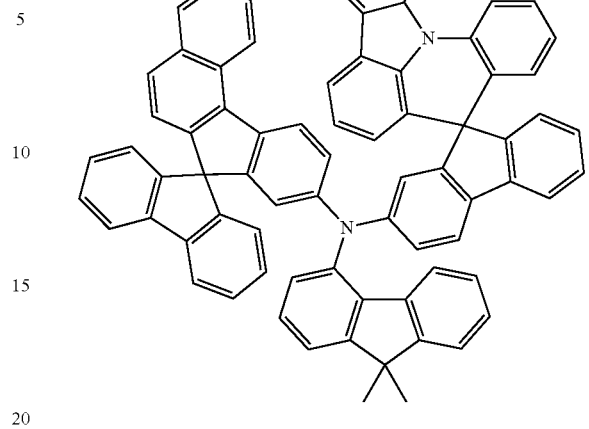
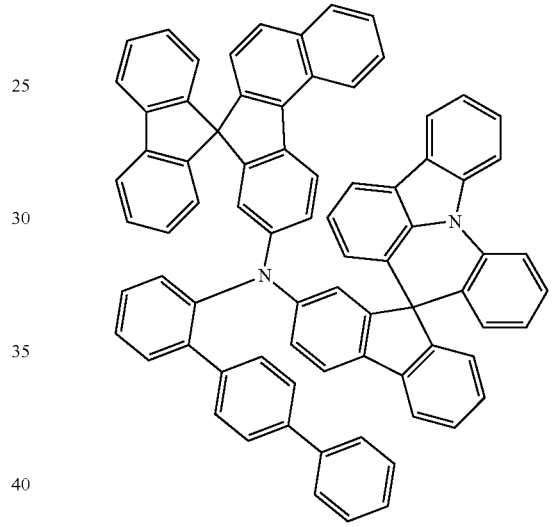
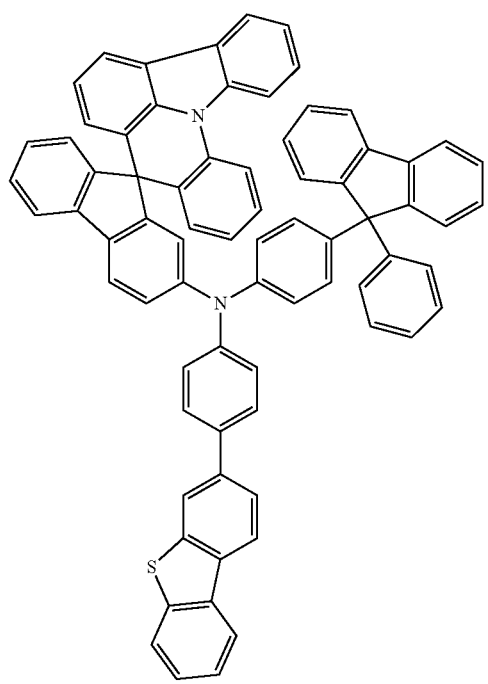
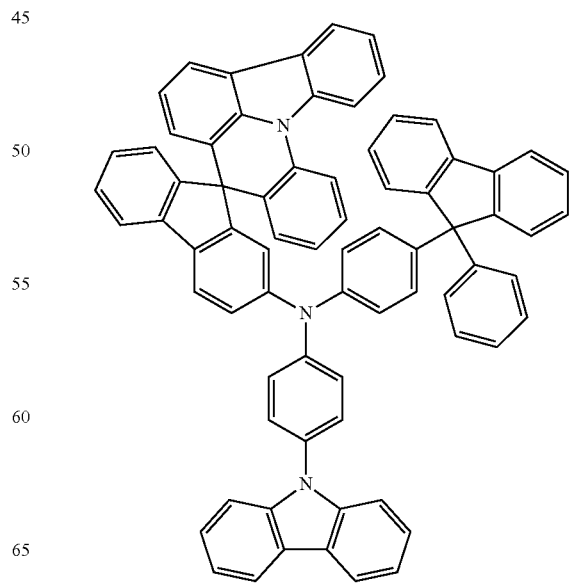

103
-continued
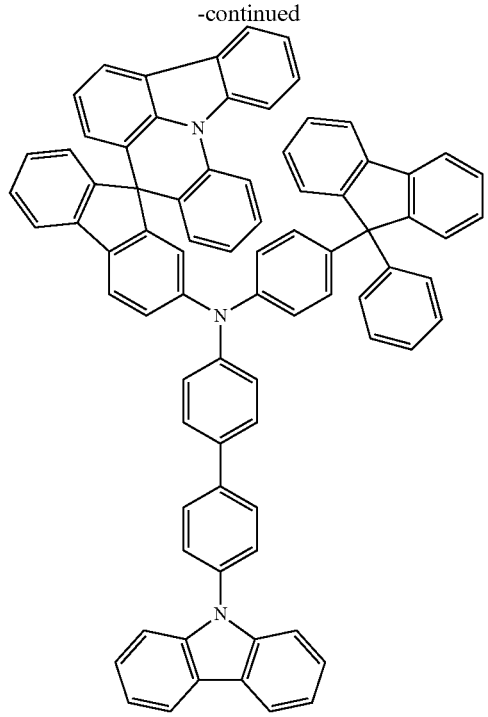
104
-continued
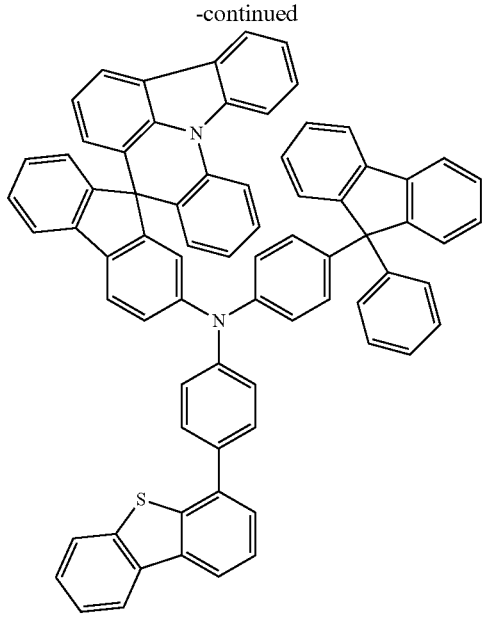
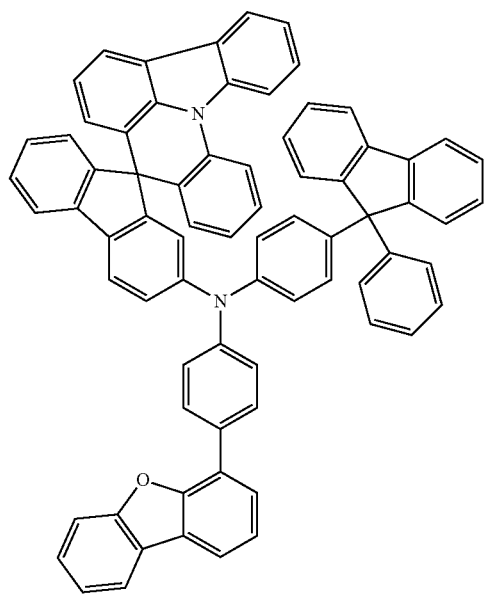
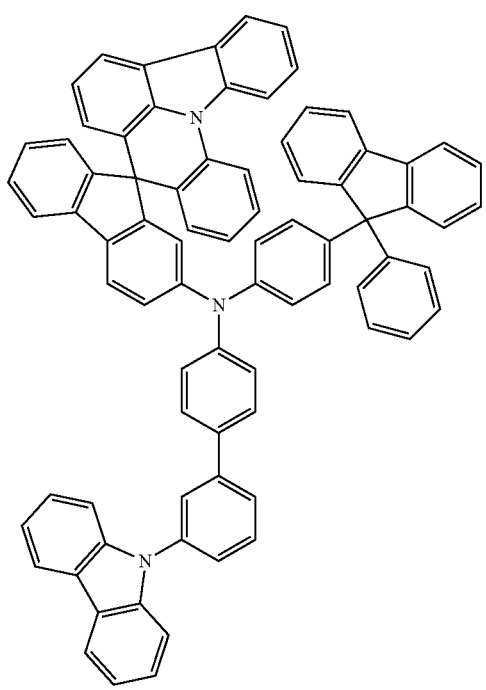

105
-continued
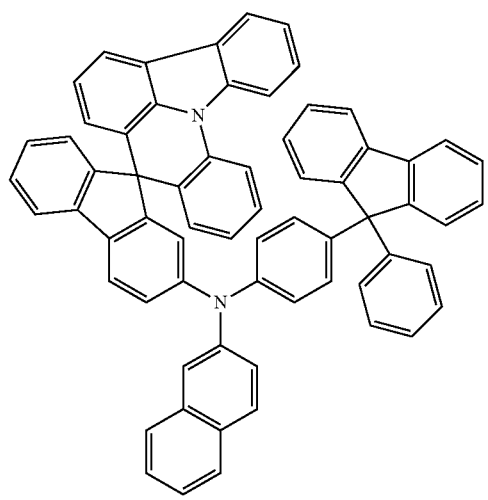
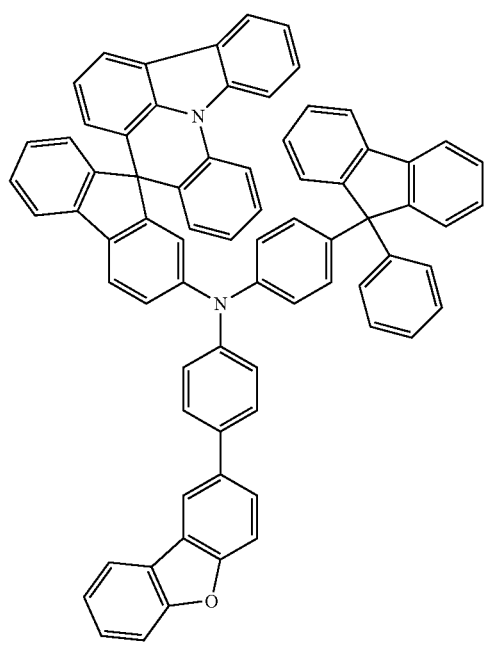
106
-continued
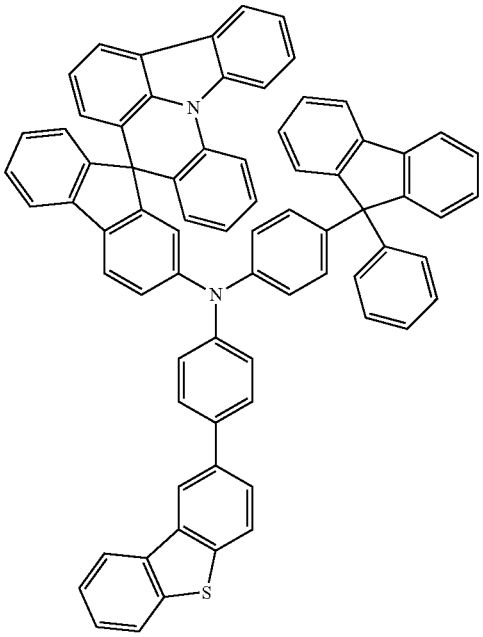
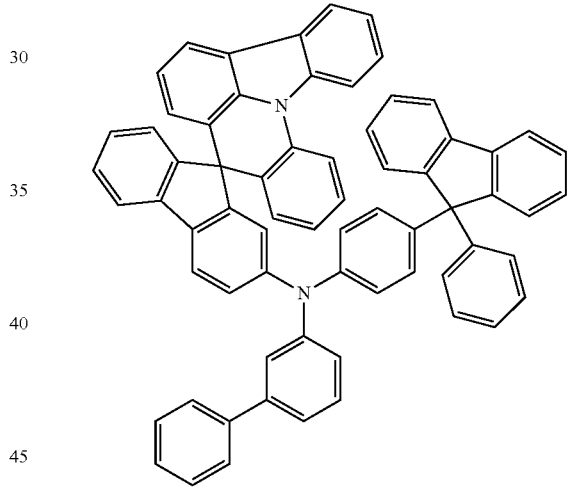
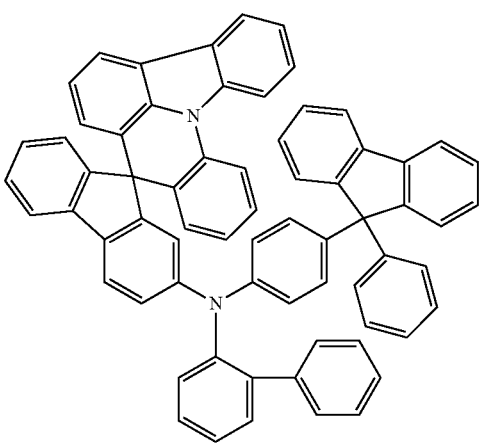

107
-continued
108
-continued
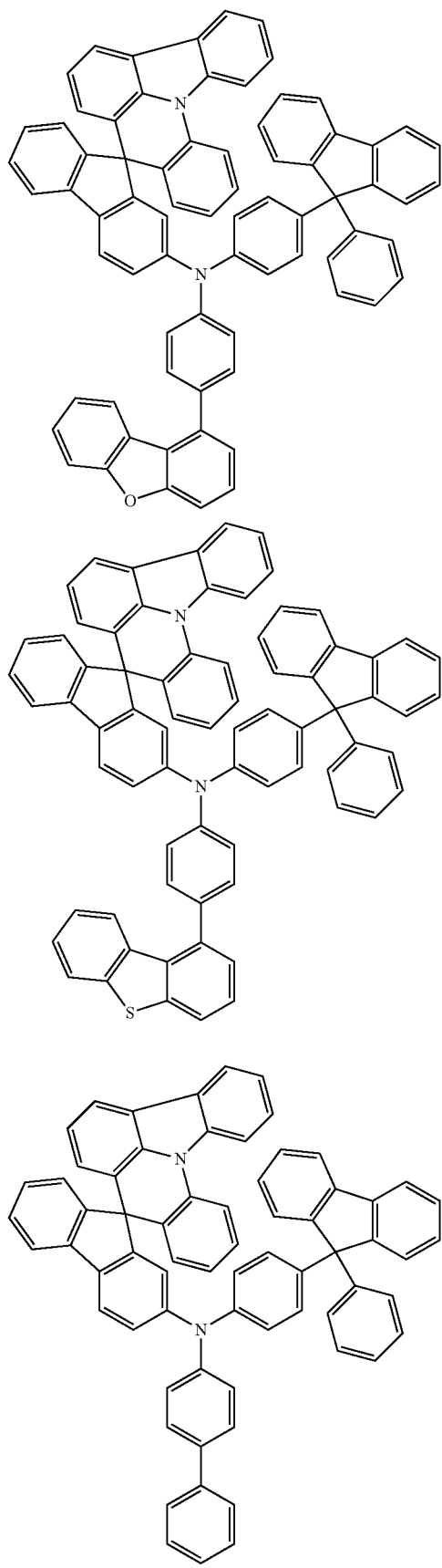
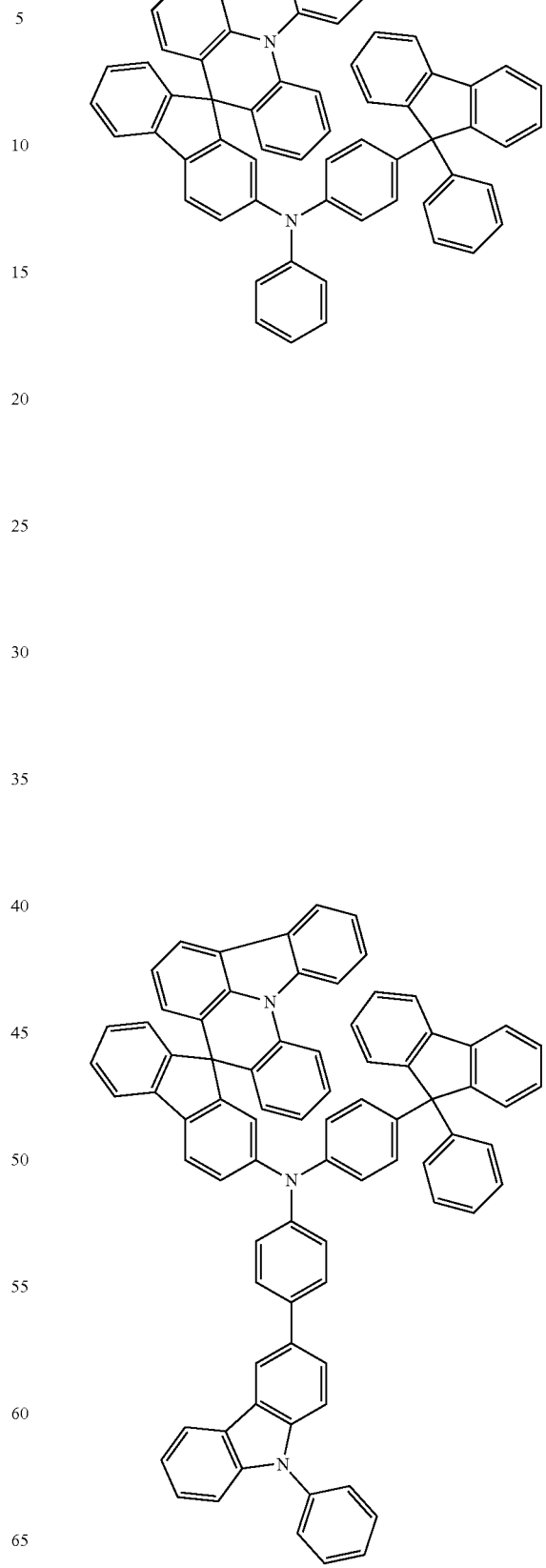

109
-continued
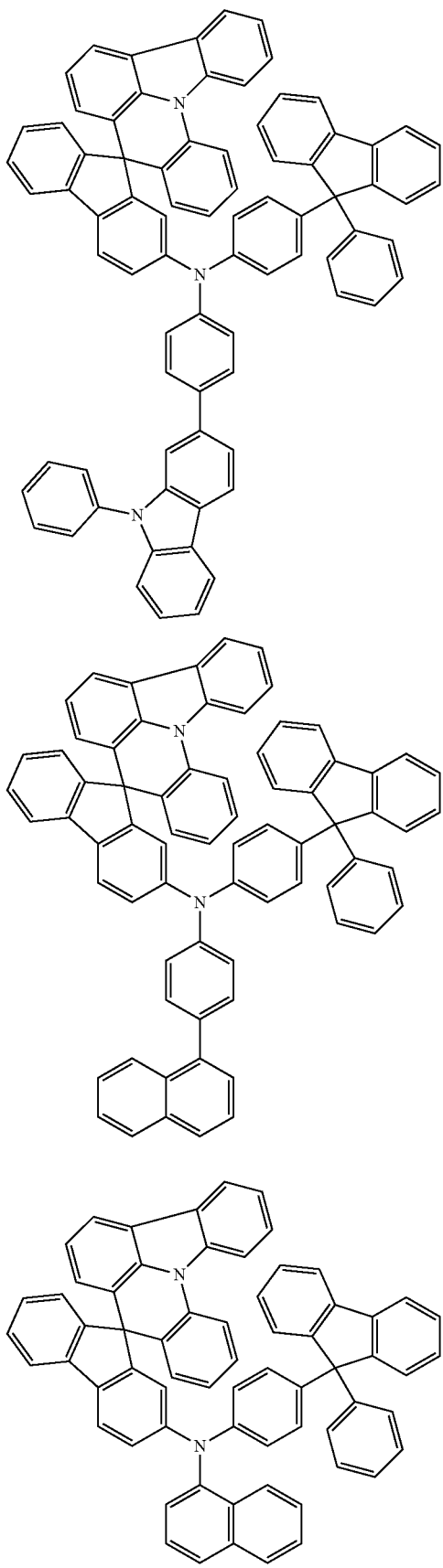
110
-continued
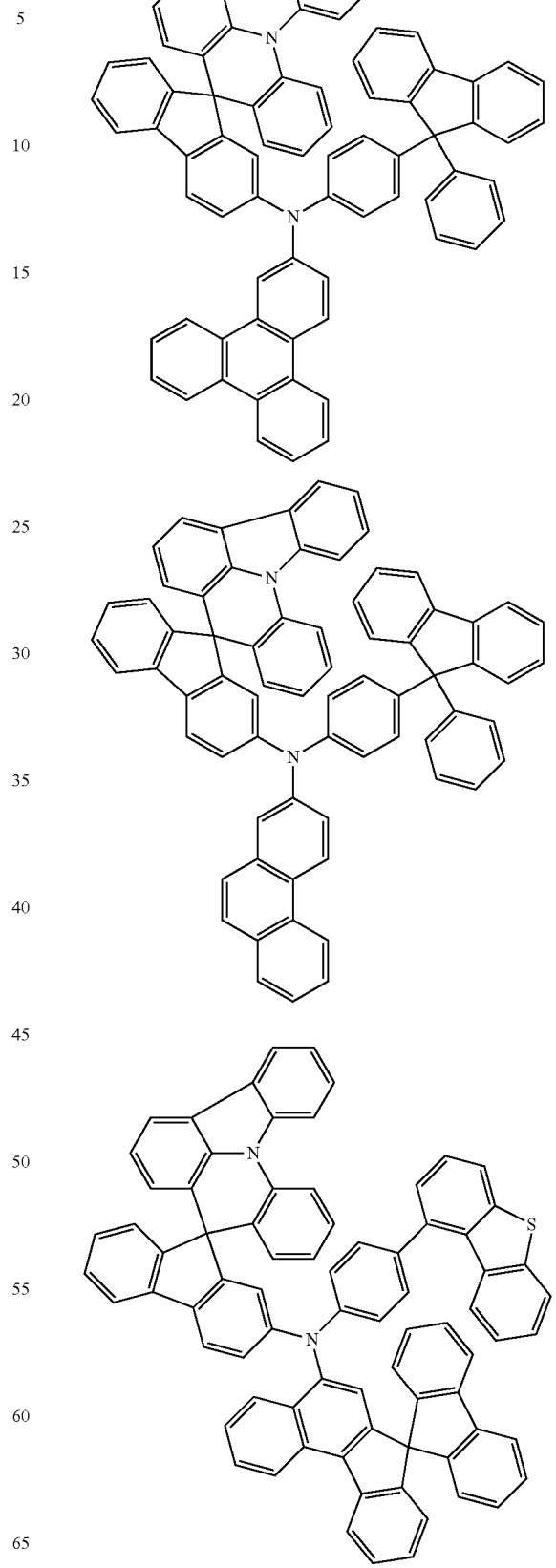

111
-continued
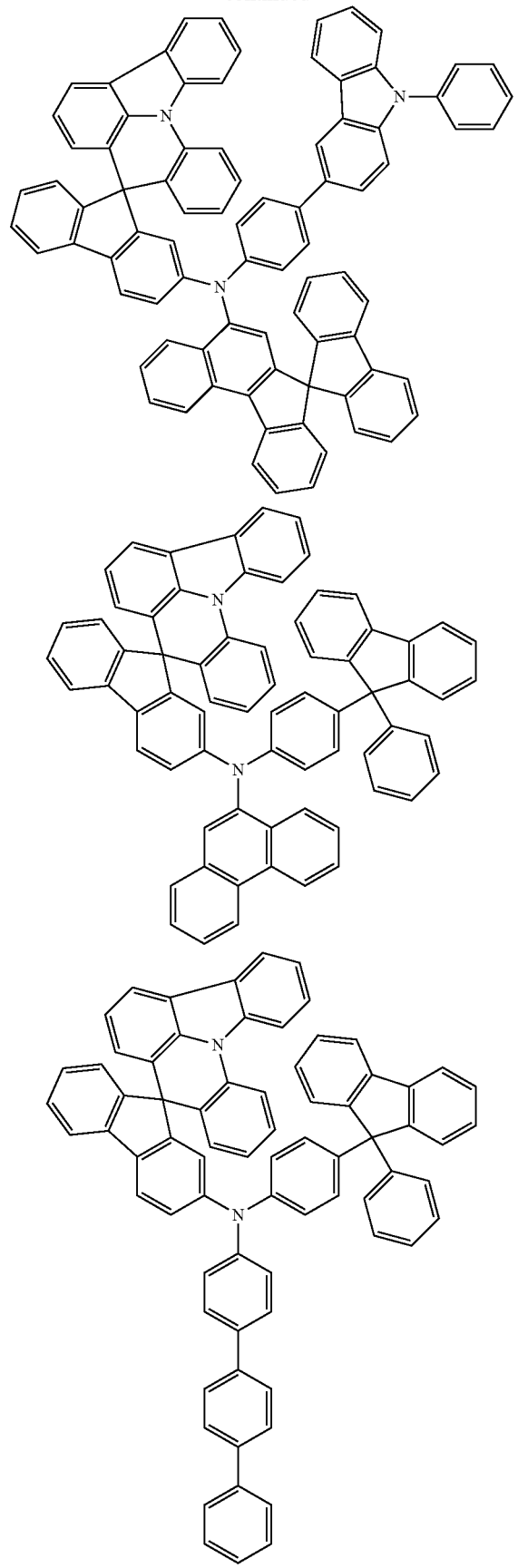
112
-continued
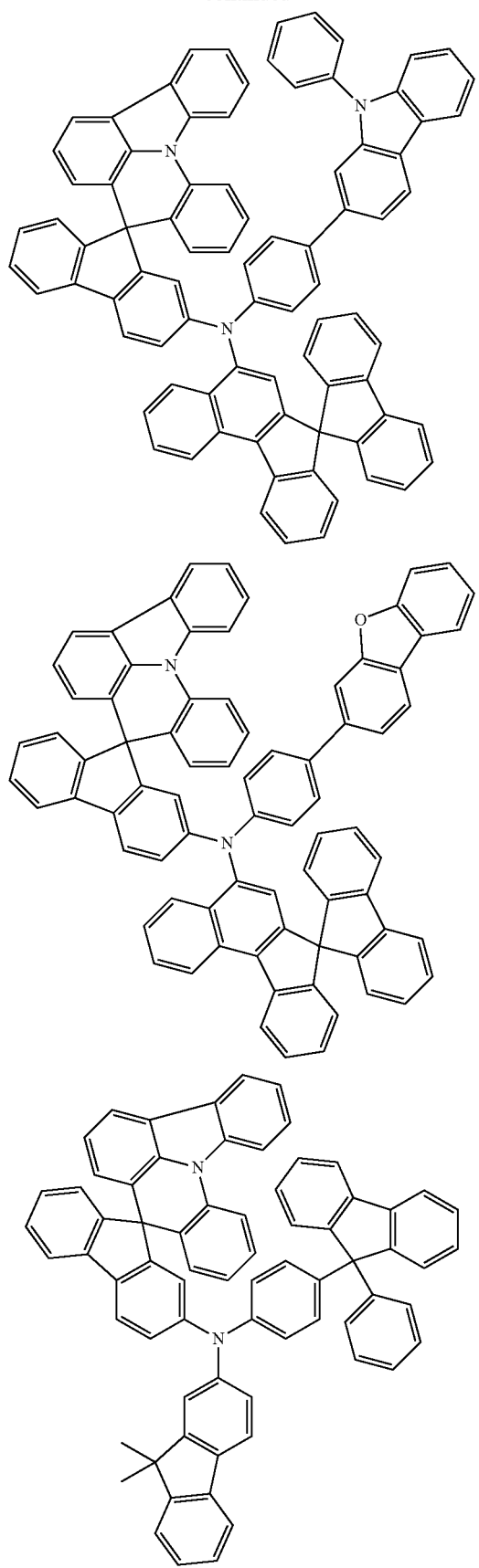

113
-continued
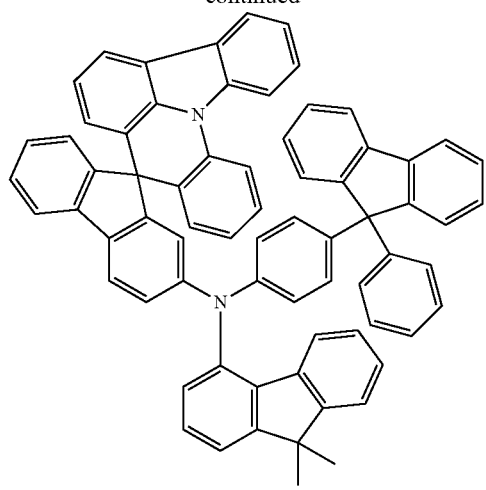
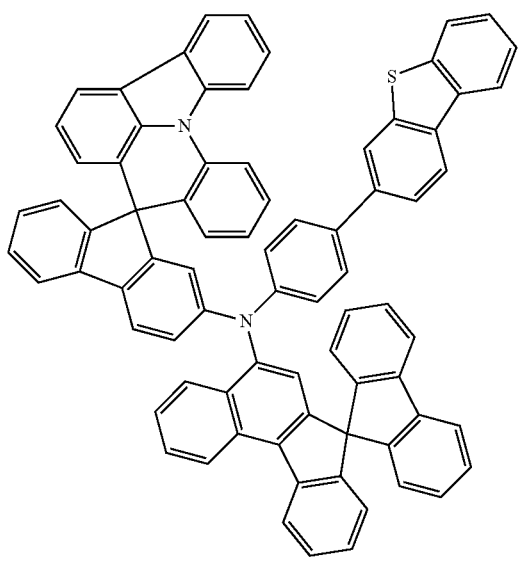
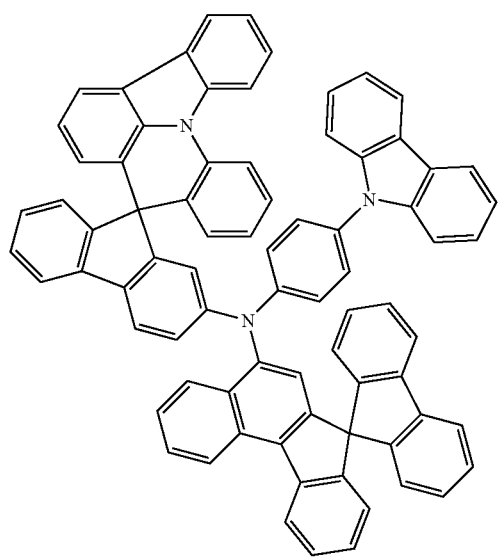
114
-continued
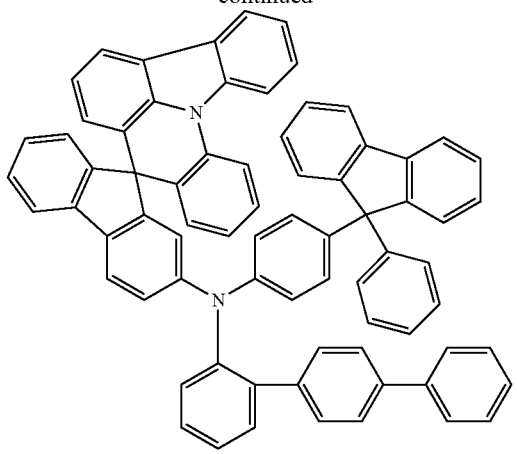
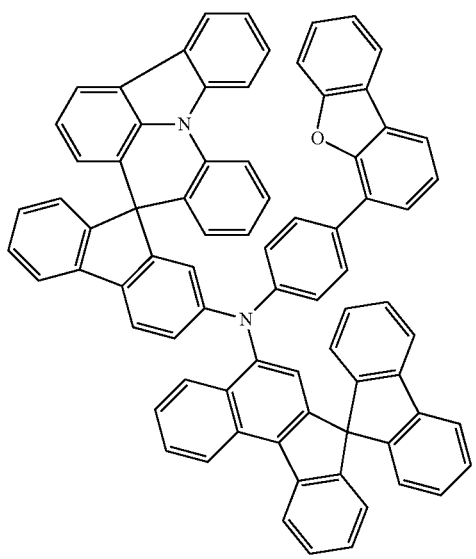
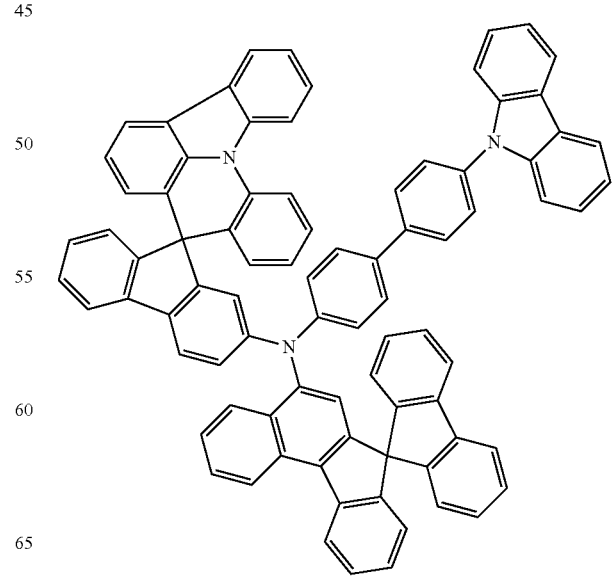

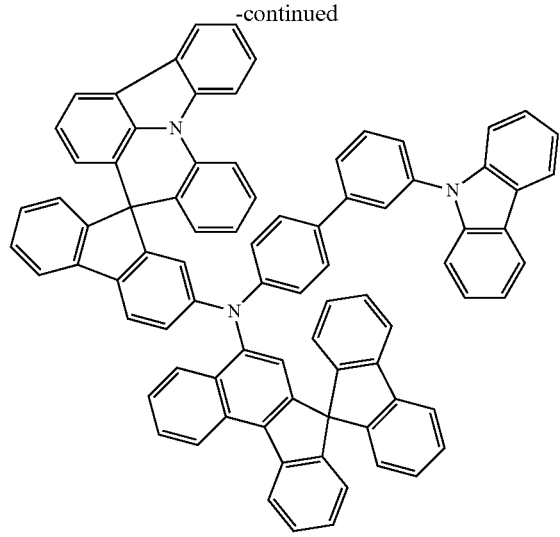
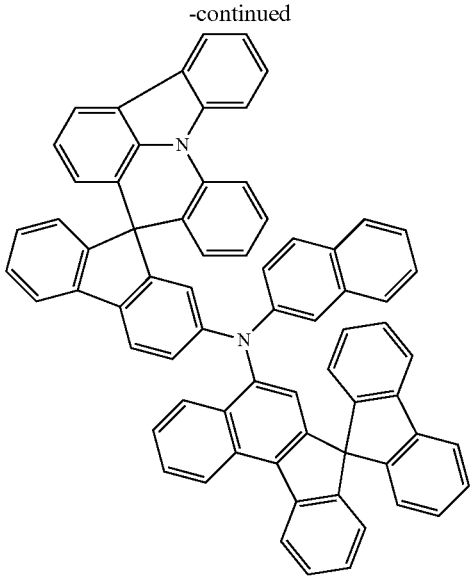
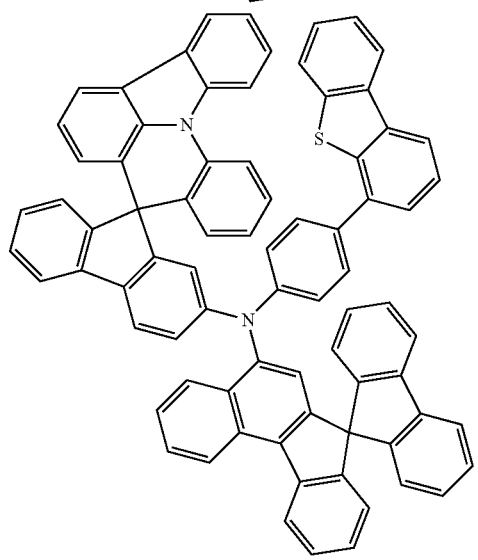
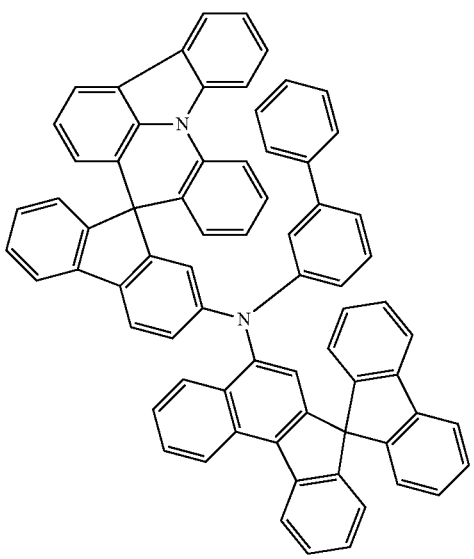
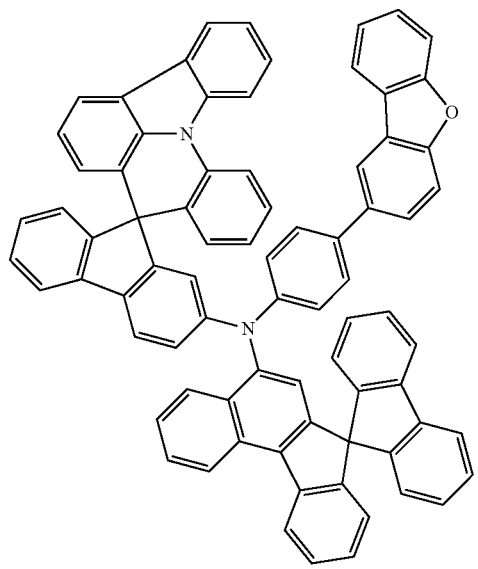
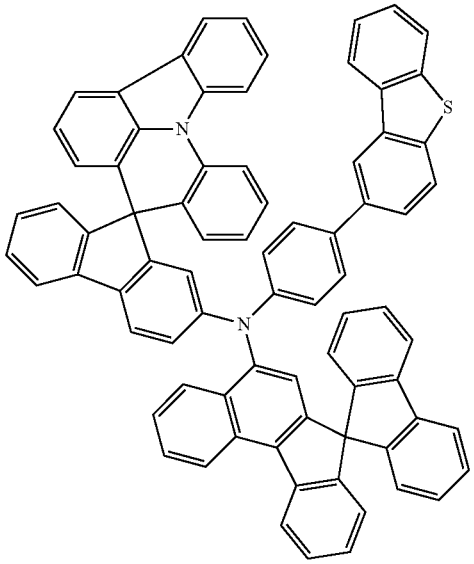

117
-continued
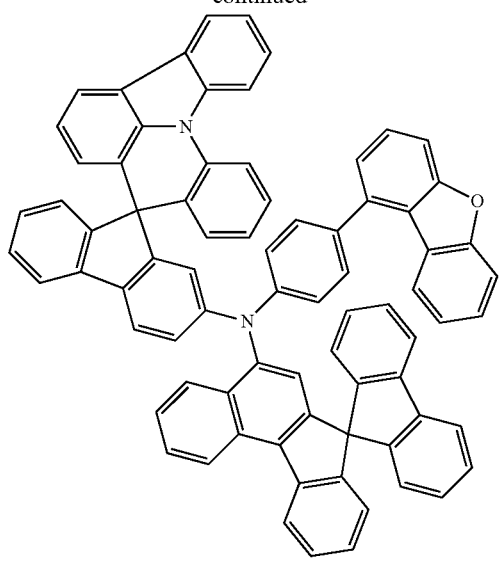
118
-continued
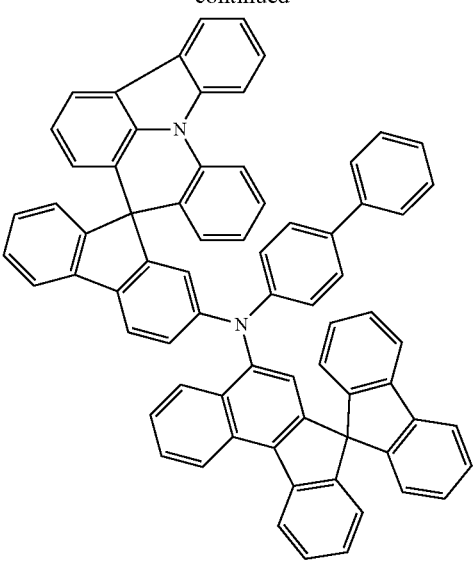
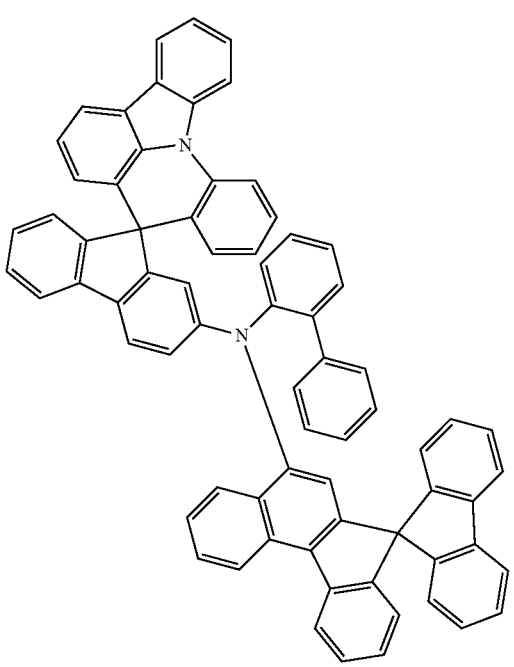
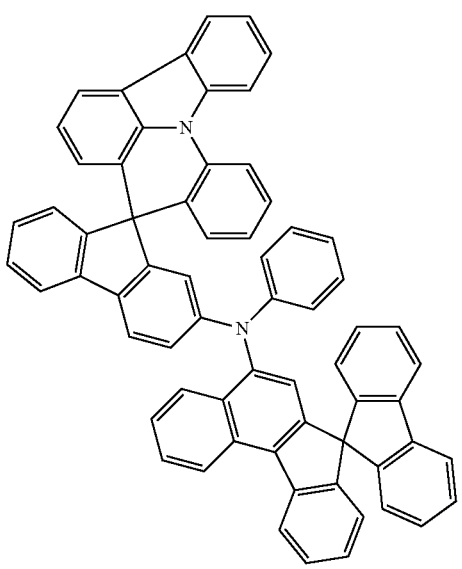

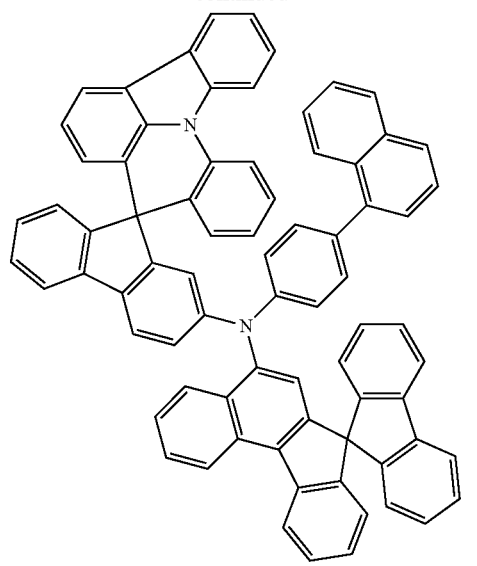
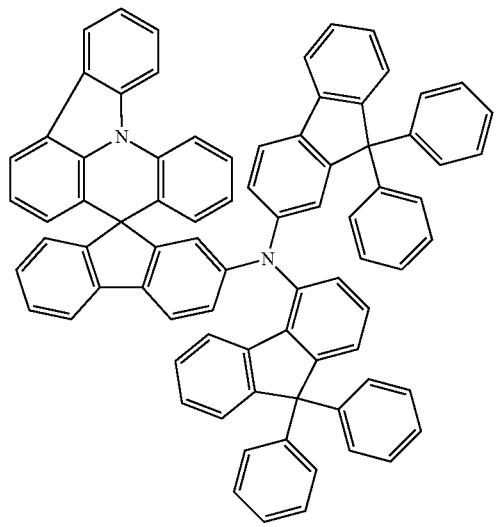
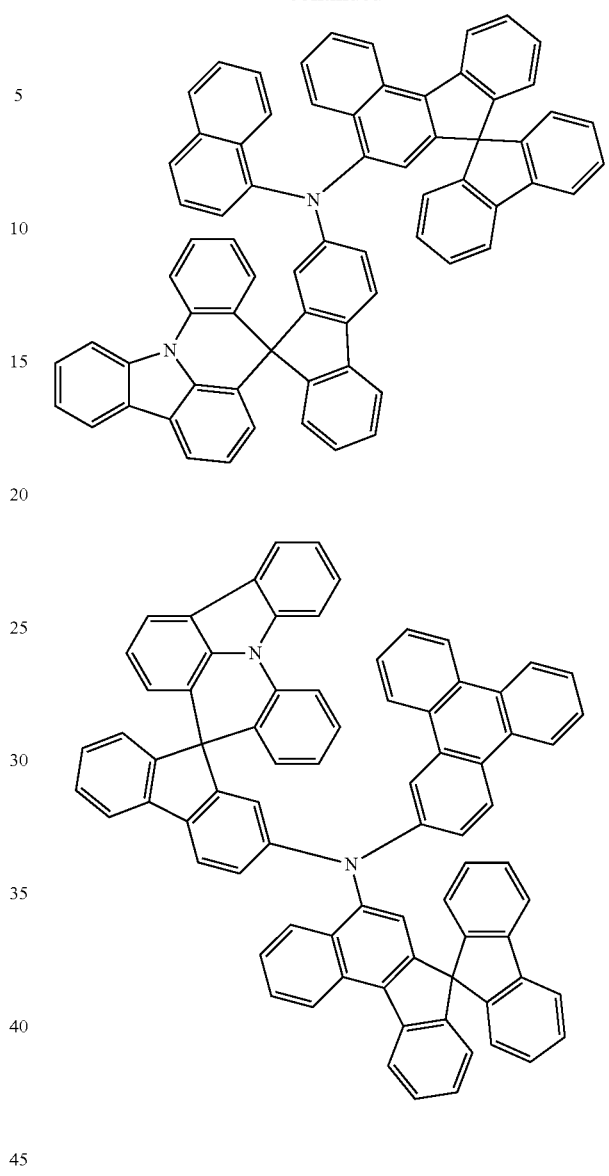

121
-continued
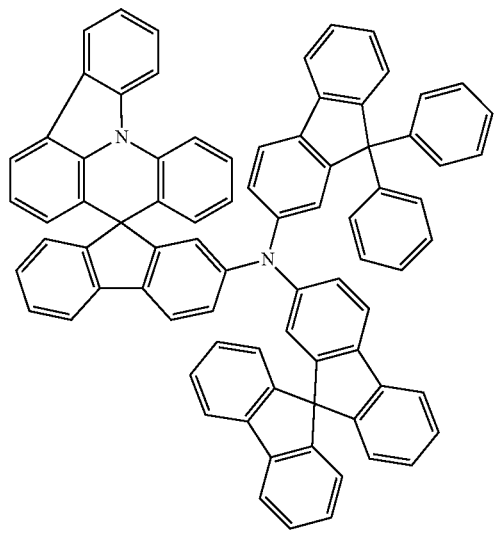
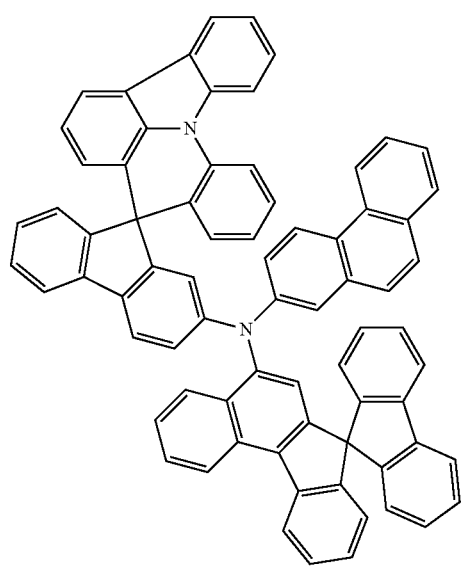
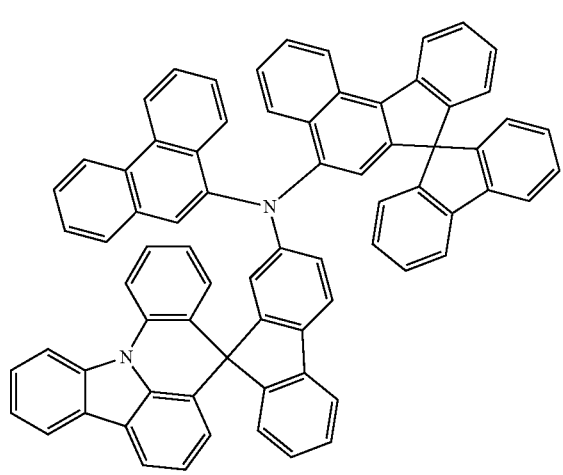
122
-continued
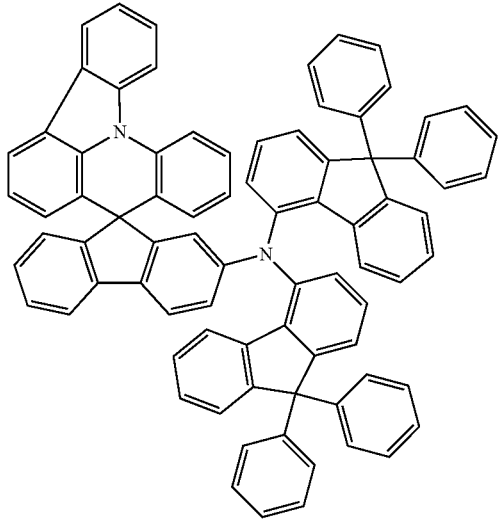
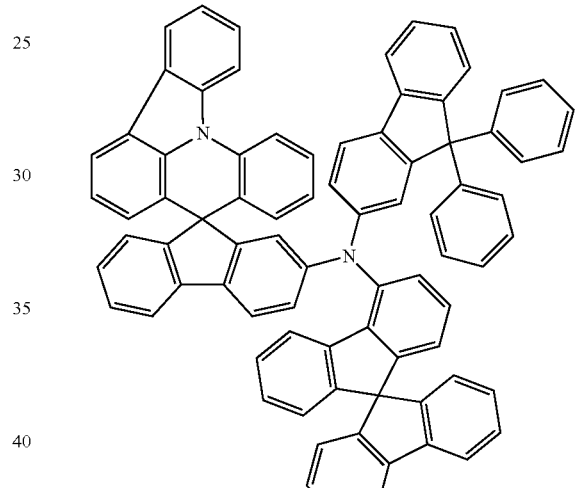
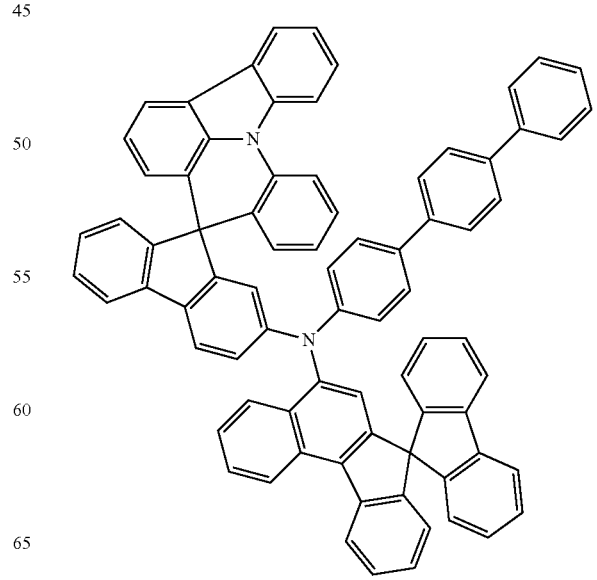

123
-continued
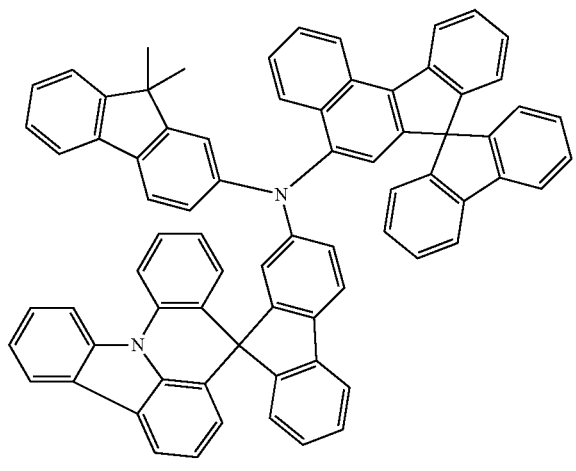
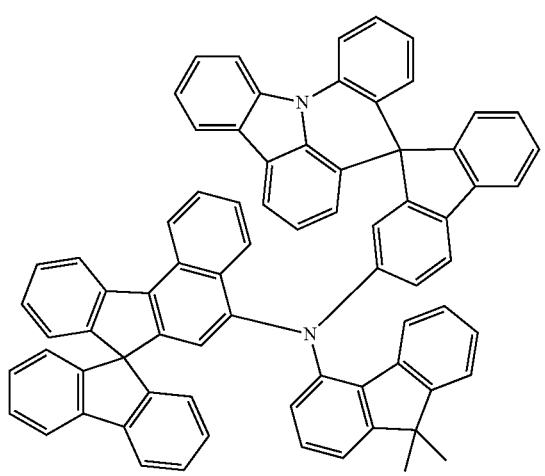
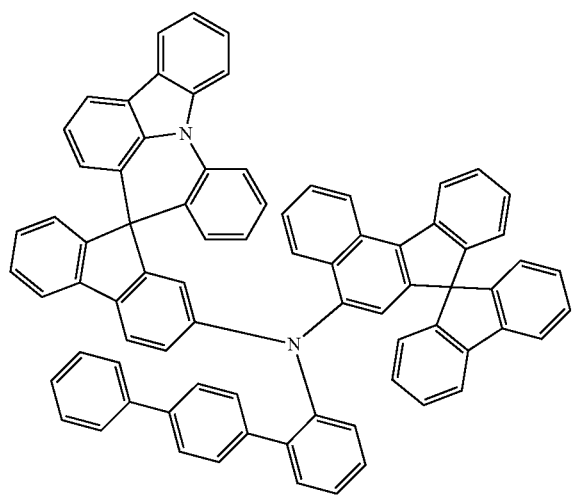
124
-continued
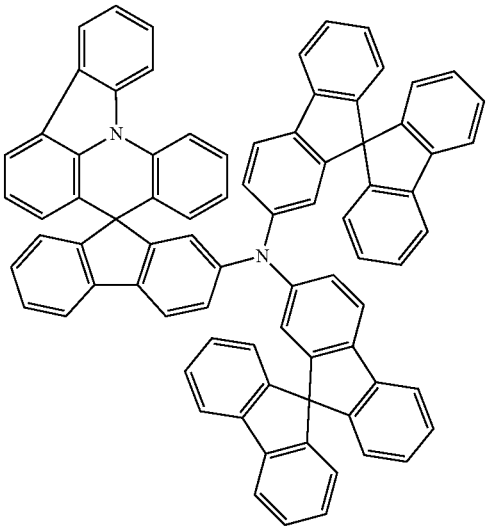
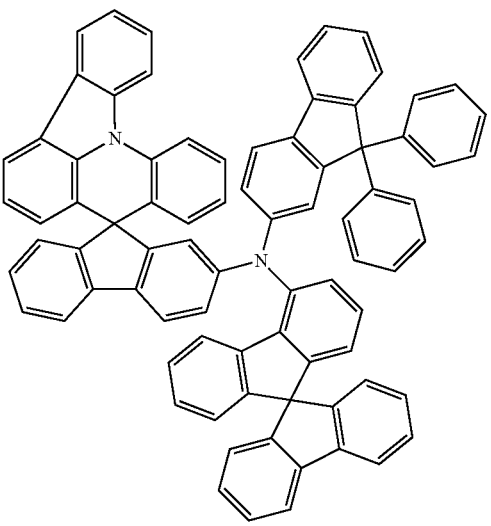
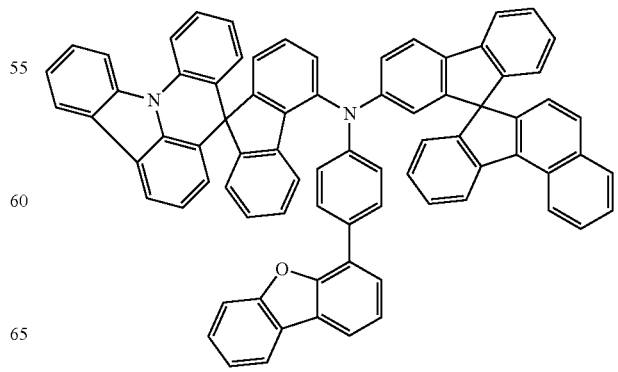

125
-continued
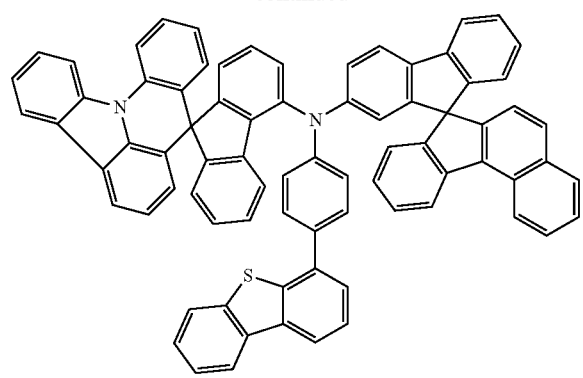
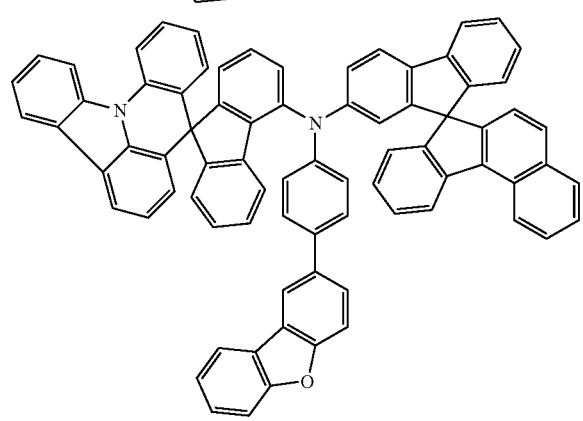
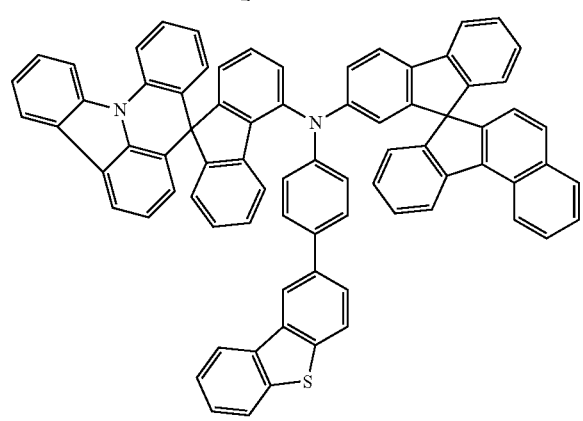
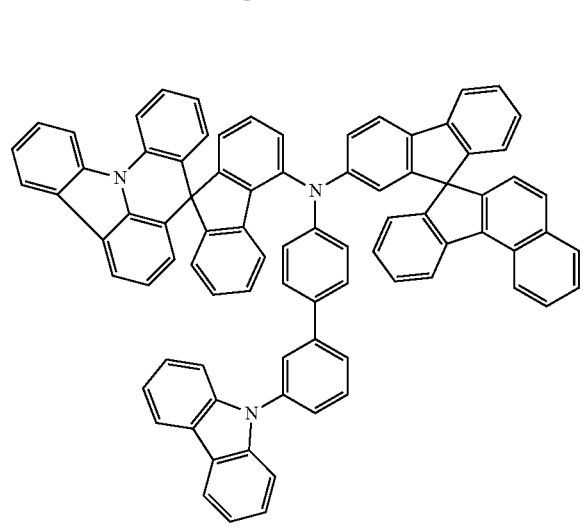
126
-continued
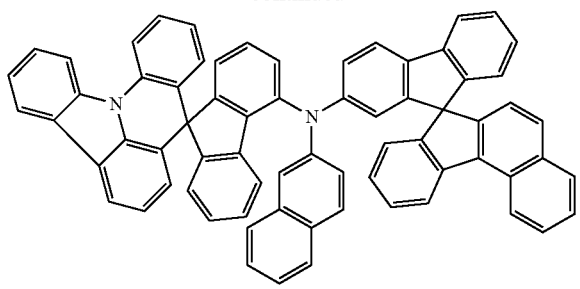
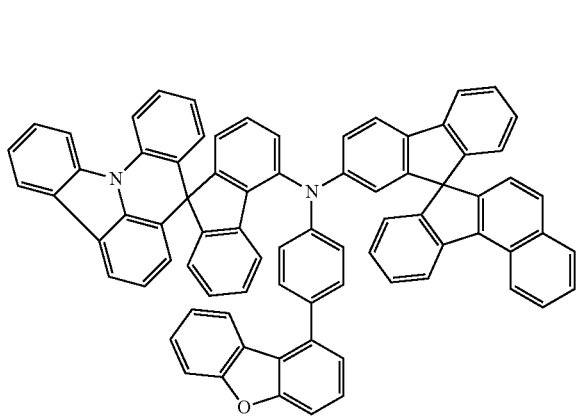
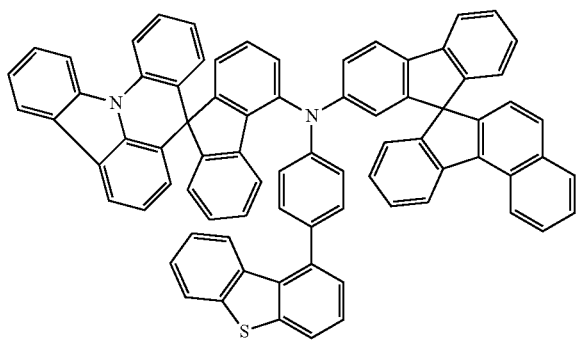
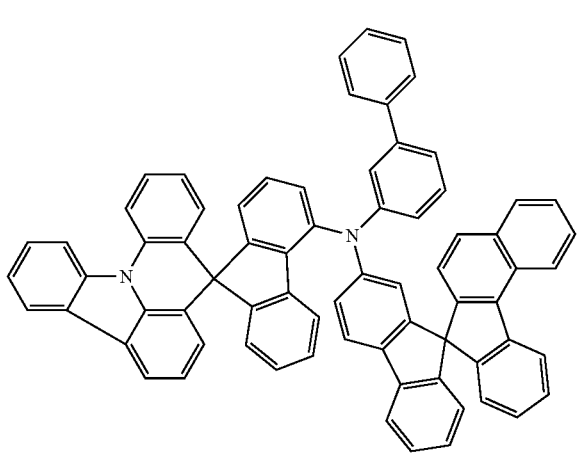

127
-continued
128
-continued
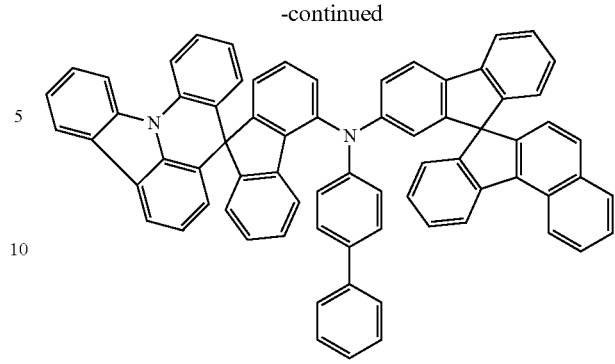
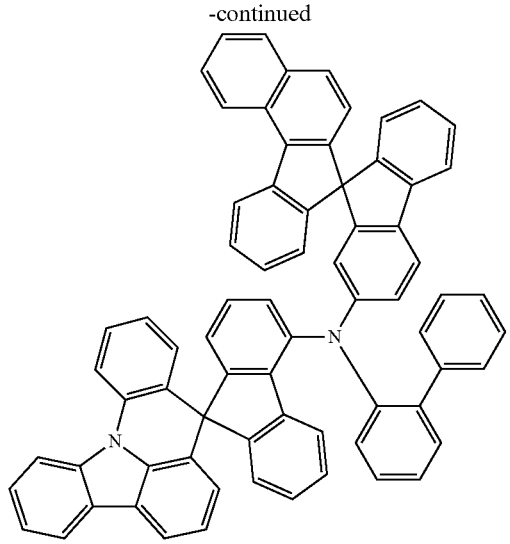
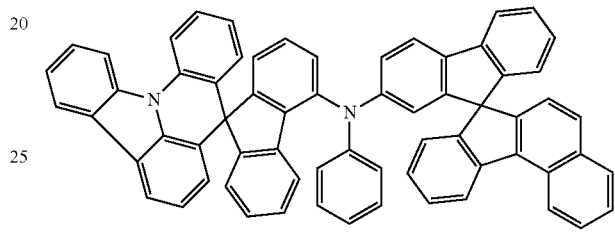
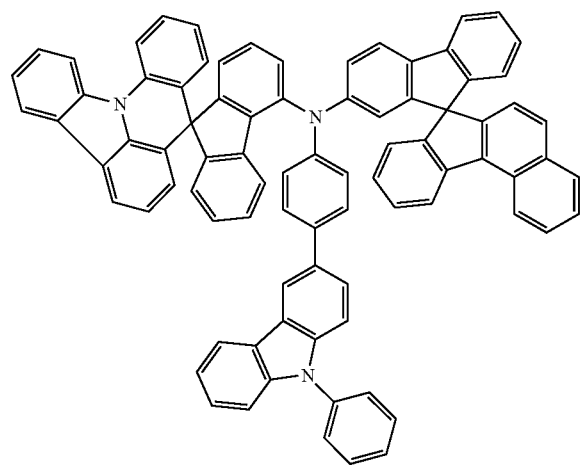
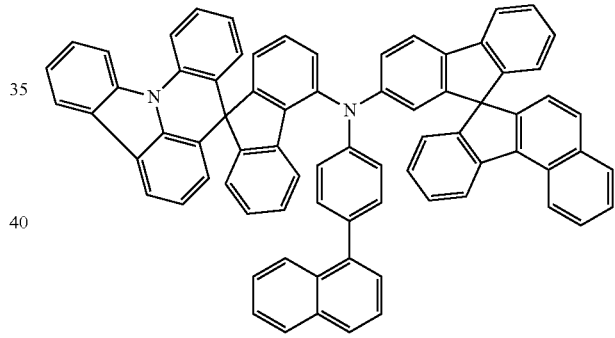
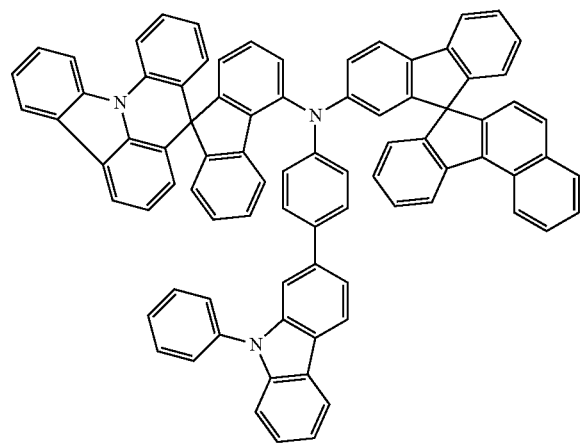
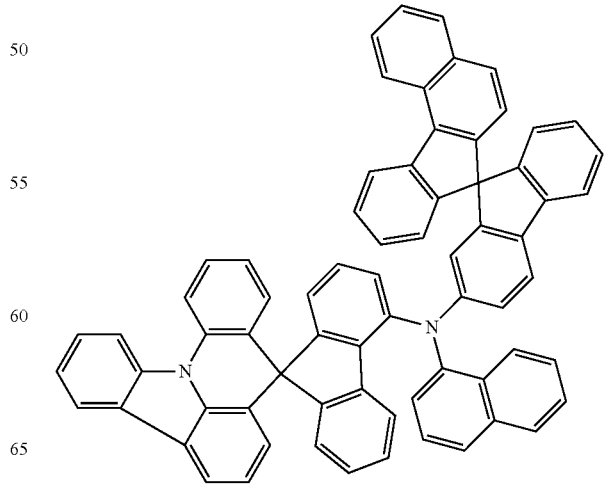

129
-continued
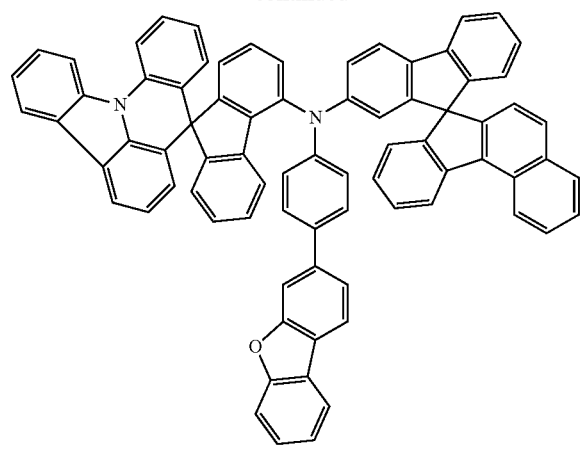
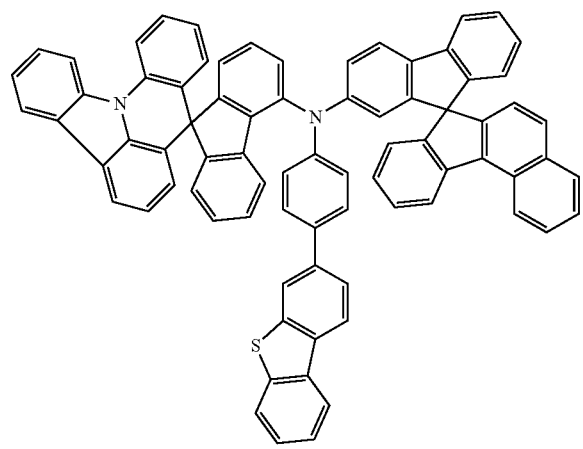
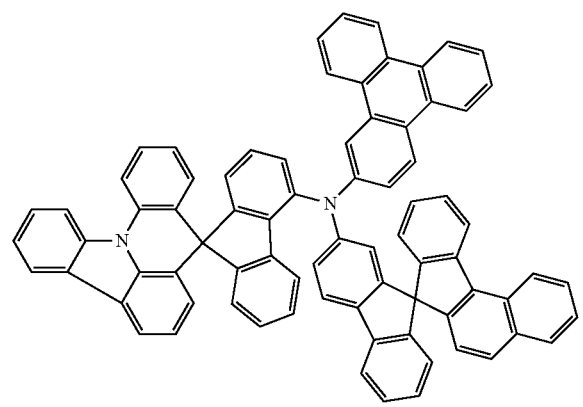
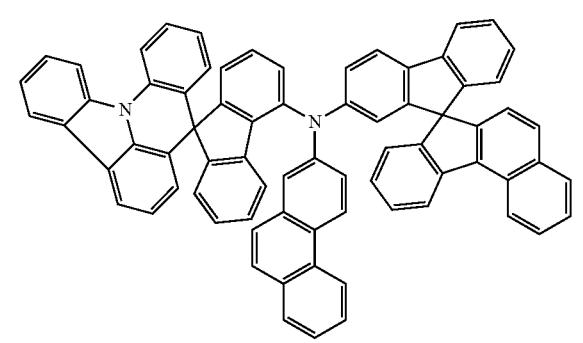
130
-continued
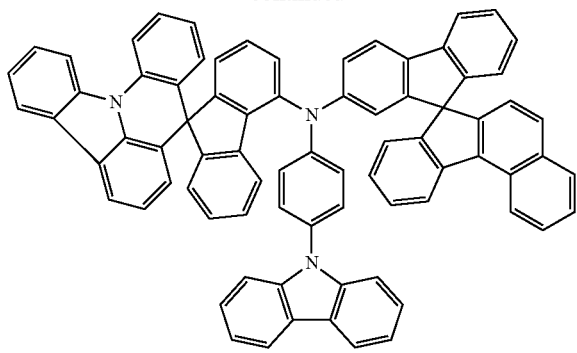
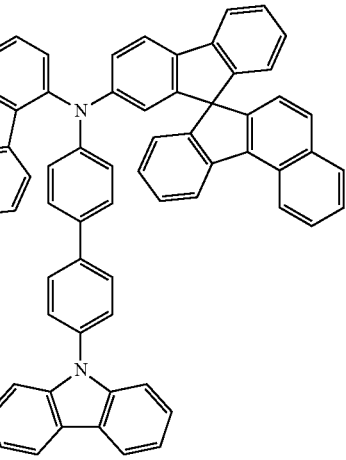
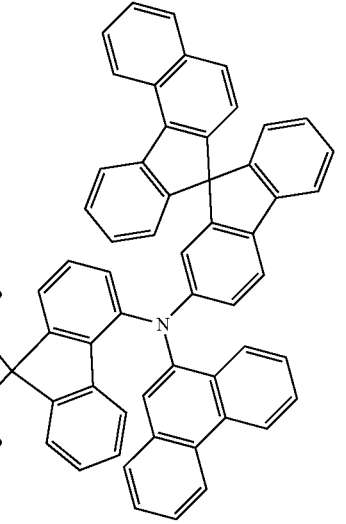

131
-continued
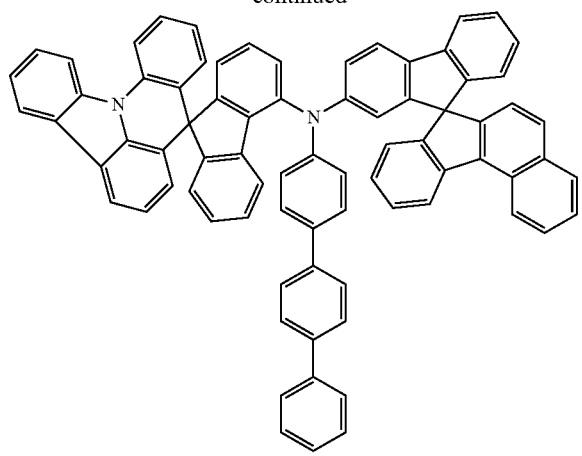
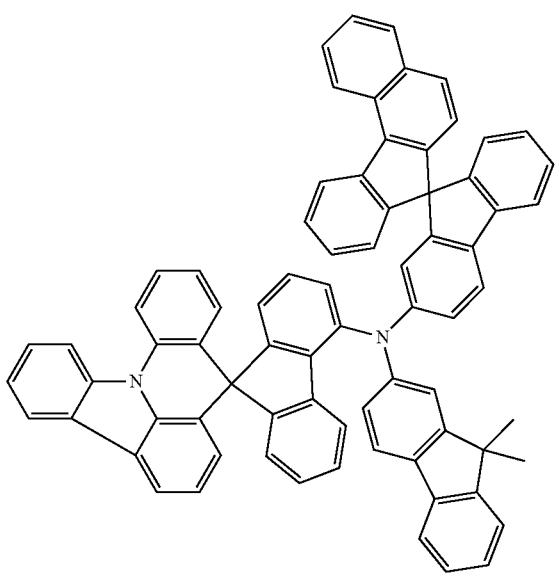
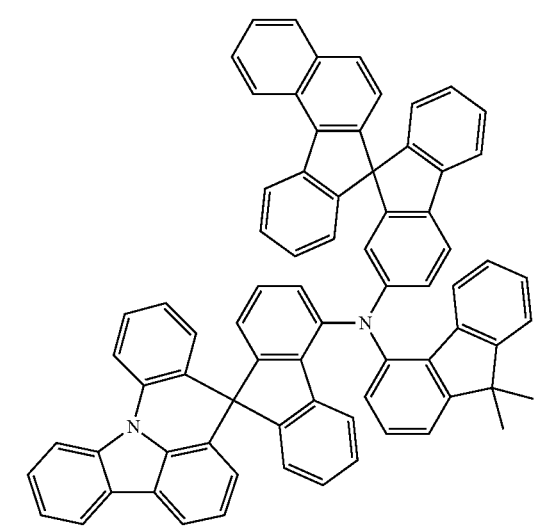
132
-continued
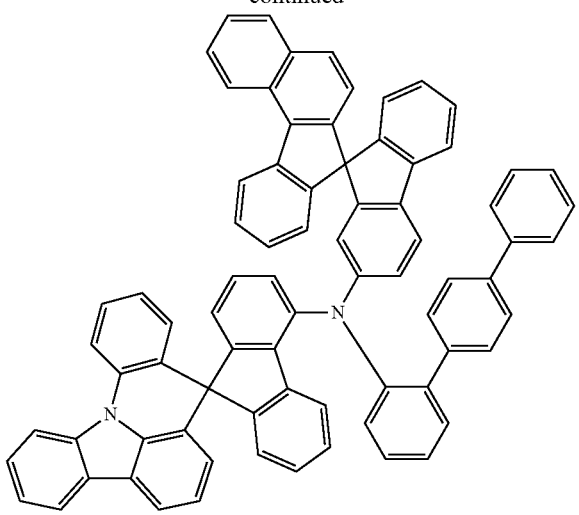
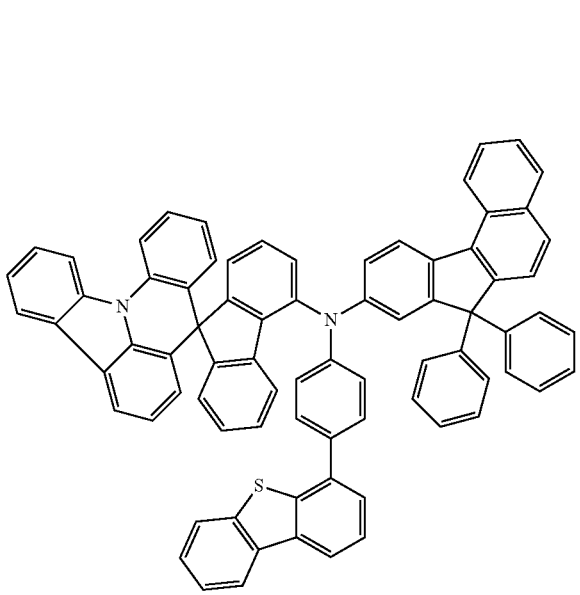

133
-continued
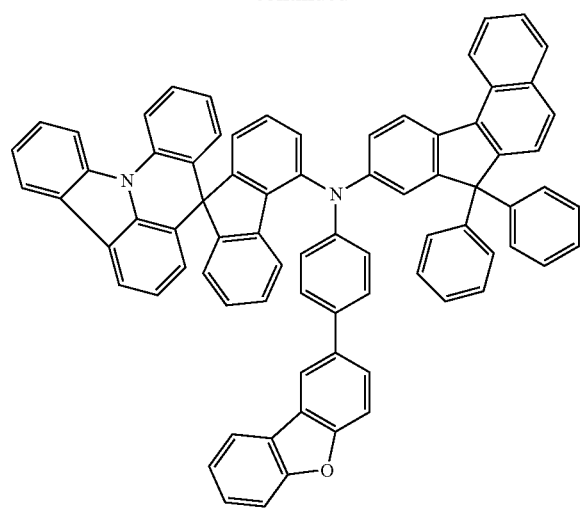
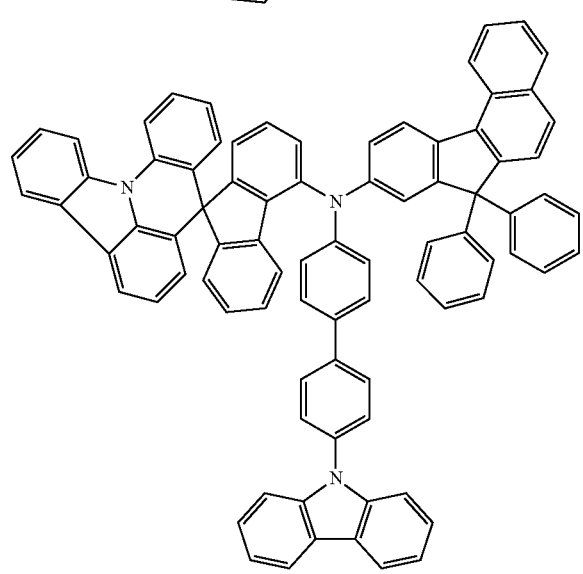
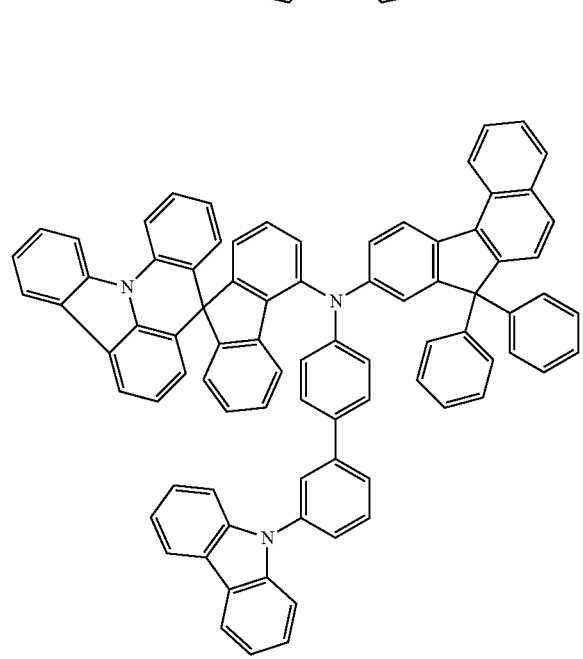
134
-continued
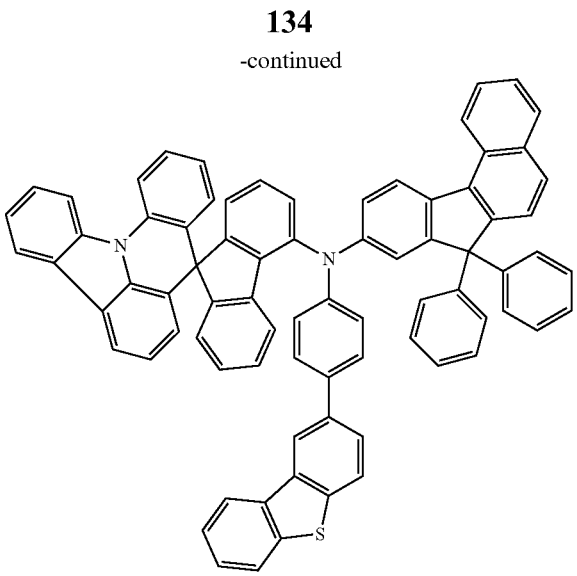
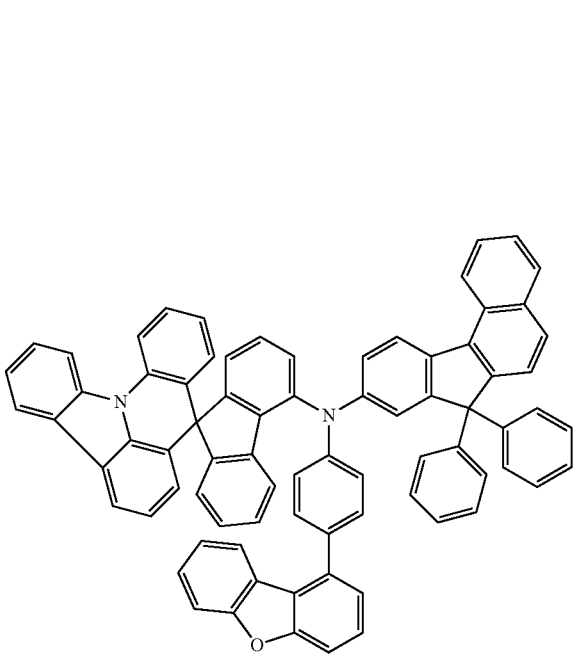
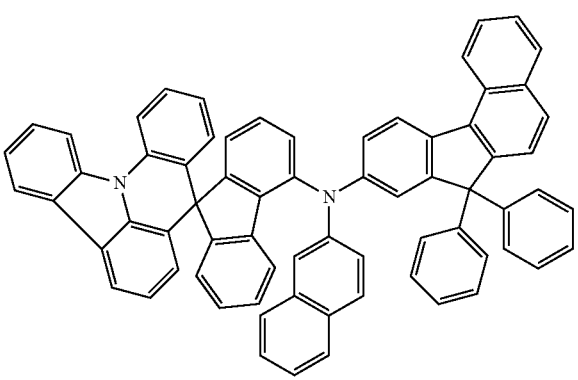

135
-continued
136
-continued
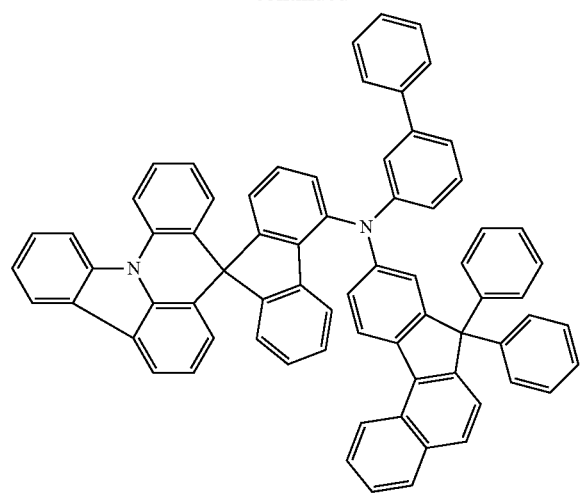
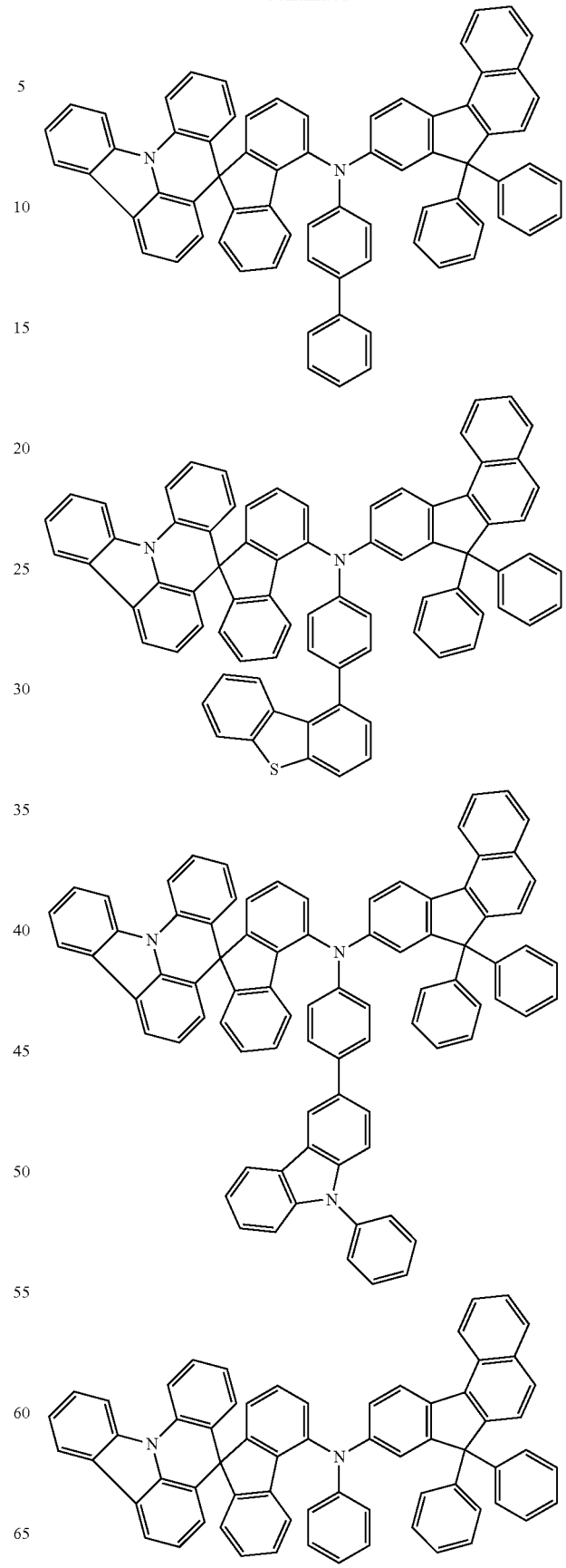

137
-continued
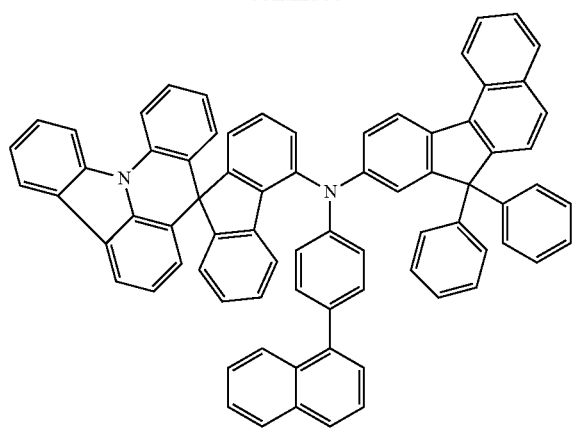
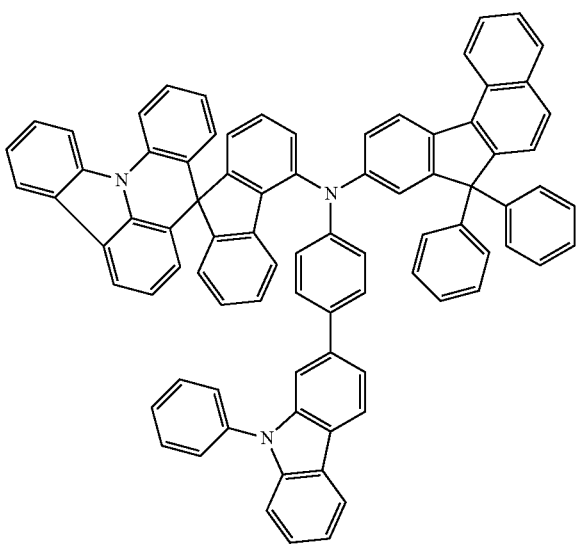
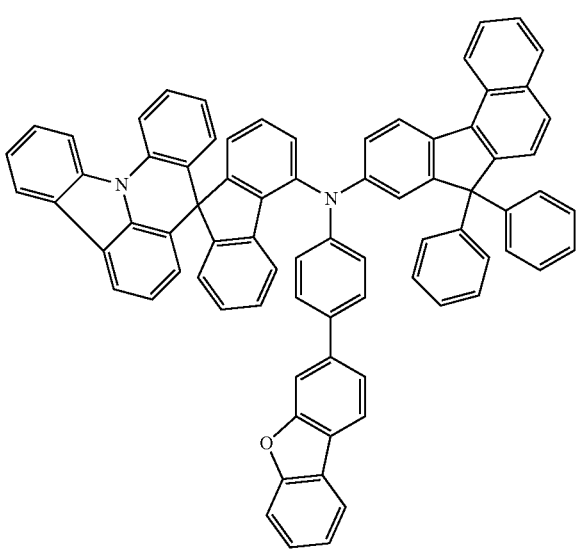
138
-continued
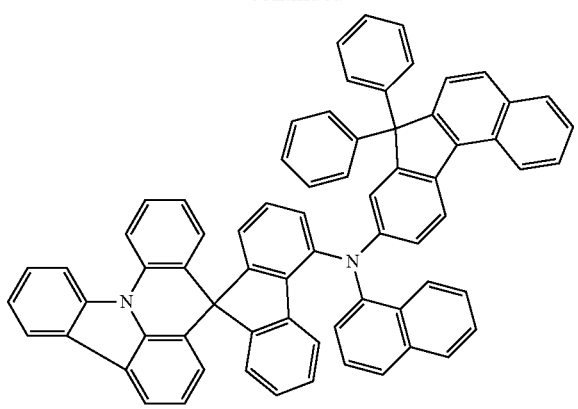
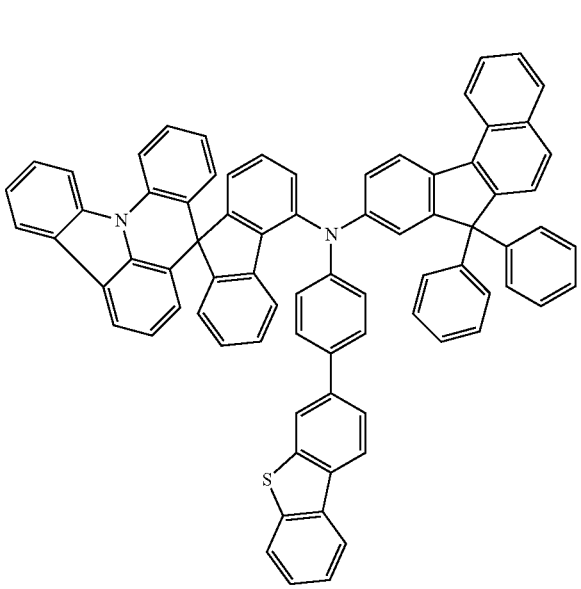
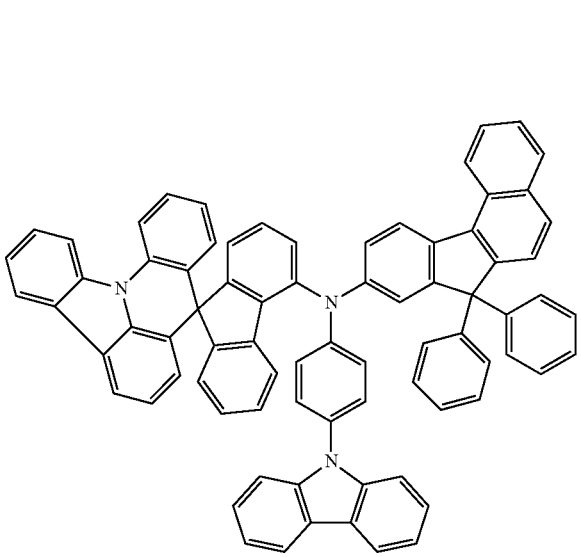

-continued
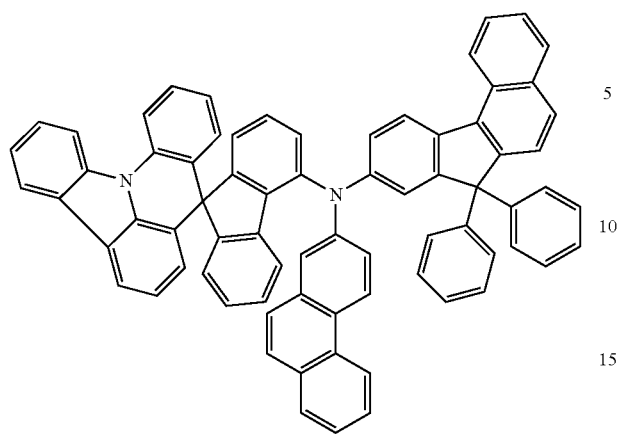
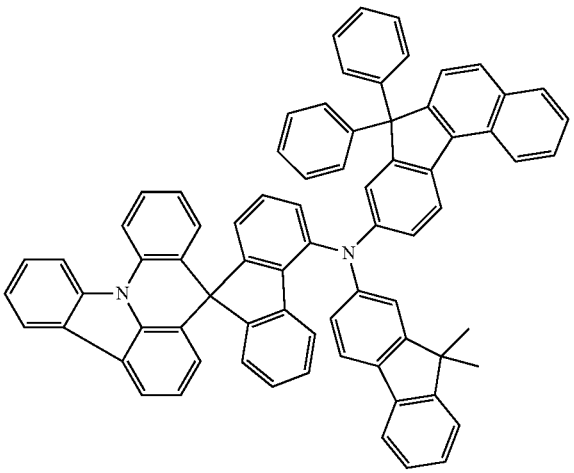
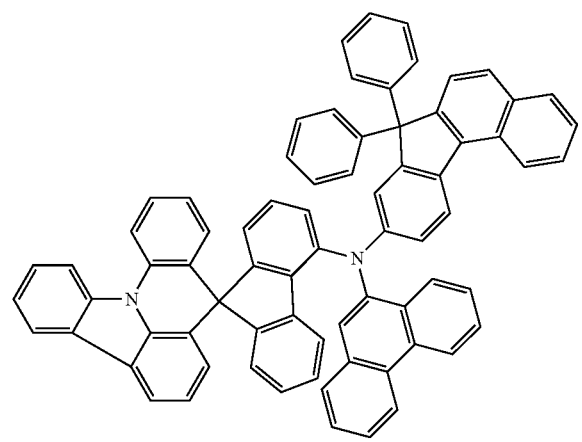
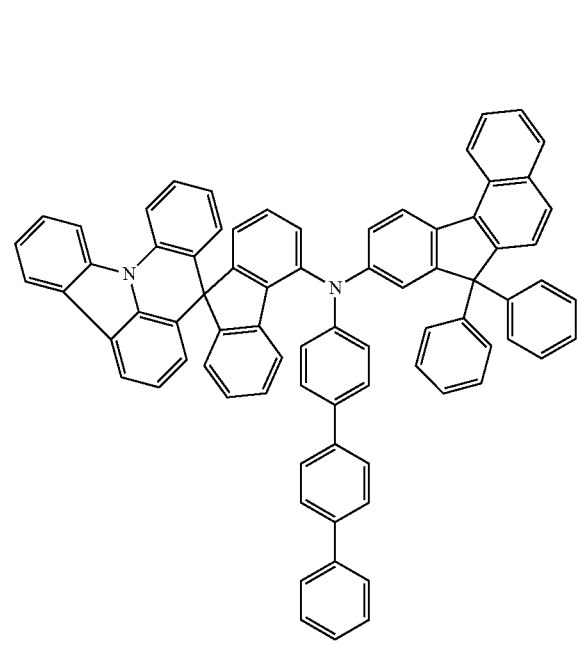
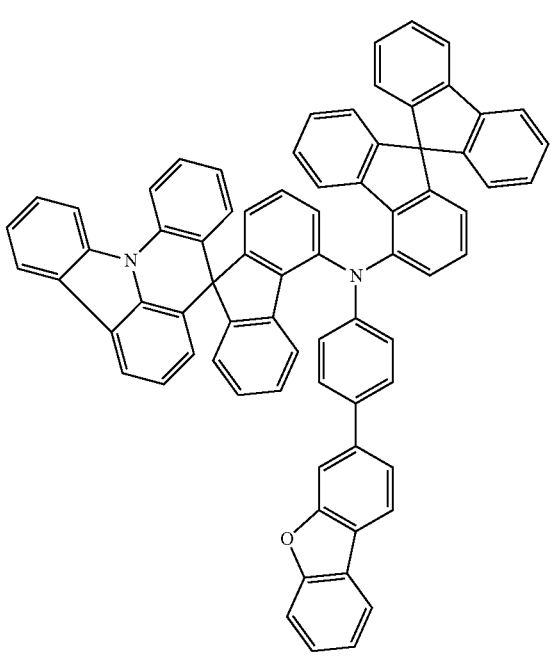

141
-continued
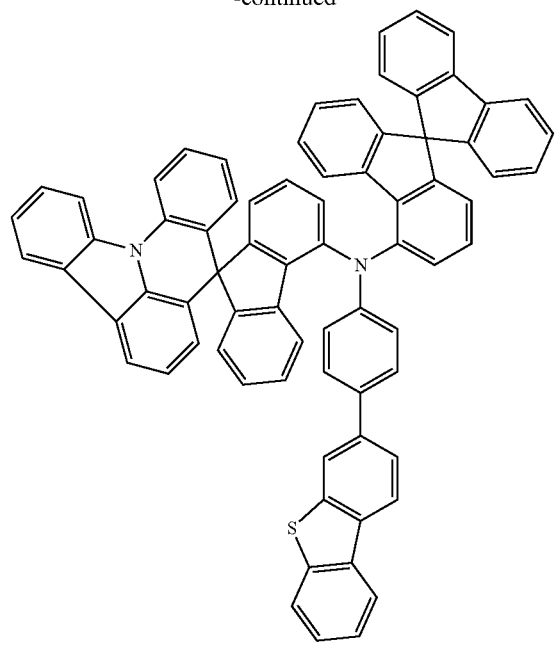
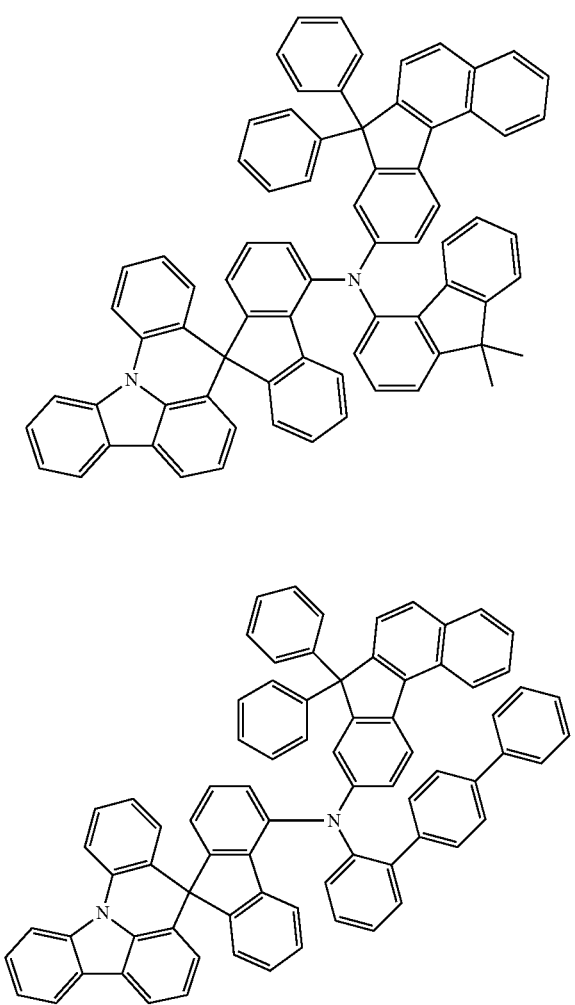
142
-continued
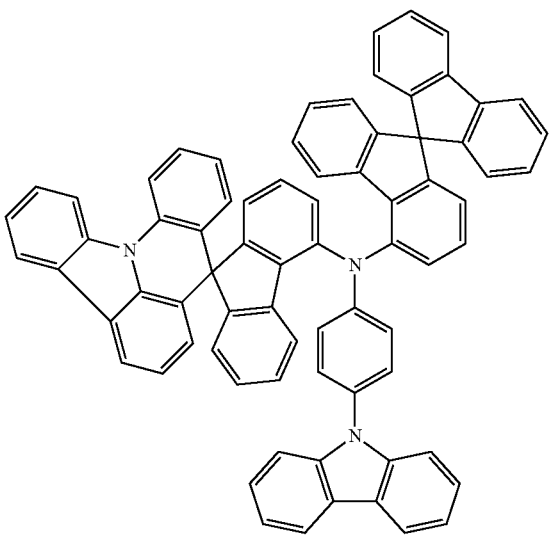
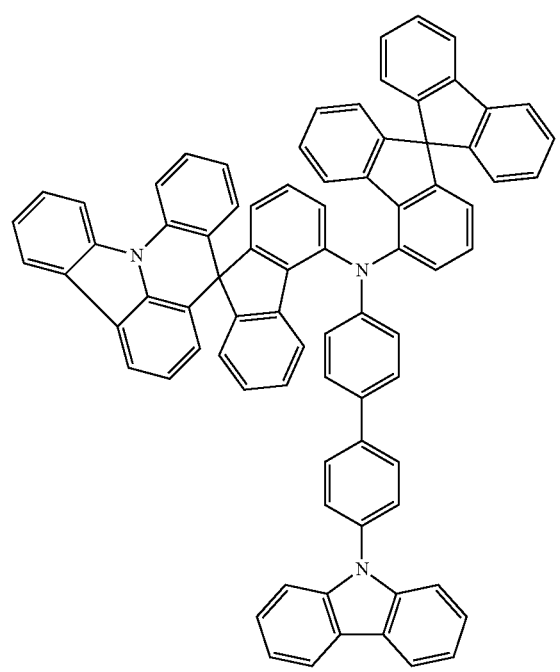

-continued
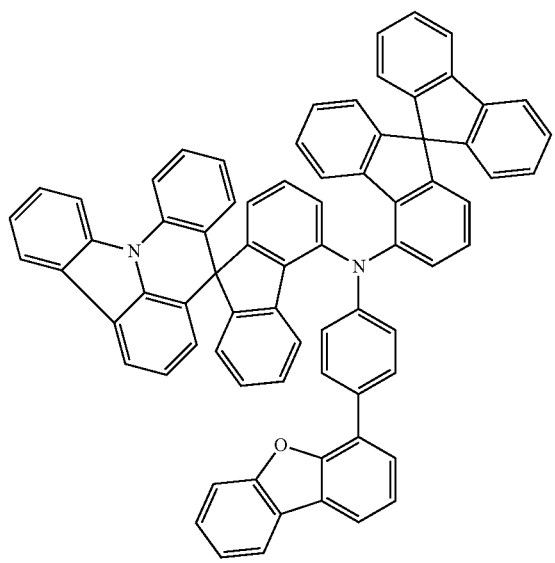
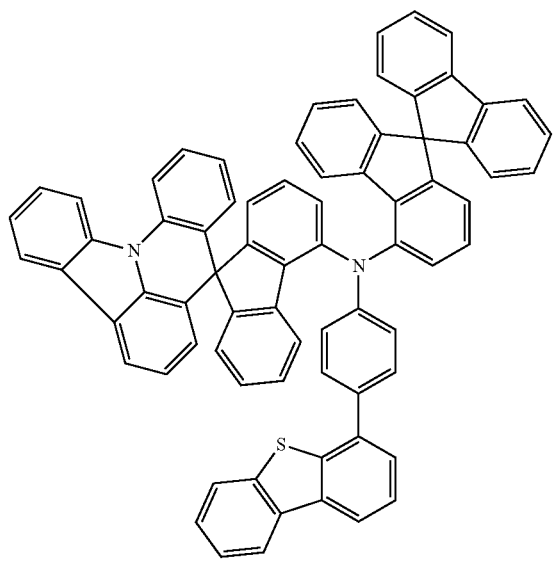
-continued
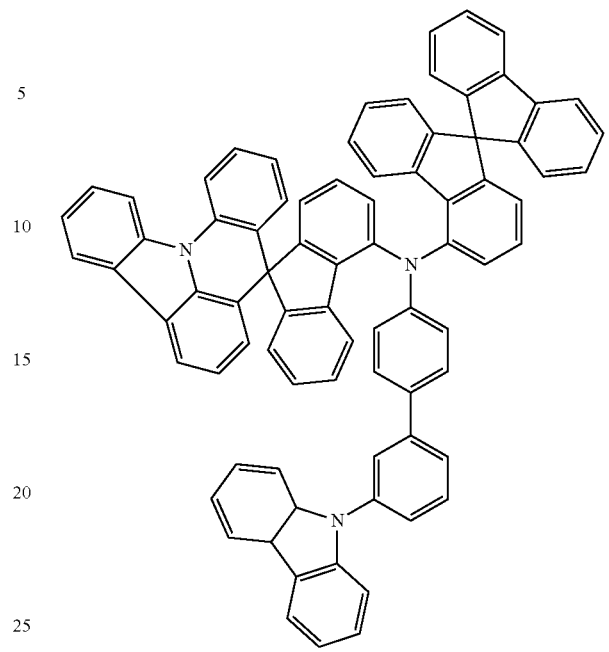
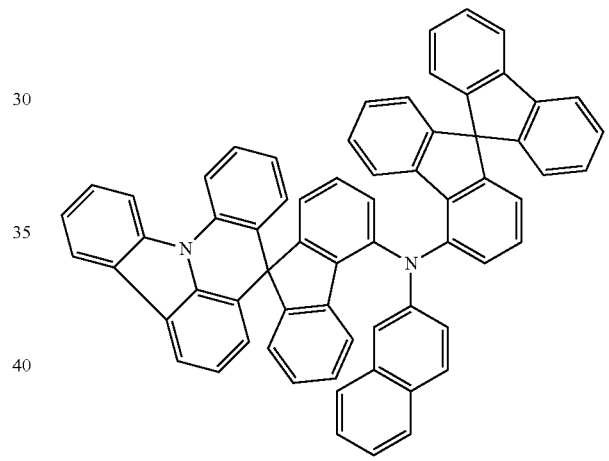
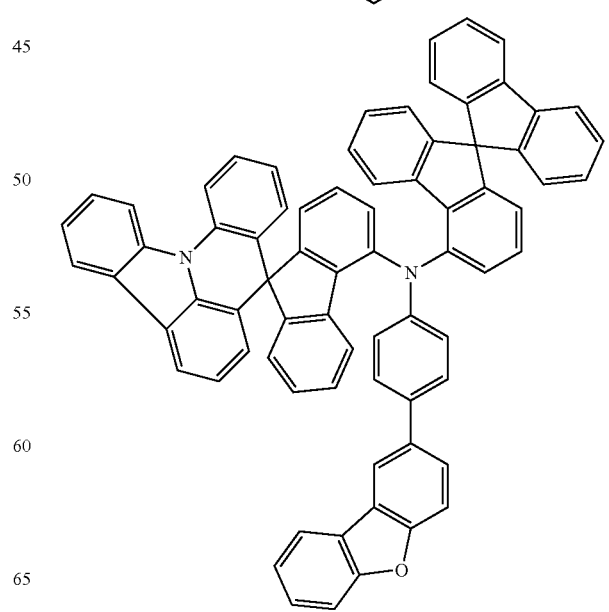

145
-continued
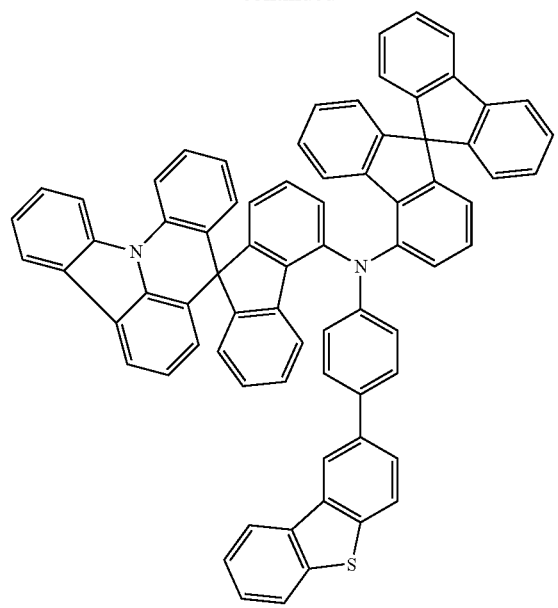
146
-continued
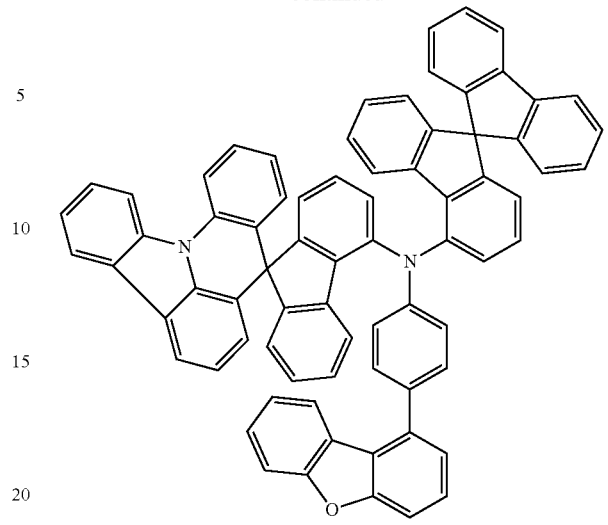
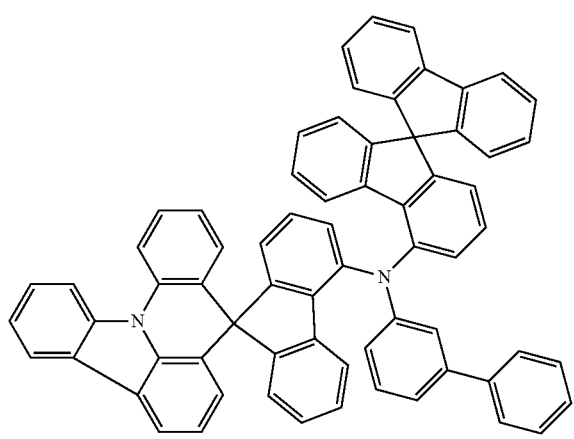
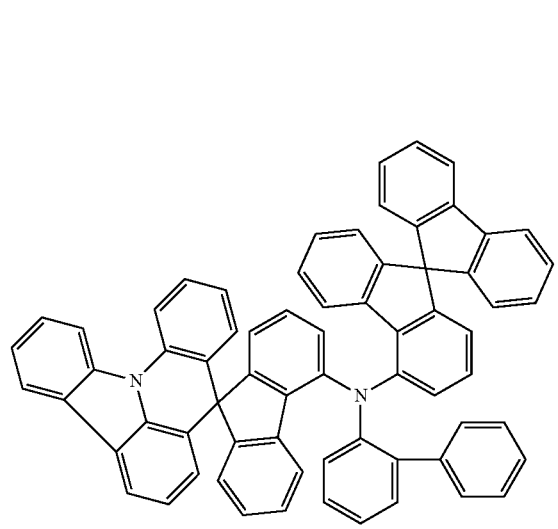
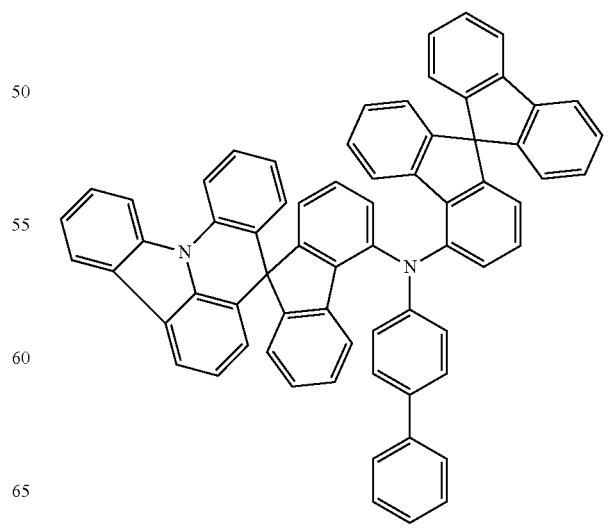

147
-continued
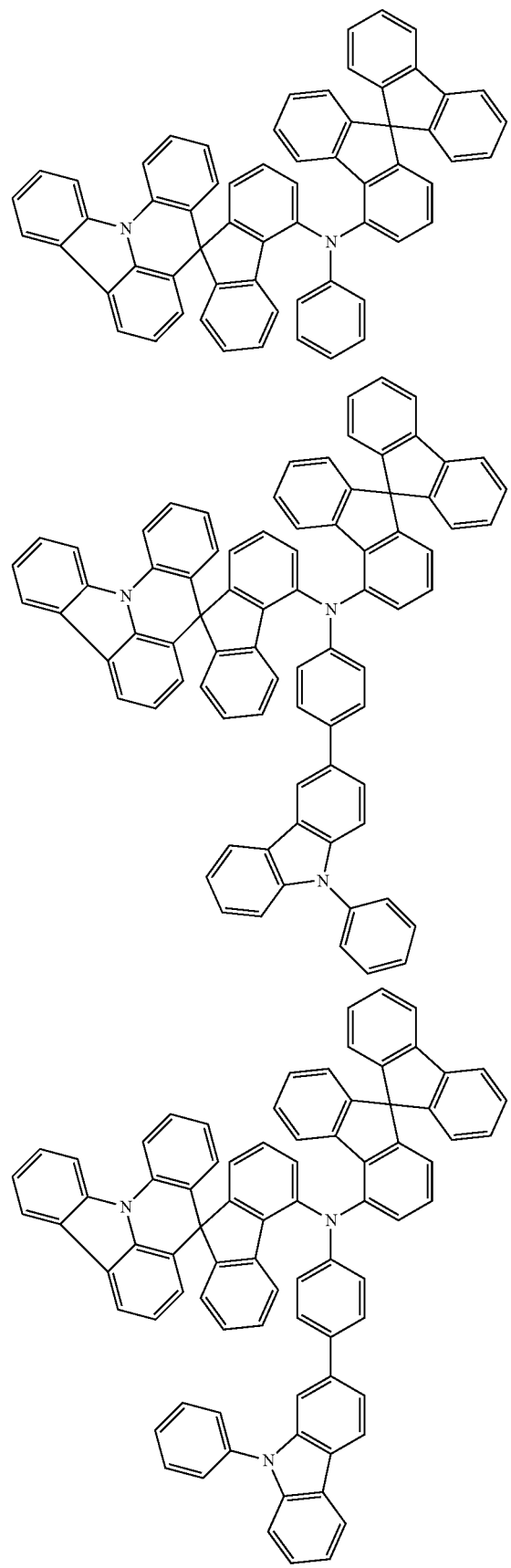
148
-continued
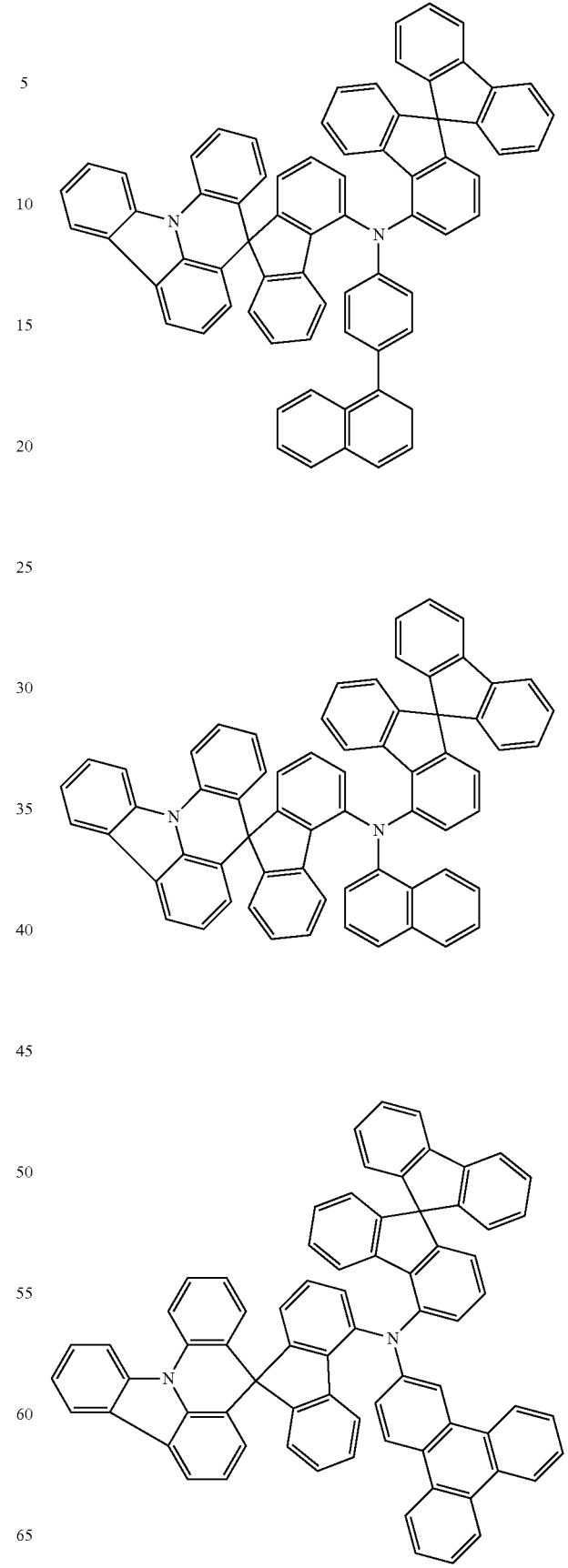

149
-continued
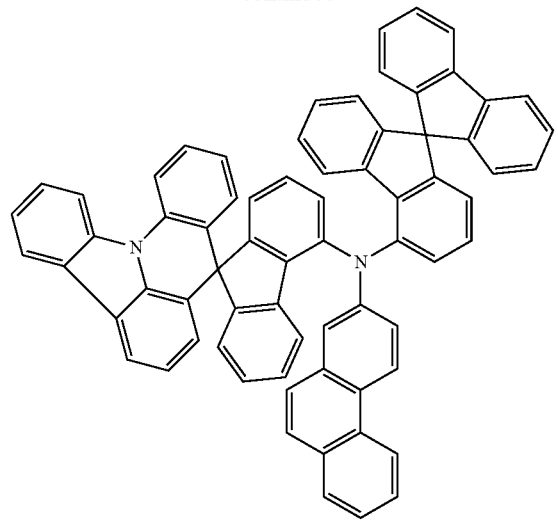
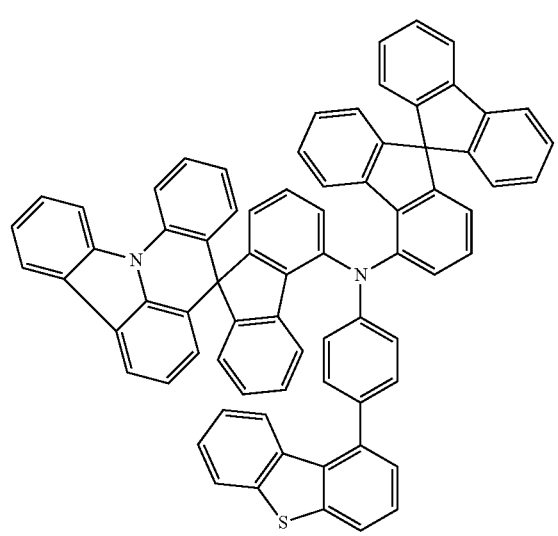
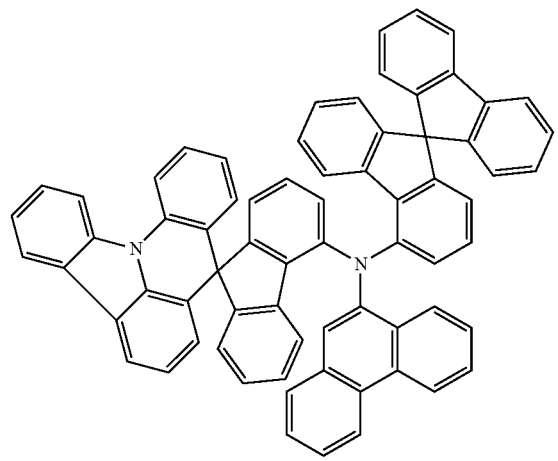
150
-continued
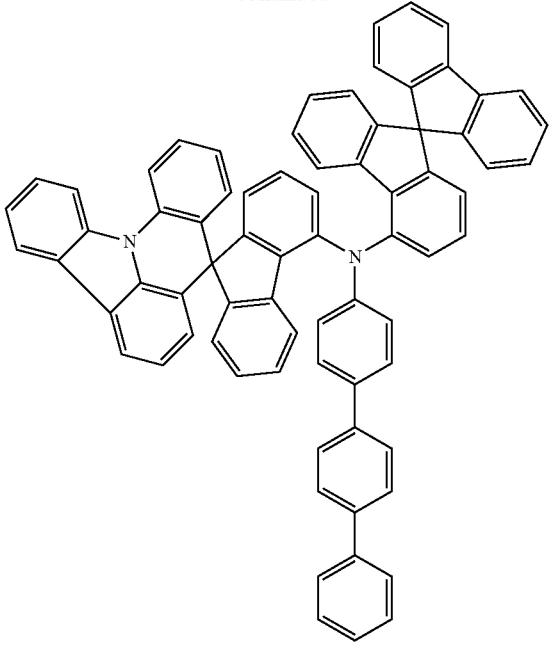
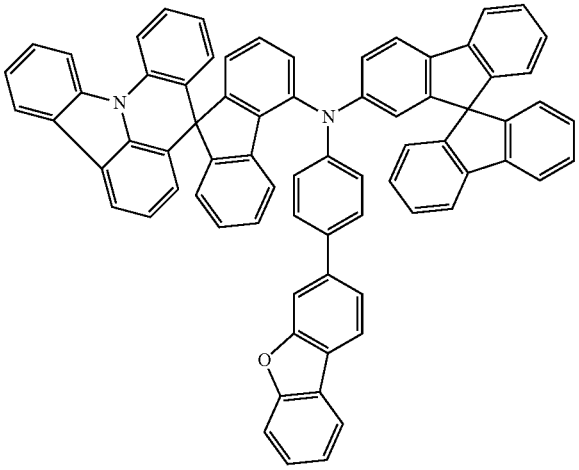

151
-continued
152
-continued
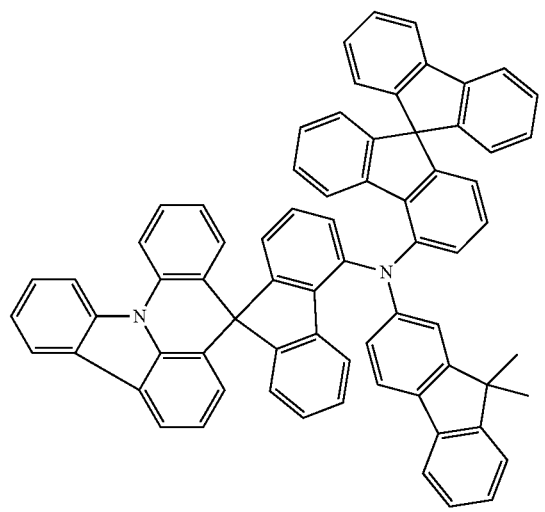
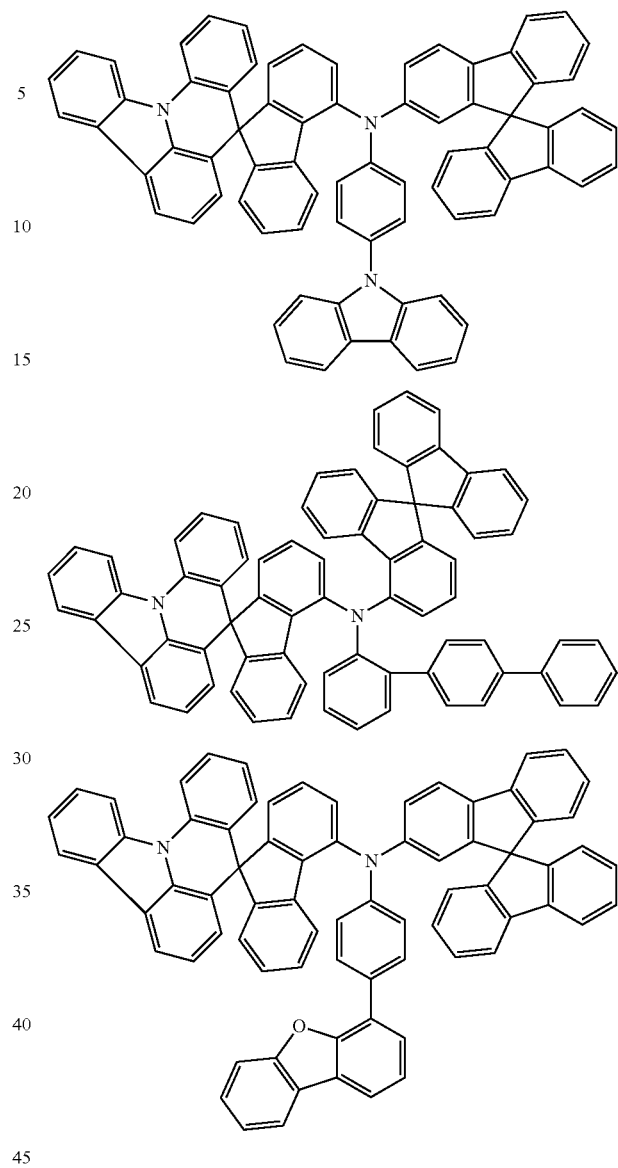
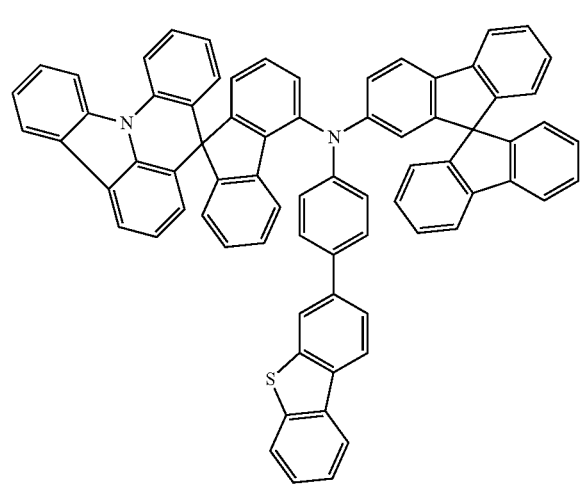
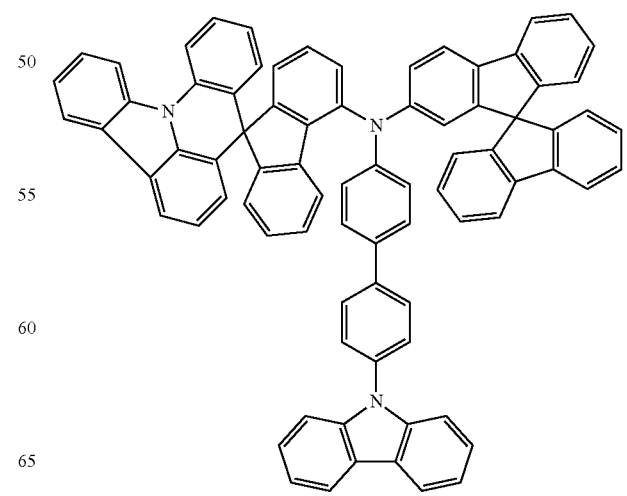

153
-continued
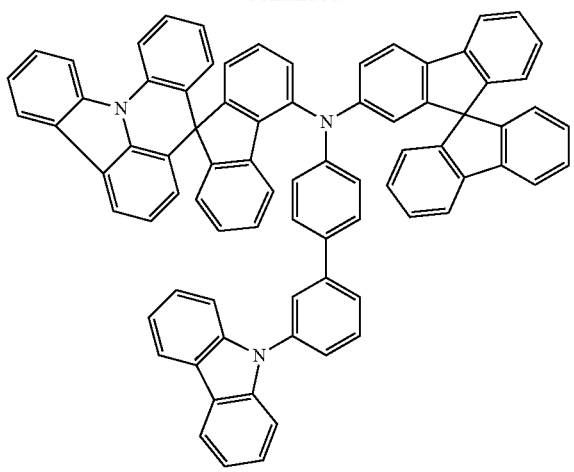
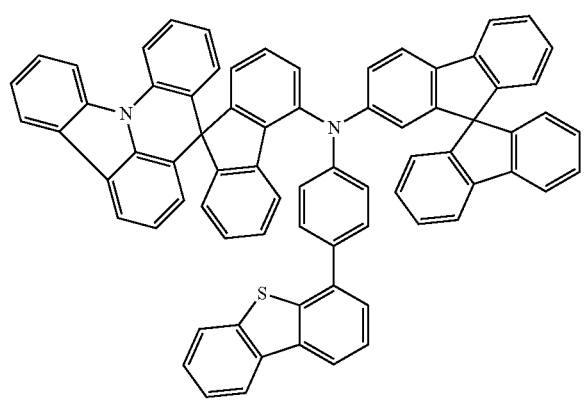
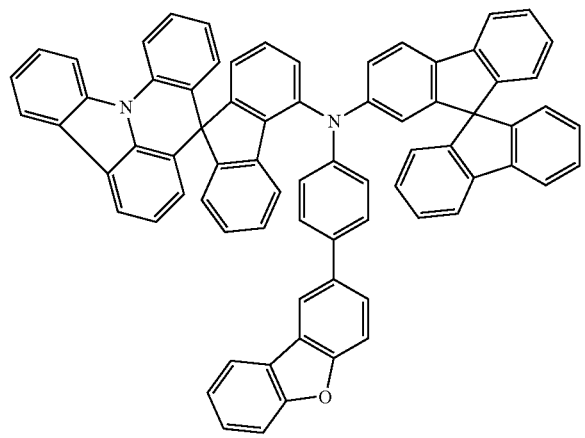
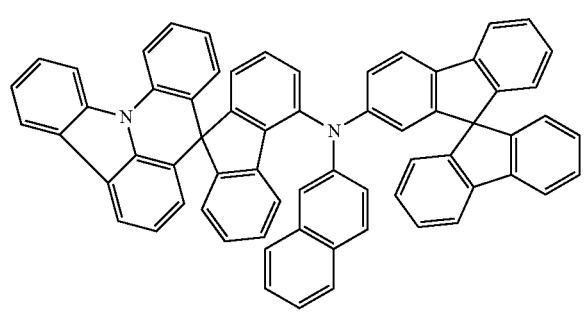
154
-continued
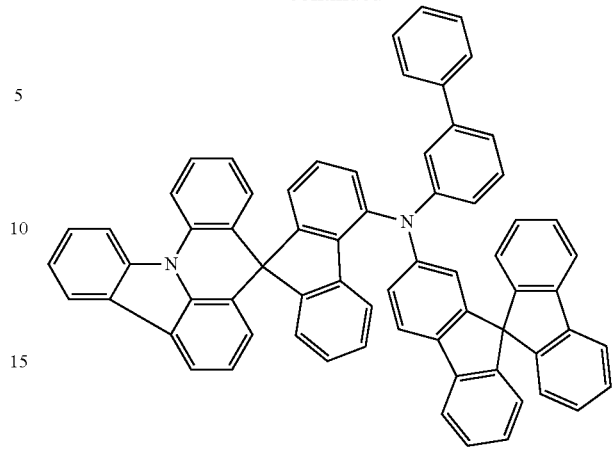
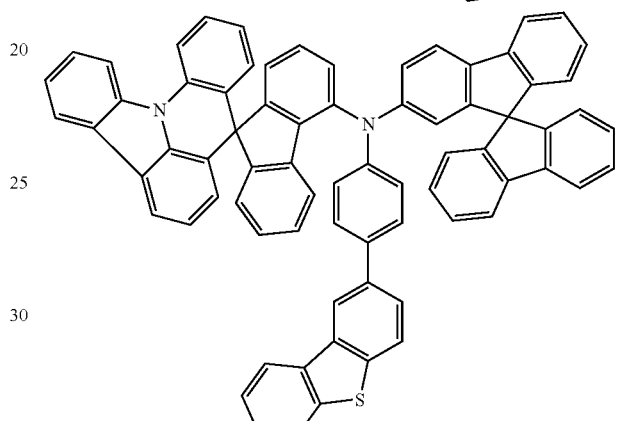
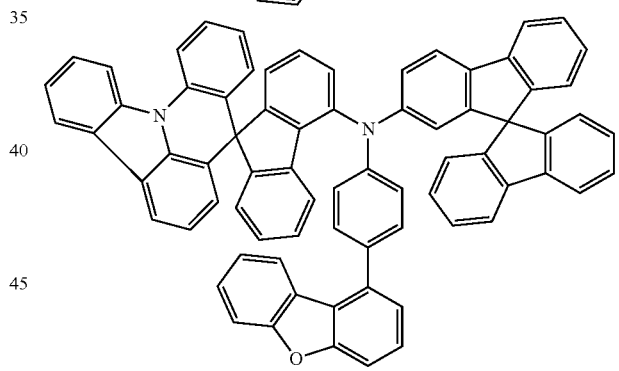
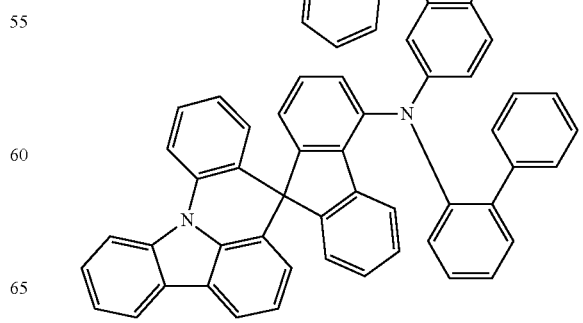

155
-continued
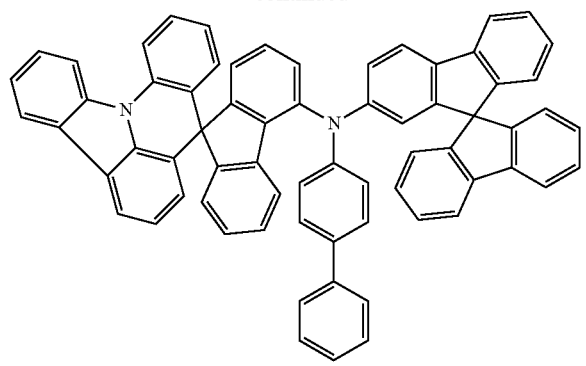
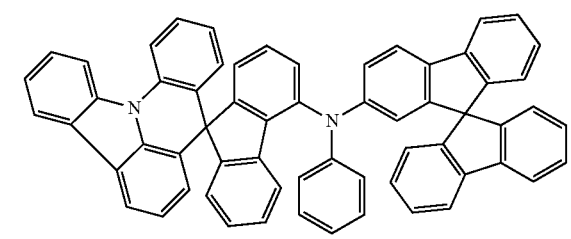
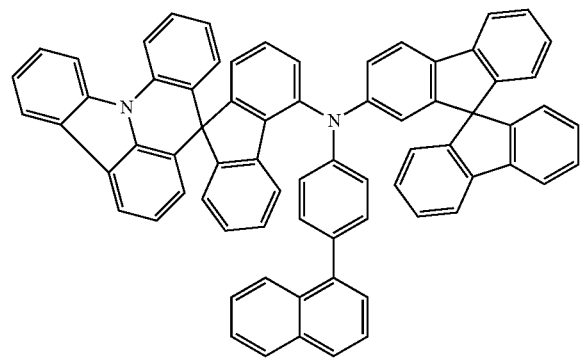
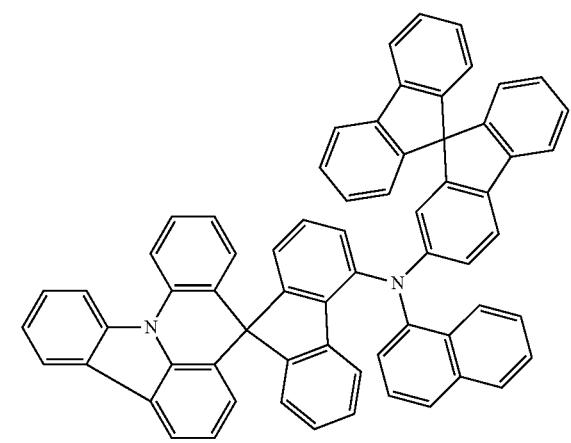
156
-continued
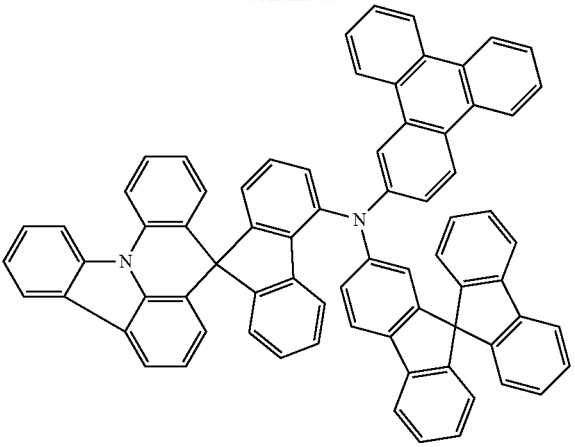
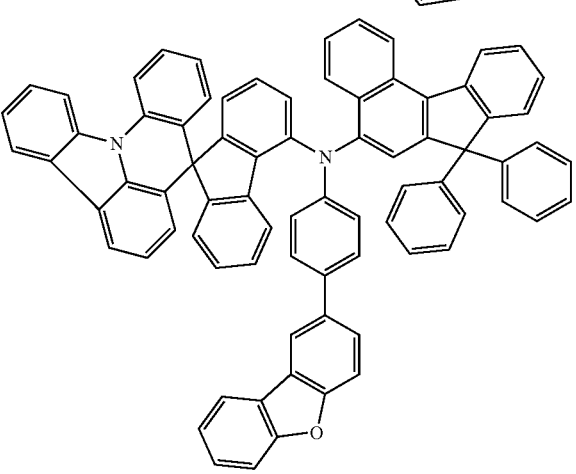
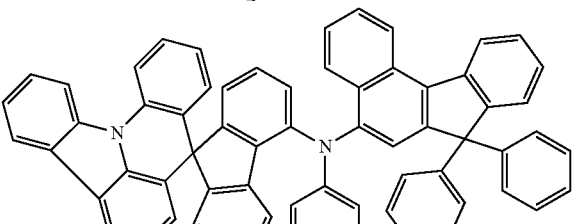
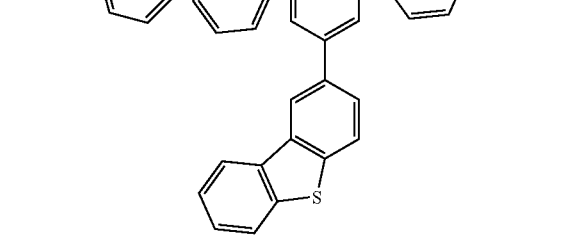
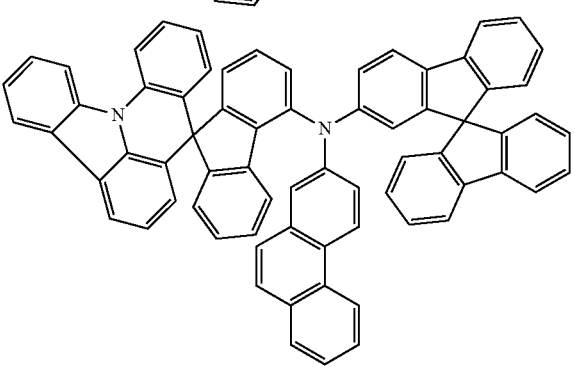

157
-continued
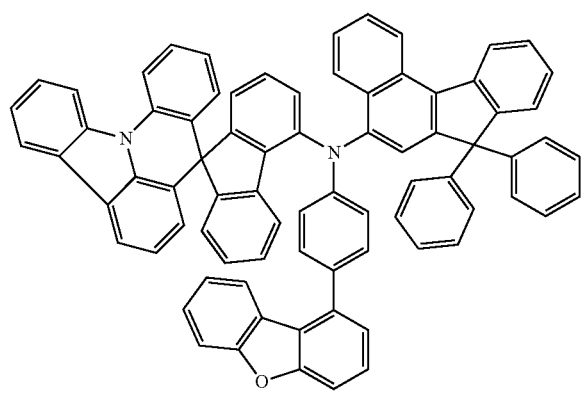
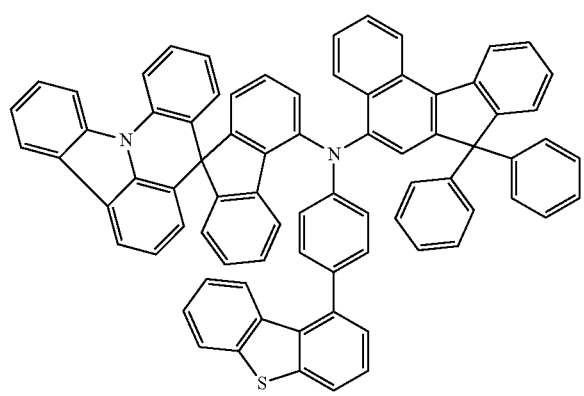
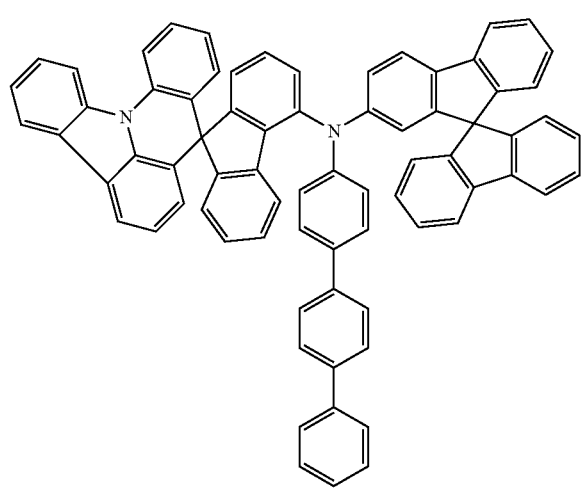
158
-continued
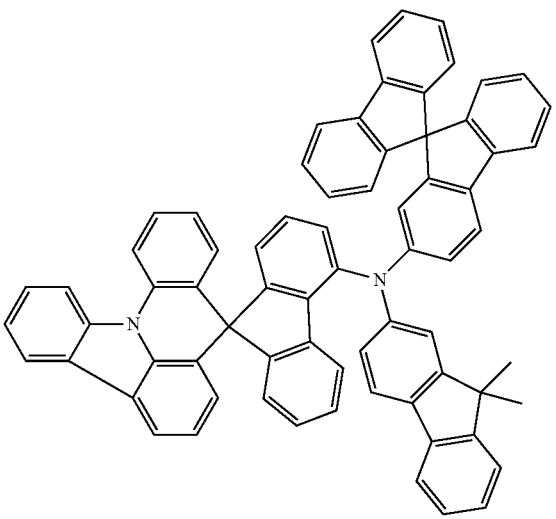
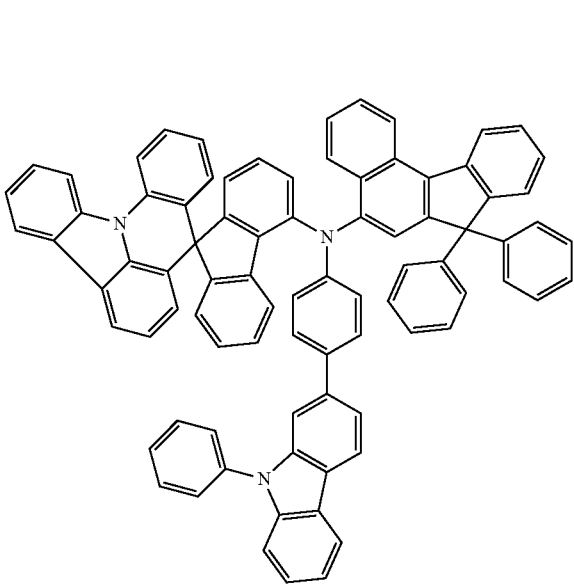

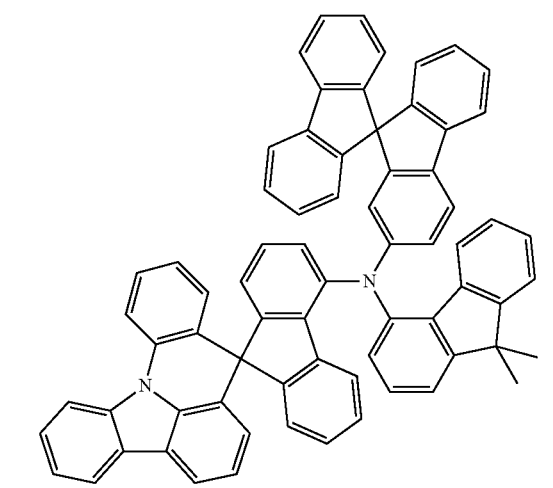
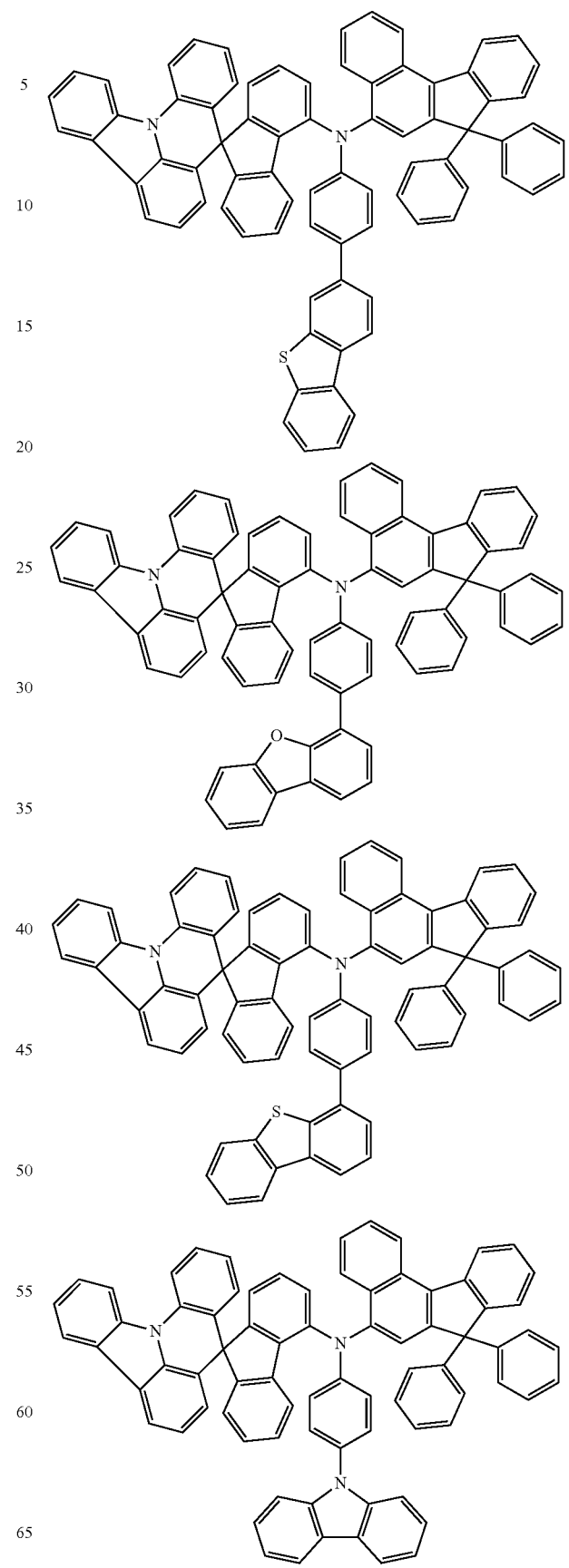

161
-continued
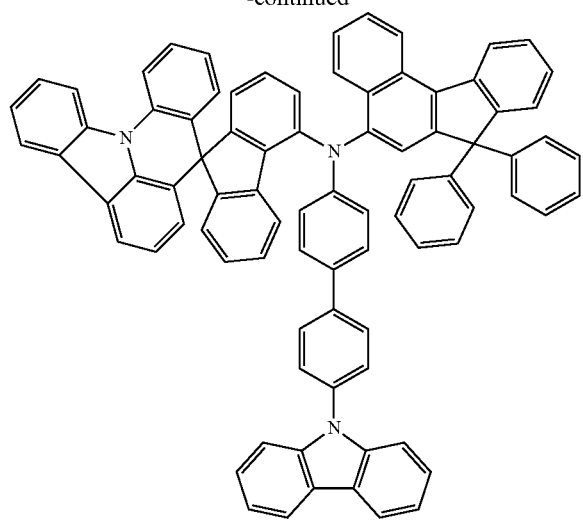
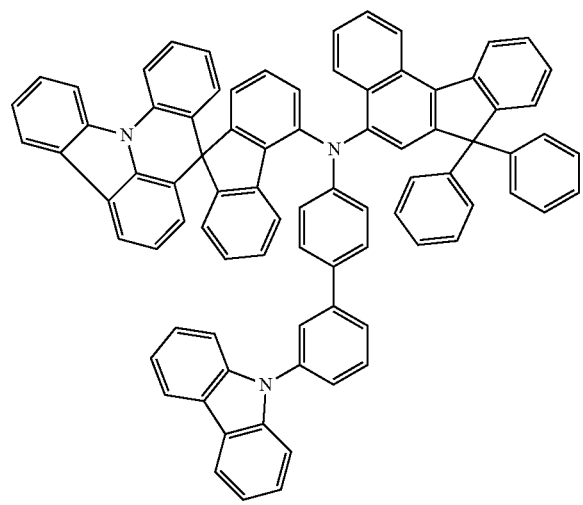
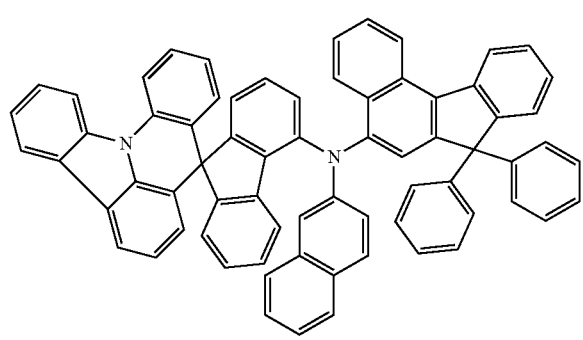
162
-continued
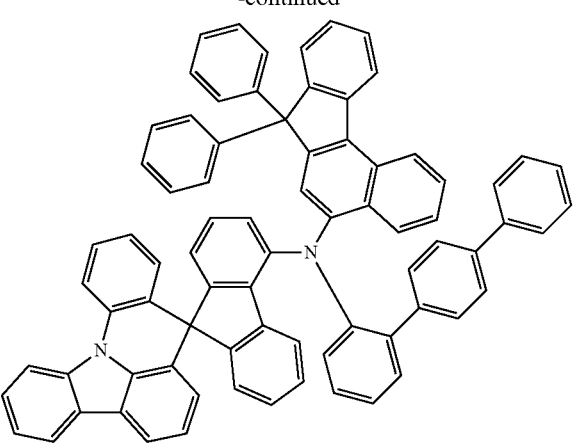
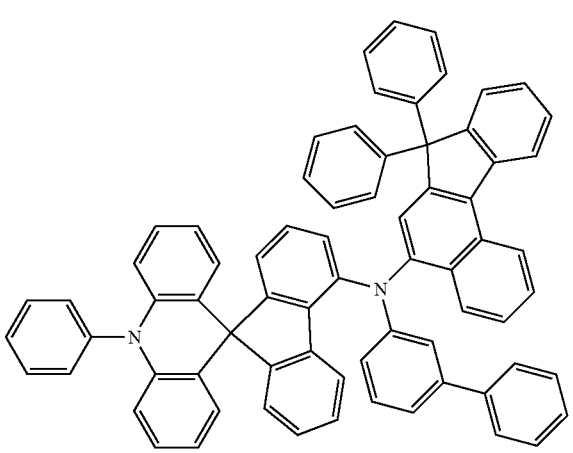

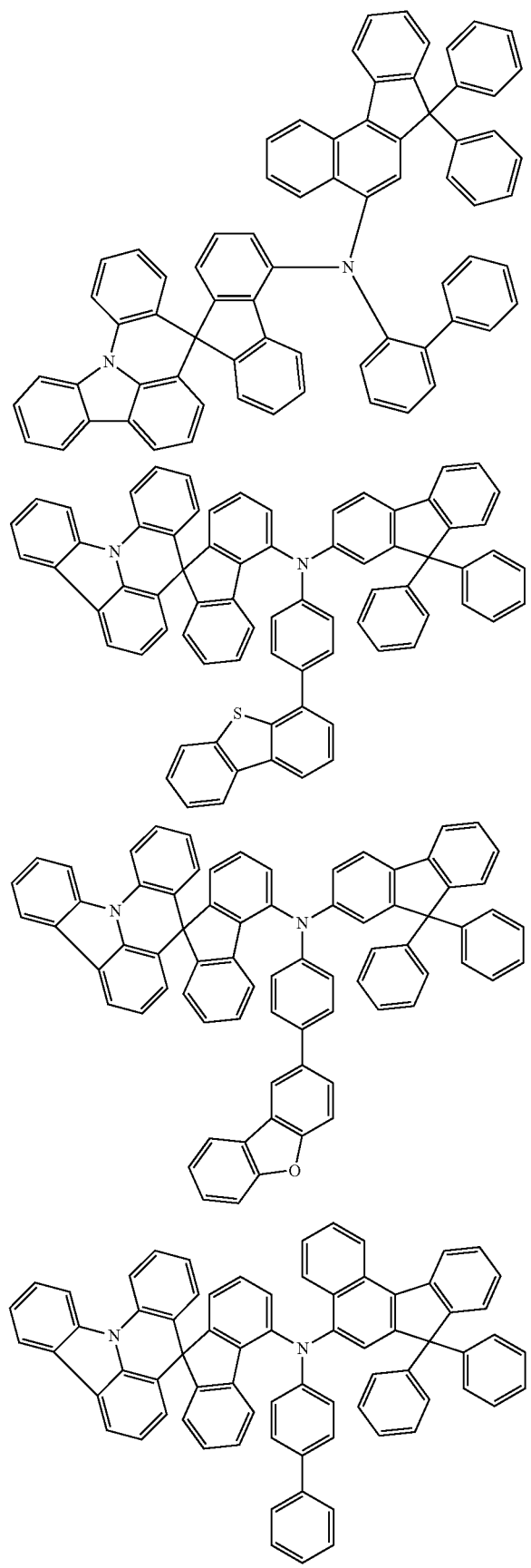
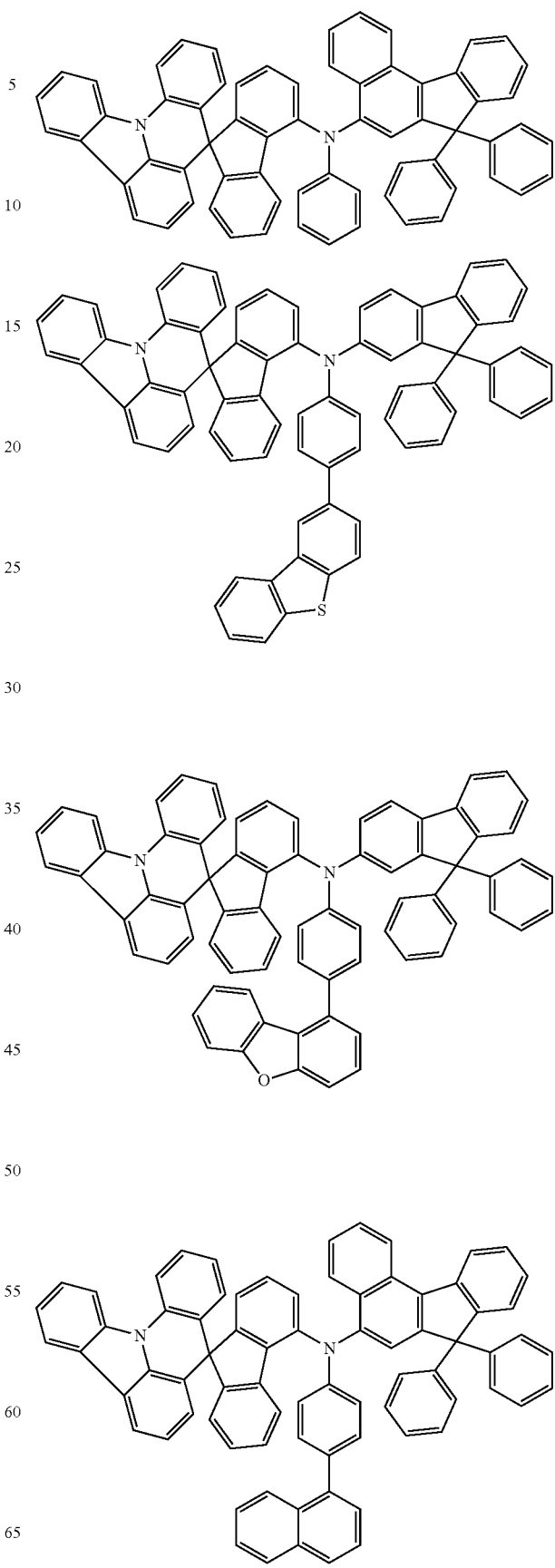

165
-continued
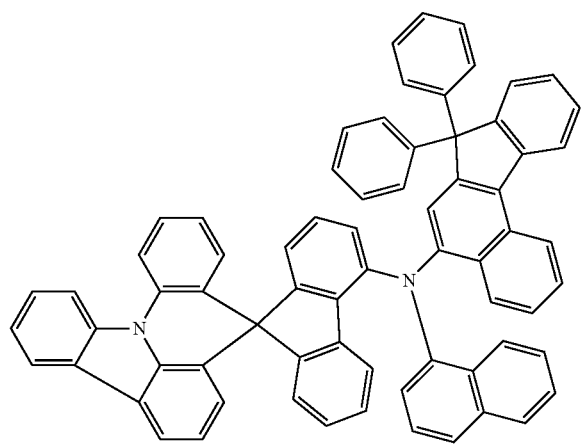
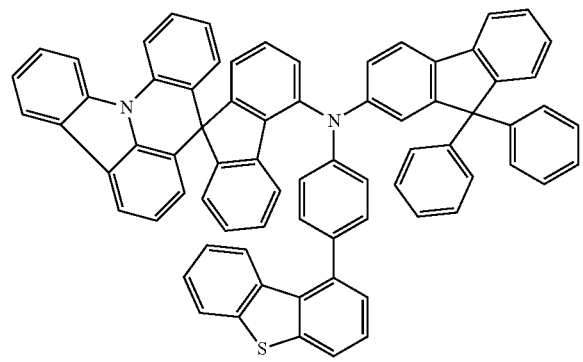
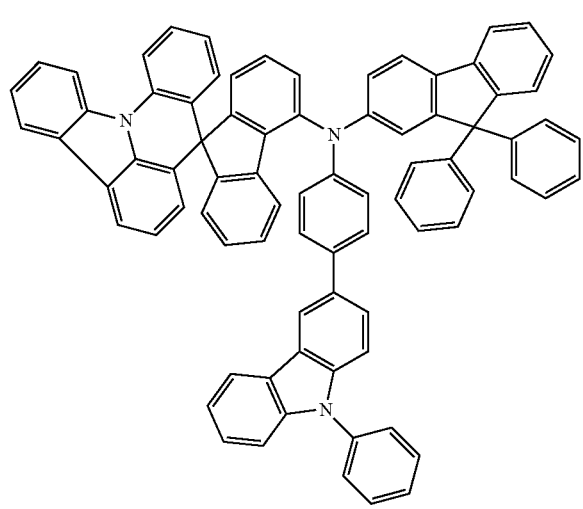
166
-continued
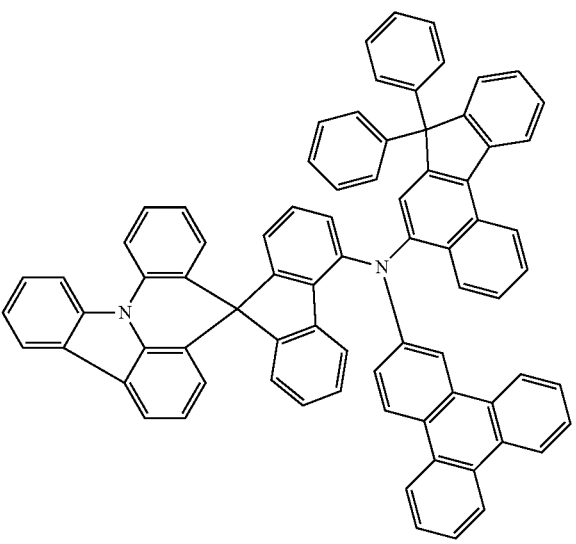
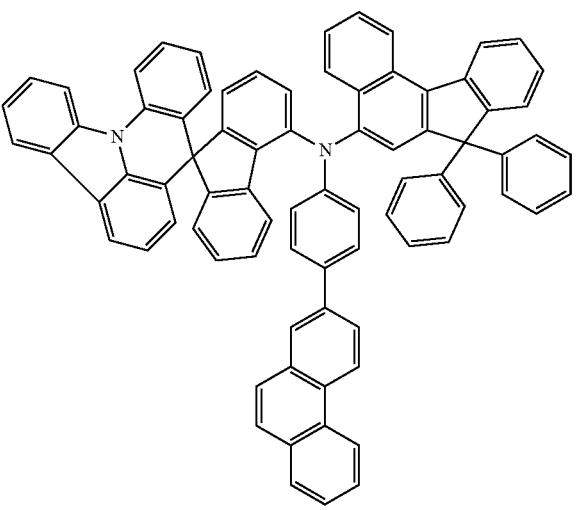
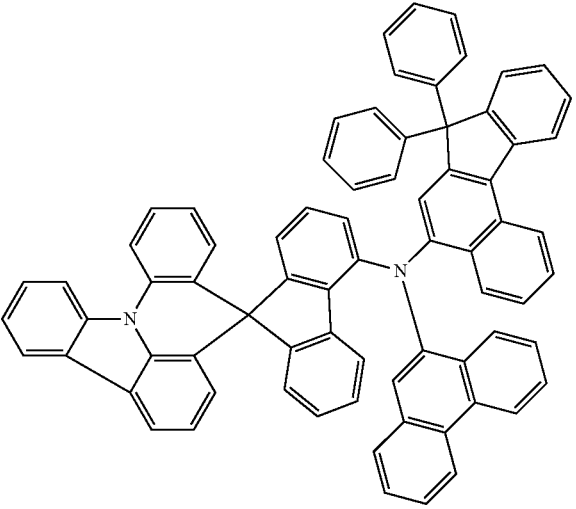

167
-continued
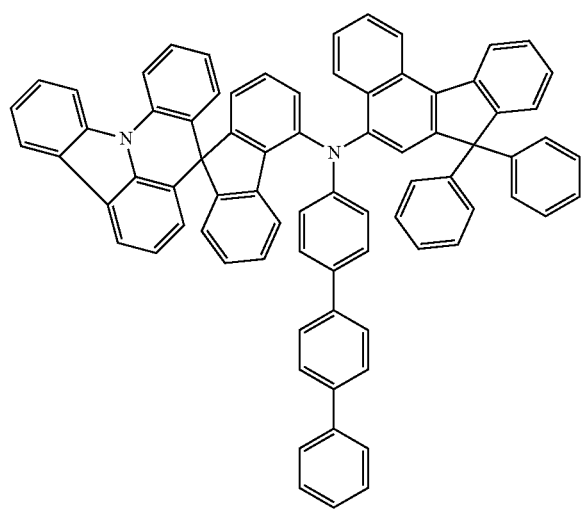
168
-continued
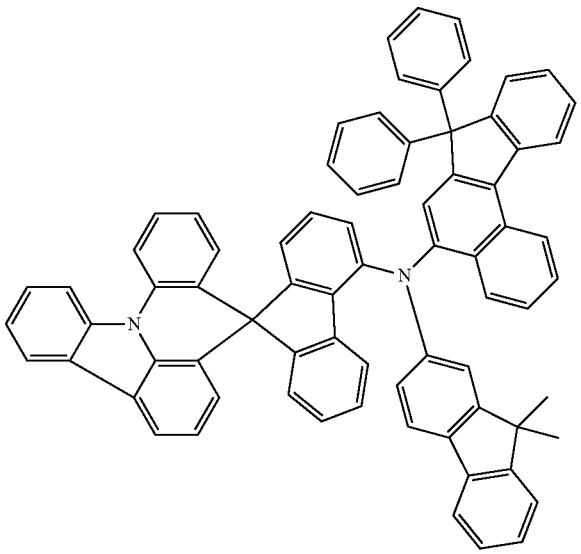
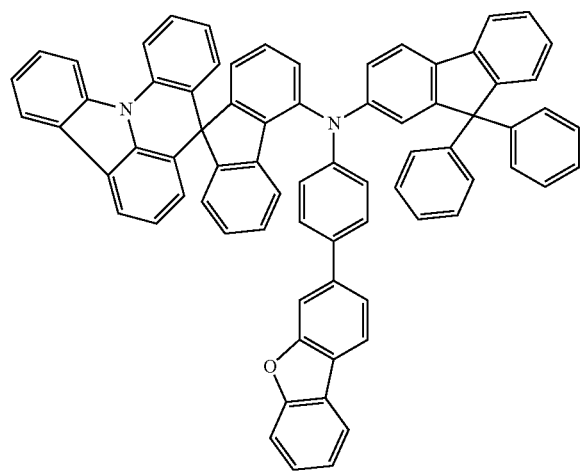
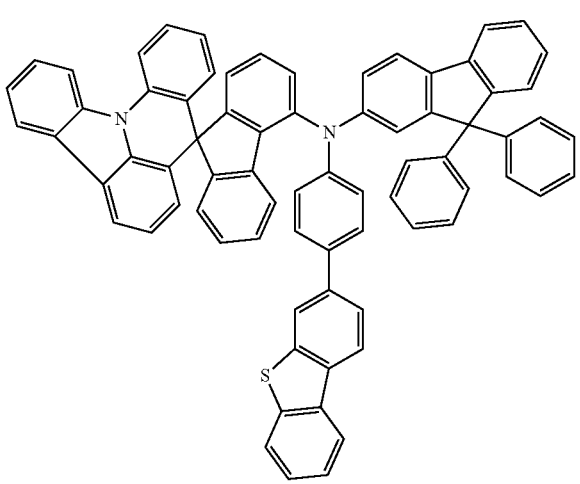

169
-continued
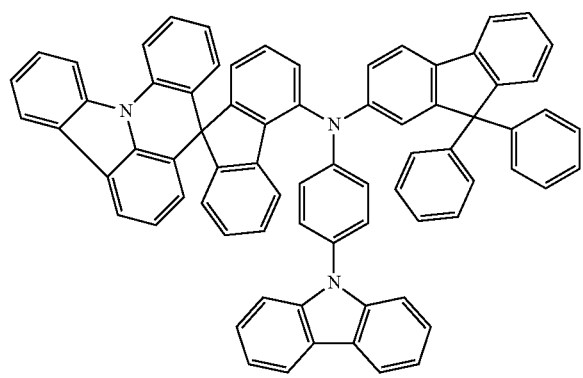
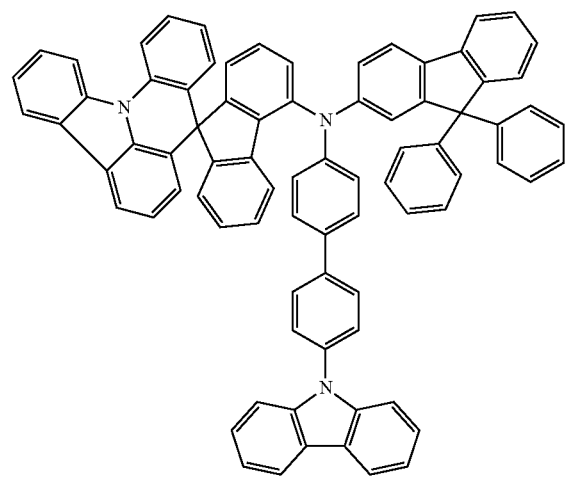
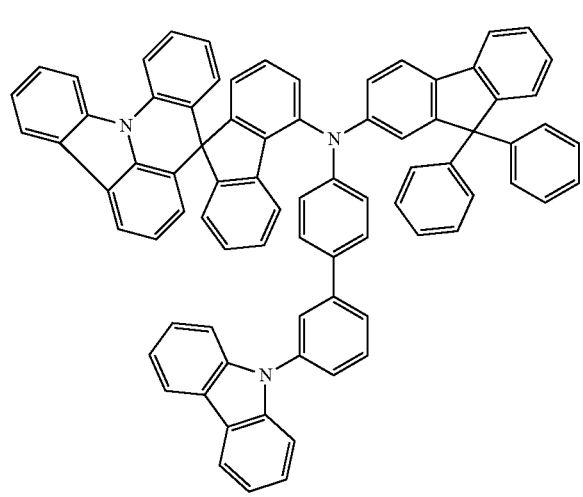
170
-continued
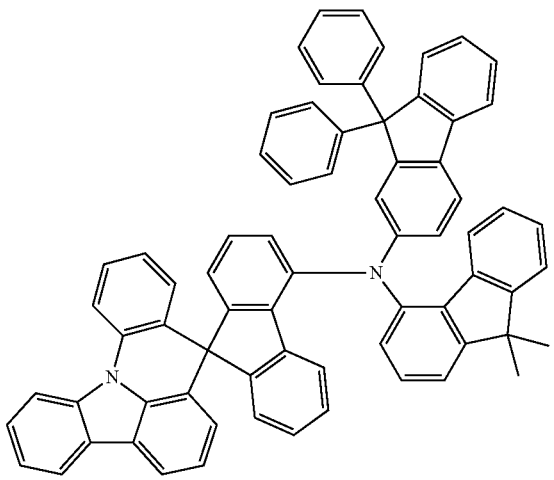
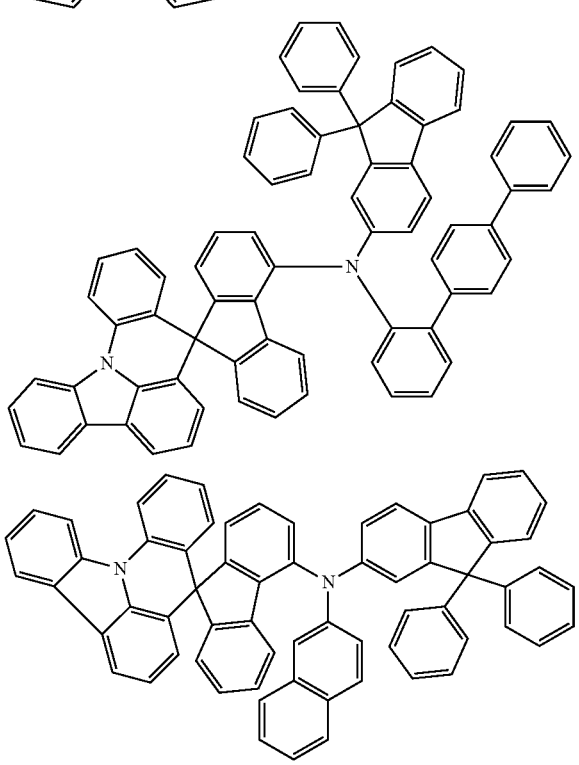
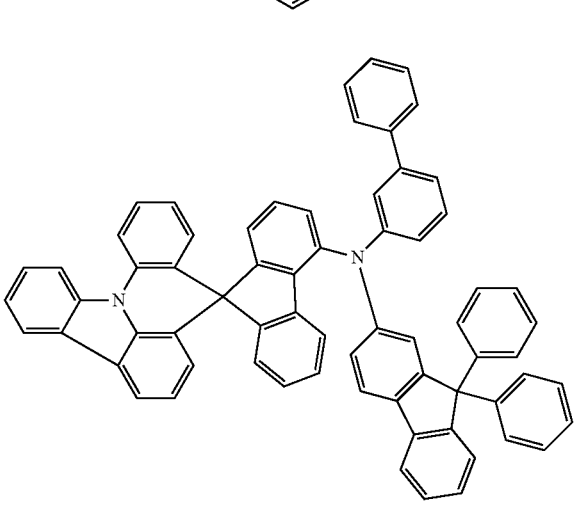

171
-continued
172
-continued
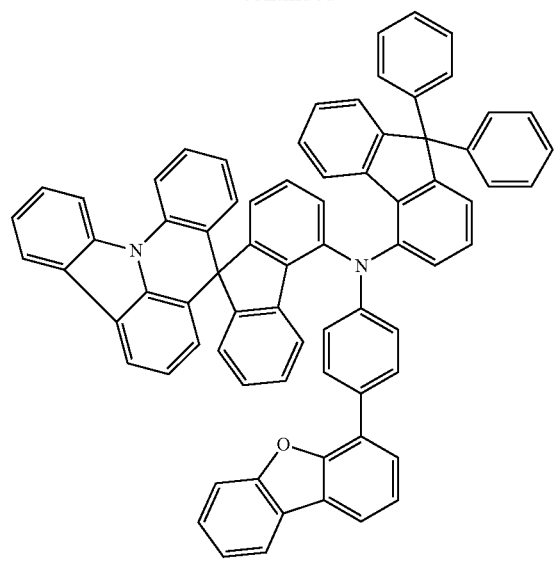
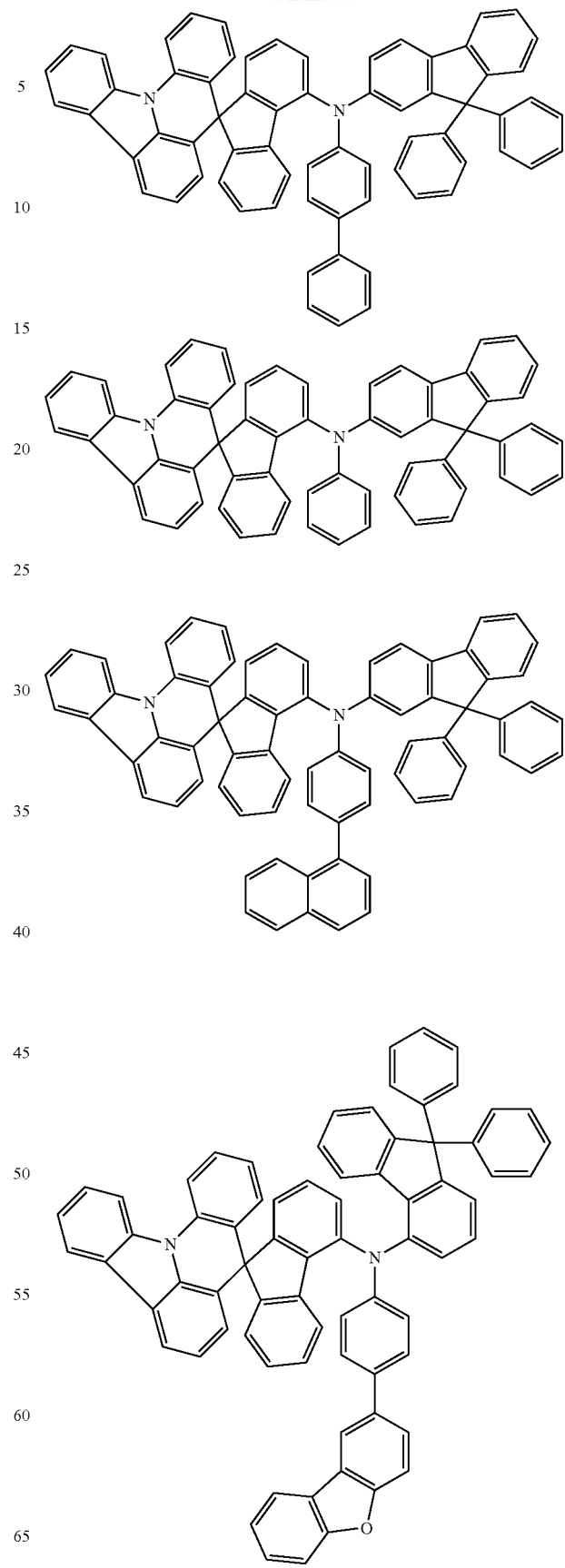

173
-continued
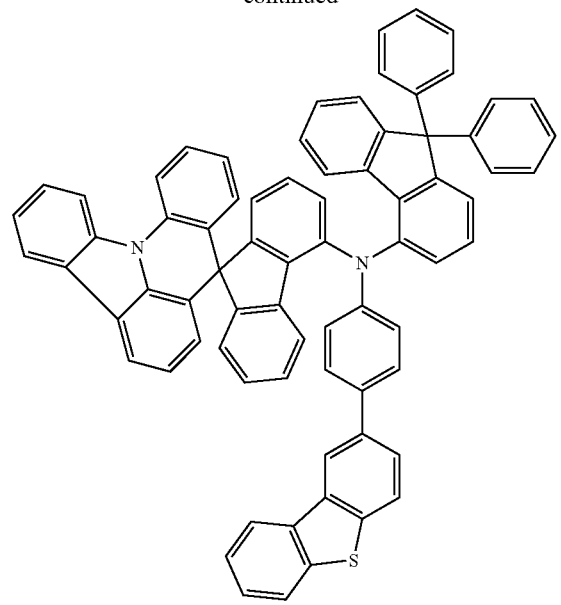
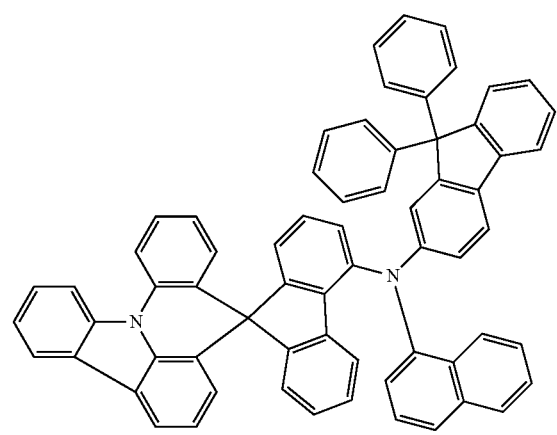
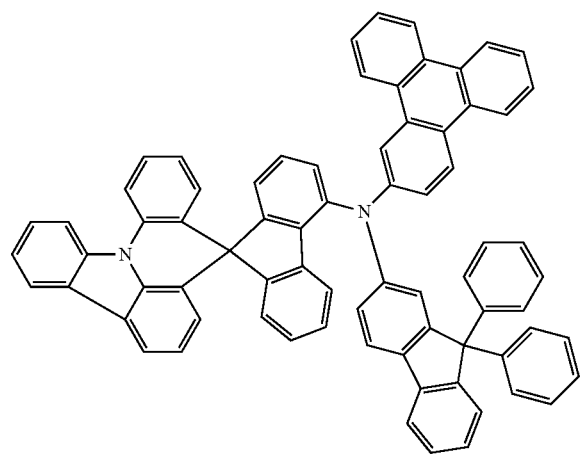
174
-continued
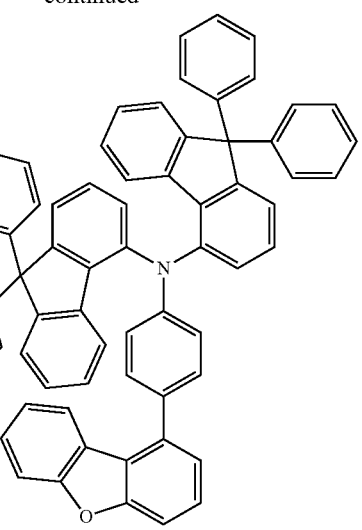
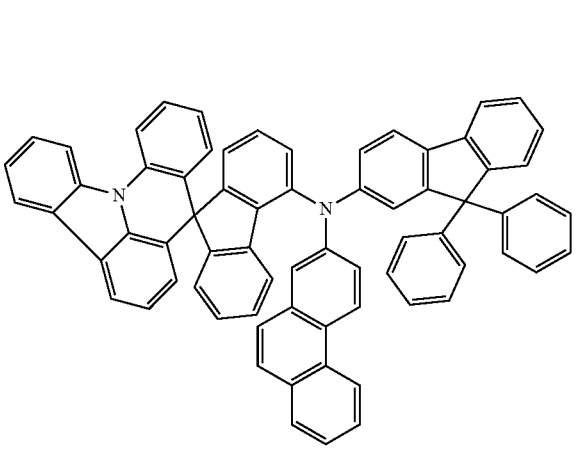

175
-continued
176
-continued
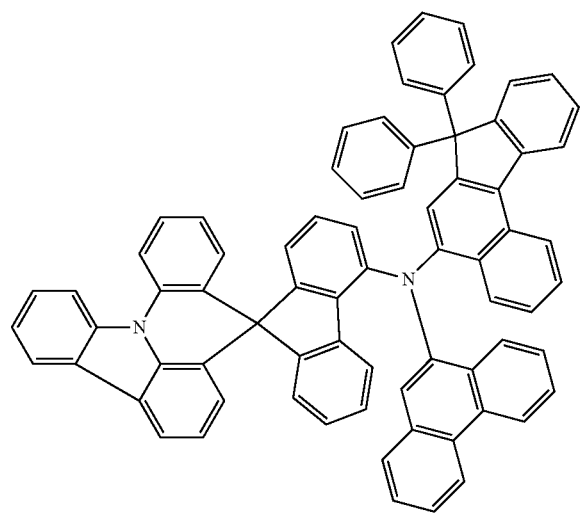
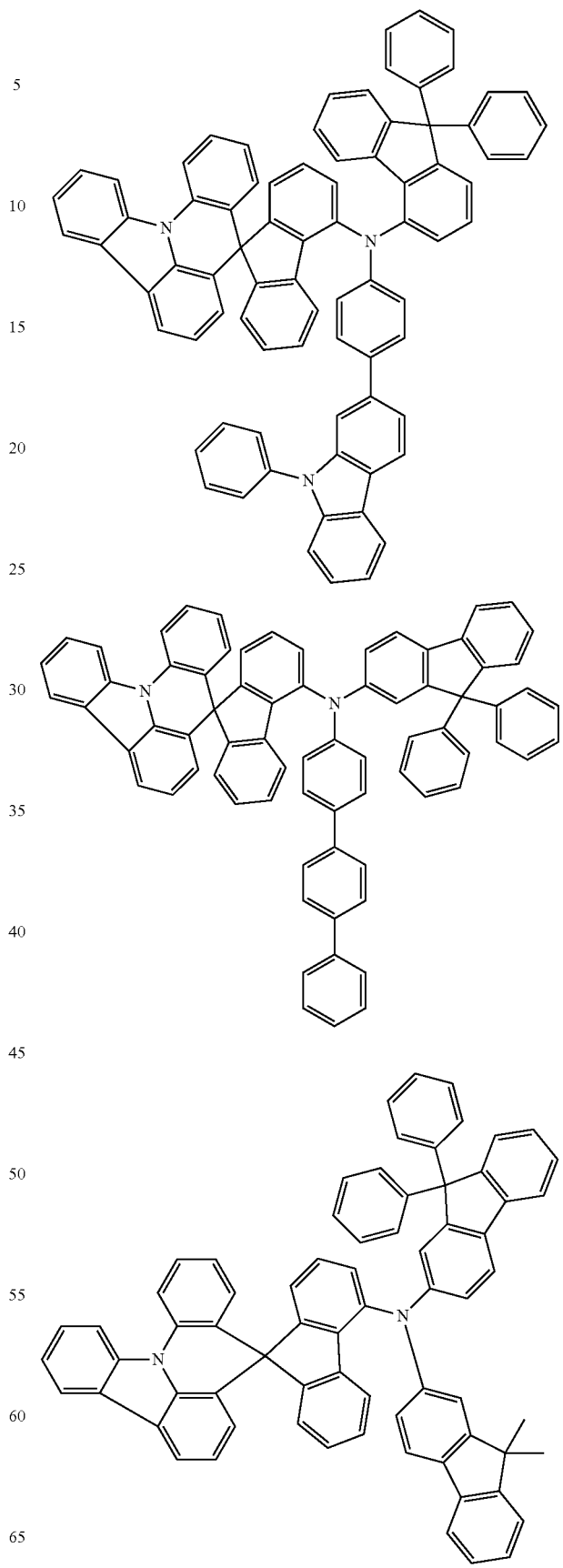

177
-continued
178
-continued
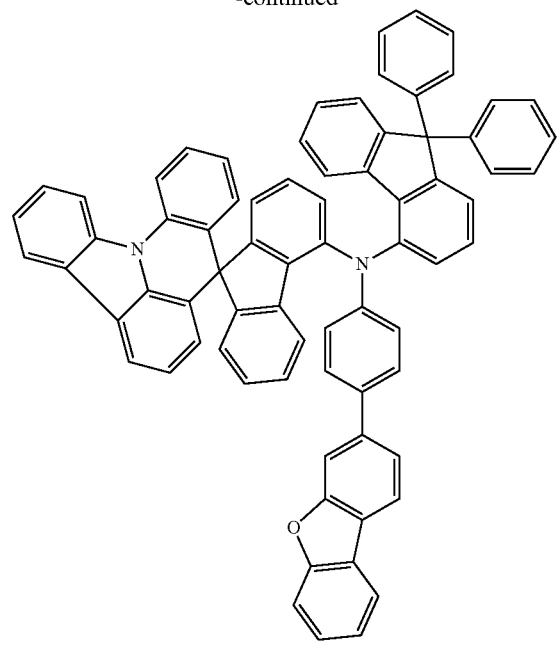
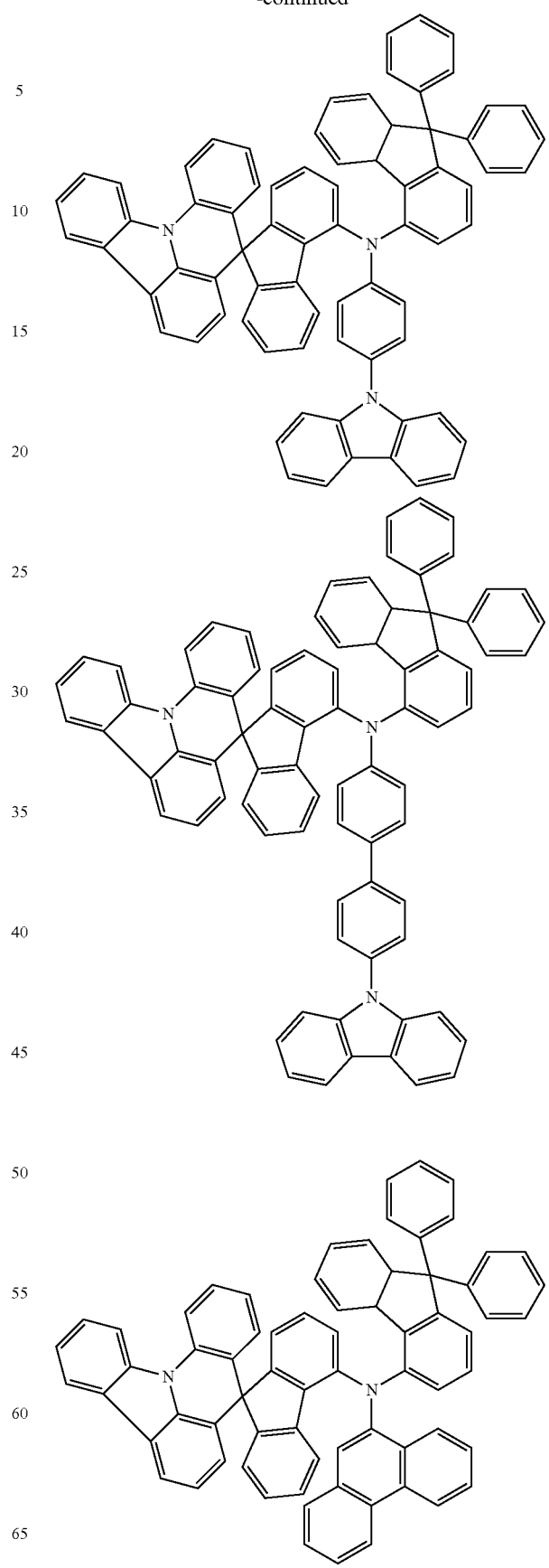

179
-continued
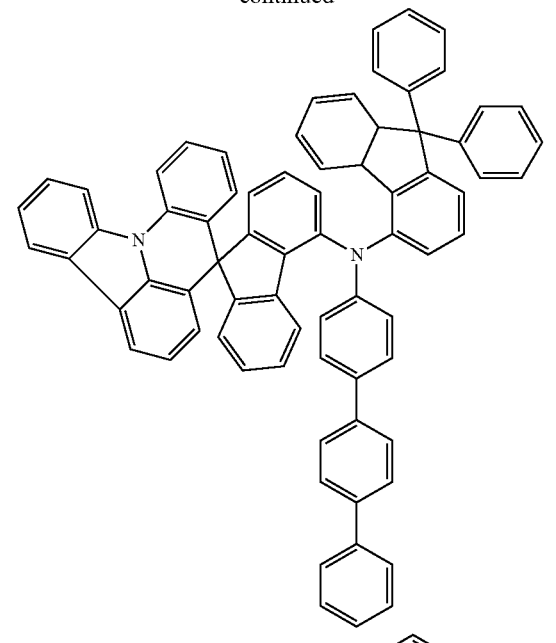
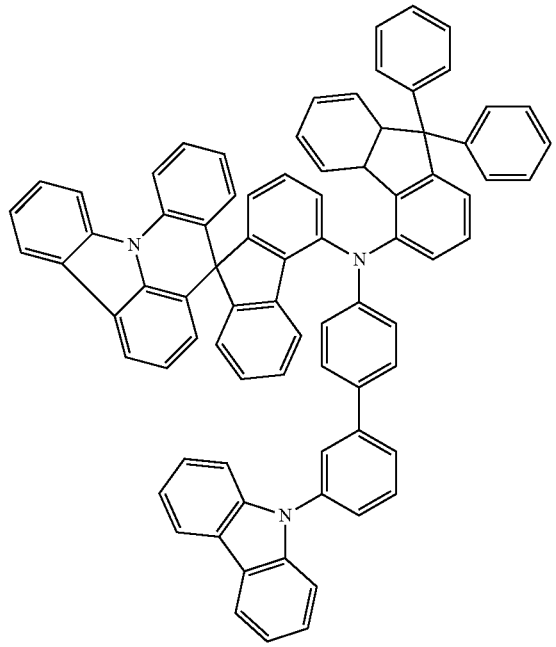
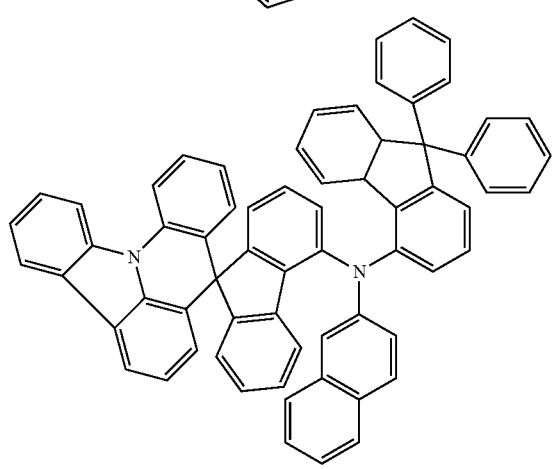
180
-continued
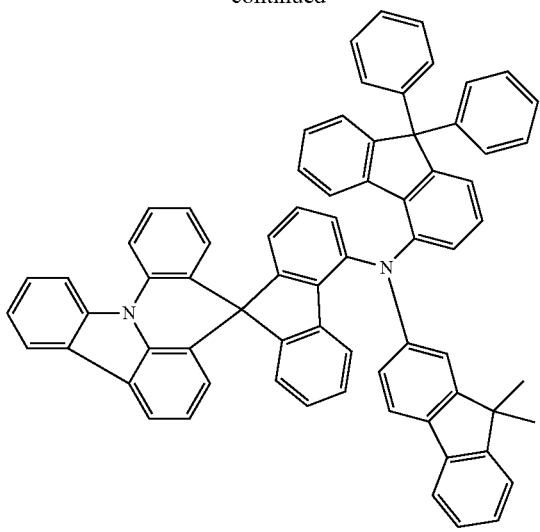
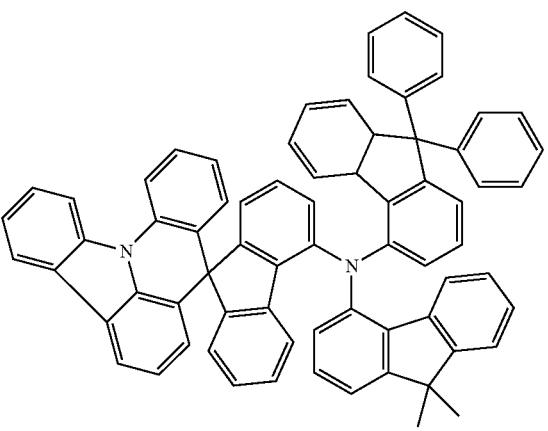
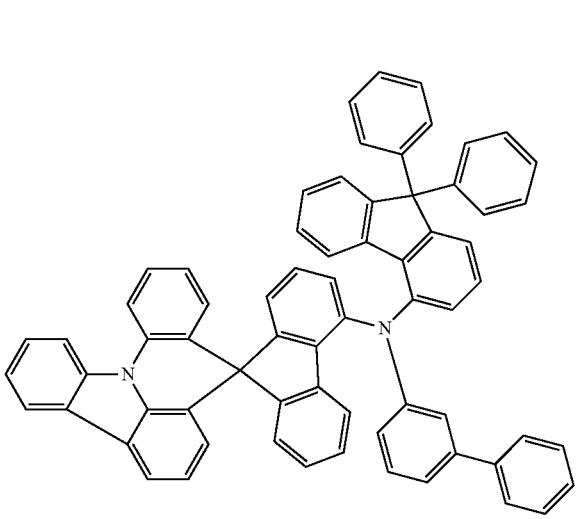

181
-continued
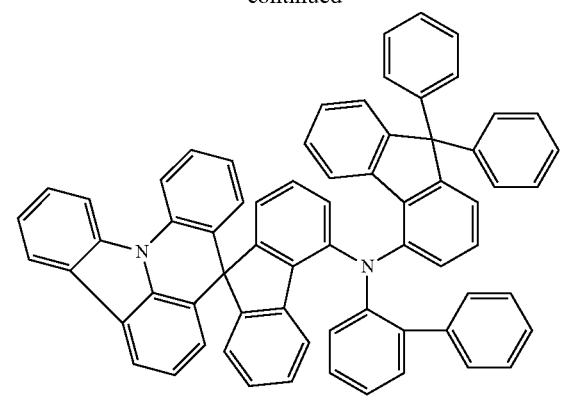
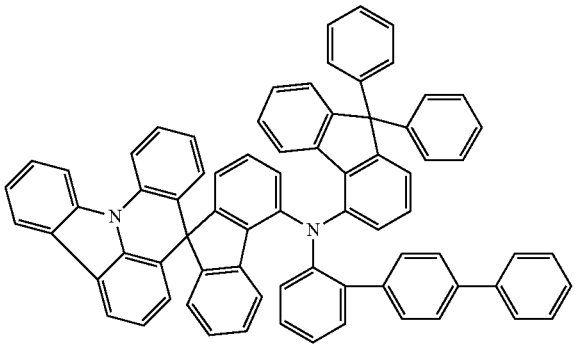
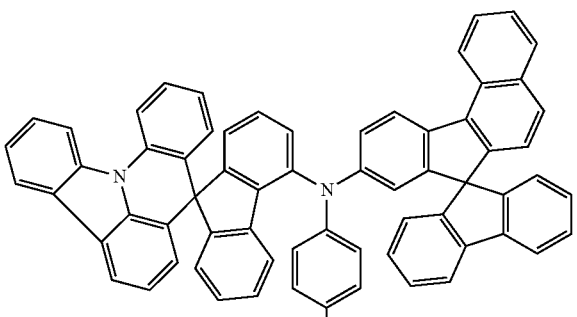
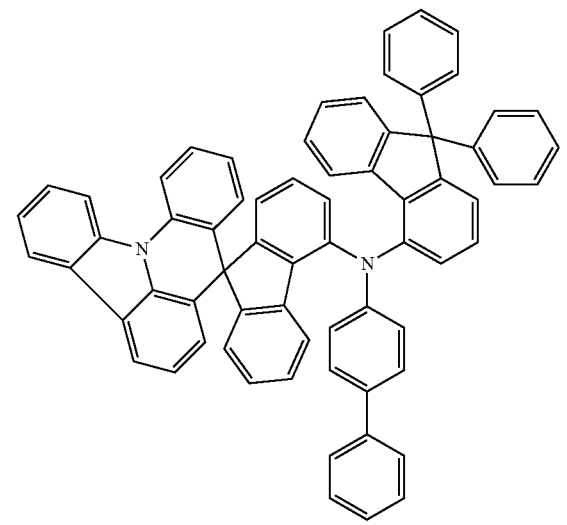
182
-continued
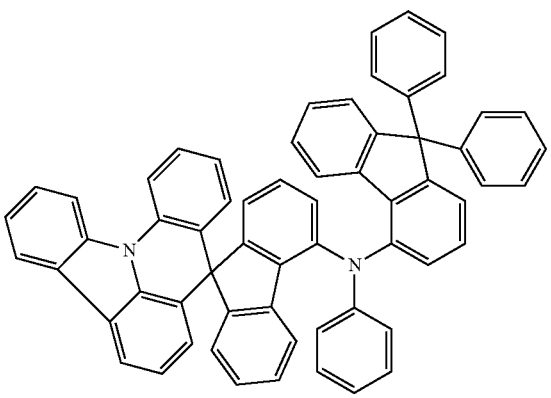
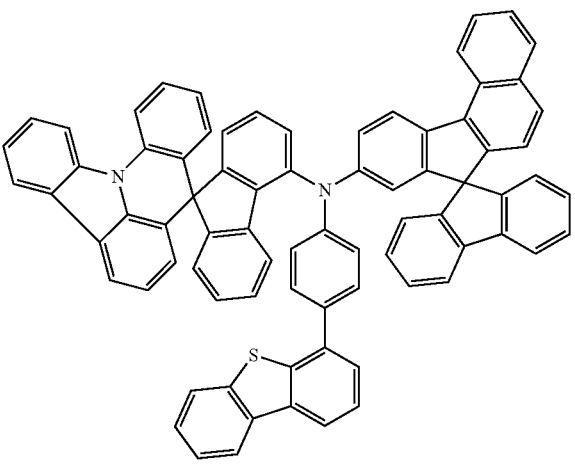
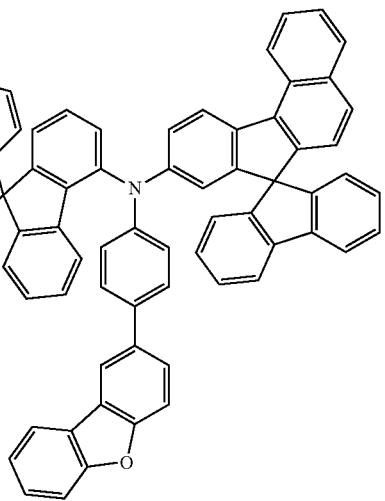

183
-continued
184
-continued
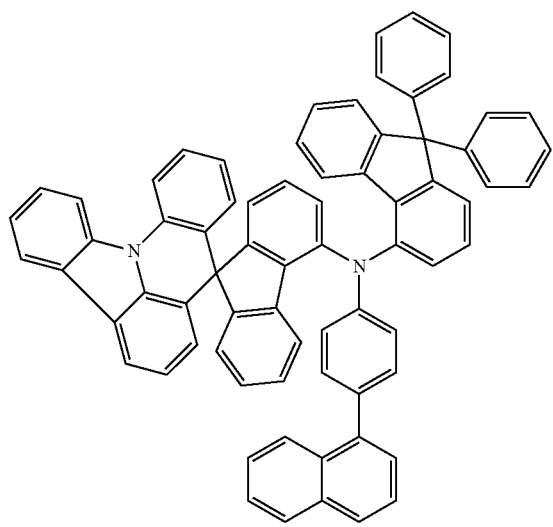
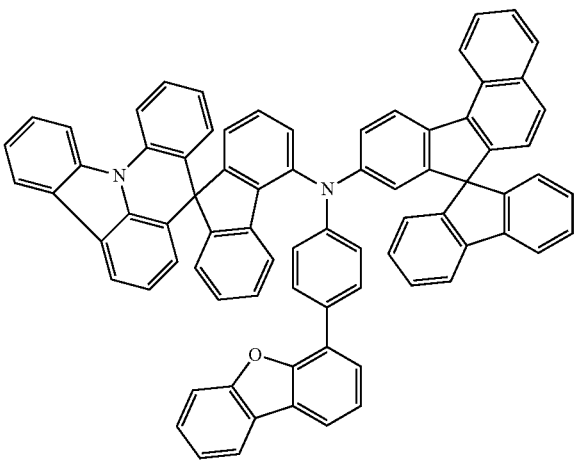
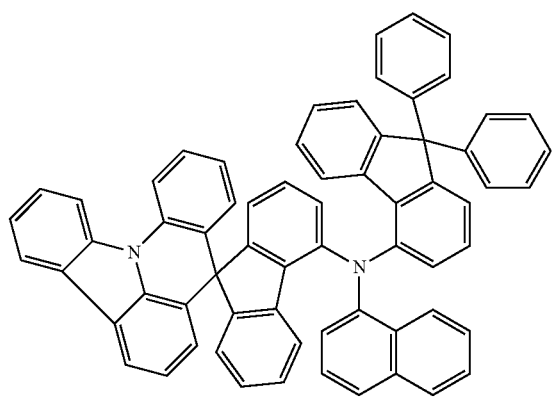
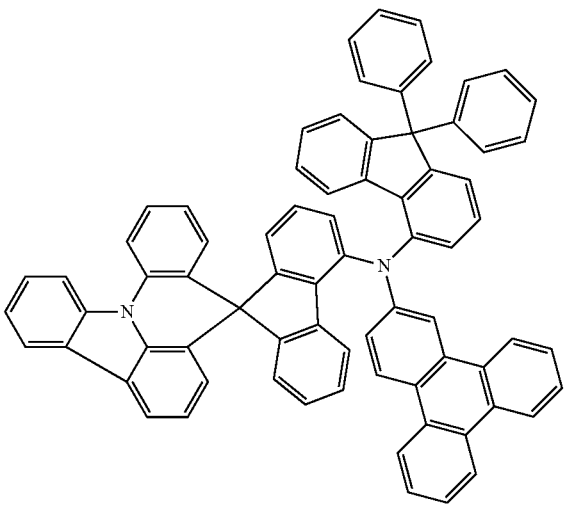
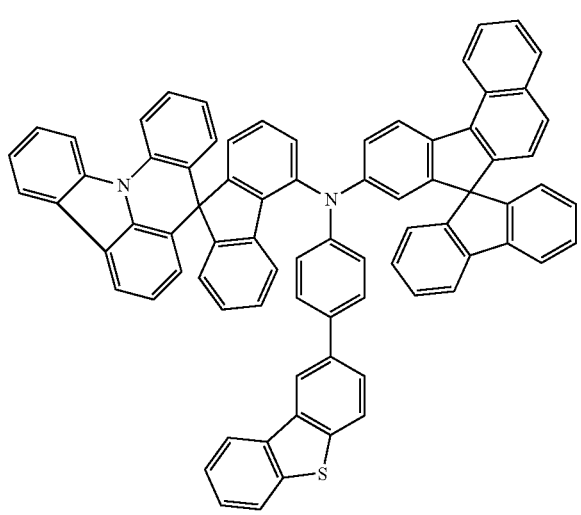
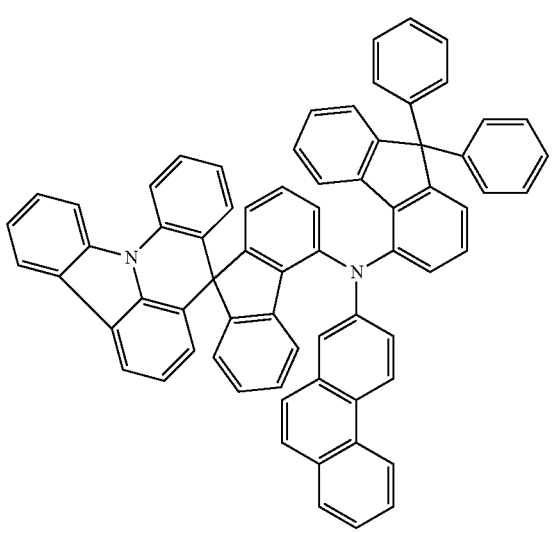

185
-continued
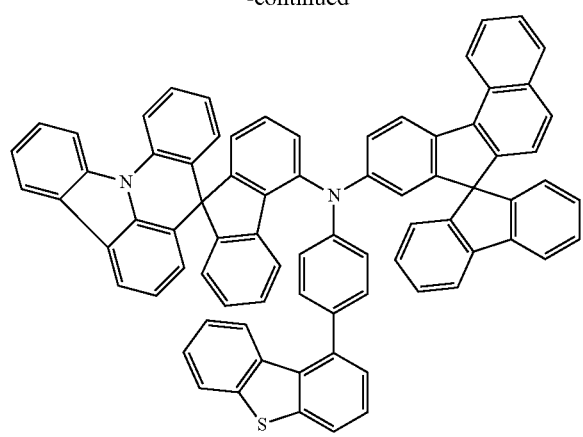
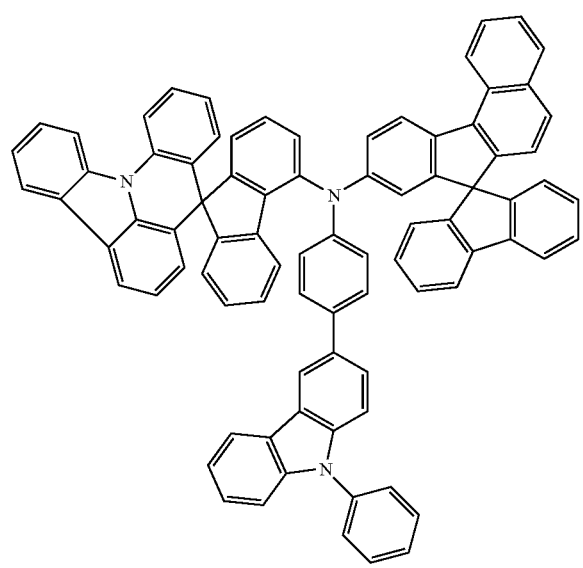
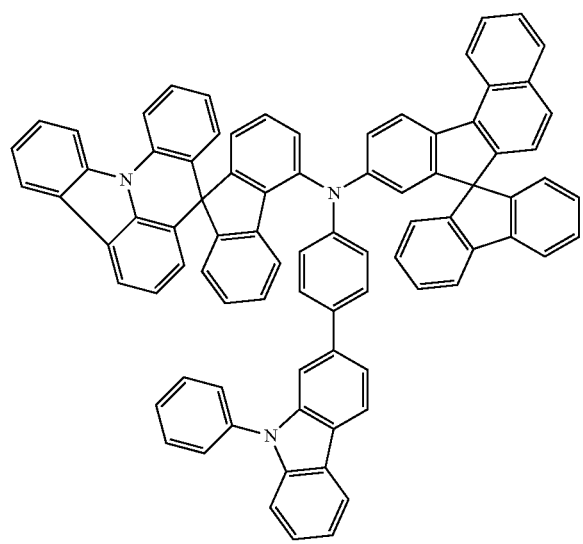
186
-continued
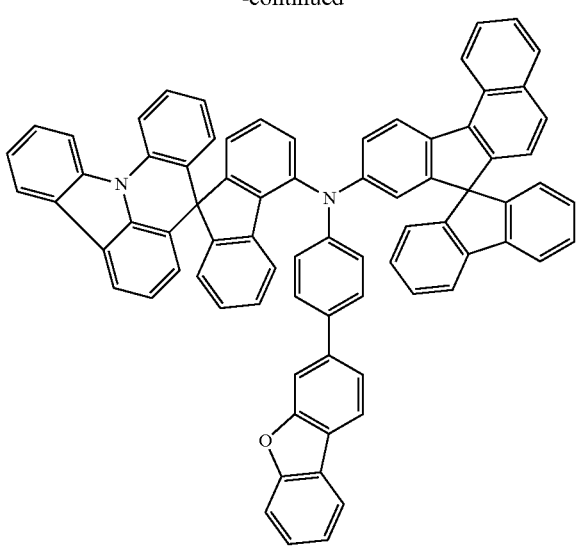
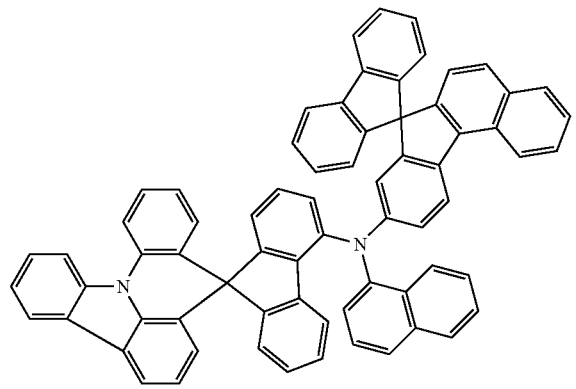
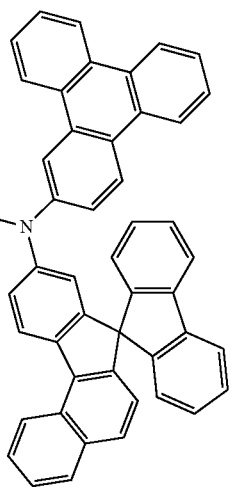

187
-continued
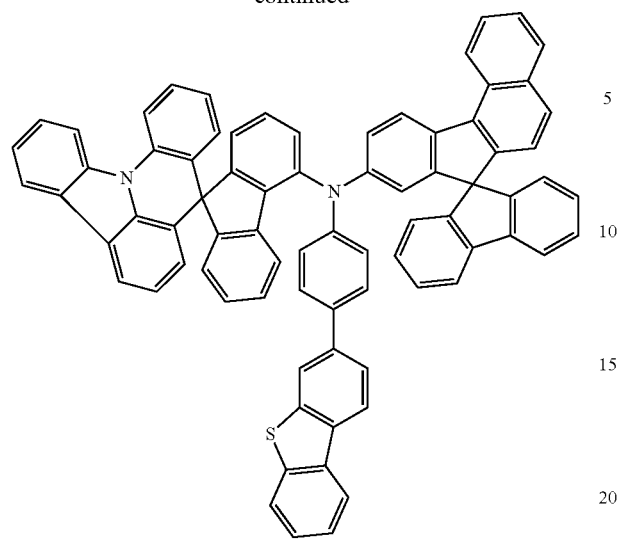
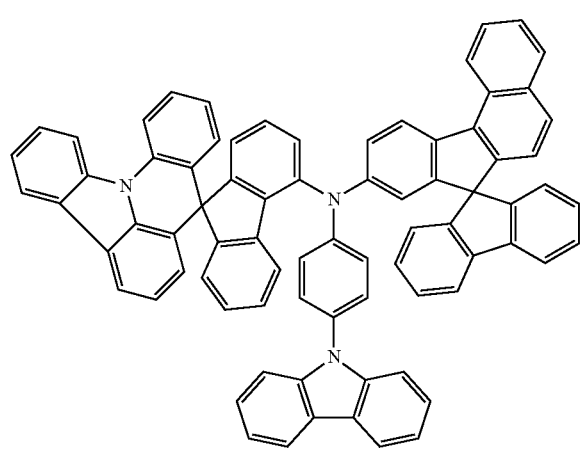
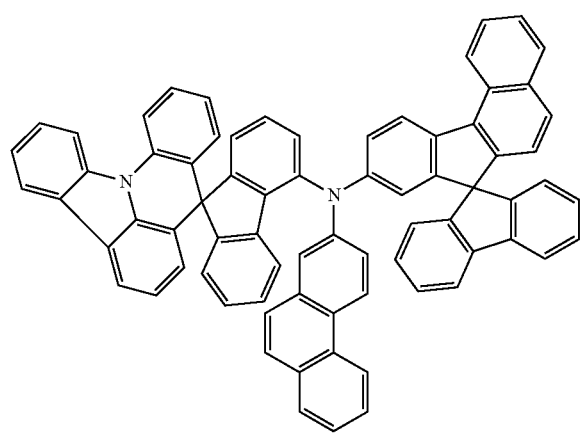
188
-continued
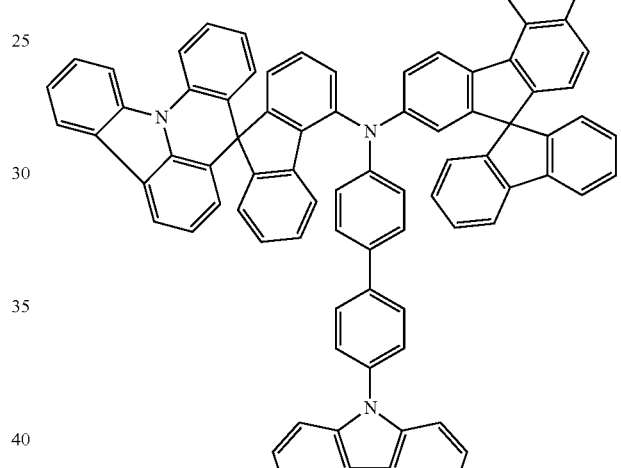
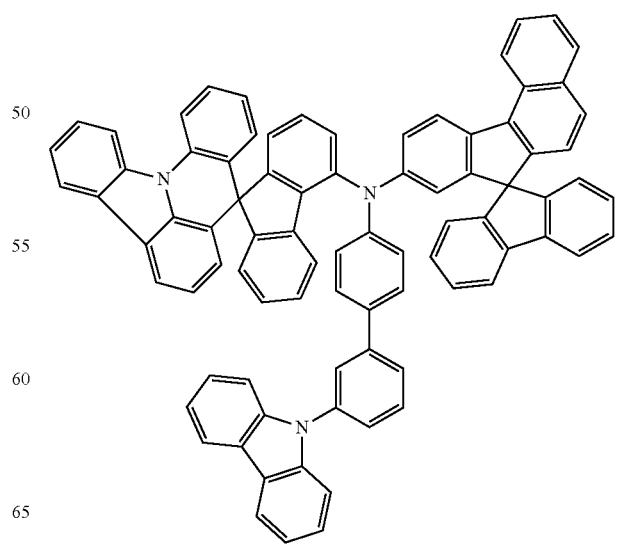

189
-continued
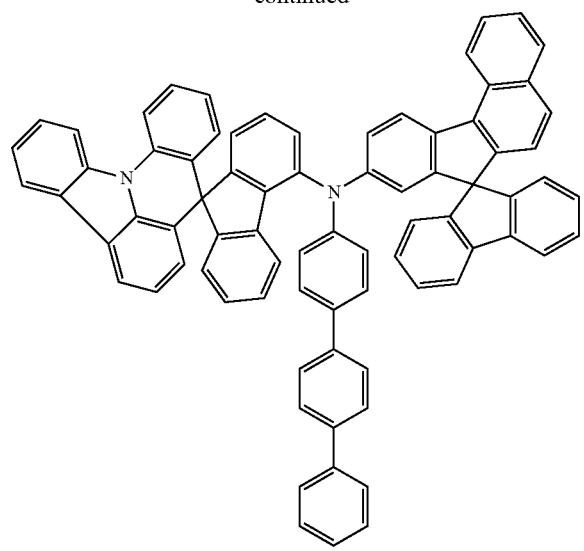
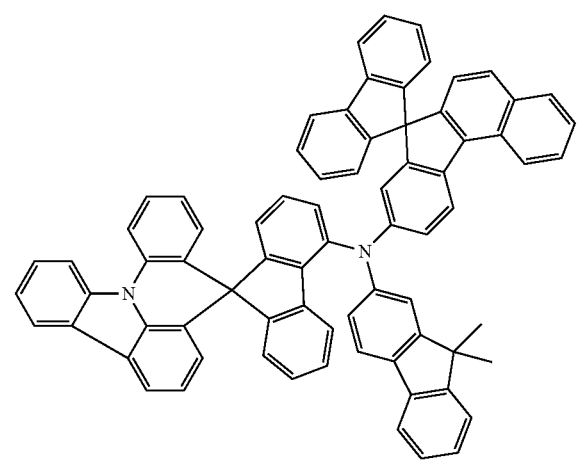
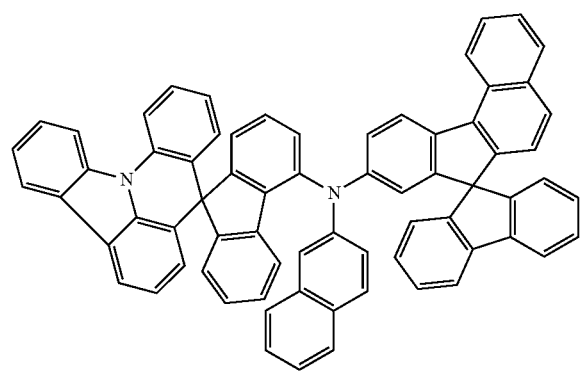
190
-continued
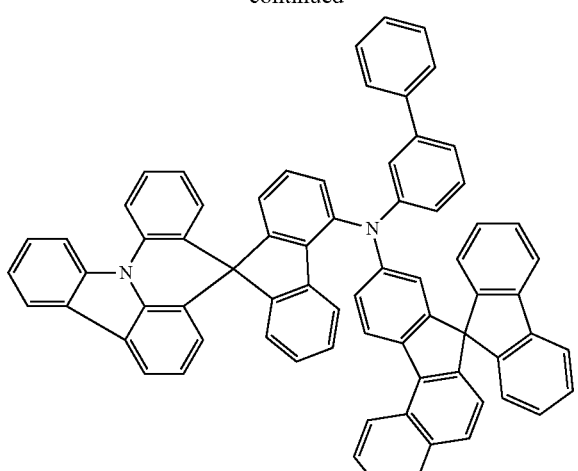
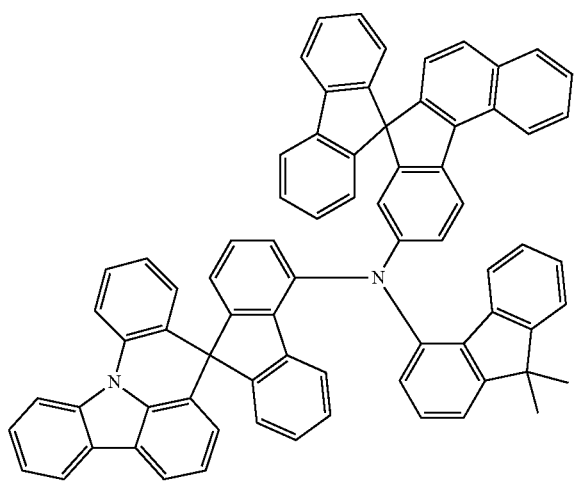
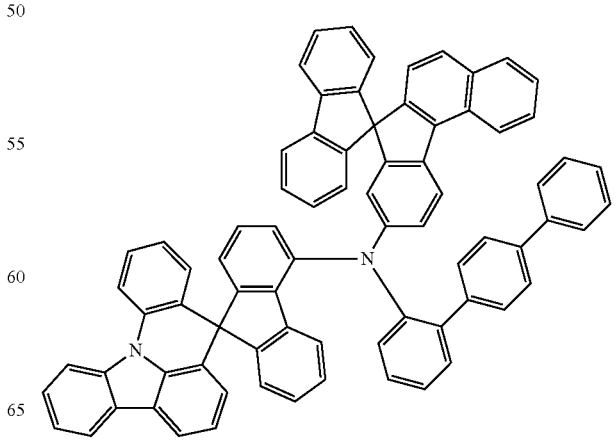

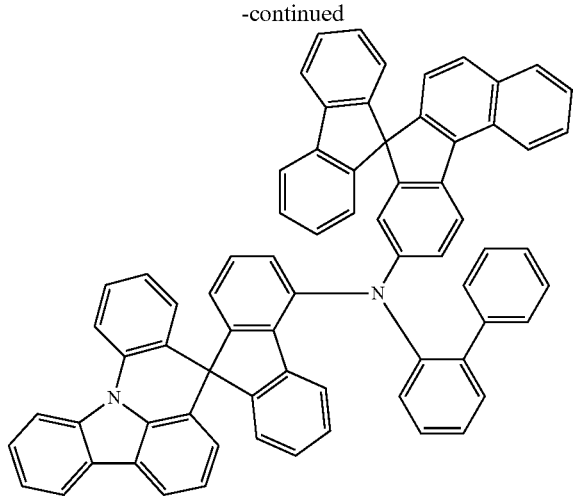
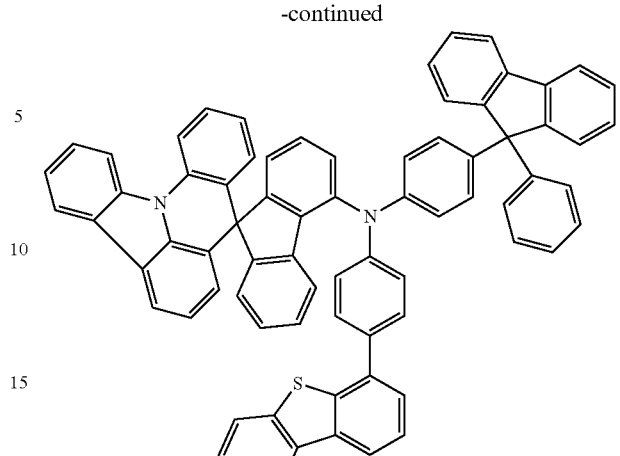
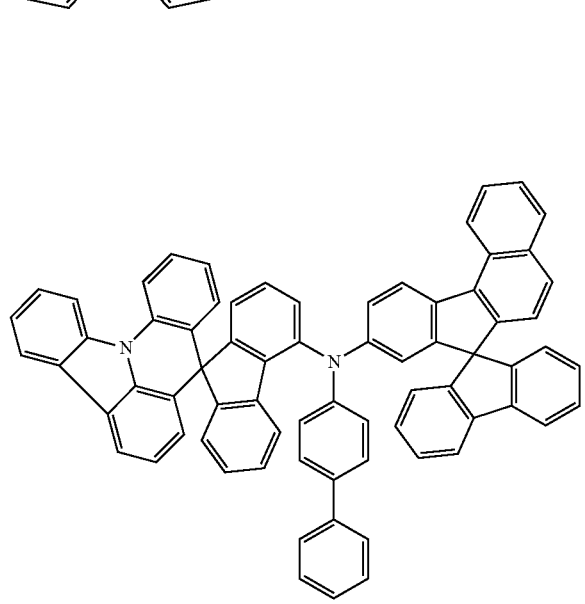
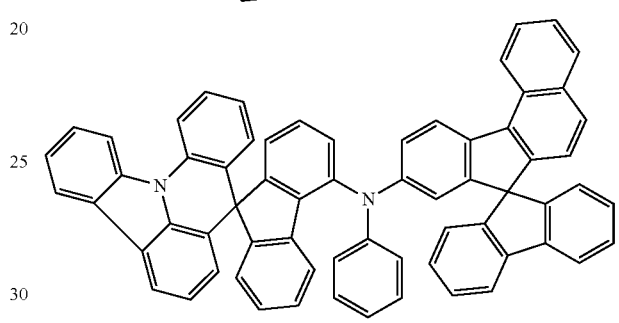
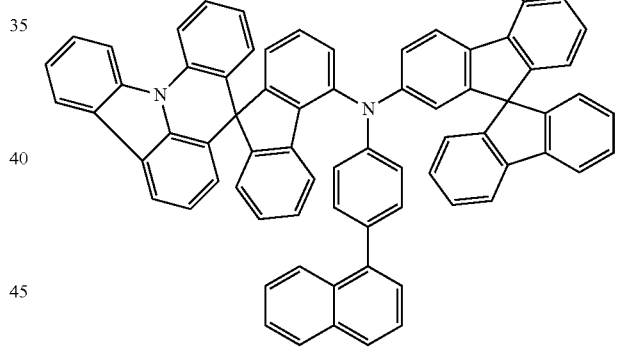
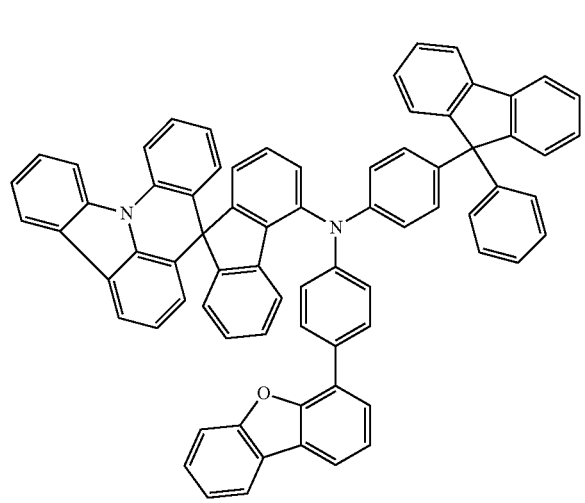
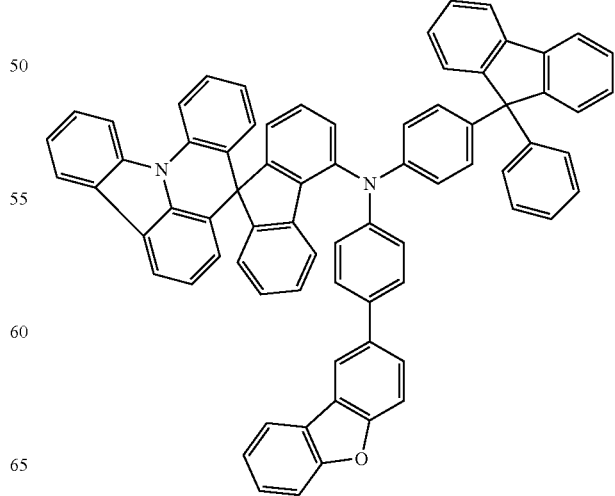

193
-continued
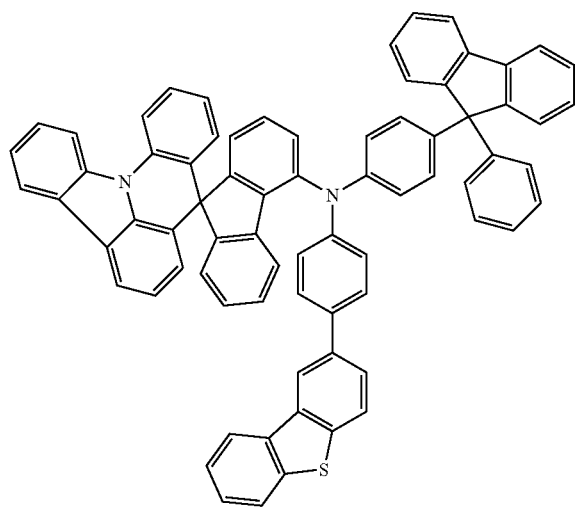
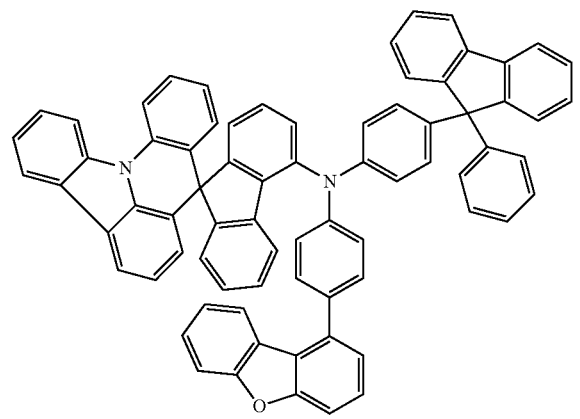
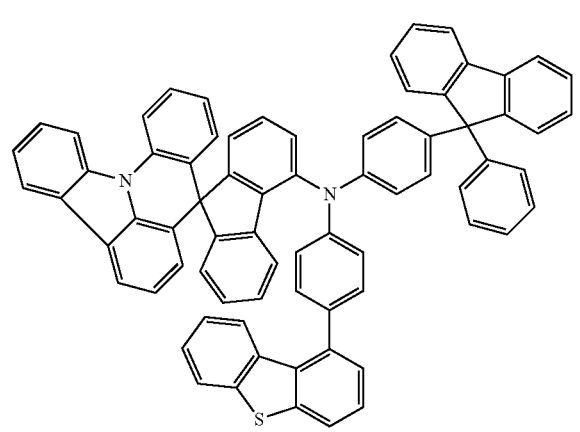
194
-continued
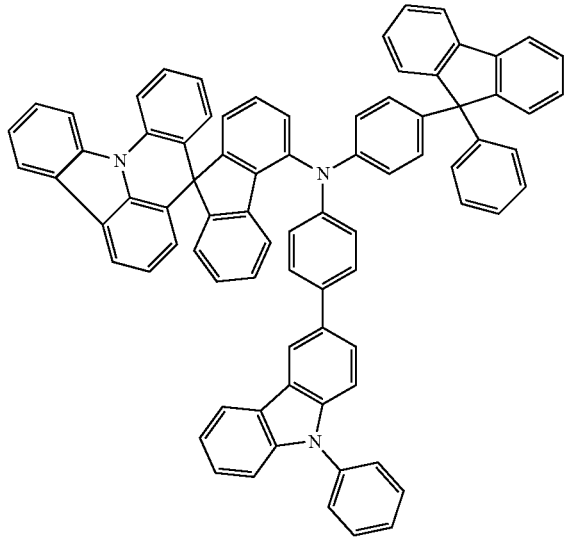
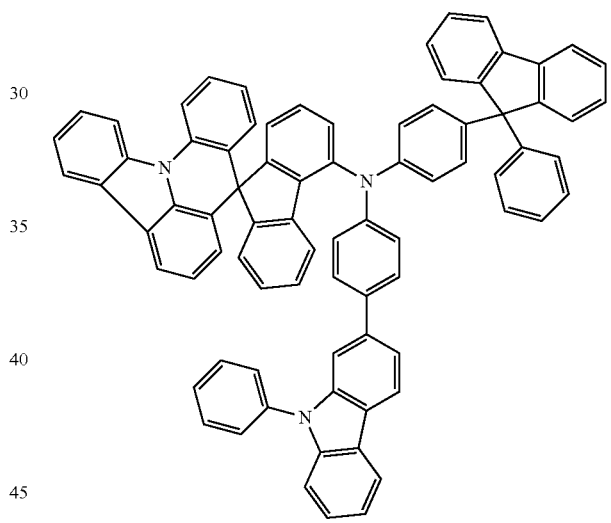
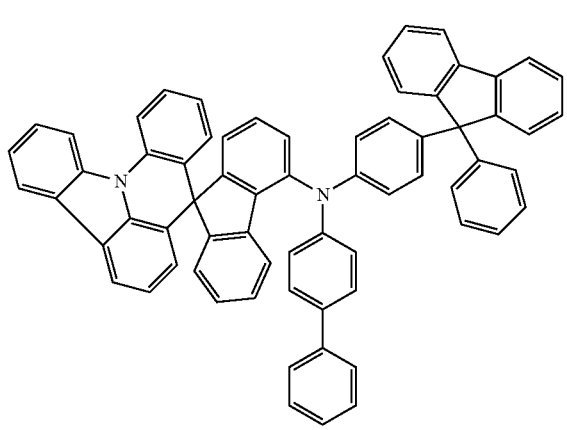

-continued
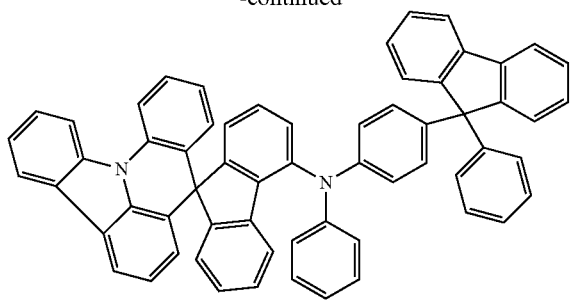
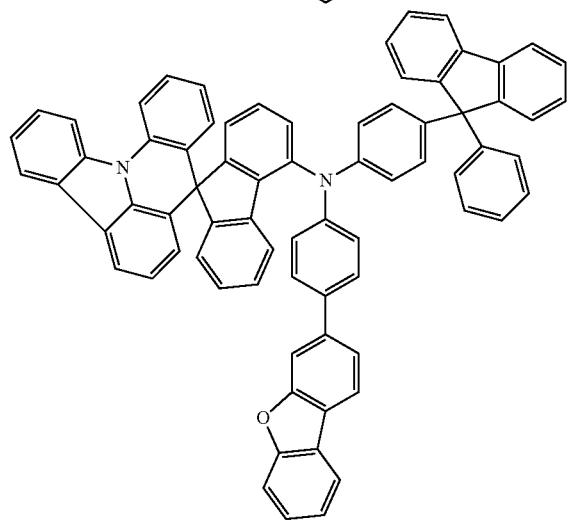
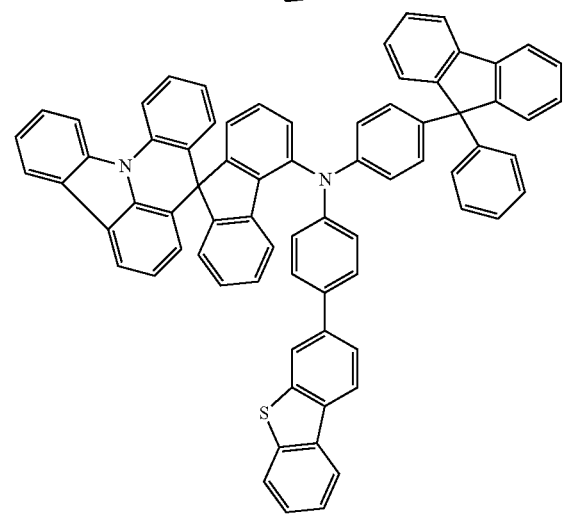
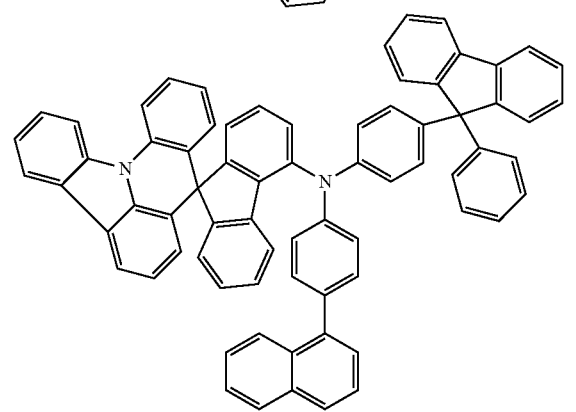
-continued
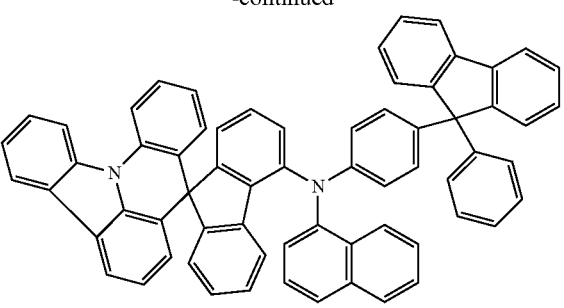
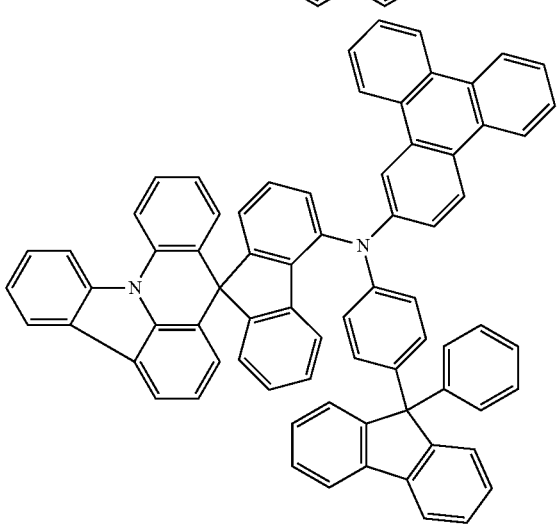
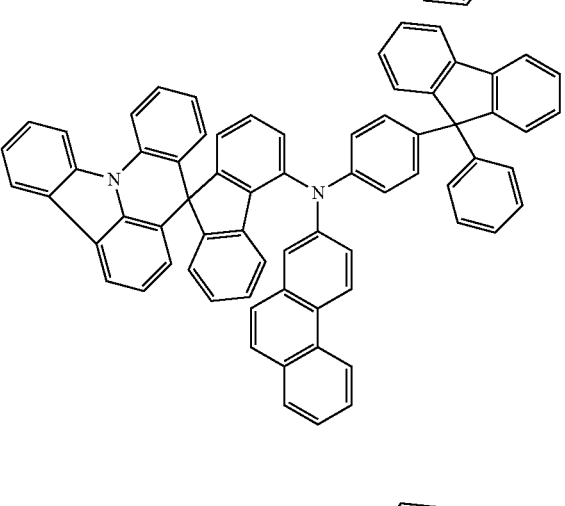
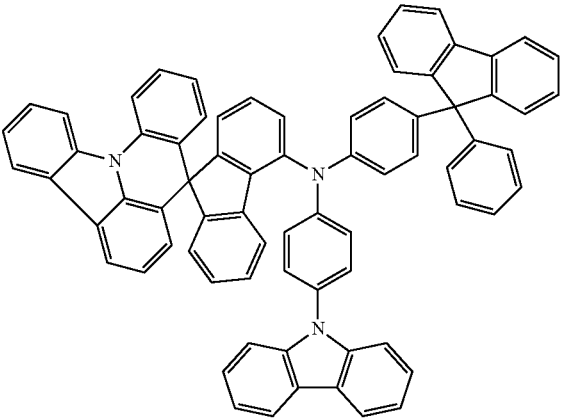

197
-continued
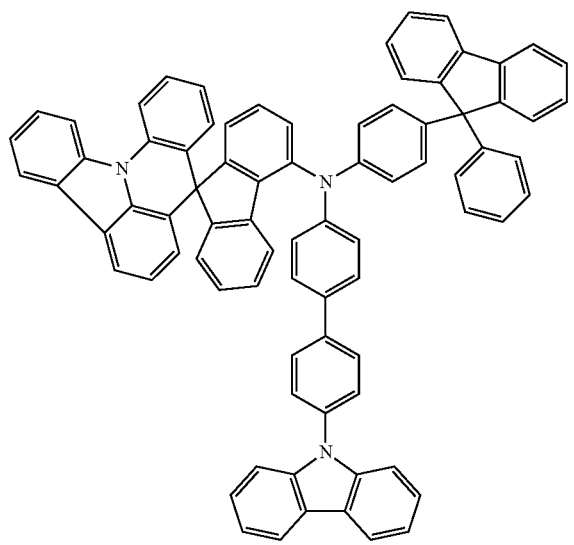
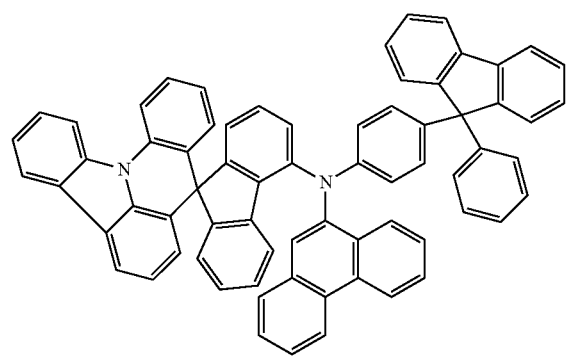
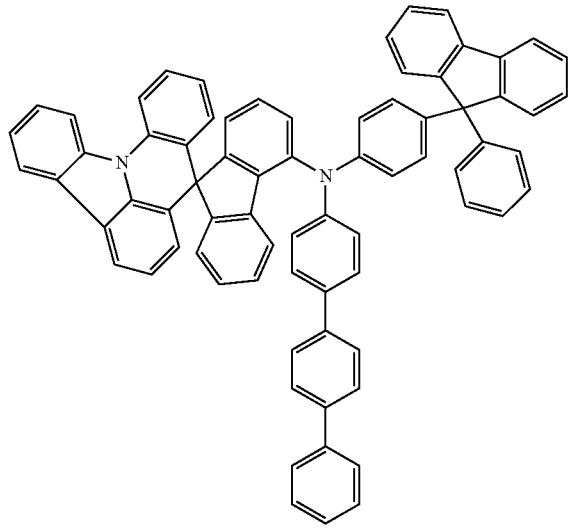
198
-continued
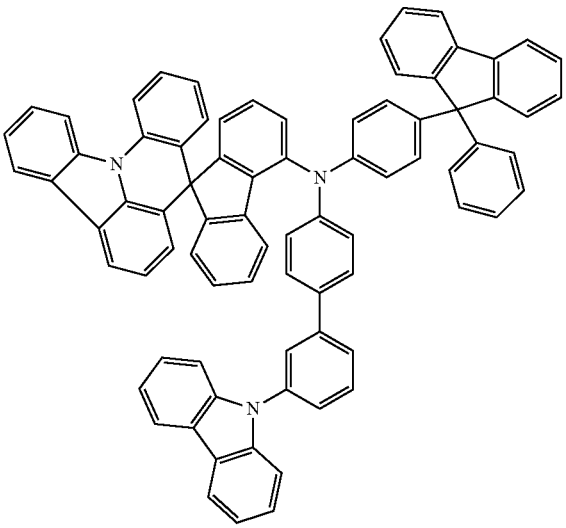
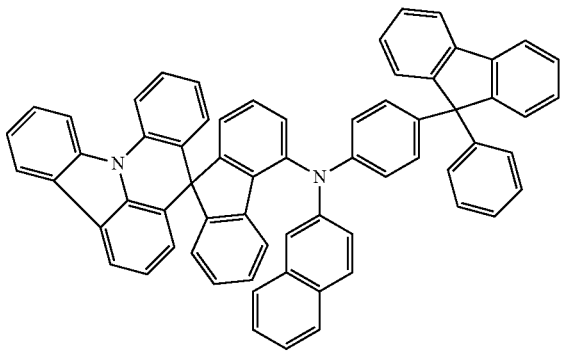
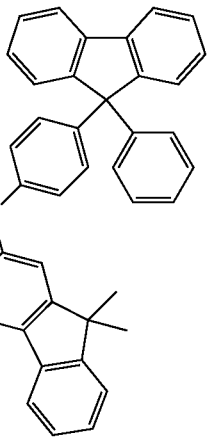
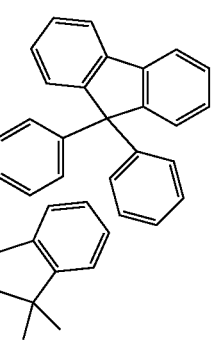

| 199 -continued | 200 -continued |
|---|---|
| 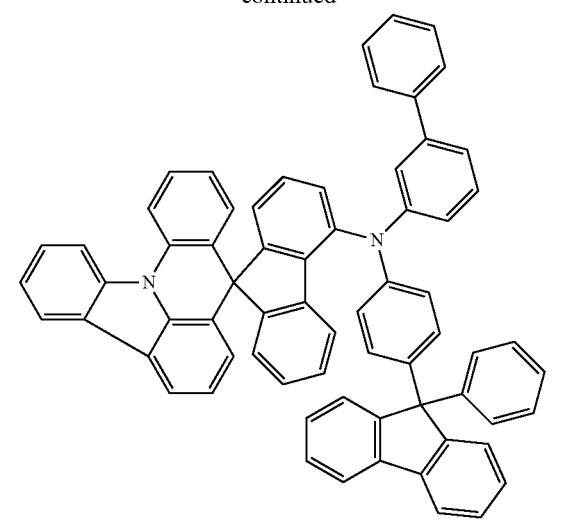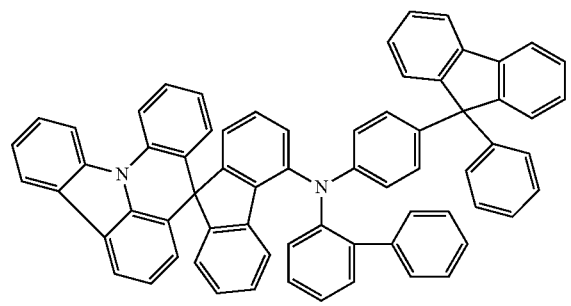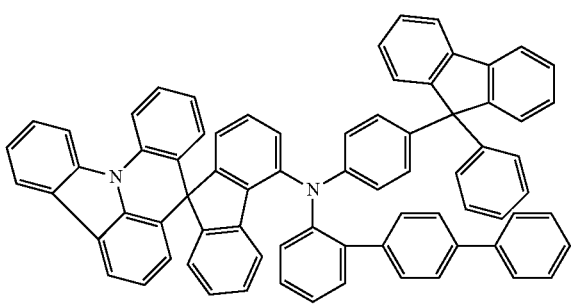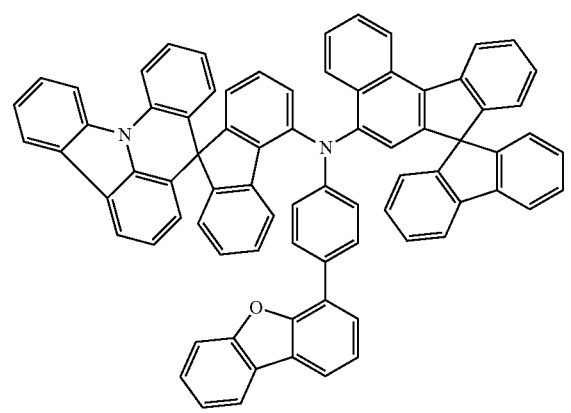 | 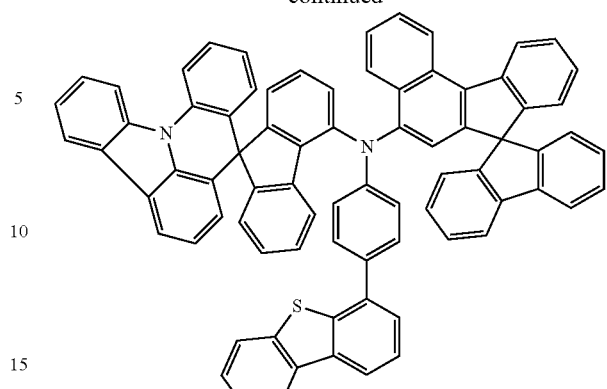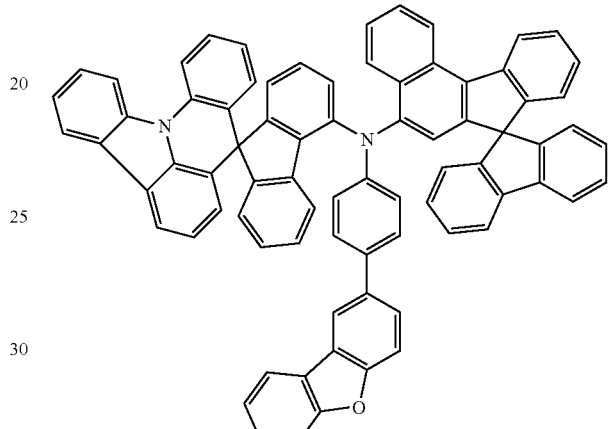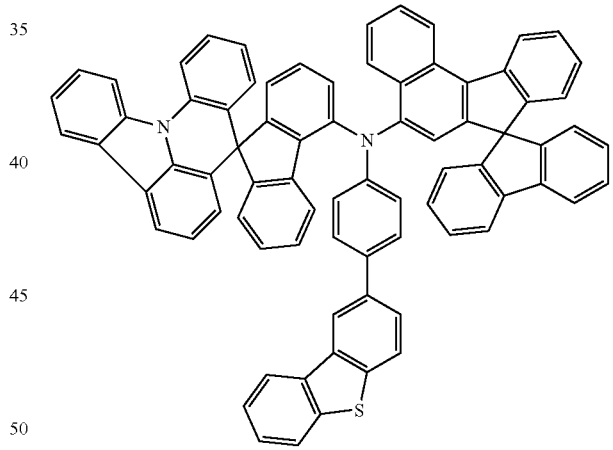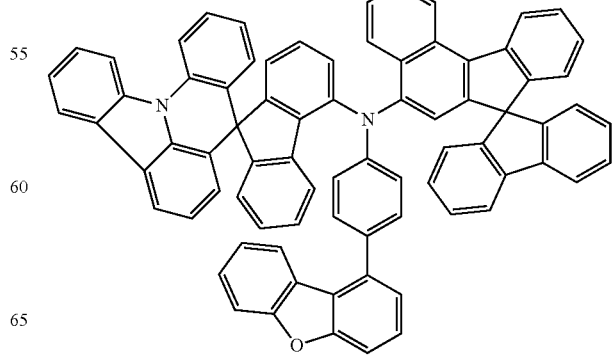 |

201
-continued
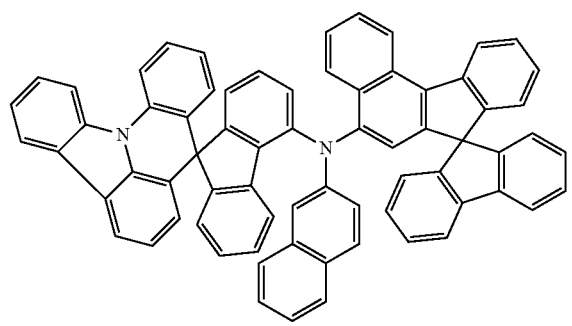
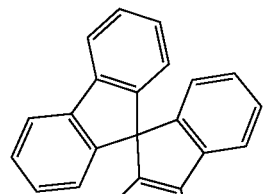
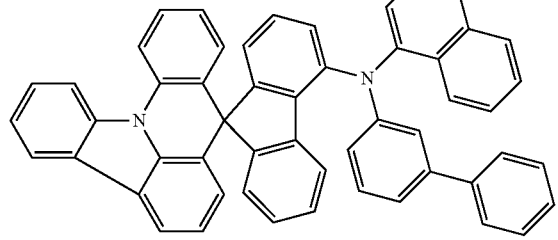
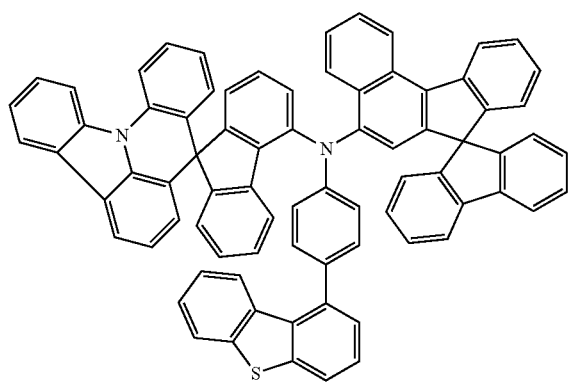
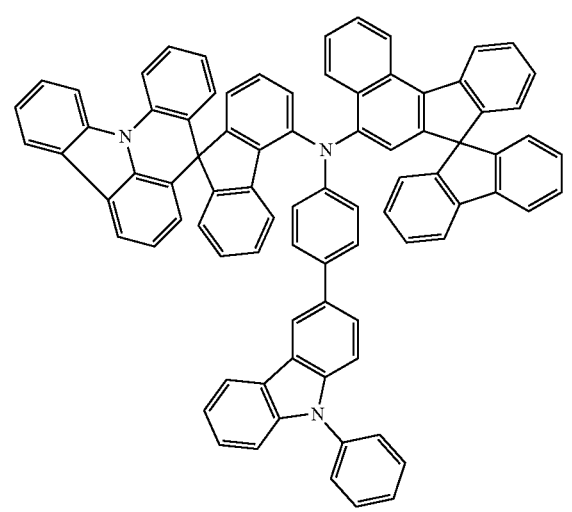
202
-continued
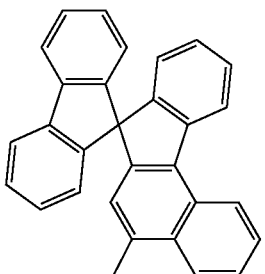
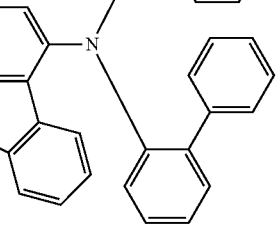
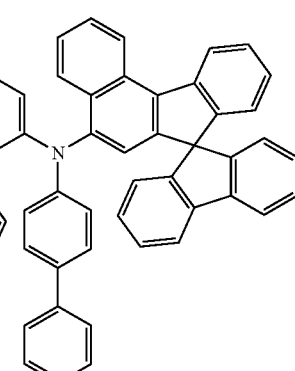
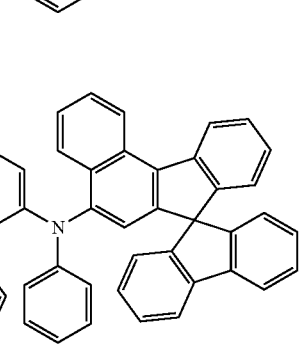
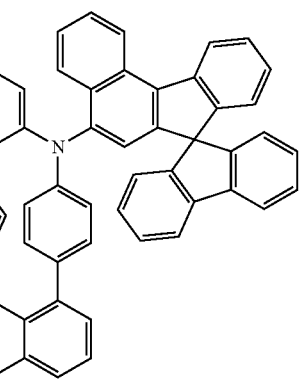

203
-continued
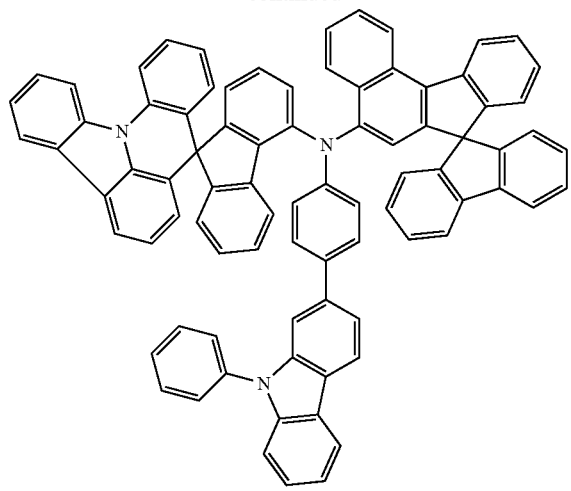
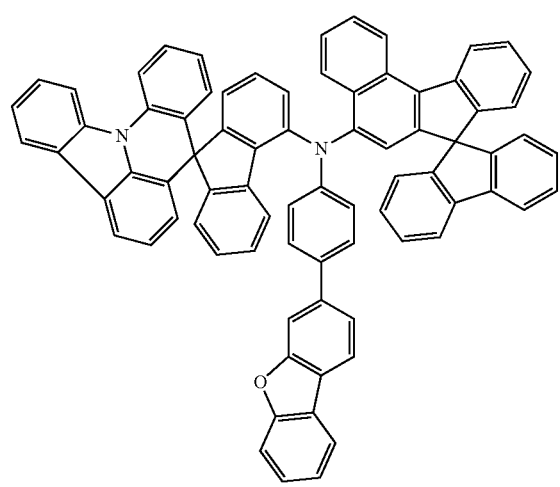
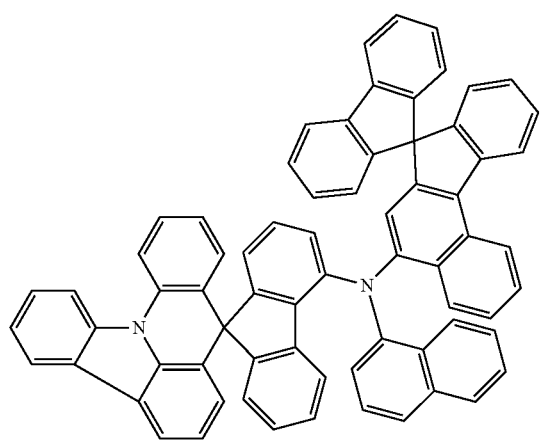
204
-continued
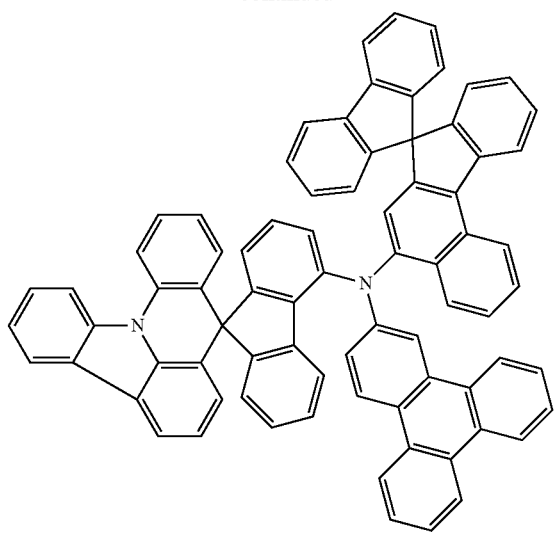
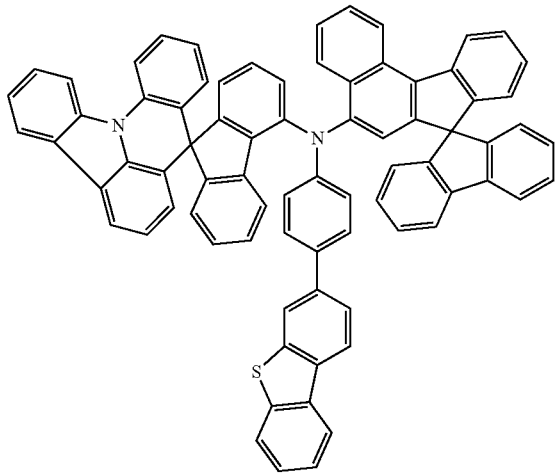
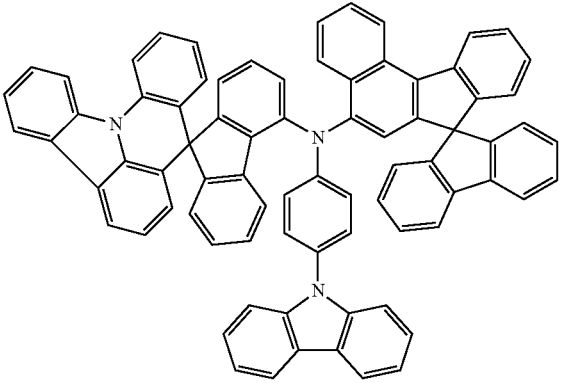

205
-continued
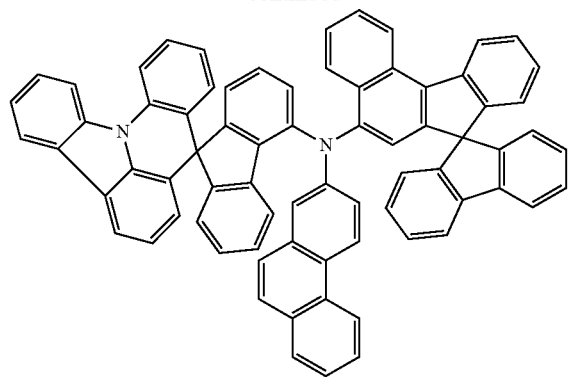
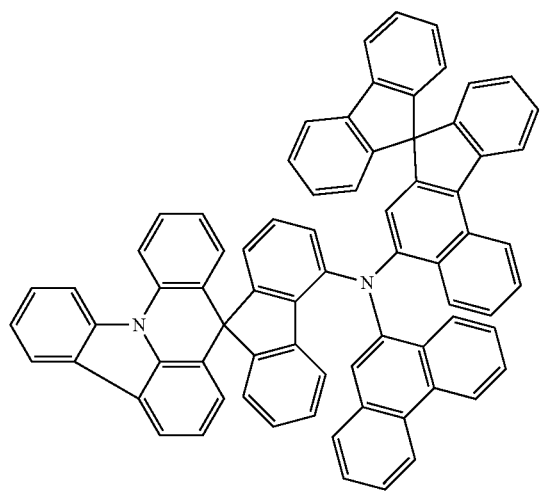
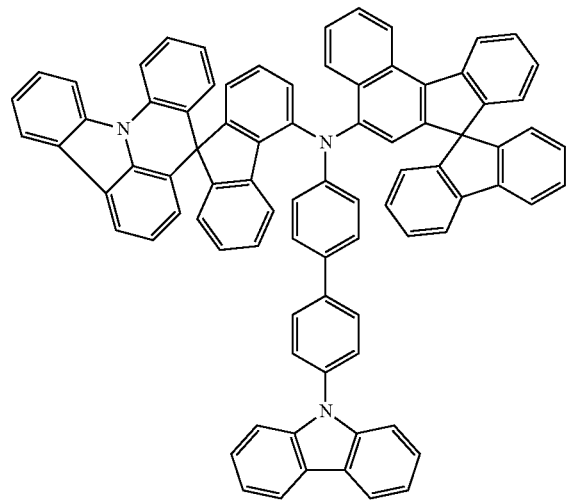
206
-continued
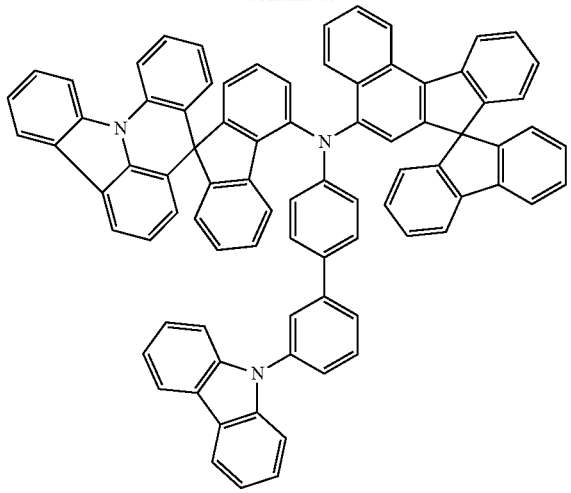
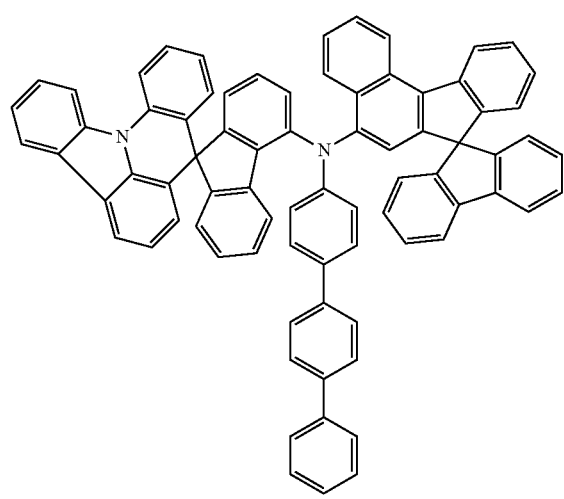
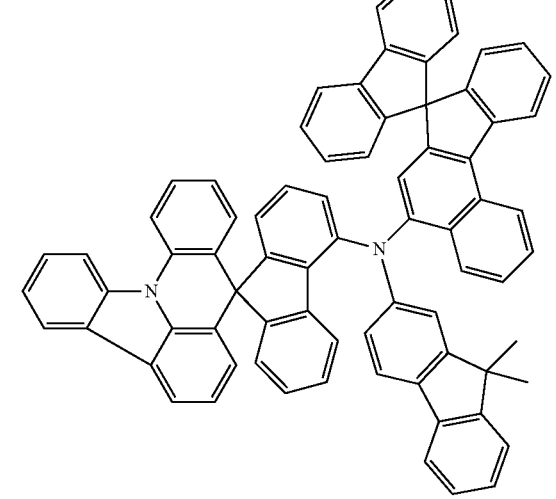

207
-continued
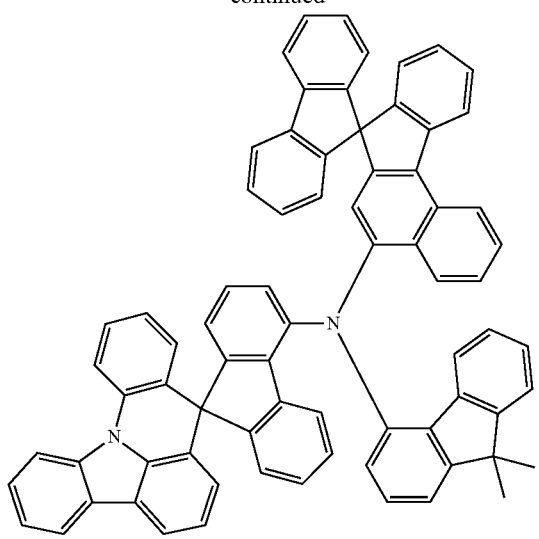
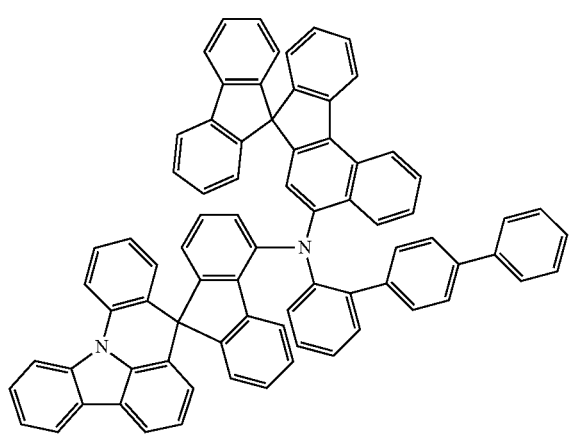
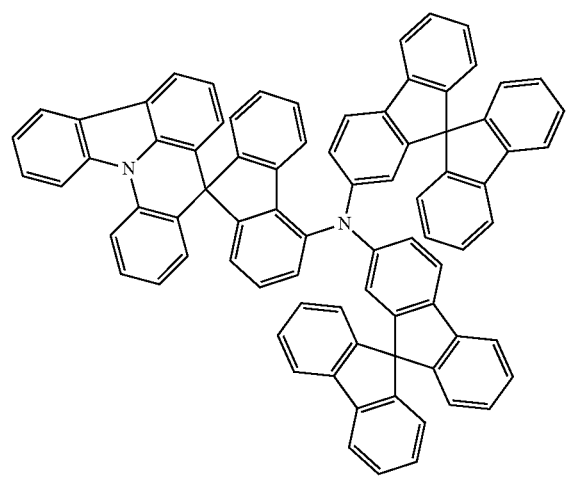
208
-continued
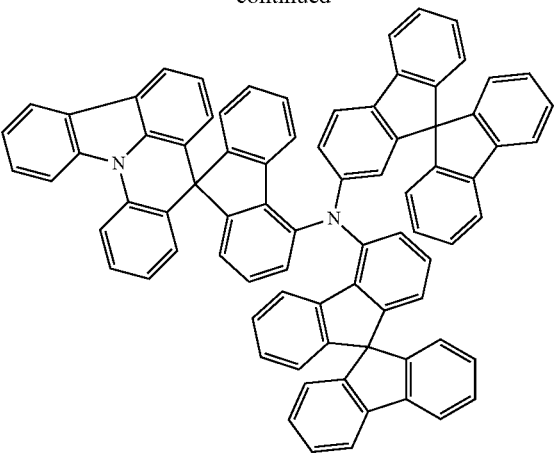
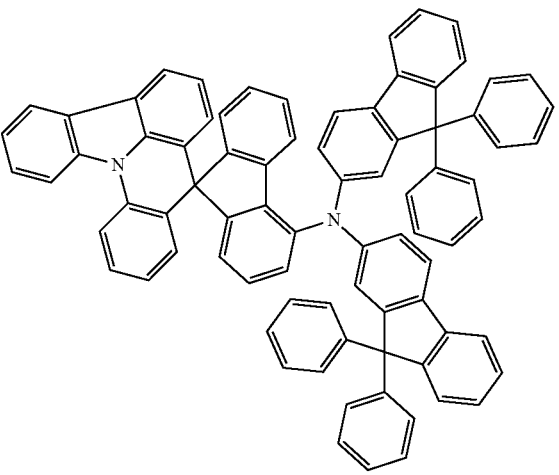
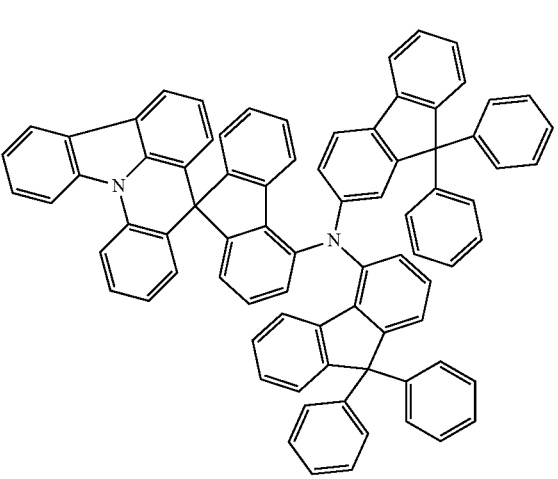

209
-continued
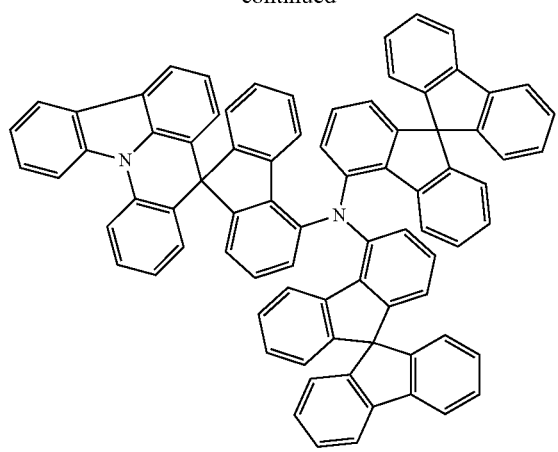
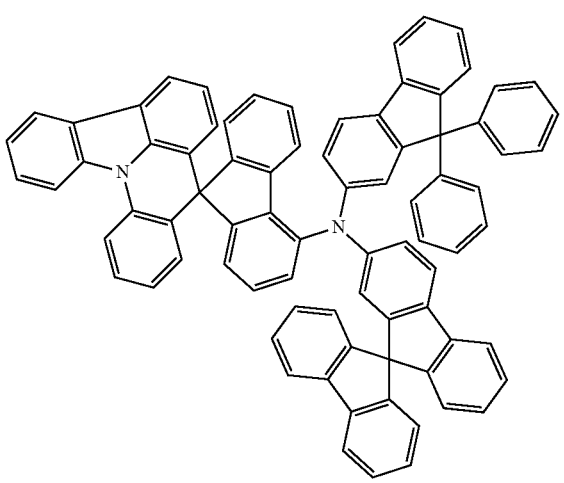
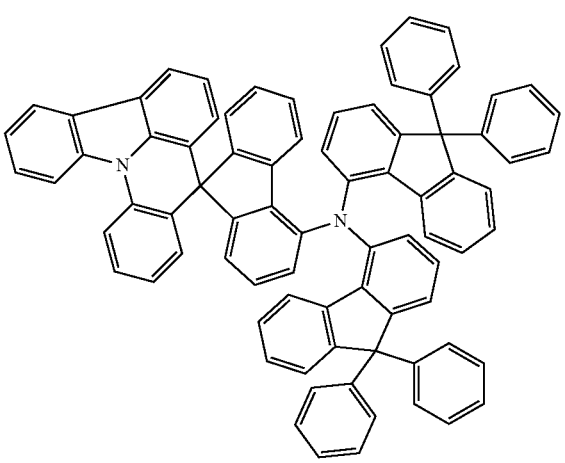
210
-continued
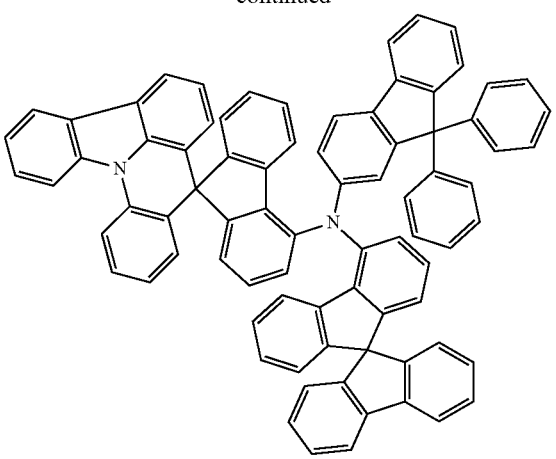
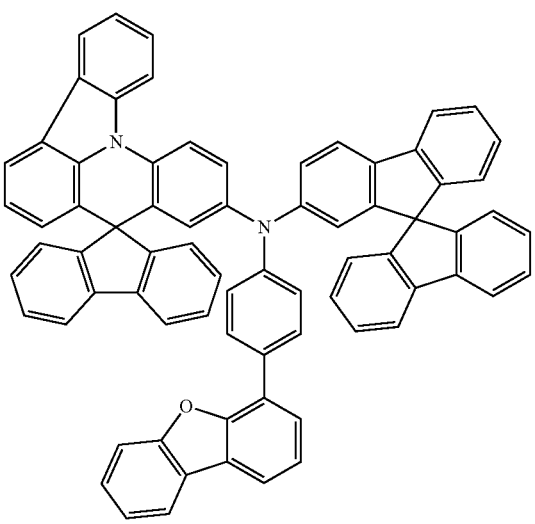
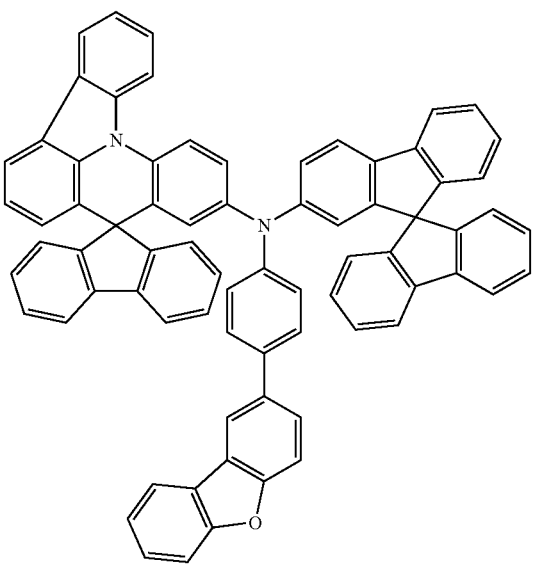

211
-continued
212
-continued
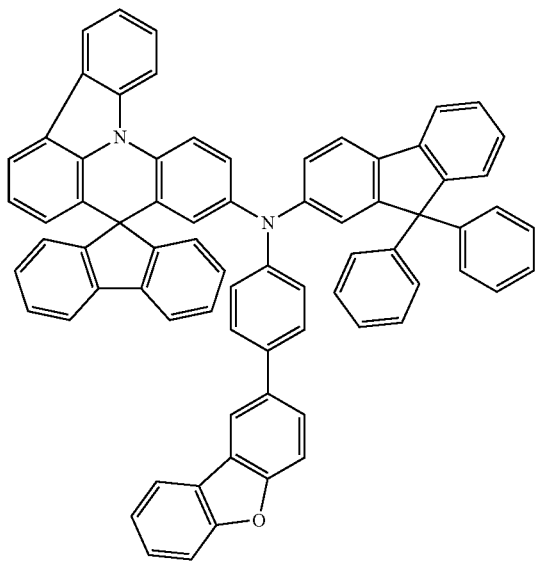
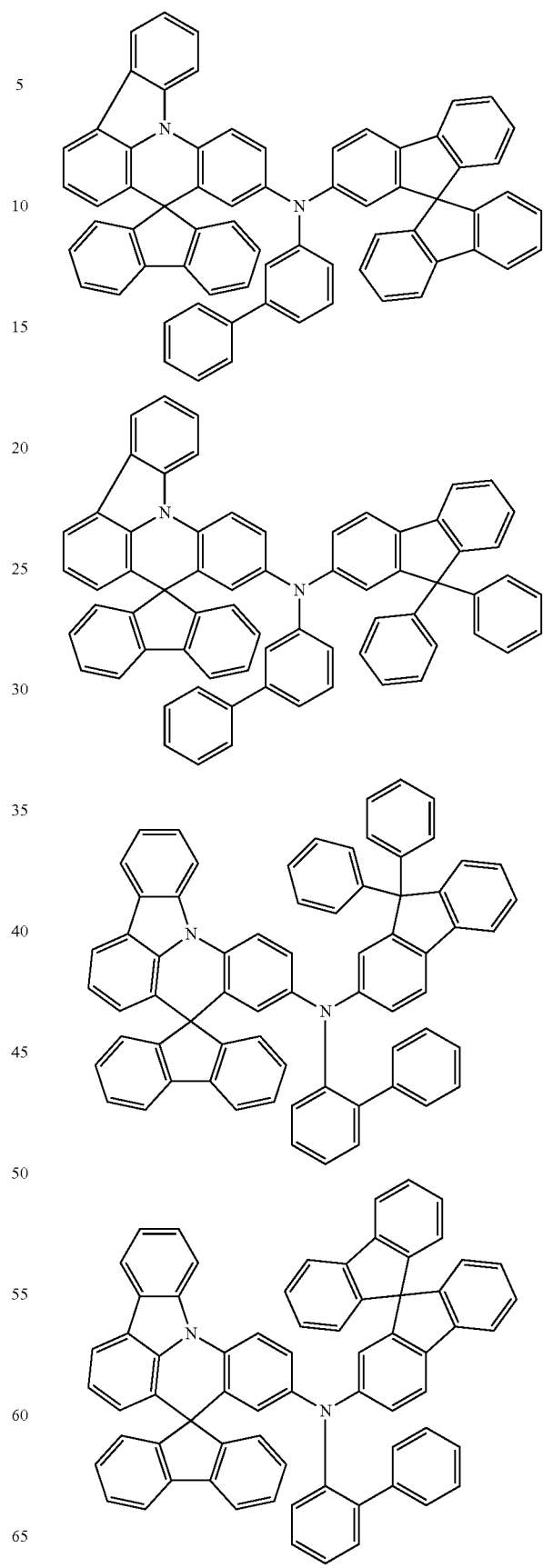

213
-continued
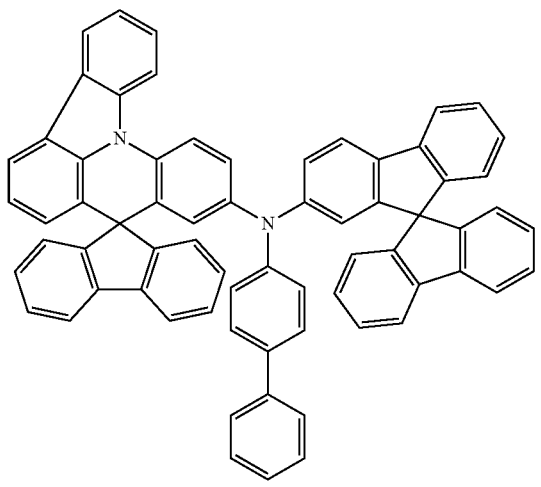
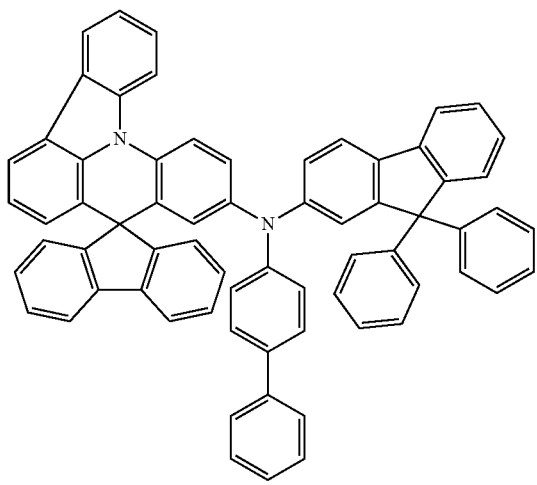
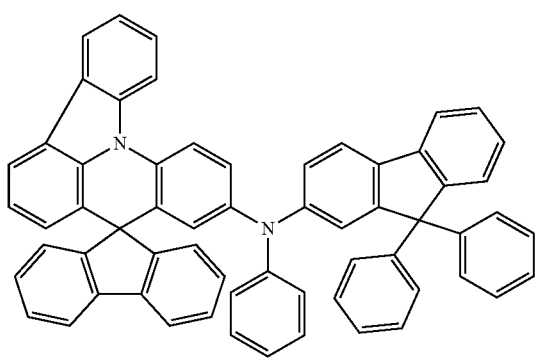
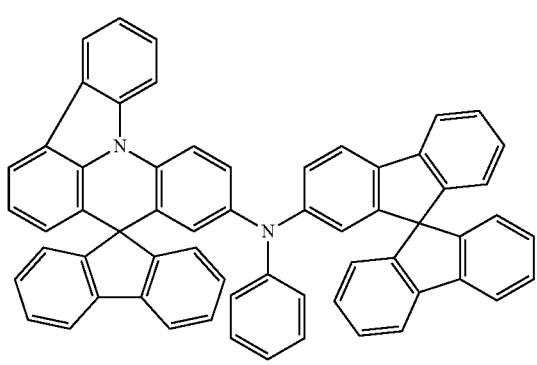
214
-continued
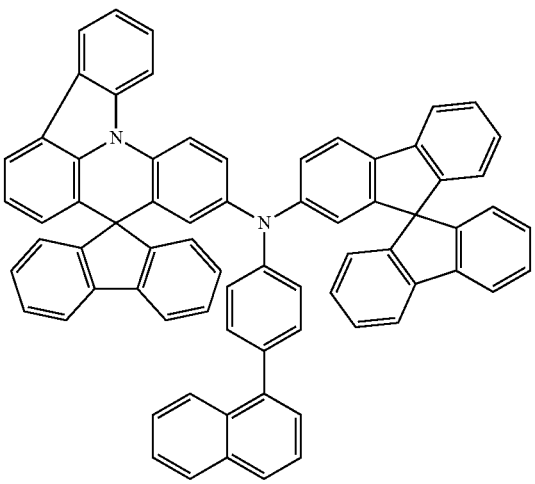
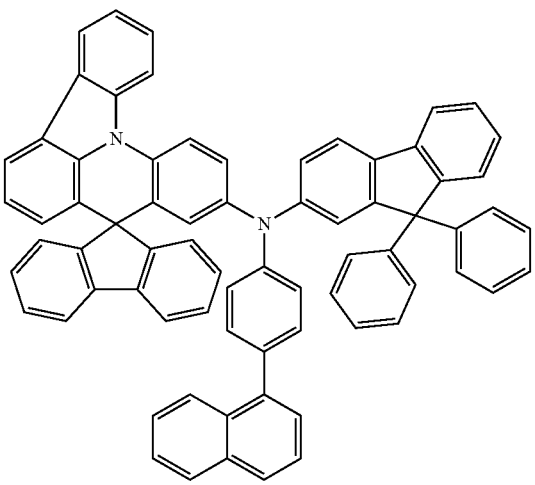
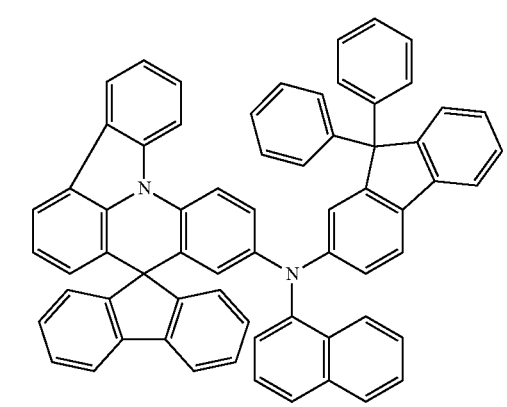

215
-continued
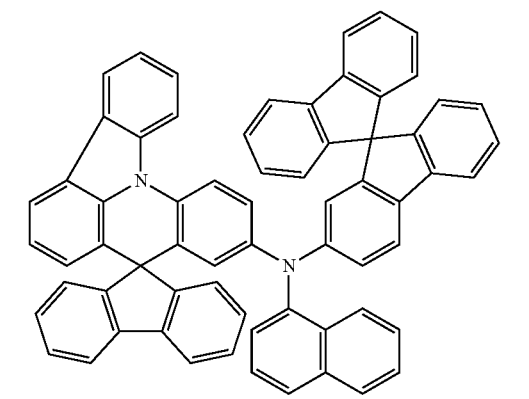
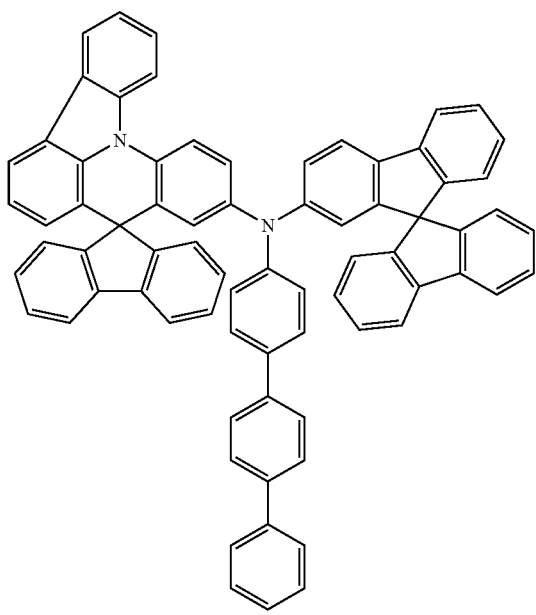
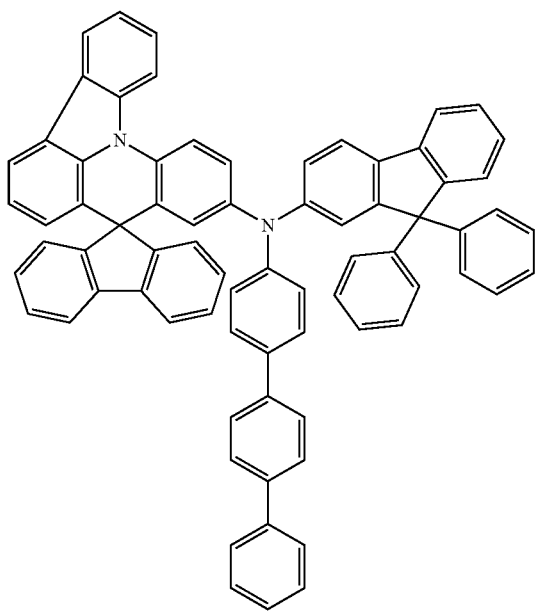
216
-continued
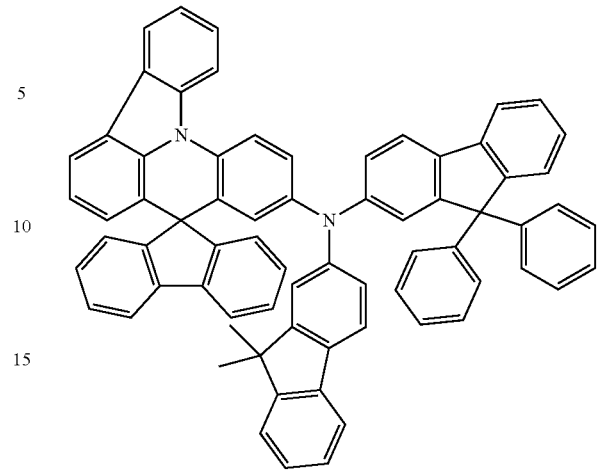
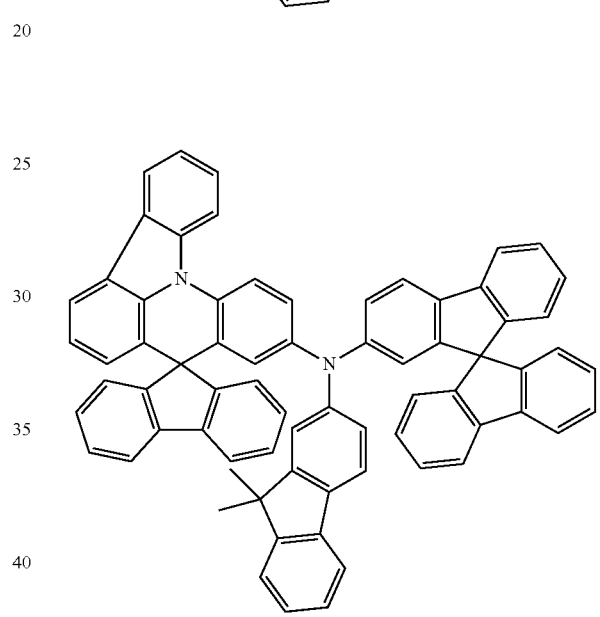
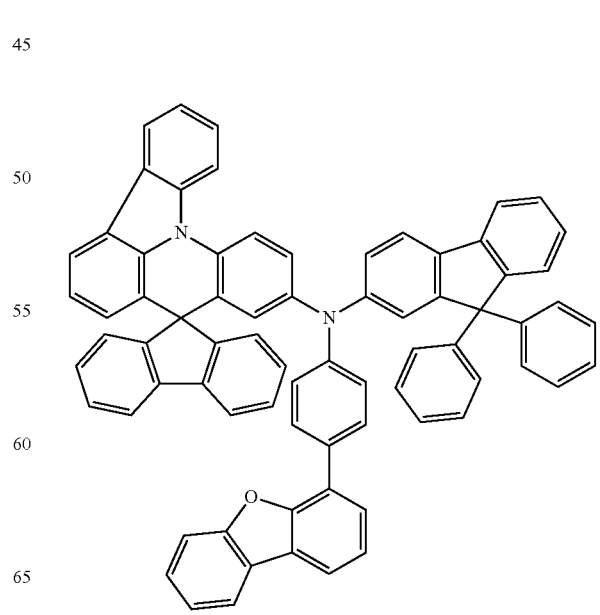

217
-continued
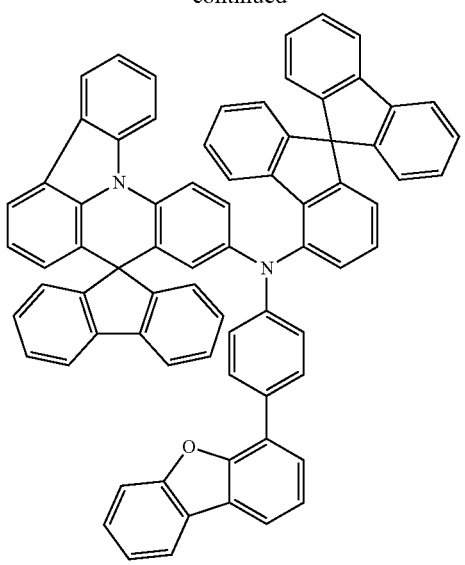
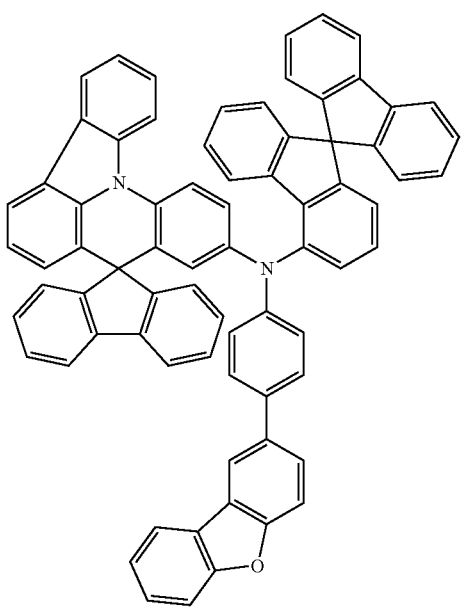
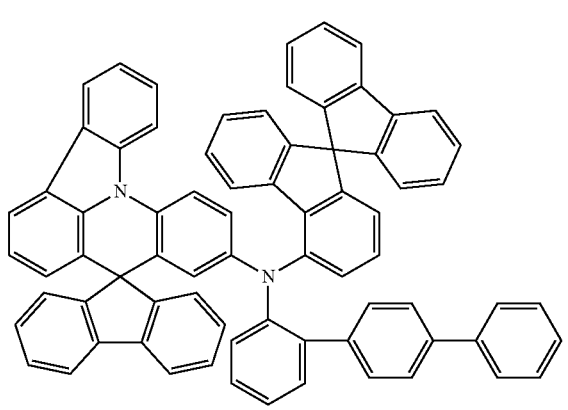
218
-continued
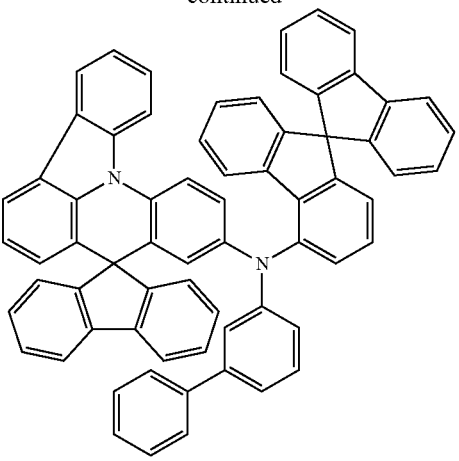
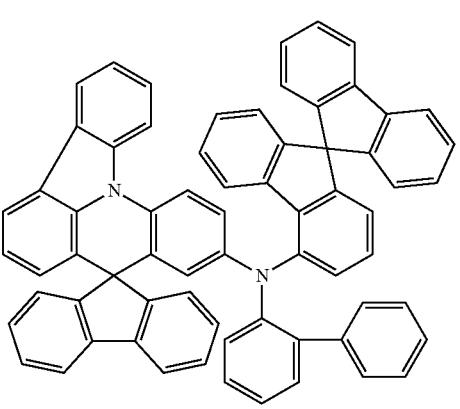
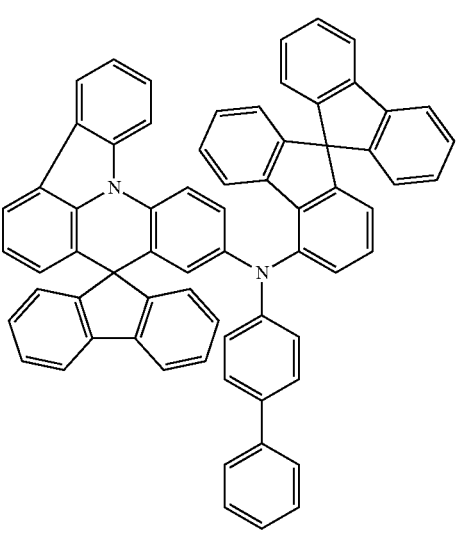

219
-continued
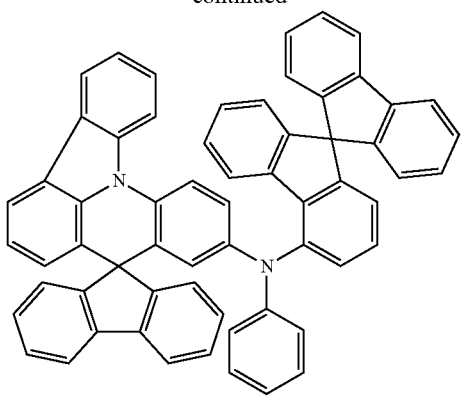
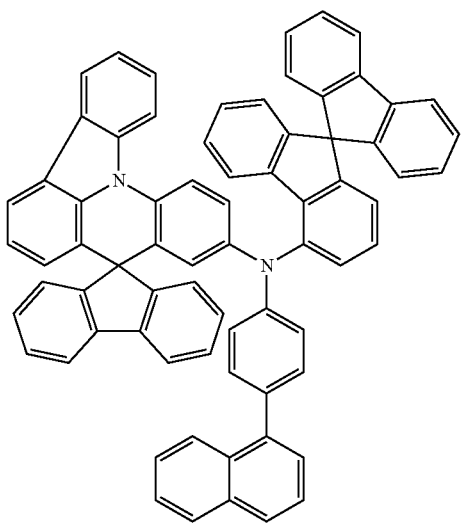
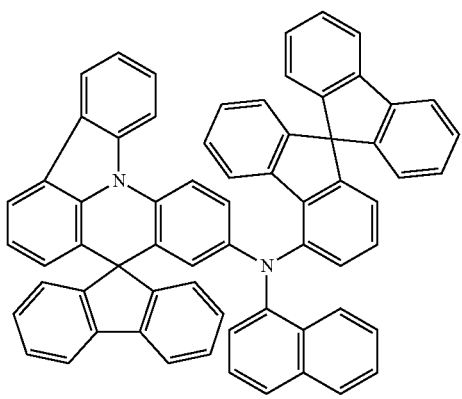
220
-continued
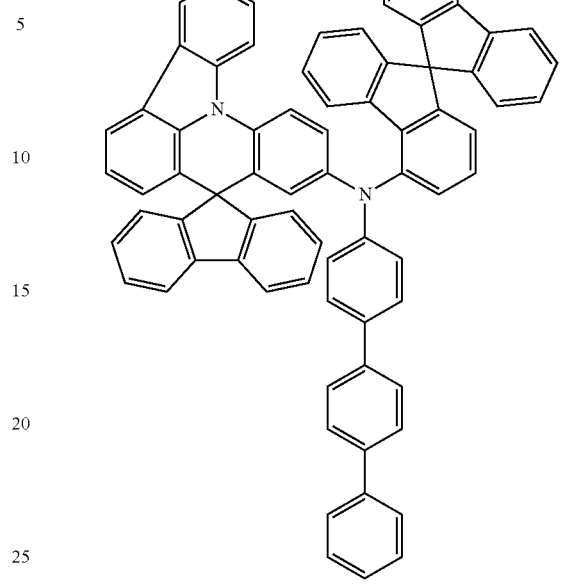
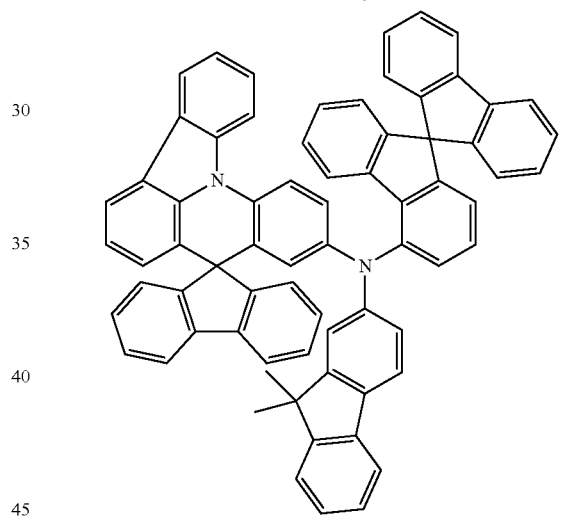

221
-continued
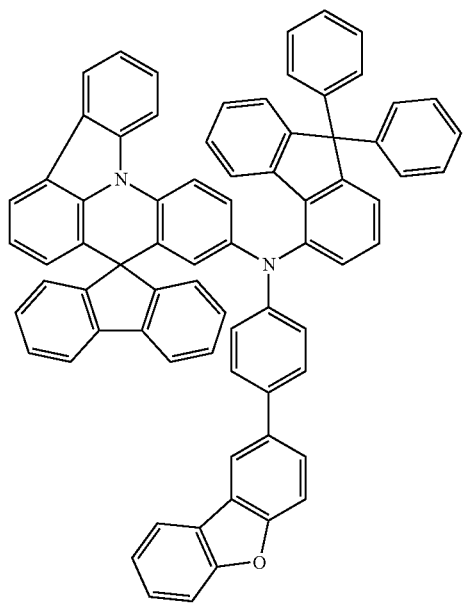
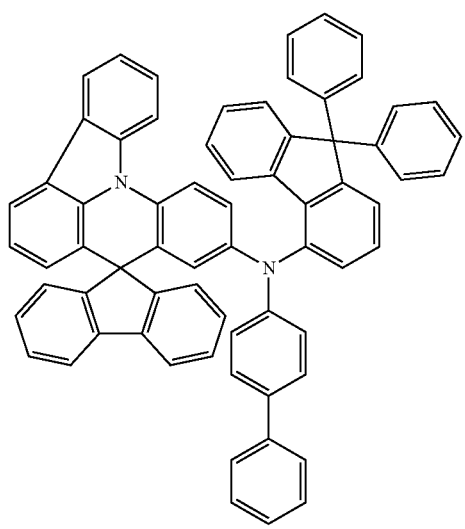
222
-continued
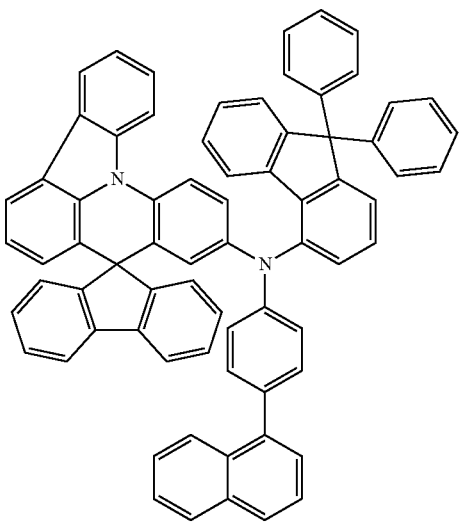
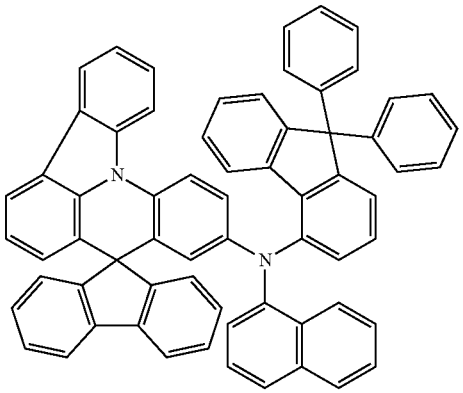

223
-continued
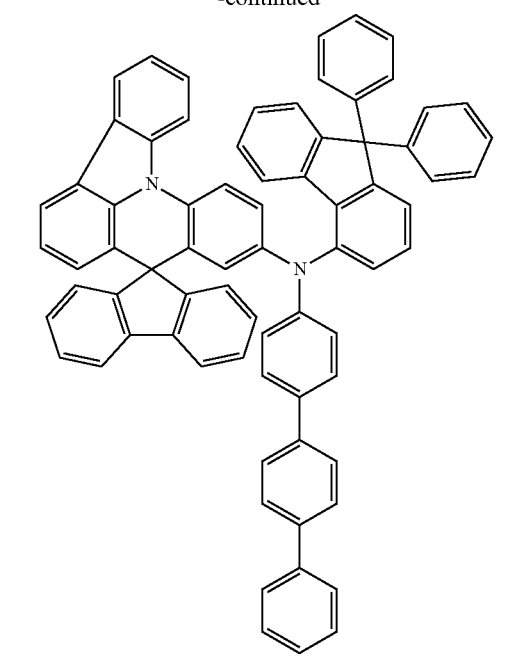
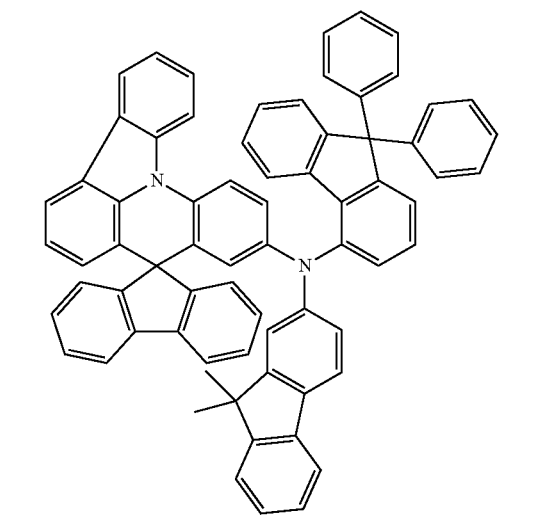
224
-continued
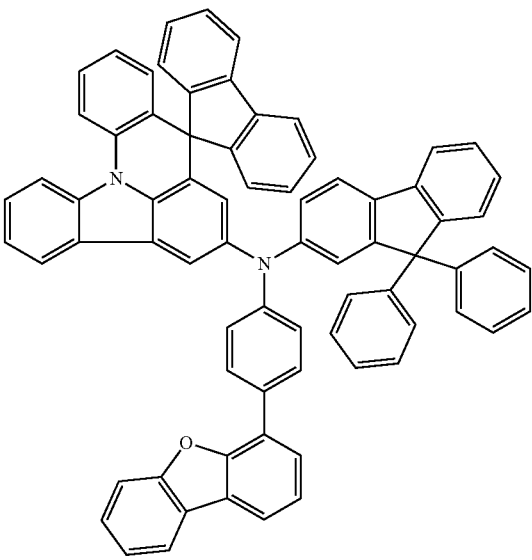
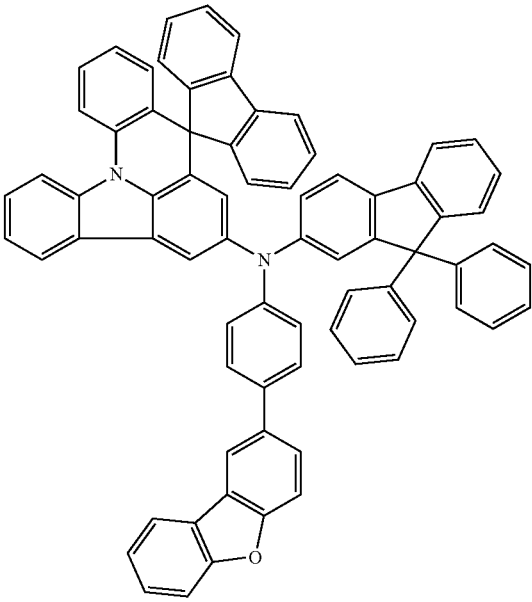

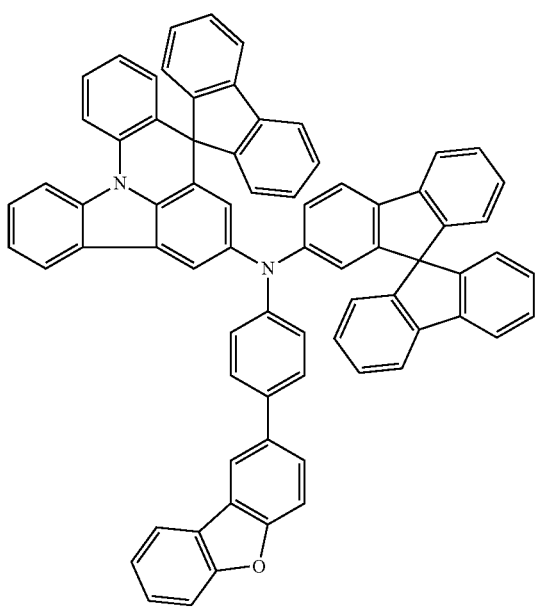
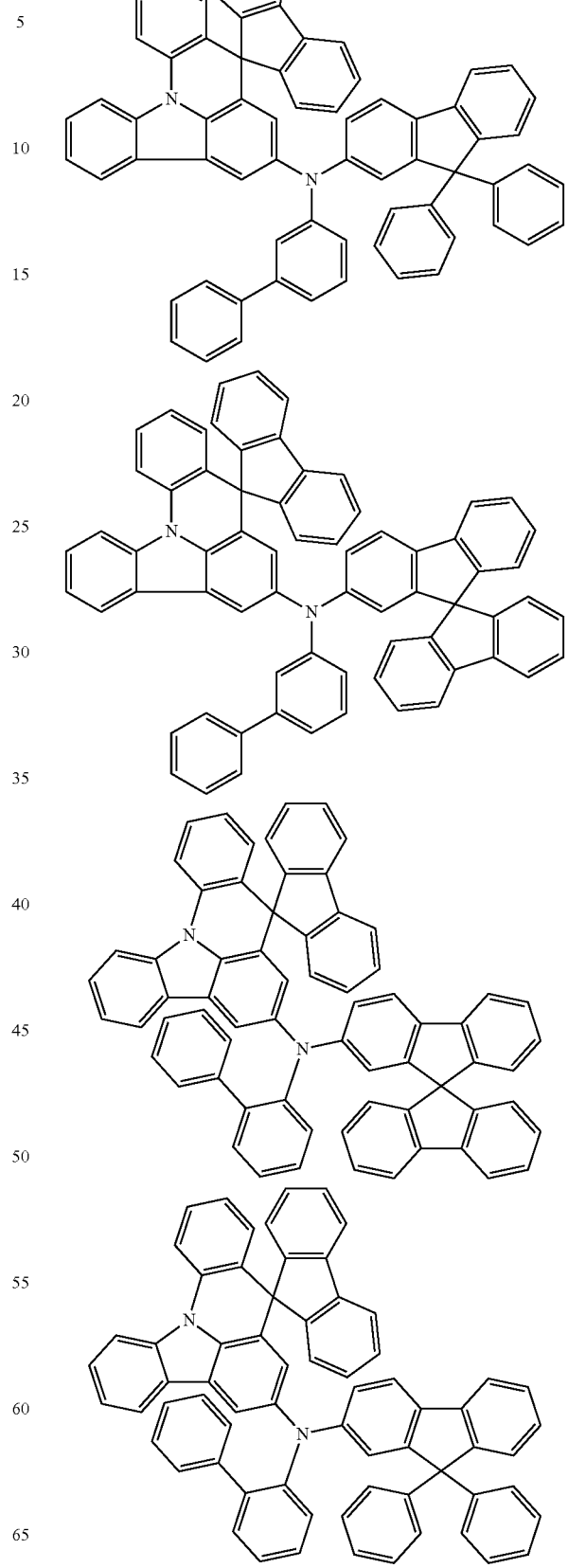

227
-continued
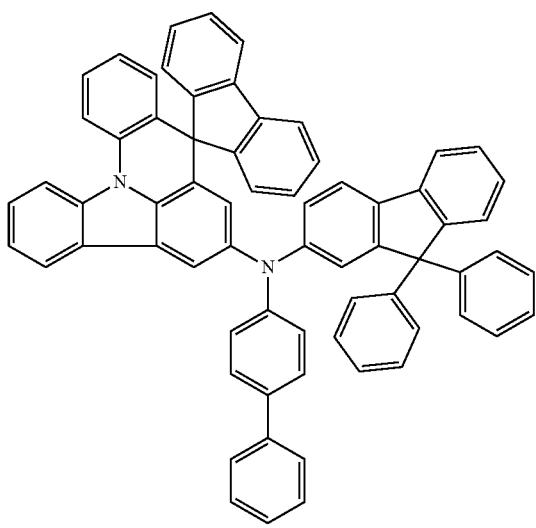
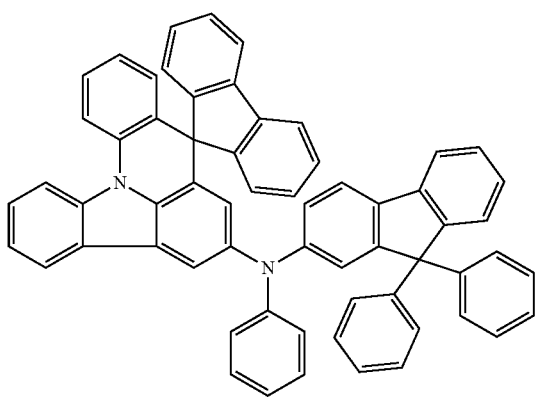
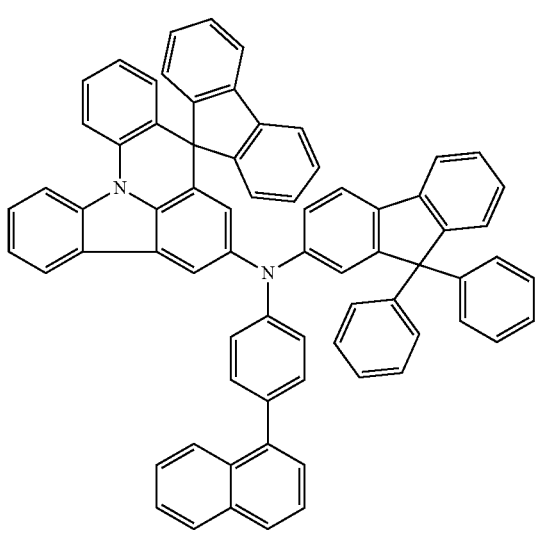
228
-continued
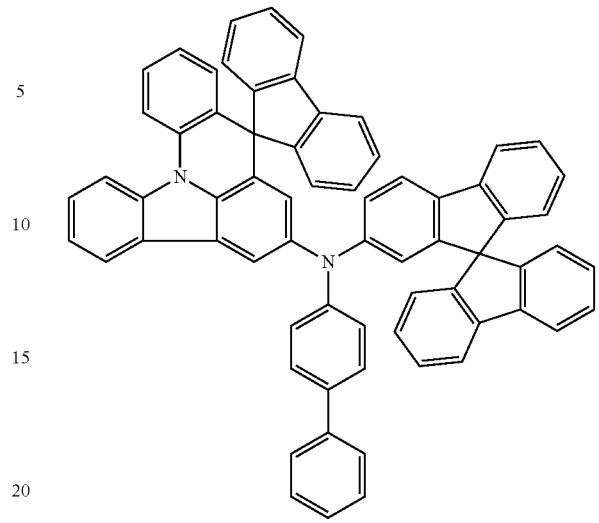
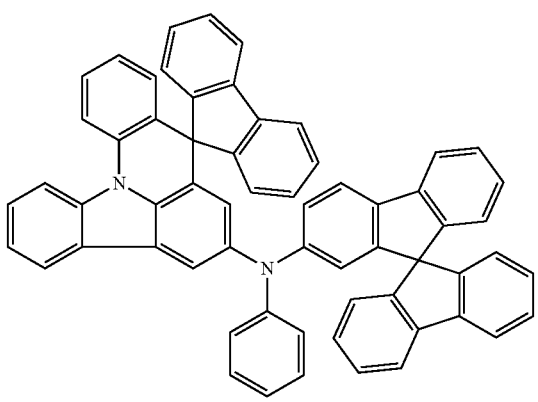
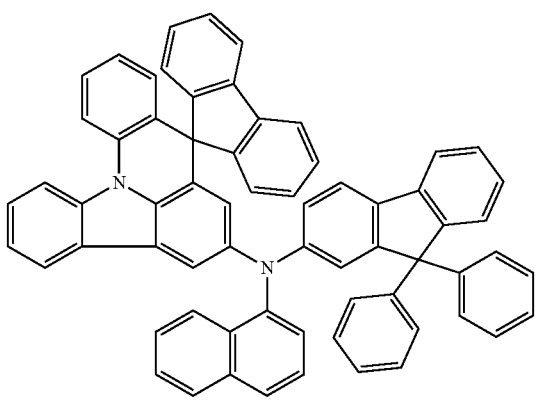

229
-continued
230
-continued
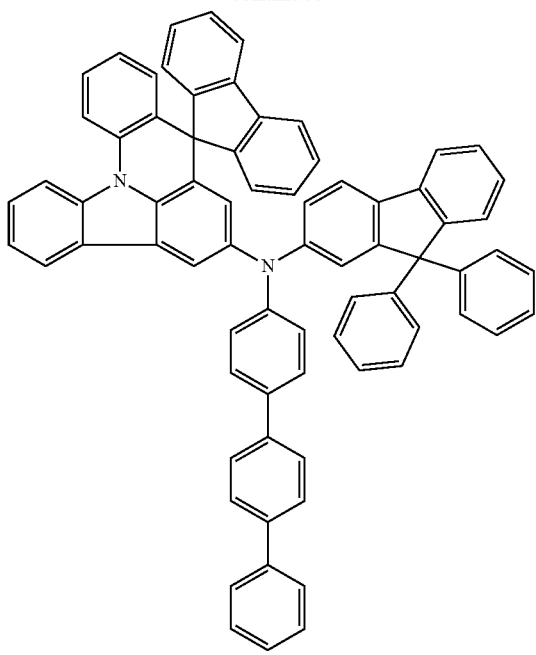
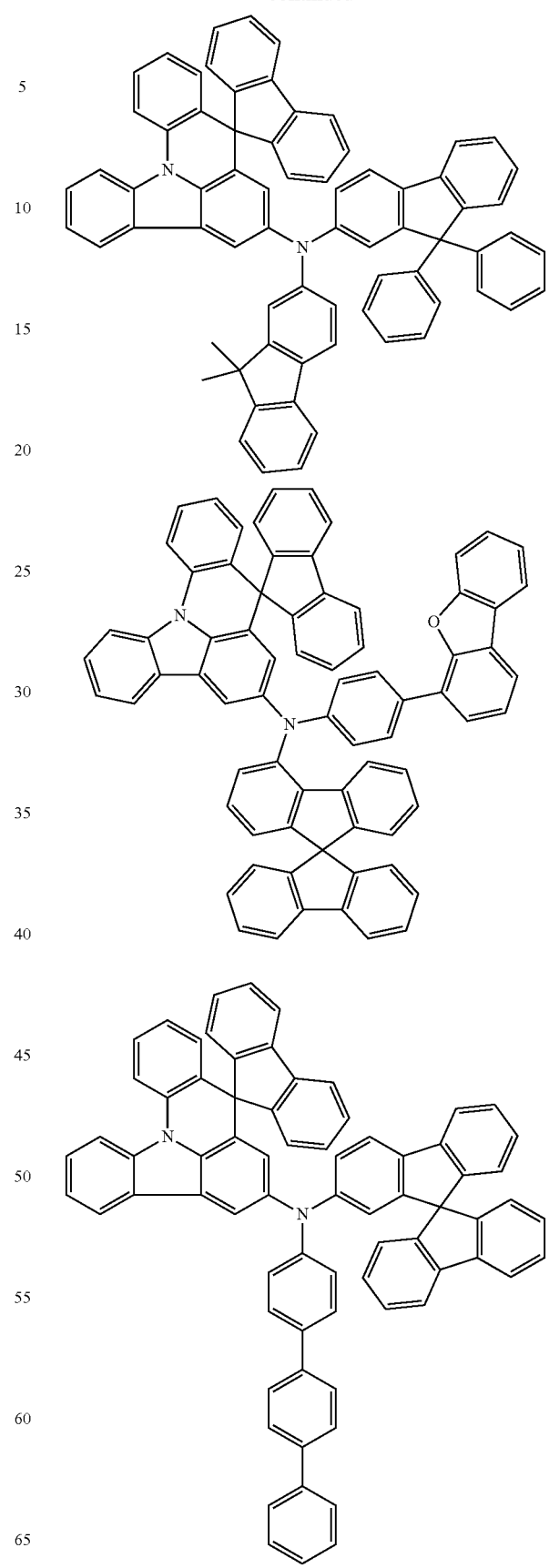

231
-continued
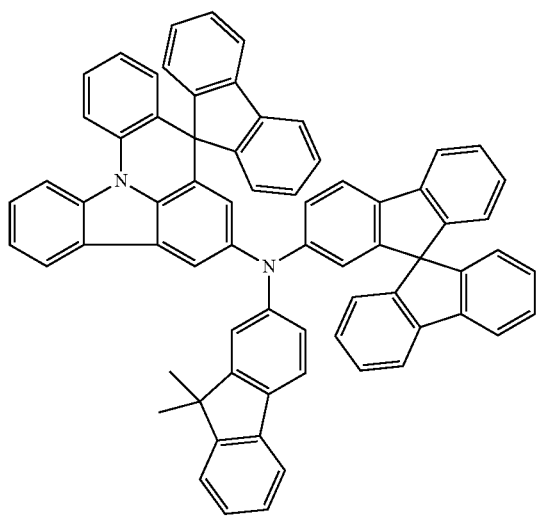
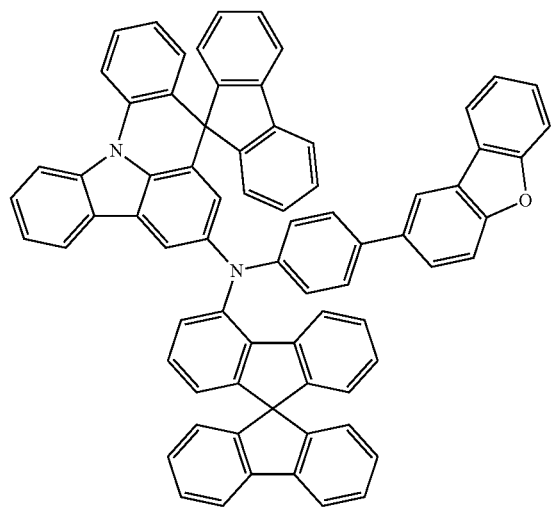
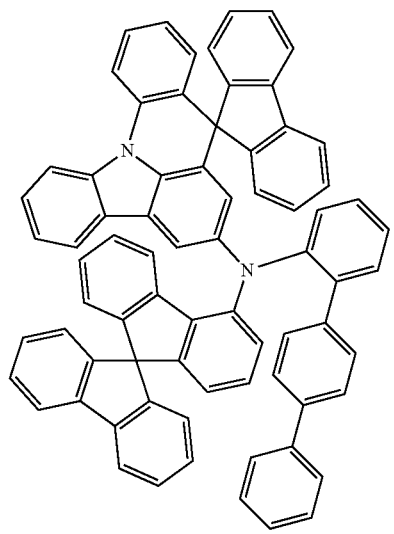
232
-continued
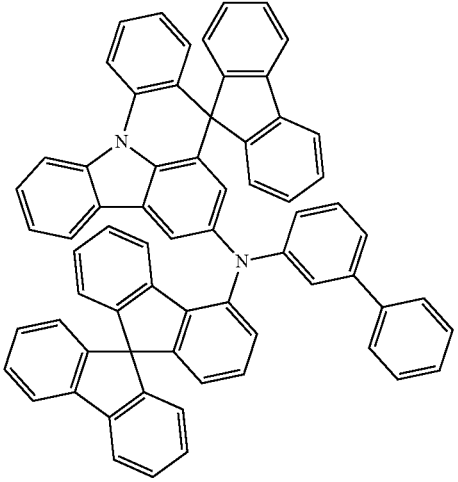
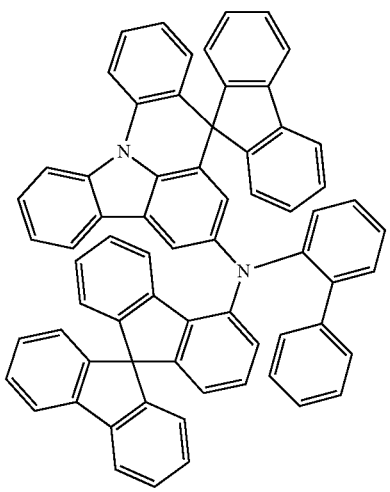
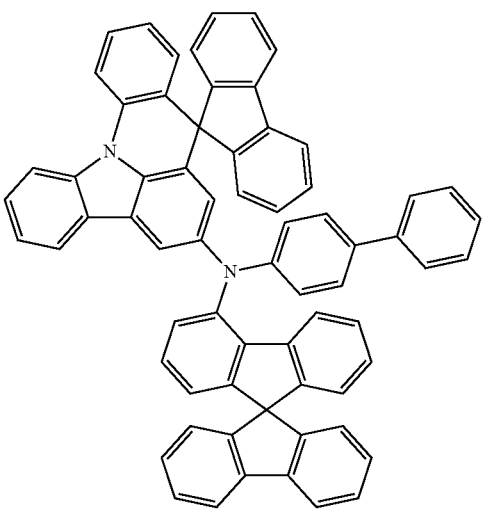

233
-continued
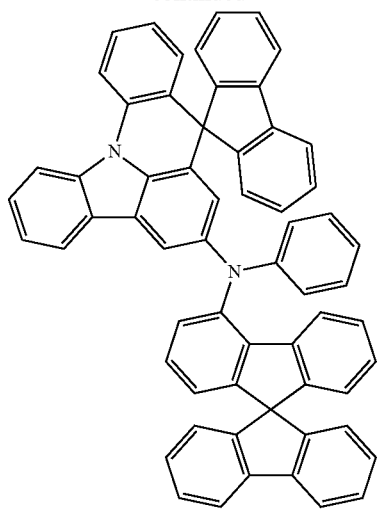
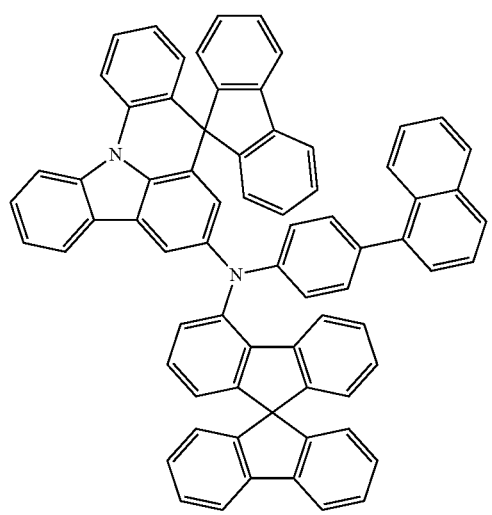
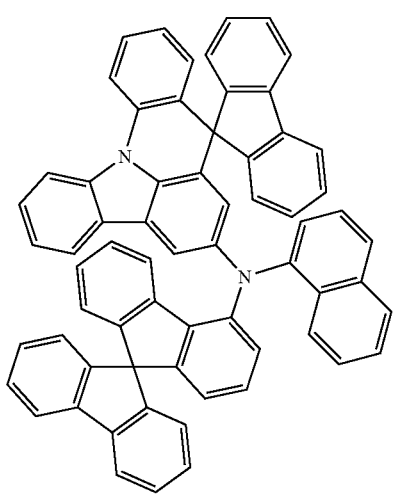
234
-continued
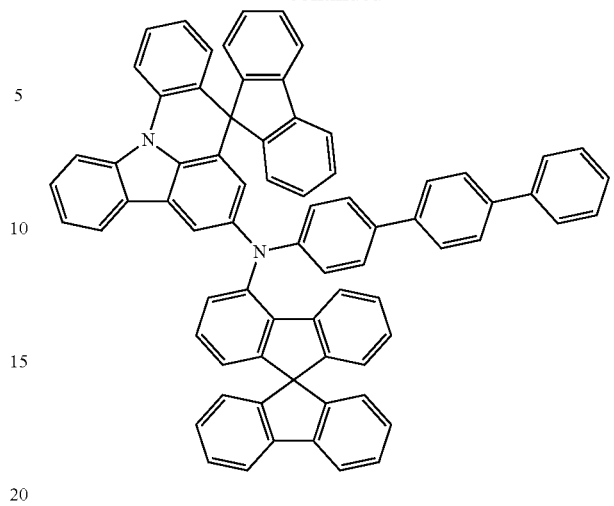
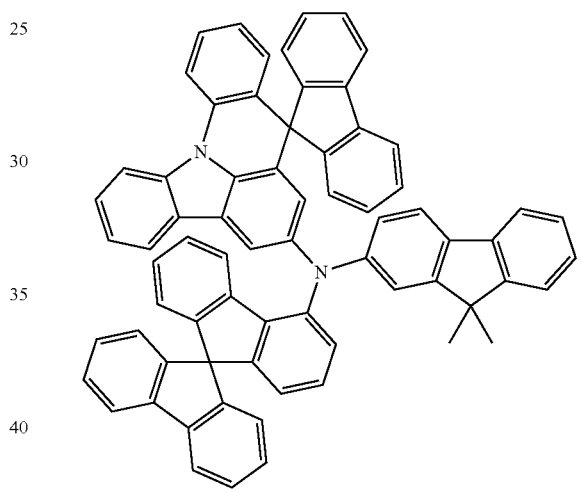
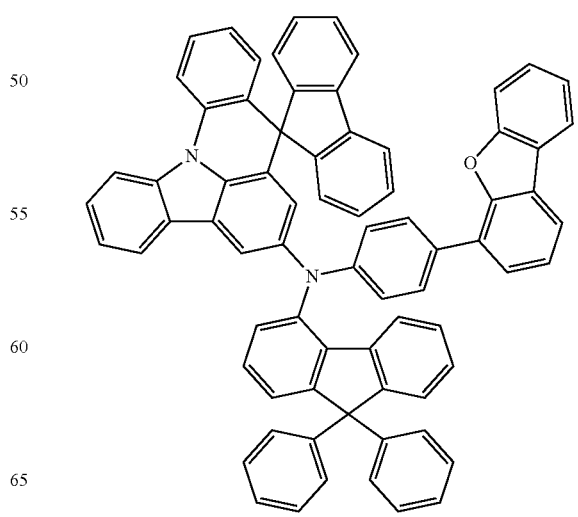

235
-continued
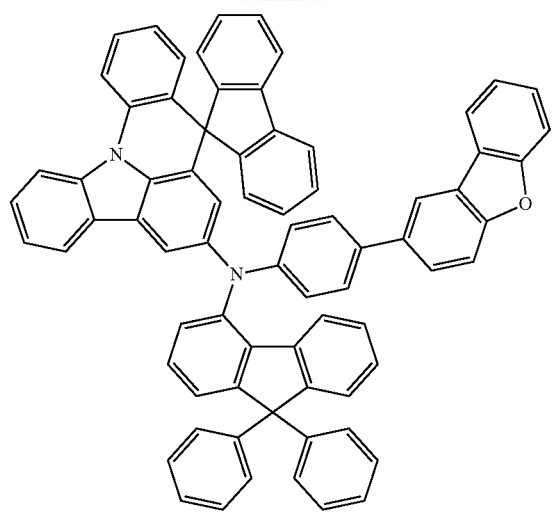
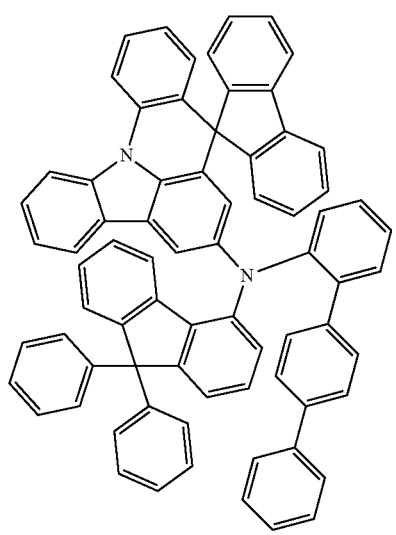
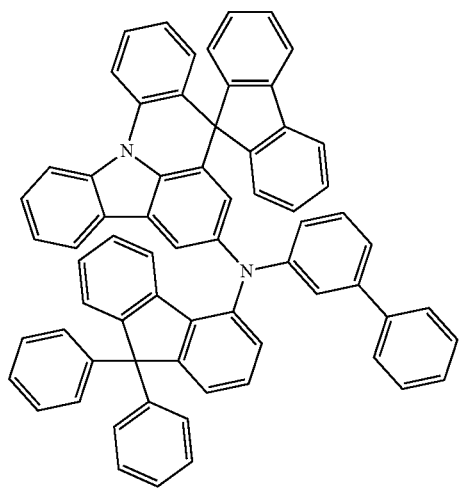
236
-continued
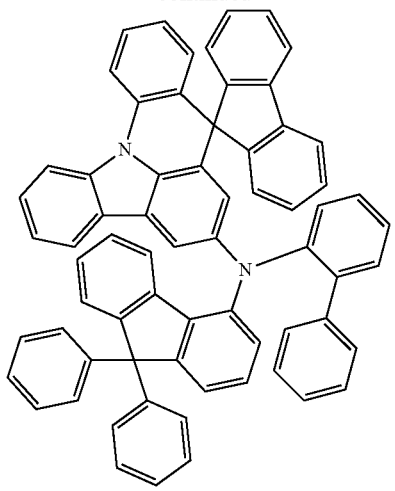
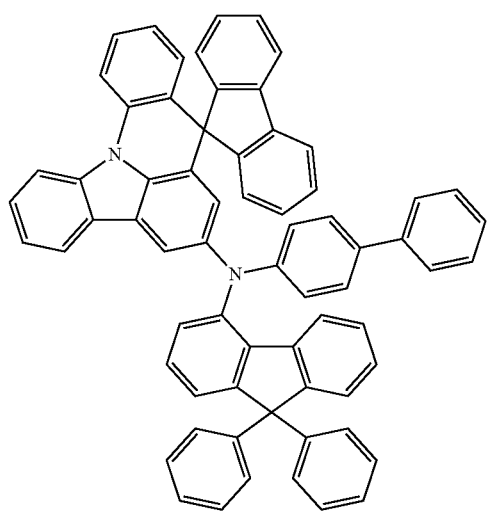
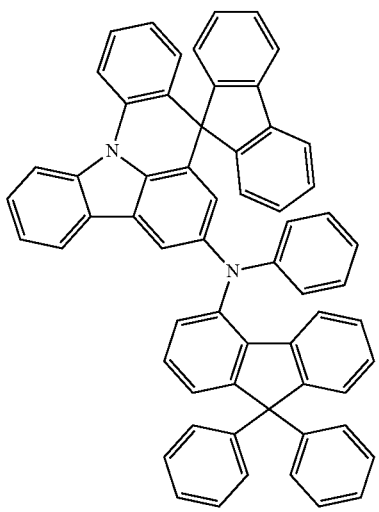

237
-continued
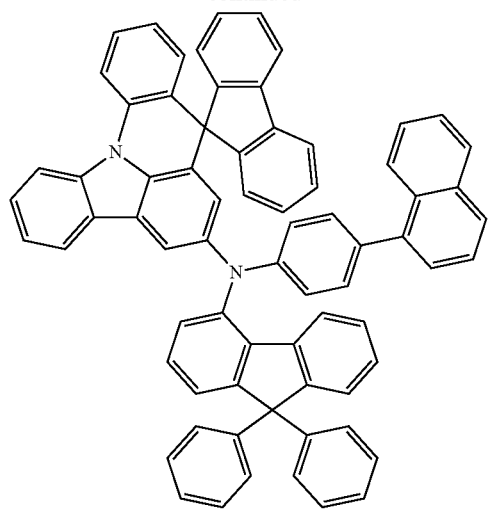
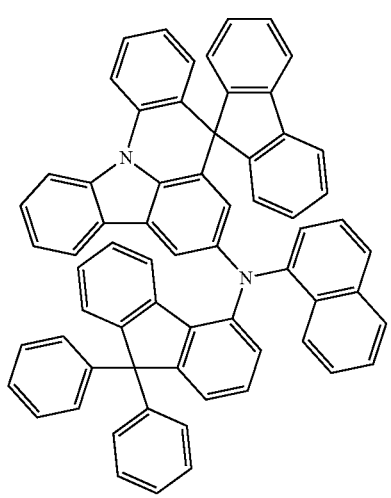
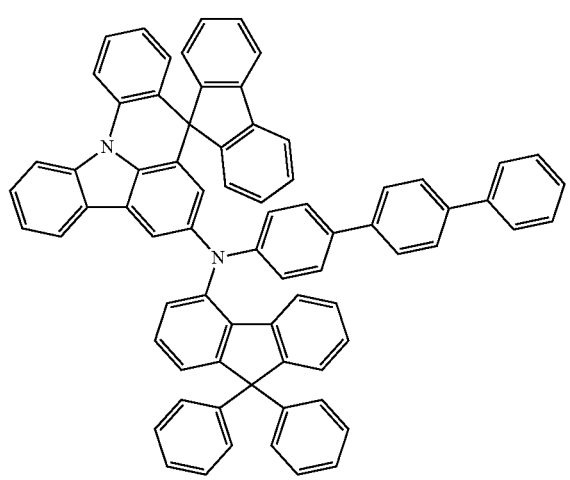
238
-continued
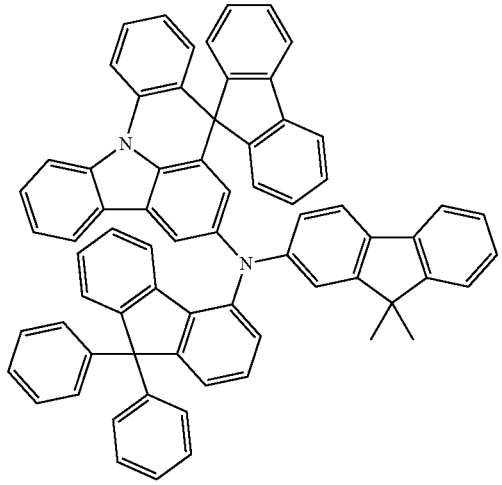
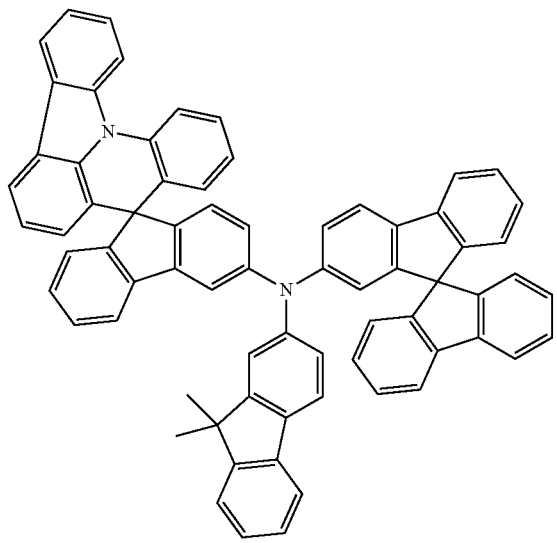
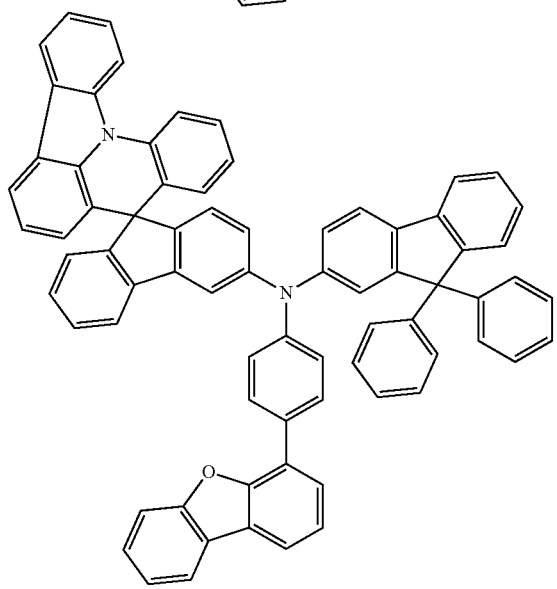

239
-continued
240
-continued
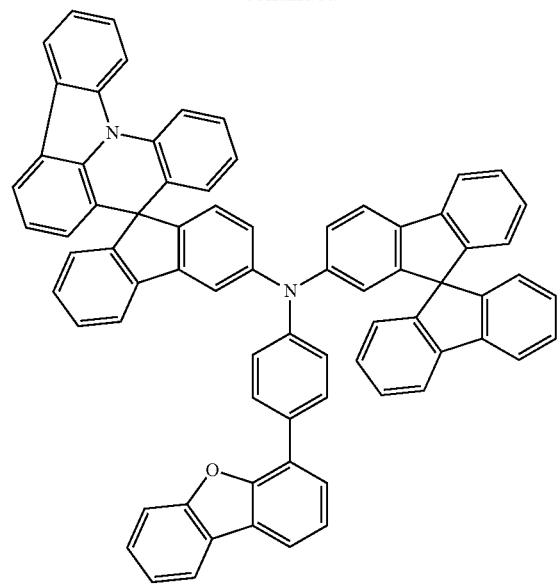
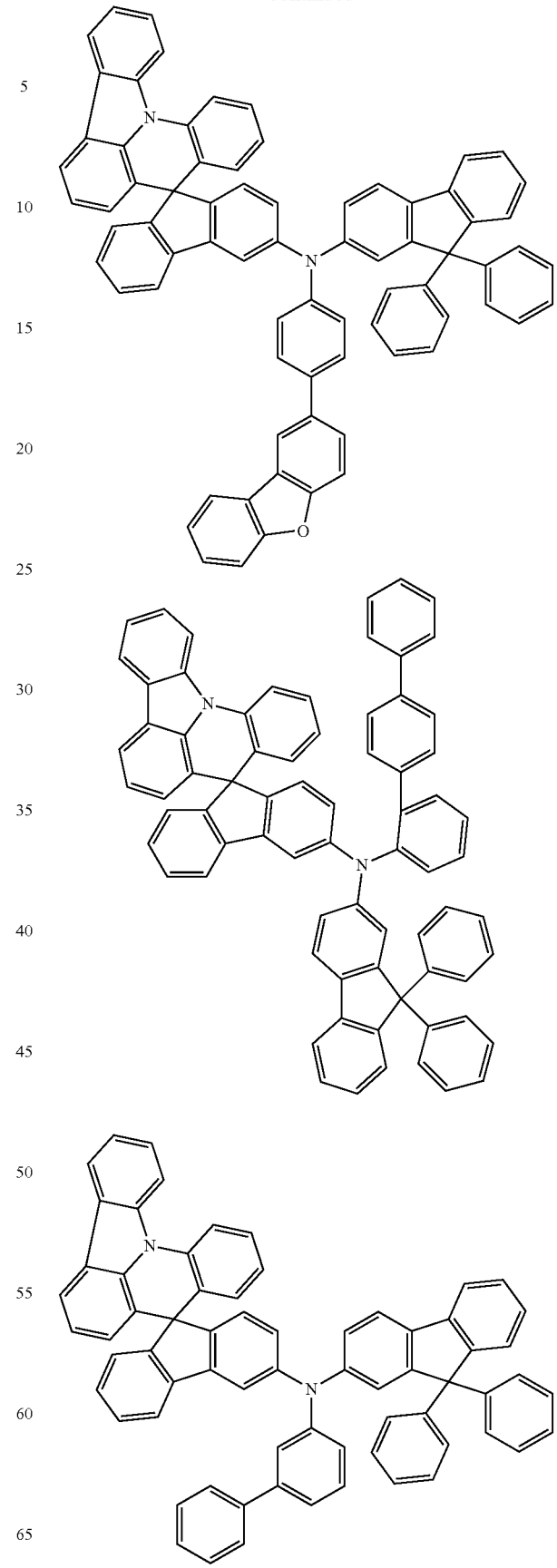

241
-continued
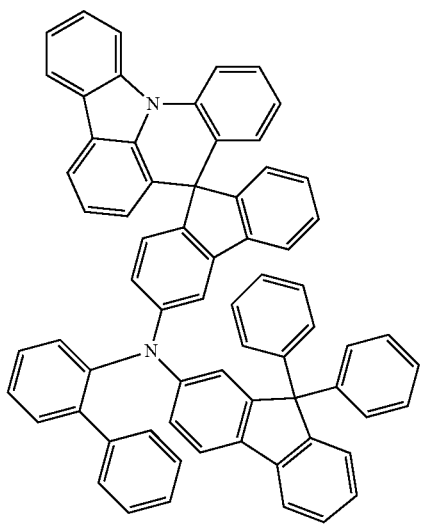
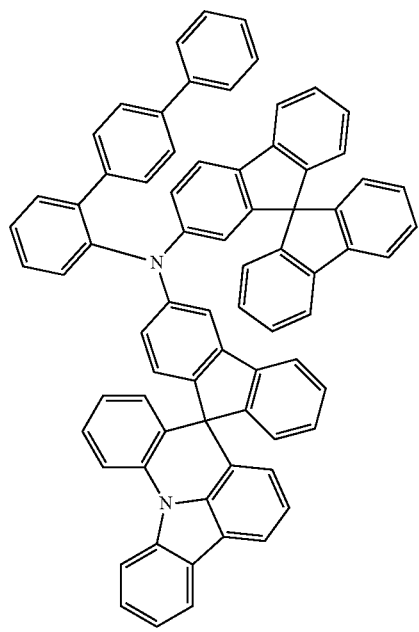
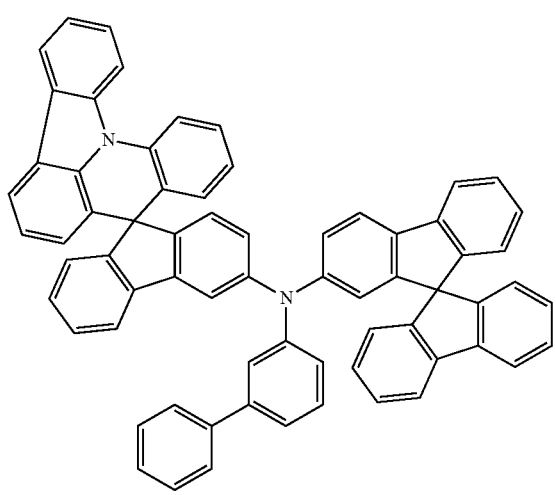
242
-continued
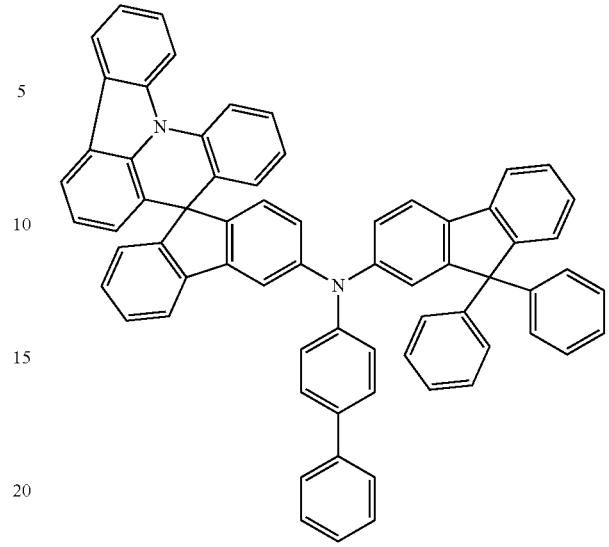
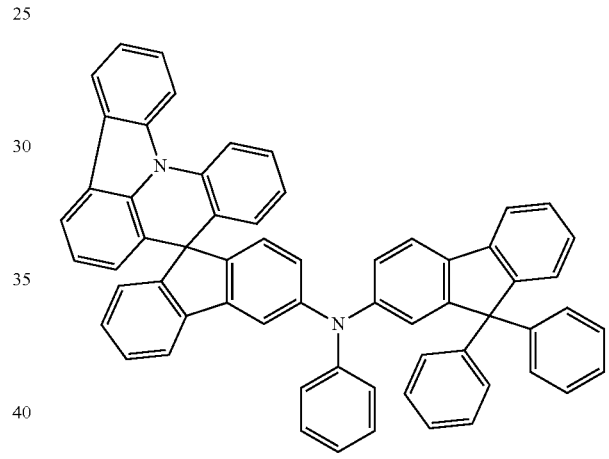
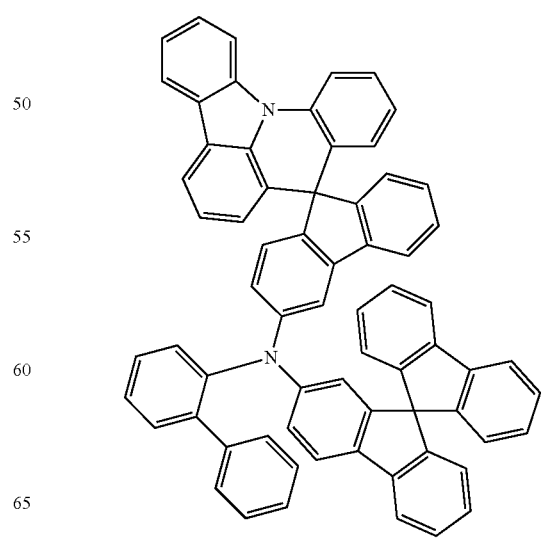

243
-continued
244
-continued
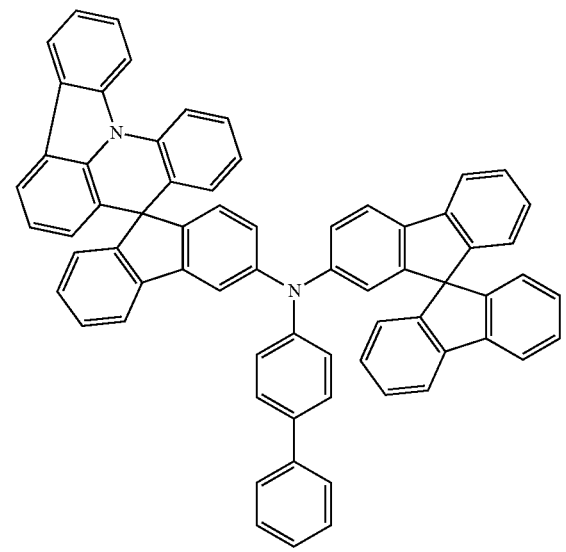
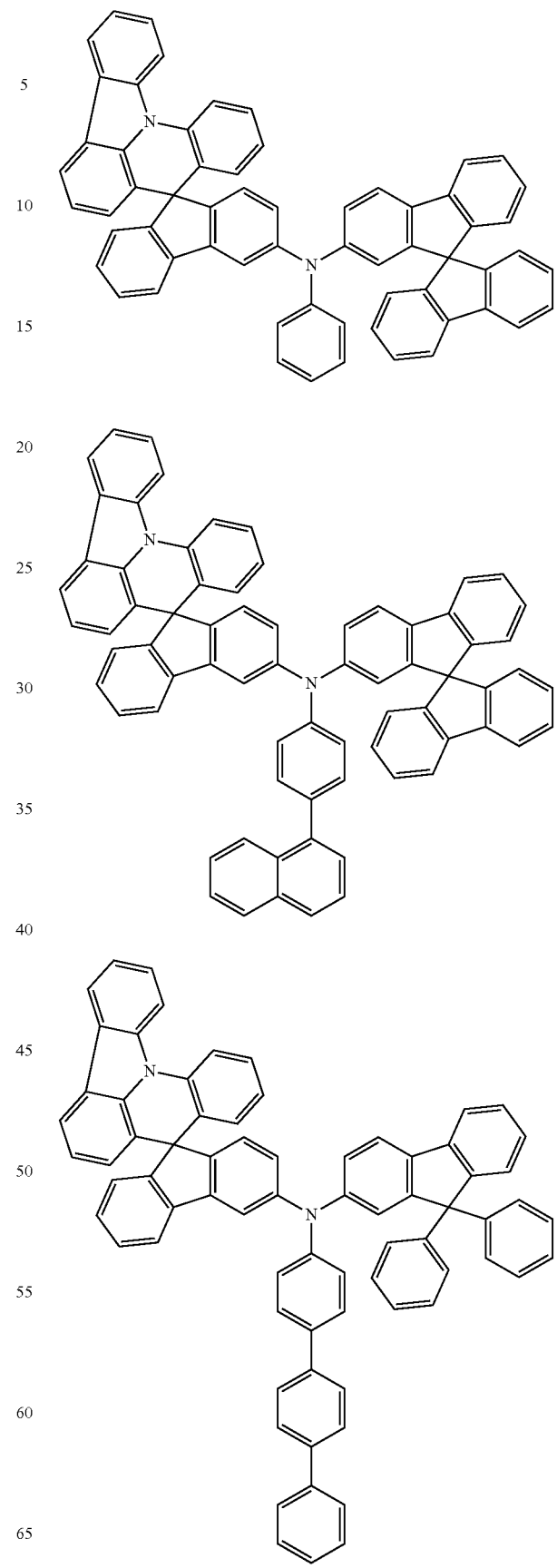

245
-continued
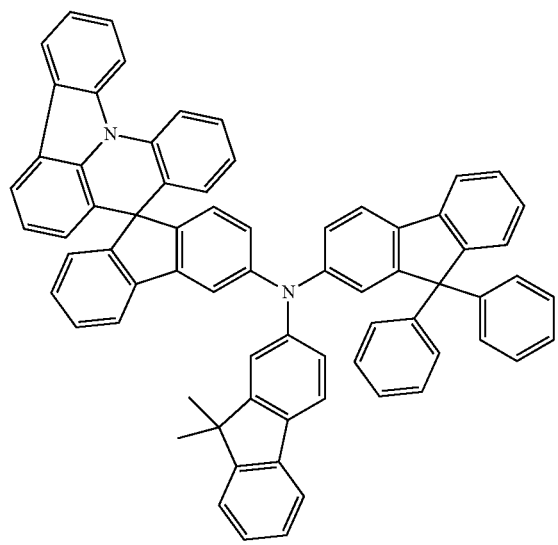
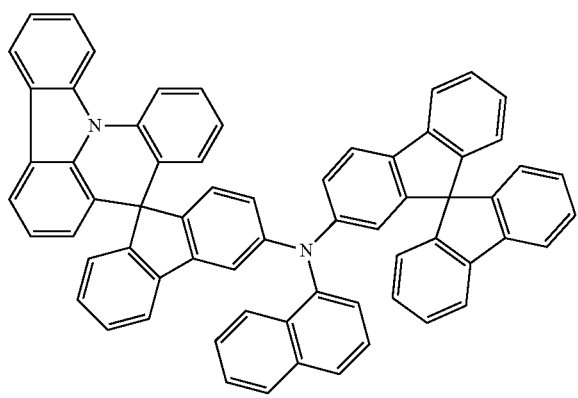
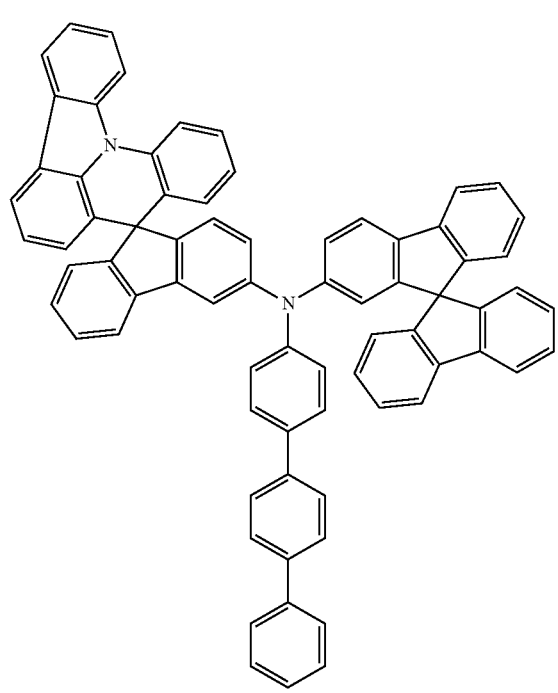
246
-continued
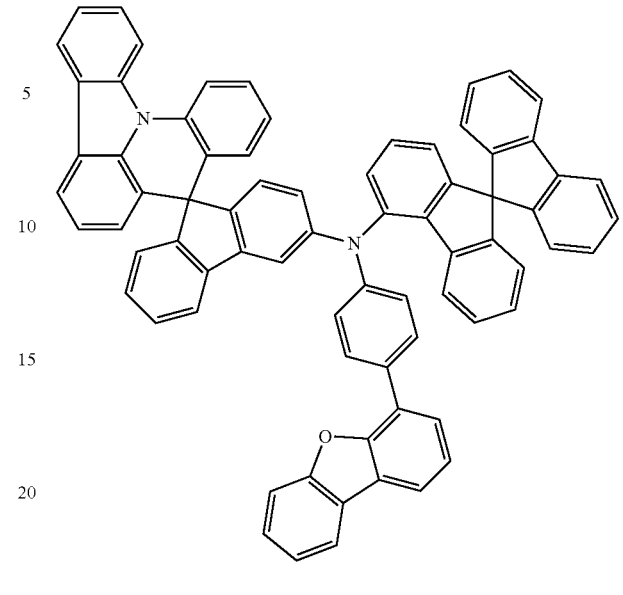
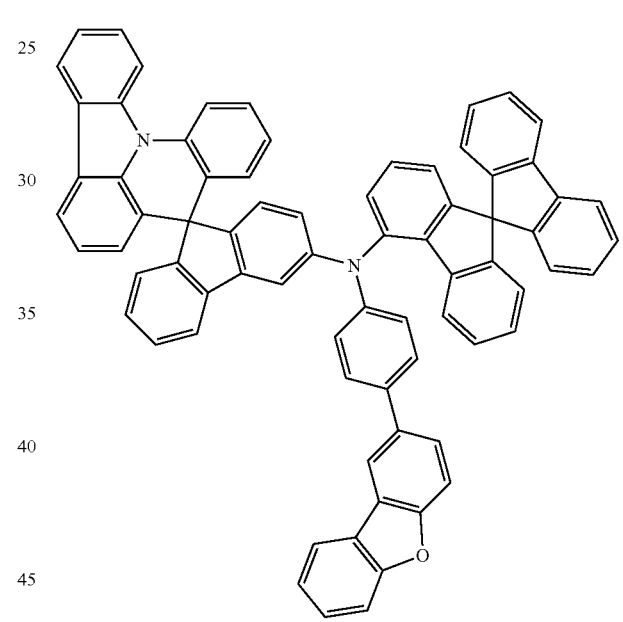
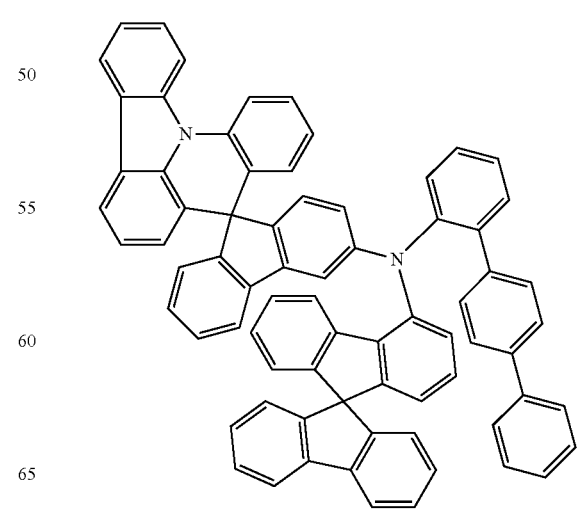

247
-continued
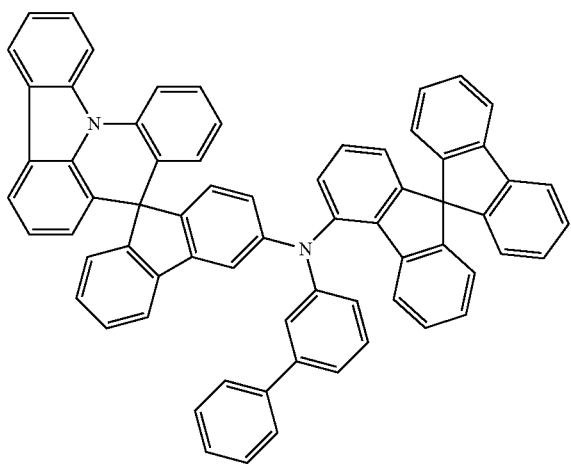
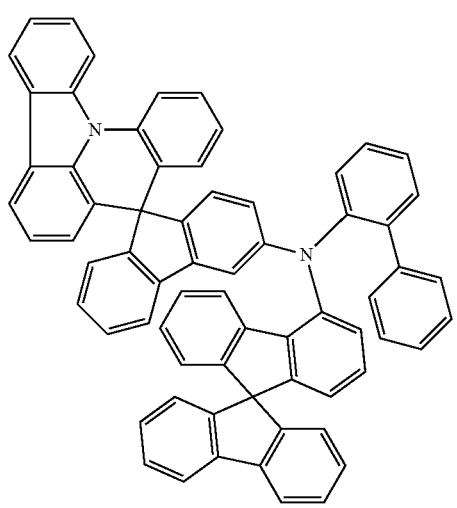
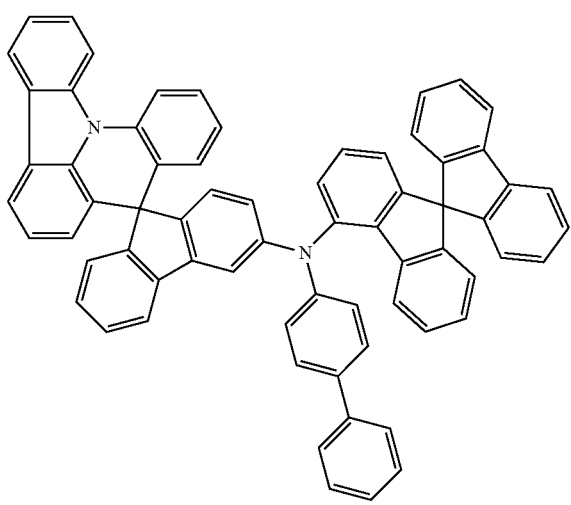
248
-continued
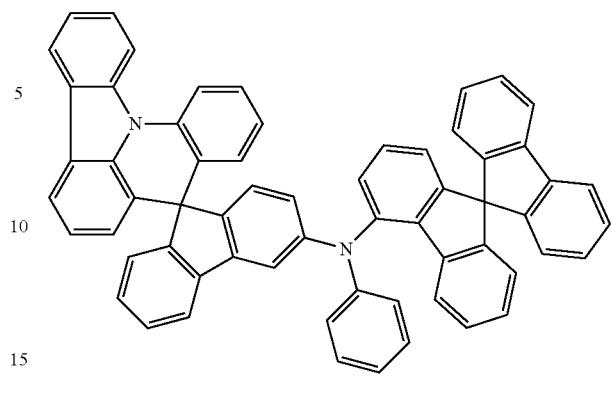
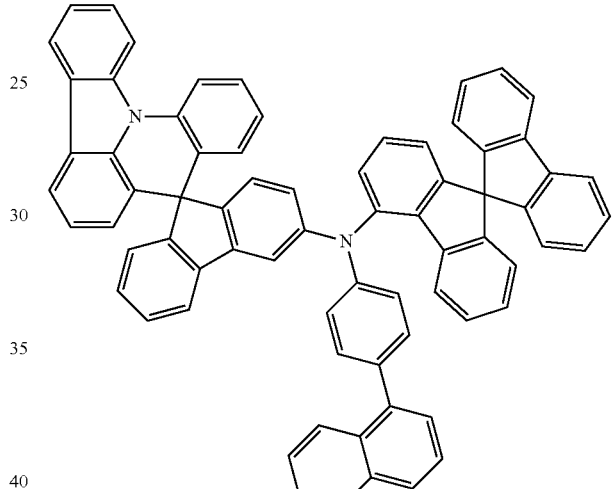
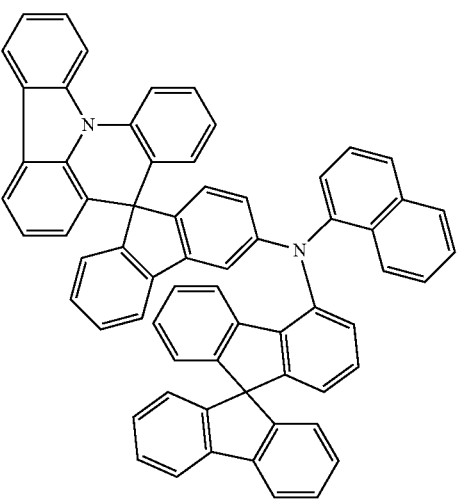

249
-continued
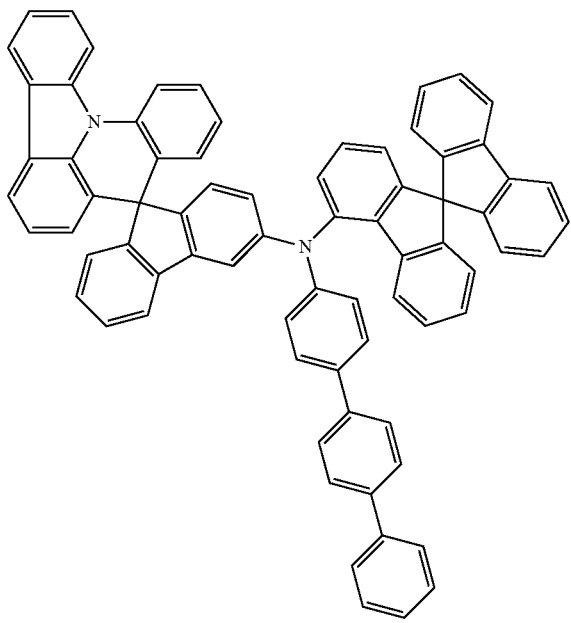
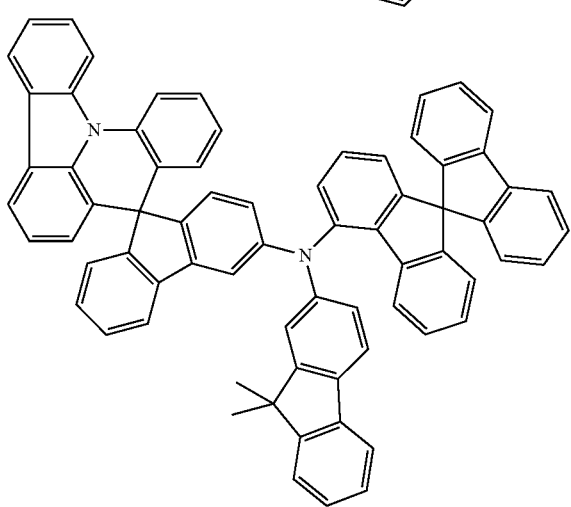
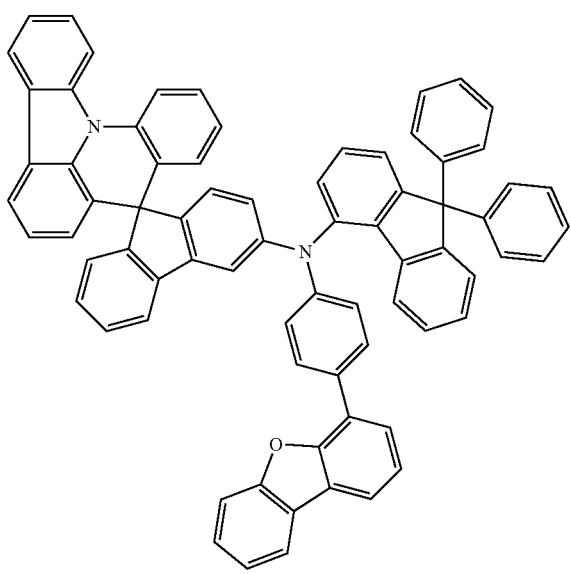
250
-continued
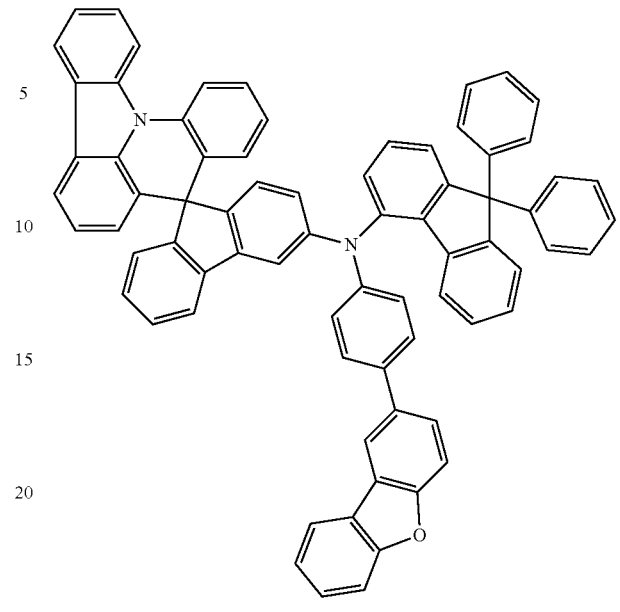
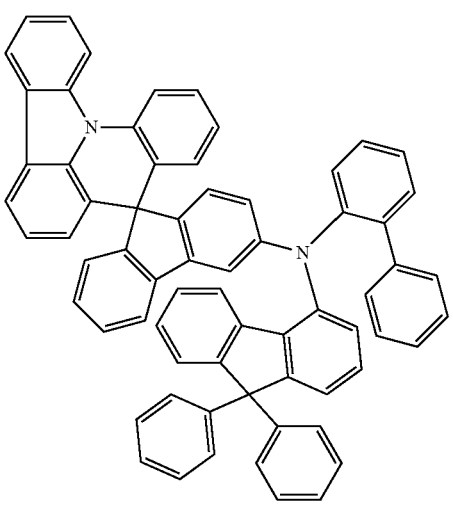
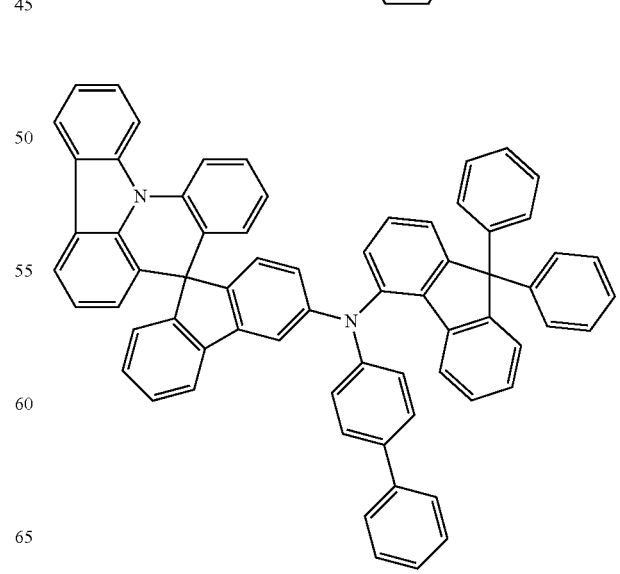

251
-continued
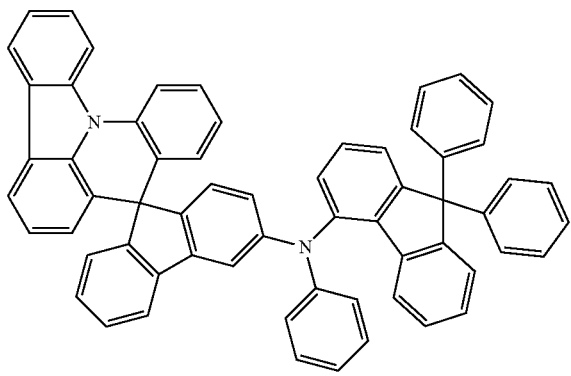
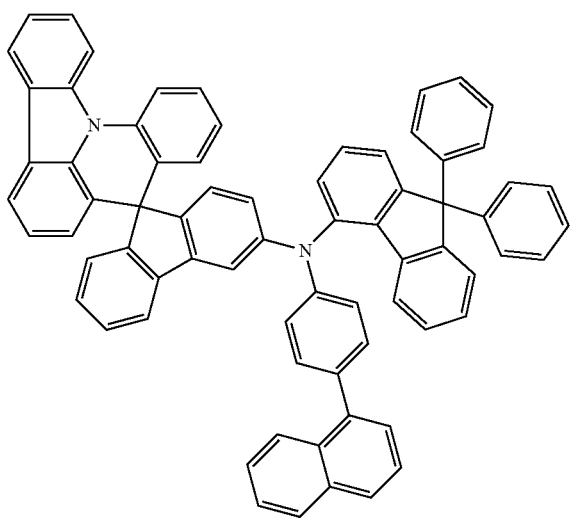
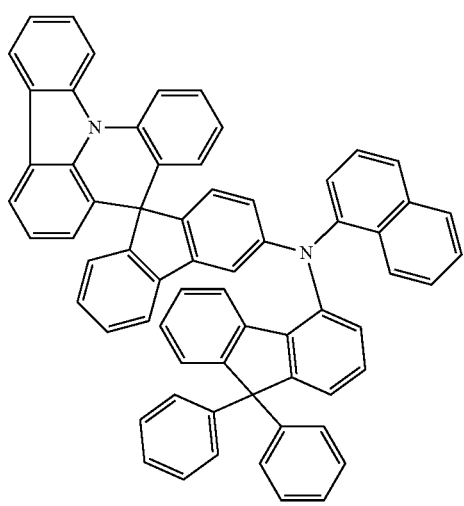
252
-continued
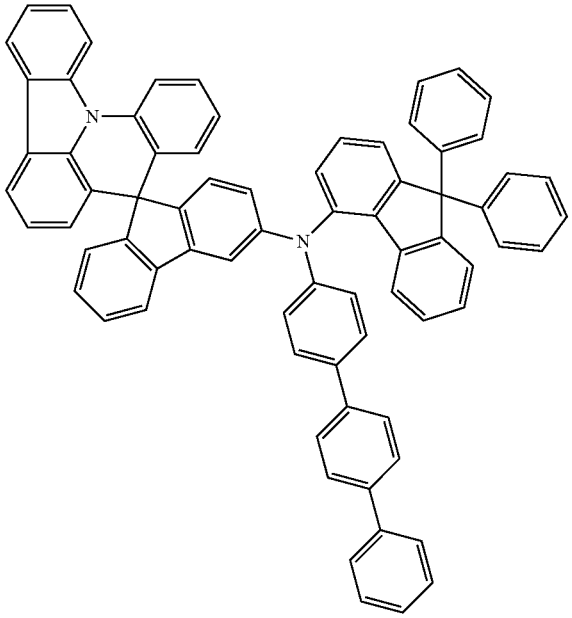
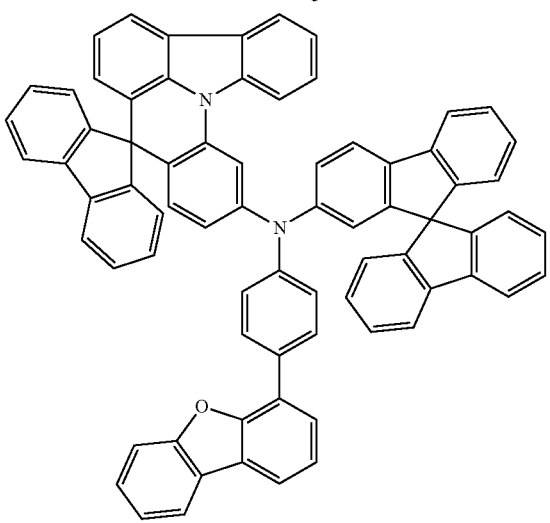

253
-continued
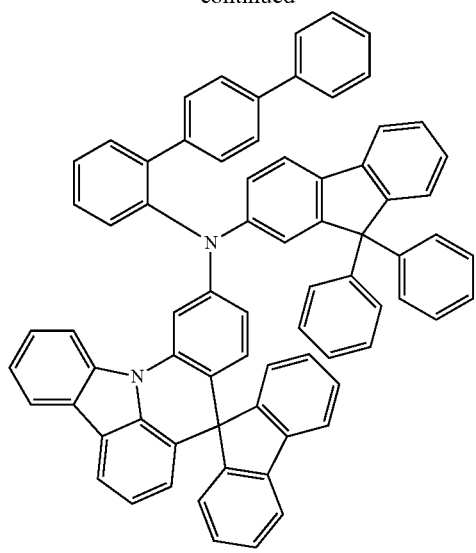
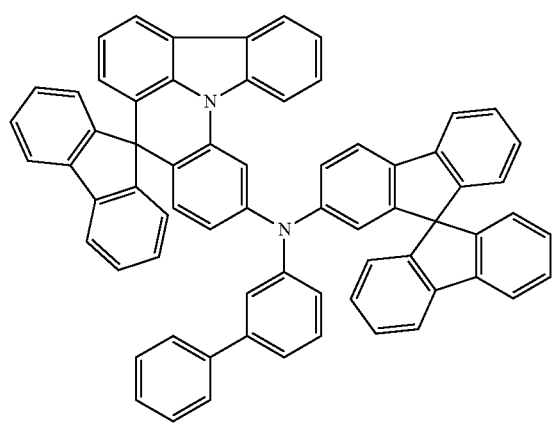
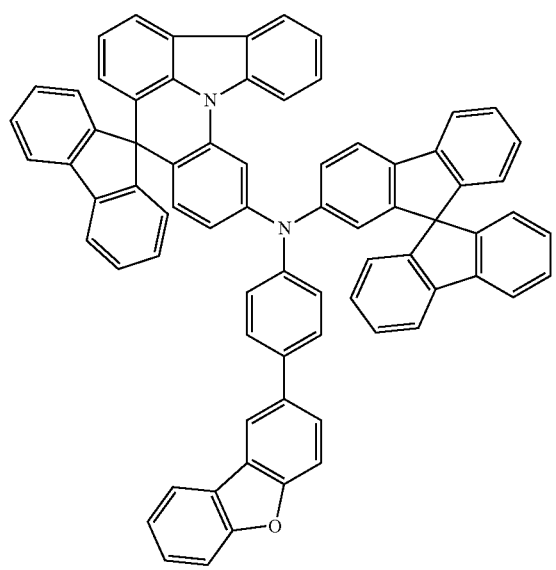
254
-continued
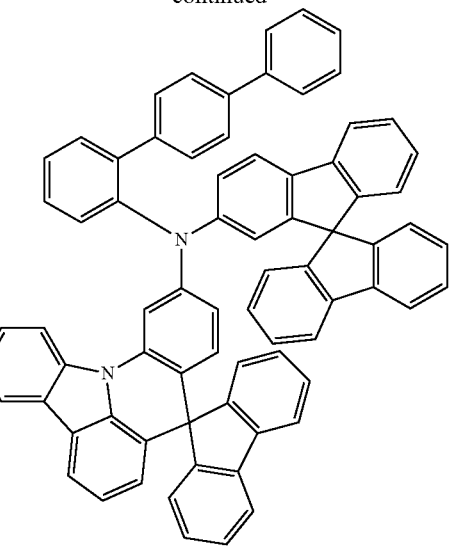
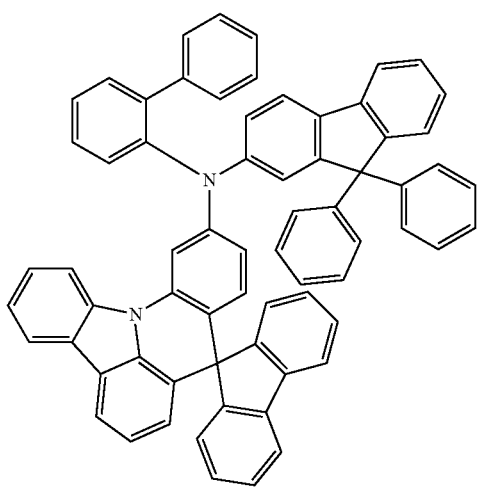
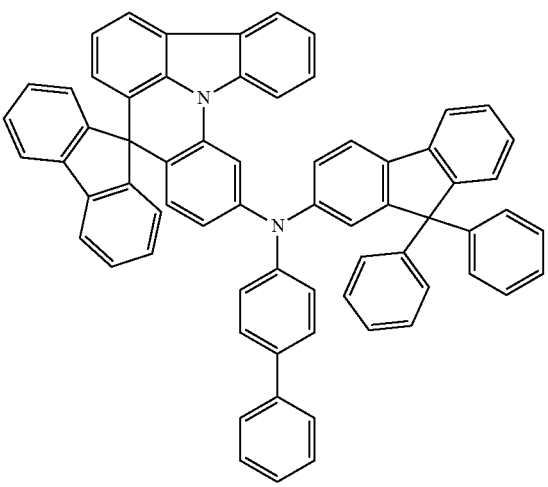

255
-continued
256
-continued
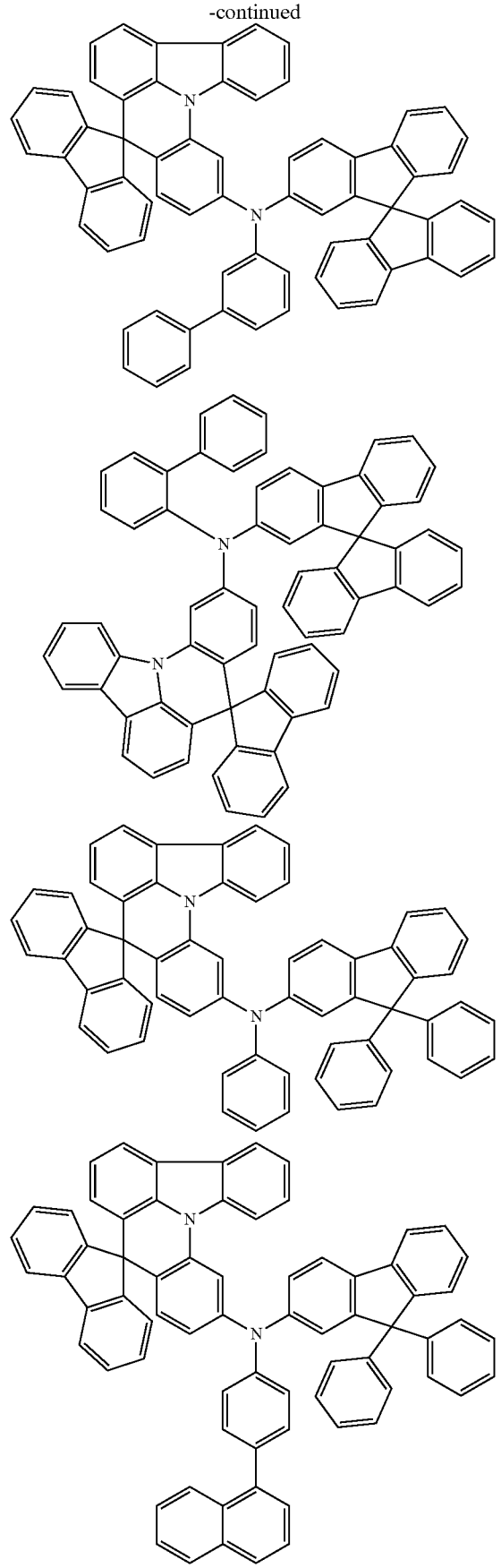
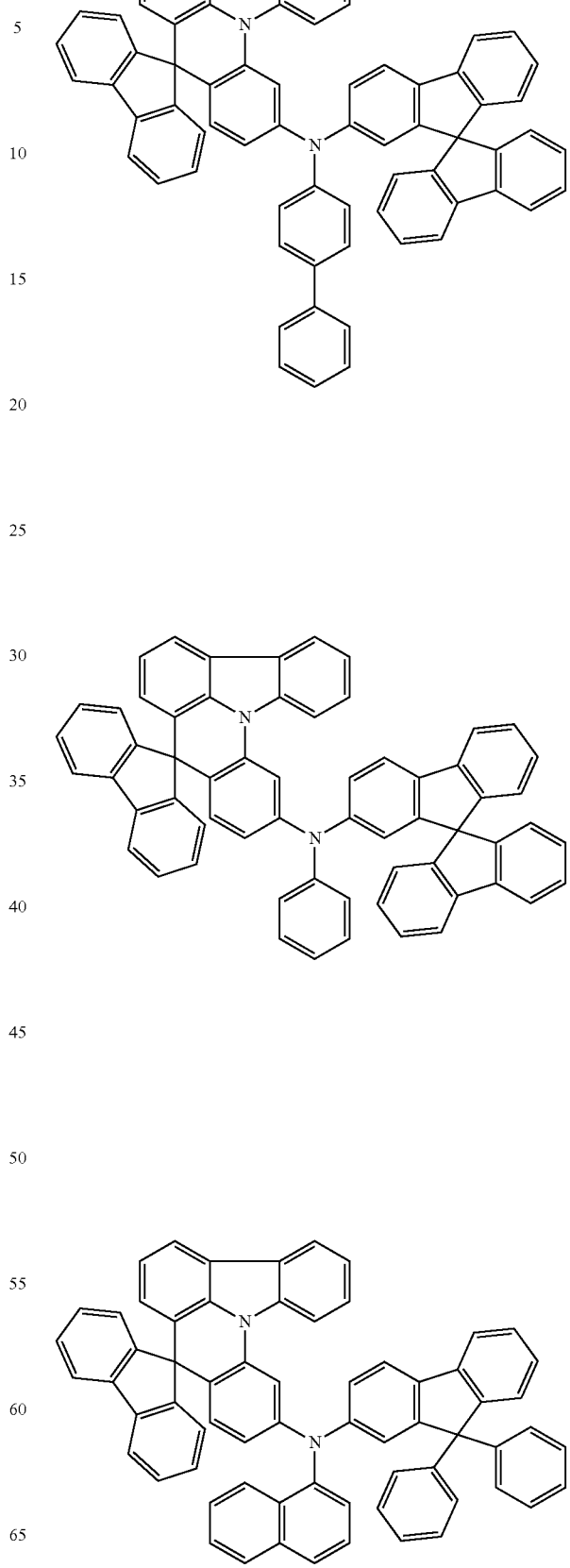

257
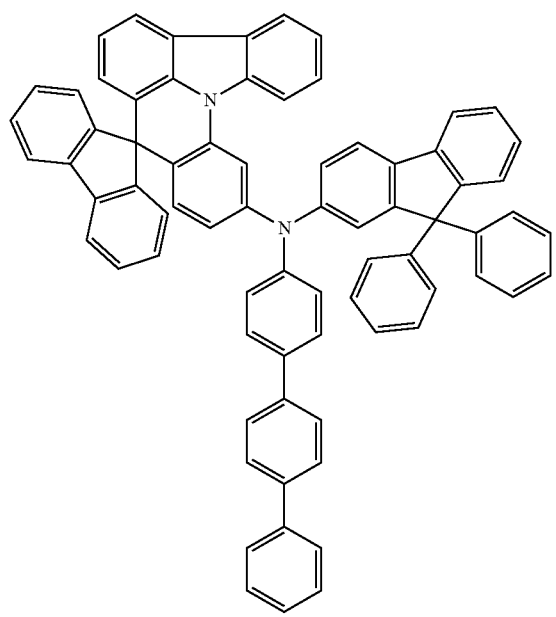
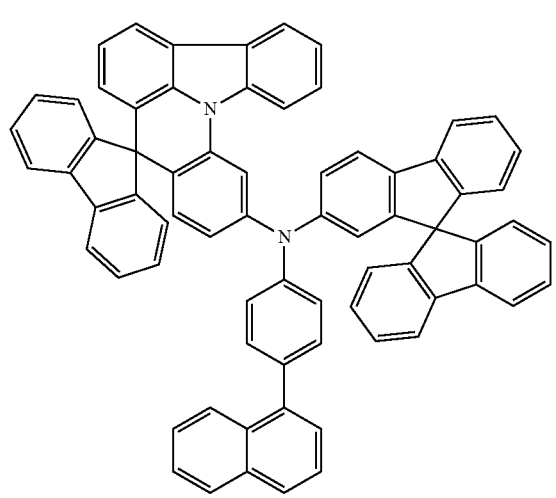
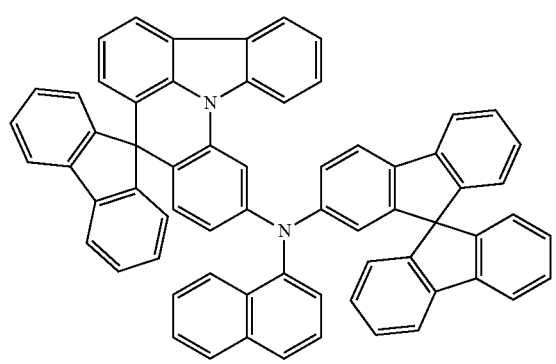
258
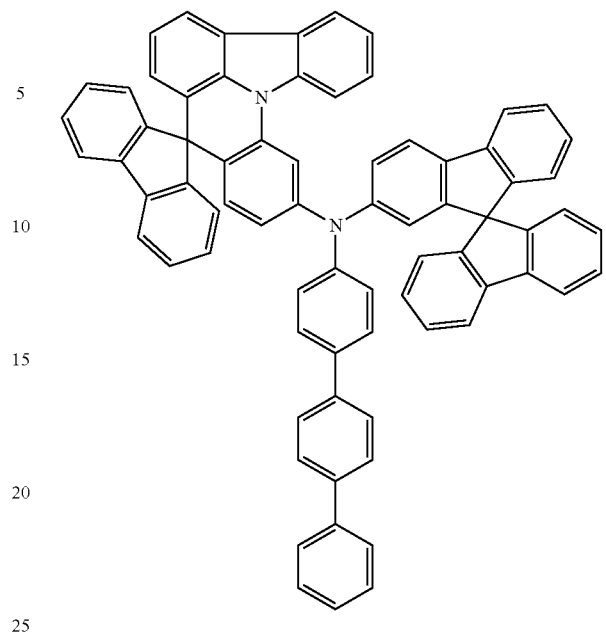
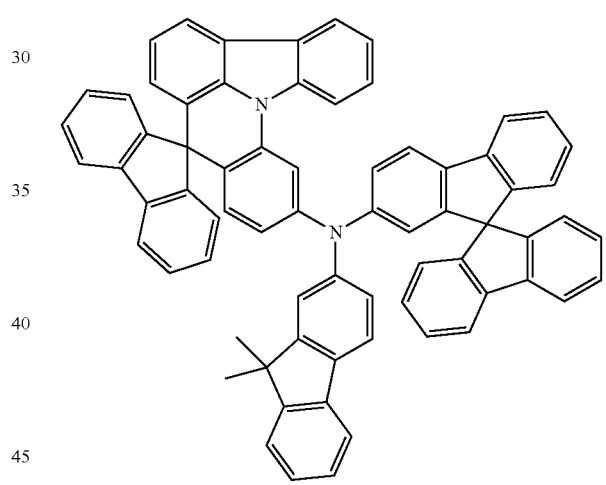
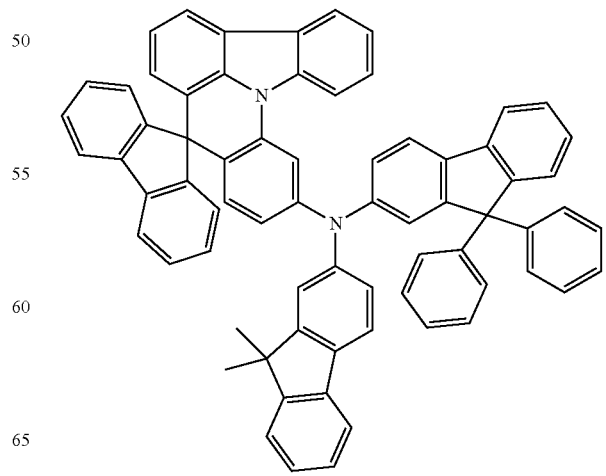

259
-continued
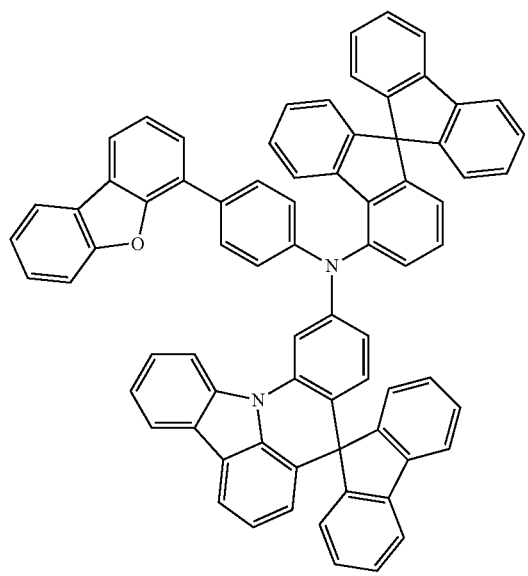
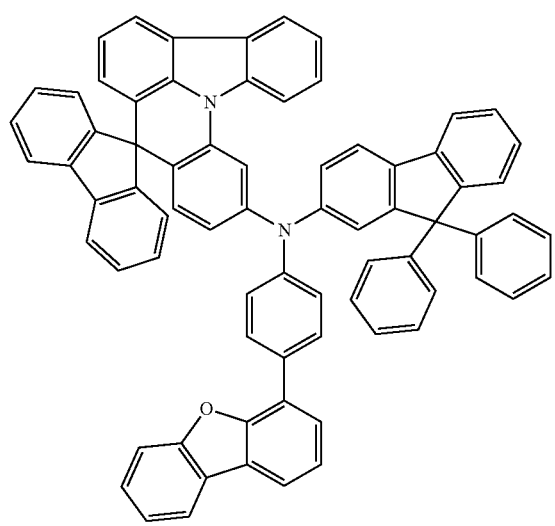
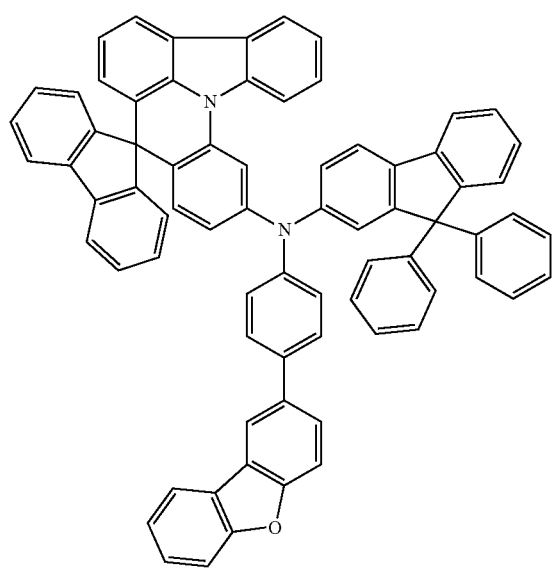
260
-continued
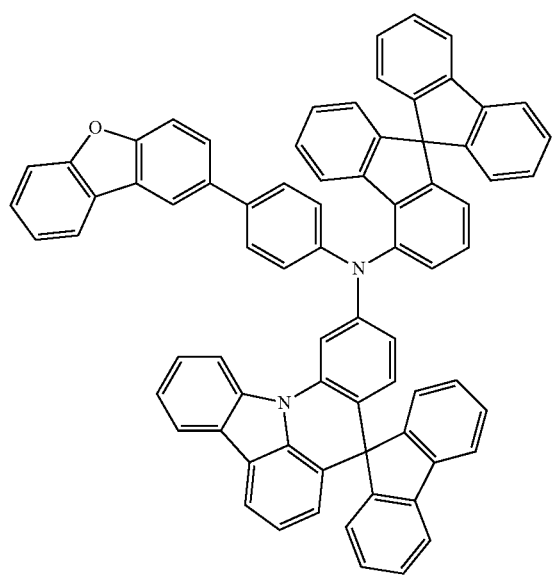
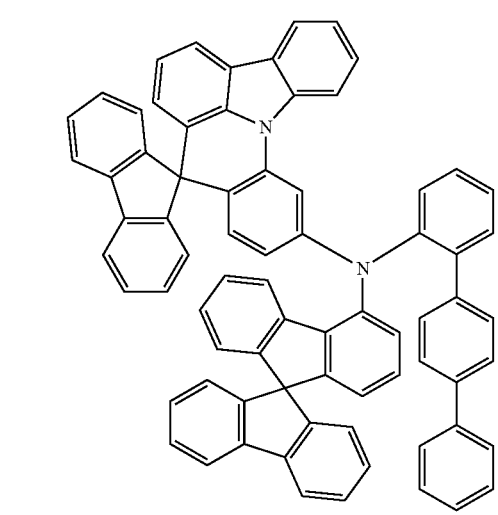
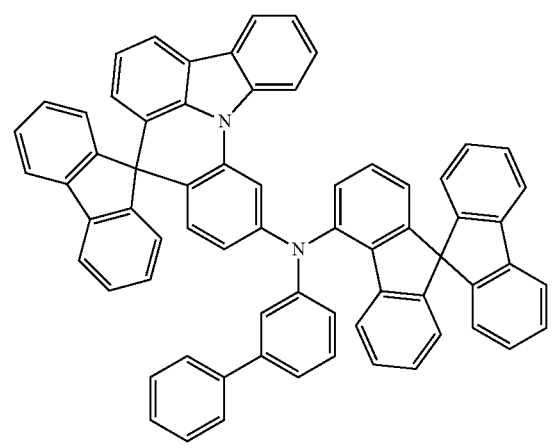

261
-continued
262
-continued
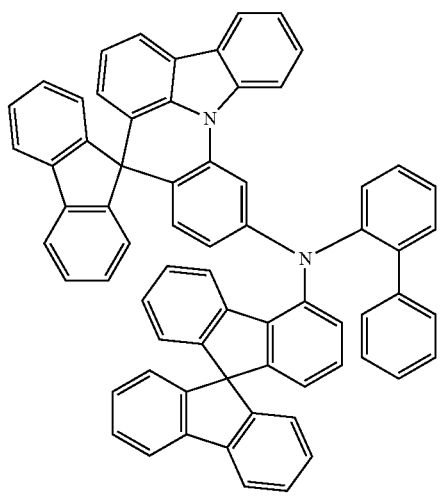
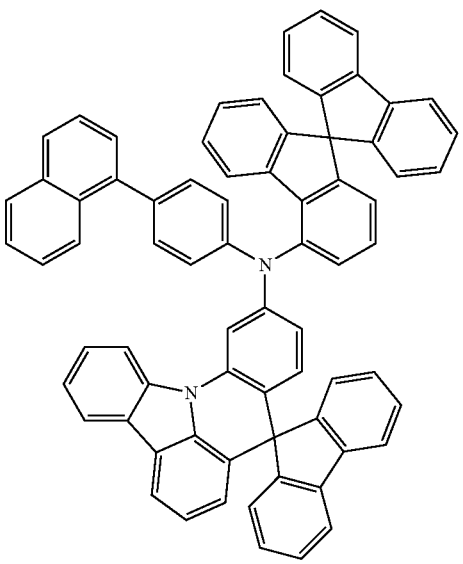
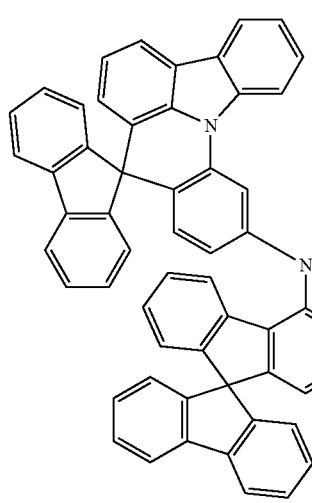
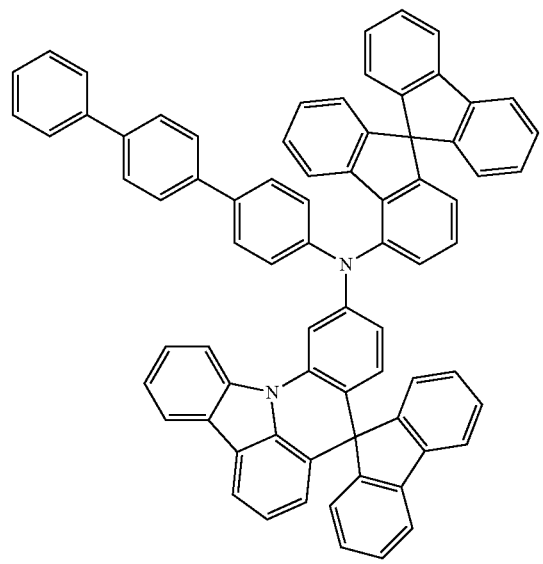

263
-continued
264
-continued
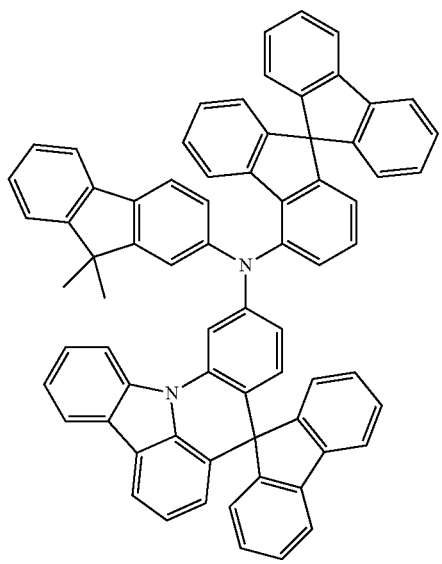
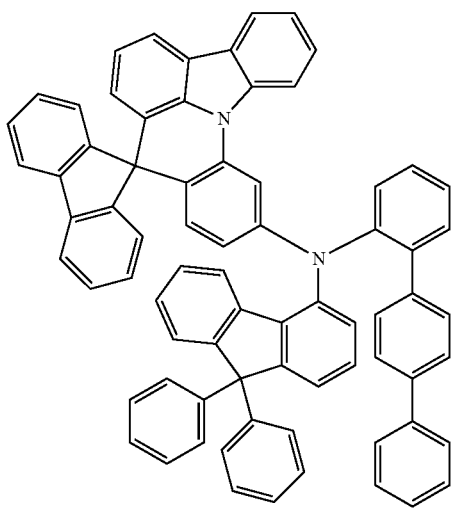
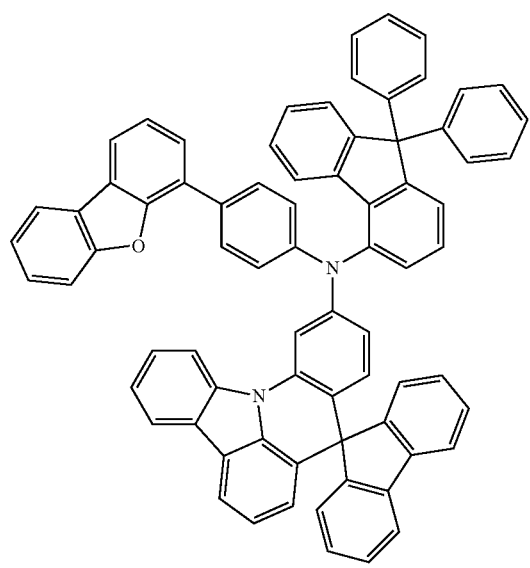
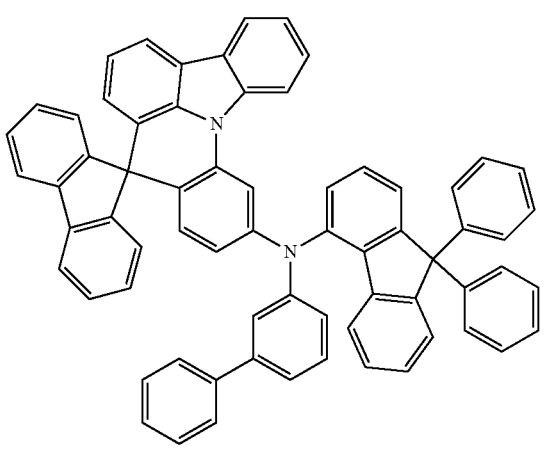
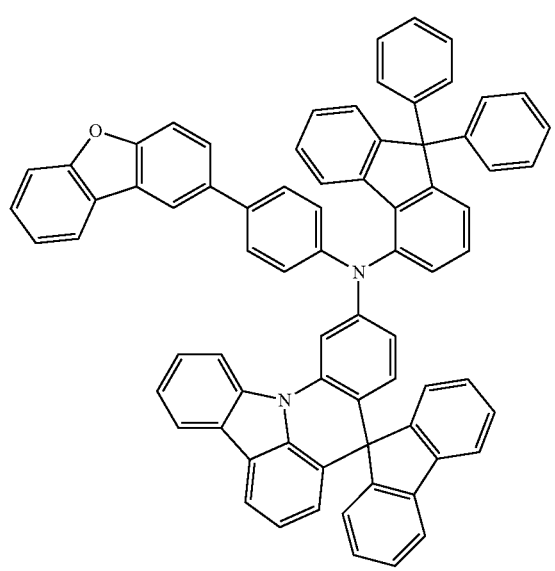
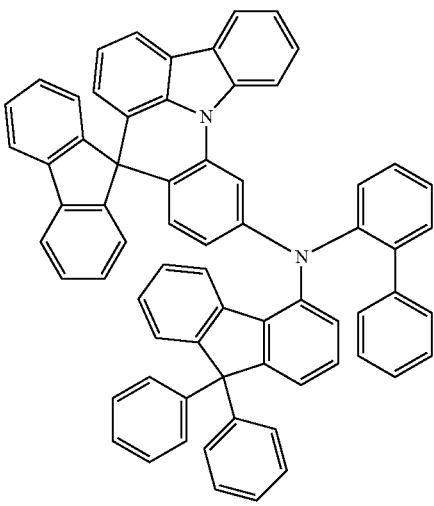

265
-continued
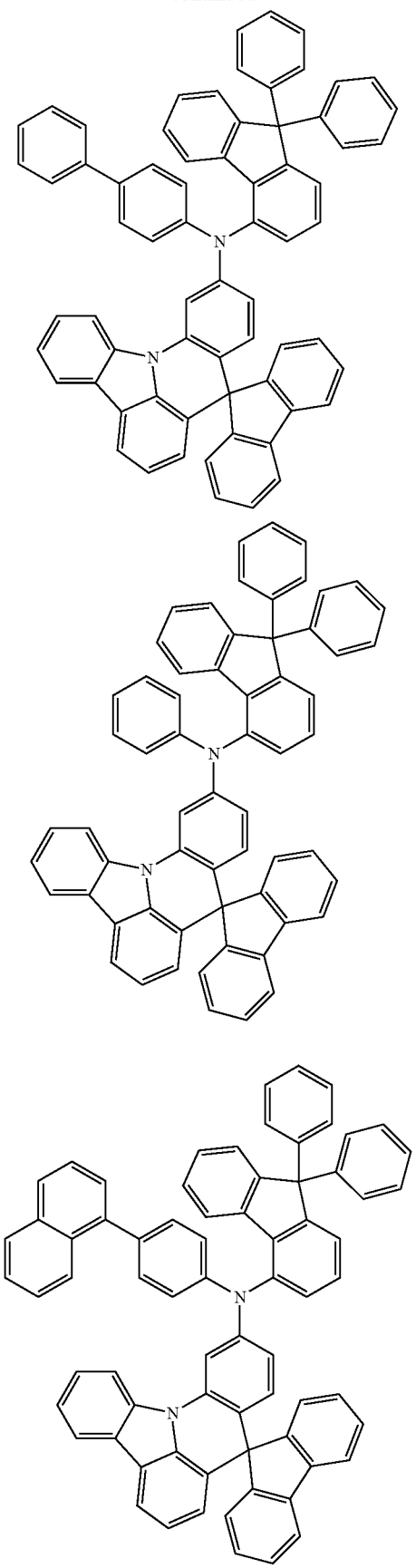
266
-continued
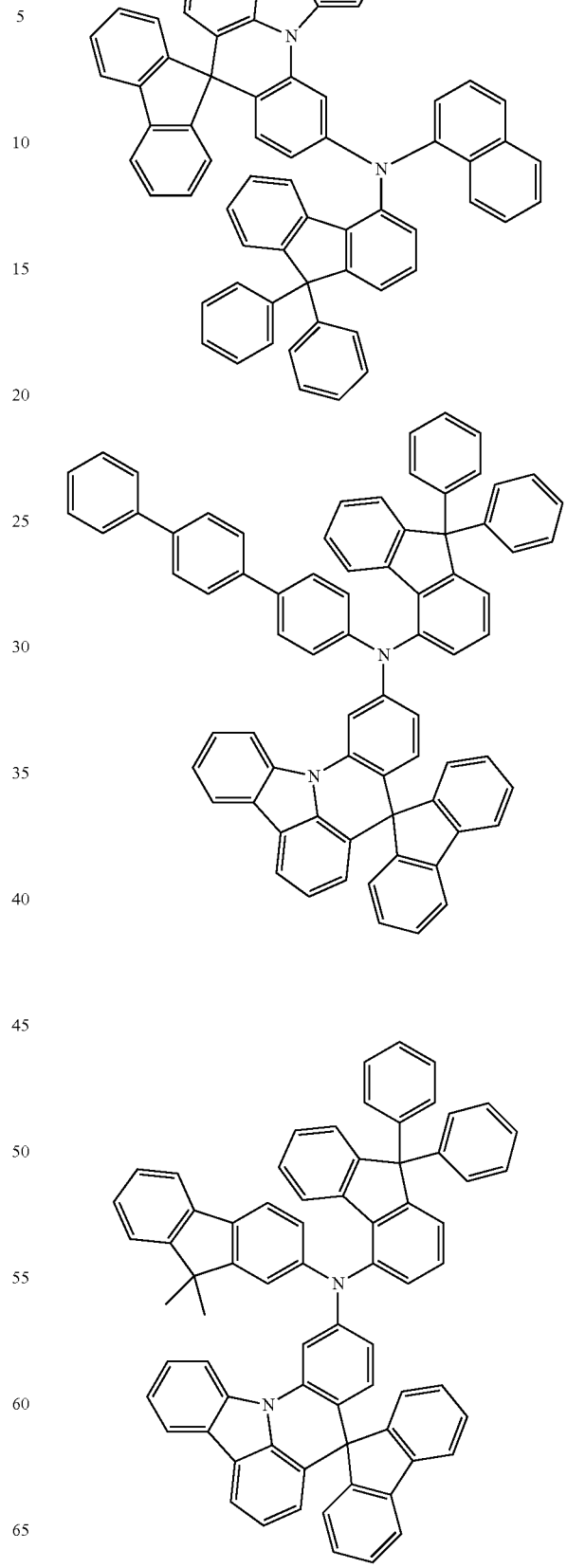

267
-continued
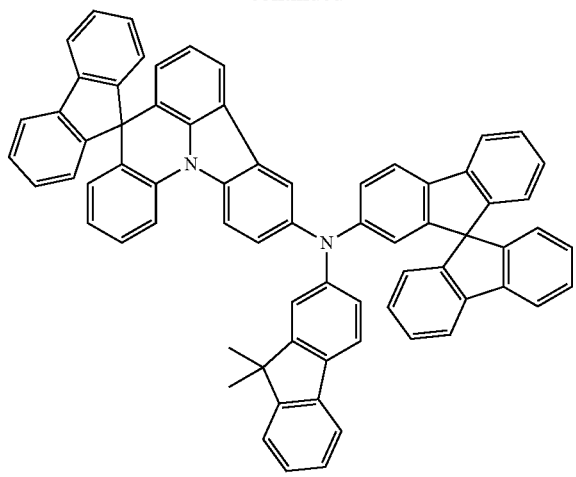
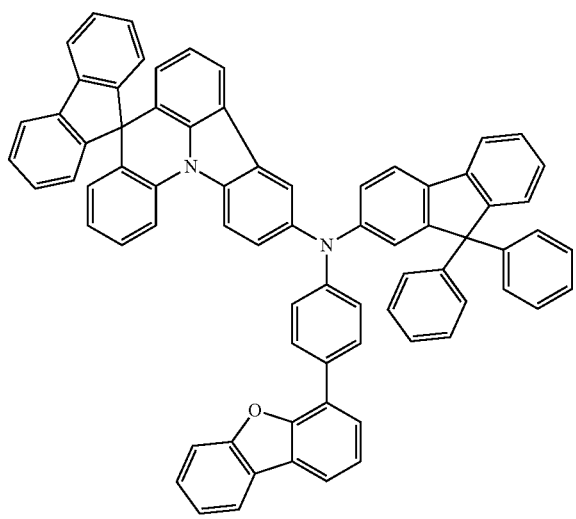
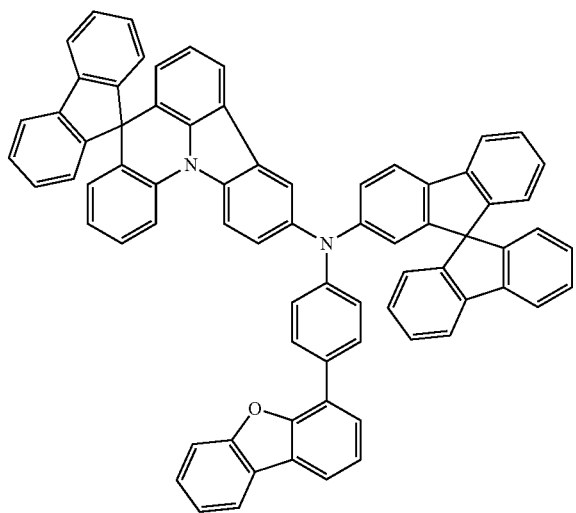
268
-continued
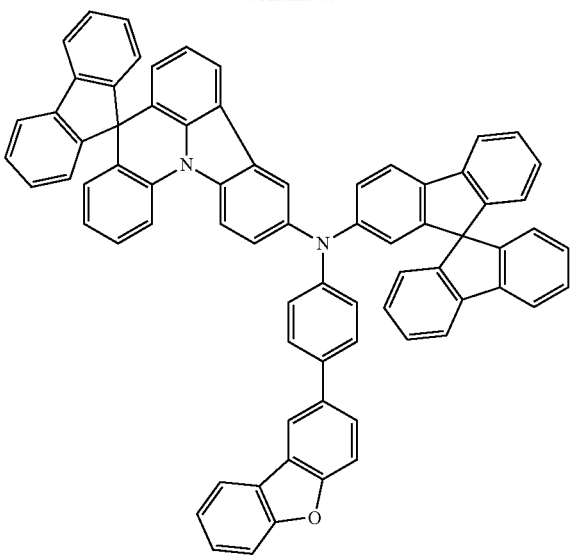
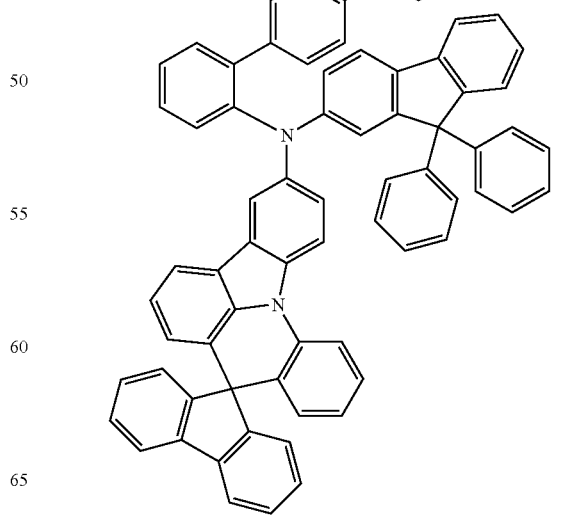

269
-continued
270
-continued
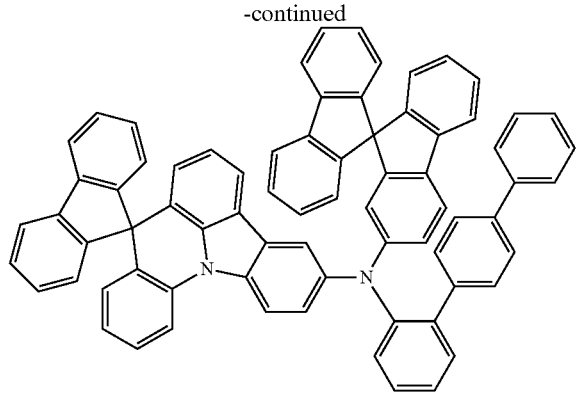
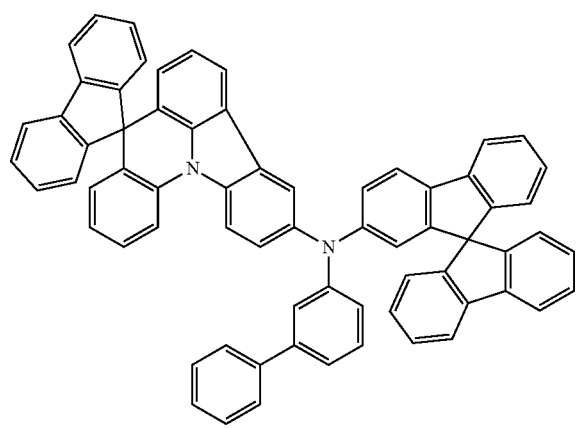
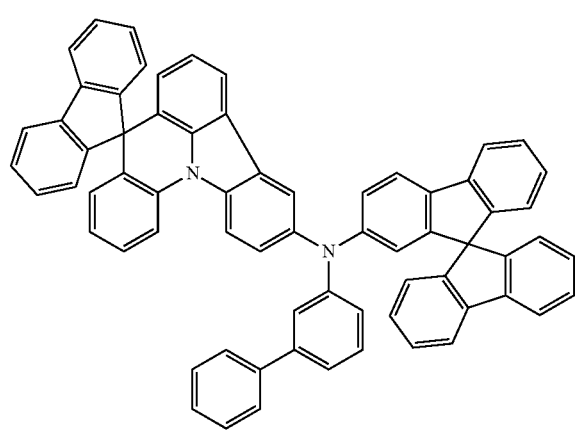
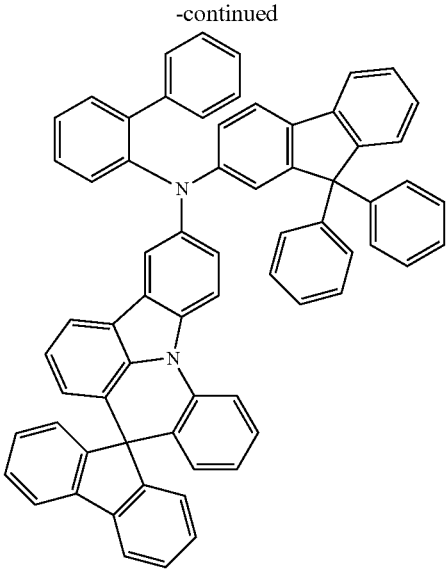
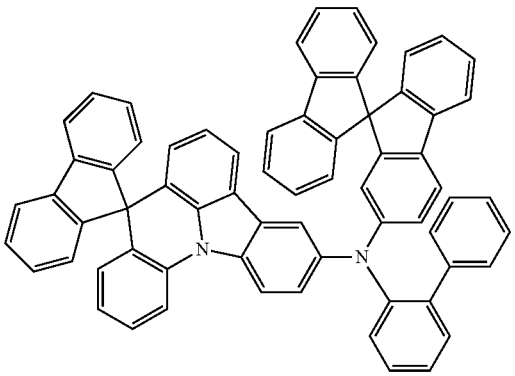
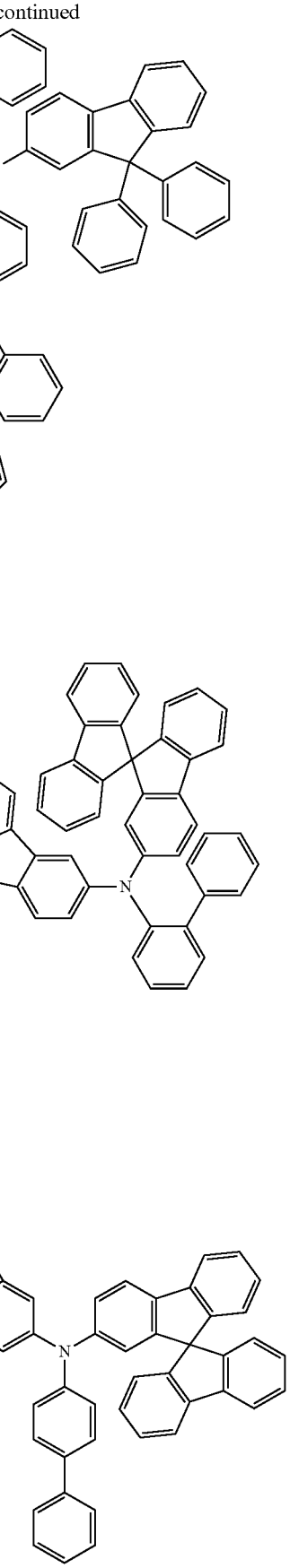

271
-continued
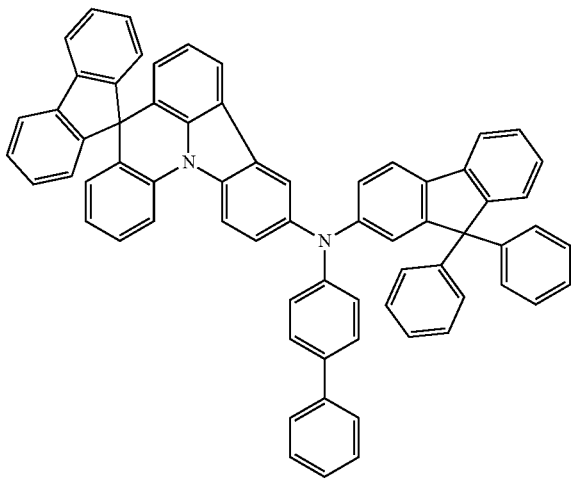
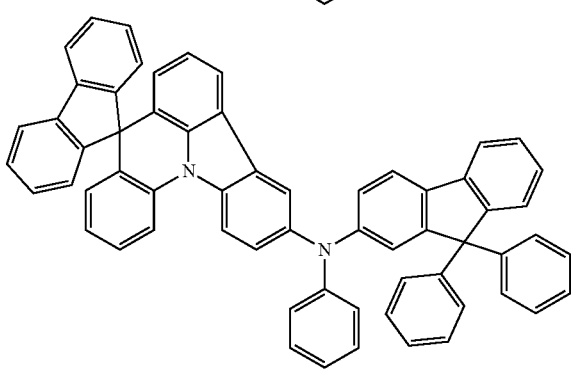
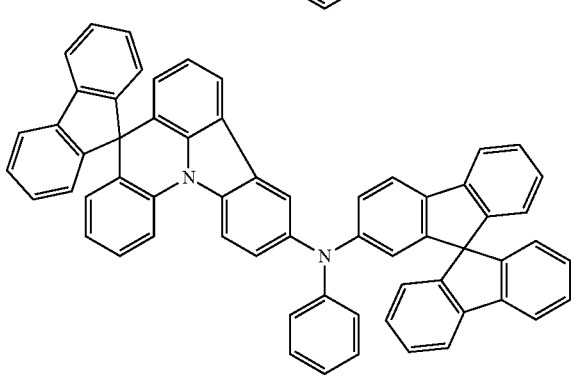
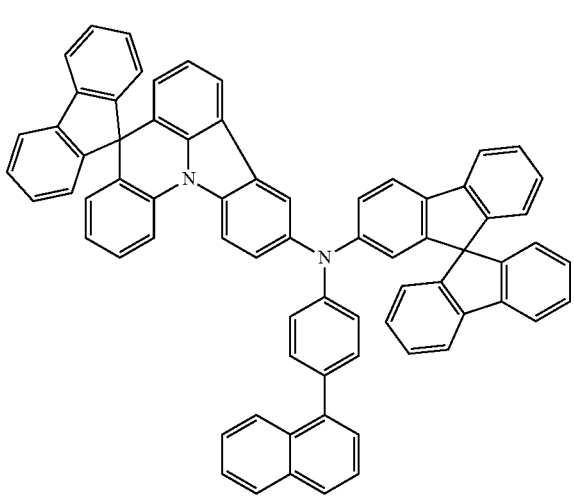
272
-continued
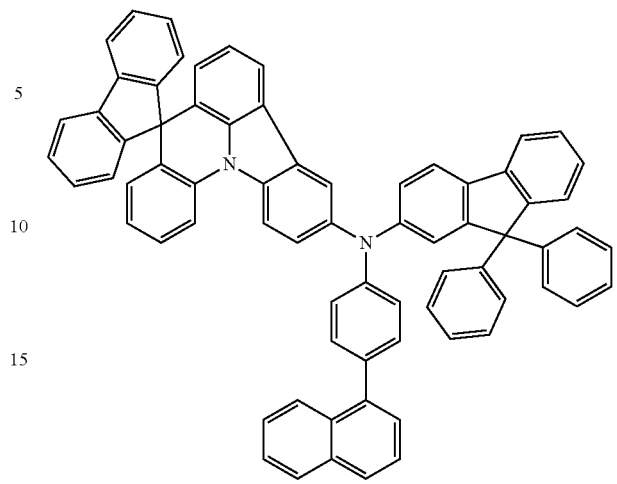
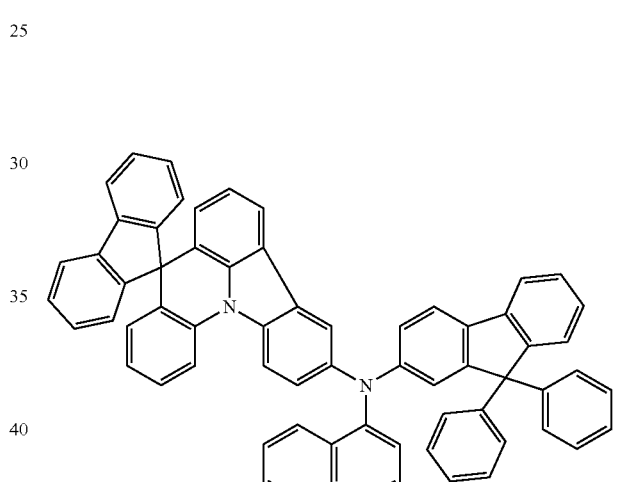
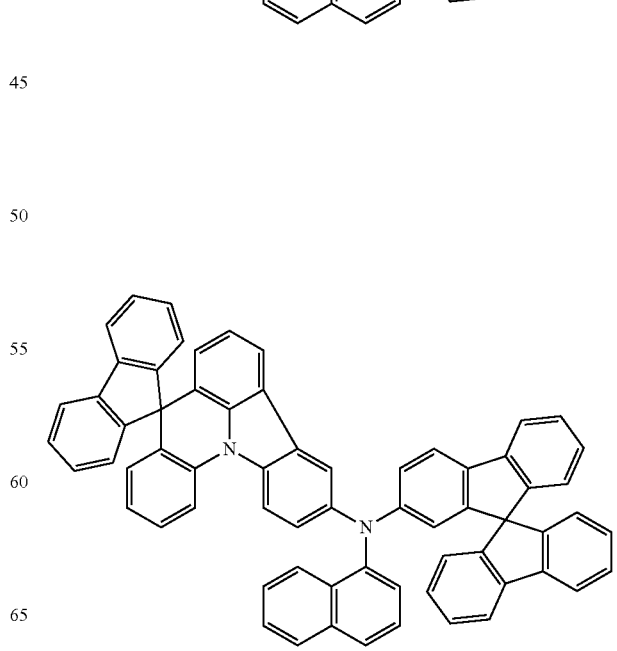

273
-continued
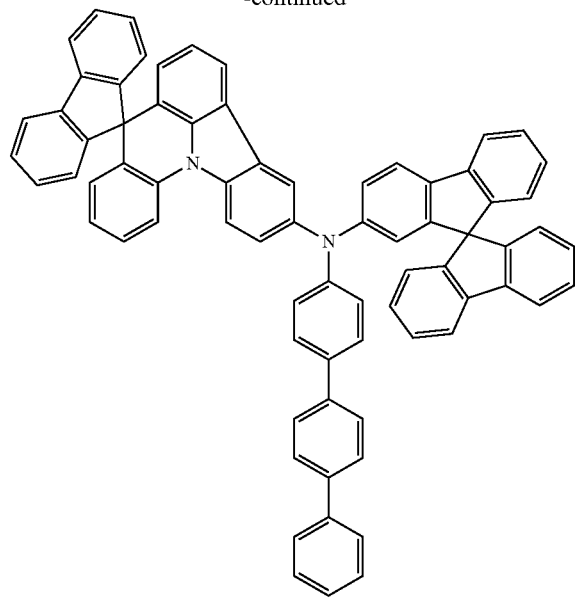
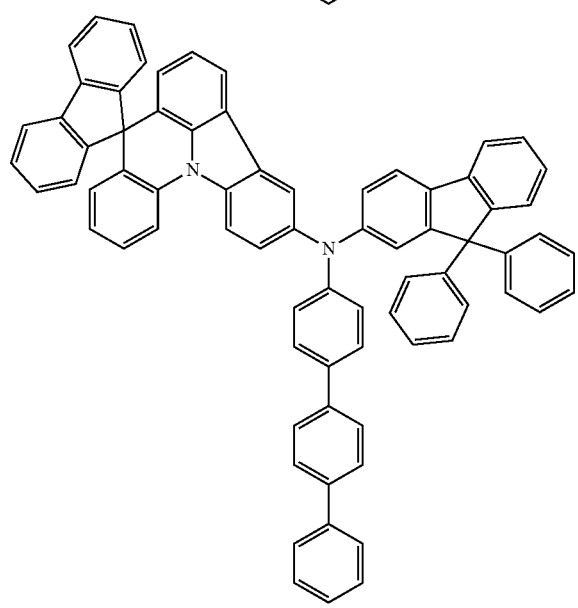
274
-continued
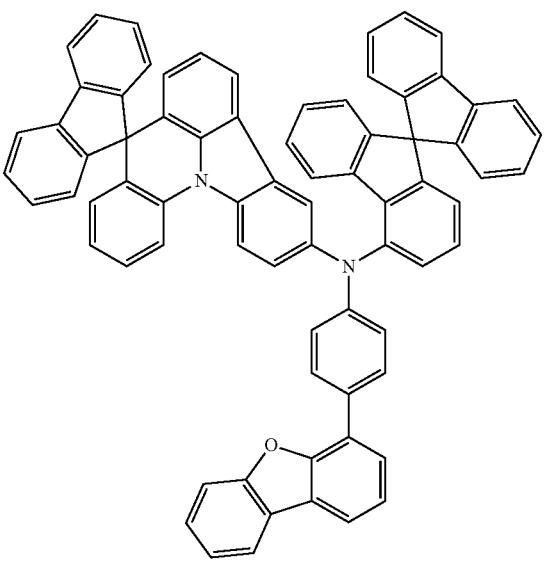
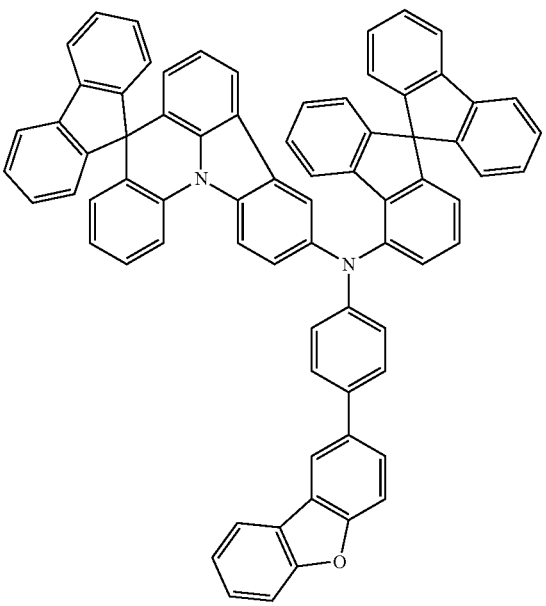

275
-continued
276
-continued
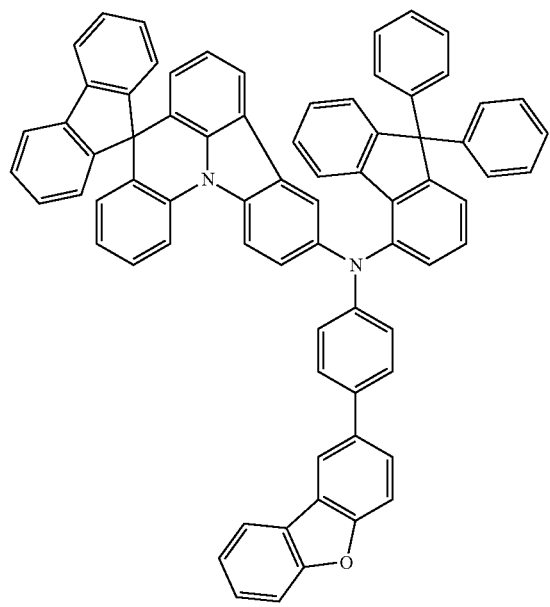
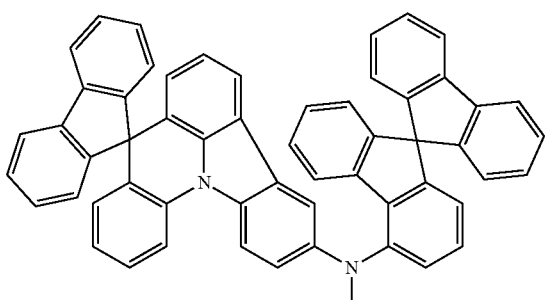
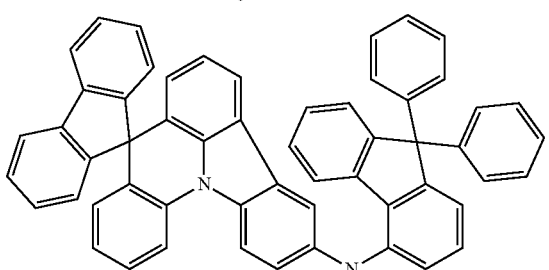
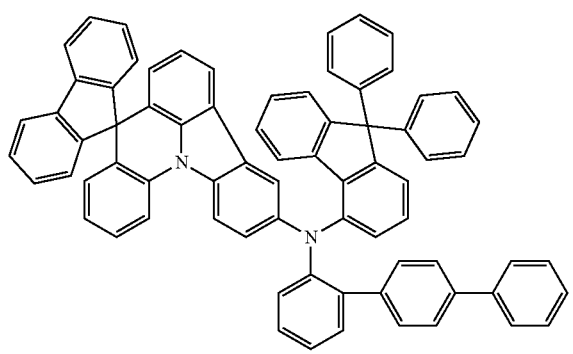
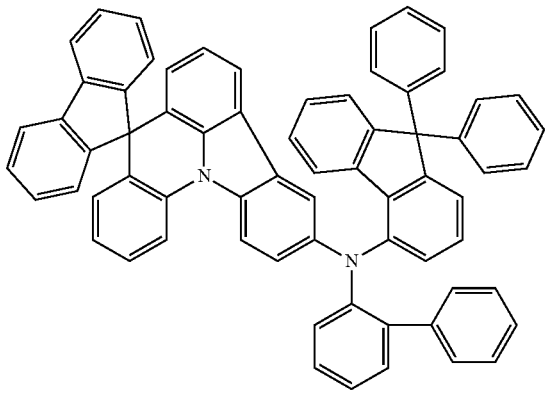
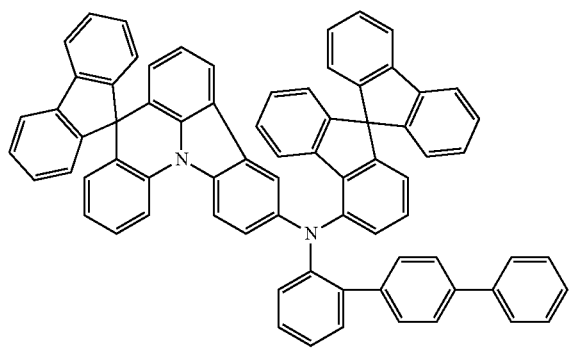
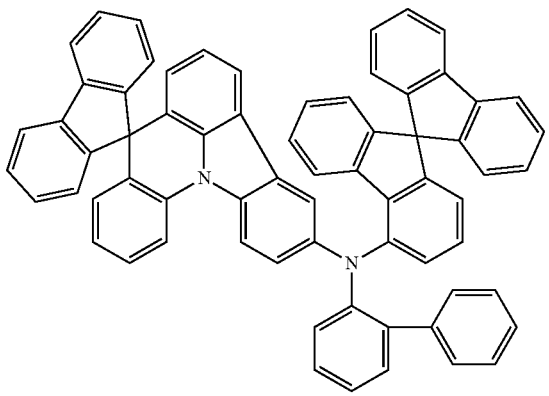

277
-continued
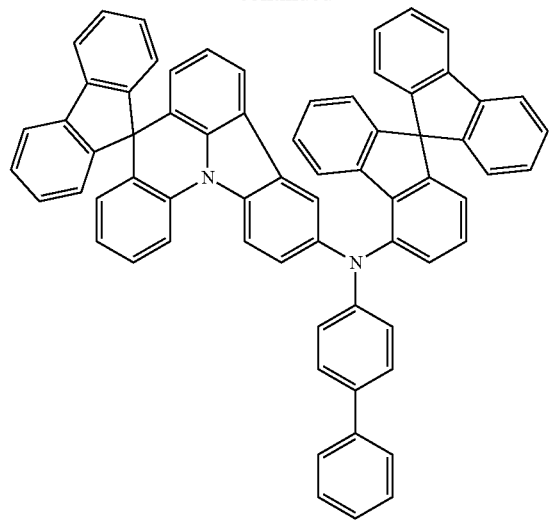
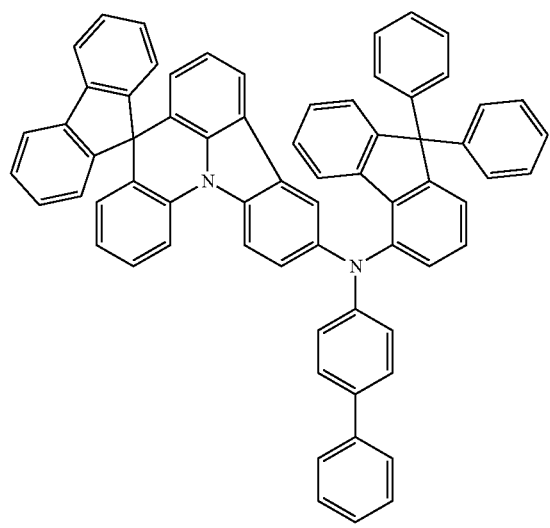
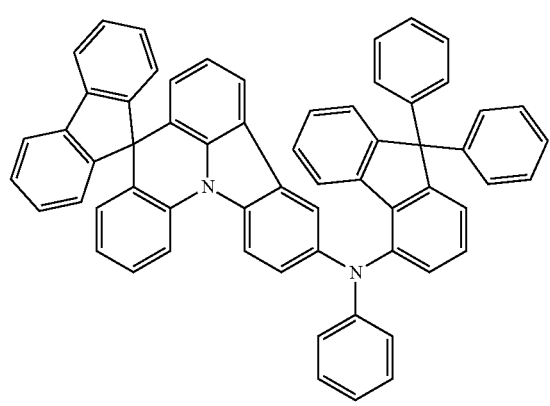
278
-continued
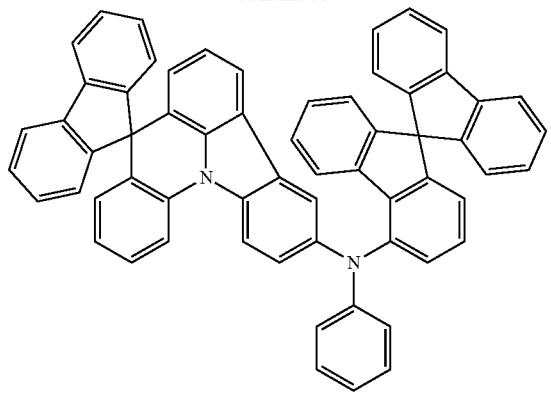
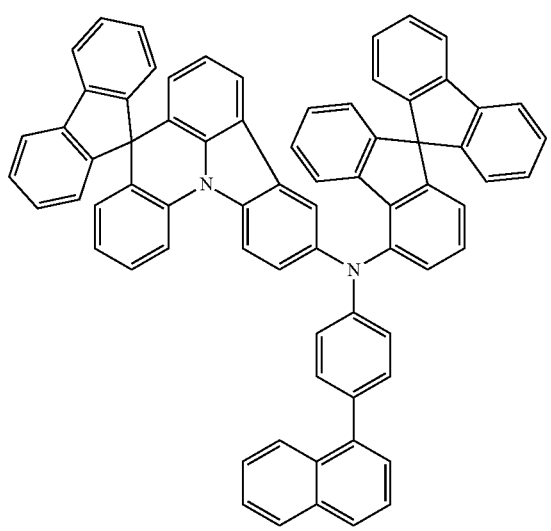
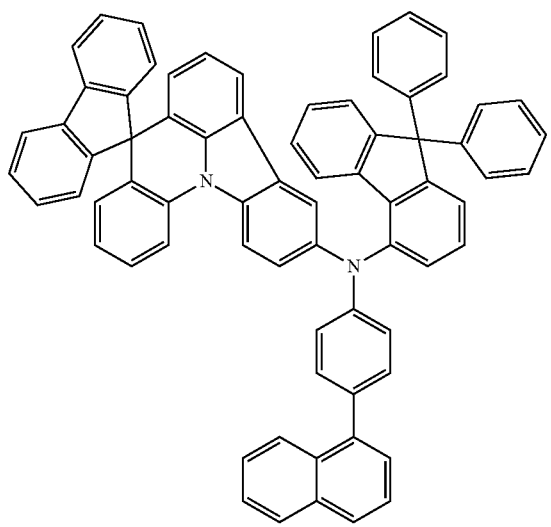

279
-continued
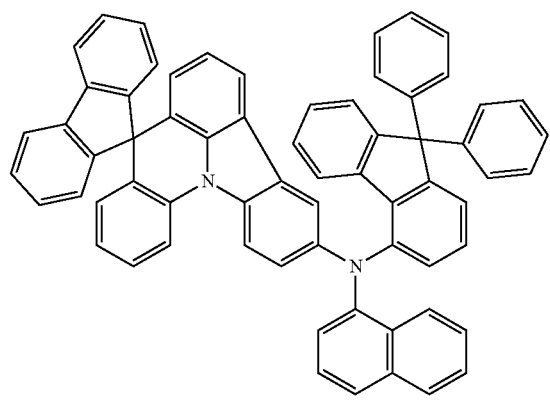
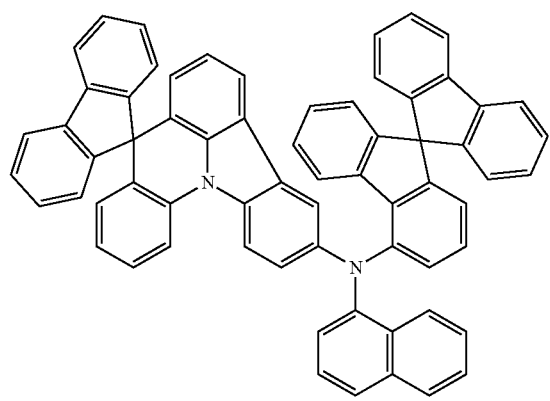
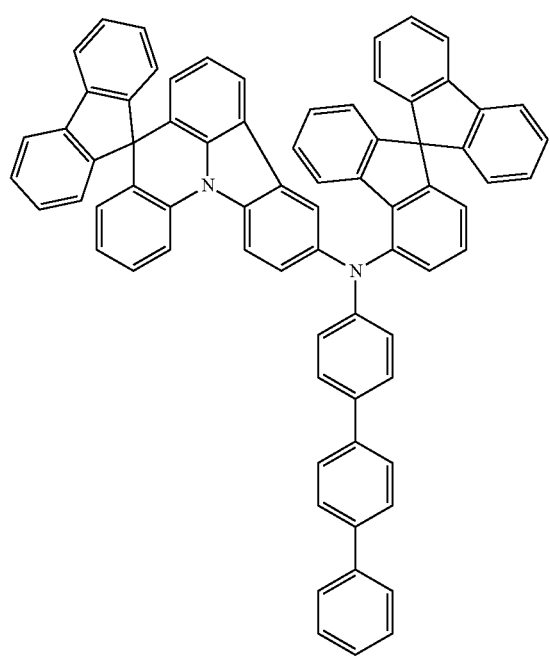
280
-continued
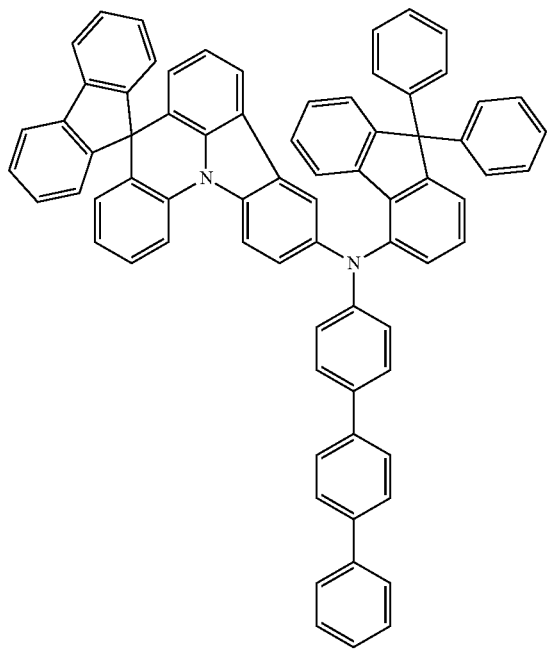
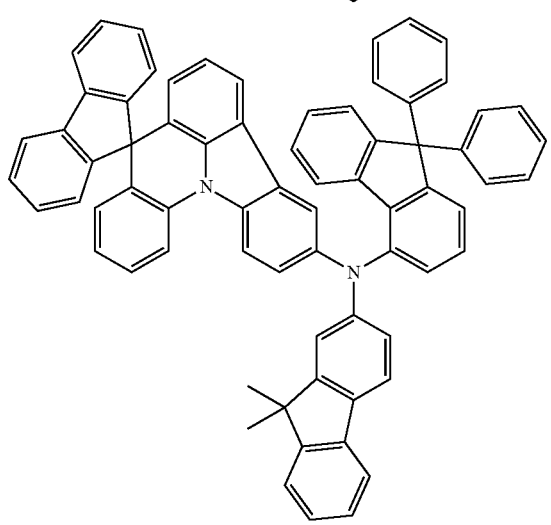
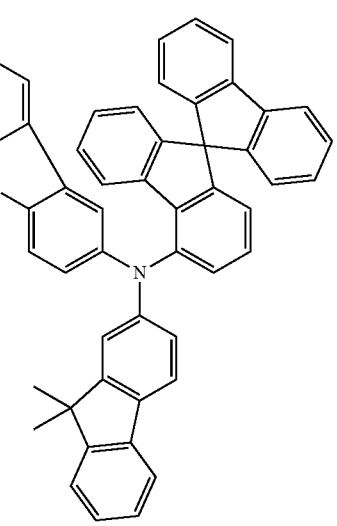

281
-continued
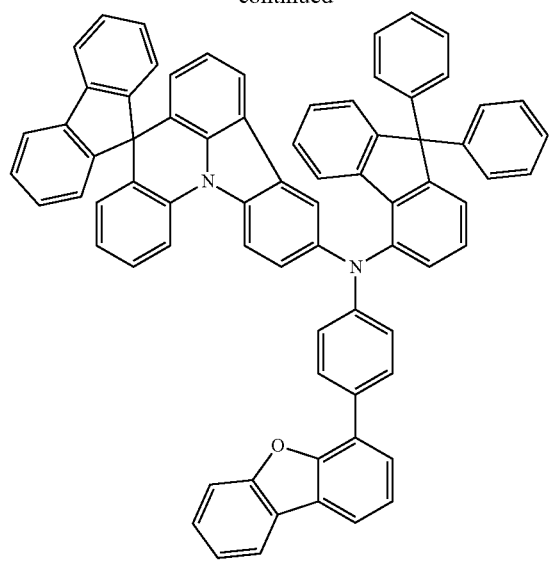
282
-continued
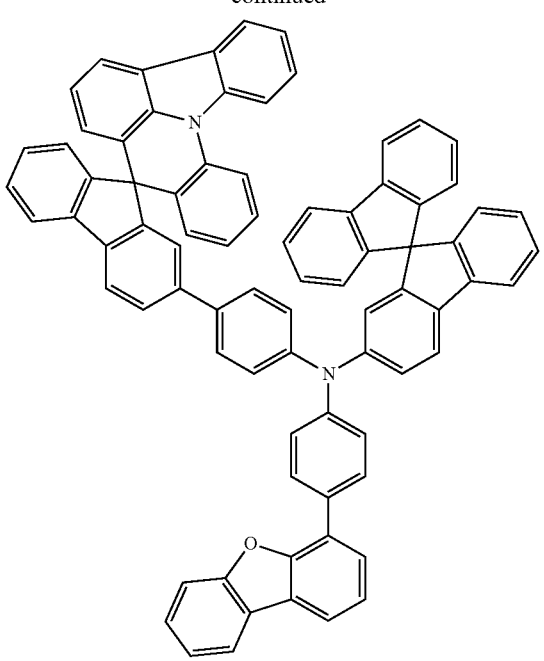
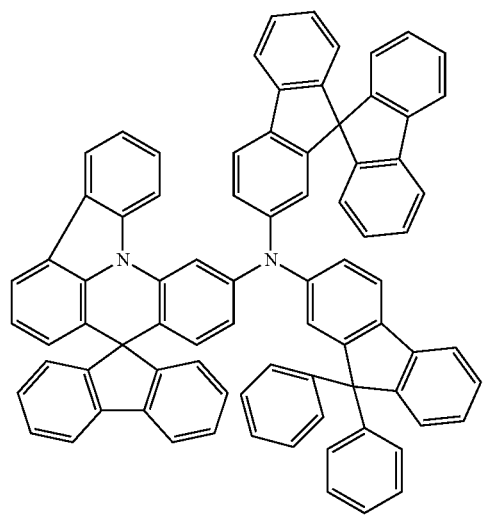
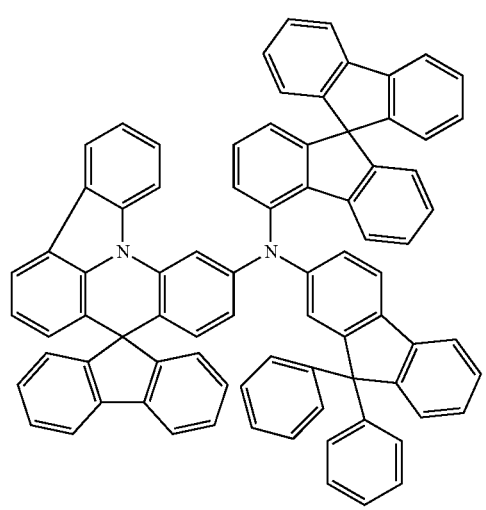
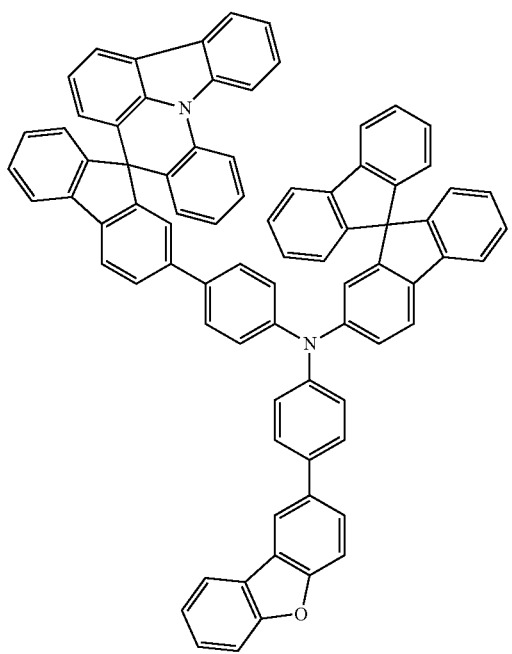

283
-continued
284
-continued
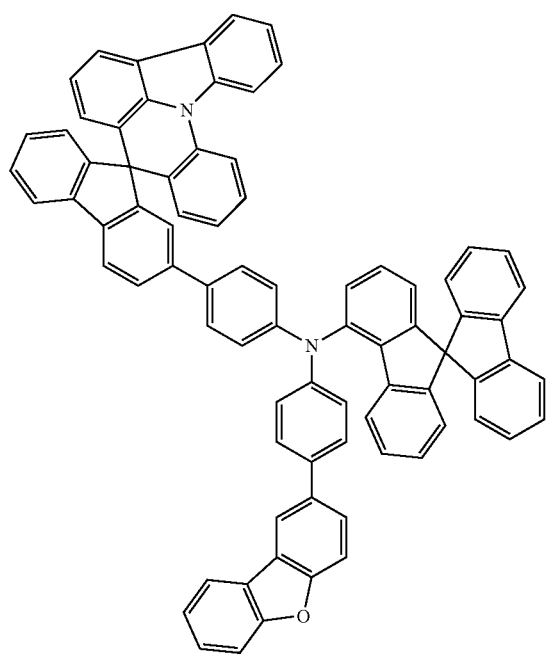
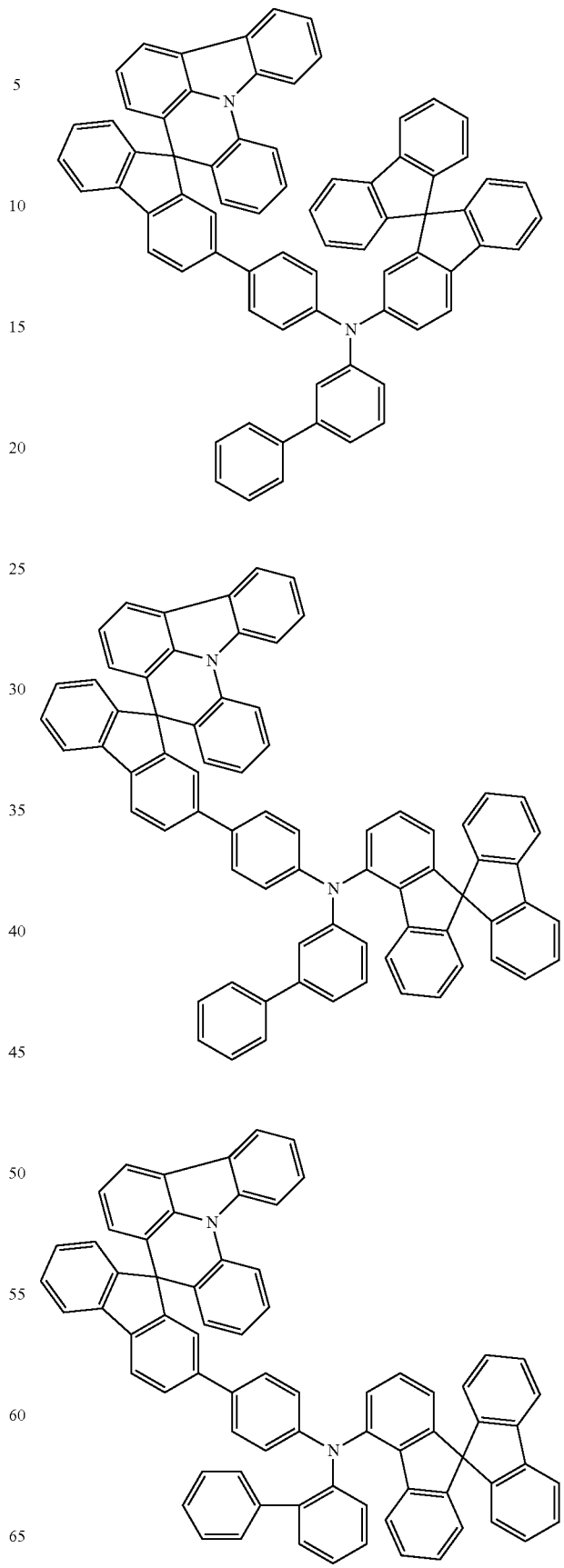

285
-continued
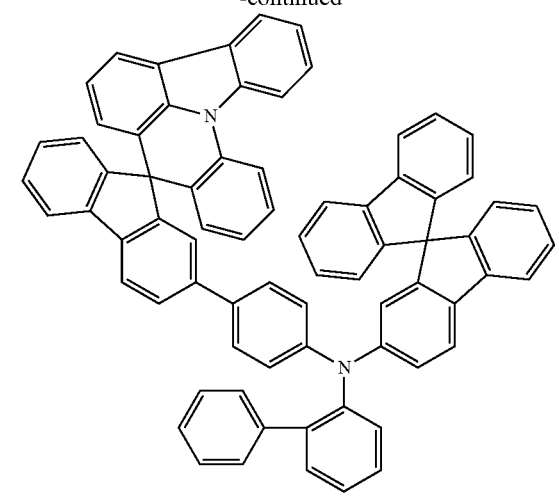
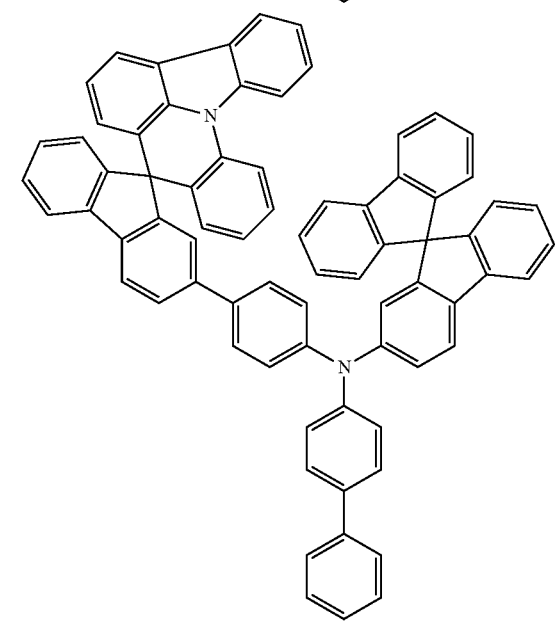
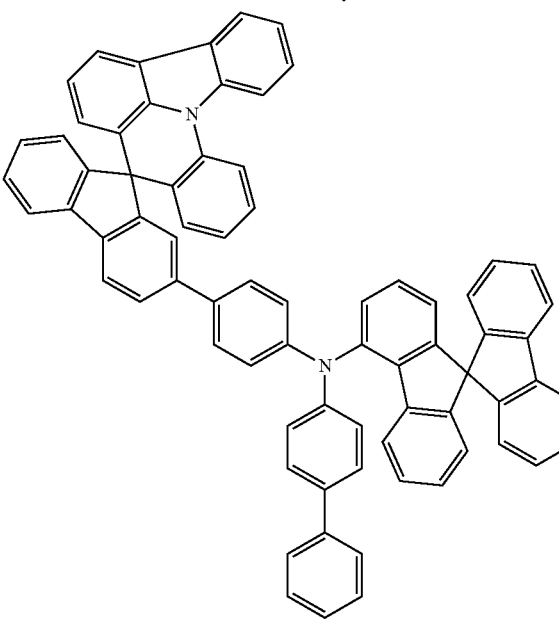
286
-continued
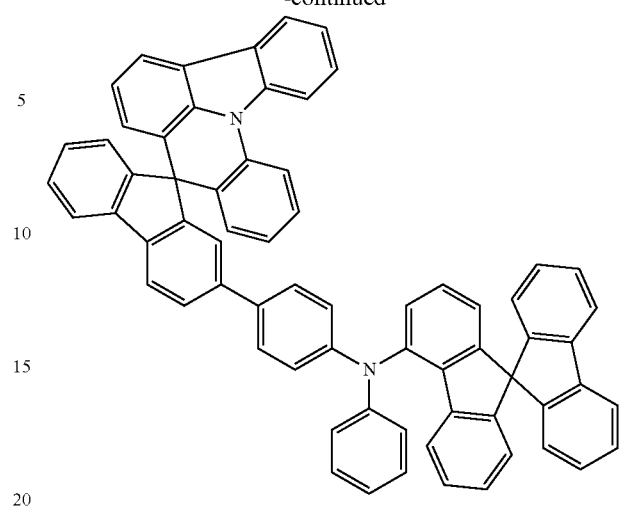
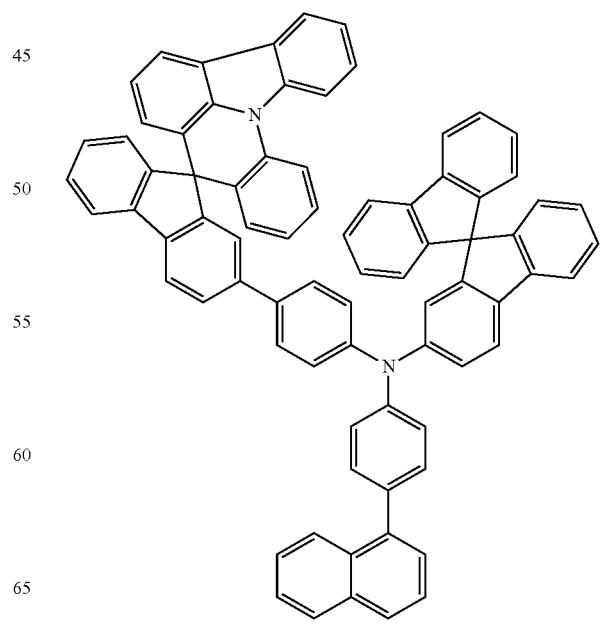

287
-continued
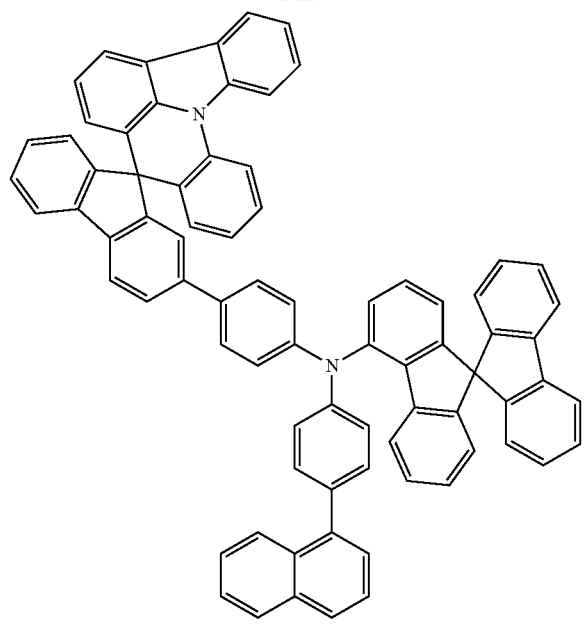
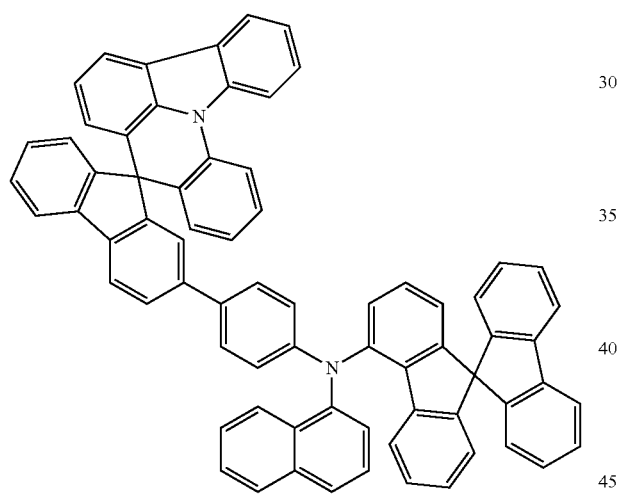
288
-continued
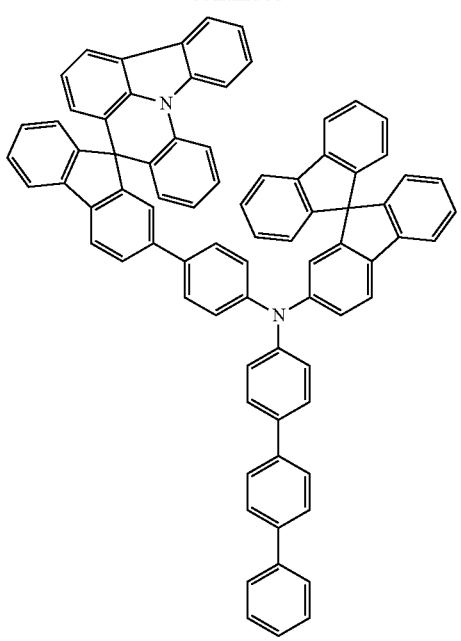
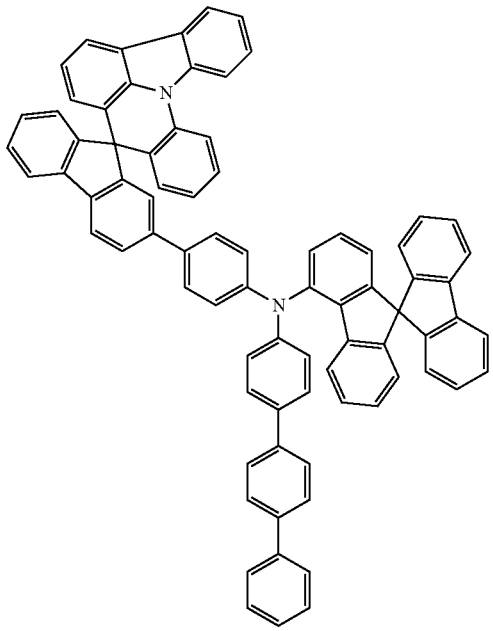

289
-continued
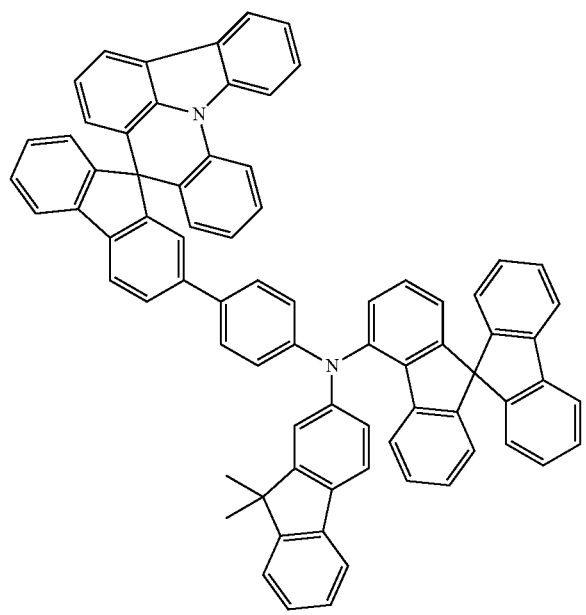
290
-continued
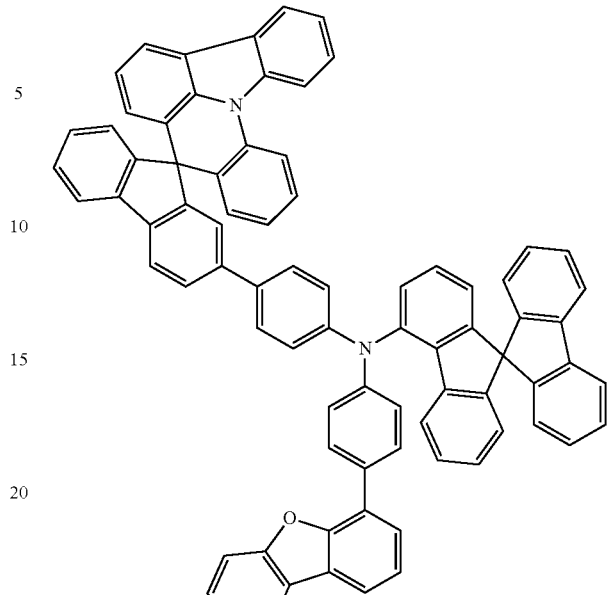
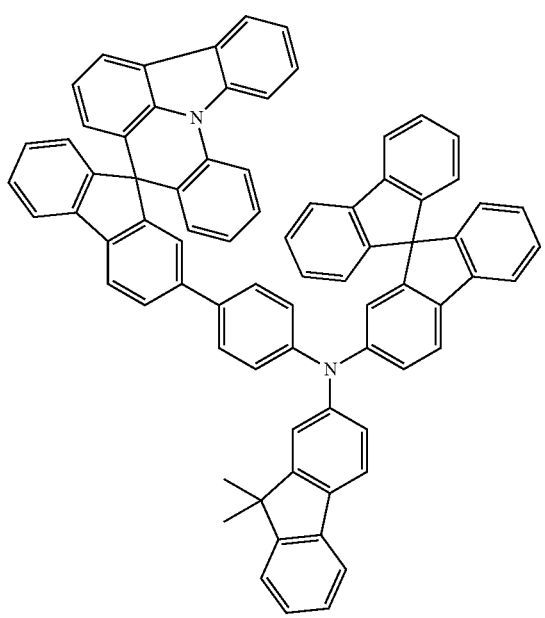
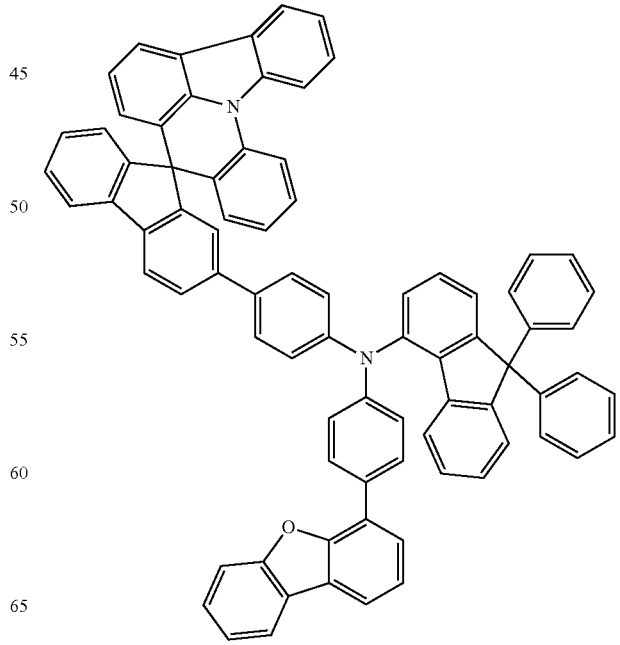

291
-continued
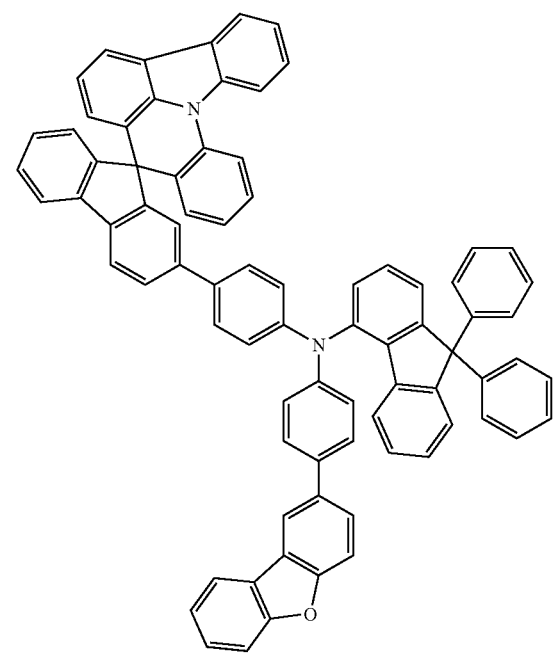
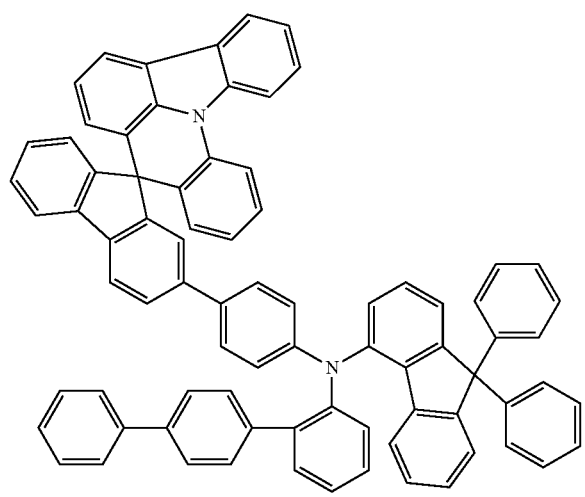
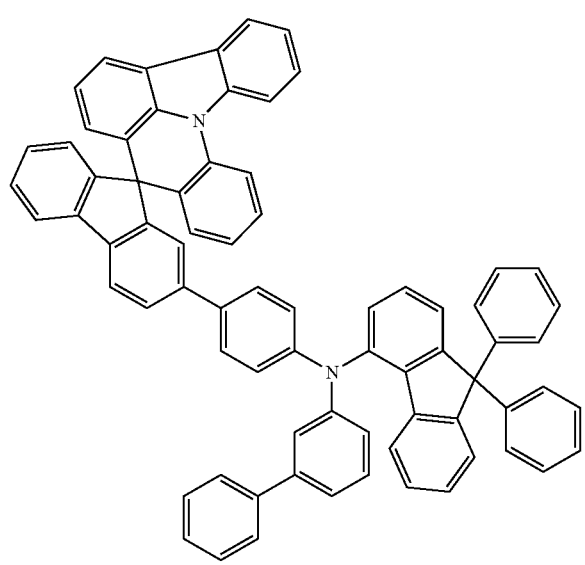
292
-continued
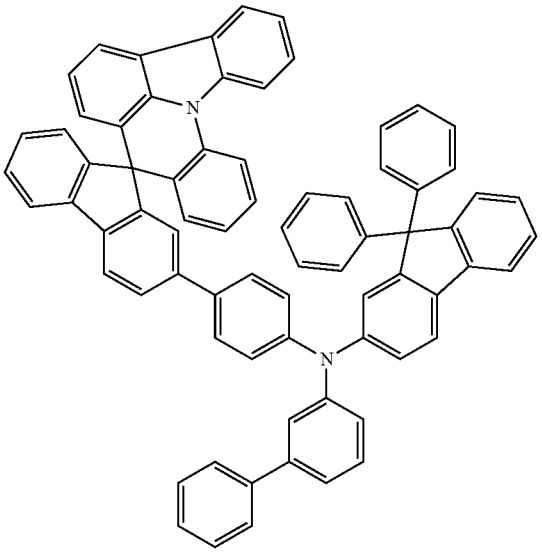
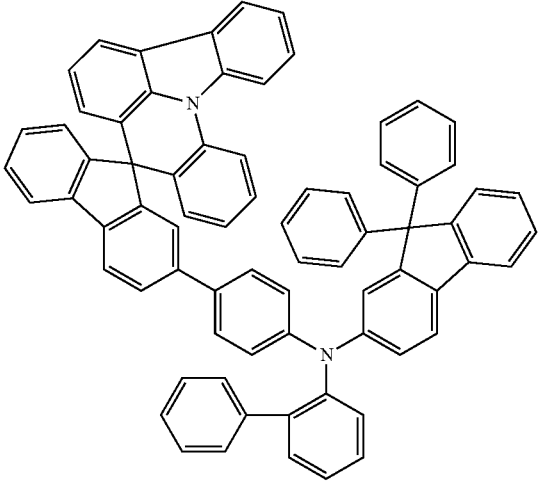
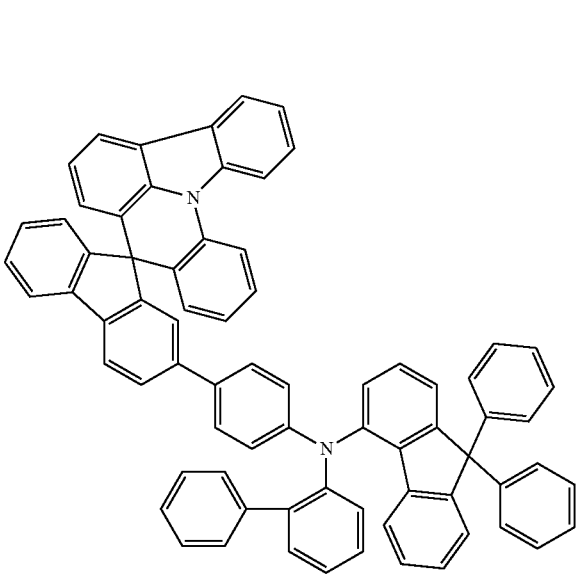

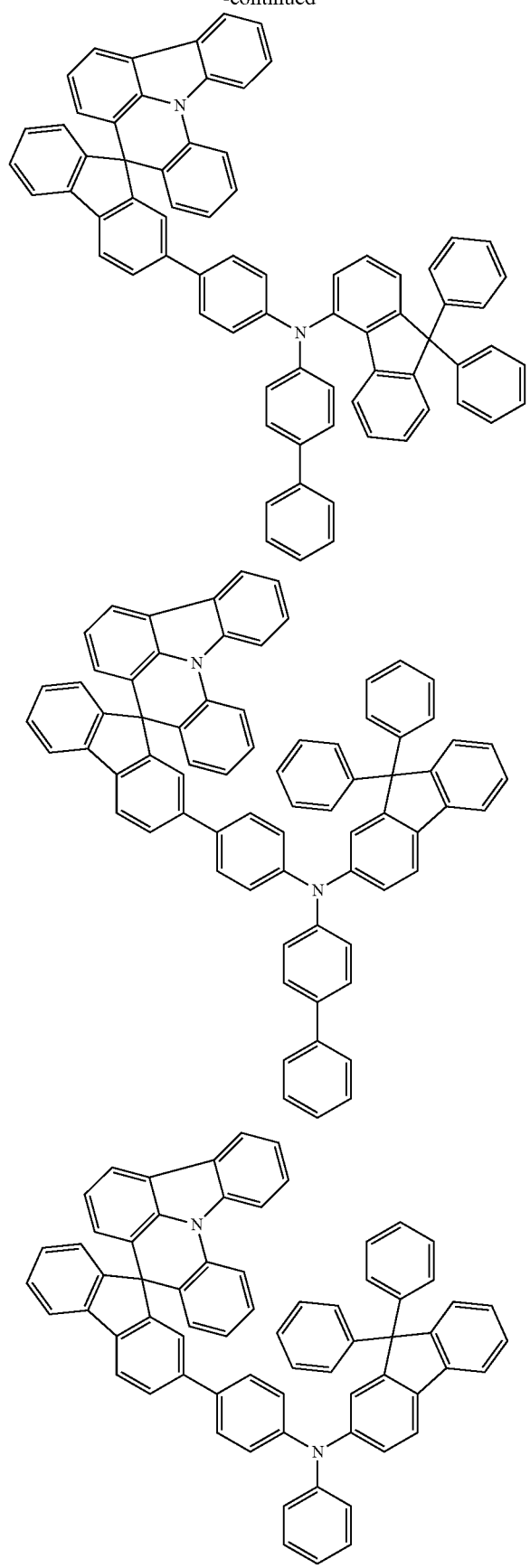
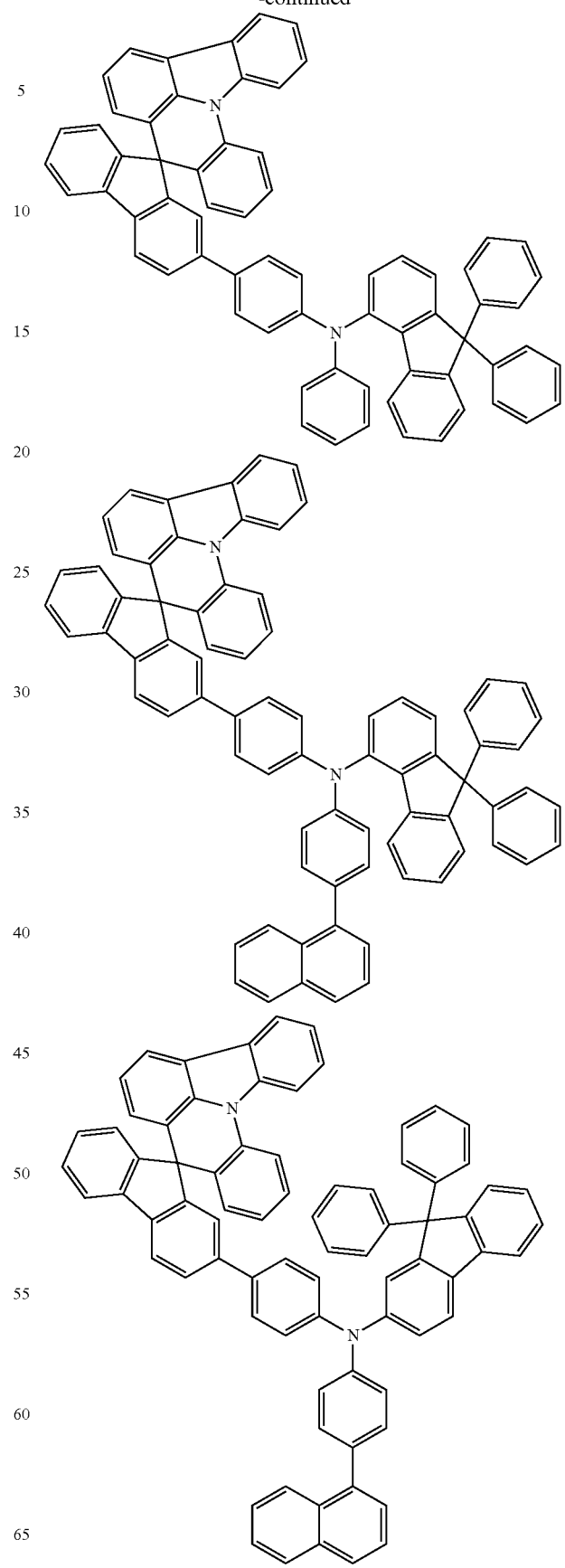

295
-continued
296
-continued
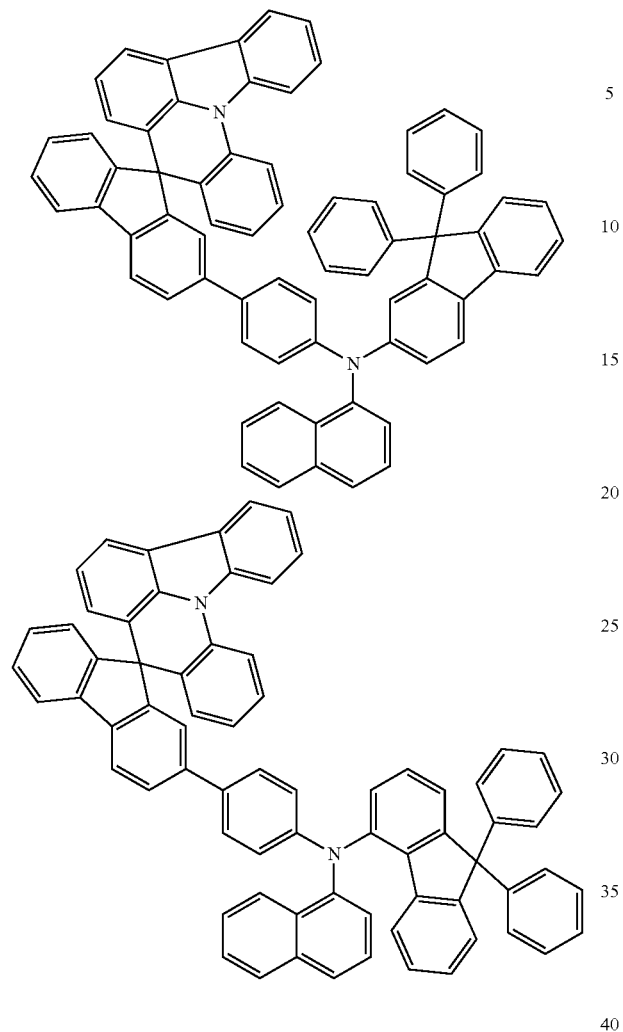
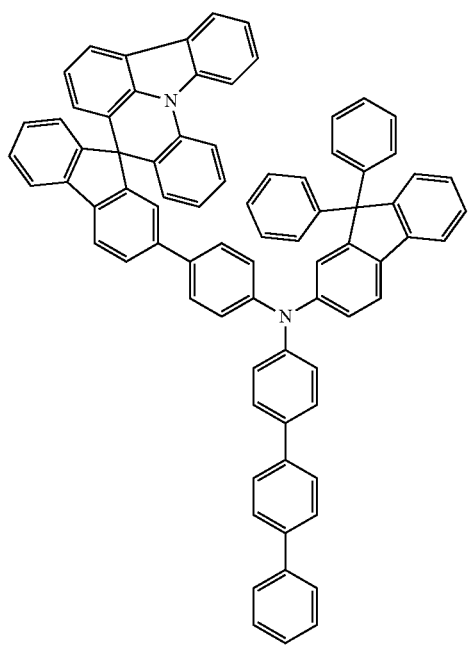
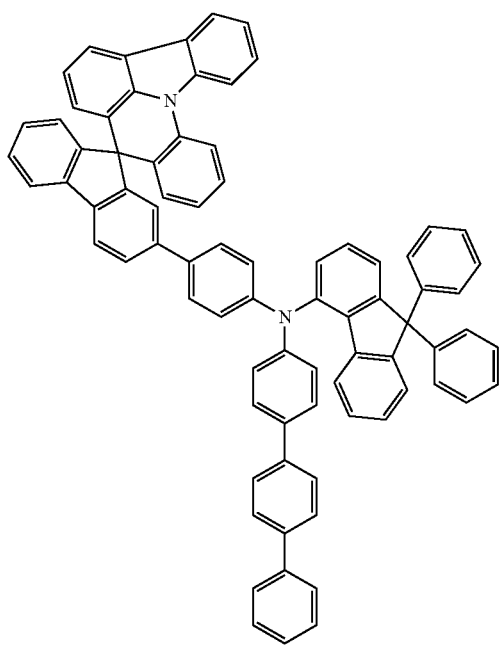

297
-continued
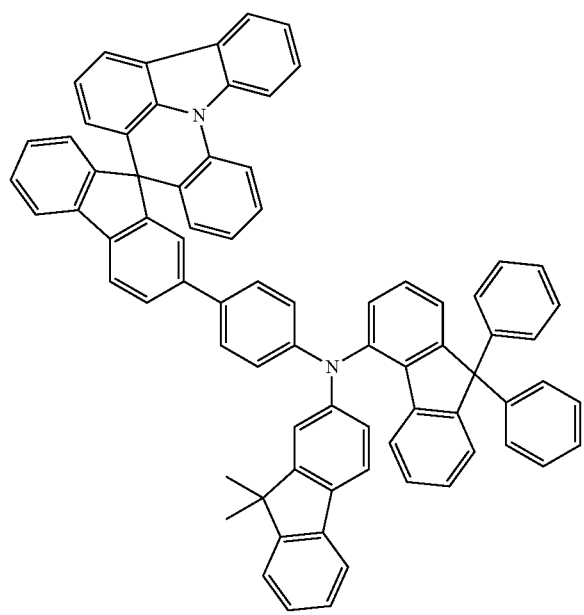
298
-continued
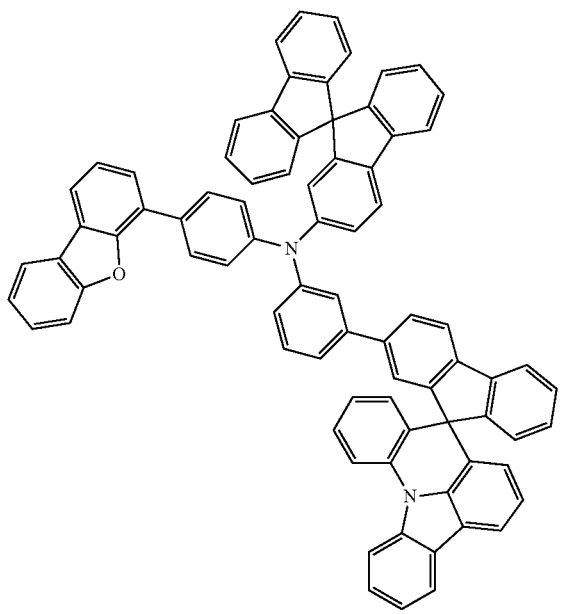
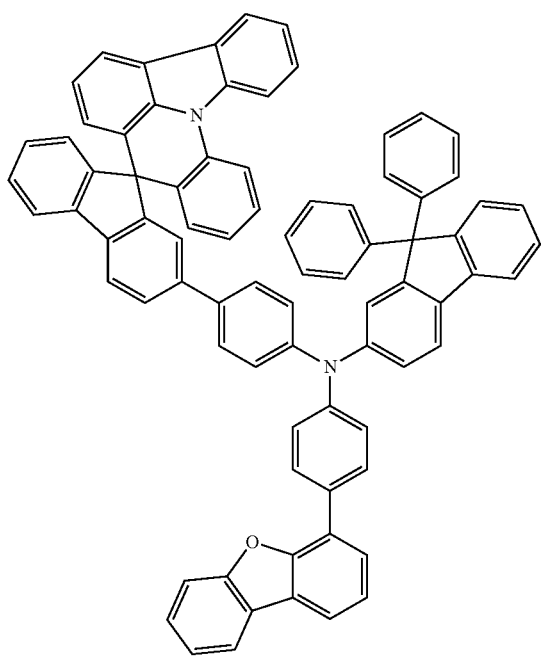
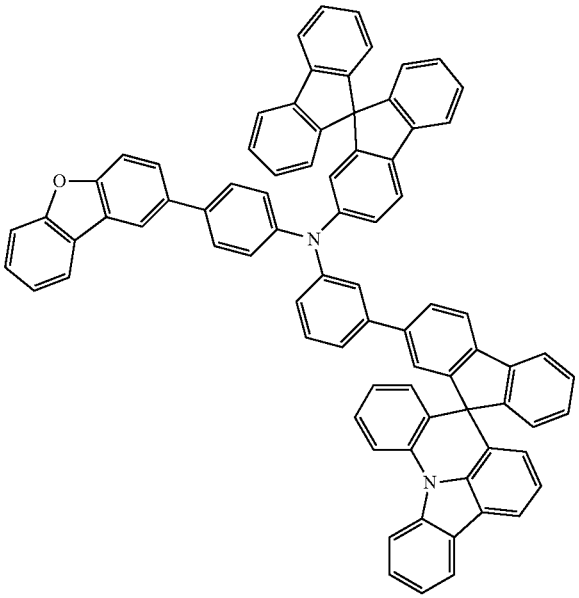

299
-continued
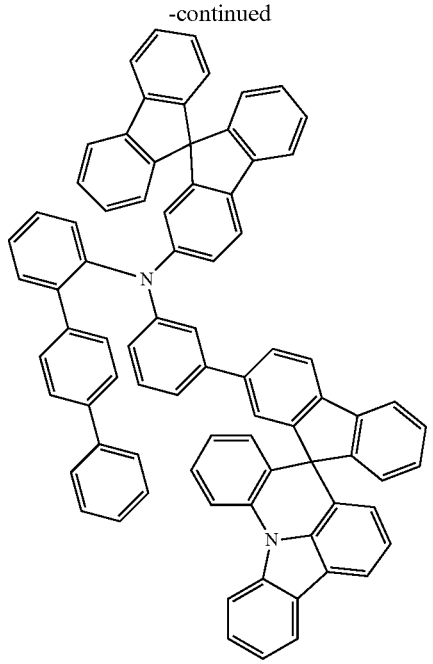
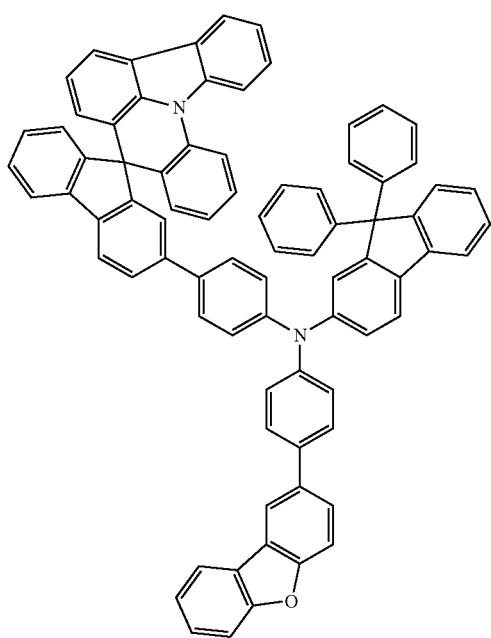
300
-continued
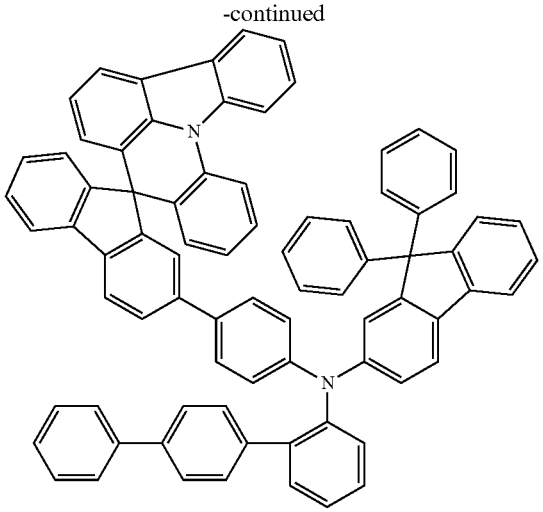
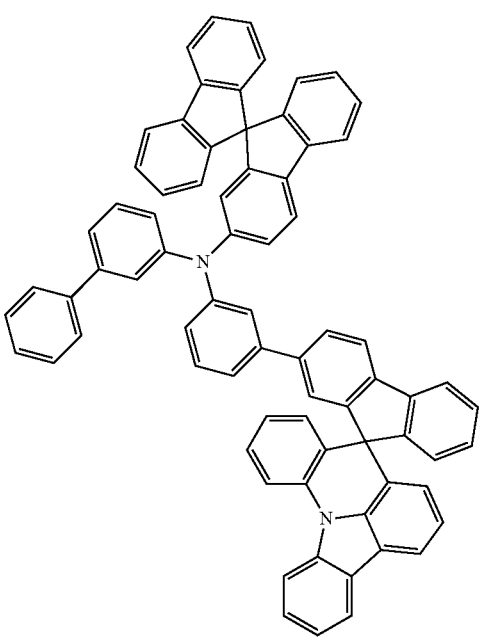

301
-continued
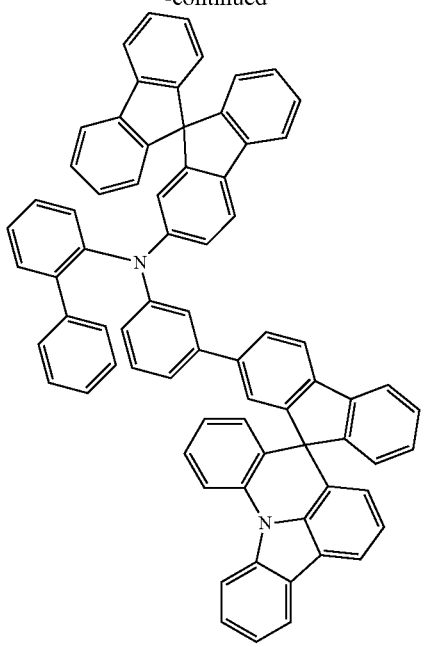
302
-continued
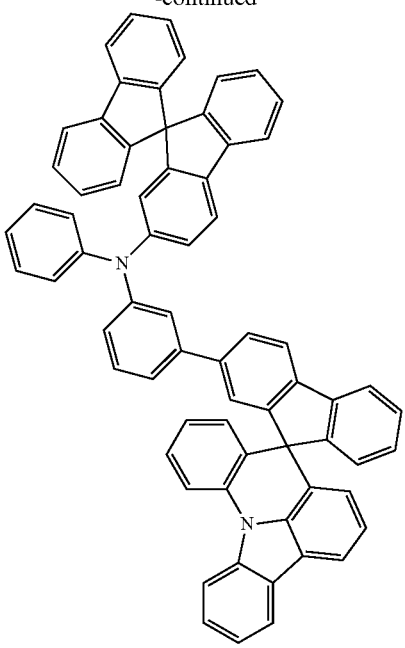
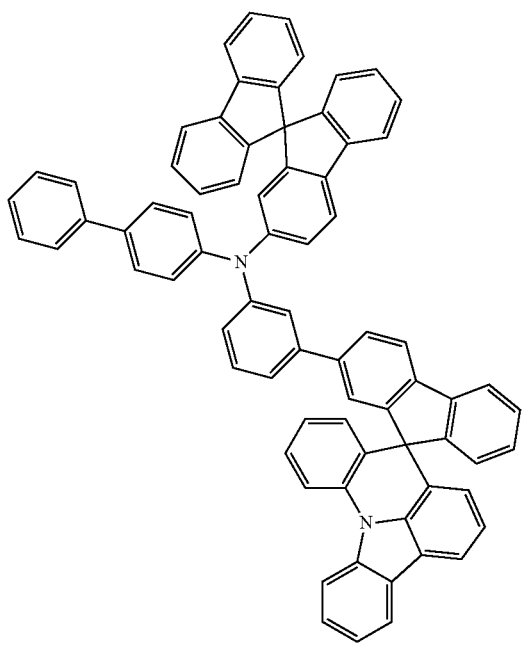
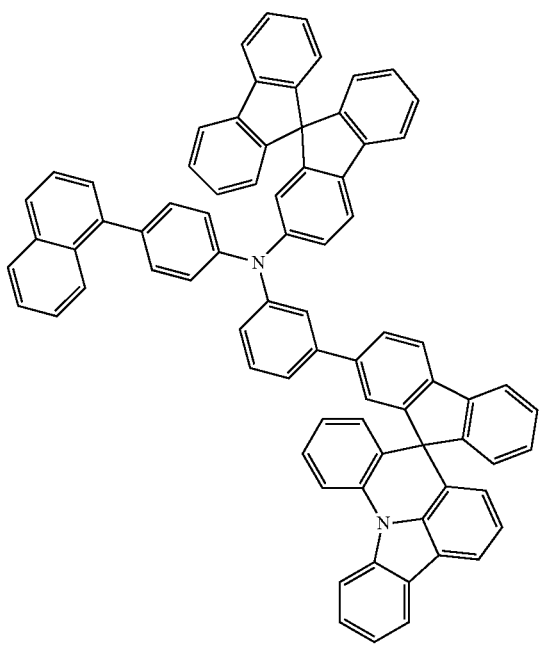

303
-continued
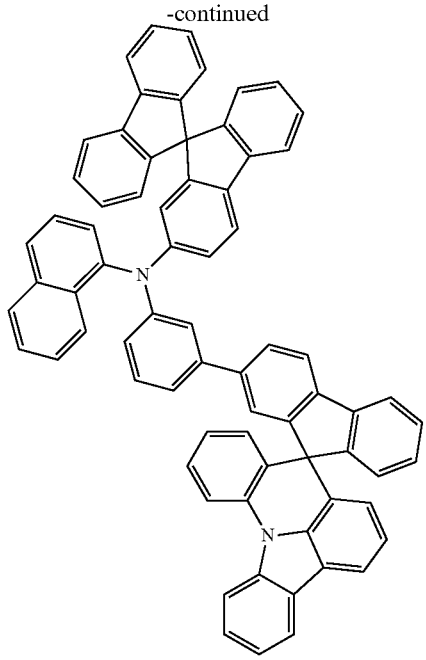
304
-continued
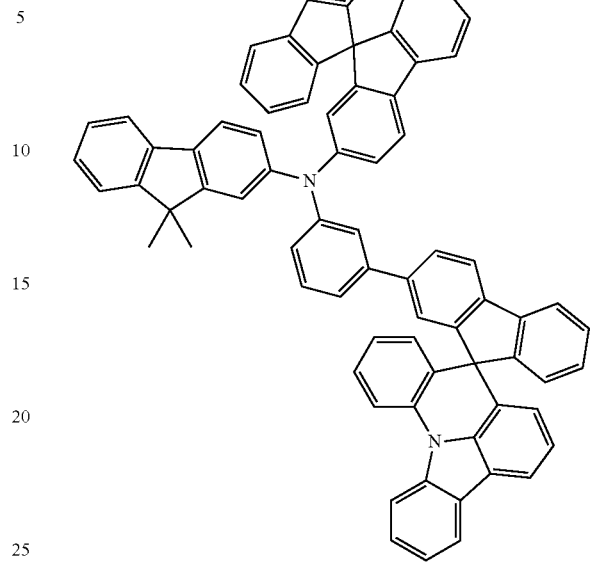
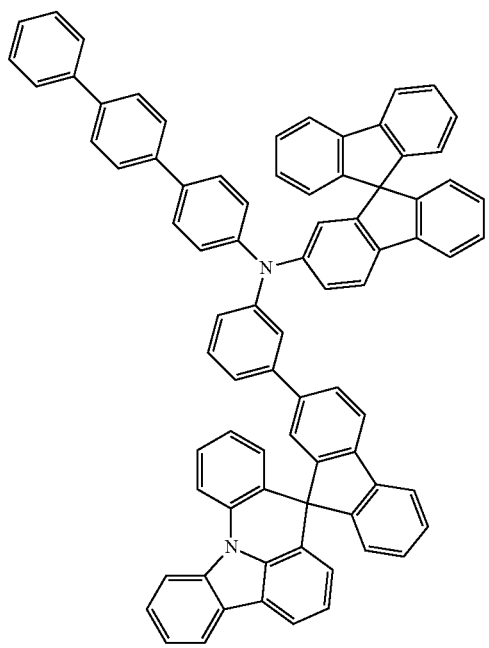
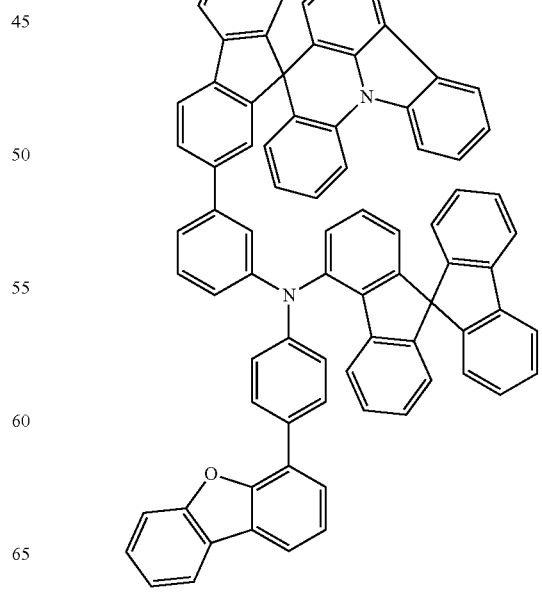

305
-continued
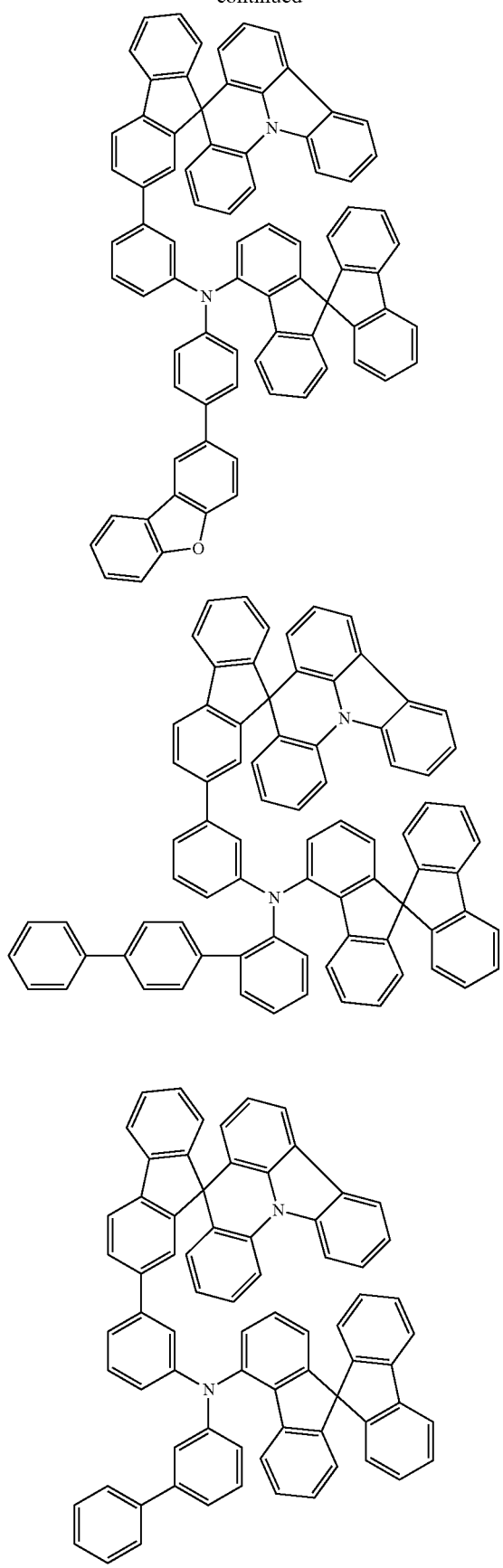
306
-continued
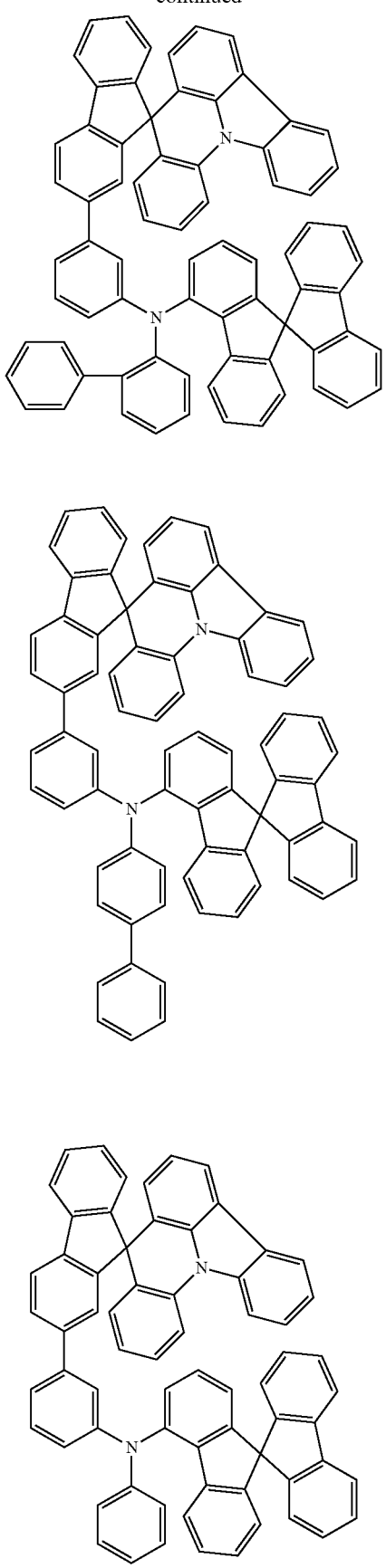

307
-continued
308
-continued
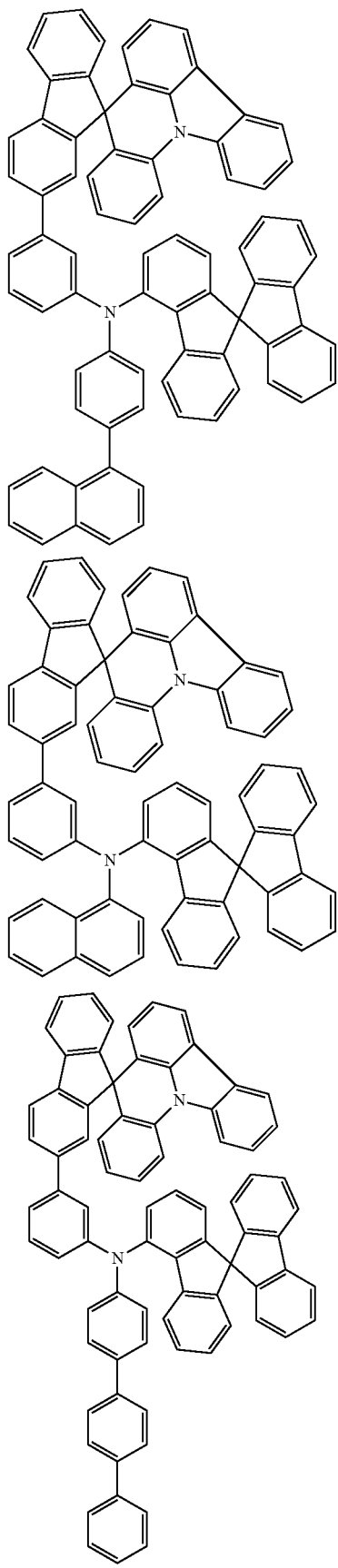

309
-continued
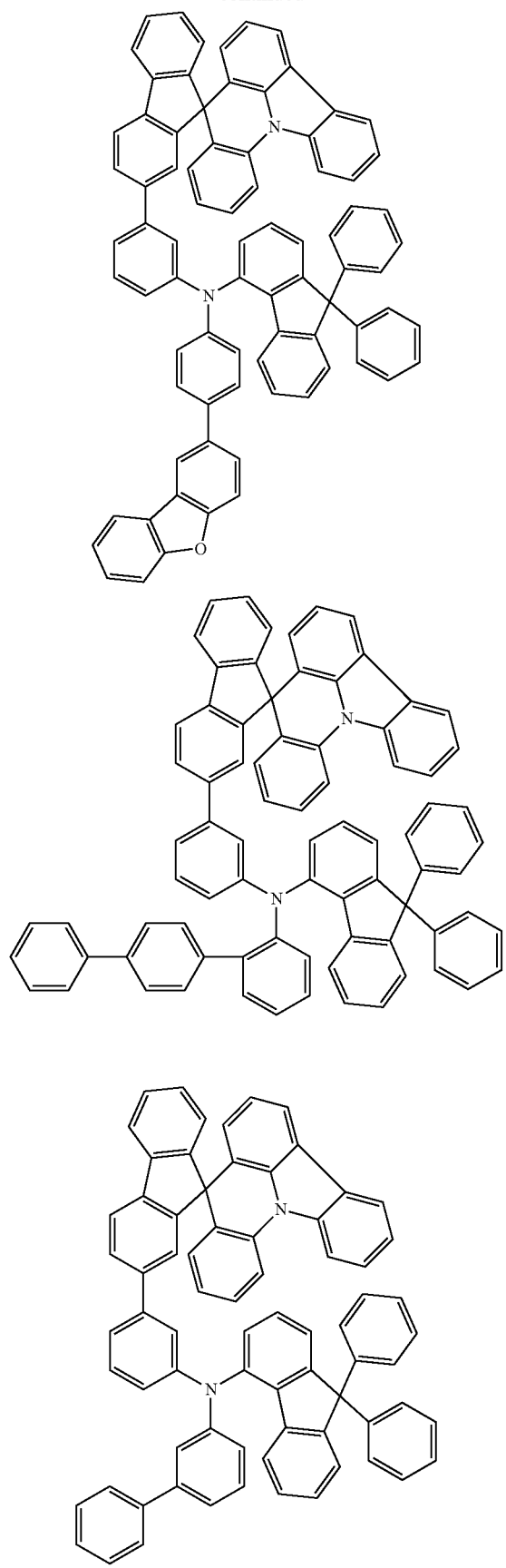
310
-continued
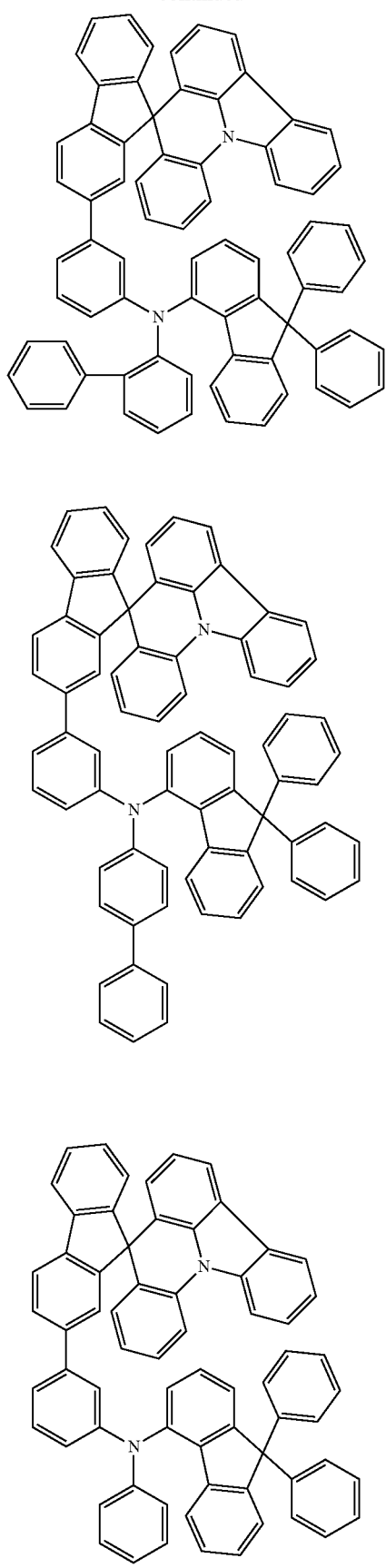

311
-continued
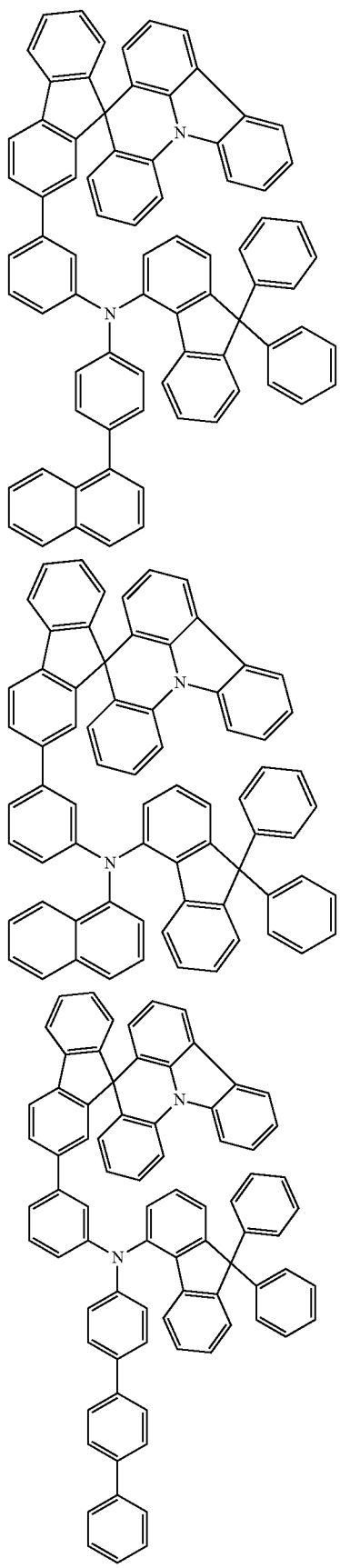
312
-continued
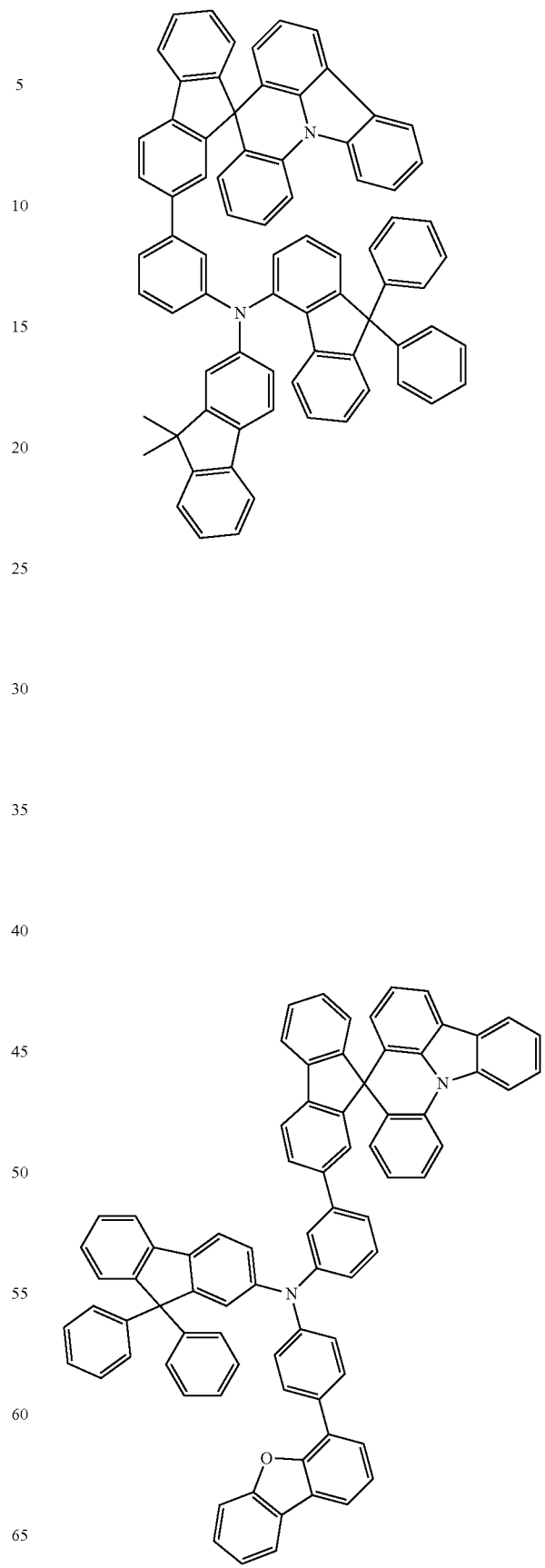

313
-continued
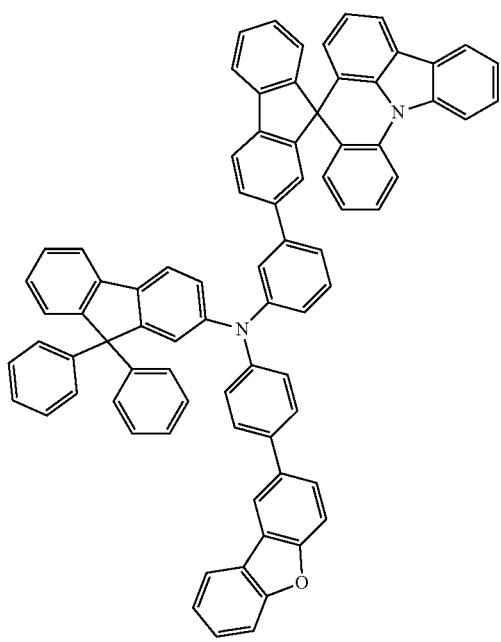
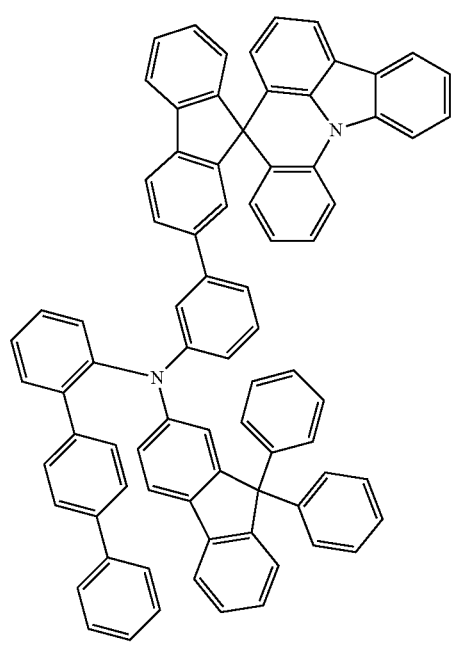
314
-continued
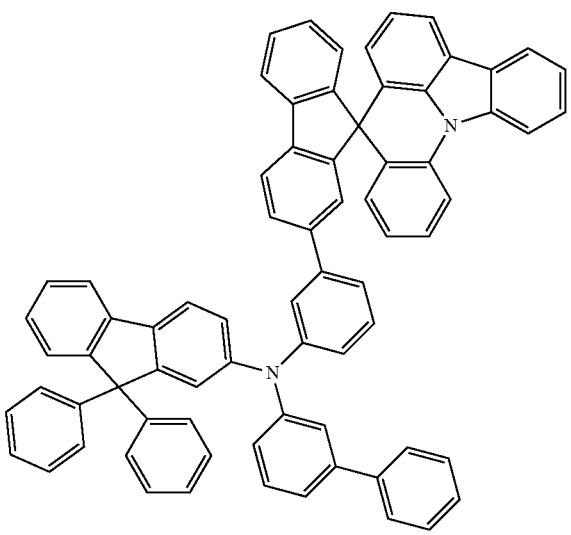
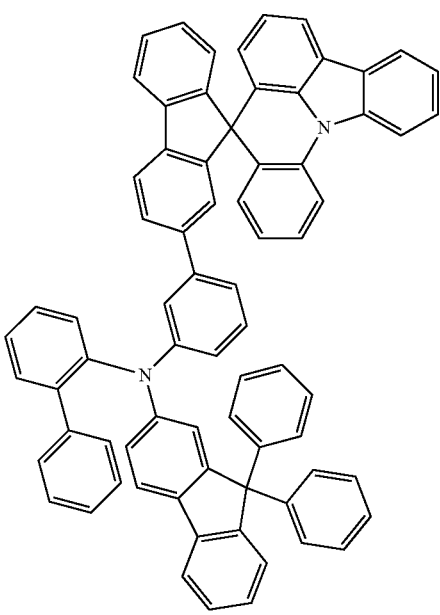

315
-continued
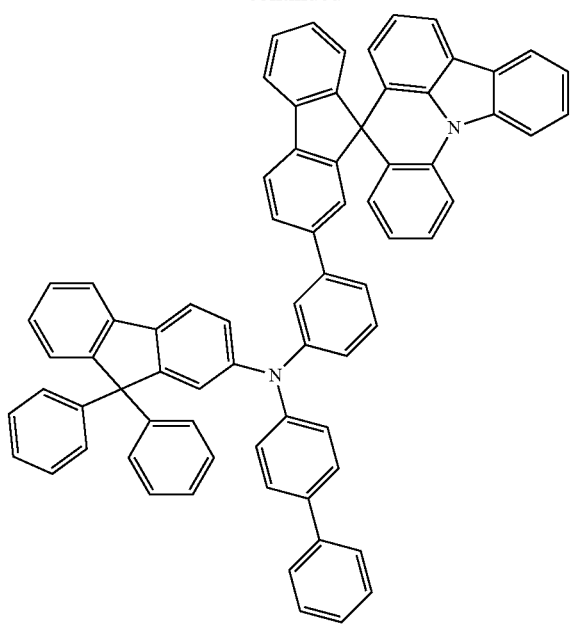
316
-continued
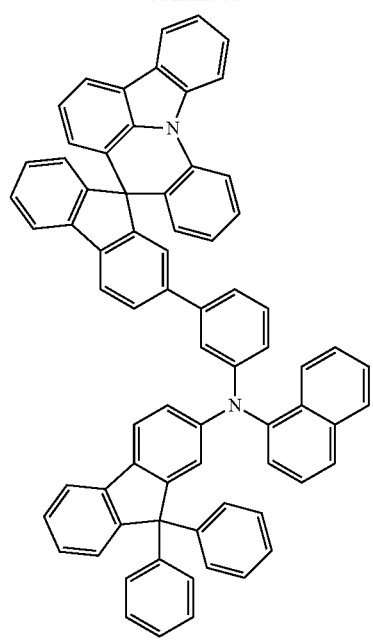
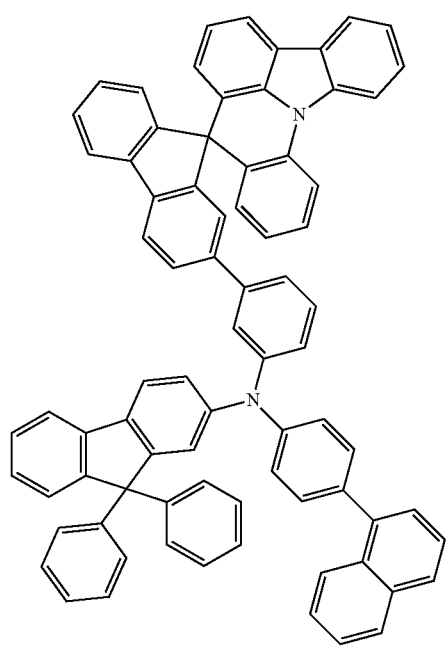
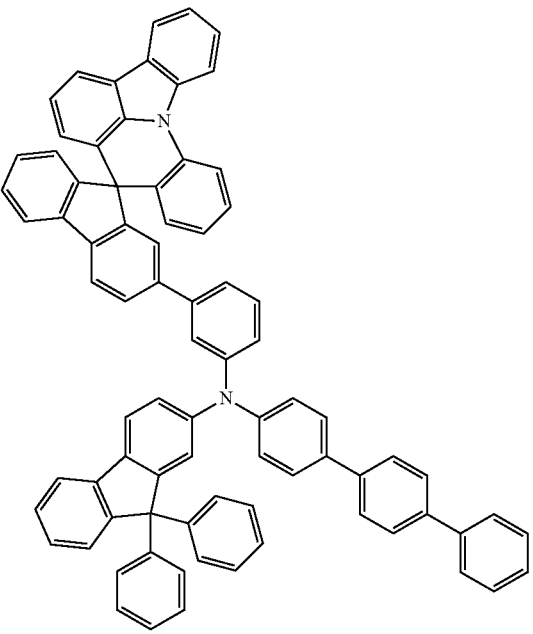

317
-continued
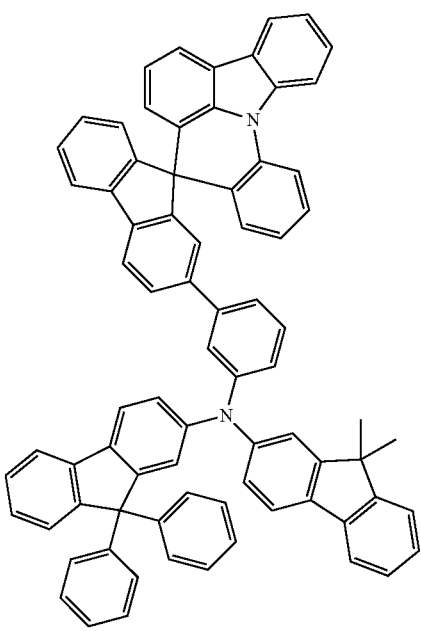
318
-continued
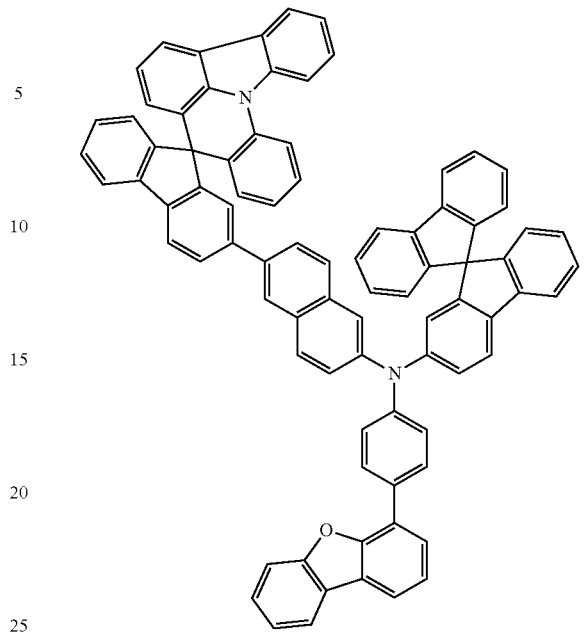
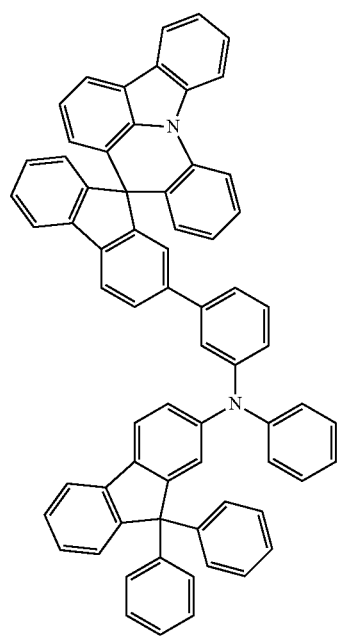
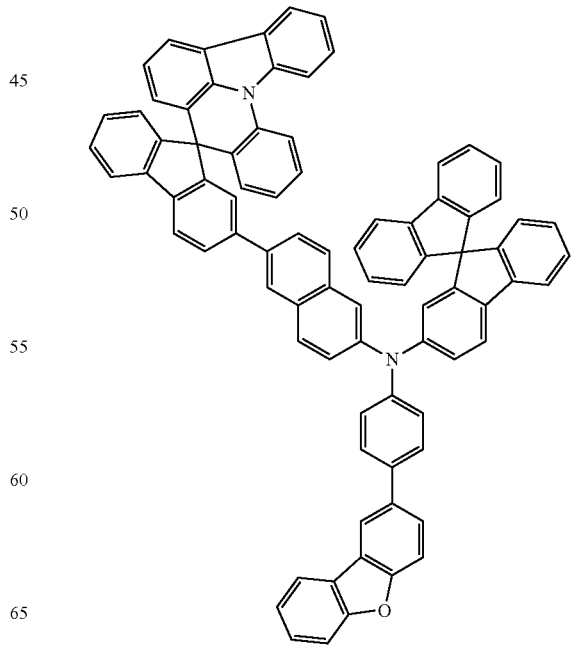

319
-continued
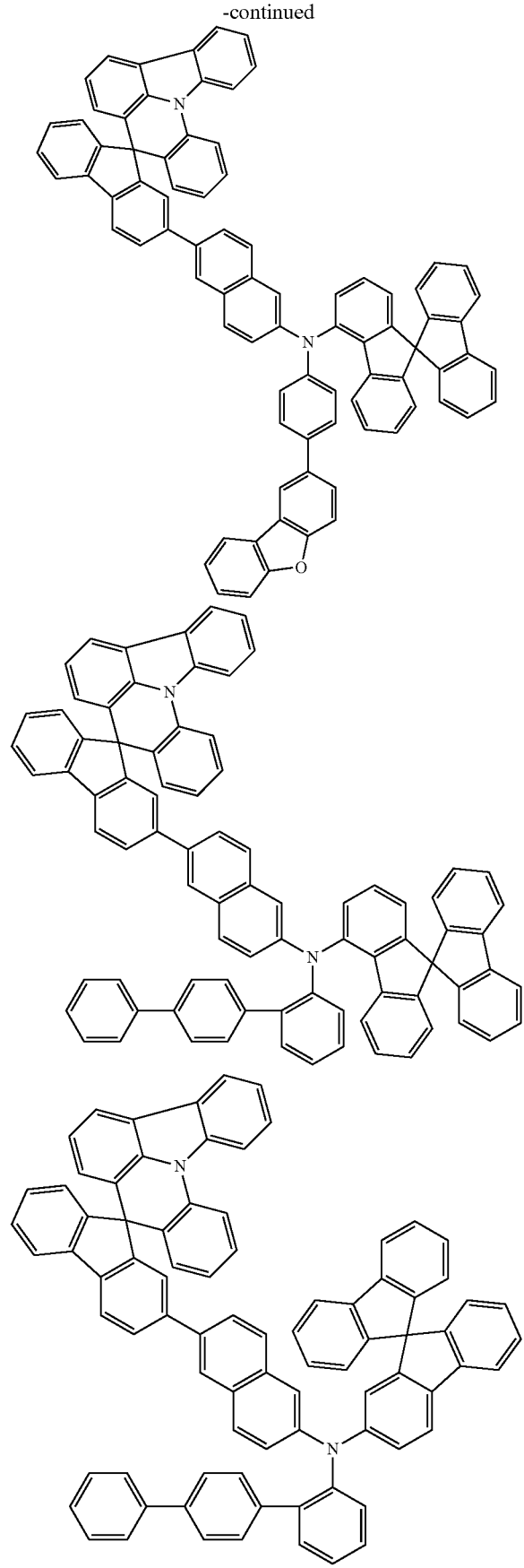
320
-continued
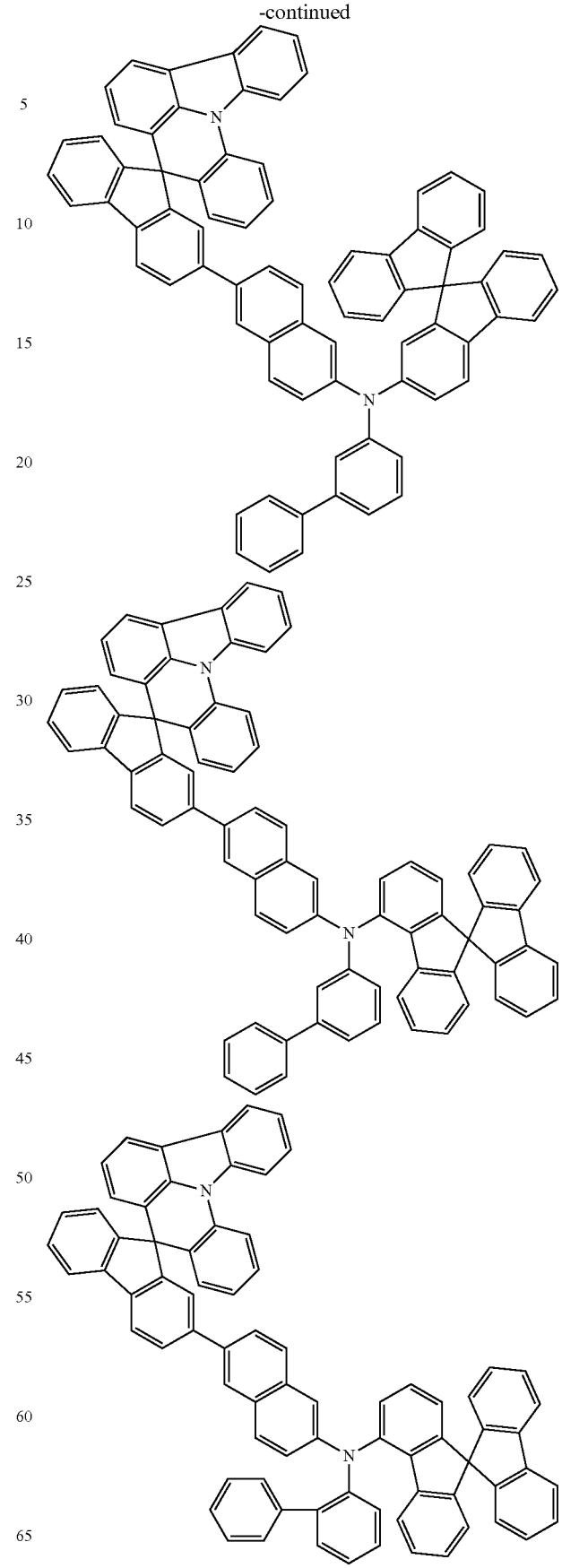

321
-continued
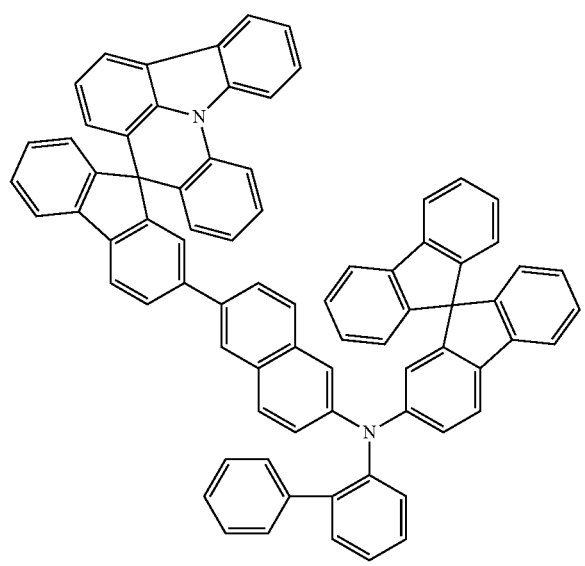
322
-continued
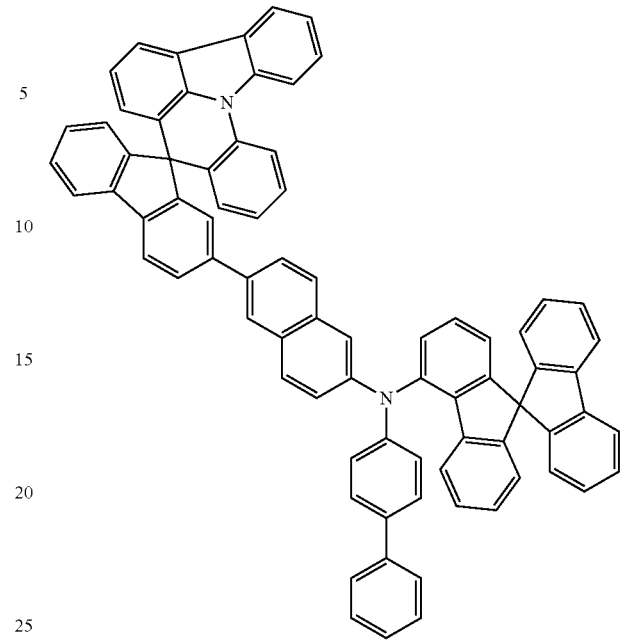
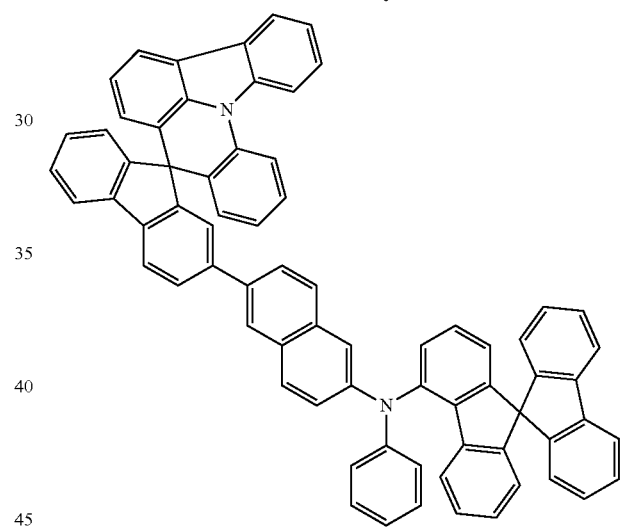
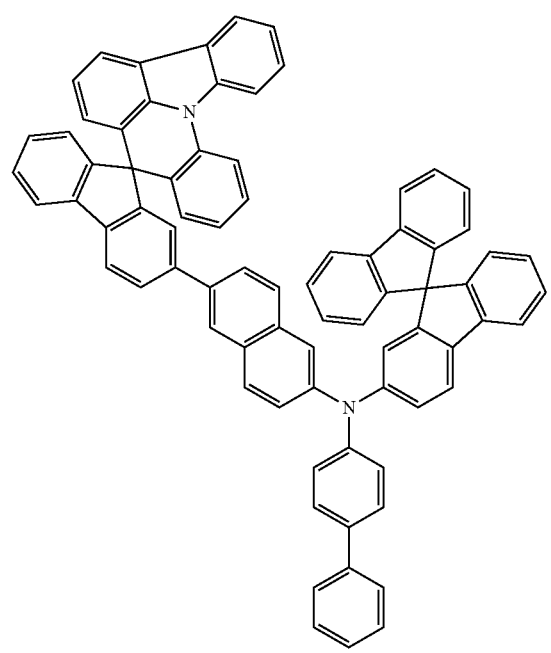

323
-continued
324
-continued
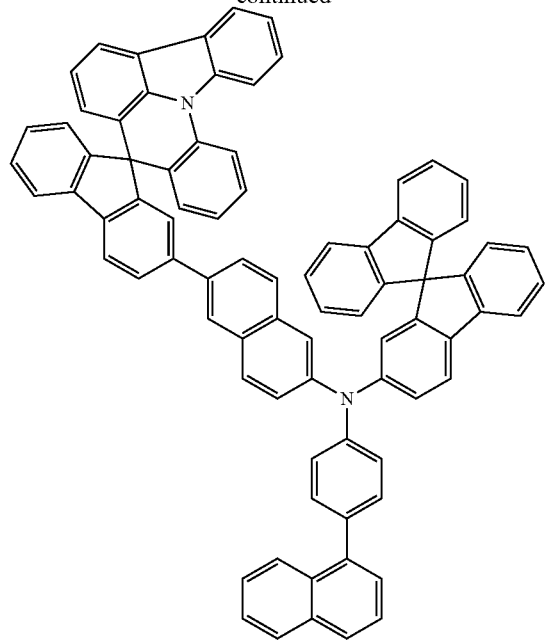
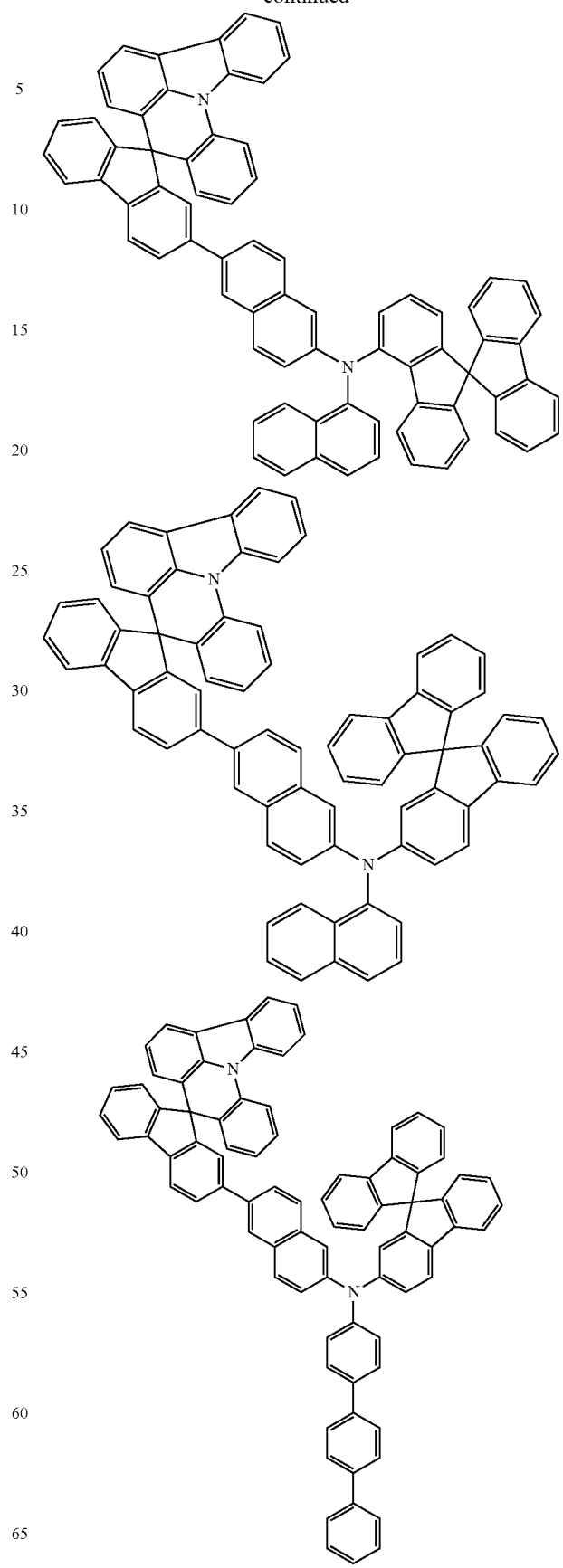

325
-continued
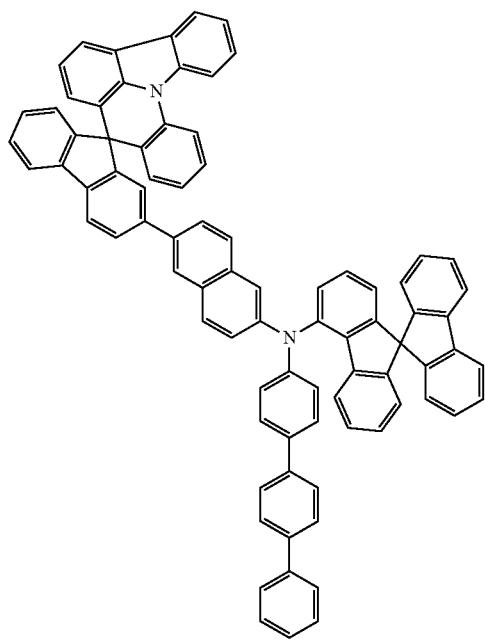
326
-continued
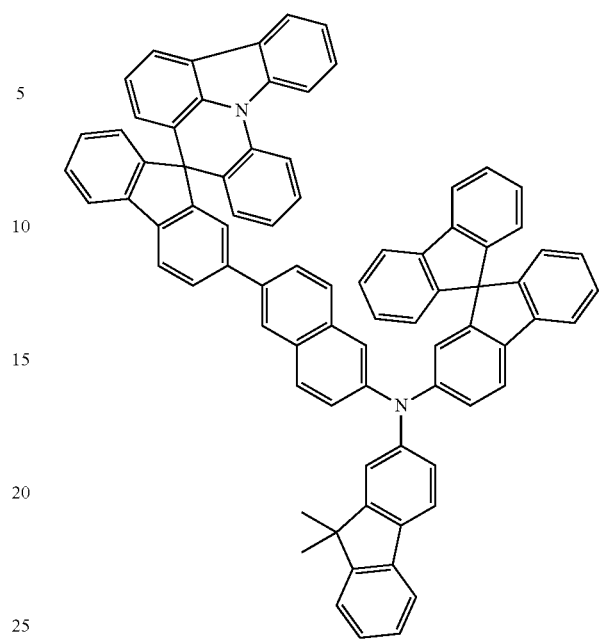
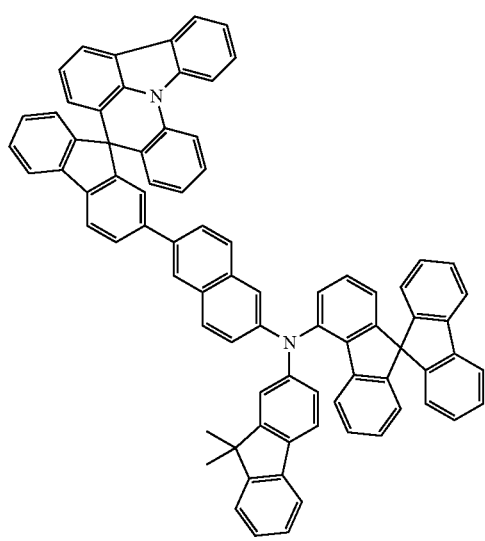
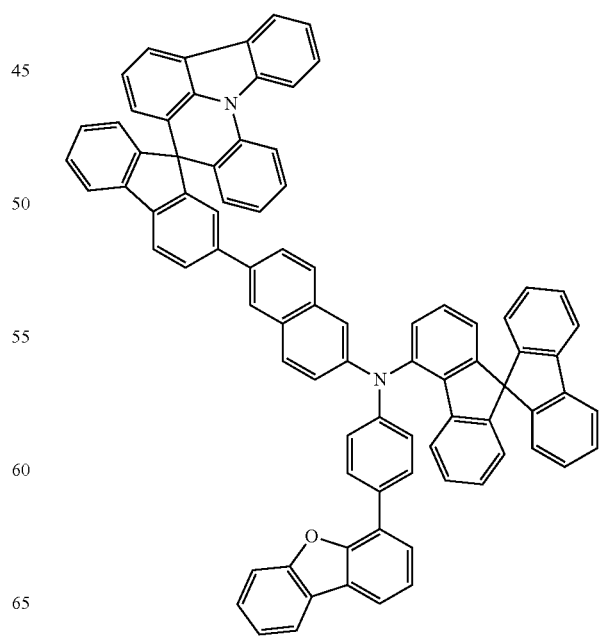

327
-continued
328
-continued
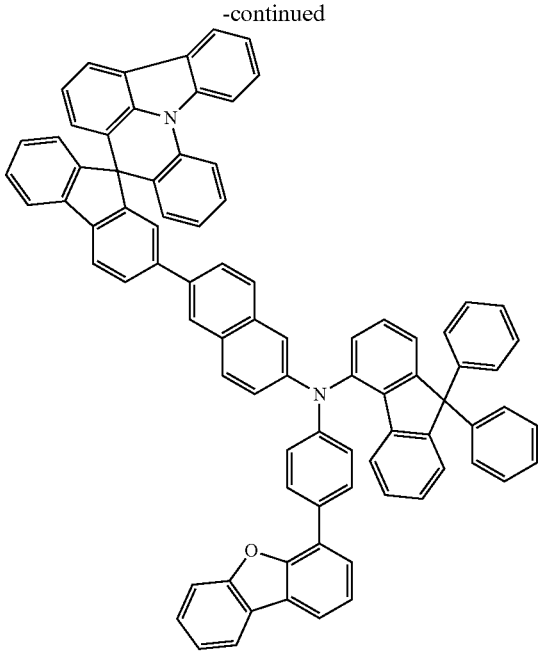
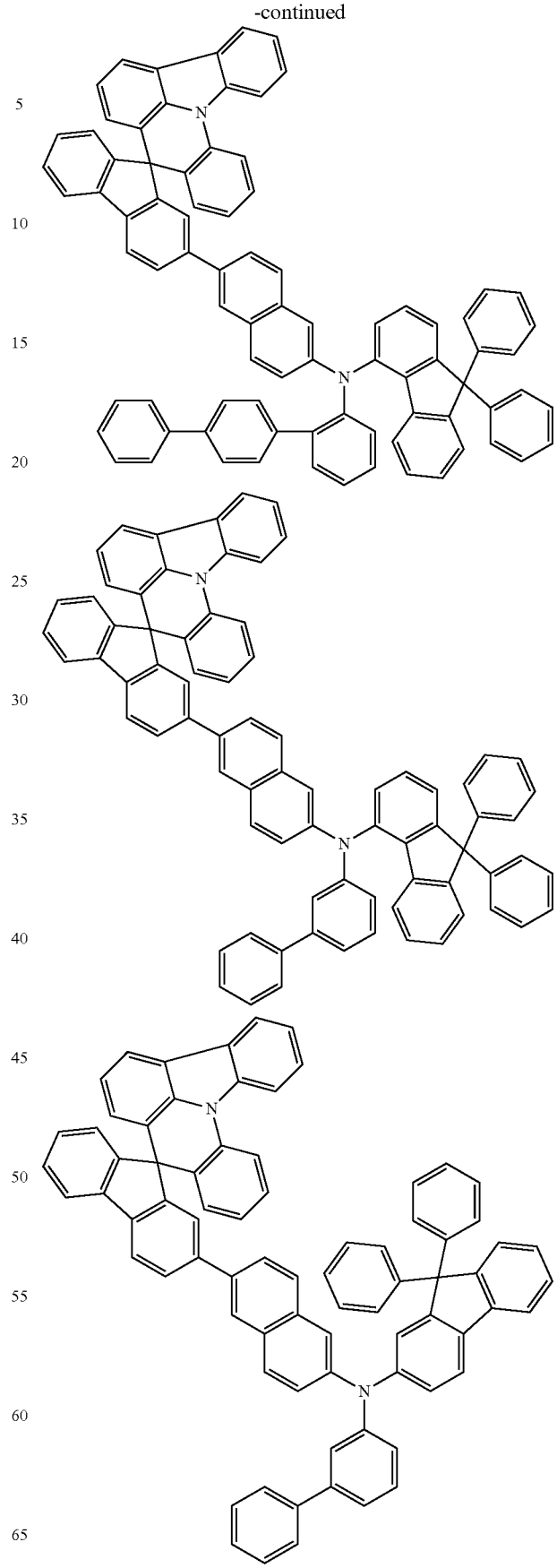

329
-continued
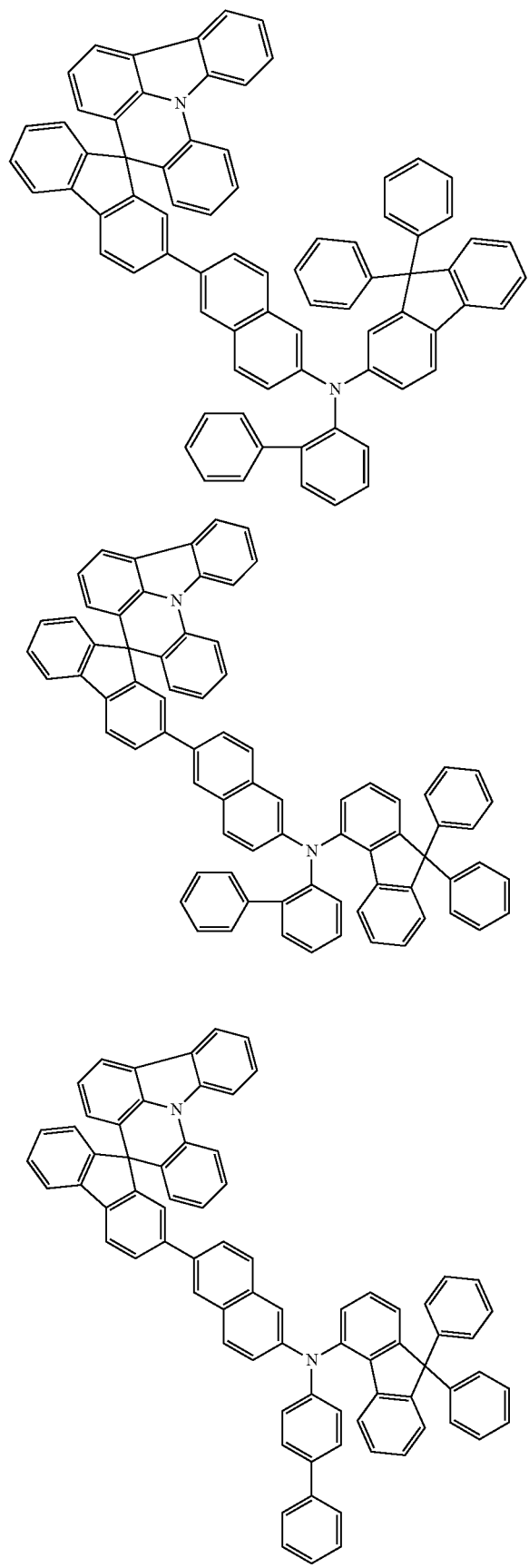
330
-continued
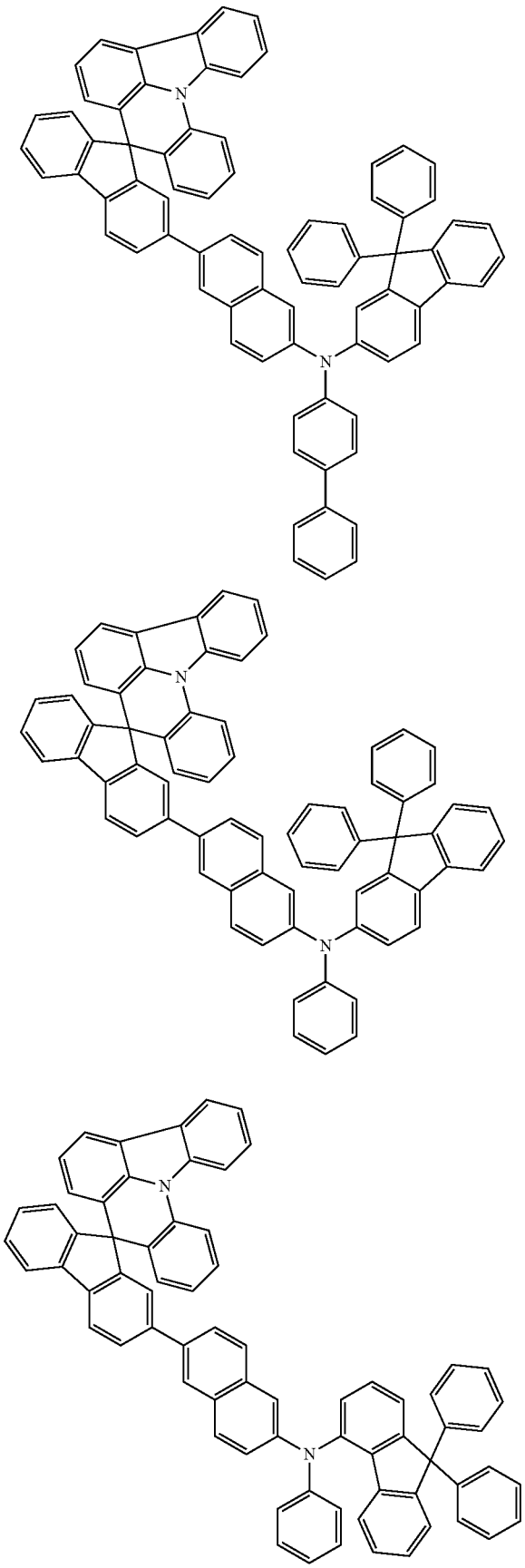

331
-continued
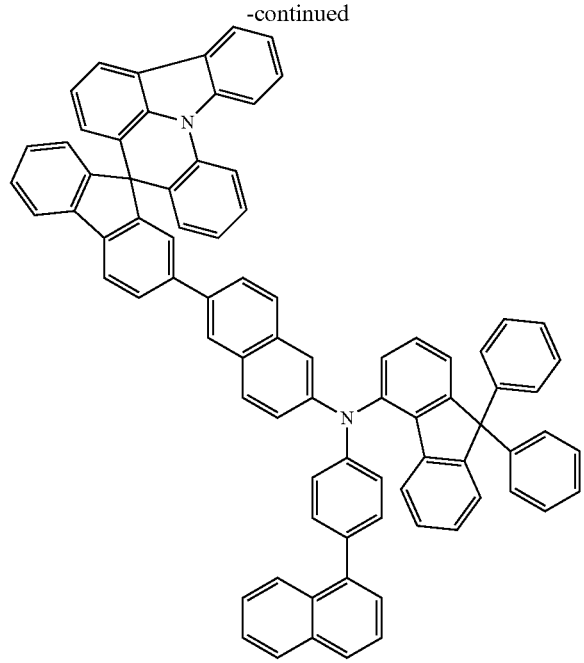
332
-continued
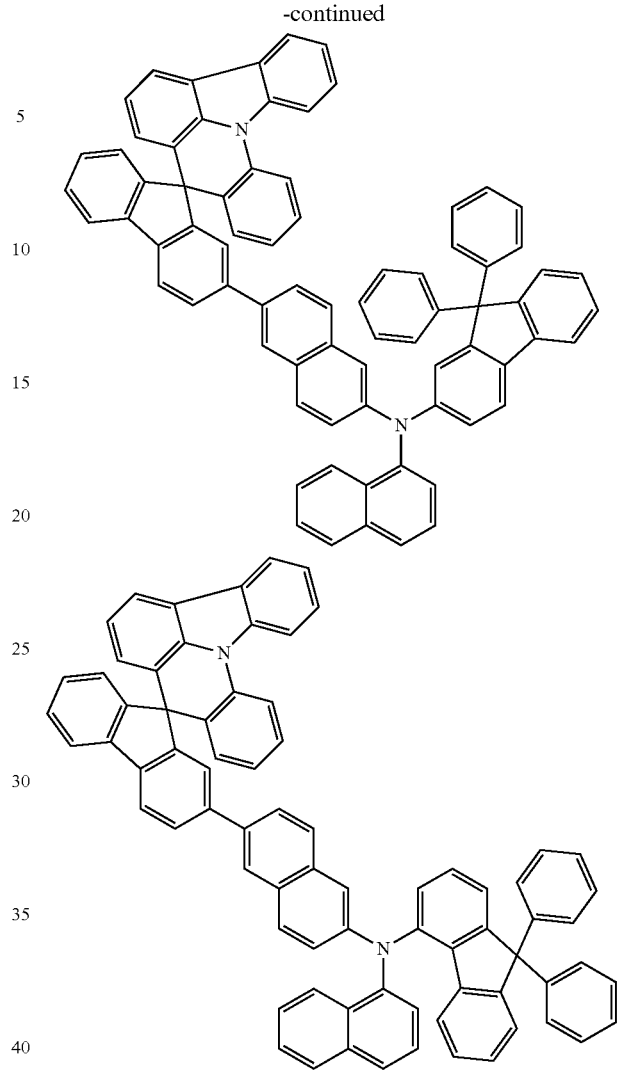
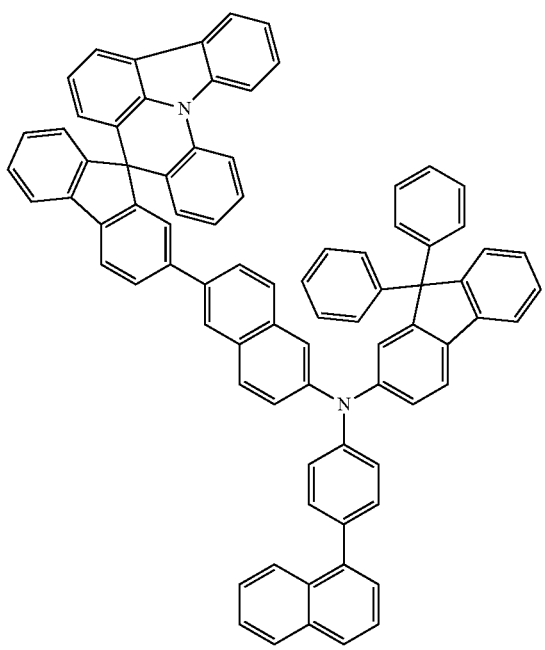
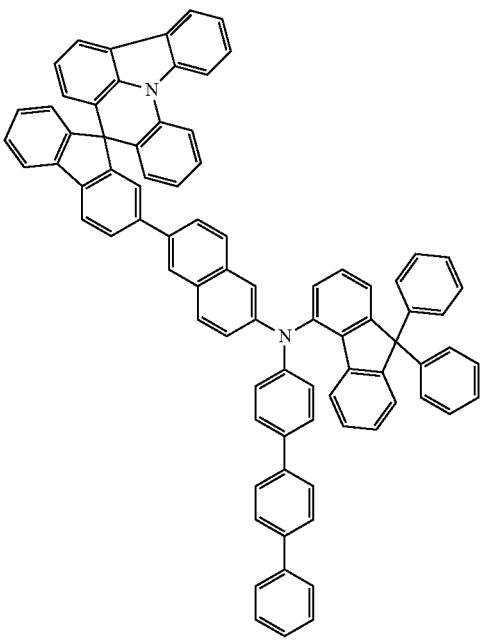

333
-continued
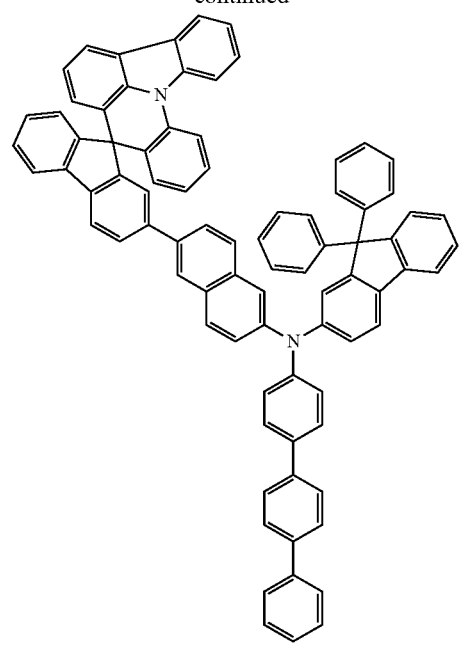
334
-continued
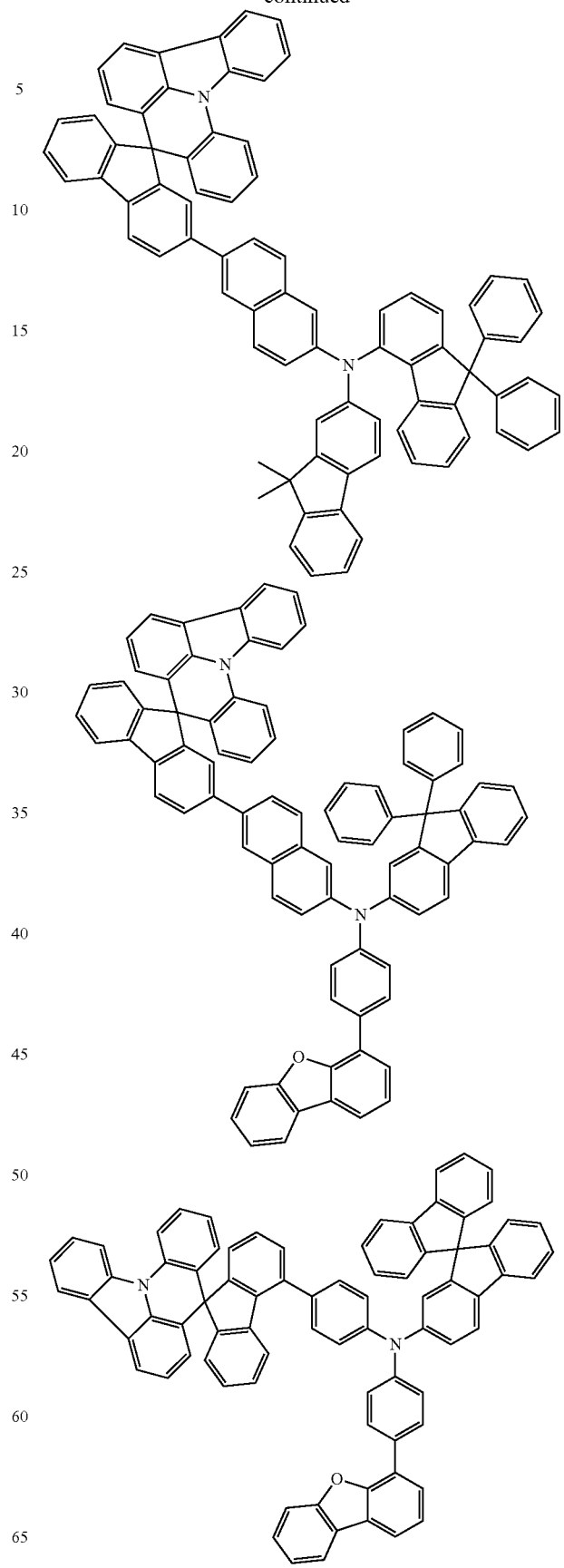

335
-continued
336
-continued
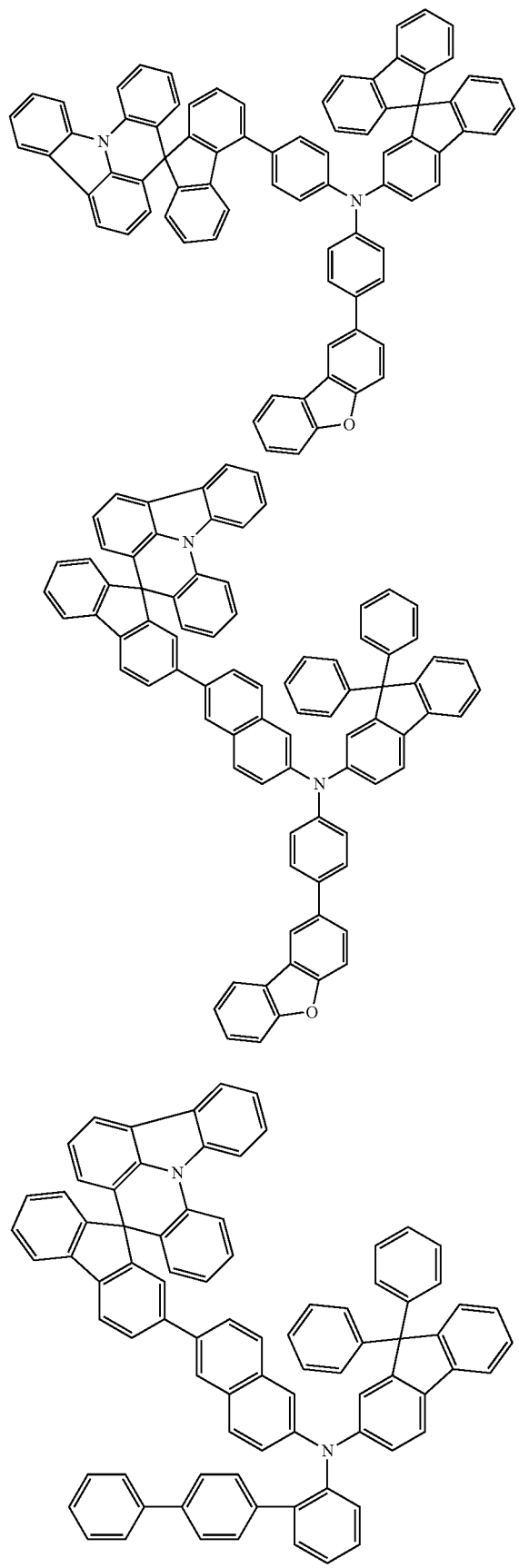
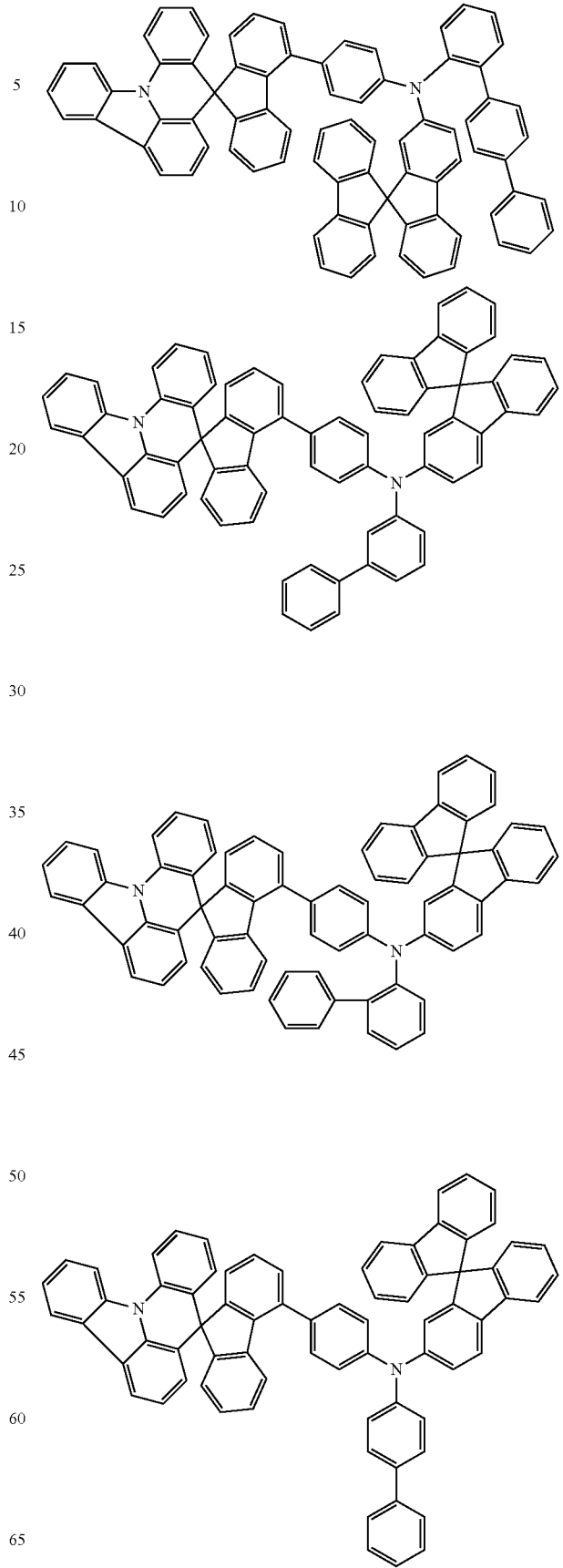

337
-continued
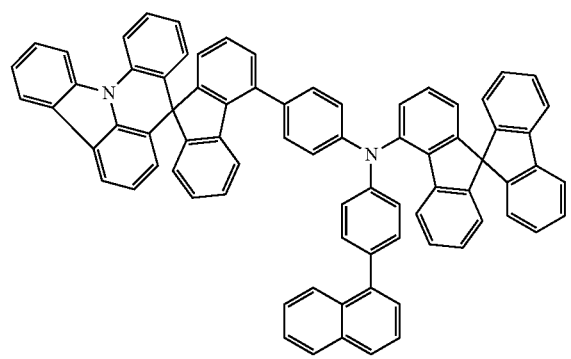
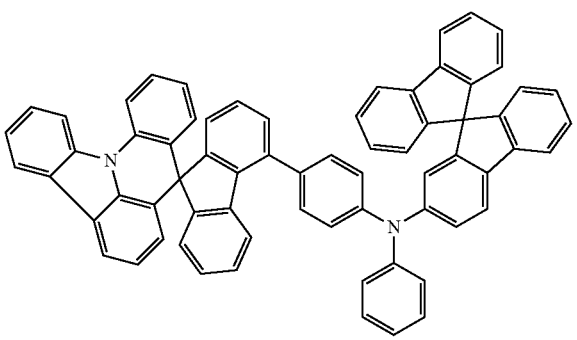
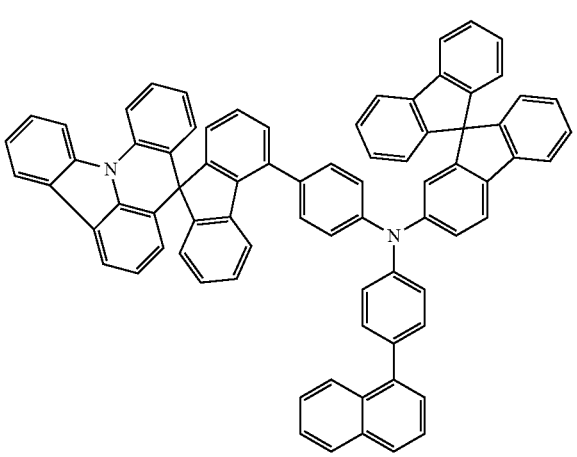
338
-continued
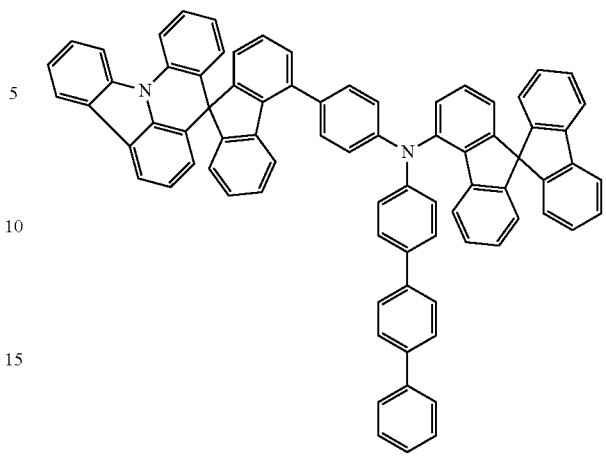
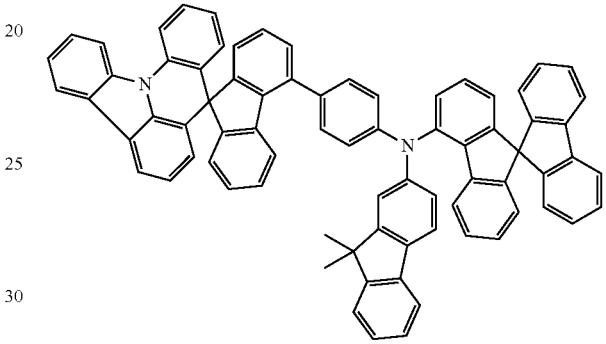
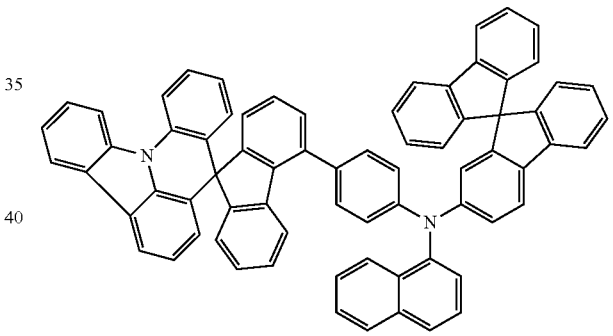
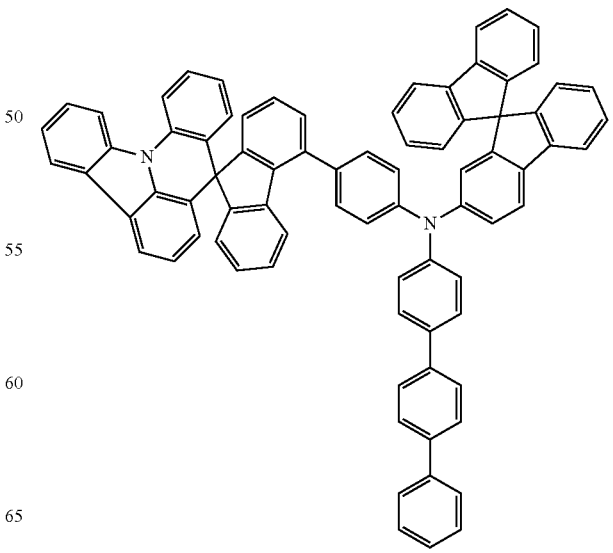

339
-continued
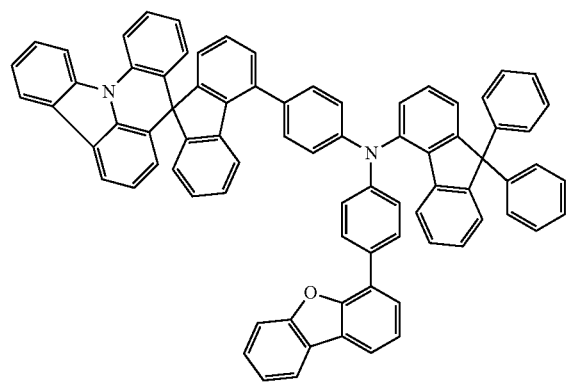
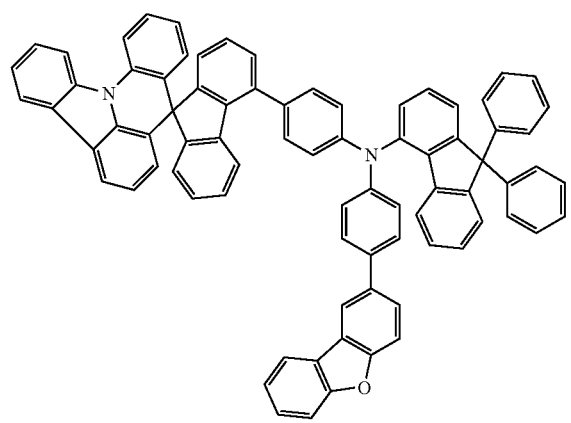
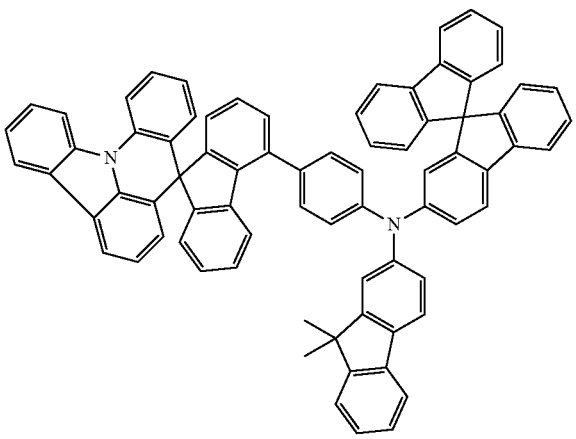
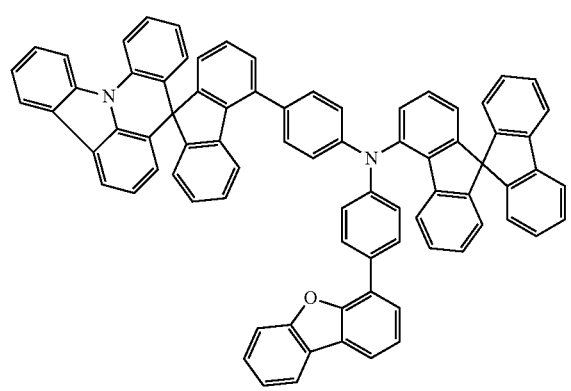
340
-continued
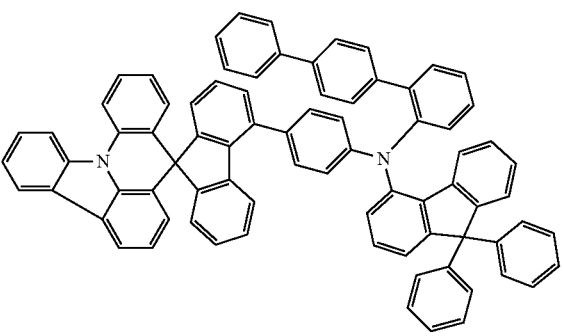
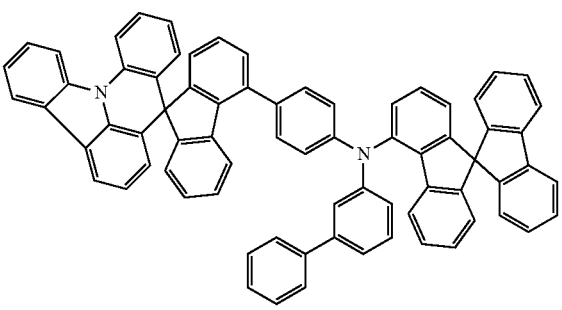
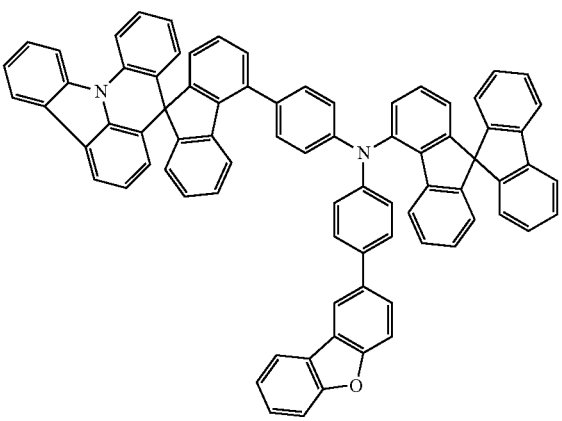
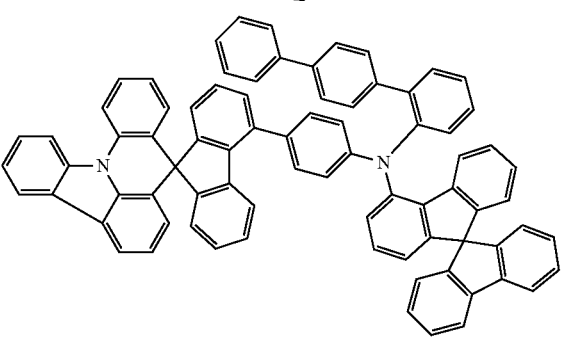
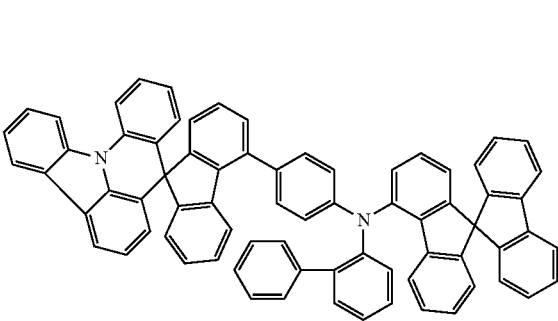

341
-continued
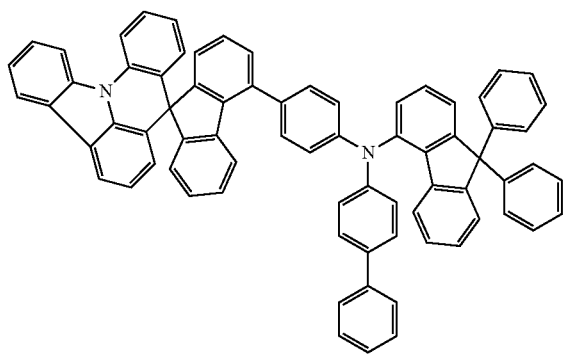
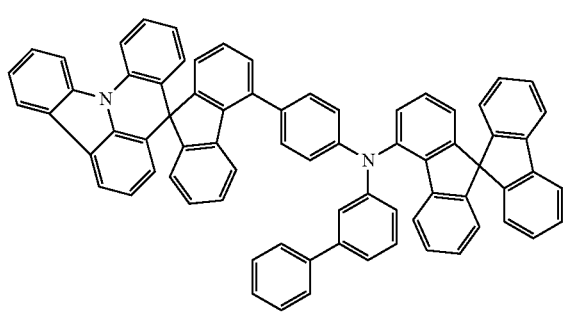
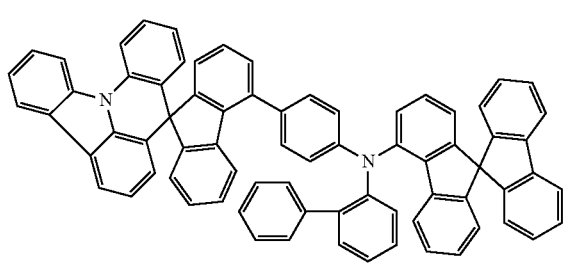
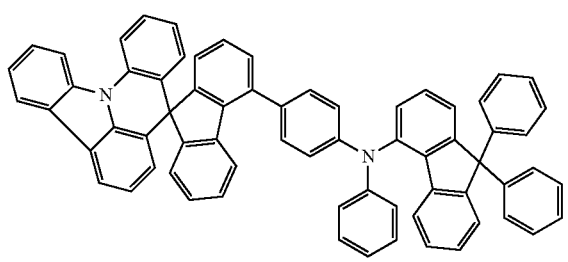
342
-continued
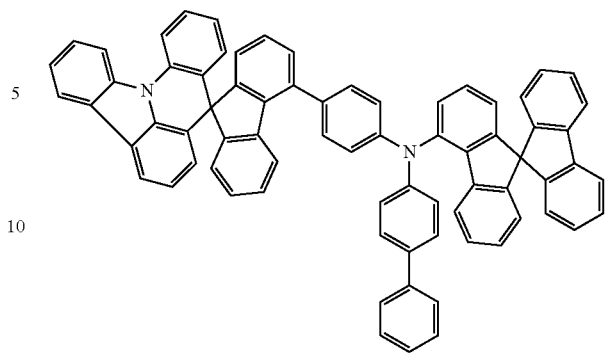
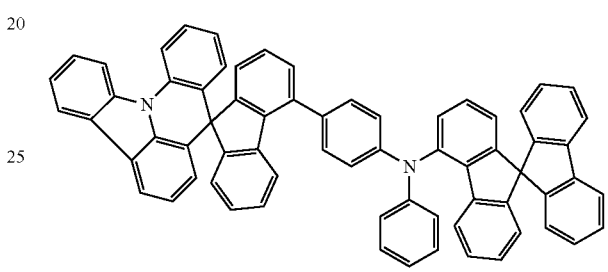
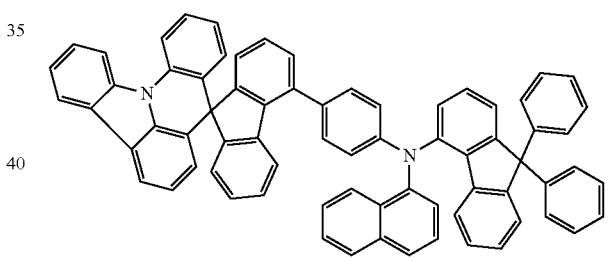
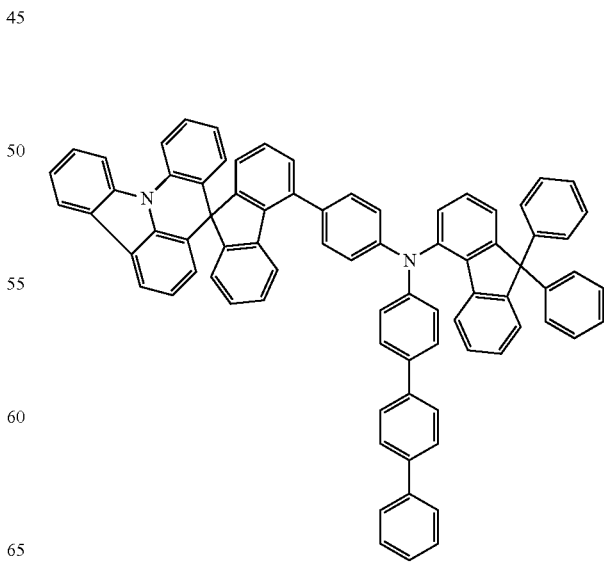

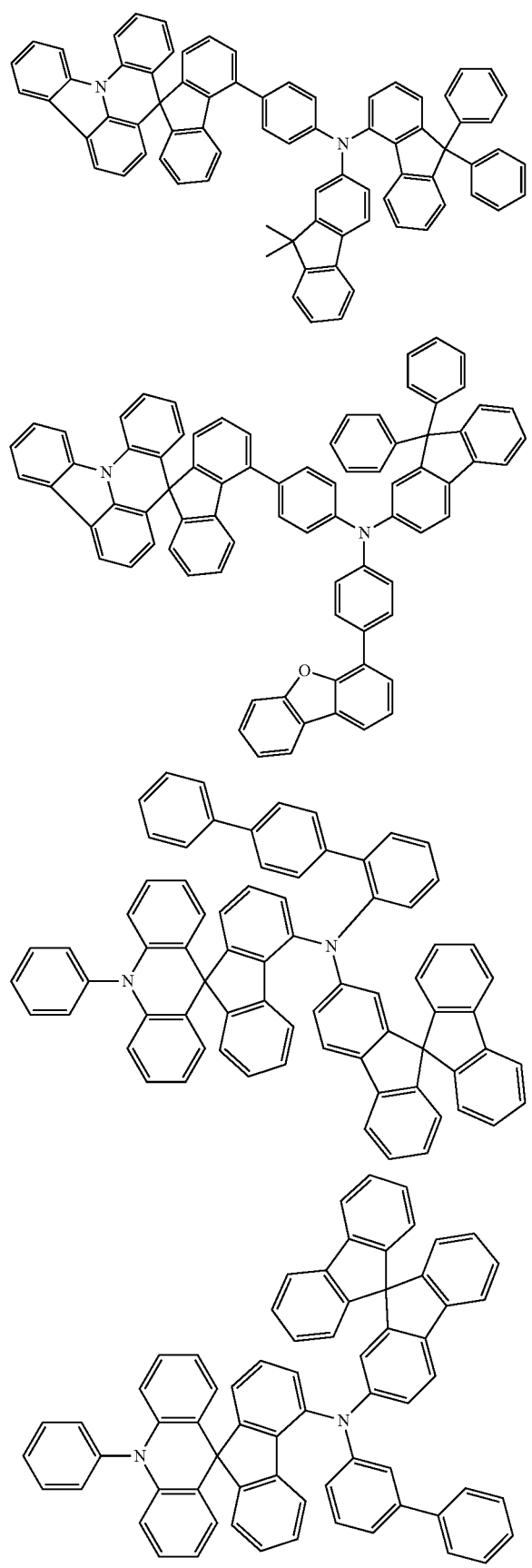
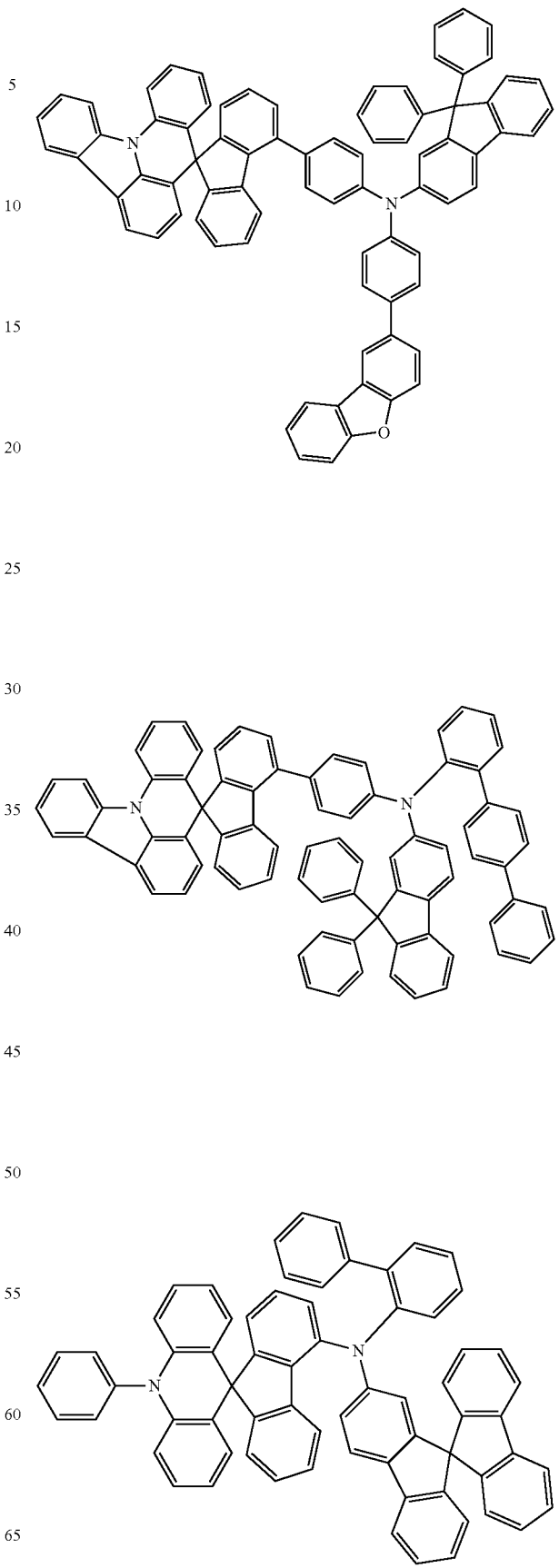

345
-continued
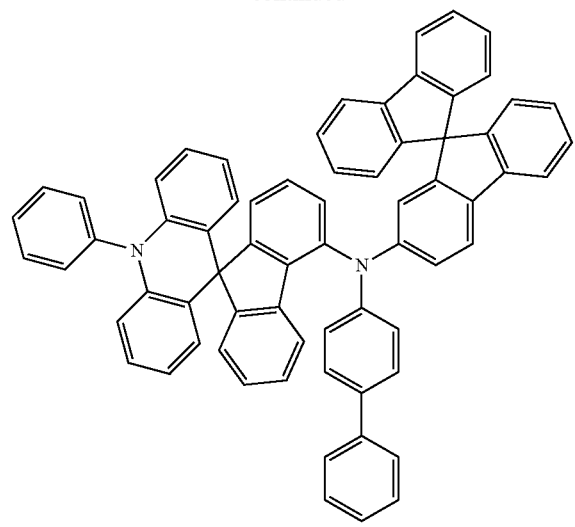
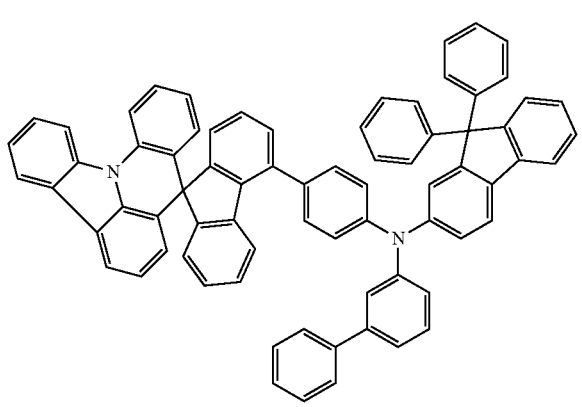
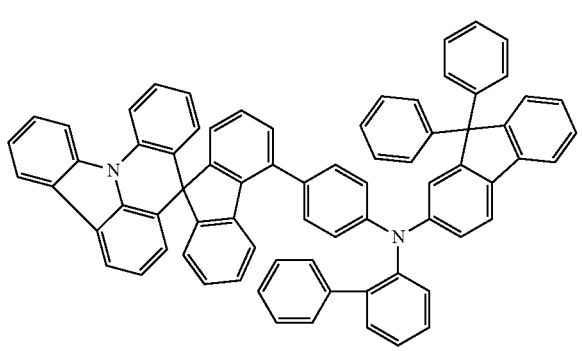
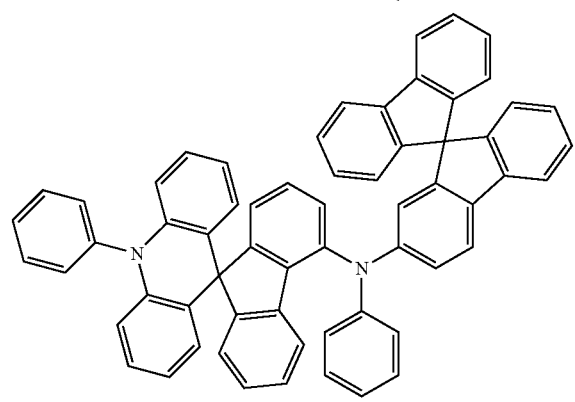
346
-continued
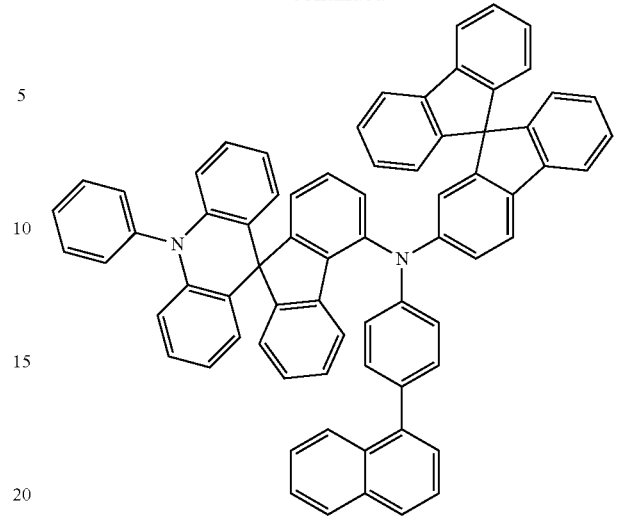
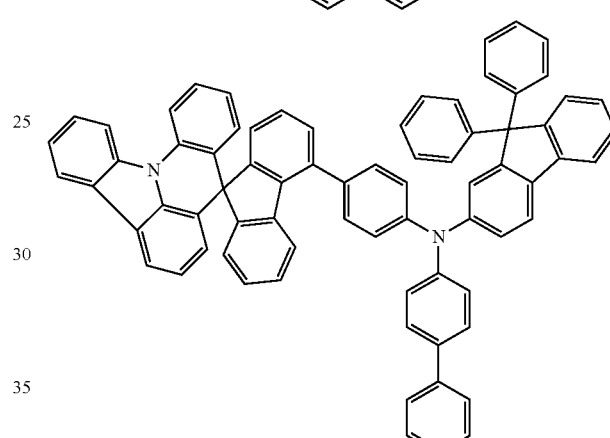
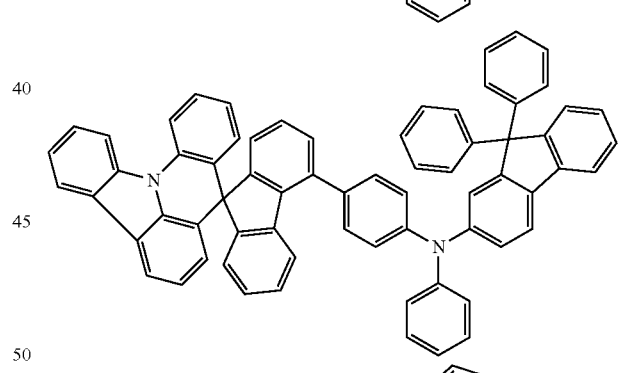
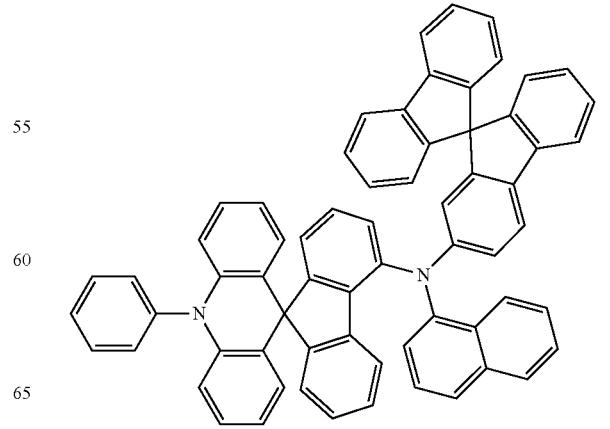

347
-continued
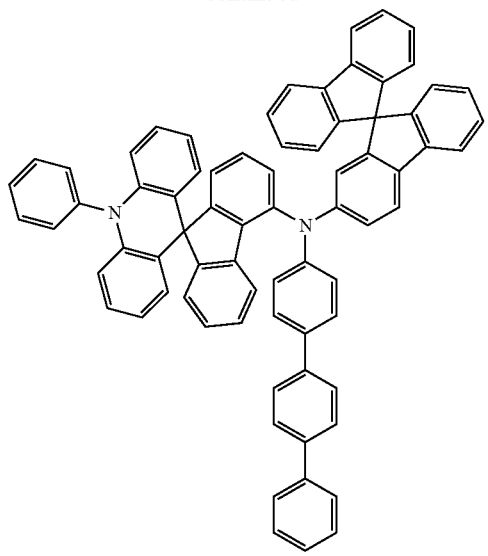
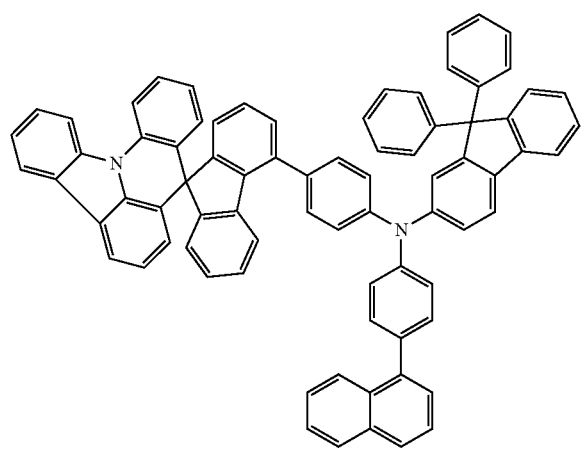
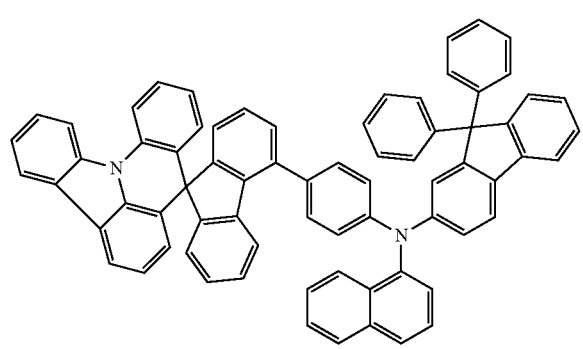
348
-continued
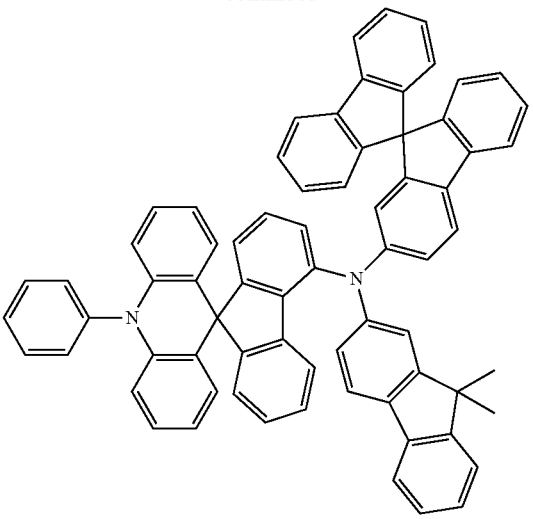
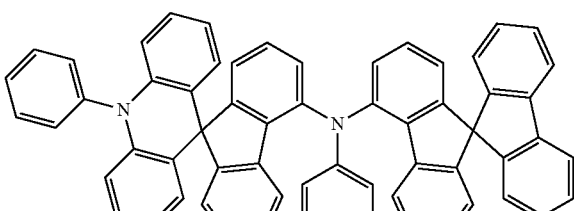
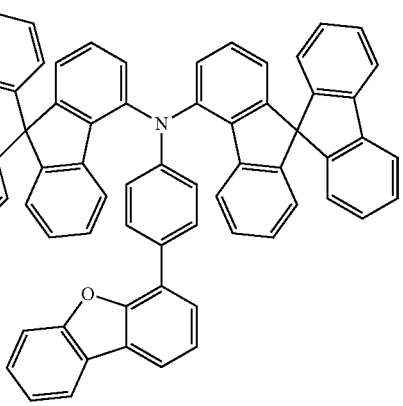
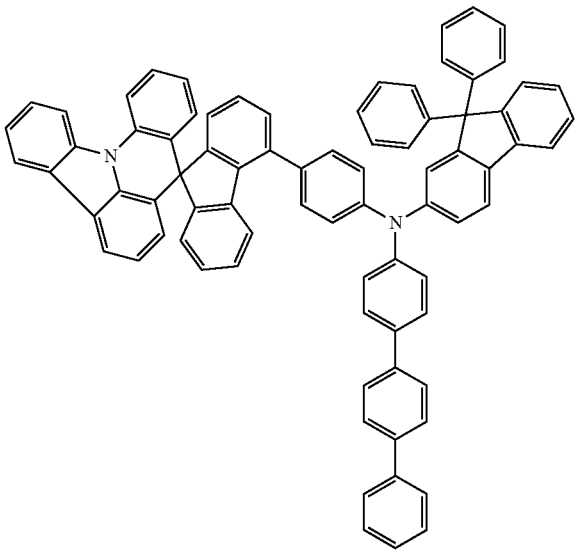

349
-continued
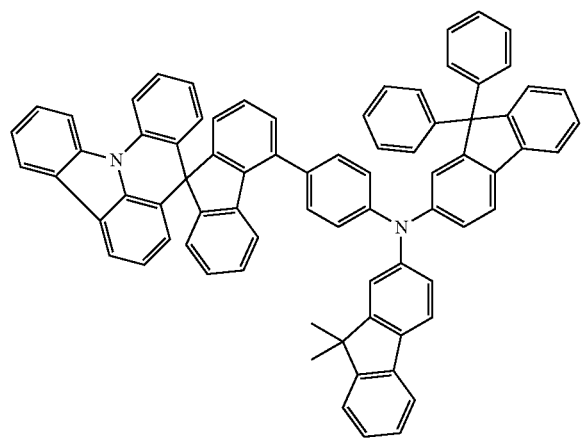
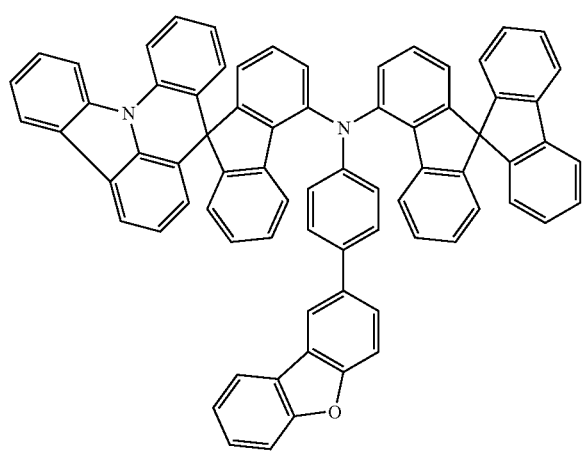
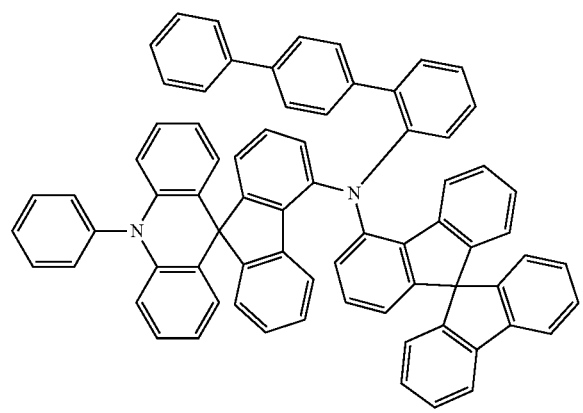
350
-continued
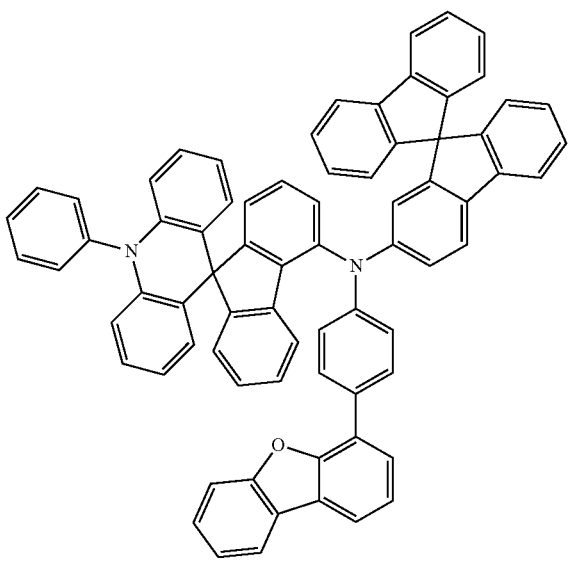
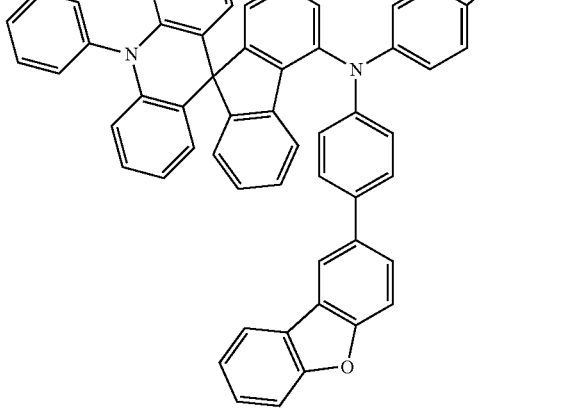
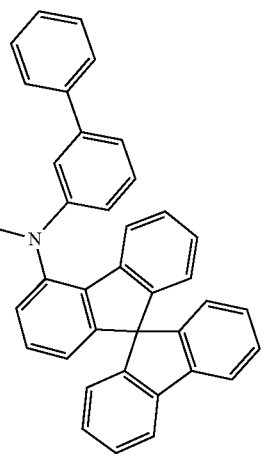

351
-continued
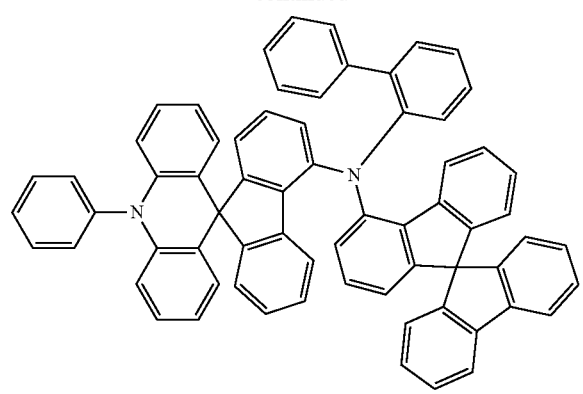
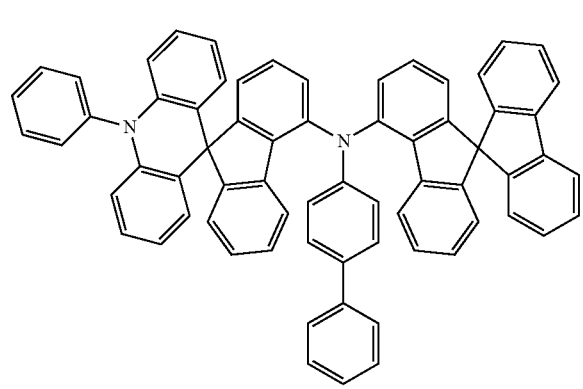
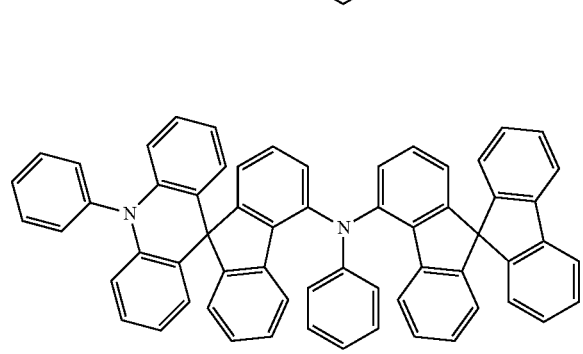
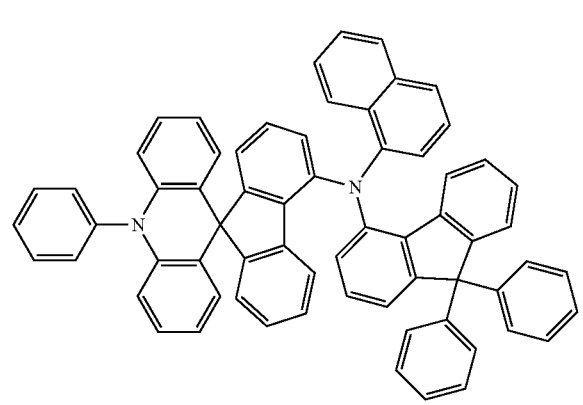
352
-continued
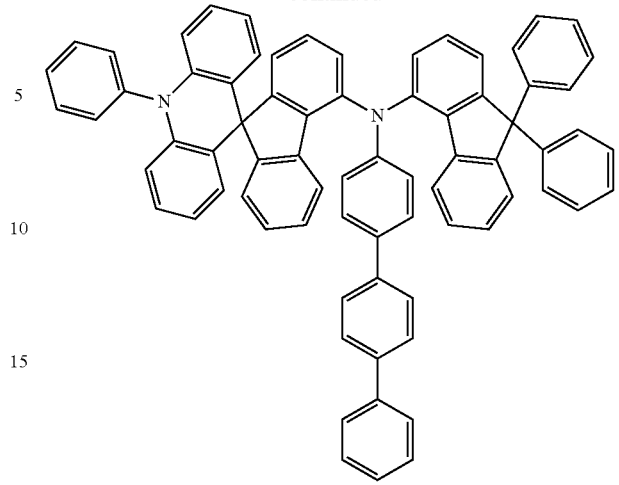

353
-continued
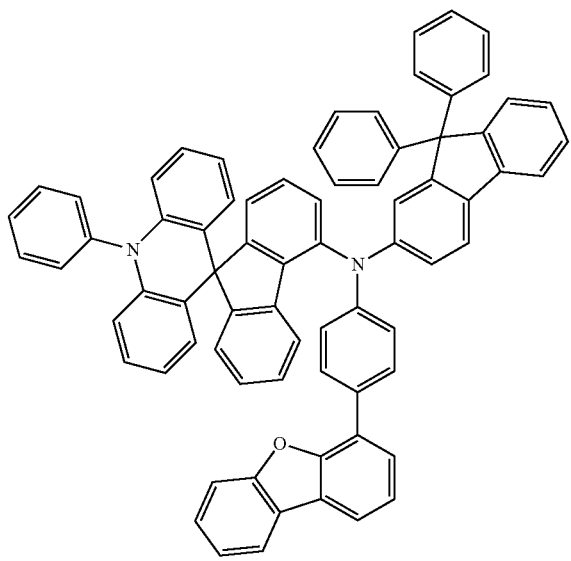
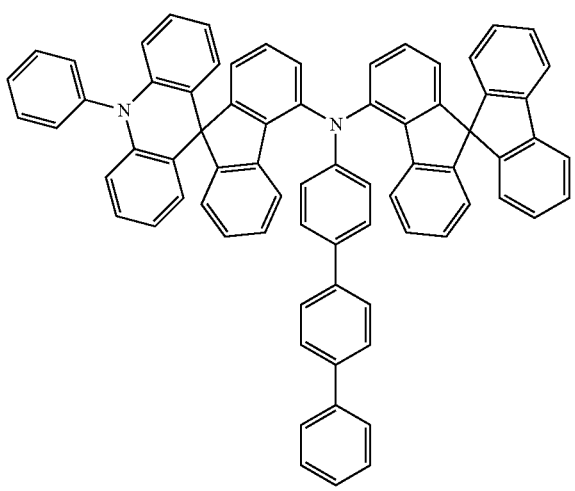
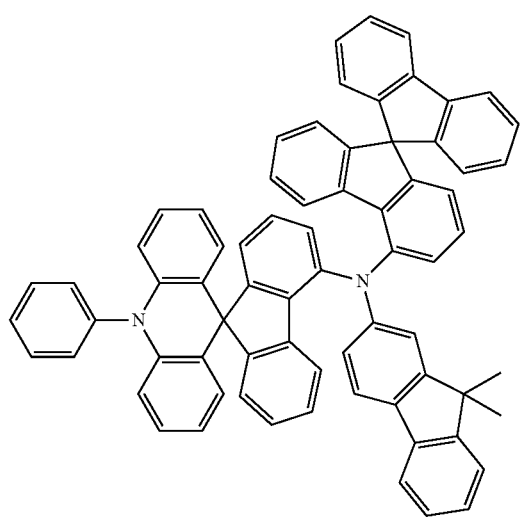
354
-continued
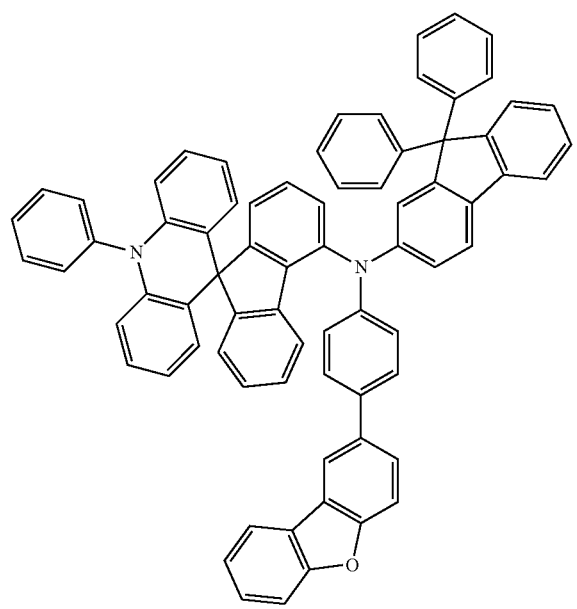
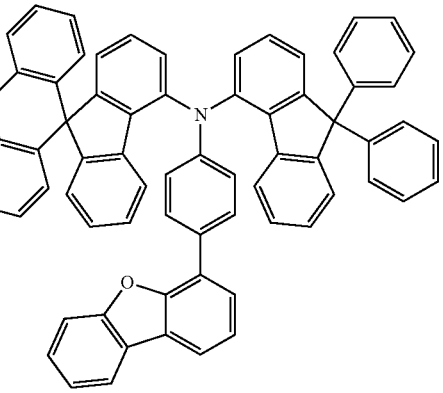

355
-continued
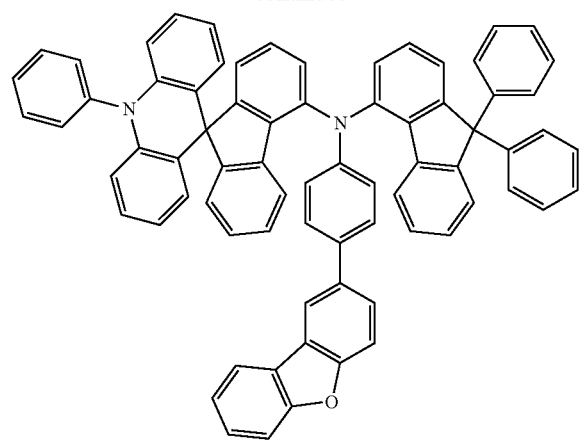
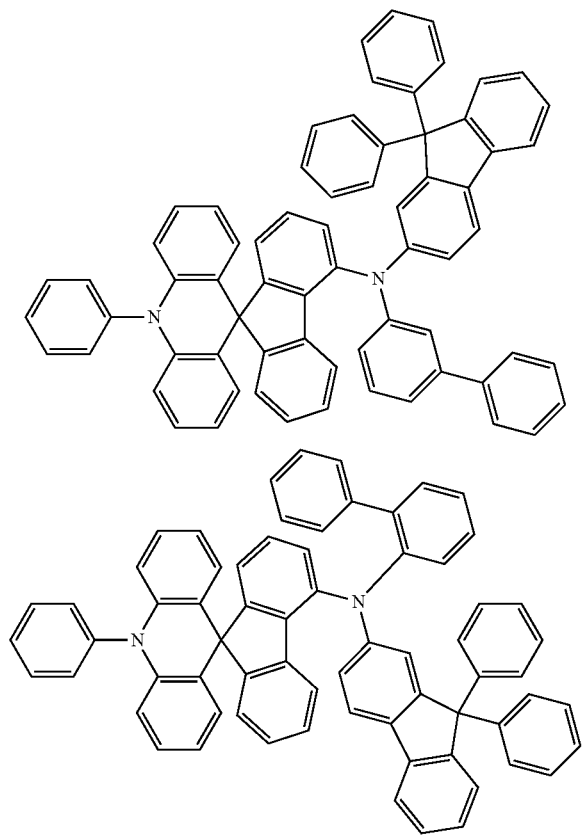
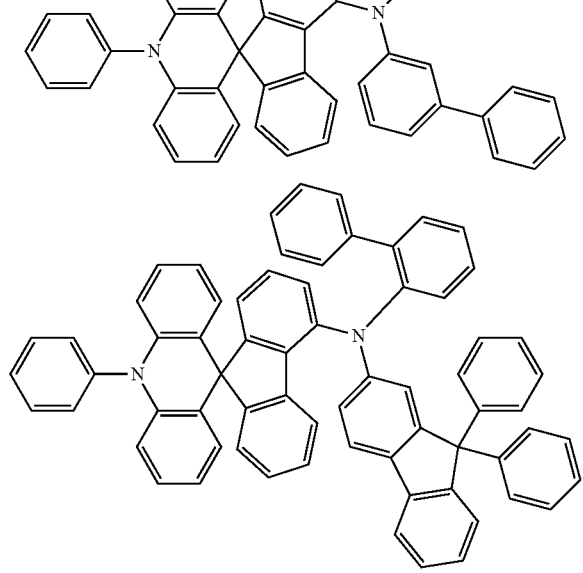
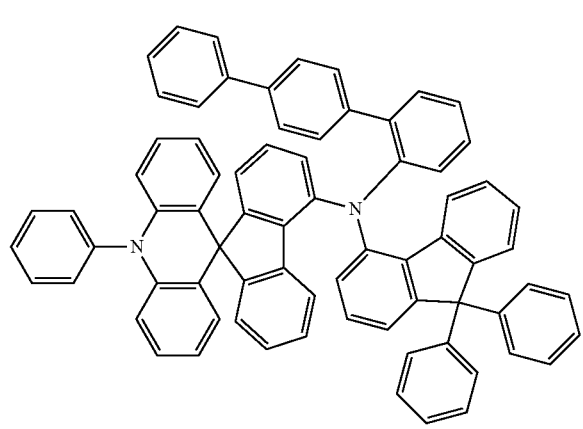
356
-continued
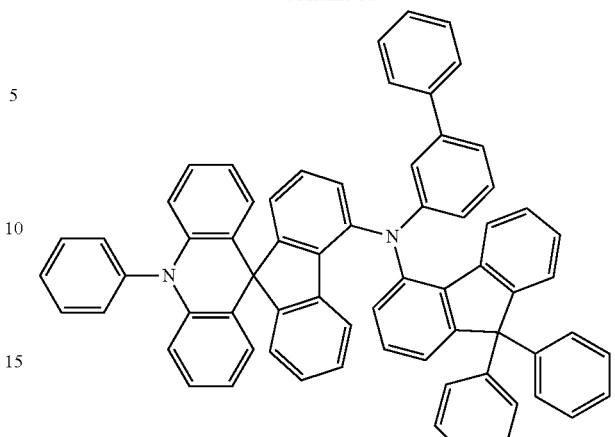
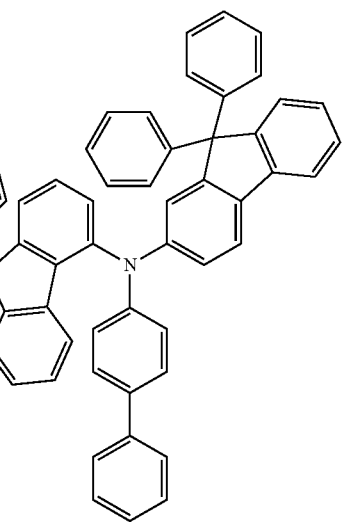
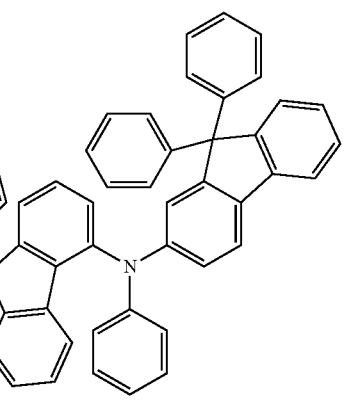

357
-continued
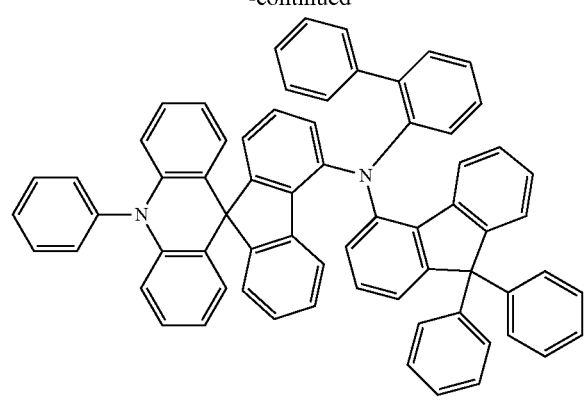
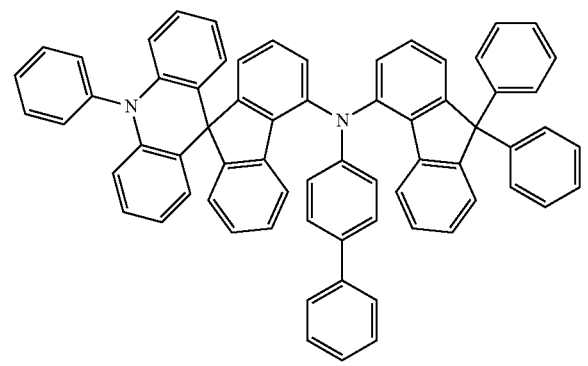
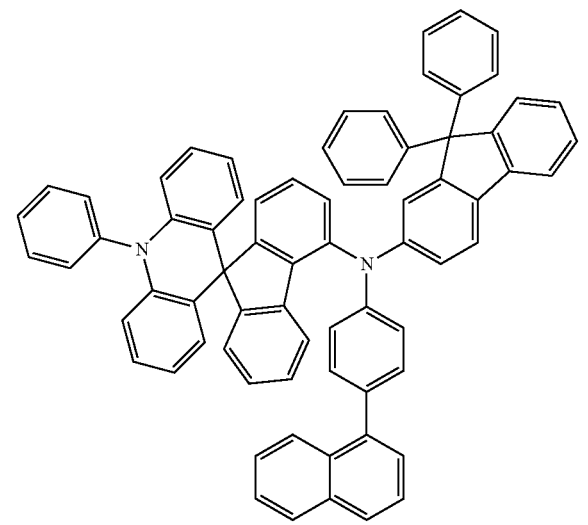
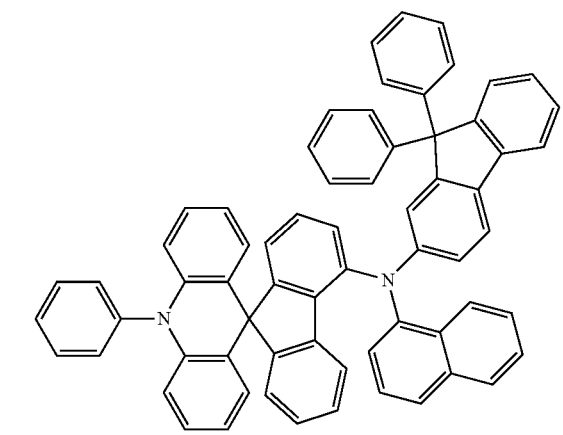
358
-continued
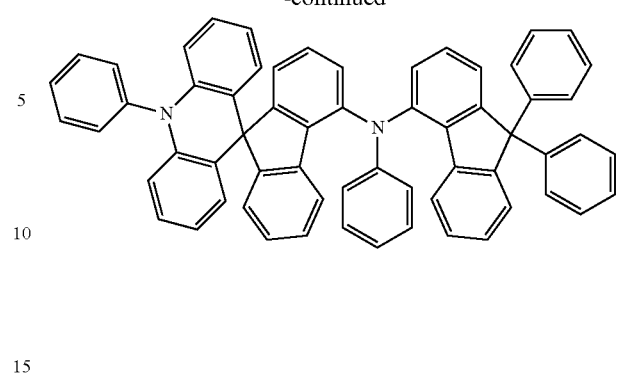
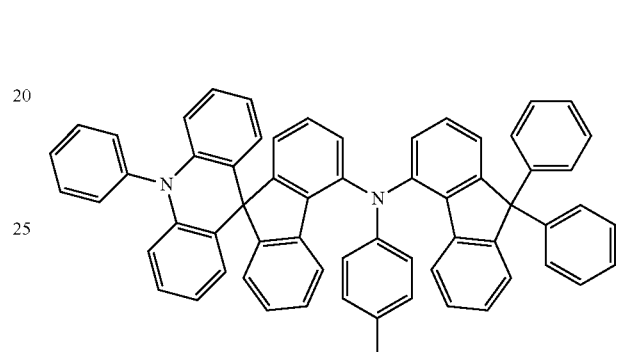
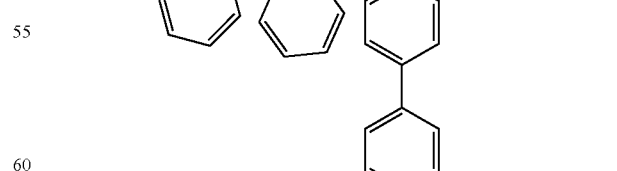

359
-continued
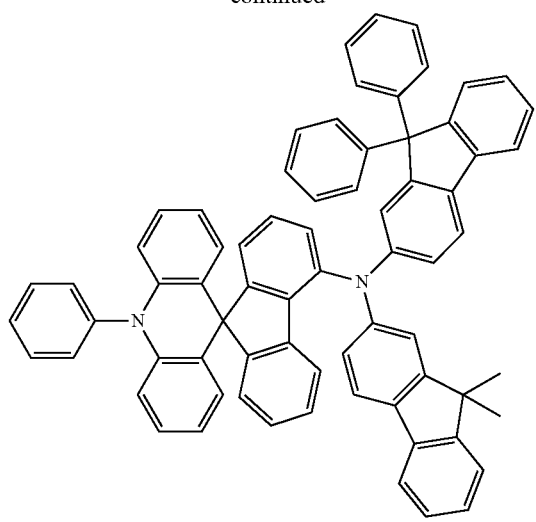
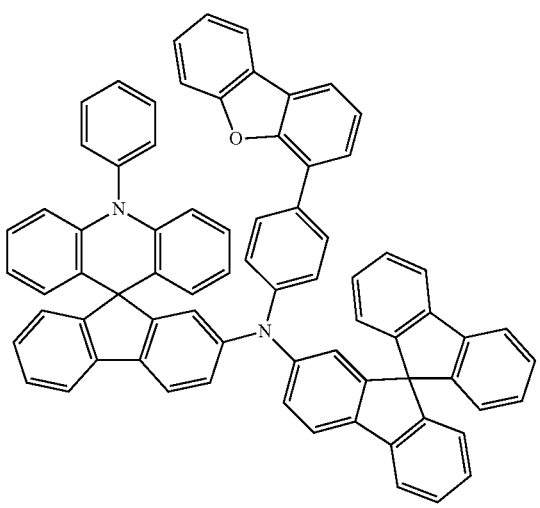
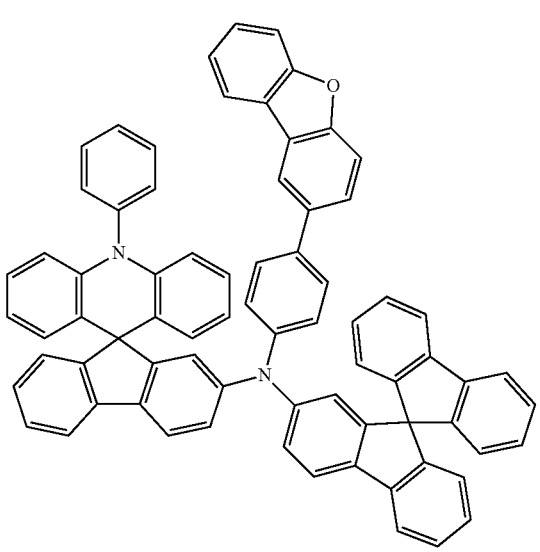
360
-continued
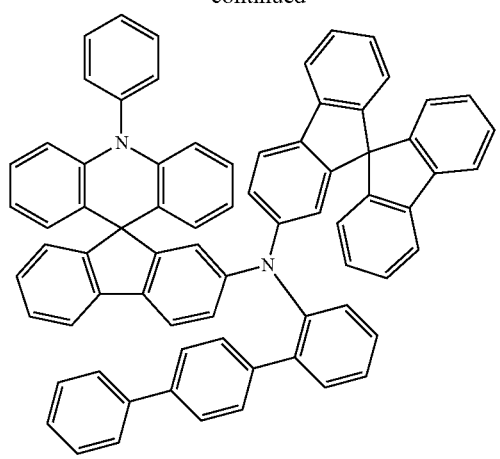
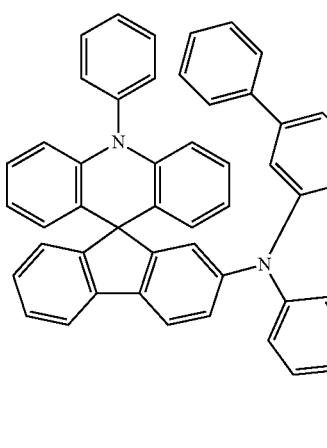
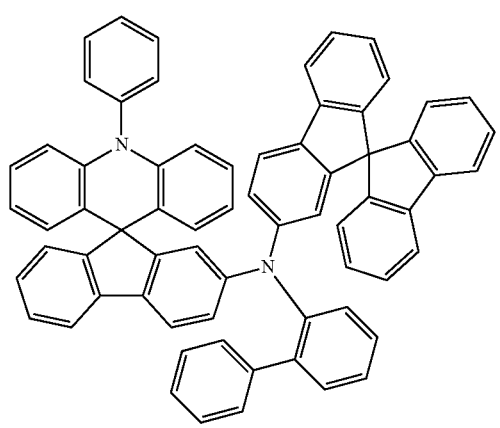

361
-continued
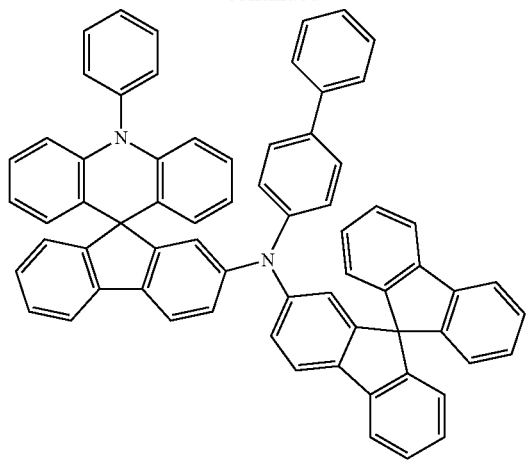
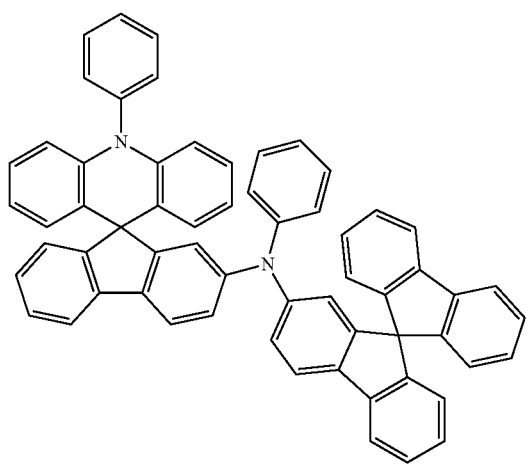
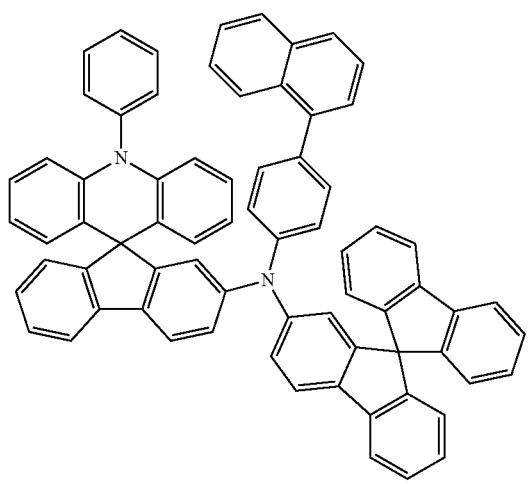
362
-continued
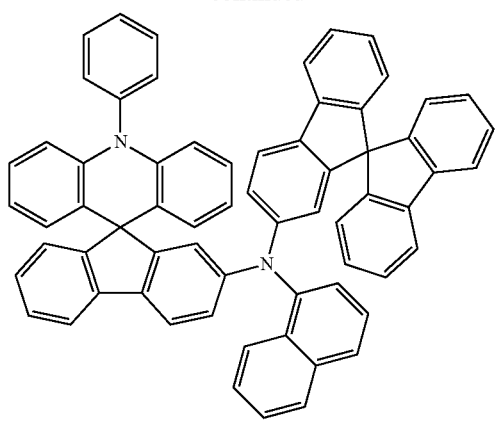
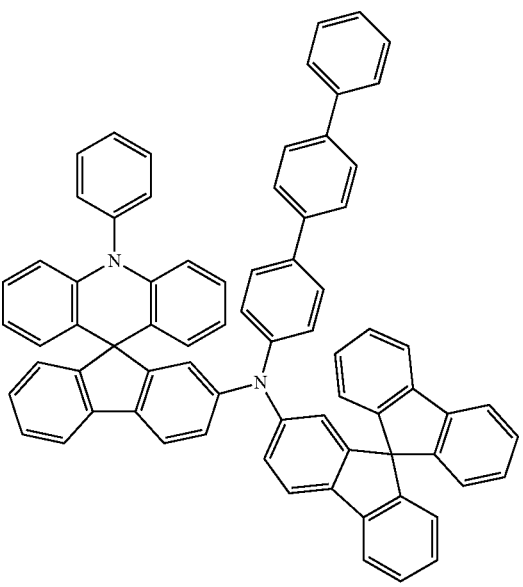
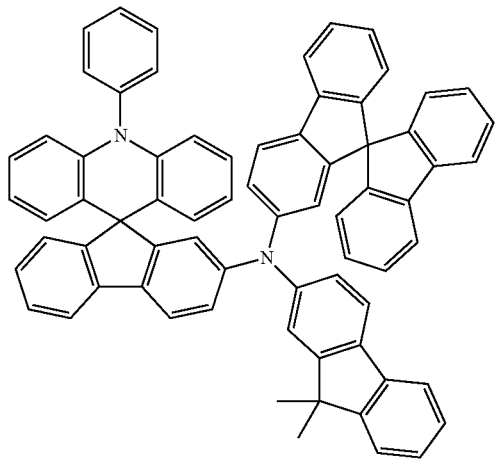

363
-continued
364
-continued
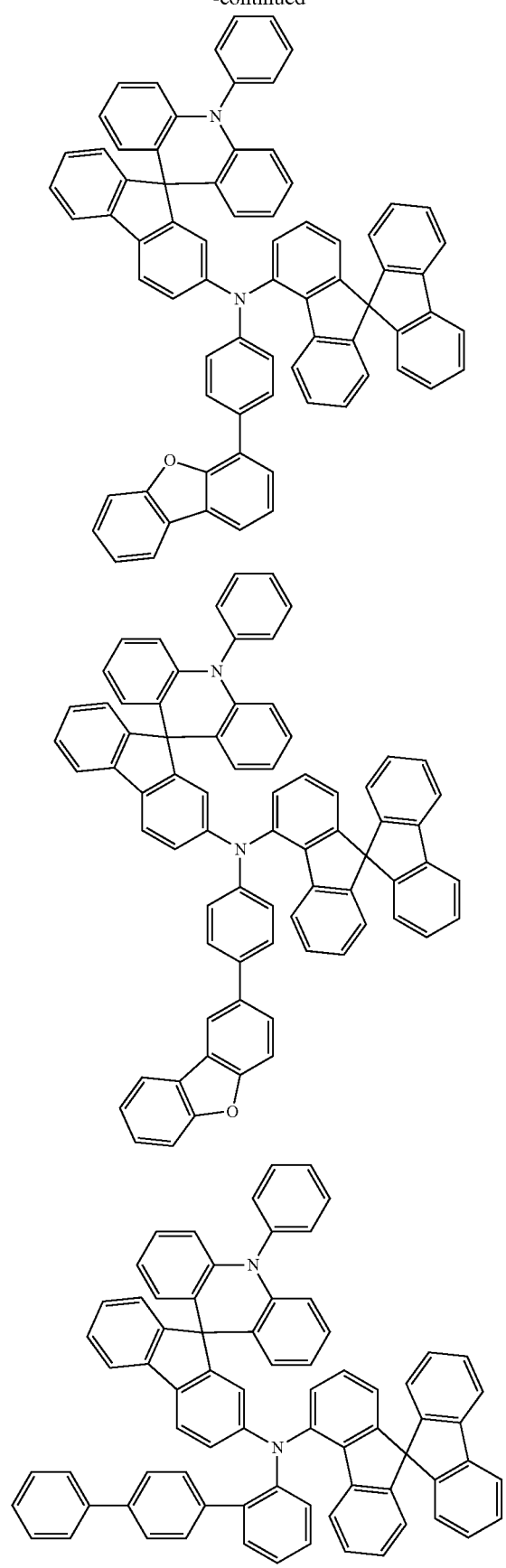
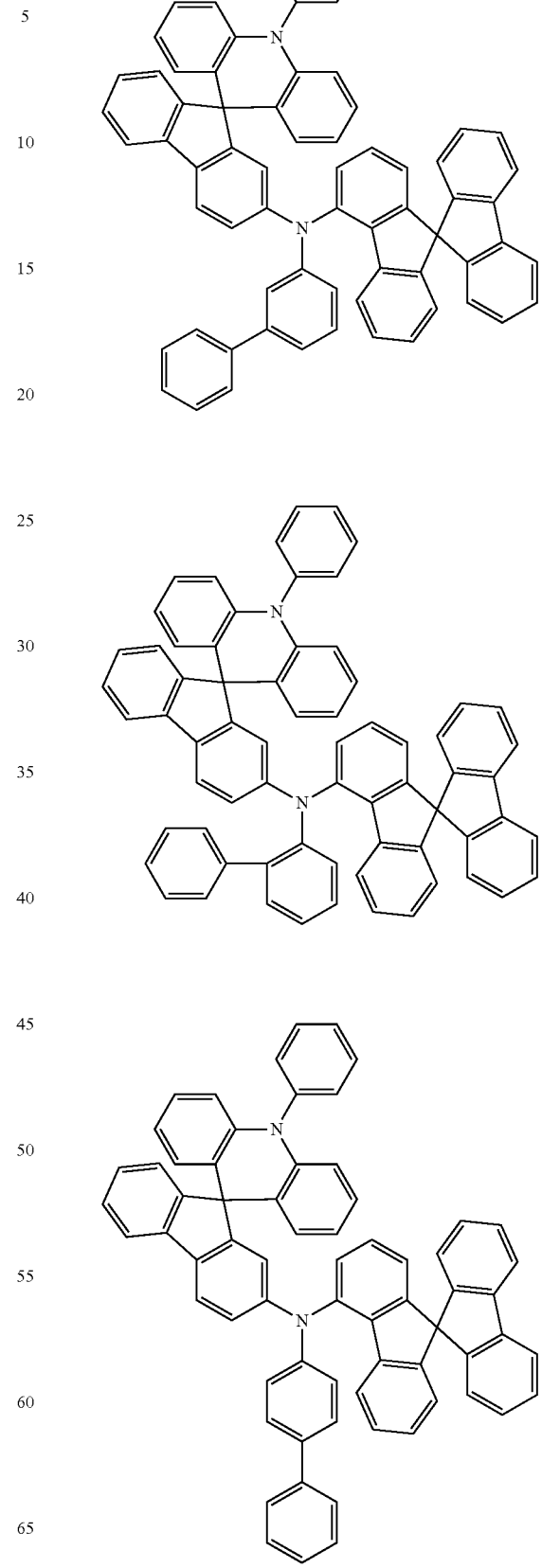

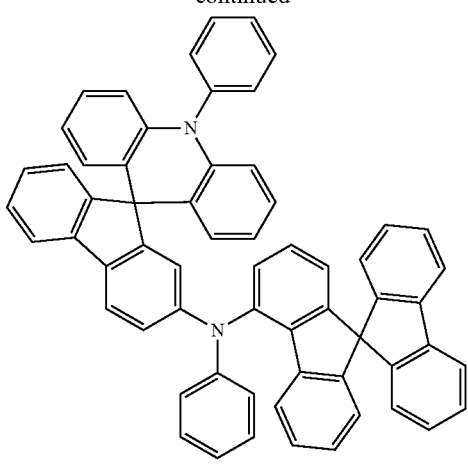
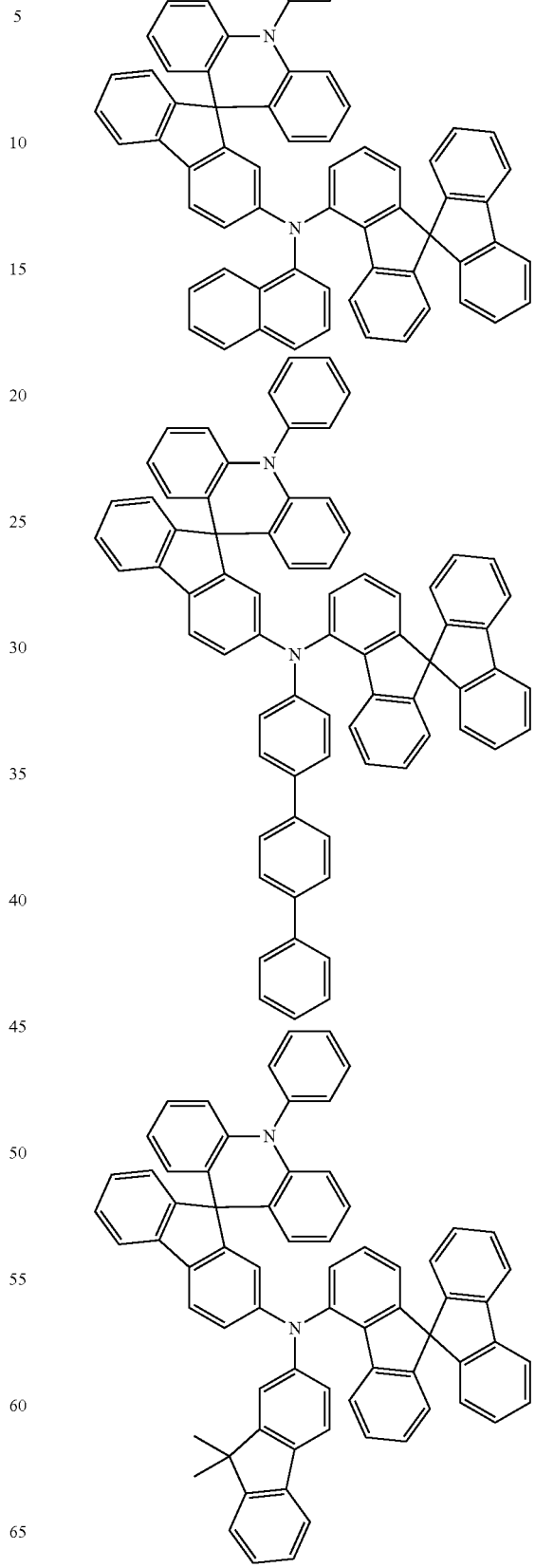

367
-continued
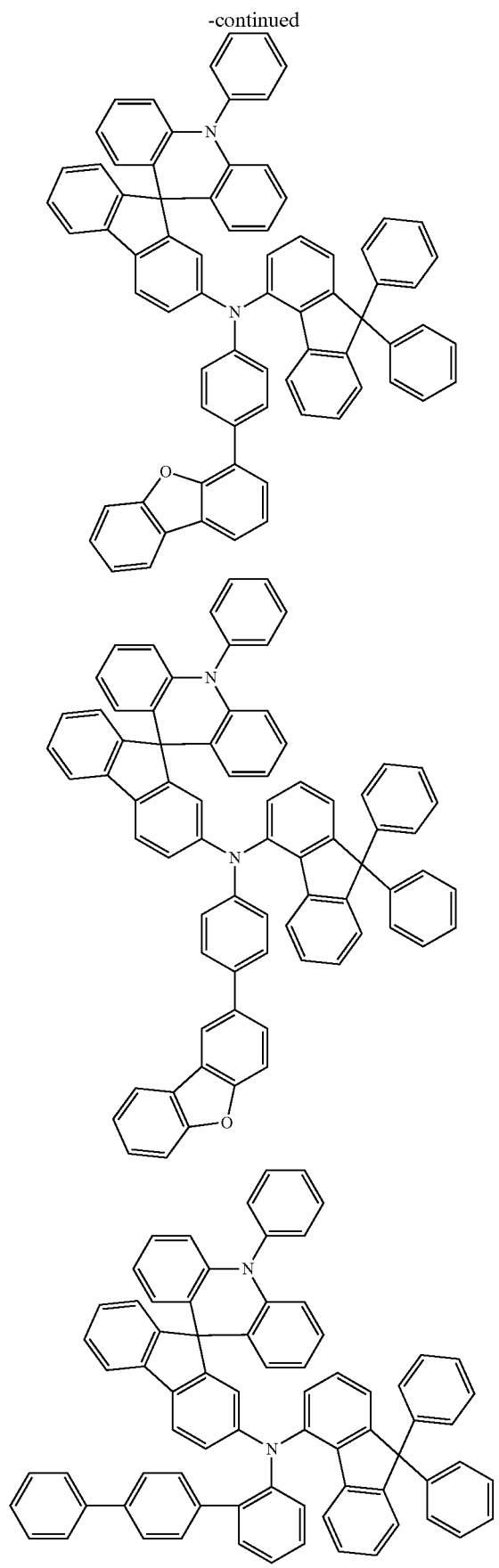
368
-continued
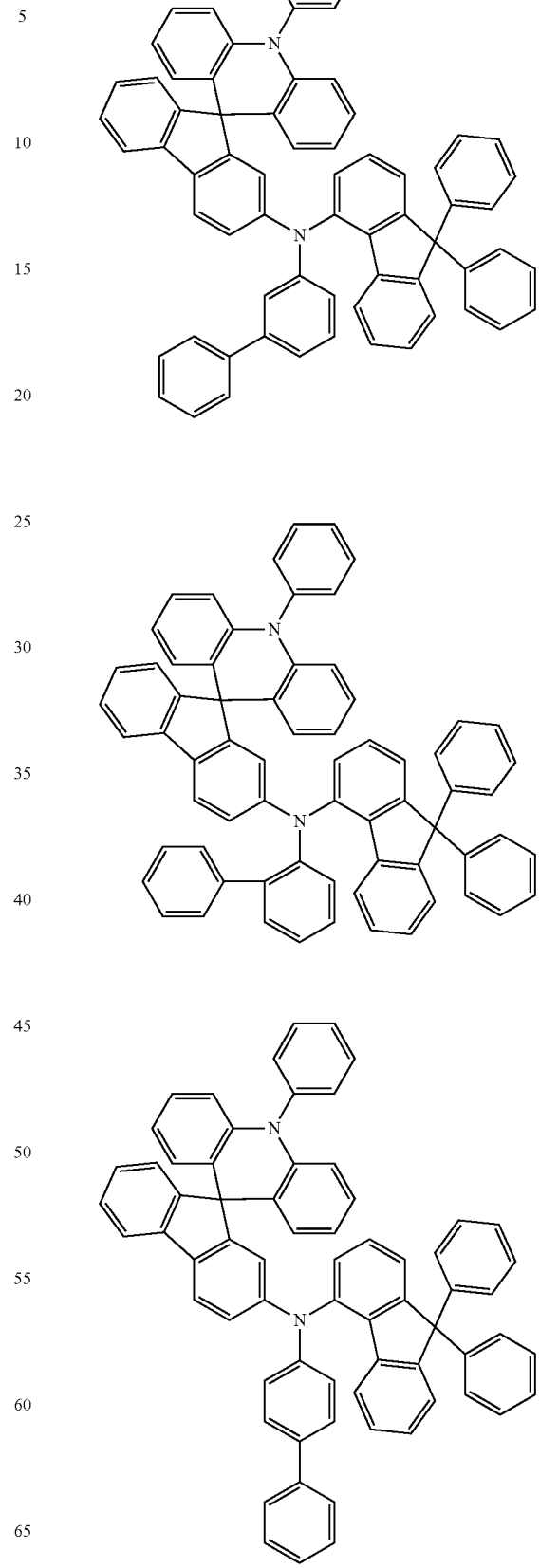

369
-continued
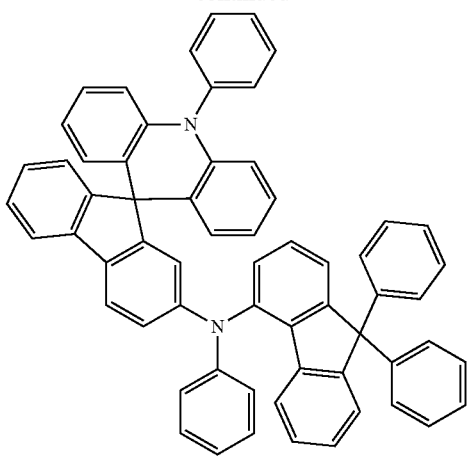
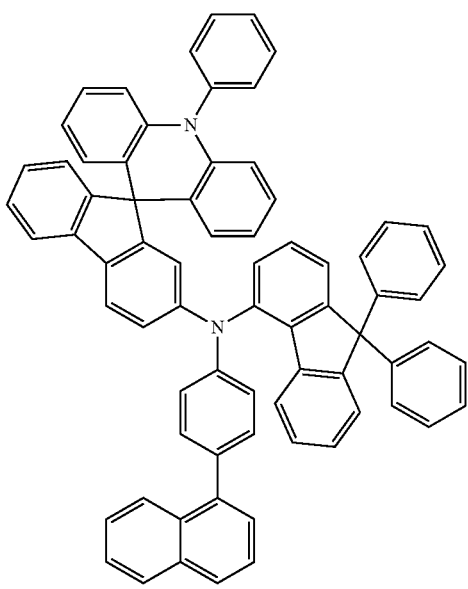
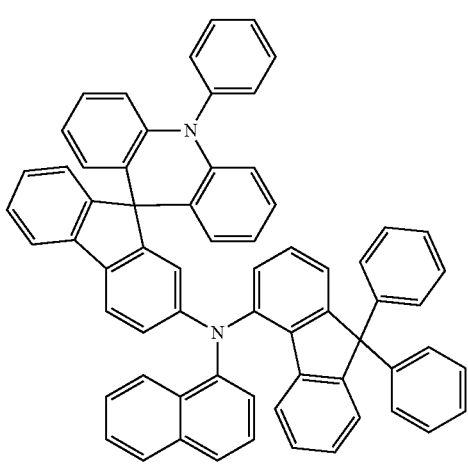
370
-continued
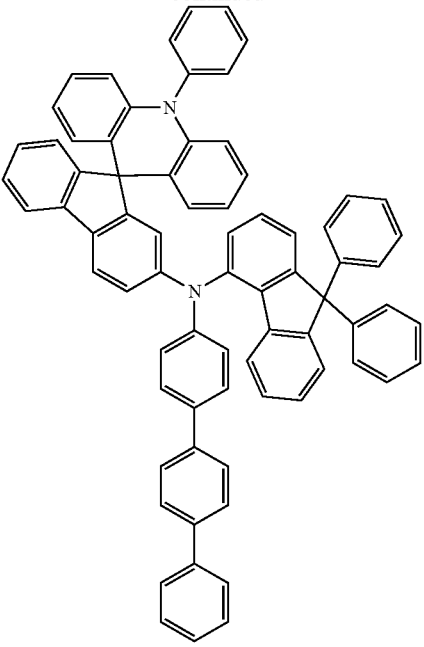
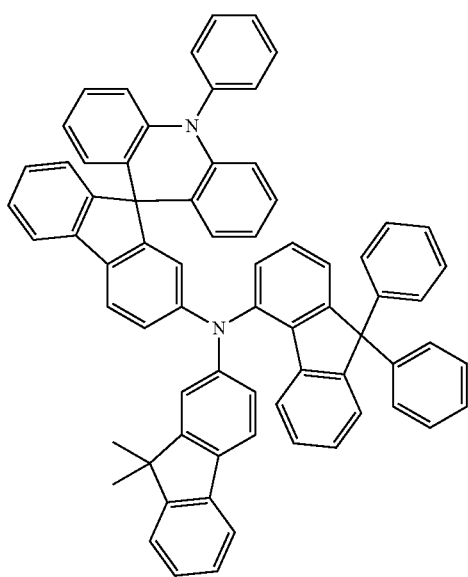

371
-continued
372
-continued
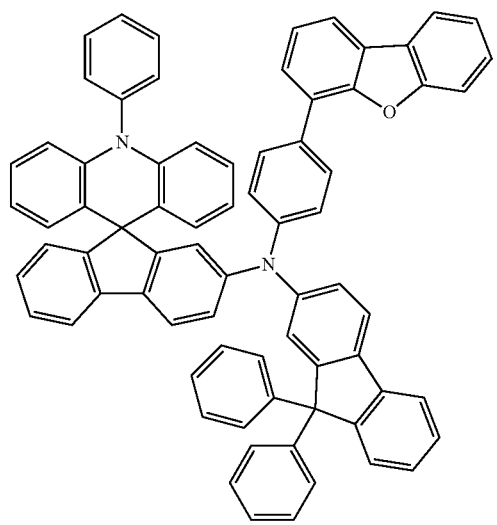
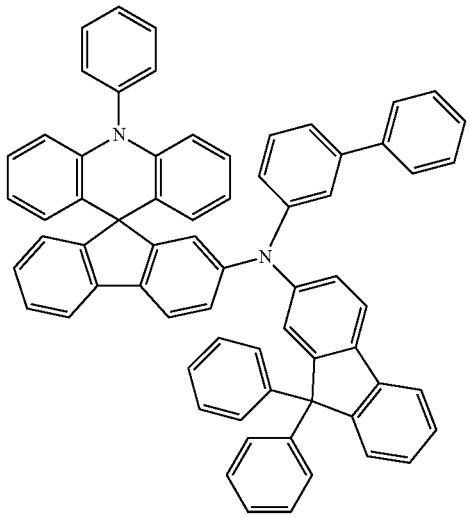
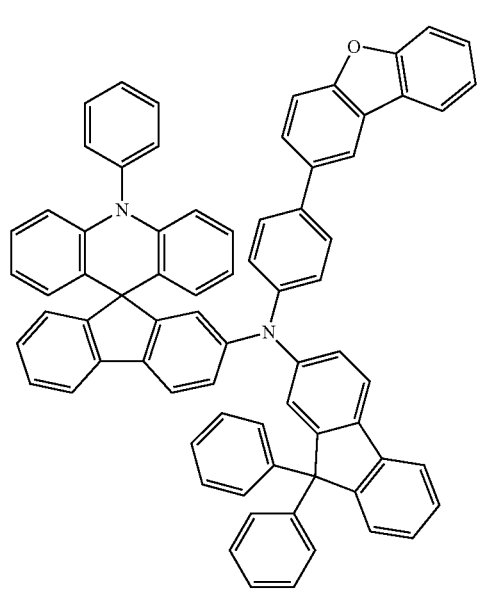
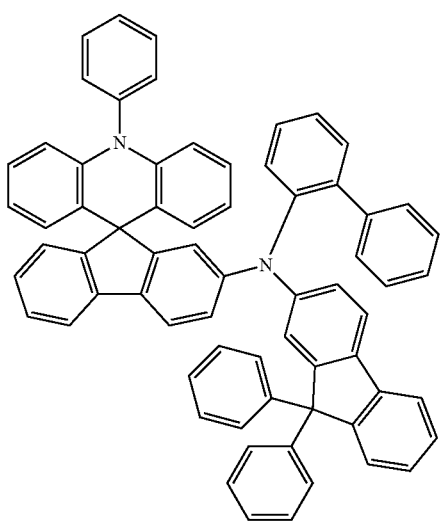
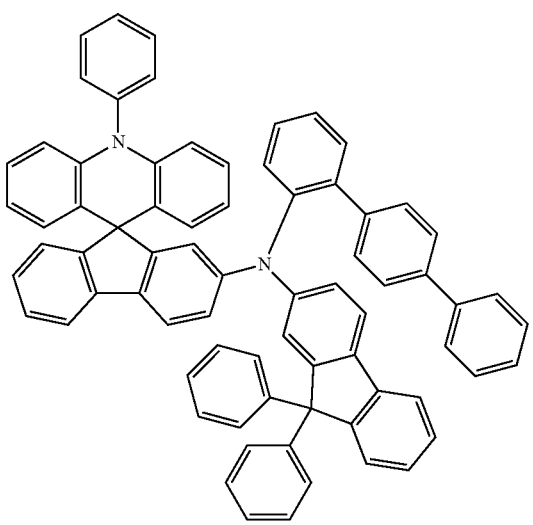
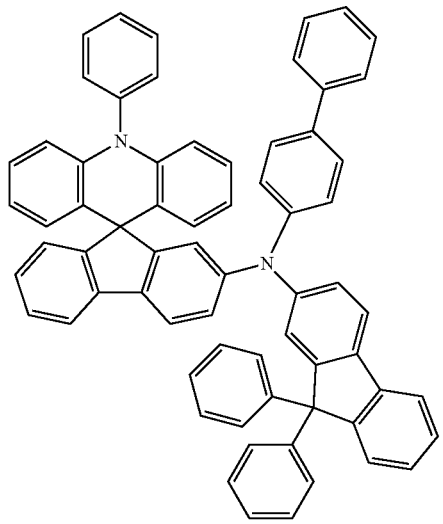

373
-continued
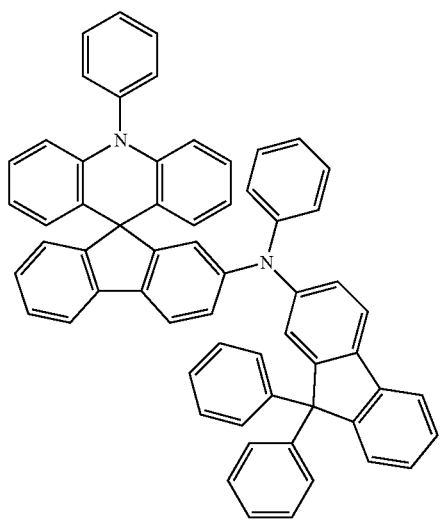
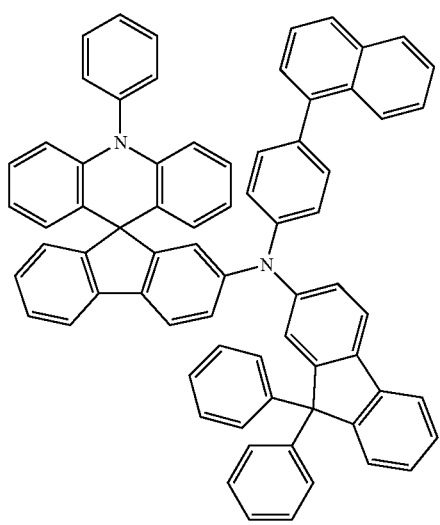
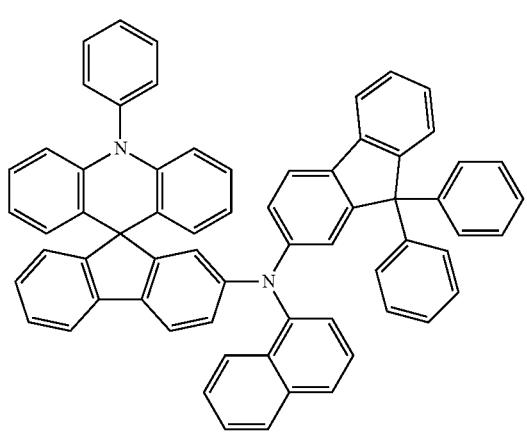
374
-continued
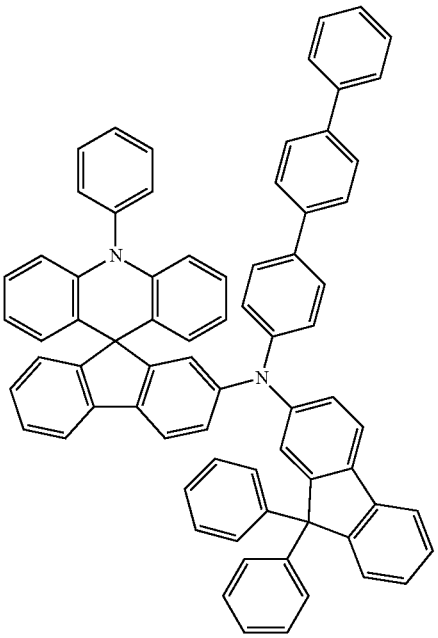
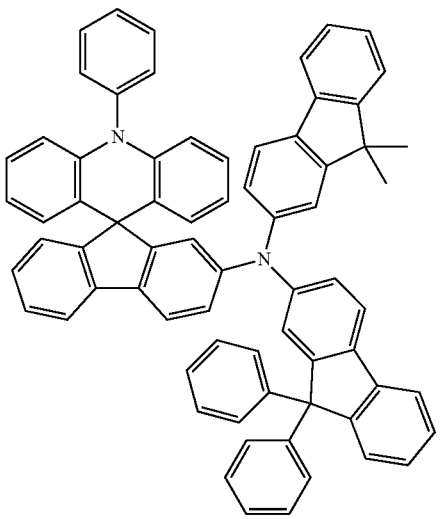

375
-continued
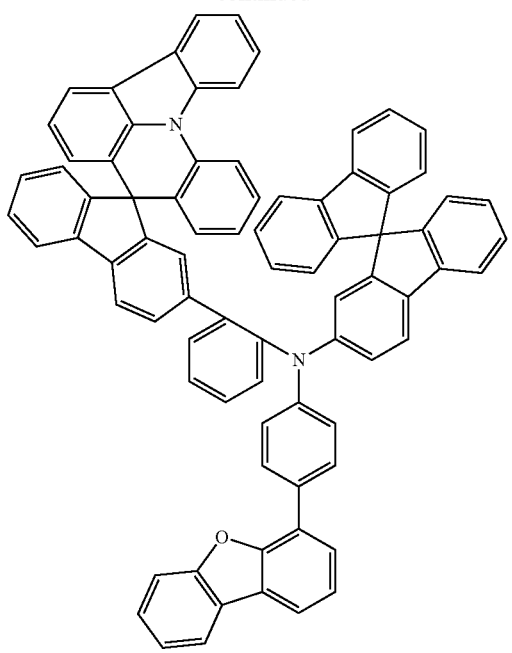
376
-continued
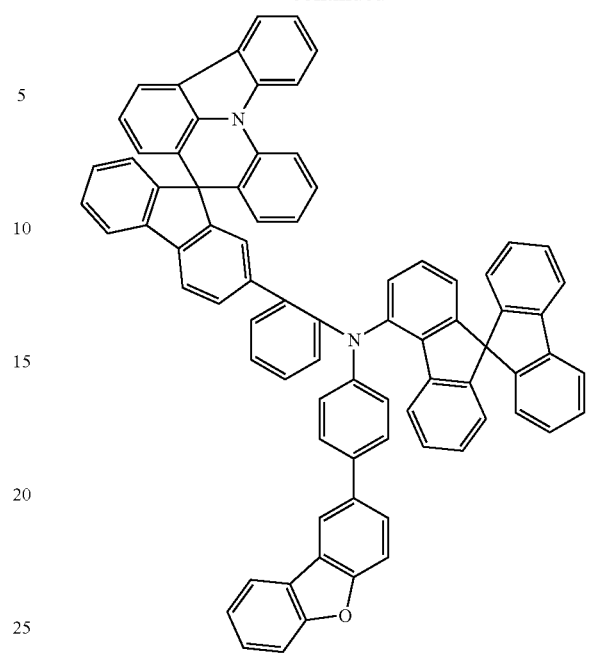
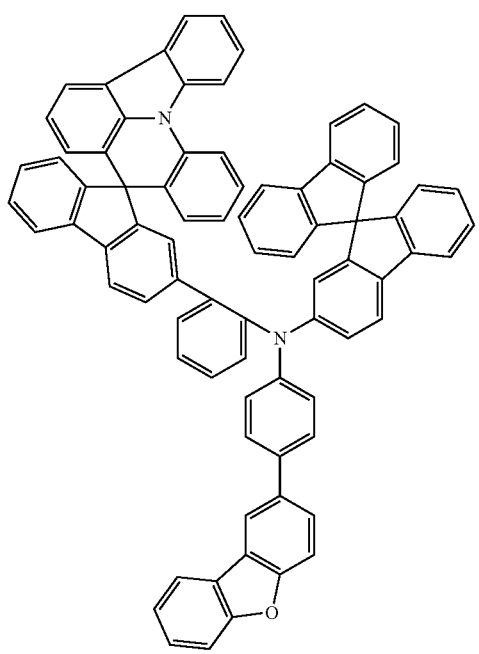
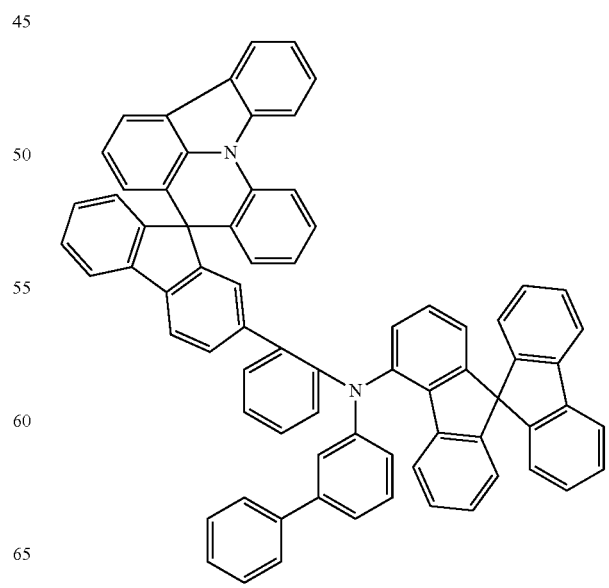

377
-continued
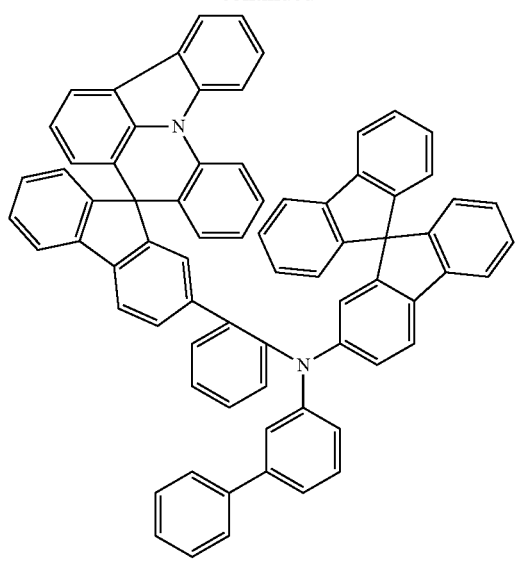
378
-continued
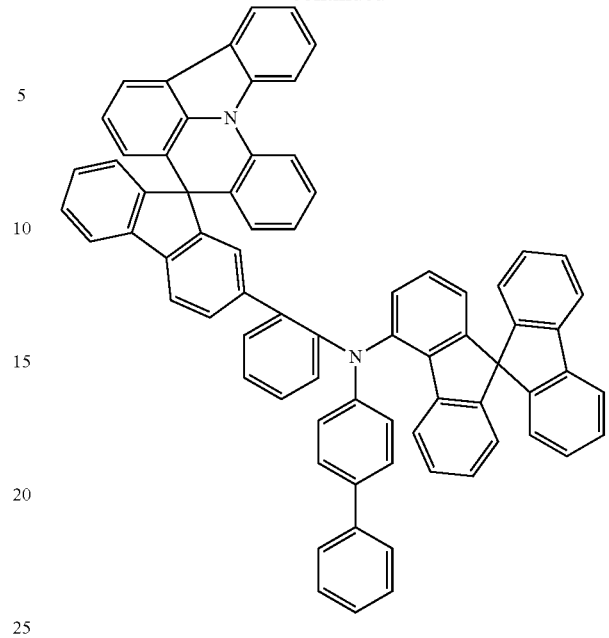
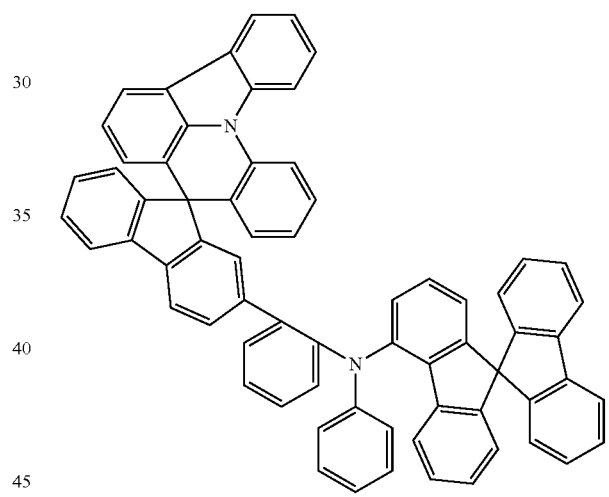
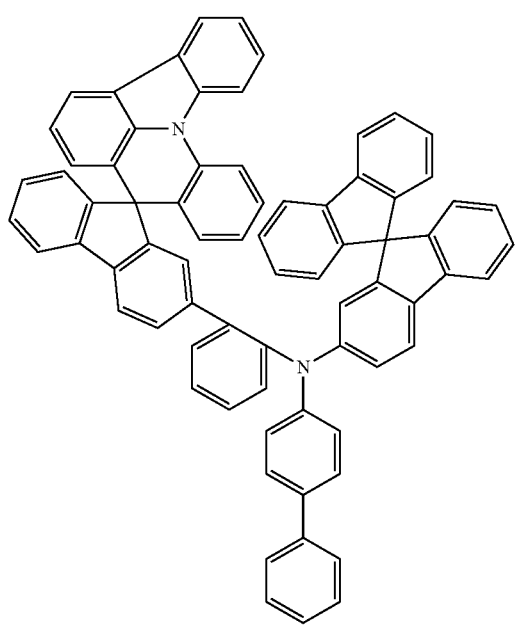
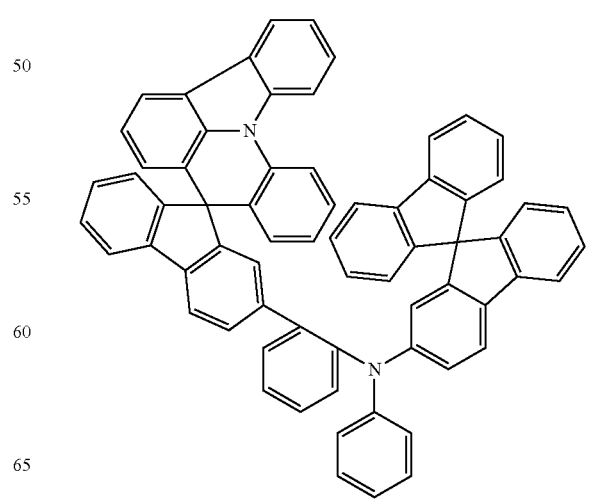

379
-continued
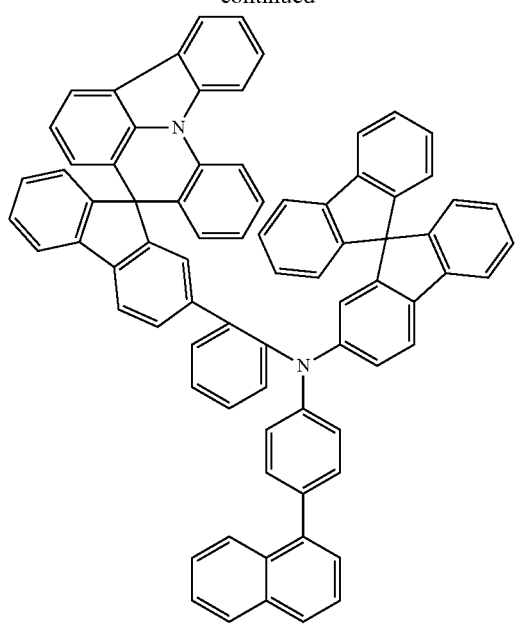
380
-continued
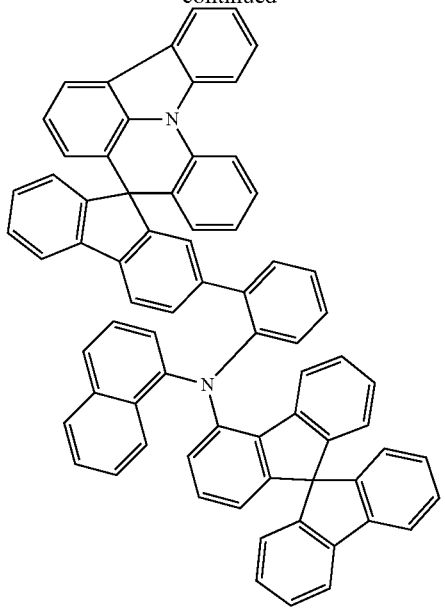
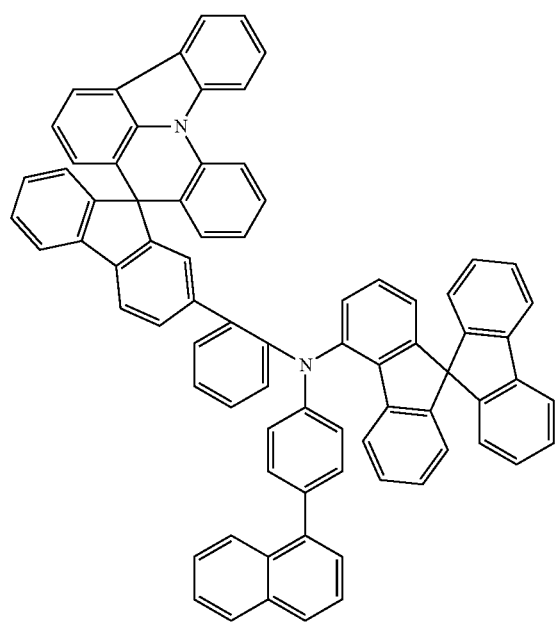
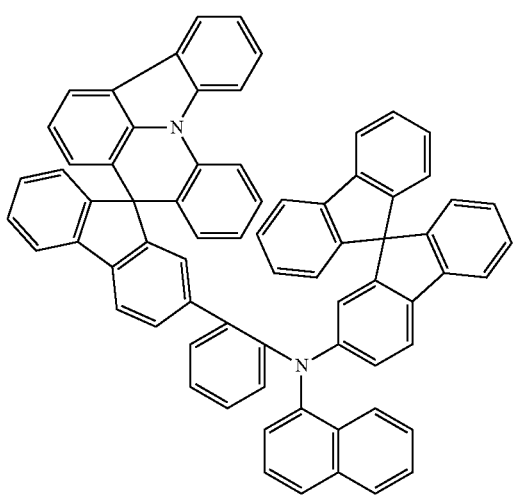

381
-continued
382
-continued
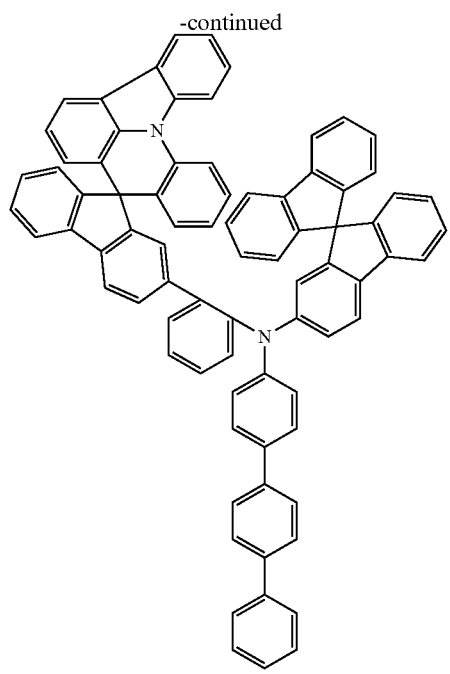
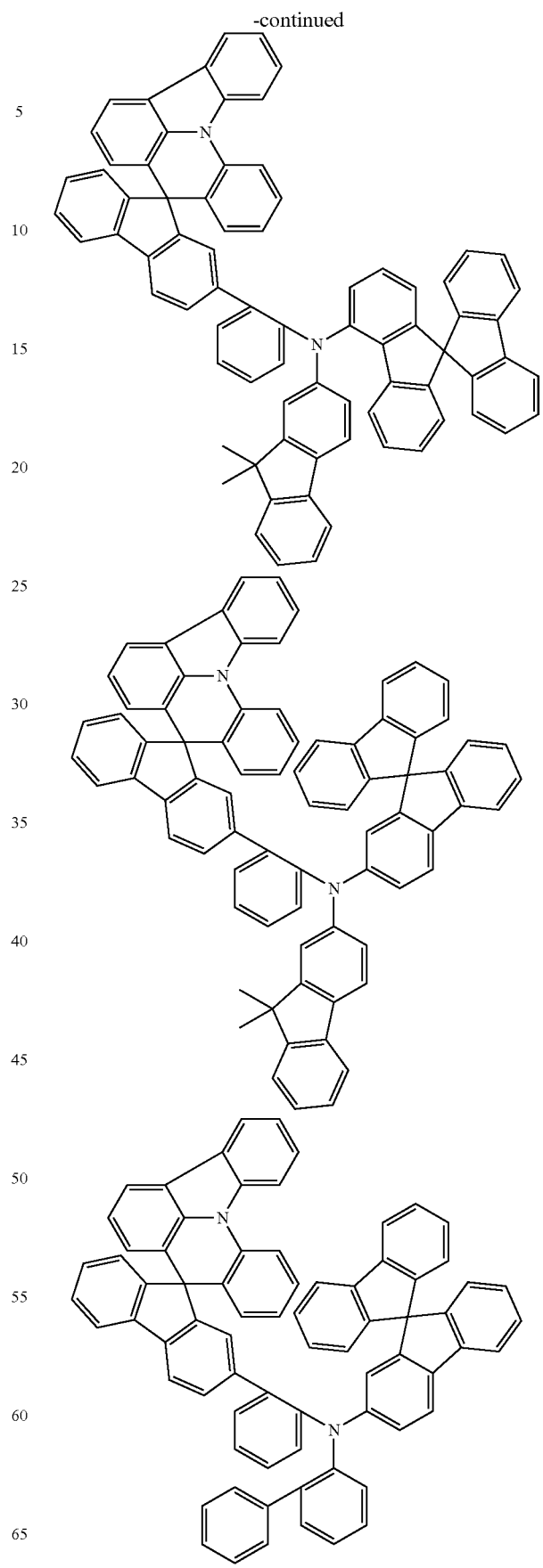

383
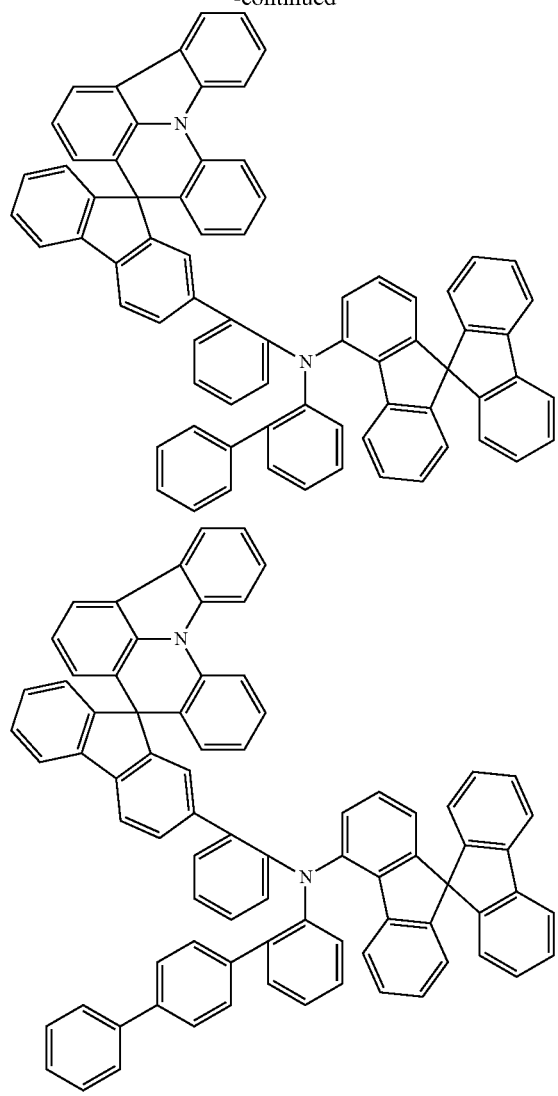
384
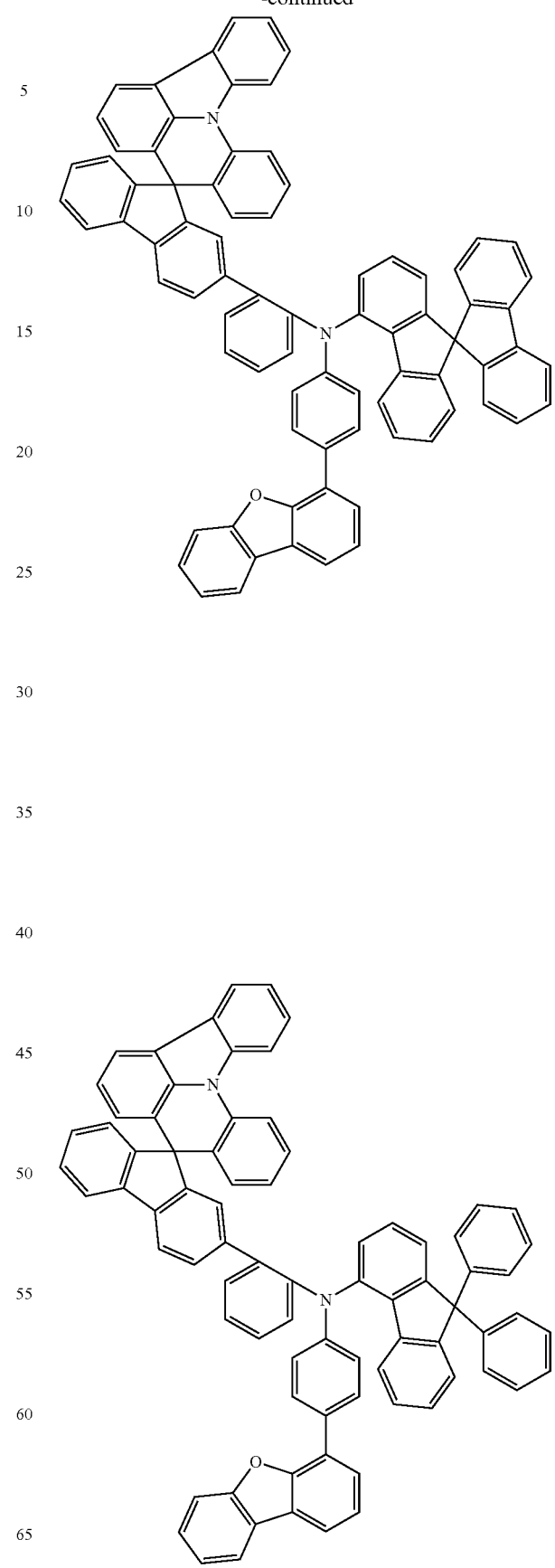

385
-continued
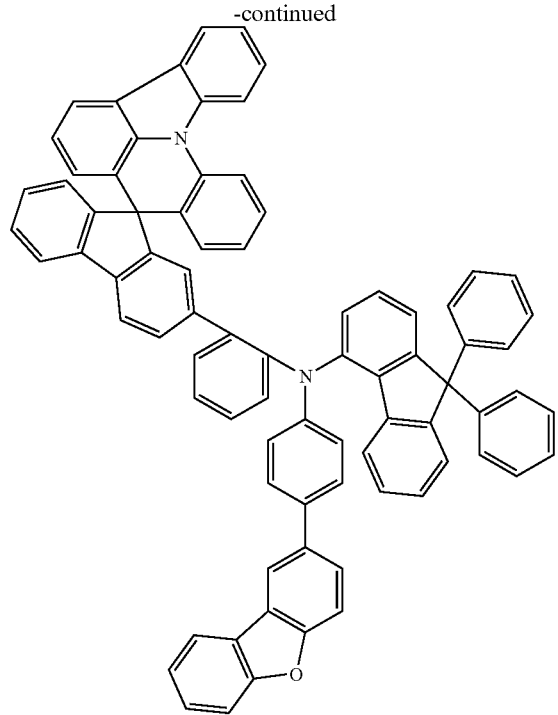
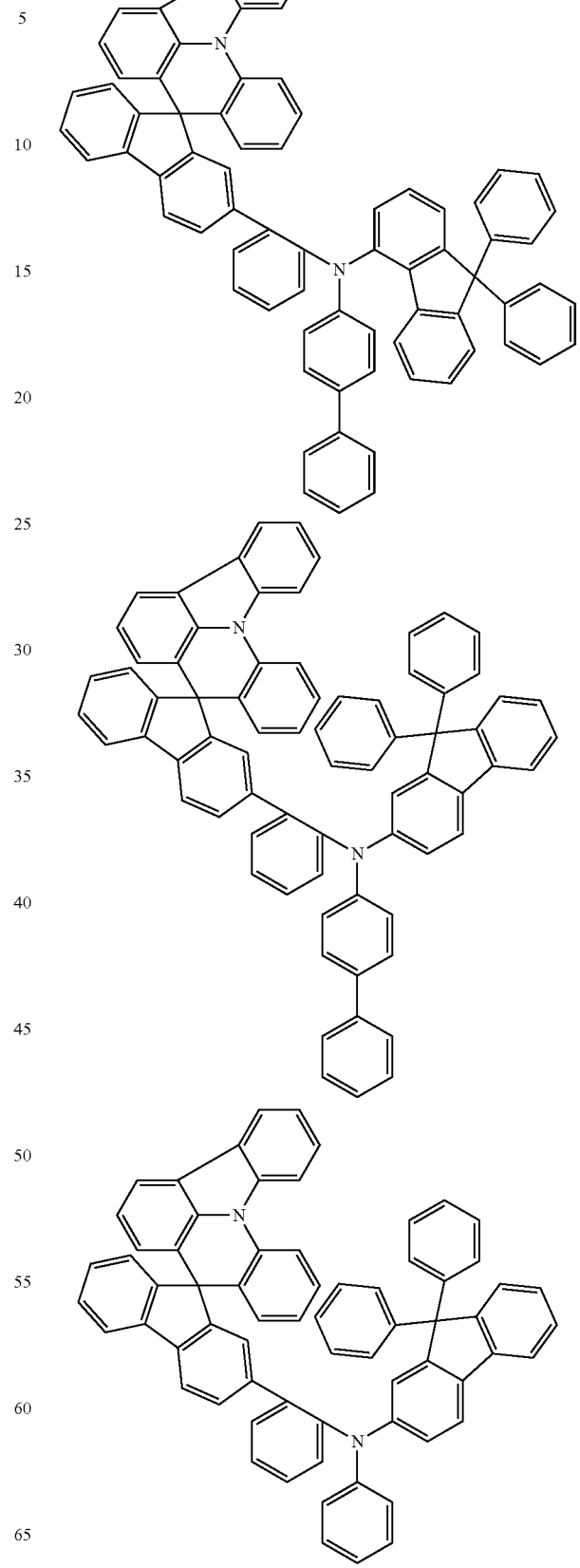
386
-continued
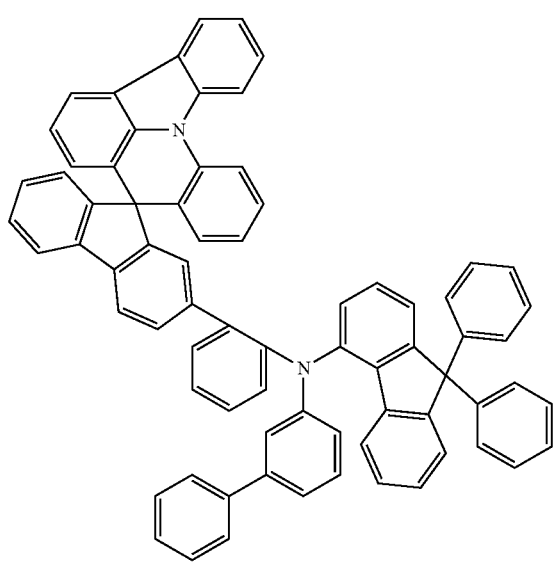

387
-continued
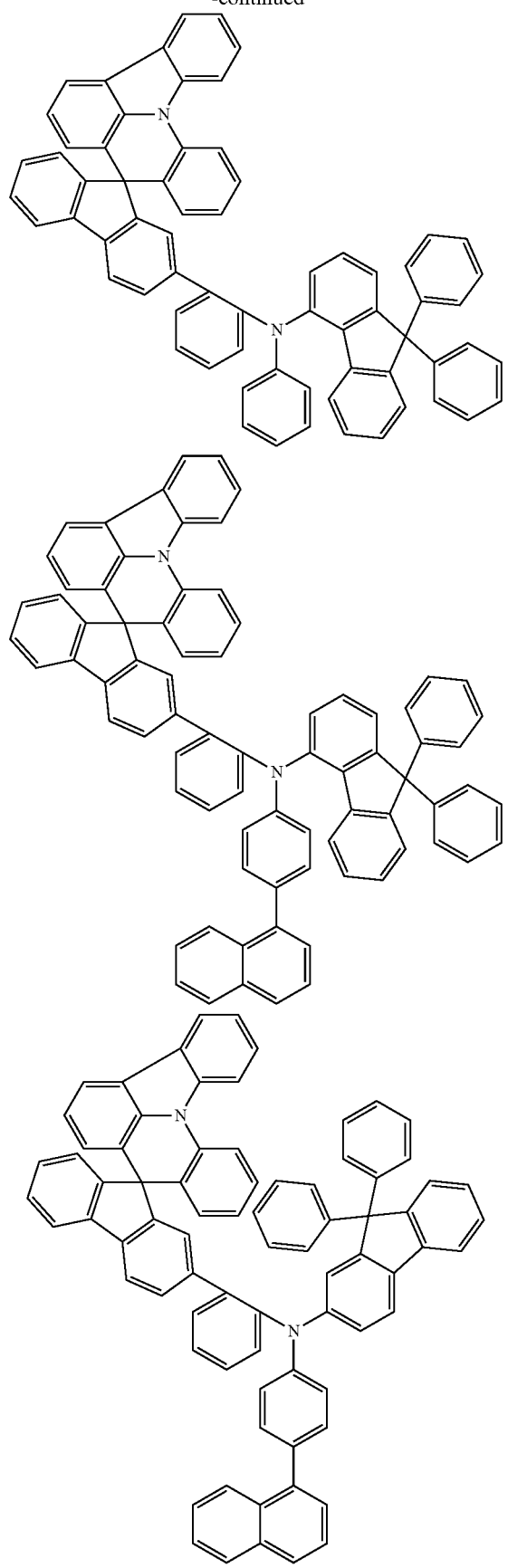
388
-continued

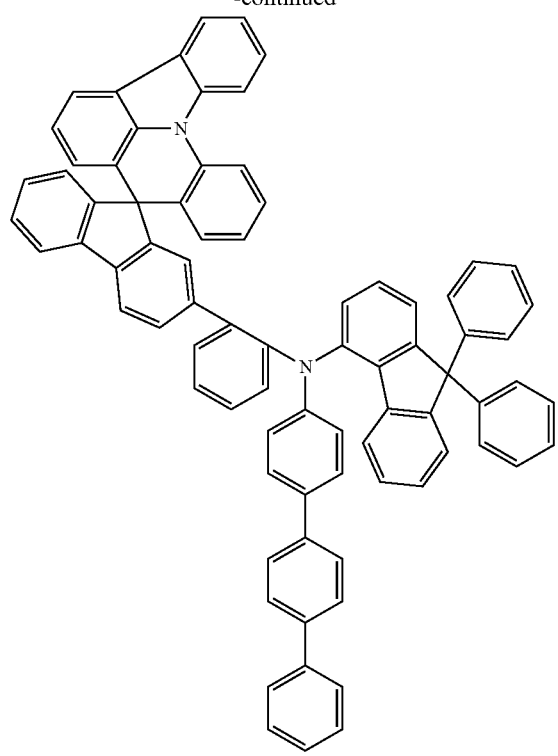
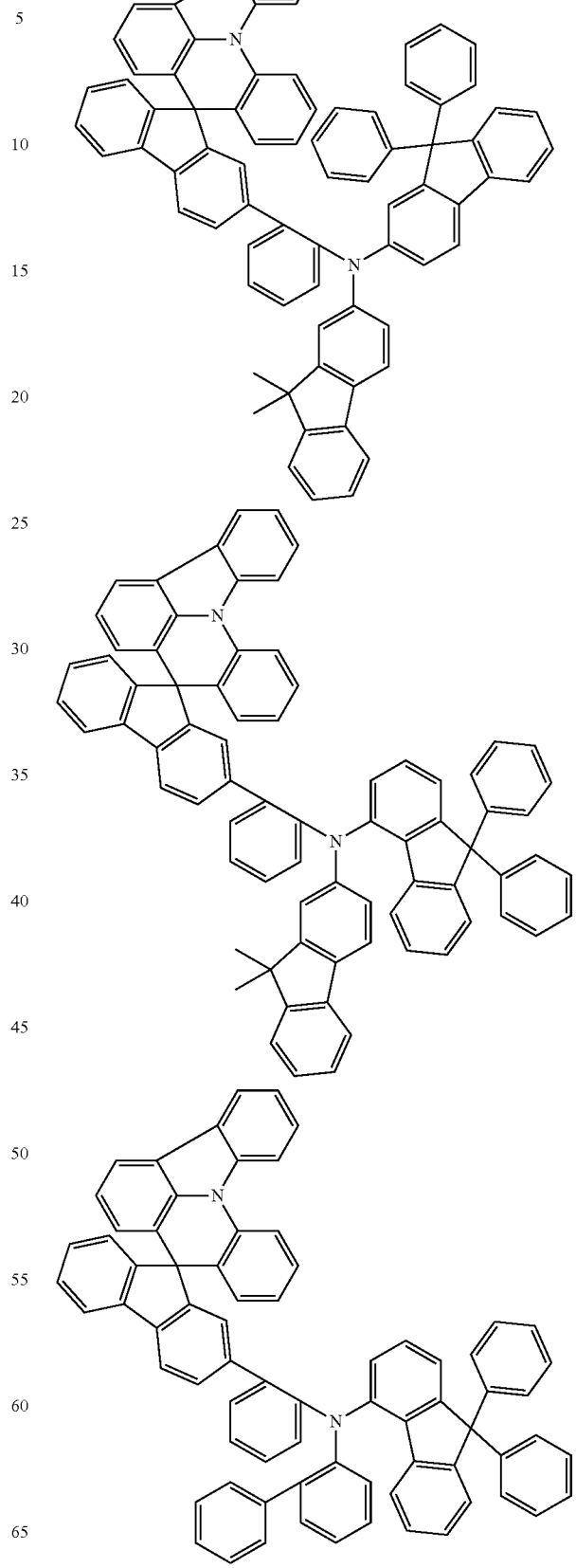

391
-continued
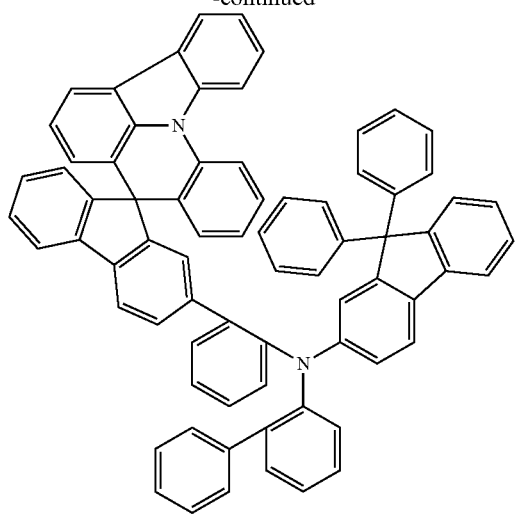
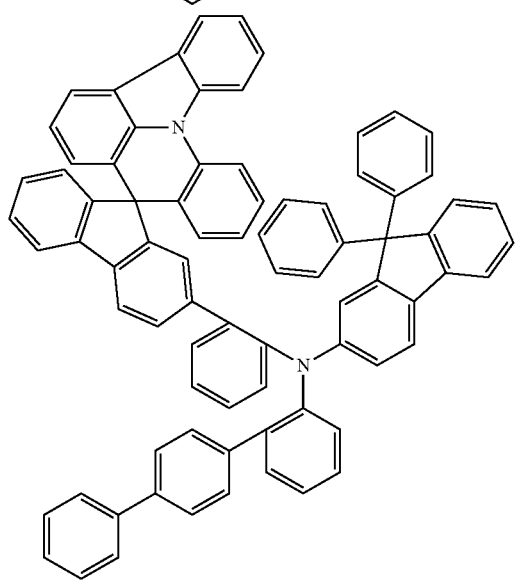
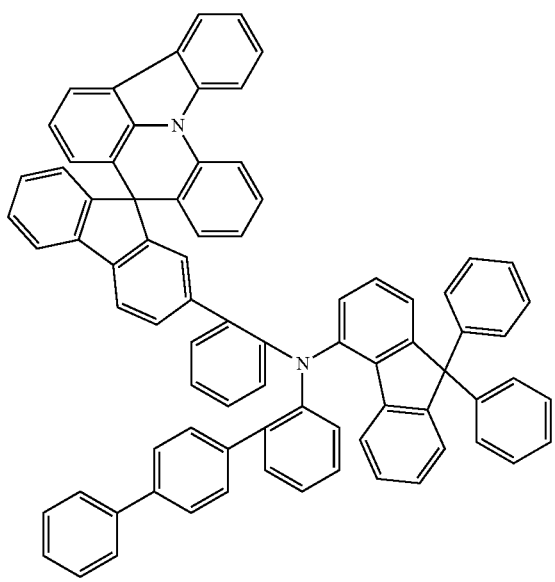
392
-continued
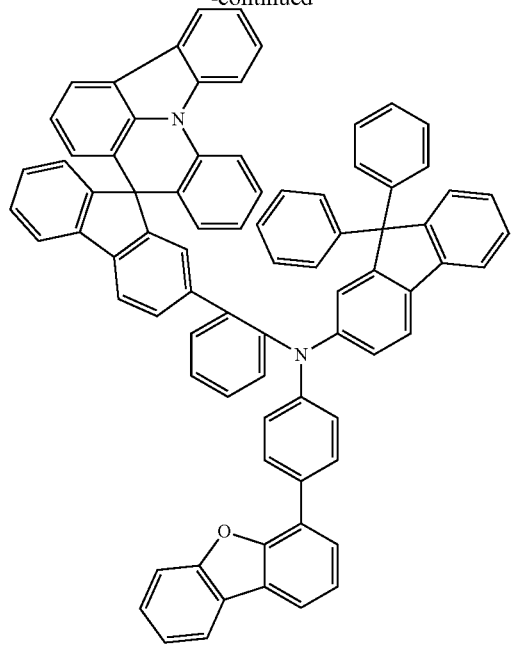
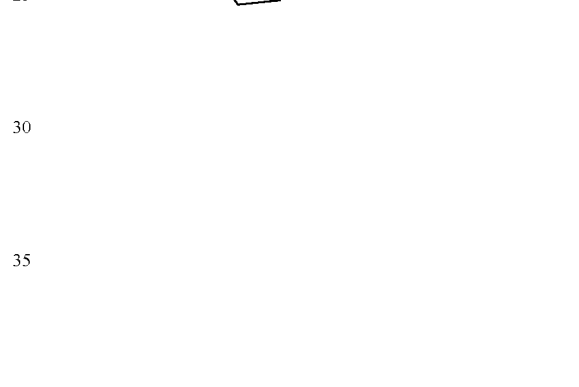
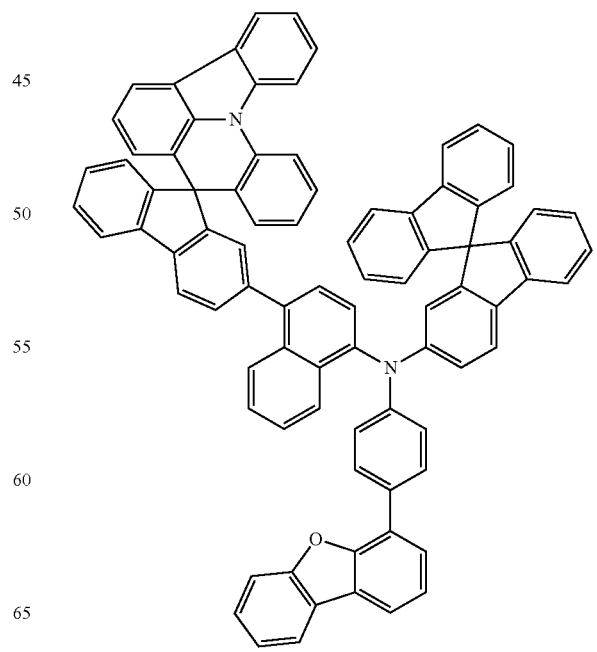

393
-continued
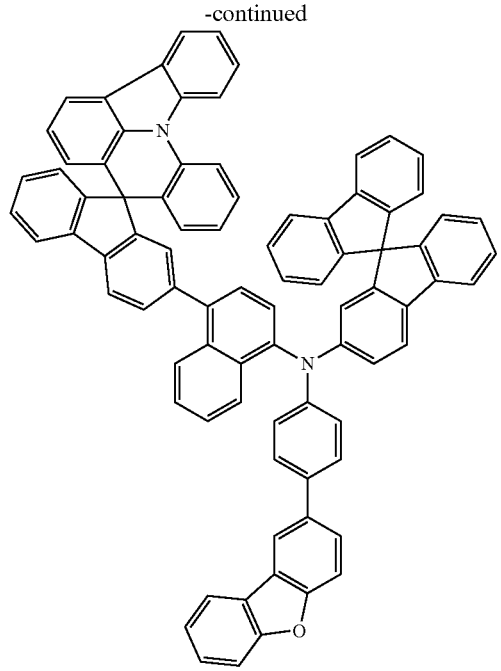
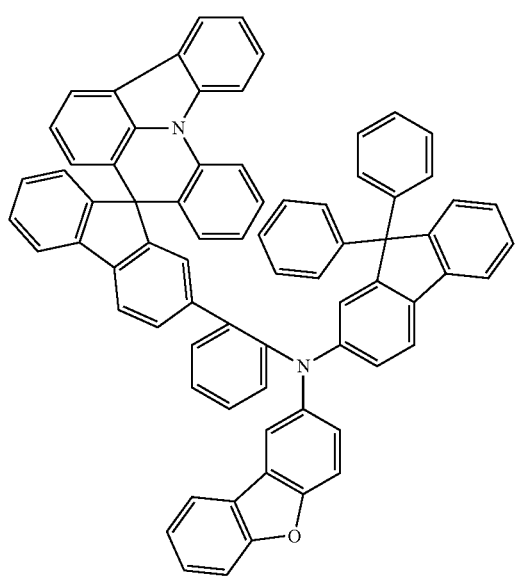
394
-continued
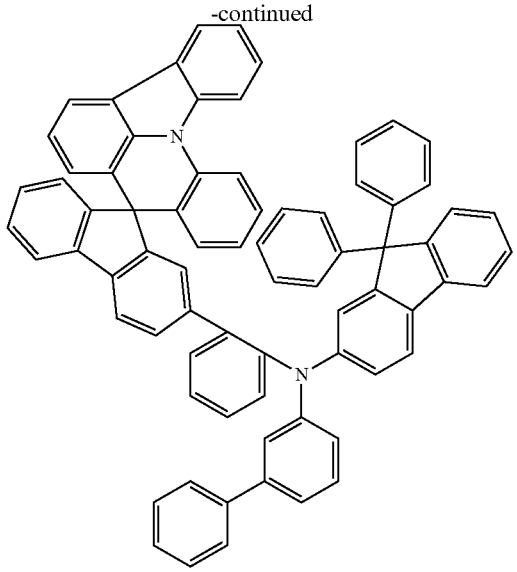
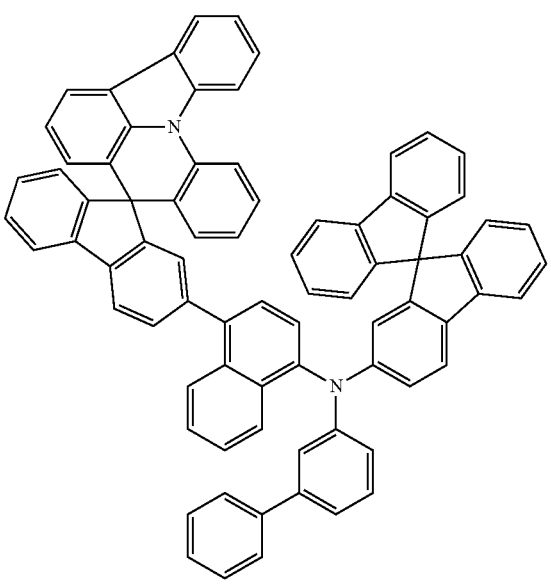

395
-continued
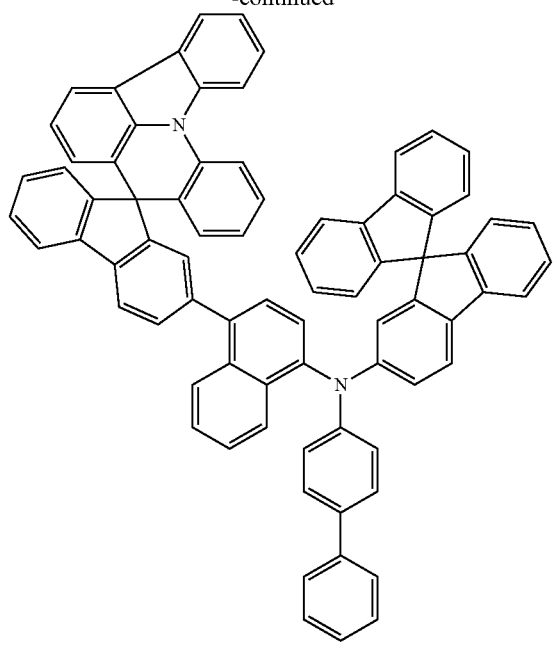
396
-continued
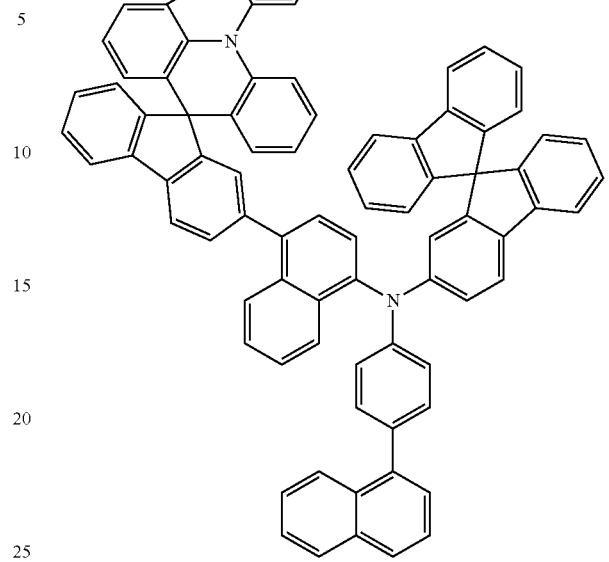
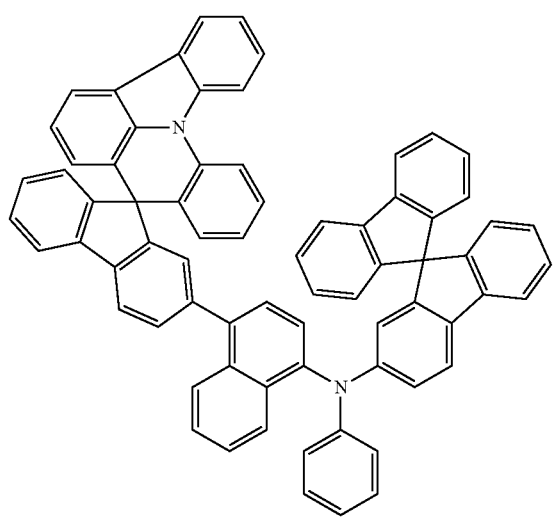
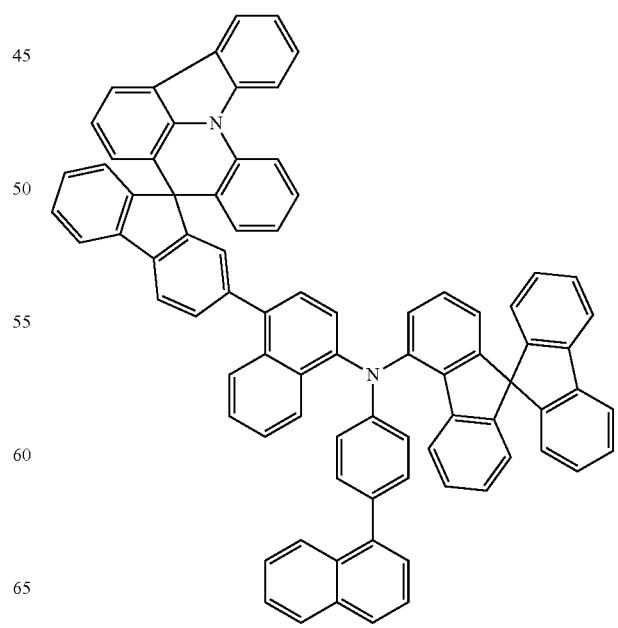

397
-continued
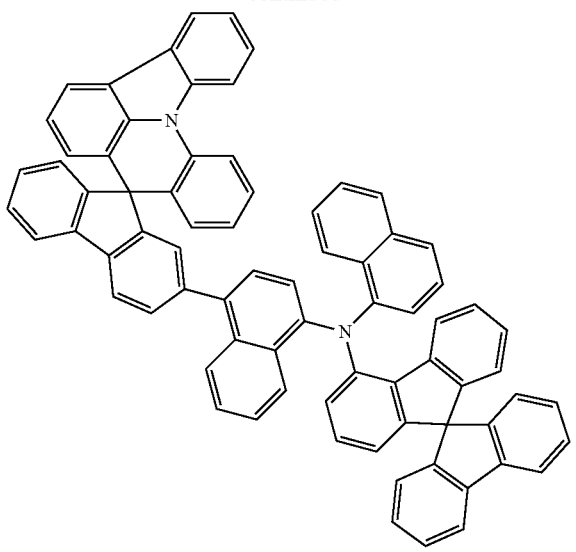
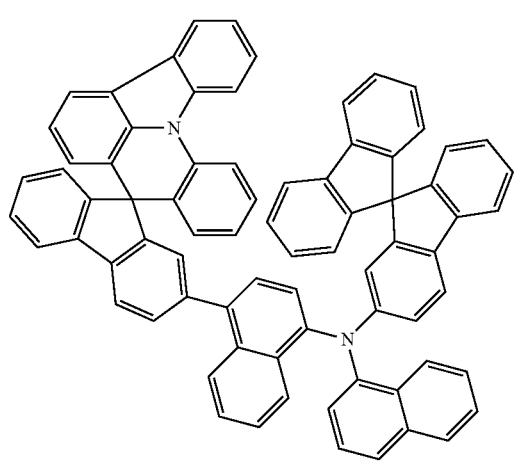
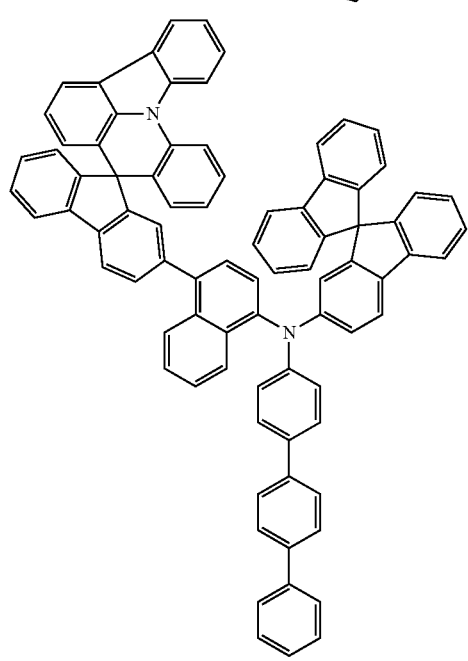
398
-continued
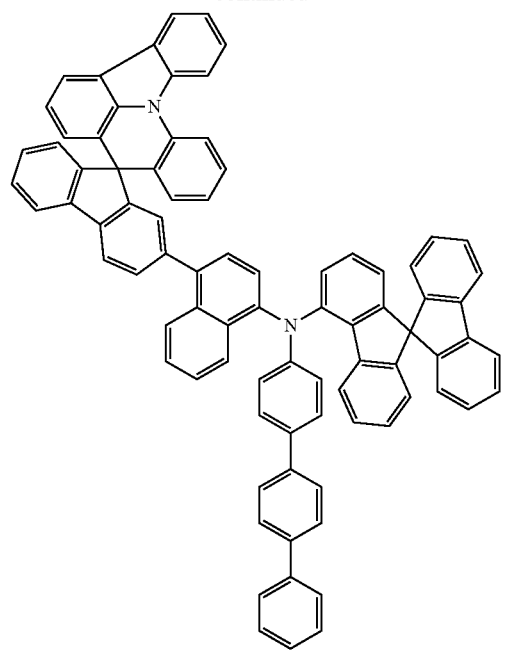
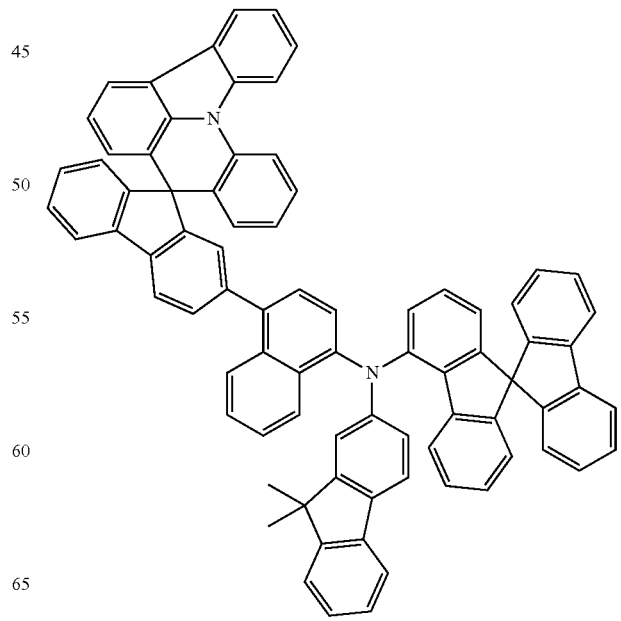

399
-continued
400
-continued
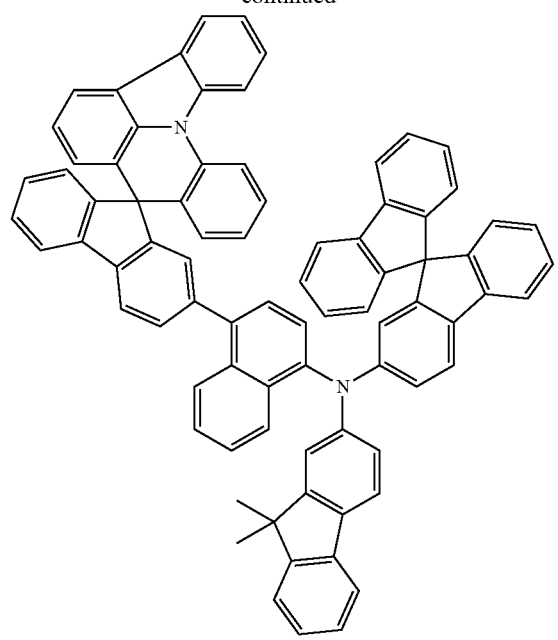
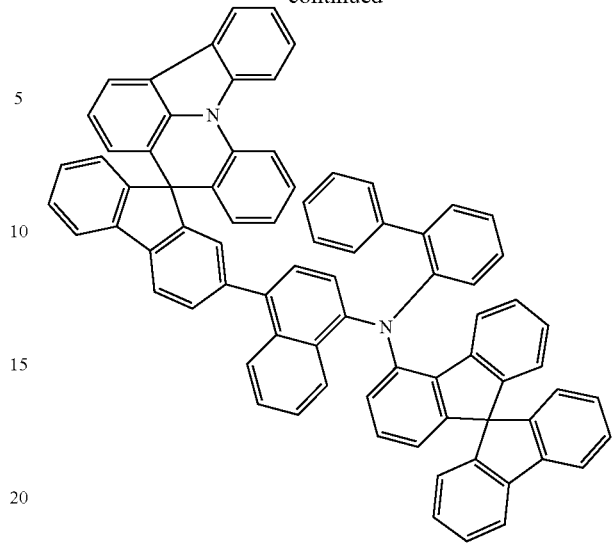
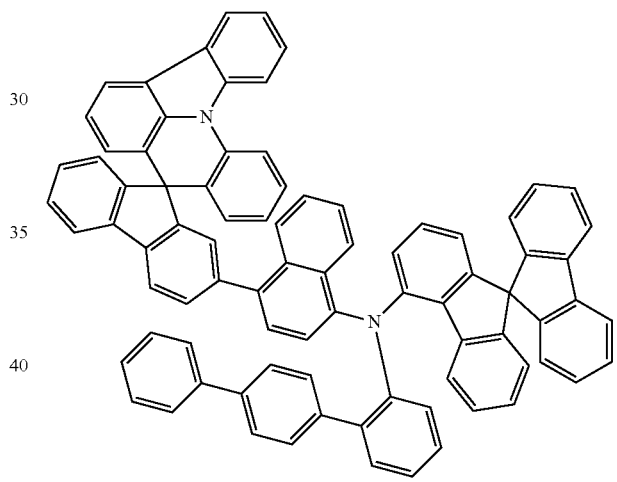
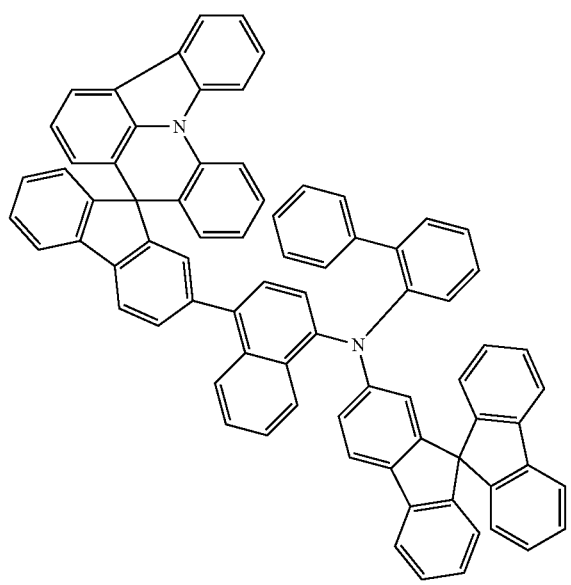

401
-continued
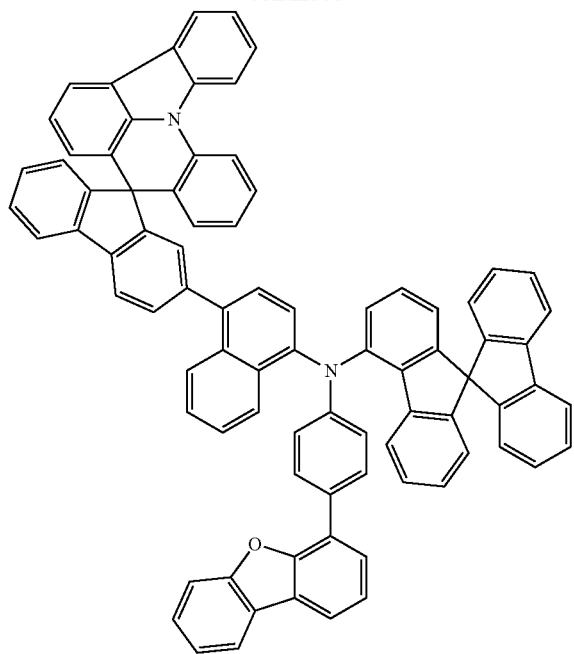
402
-continued
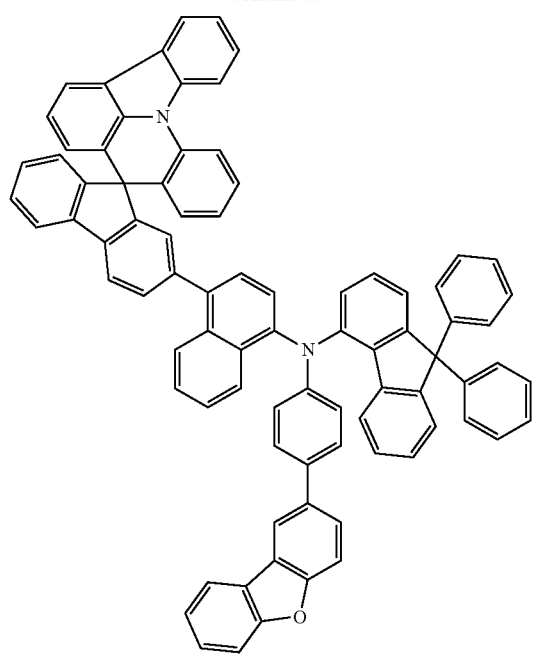
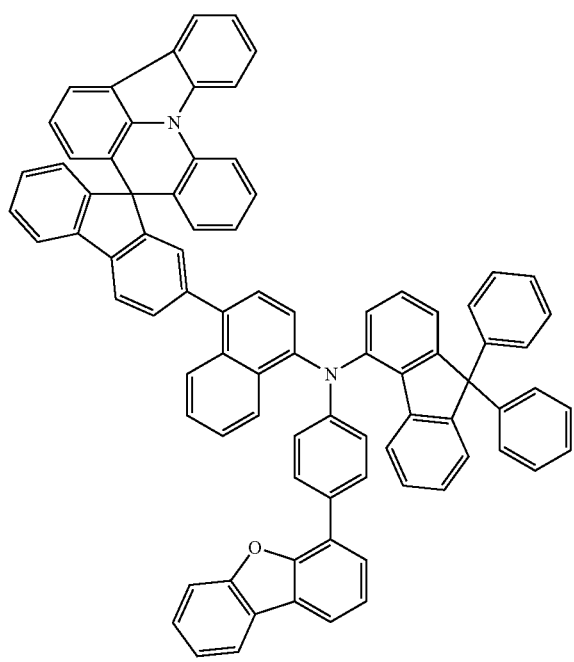
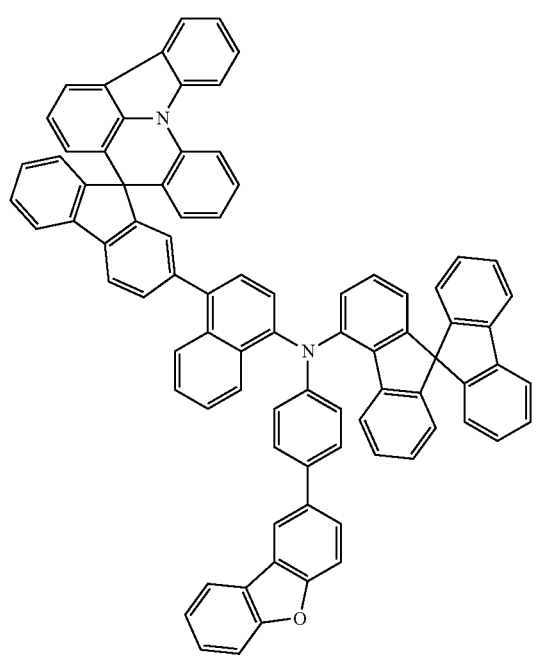

403
-continued
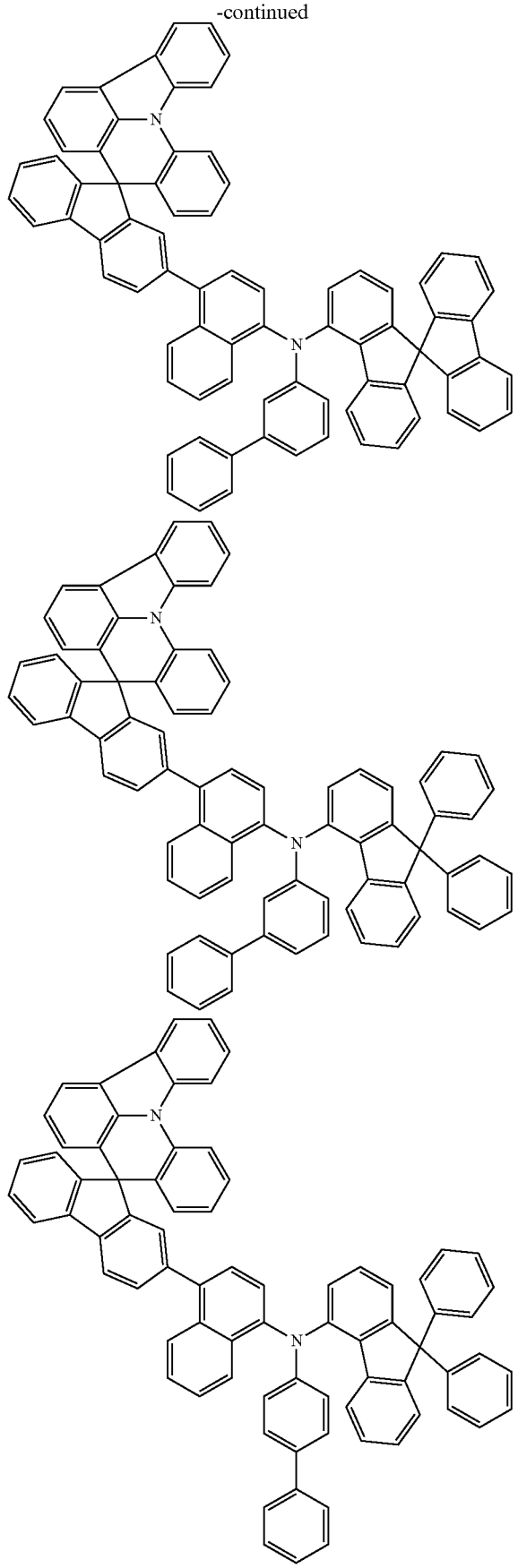
404
-continued
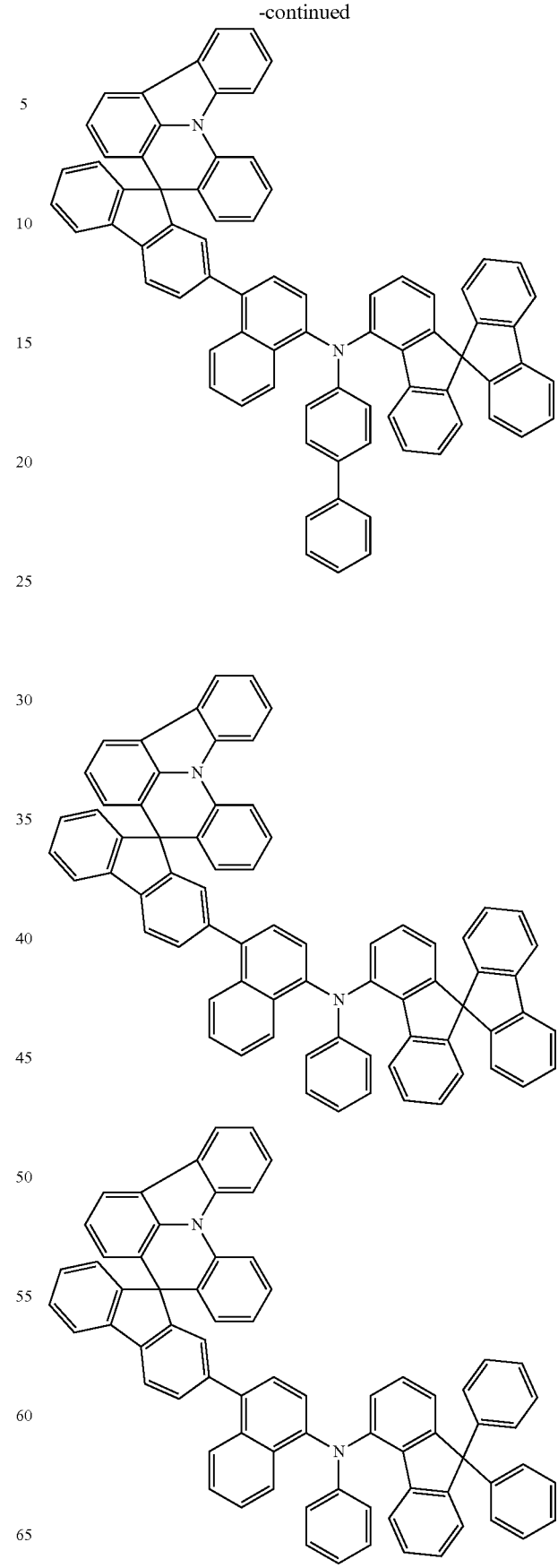

405
-continued
406
-continued
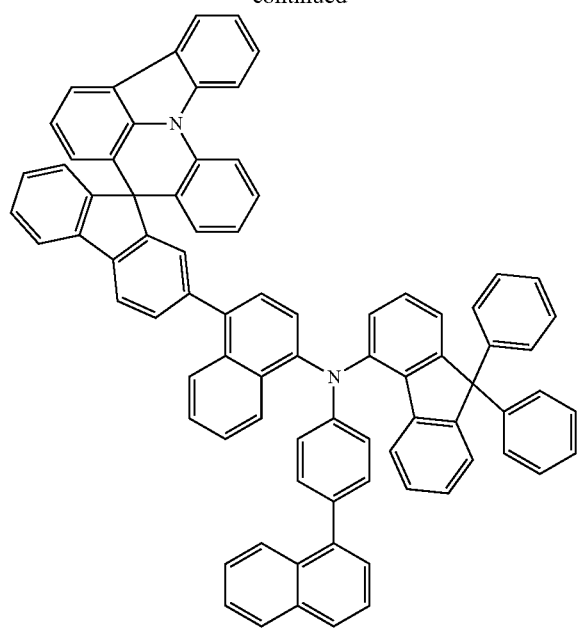

407
-continued
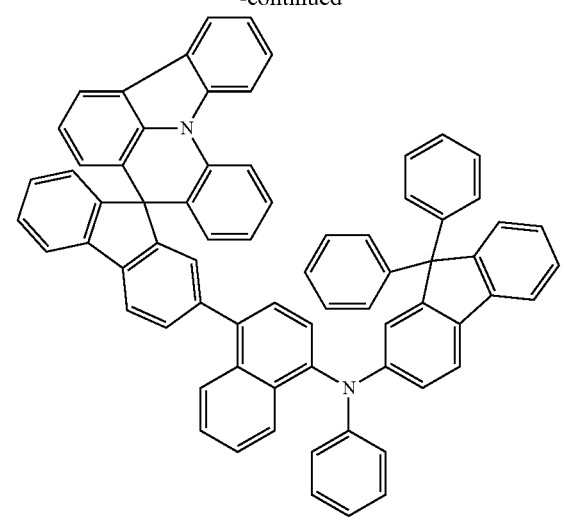
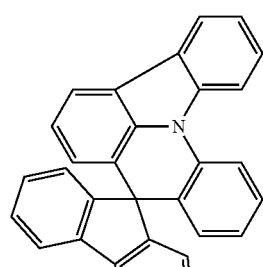
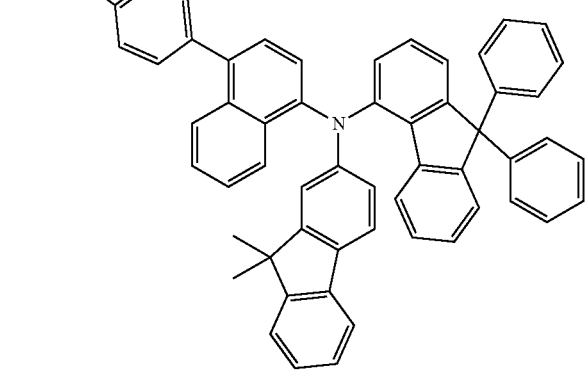
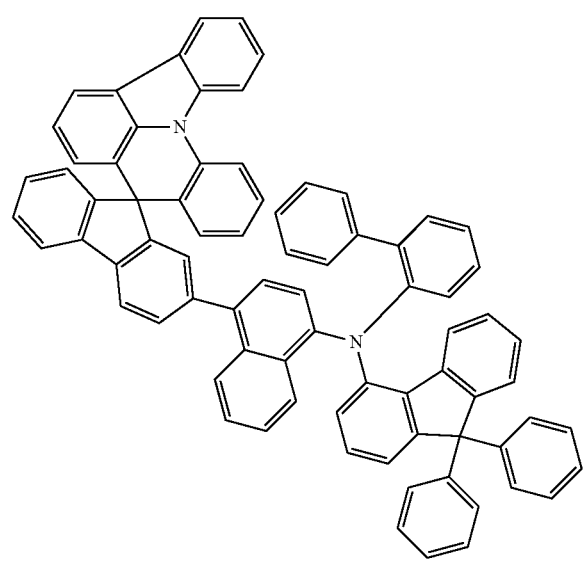
408
-continued
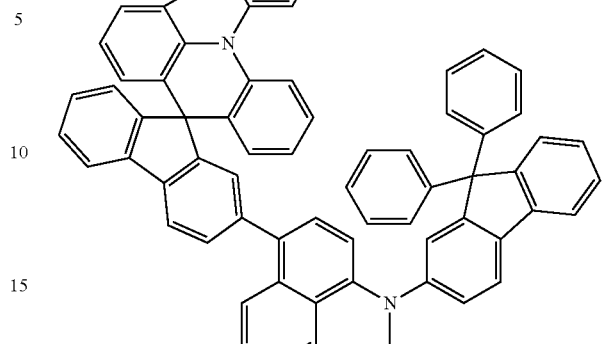
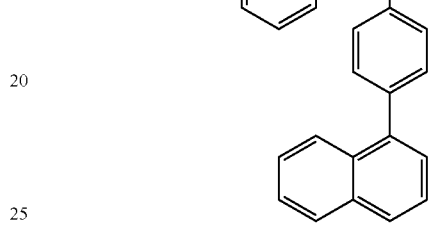
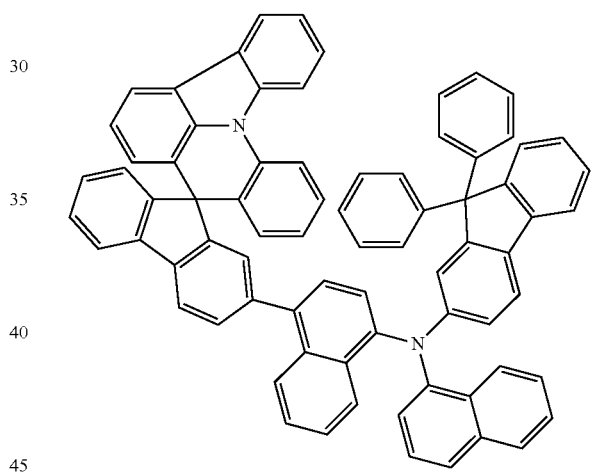
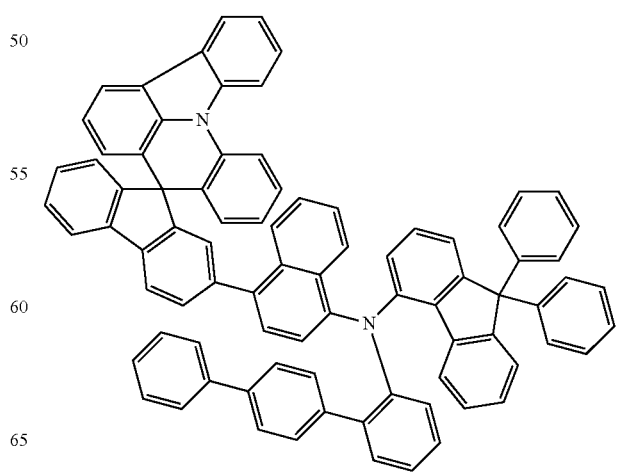

409
-continued
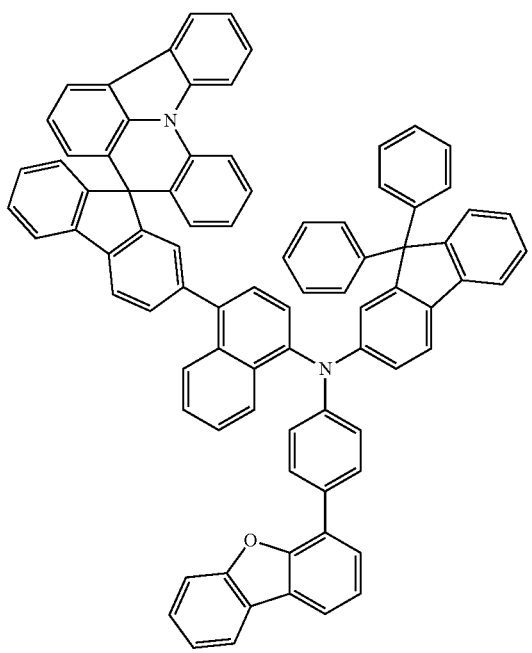
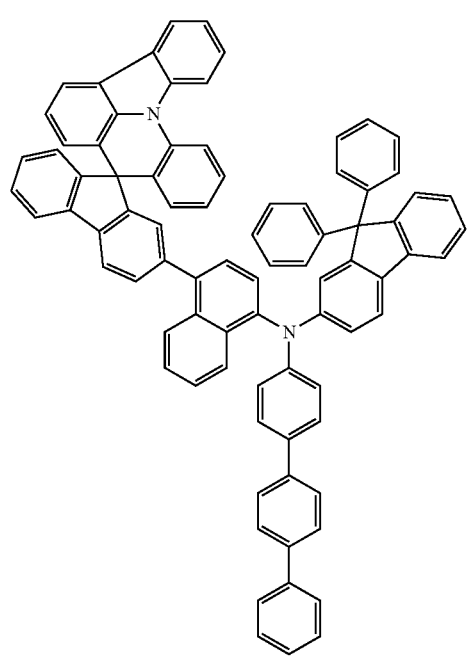
410
-continued
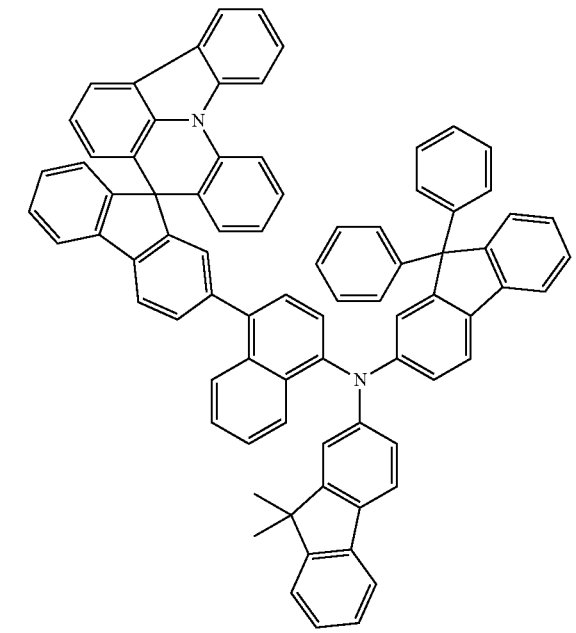
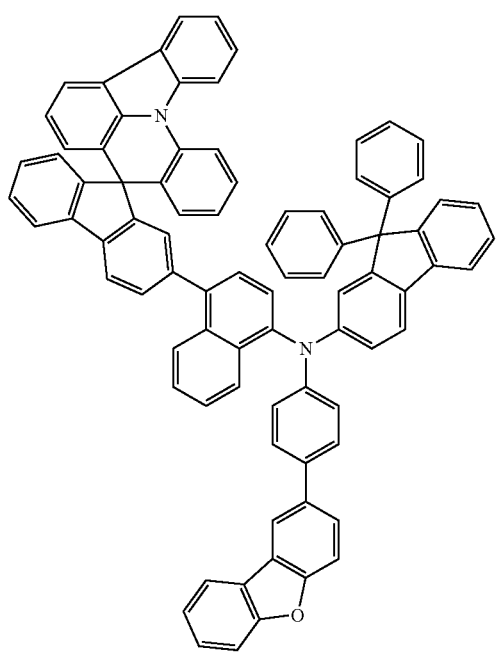

411
-continued
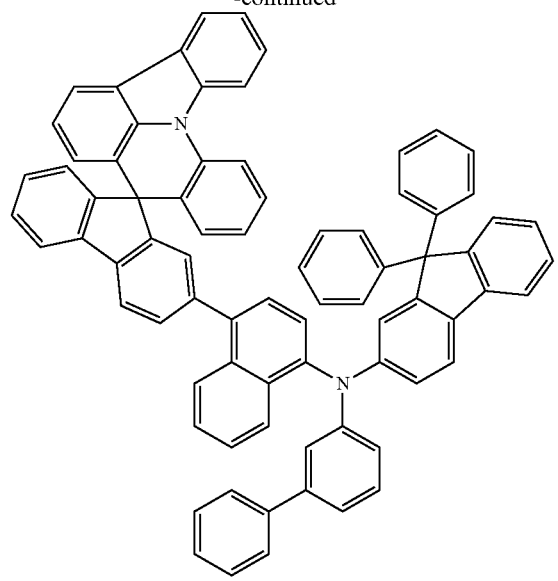
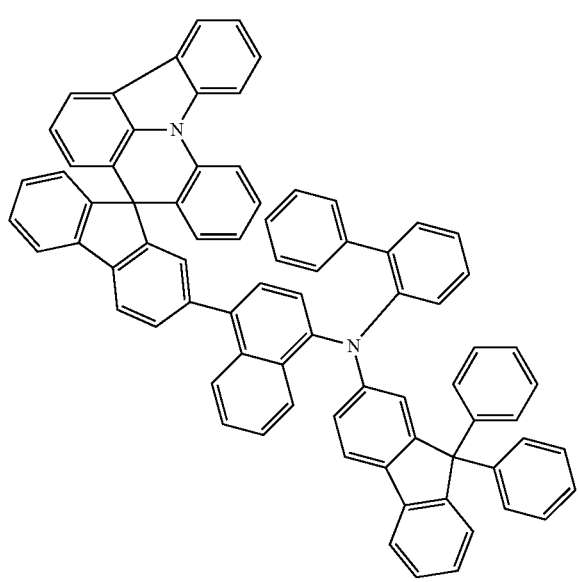
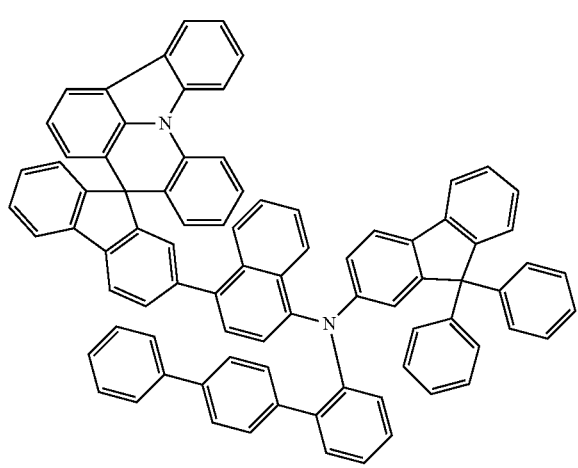
412
-continued
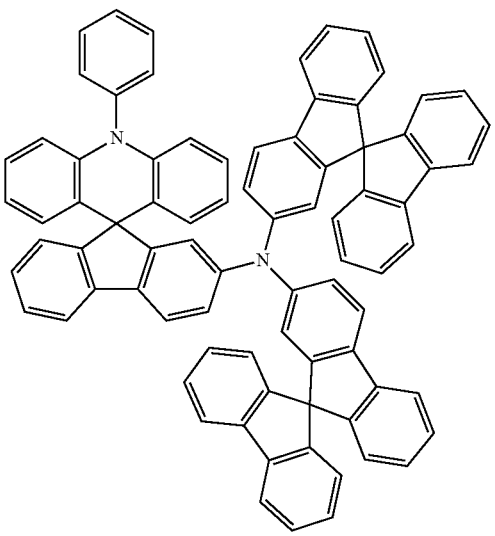
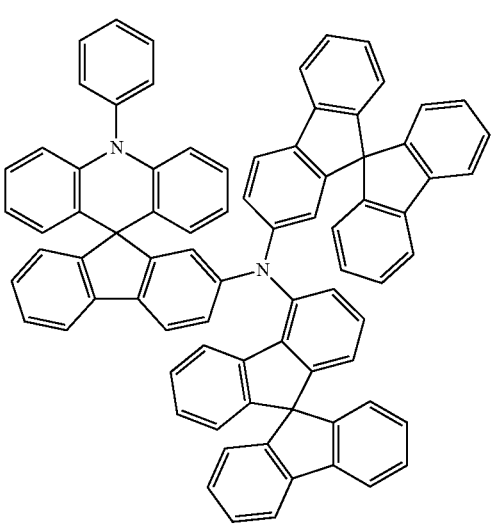
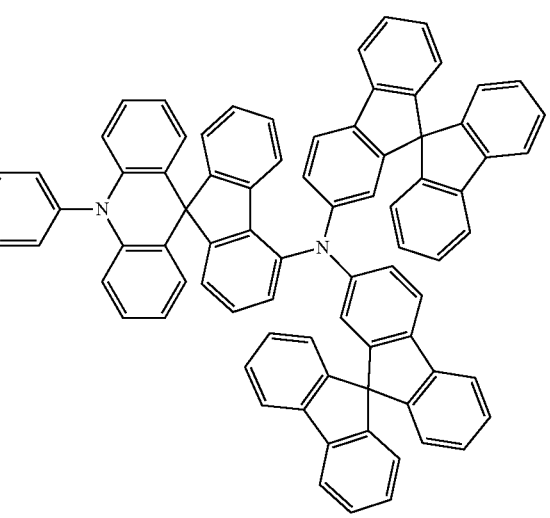

413
-continued
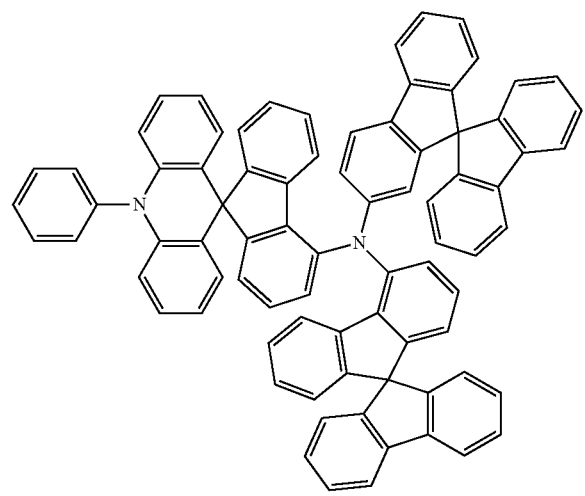
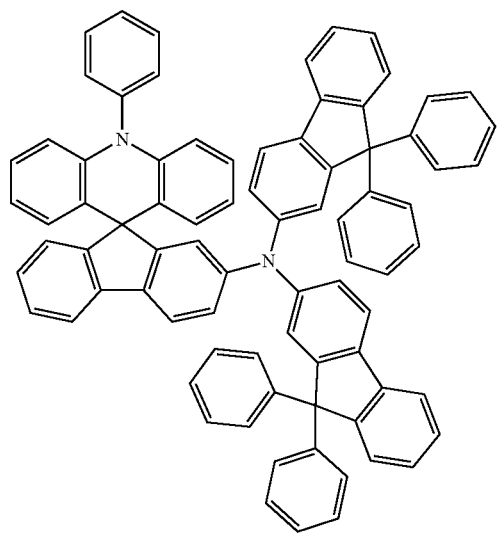
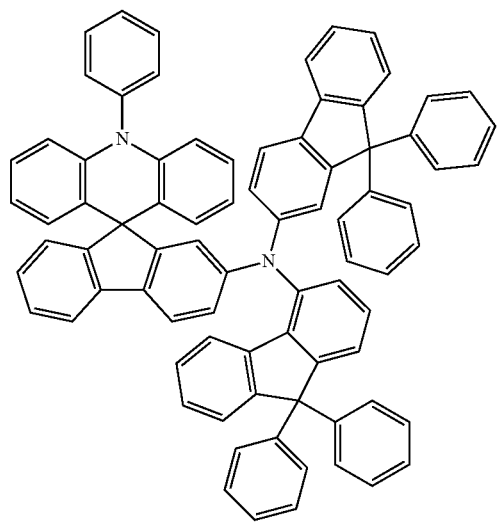
414
-continued
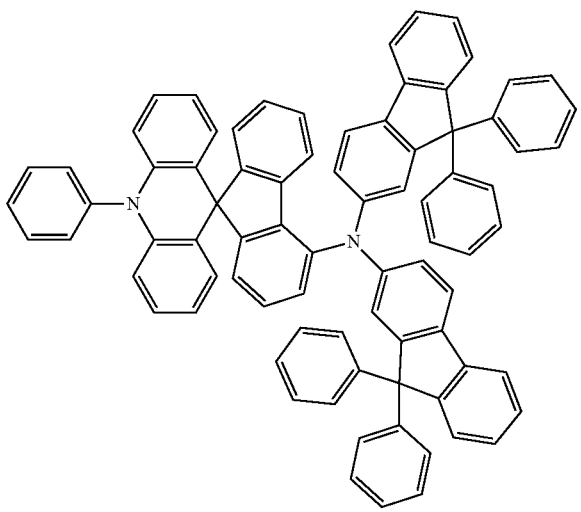
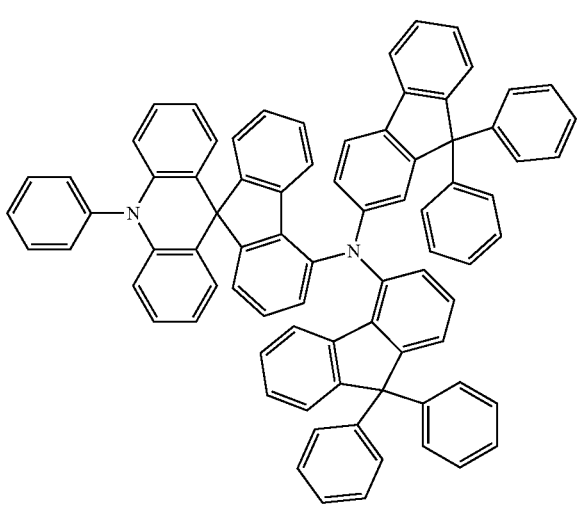
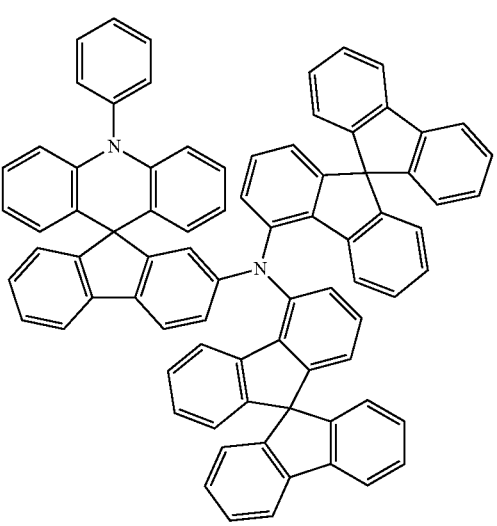

415
-continued
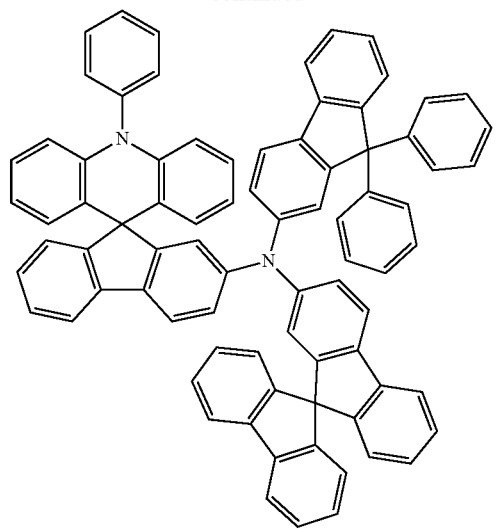
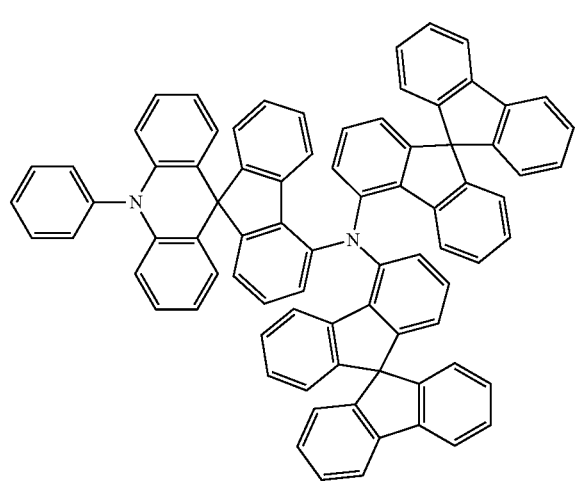
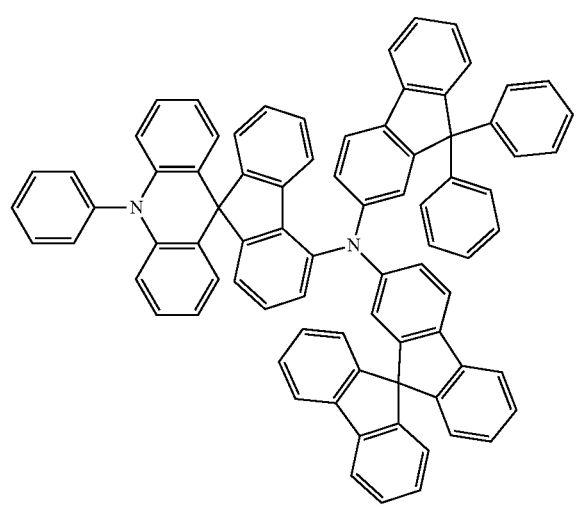
416
-continued
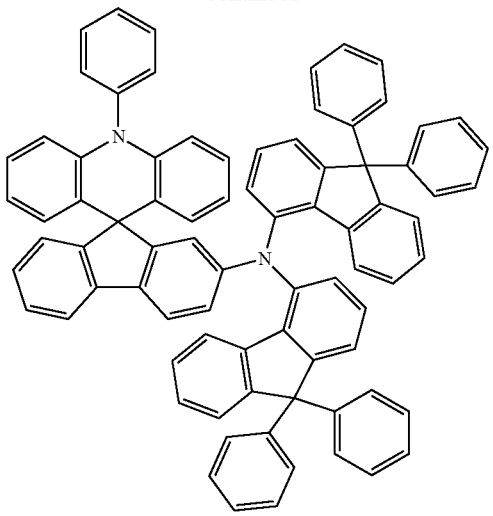
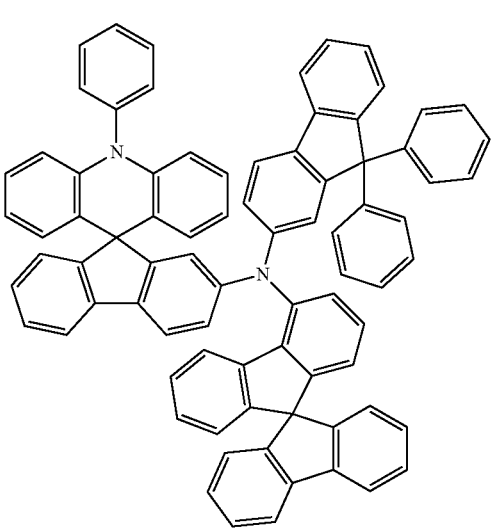
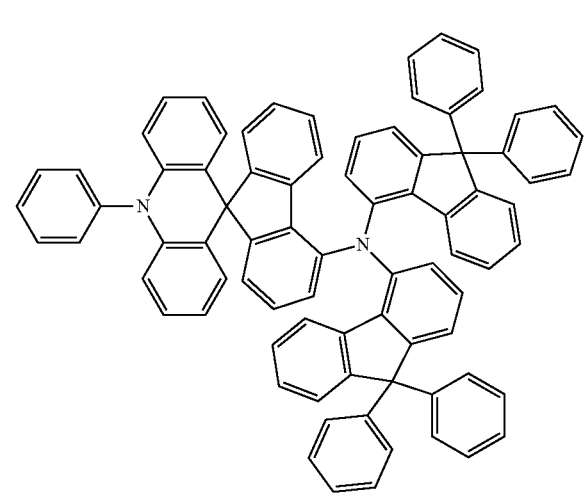

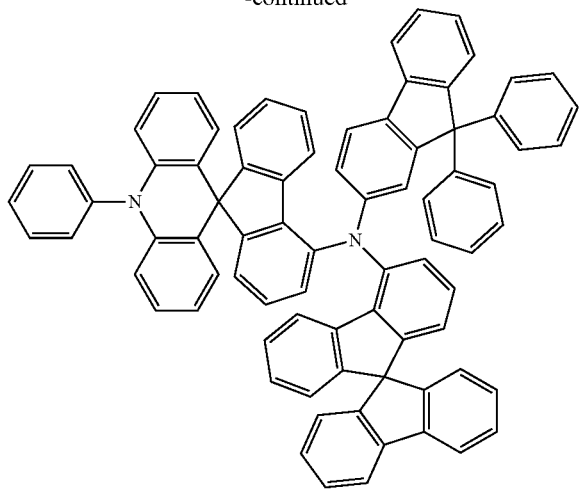

The method of producing the compound of the invention is not particularly limited. A person skilled in the art could easily produce the compound by using or modifying known synthesis reactions with reference to the examples described below.

Organic EL Device

The organic EL device of the invention will be described below.

The organic electroluminescence device comprises a cathode, an anode and an organic layer between the cathode and the anode. The organic layer comprises a light emitting layer and at least one layer of the organic layer comprises the compound of the invention.

Preferably, the organic layer comprises a hole transporting region between the anode and the light emitting layer, and the hole transporting region comprises the compound.

Preferably, the hole transporting region comprises a first hole transporting layer and a second hole transporting layer from the anode toward the light emitting layer in this order, and one of the first hole transporting layer and the second hole transporting layer comprises the compound.

Also preferably, the first hole transporting layer and the second hole transporting layer both comprise the compound because the performance of organic EL device, such as the efficiency, is expected to be improved by the optimization.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent emitting device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, with the layers in parentheses being optional:

(a) (Hole injecting layer/) Hole transporting layer/Fluorescent emitting layer/Electron transporting layer;
(b) (Hole injecting layer/) Hole transporting layer/Phosphorescent emitting layer/Electron transporting layer;
(c) (Hole injecting layer/) Hole transporting layer/First fluorescent emitting layer/Second fluorescent emitting layer/Electron transporting layer;
(d) (Hole injecting layer/) Hole transporting layer/First phosphorescent emitting layer/Second phosphorescent emitting layer/Electron transporting layer;
(e) (Hole injecting layer/) Hole transporting layer/Phosphorescent emitting layer/Space layer/Fluorescent emitting layer/Electron transporting layer;
(f) (Hole injecting layer/) Hole transporting layer/First phosphorescent emitting layer/Second phosphorescent emitting layer/Space layer/Fluorescent emitting layer/Electron transporting layer;
(g) (Hole injecting layer/) Hole transporting layer/First phosphorescent emitting layer/Space layer/Second phosphorescent emitting layer/Space layer/Fluorescent emitting layer/Electron transporting layer;
(h) (Hole injecting layer/) Hole transporting layer/Phosphorescent emitting layer/Space layer/First fluorescent emitting layer/Second fluorescent emitting layer/Electron transporting layer;
(i) (Hole injecting layer/) Hole transporting layer/Electron blocking layer/Fluorescent emitting layer/Electron transporting layer;
(j) (Hole injecting layer/) Hole transporting layer/Electron blocking layer/Phosphorescent emitting layer/Electron transporting layer;
(k) (Hole injecting layer/) Hole transporting layer/Exciton blocking layer/Fluorescent emitting layer/Electron transporting layer;
(l) (Hole injecting layer/) Hole transporting layer/Exciton blocking layer/Phosphorescent emitting layer/Electron transporting layer;
(m) (Hole injecting layer/) First hole transporting layer/Second hole transporting layer/Fluorescent emitting layer/Electron transporting layer;
(n) (Hole injecting layer/) First hole transporting layer/Second hole transporting layer/Phosphorescent emitting layer/Electron transporting layer;
(o) (Hole injecting layer/) Hole transporting layer/Fluorescent emitting layer/Electron transporting layer;
(p) (Hole injecting layer/) Hole transporting layer/Phosphorescent emitting layer/Electron transporting layer;
(q) (Hole injecting layer/) Hole transporting layer/Fluorescent emitting layer/Triplet blocking layer/Electron transporting layer; and
(r) (Hole injecting layer/) Hole transporting layer/Phosphorescent emitting layer/Triplet blocking layer/Electron transporting layer.

The emission color of the fluorescent emitting layer and that of the phosphorescent emitting layer may be different. For example, the layered structure of the laminated emission unit (f) may be (Hole injecting layer/) Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between the light emitting layer and the hole transporting layer or between the light emitting layer and the space layer, if necessary. With such an electron blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be independently selected from, for example, those exemplified above.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 7. A first hole transporting layer 6 and a second hole transporting layer 5 (anode-side organic layers) are disposed between the light emitting layer 7 and the anode 3. An electron transporting layer 8 (cathode-side organic layer) is disposed between the light emitting layer 7 and the cathode 4. An electron injecting layer may be formed between the electron transporting layer 8 and the cathode 4. An electron blocking layer may be formed on the side of the anode 3 of the light emitting layer 7. With the electron blocking layer, electrons and holes are confined in the light emitting layer 7 to increase the exciton generation in the light emitting layer 7.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). In addition to a hole injecting material, the hole injecting layer may comprise the same material as that contained in the adjacent hole transporting layer. The compound (1) may be used in the hole injecting layer alone or in combination with the hole injecting material mentioned below.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4"-tris(N,N-diphenylamino)triphenylamine (TDATA), 4,4',4"-tris[N-(3-methylphenyl)-N-phenylamino]triphenylamine (MT-DATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino) biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1). Further, the radialene compound, such as 4-({2,3-bis[cyano-(4-cyano-2,3,5,6-tetrafluorophenyl) methylene]cyclopropylidene}cyanomethyl)-2,3,5,6-tetrafluorobenzonitrile, is also usable as the hole injecting material. In addition to the radialene compound as the hole injecting material, the hole injecting layer may further comprise the same material as that contained in the adjacent hole transporting layer. The compound (1) may be used in the hole injecting layer in combination with the radialene compound.

A macro molecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macro molecular compound, such as poly(3,4-ethylenedioxythiophene)/poly(styrenesulfonic acid) (PEDOT/PSS) and polyaniline/poly(styrenesulfonic acid) (PAni/PSS), is also usable.

The compound represented by (2-1) or (2-2) is preferably used as the hole injecting material:

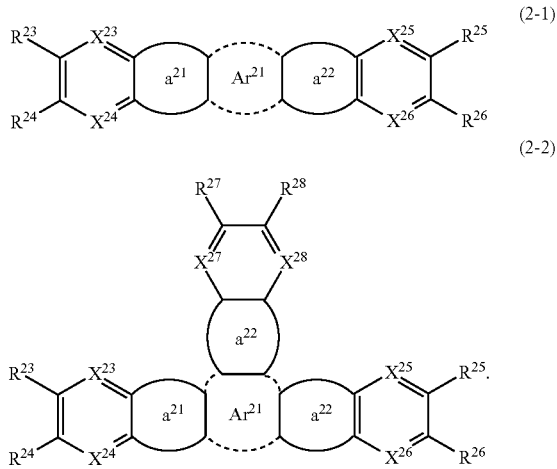

In formulae (2-1) and (2-2), $Ar^{21}$ is a substituted or unsubstituted aromatic hydrocarbon ring having 6 to 30 ring carbon atoms or a substituted or unsubstituted aromatic heterocyclic ring having 5 to 30 ring atoms. The aromatic hydrocarbon ring is preferably a benzene ring. The aromatic heterocyclic ring is preferably a ring having 6 ring atoms, for example, a pyridine ring, a pyrazine ring, and a pyridazine ring.

In formulae (2-1) and (2-2), each of $X^{23}$ to $X^{28}$ is independently C(R) or a nitrogen atom.

Each R is independently a hydrogen atom, a halogen atom, a hydroxyl group, a cyano group, a substituted or unsubstituted alkyl group having 1 to 30 carbon atoms, a substituted or unsubstituted aryl group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, an alkoxy group having a substituted or unsubstituted alkyl group having 1 to 30 carbon atoms, an aryloxy group having a substituted or unsubstituted aryl group having 6 to 30 ring carbon atoms, a mono- or di-substituted amino group having a substituent selected from a substituted or unsubstituted alkyl group having 1 to 30 carbon atoms and a substituted or unsubstituted aryl group having 6 to 30 ring carbon atoms, an alkylthio group having a substituted or unsubstituted alkyl group having 1 to 30 carbon atoms, an arylthio group having a substituted or unsubstituted aryl group having 6 to 30 ring carbon atoms, or a substituted or unsubstituted heteroaryl group having 5 to 30 ring atoms.

The details of the alkyl group, the aryl group, the mono-, di-, or tri-substituted silyl group, the alkoxy group, the aryloxy group, the mono- or di-substituted amino group, the alkylthio group, the arylthio group, and the heteroaryl group are the same as those of the corresponding groups mentioned above with respect to the substituent simply referred to by "substituent" and the optional substituent referred to by "substituted or unsubstituted."

In formulae (2-1) and (2-2), each of $a^{21}$ to $a^{23}$ is a ring structure represented by formula (2b):

wherein $X^{20}$ is represented by any of formulae (2b-1) to (2b-12):

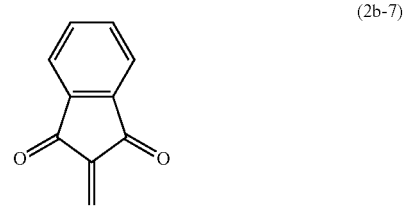

(2b-10)
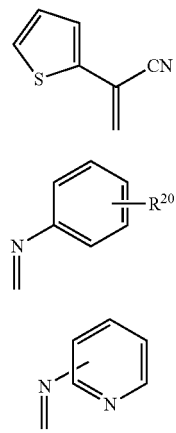
(2b-11)
(2b-12)
wherein $R^{20}$ is the same as defined with respect to R.
In formulae (2-1) and (2-2), each of $R^{23}$ to $R^{28}$ is independently the same as defined with respect to R.
Examples of the compound represented by formula (2-1) or (2-2) are shown below, although not limited thereto.
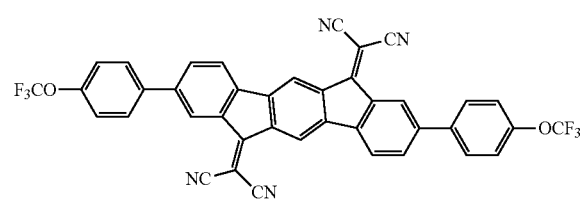
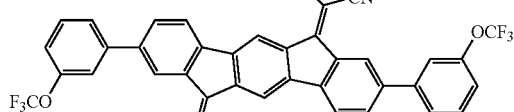
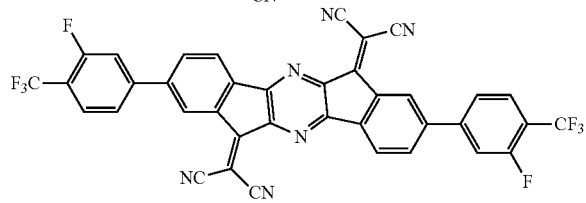
(A-1)
(A-2)
(A-3)
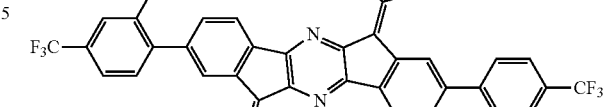
(A-4)
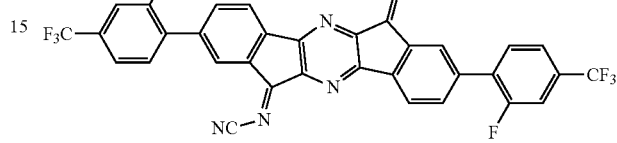
(A-5)
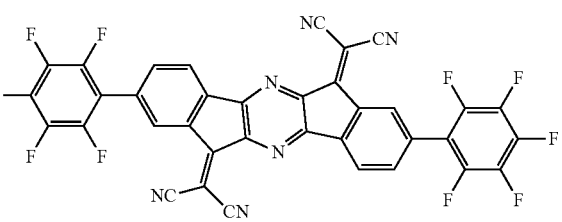
(A-6)
(A-7)
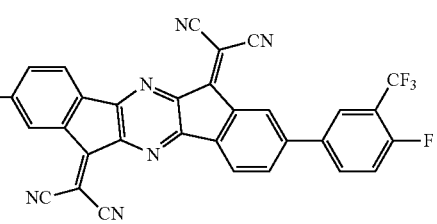
(A-8)
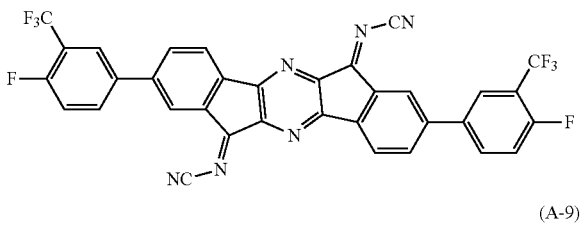
(A-9)
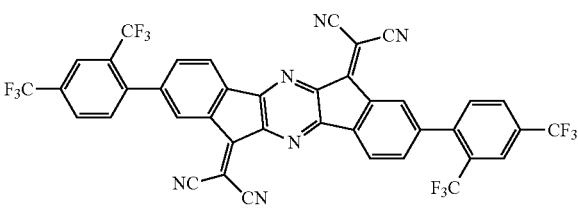

-continued
(A-10)
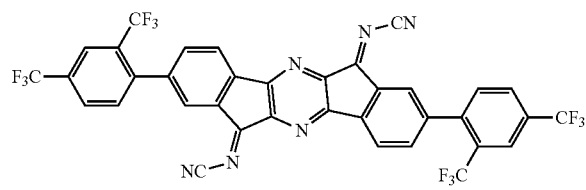
(A-11)
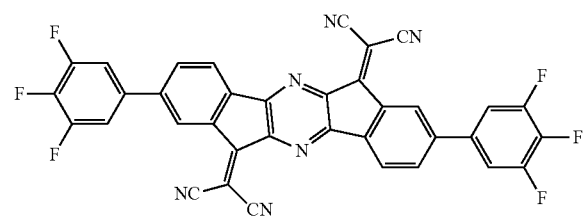
(A-12)
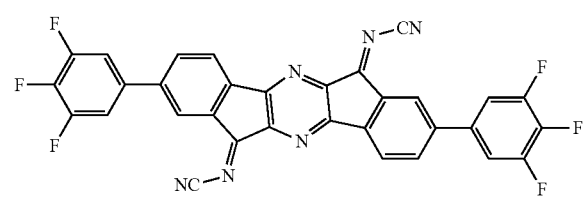
(A-13)
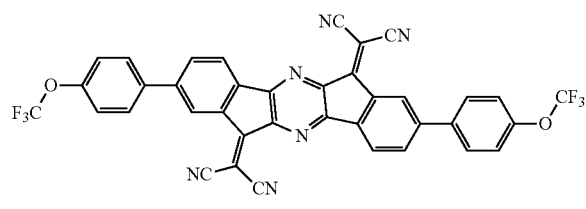
(A-14)
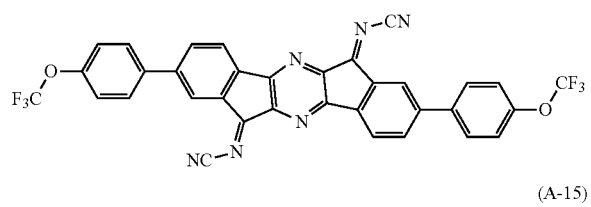
(A-15)
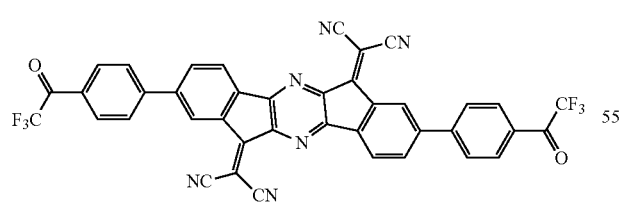
(A-16)
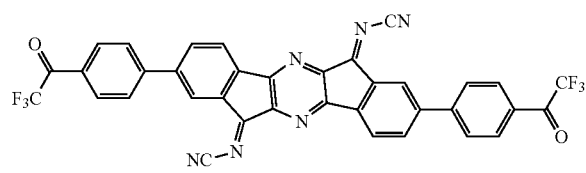
-continued
(A-17)
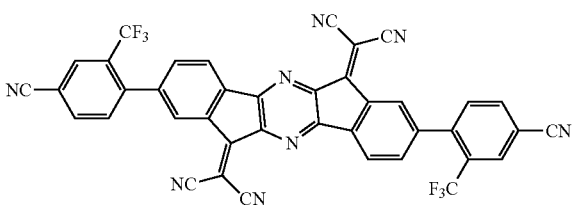
(A-18)
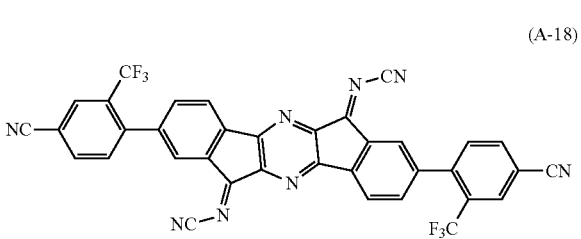
(A-19)
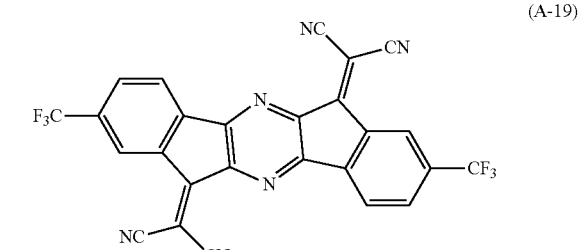
(A-20)
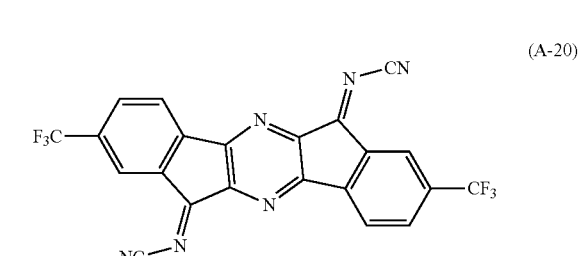
(A-21)
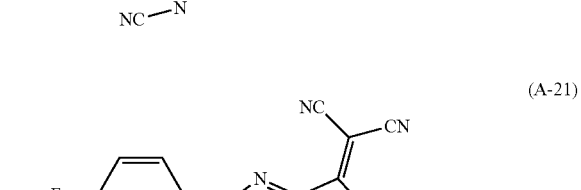
(A-22)
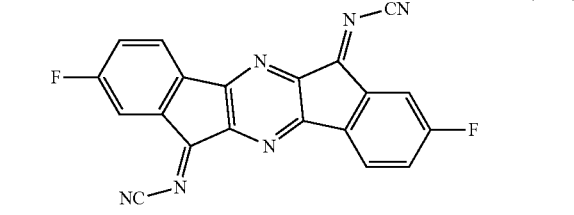

-continued
(A-23)
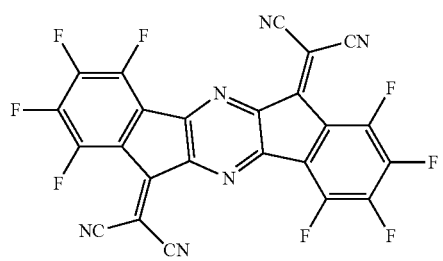
(A-24)
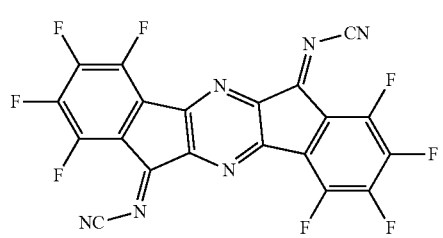
(A-25)
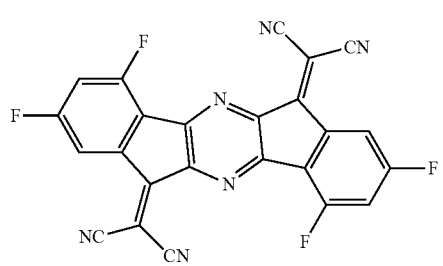
(A-26)
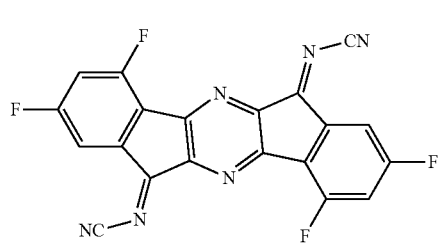
(A-31)
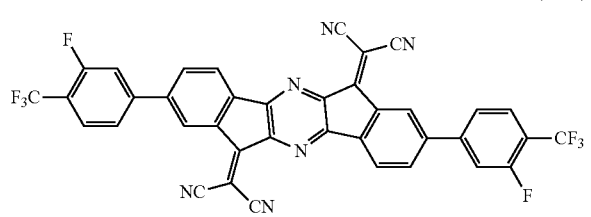
(A-32)
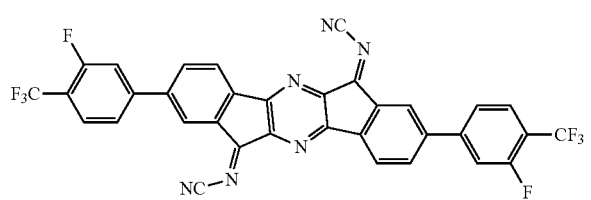
-continued
(A-33)
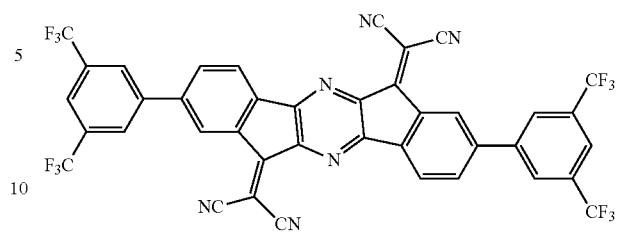
(A-34)
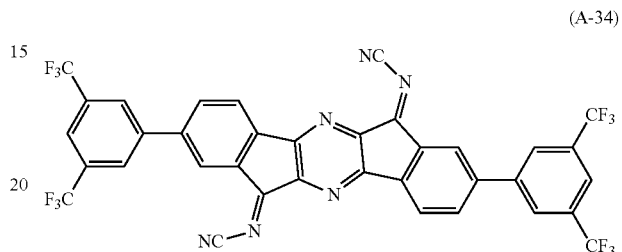
(A-35)
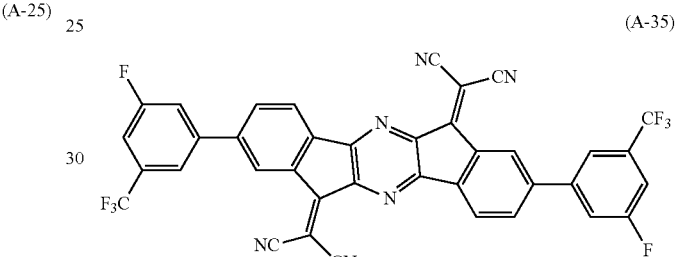
(A-36)
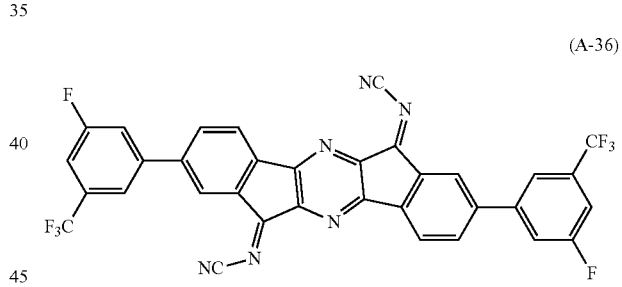
(A-37)
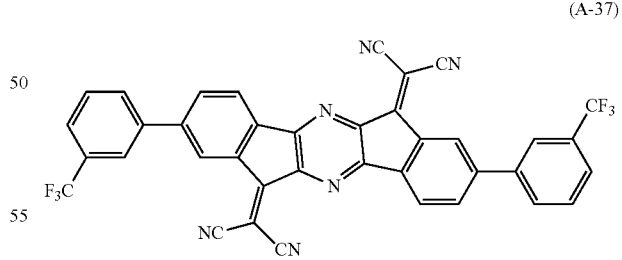
(A-38)
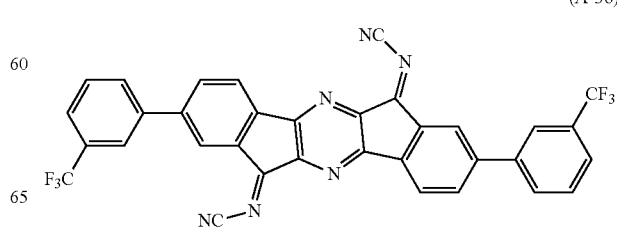

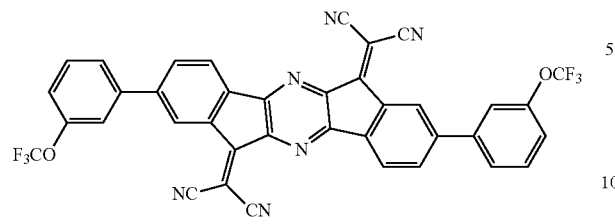
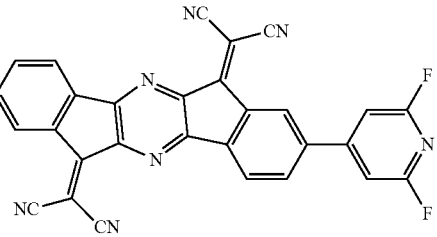
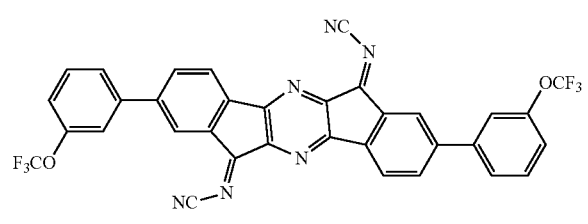
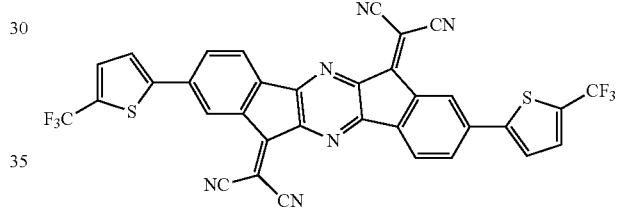

-continued
(A-51)
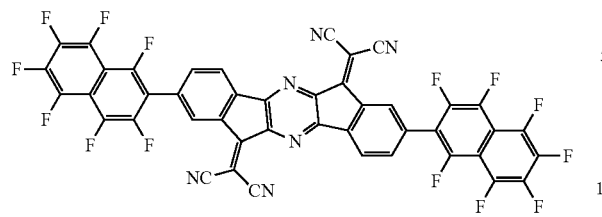
(A-52)
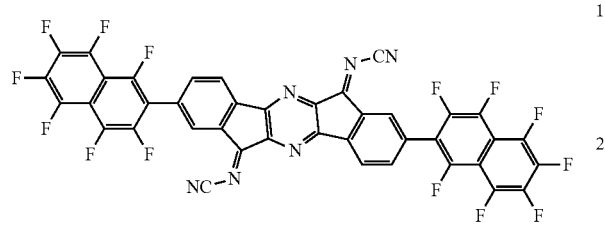
(A-53)
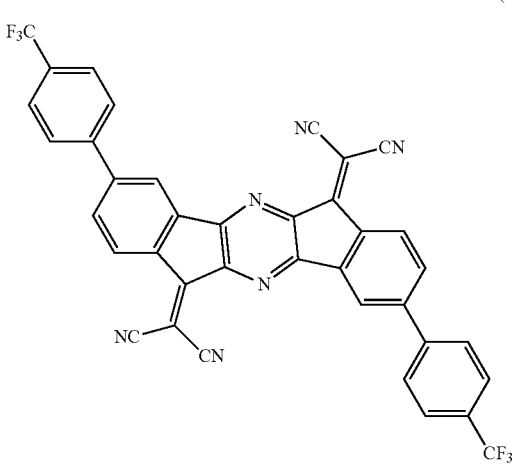
(A-54)
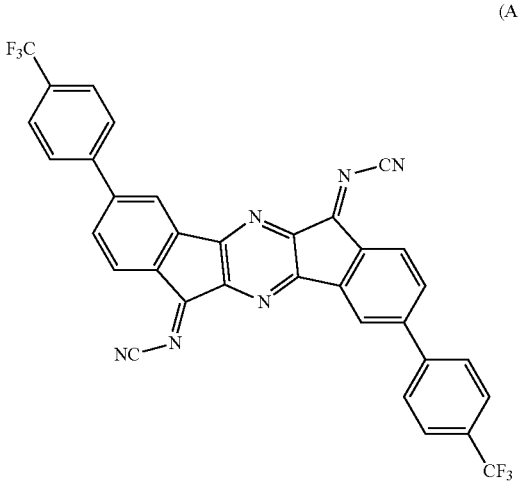
-continued
(A-55)
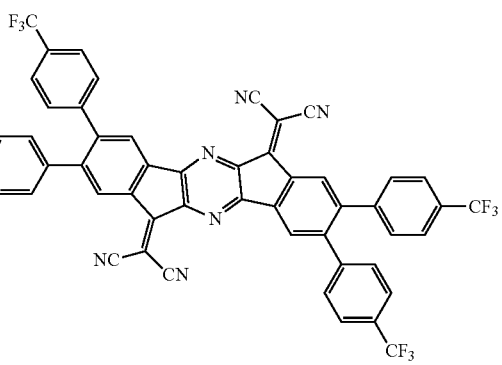
(A-56)
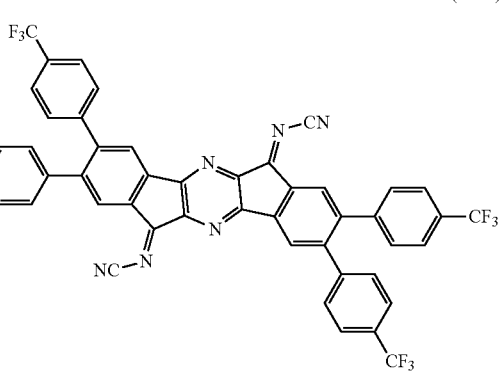
(A-57)
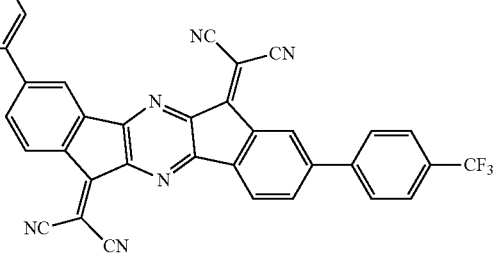
(A-58)

(A-59)
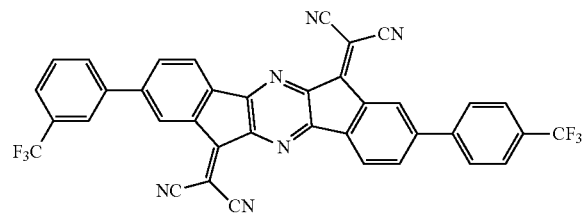
(A-60)
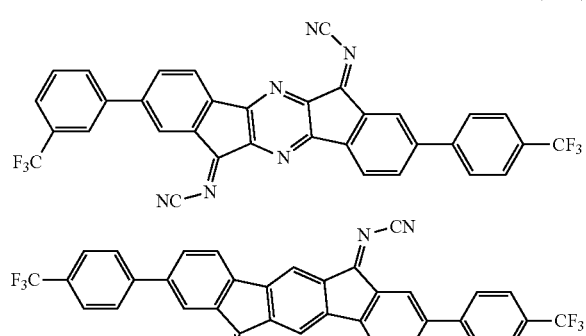
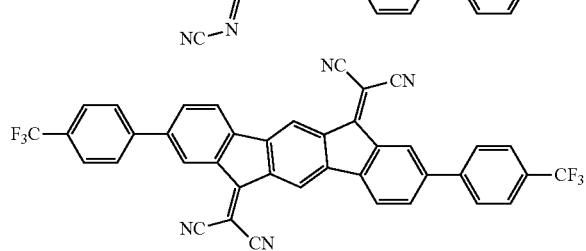
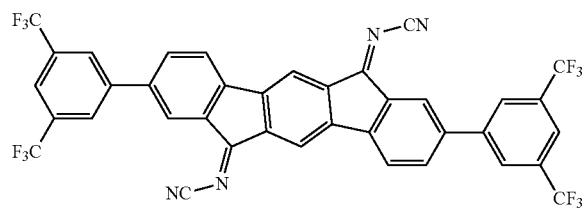
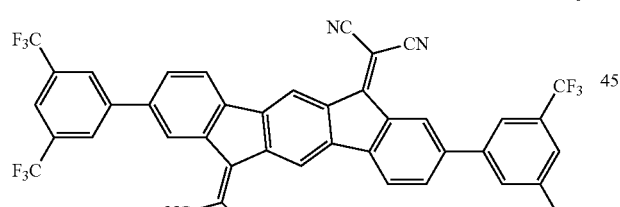
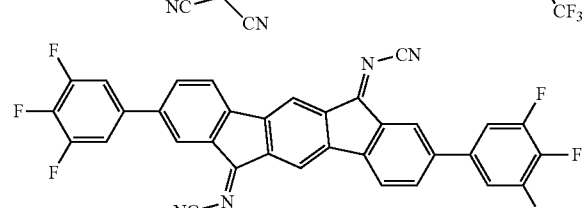
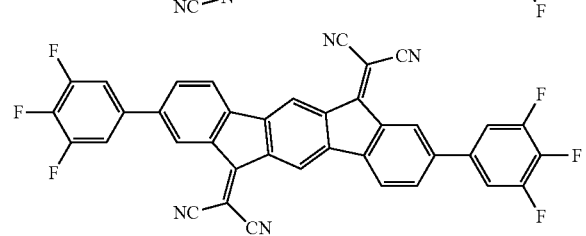
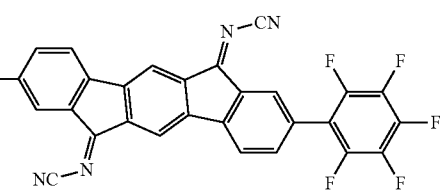
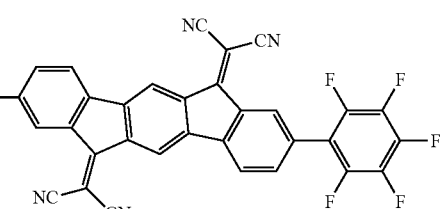
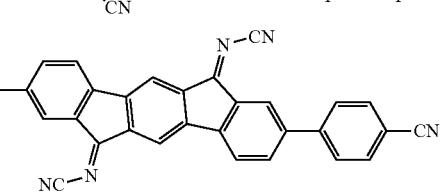
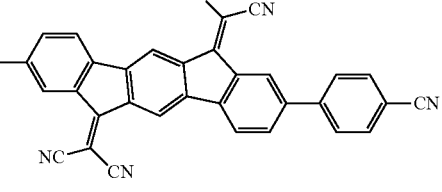
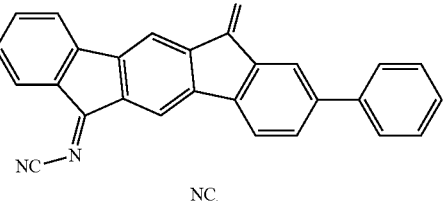
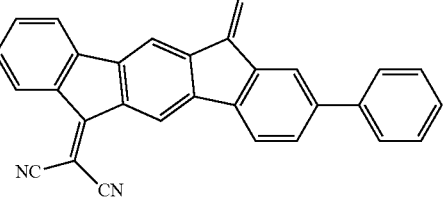
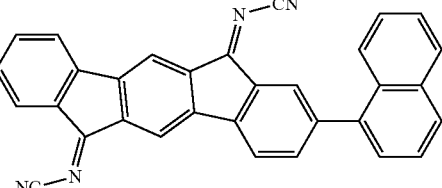
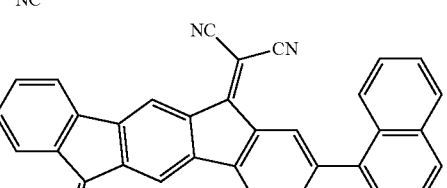
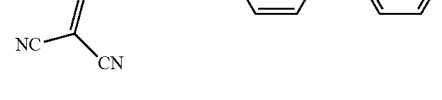

435
-continued
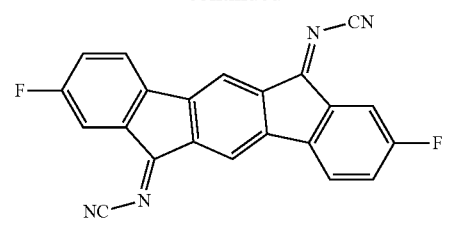
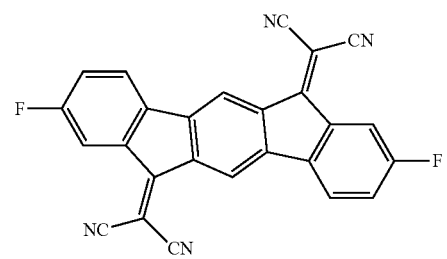
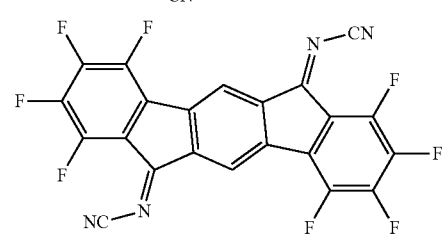
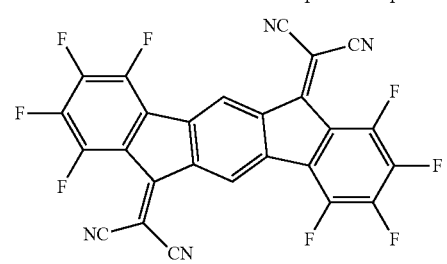
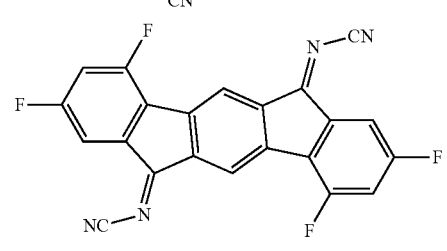
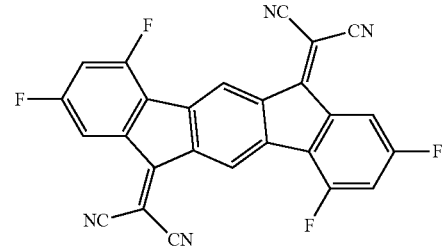
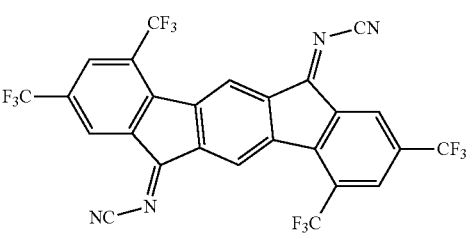
436
-continued
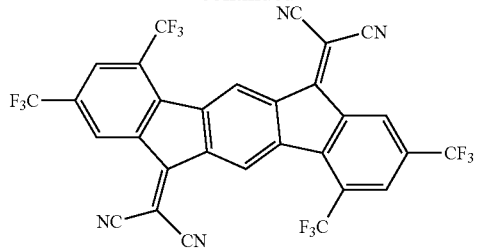
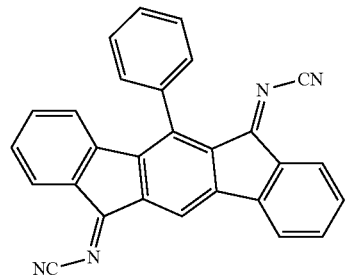
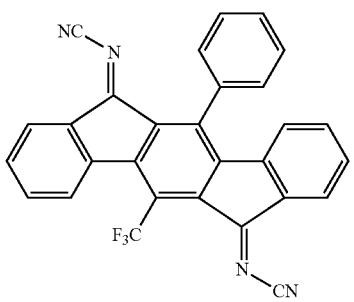
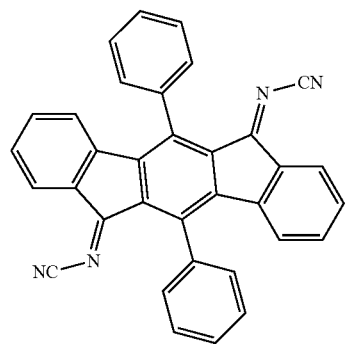
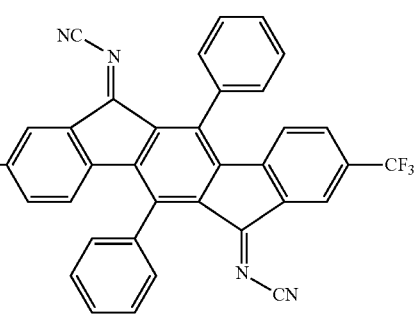

-continued
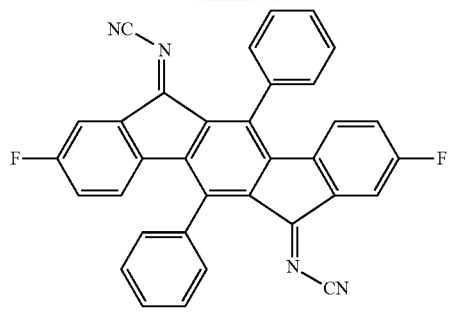
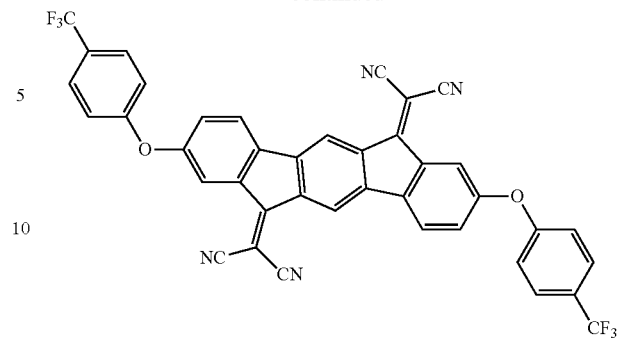
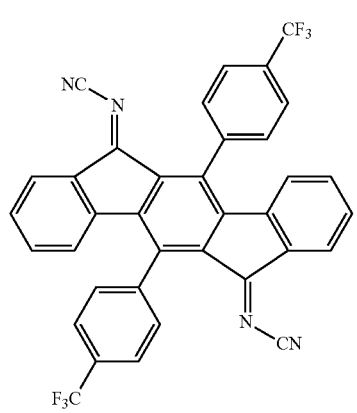
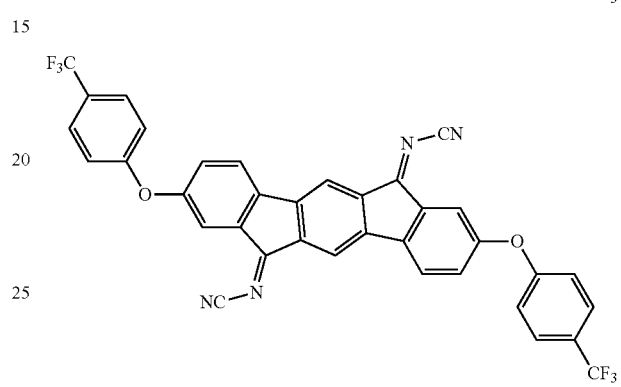
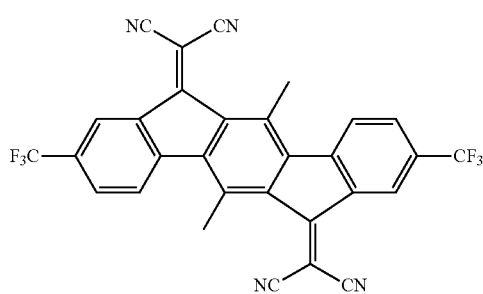
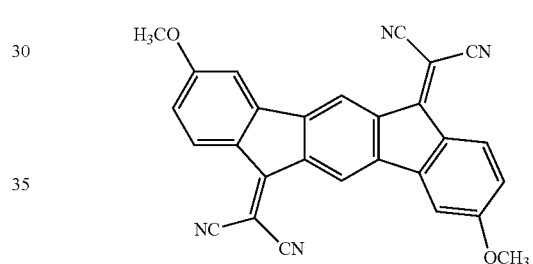
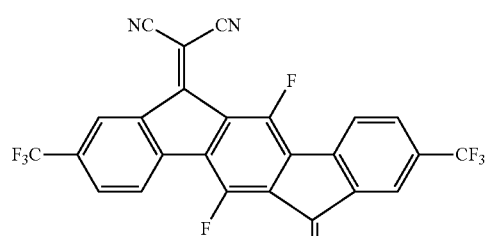
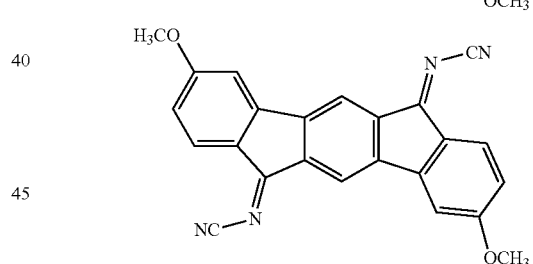
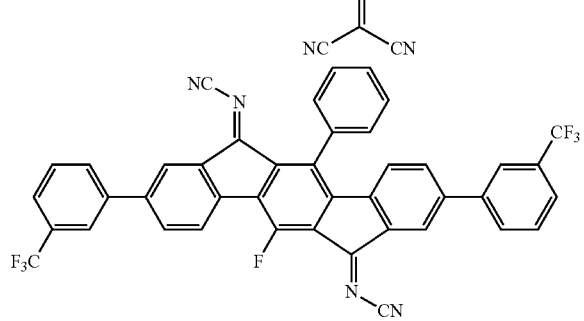
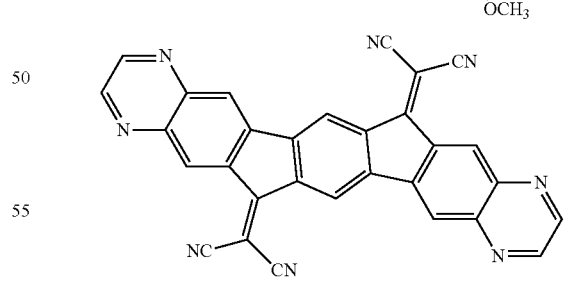
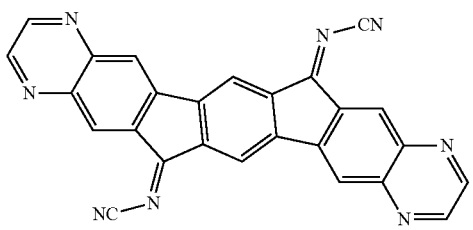

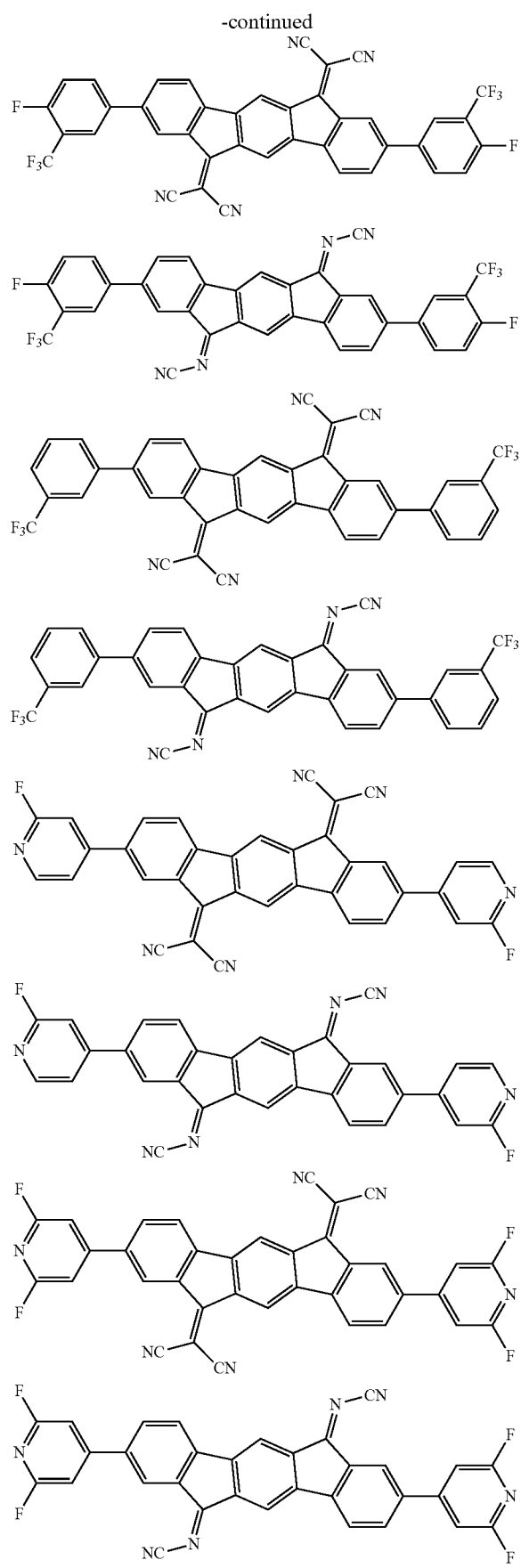

-continued
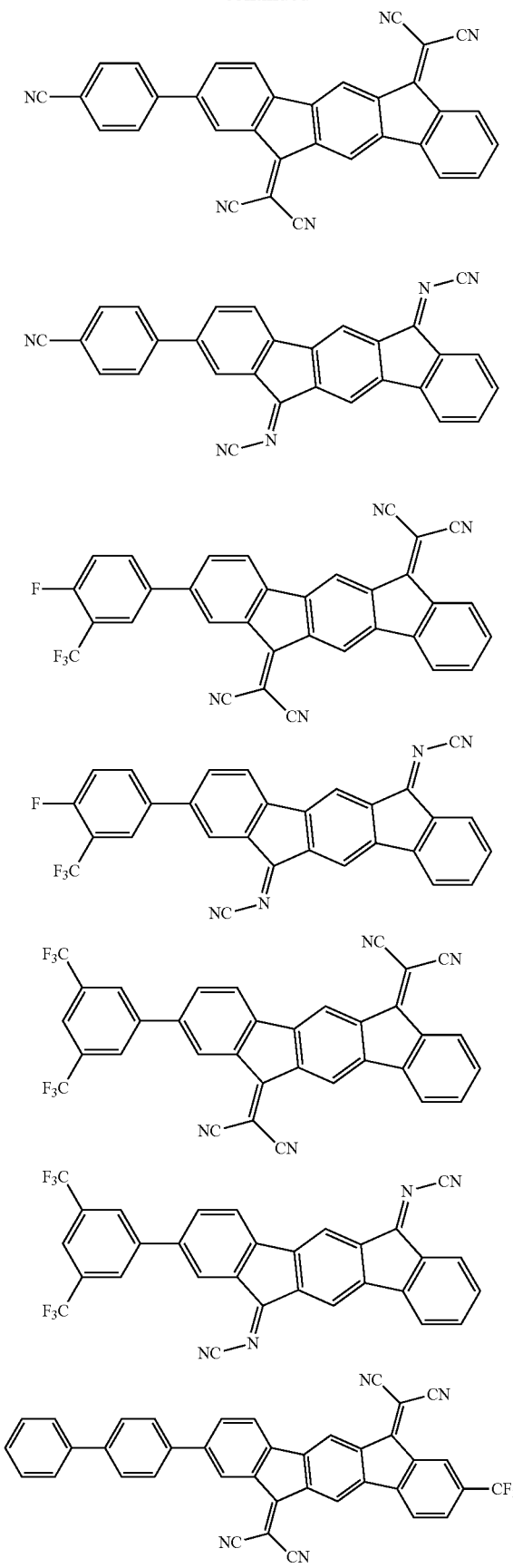
-continued
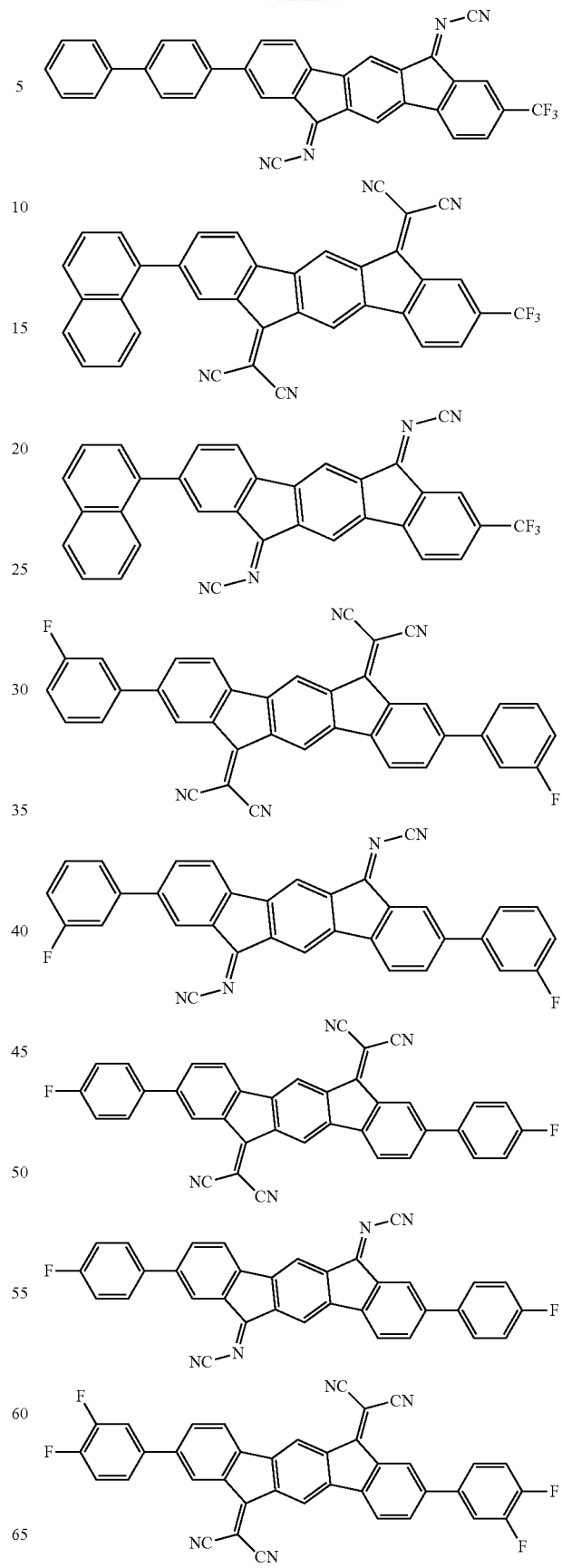

443
-continued
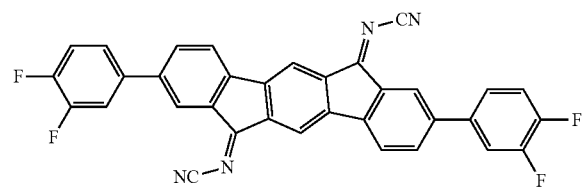
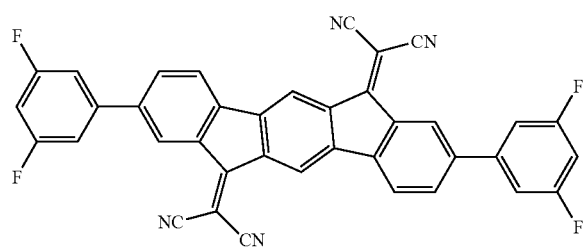
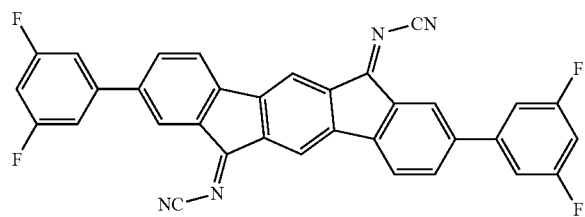
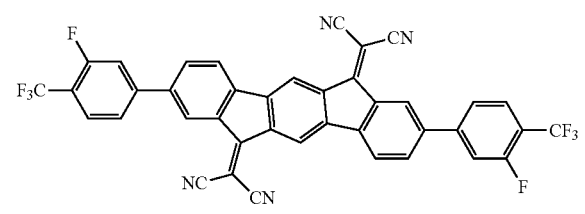
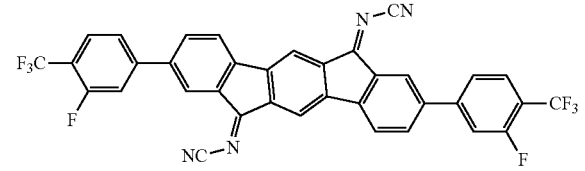
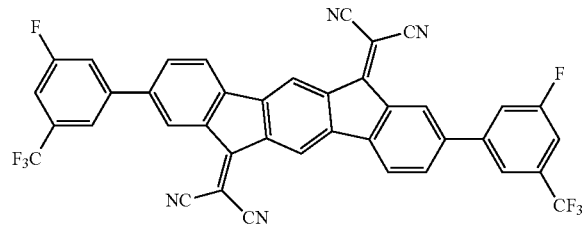
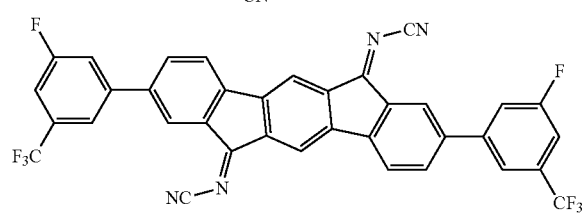
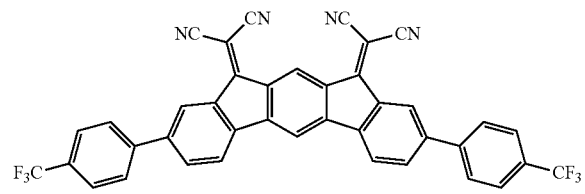
444
-continued
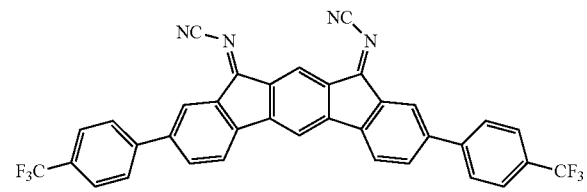
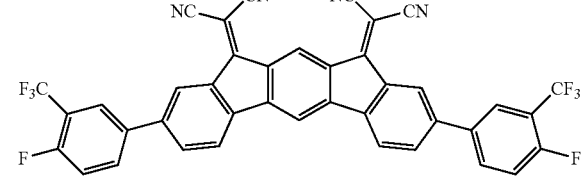
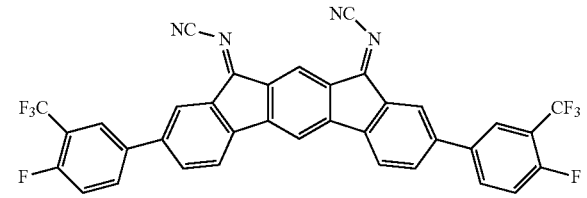
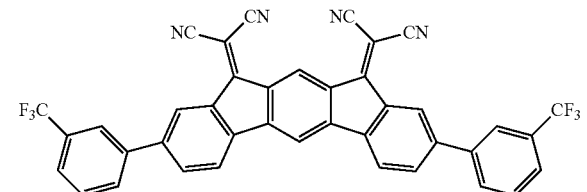
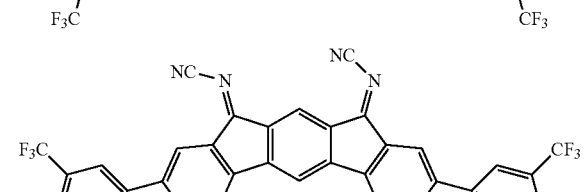
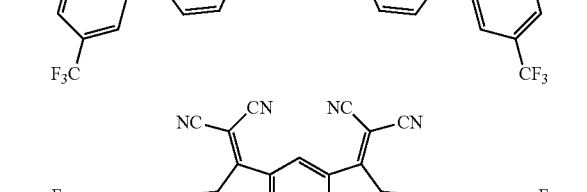
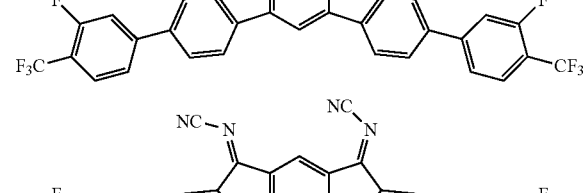
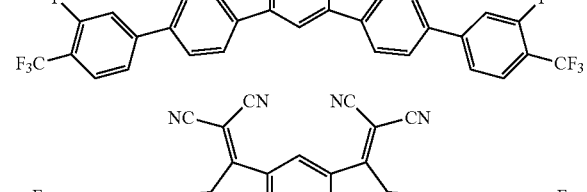
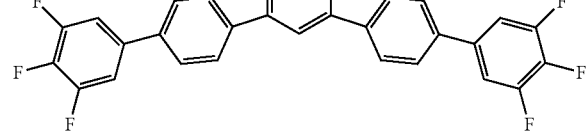

445
-continued
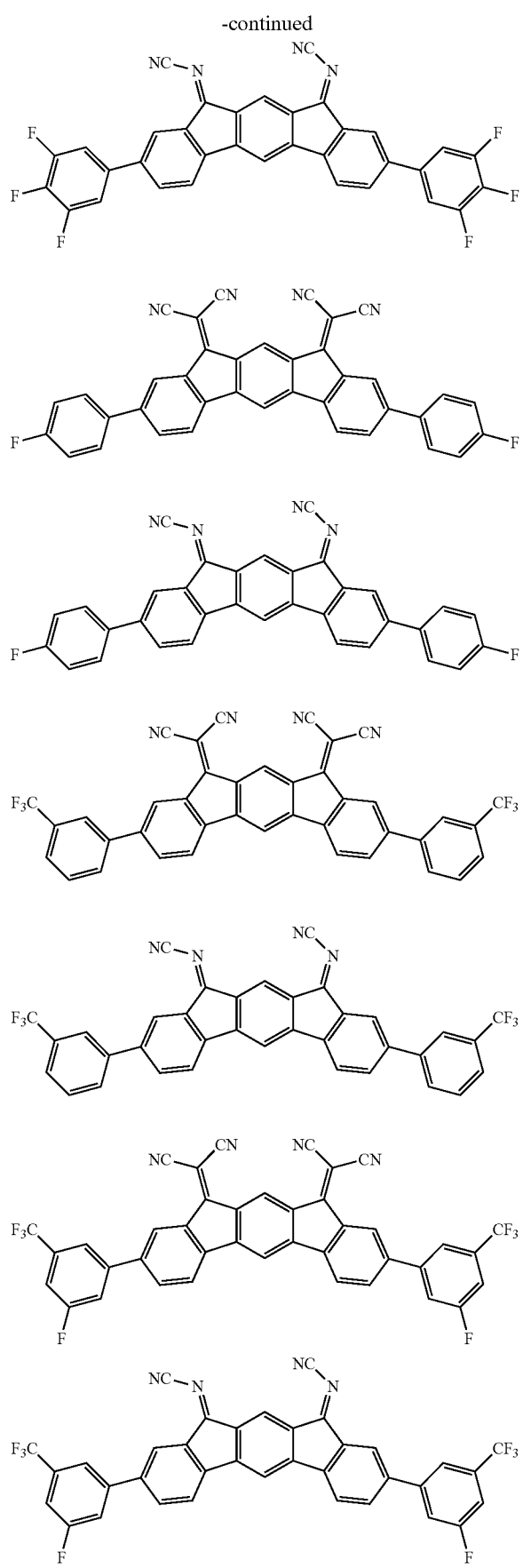
446
-continued
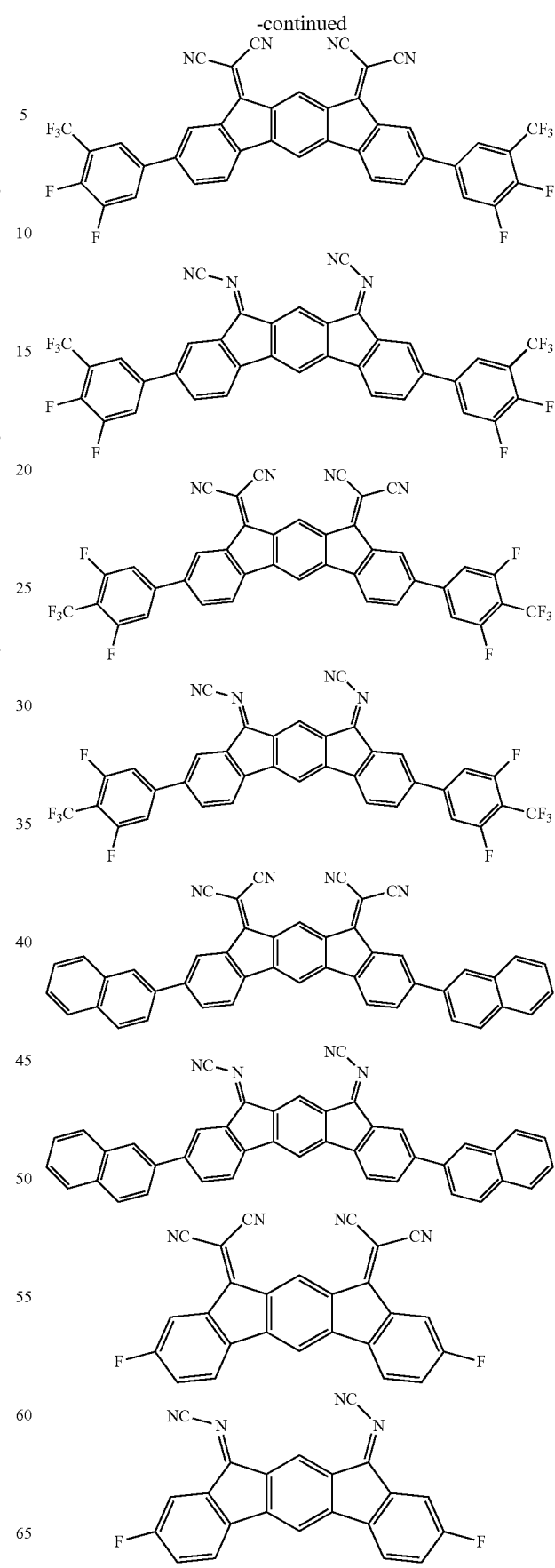

447
-continued
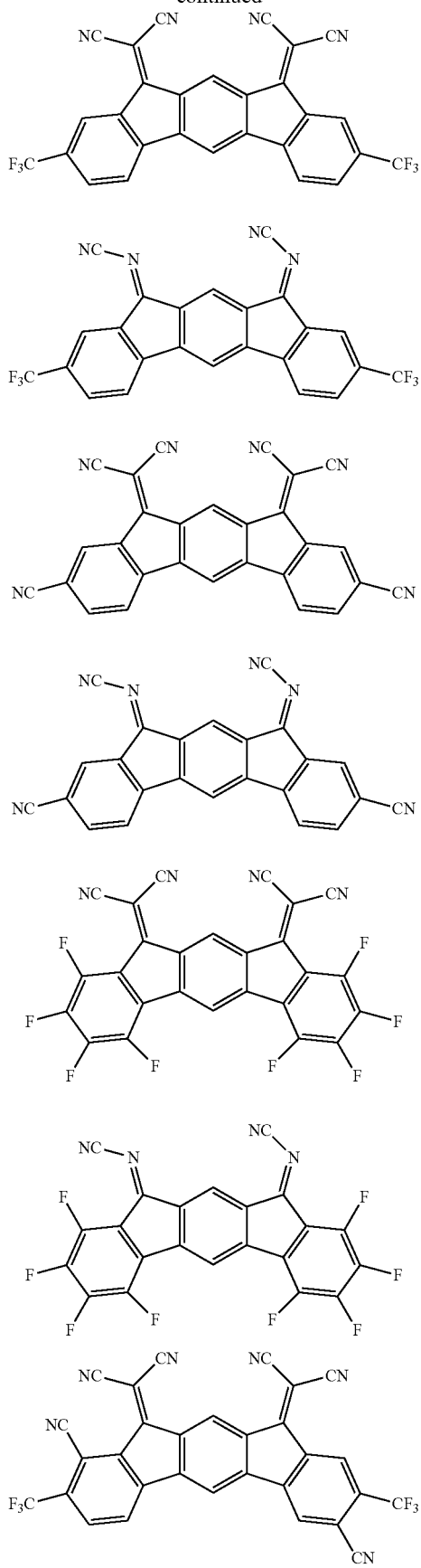
448
-continued
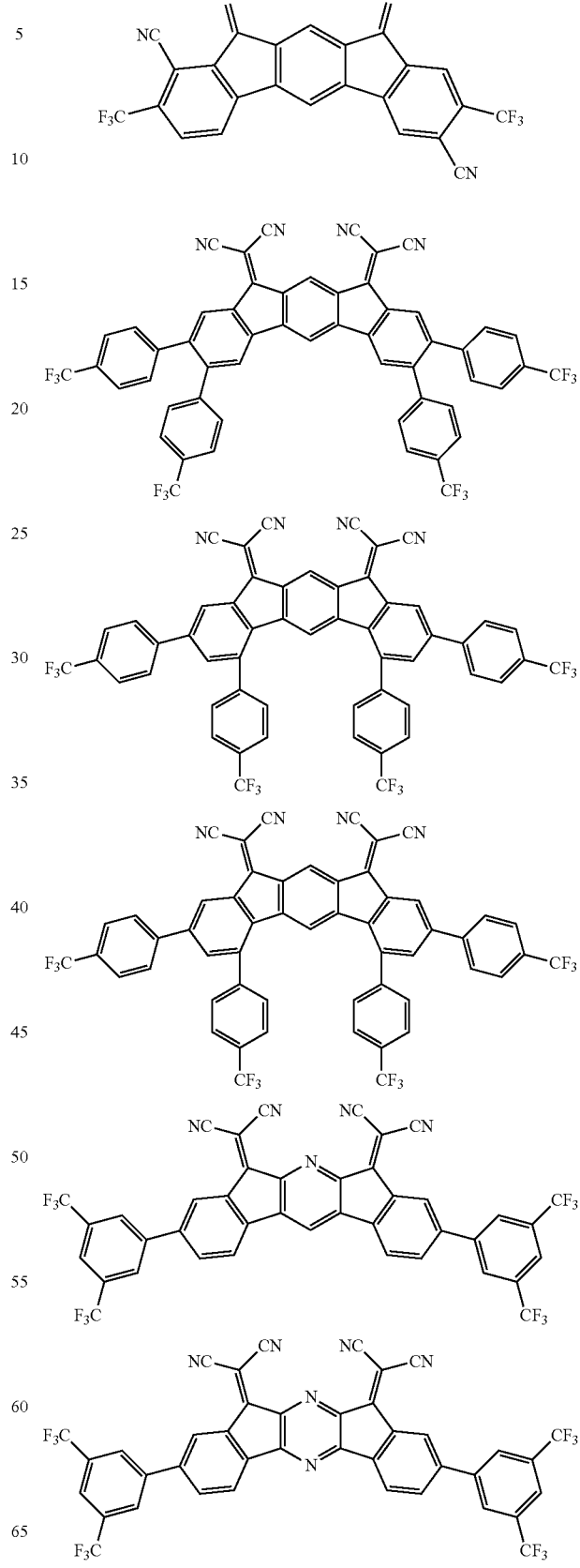

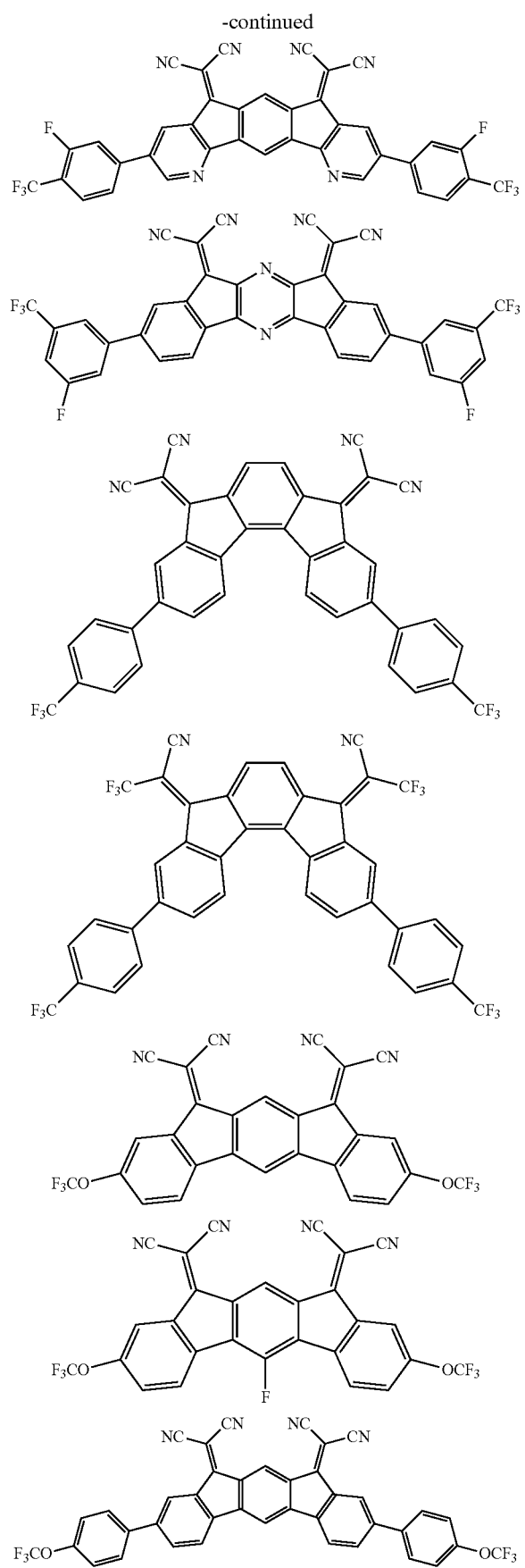
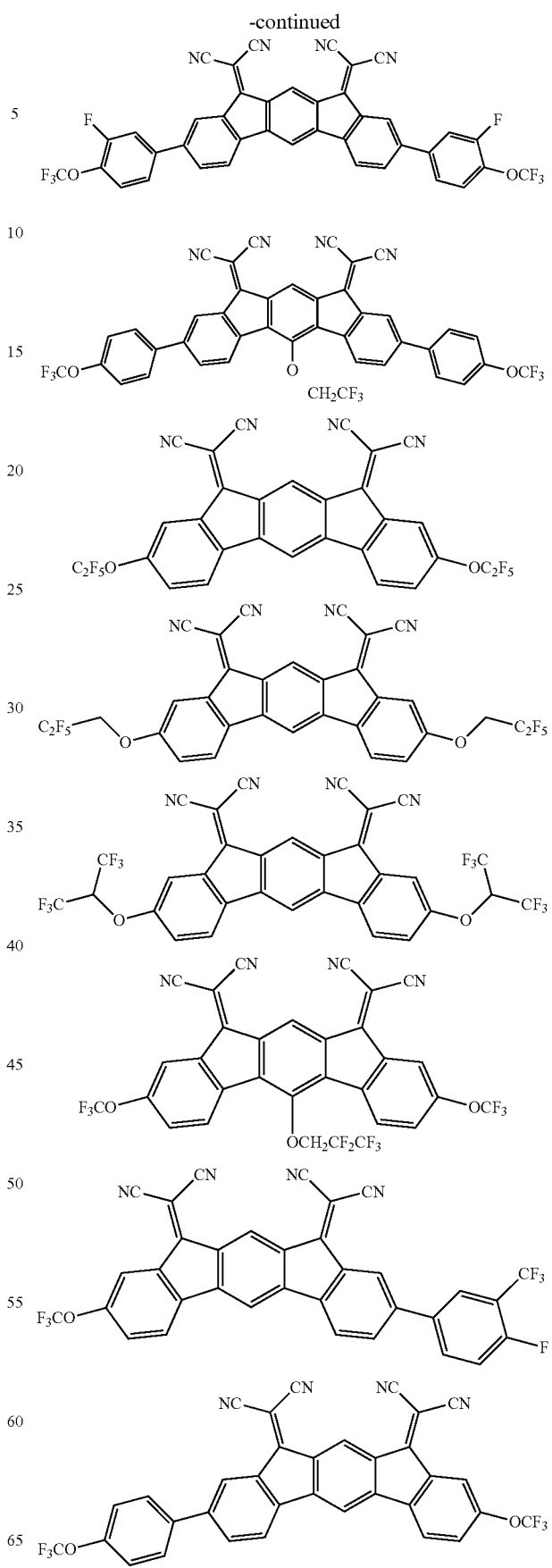

451
-continued
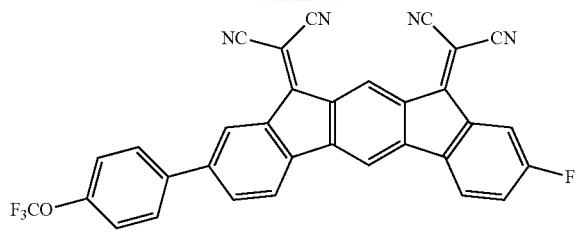
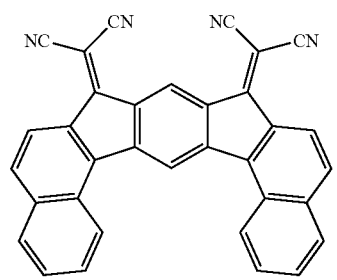
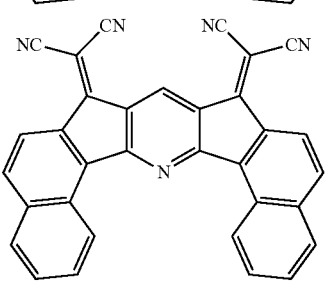
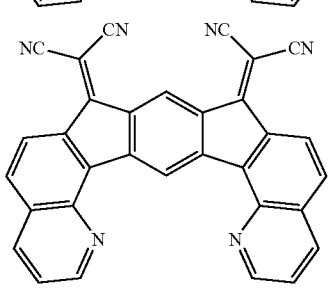
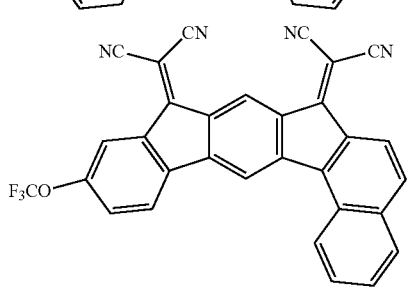
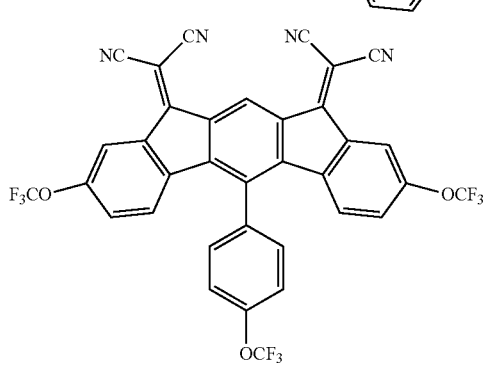
452
-continued
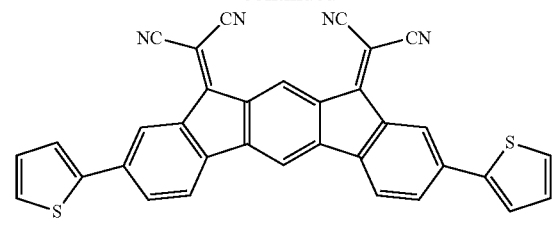
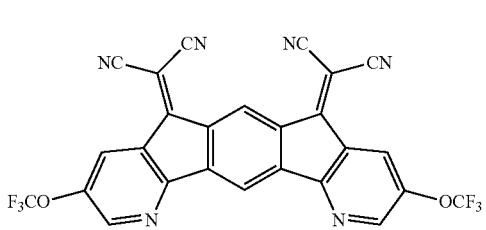
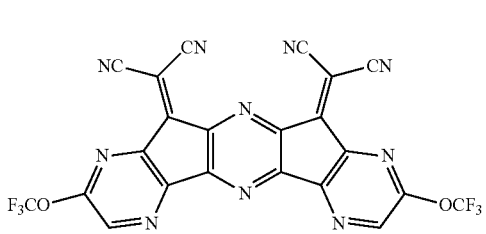
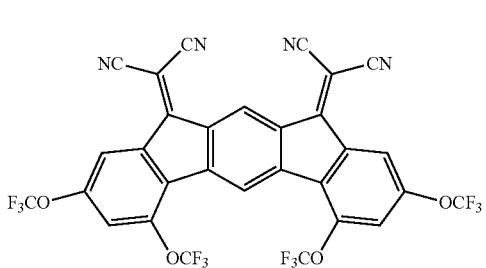
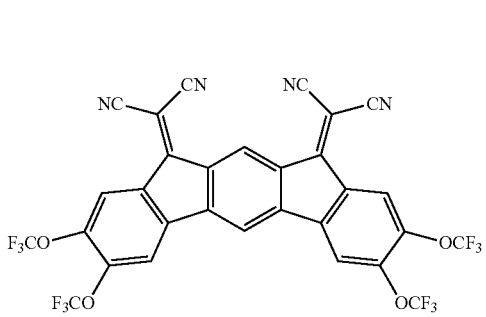
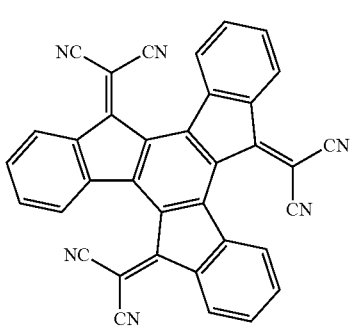

453
-continued
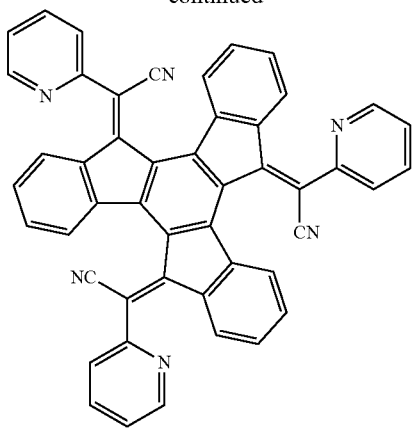
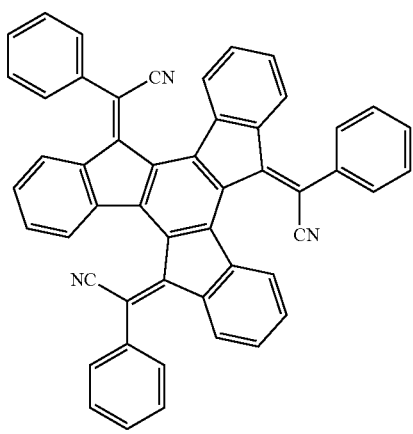
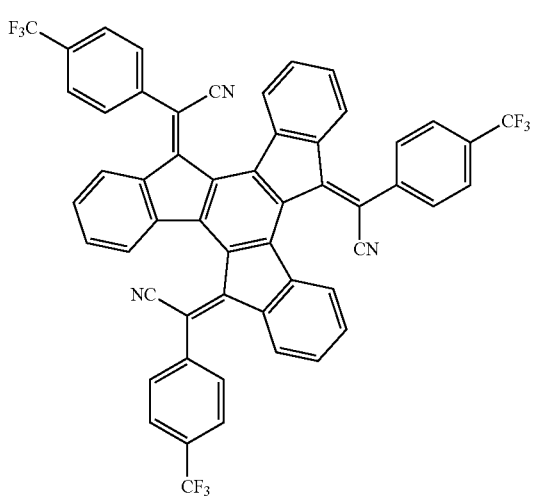
454
-continued
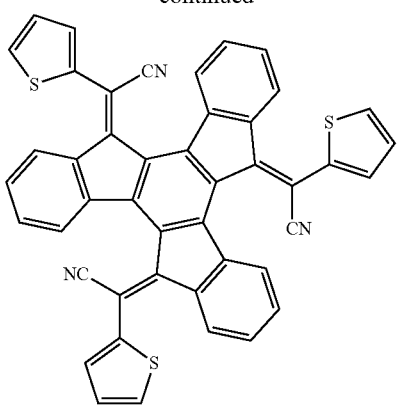
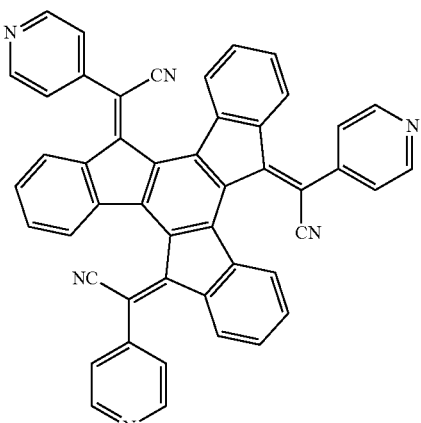
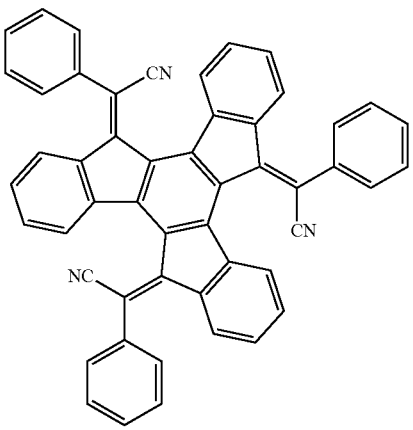
In addition, an acceptor material, such as a hexaazatriphenylene (HAT) compound represented by formula (K), is usable as the hole injecting layer material:

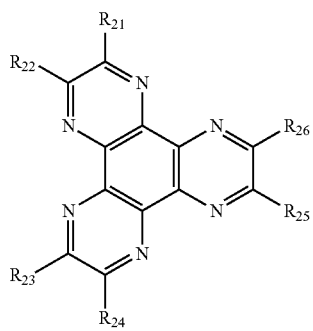

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or $R_{21}$ and $R_{22}$, $R_{23}$ and $R_{24}$, or $R_{25}$ and $R_{26}$ may be bonded to each other to form a group represented by —CO—O—CO—.

$R_{27}$ is a methyl group, an ethyl group, a n-propyl group, an isopropyl group, a n-butyl group, an isobutyl group, a t-butyl group, a cyclopentyl group, or a cyclohexyl group.

Hole Transporting Layer

The hole transporting layer comprises a highly hole transporting material (hole transporting material).

The compound of the invention is preferably used in a hole transporting layer. Examples of the hole transporting material other than the compound of the invention include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N, N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ $cm^2/Vs$ or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macro molecular compound, such as poly (N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side).

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound which emits light from a singlet excited state, and the phosphorescent emitting material is a compound which emits light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato ($FIr_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato ($Ir(CF_3ppy)_2(pic)$), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) ($Ir(ppy)_3$), bis(2-phenylpyridinato-N,C2')iridium(III) acetylacetonato ($Ir(ppy)_2(acac)$), bis(1,2-diphenyl-1H-benzimidazolato)iridium(III) acetylacetonato ($Ir(pbi)_2(acac)$), and bis (benzo[h]quinolinato)iridium(III) acetylacetonato ($Ir(bzq)_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato ($Ir(btp)_2$(acac)), bis(1-phenylisoquinolinato-N,C2')iridium(III) acetylacetonato ($Ir(piq)_2(acac)$), (acetylacetonato)bis[2,3-bis(4-fluorophenyl) quinoxalinato]iridium(III) ($Ir(Fdpq)_2$(acac)), and 2,3,7,8,12,13,17,18-octaethyl-21H,23H-porphyrin platinum(II) (PtOEP).

A rare earth metal complex, such as tris(acetylacetonato) (monophenanthroline)terbium(III) ($Tb(acac)_3(Phen)$), tris(1,3-diphenyl-1,3-propanedionato) (monophenanthroline)europium(III) ($Eu(DBM)_3(Phen)$), and tris[1-(2-thenoyl)-3,3,3-trifluoroacetonato](monophenanthroline)europium(III)

(Eu(TTA)₃(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). Various compounds may be used as the host material. The host material preferably has a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq₃), bis(10-hydroxybenzo[h]quinolinato)beryllium(II) (BeBq₂), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used in combination of two or more.

In an embodiment of the invention, an organic EL device which comprises the combination of a light emitting layer comprising an anthracene compound represented by formula (7) as a host and a hole transporting layer comprising the compound mentioned above is preferred, because the EL device performance, for example, the emission efficiency is good.

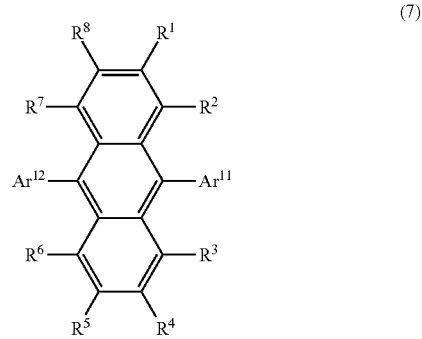

(7)

In formula (7), each of $Ar^{11}$ and $Ar^{12}$ is independently a substituted or unsubstituted aryl group having 6 to 50 ring carbon atoms or a substituted or unsubstituted heterocyclic group having 5 to 50 ring atoms. Each of $R^1$ to $R^8$ is independently selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxy group, a halogen atom, a cyano group, a nitro group, and a hydroxyl group.

The anthracene compound is preferably any of the anthracene compounds (A), (B), and (C), which are selected according to the structure of organic EL device and the required properties.

Anthracene Compound (A)

The anthracene compound (A) is a compound, wherein each of $Ar^{11}$ and $Ar^{12}$ of formula (7) is independently a substituted or unsubstituted fused aryl group having 10 to 50 ring carbon atoms. The anthracene compound (A) is classified into a compound wherein $Ar^{11}$ and $Ar^{12}$ are the same fused aryl group optionally having a substituent and a compound wherein $Ar^{11}$ and $Ar^{12}$ are different fused aryl groups each optionally having a substituent.

Examples thereof include an anthracene compound represented by any of formulae (7-1) to (7-3) and an anthracene derivative wherein $Ar^{11}$ and $Ar^{12}$ of formula (7) are different fused aryl groups each optionally having a substituent.

In the anthracene compound represented by formula (7-1), each of $Ar^{11}$ and $Ar^{12}$ is a 9-phenanthrenyl group optionally having a substituent:

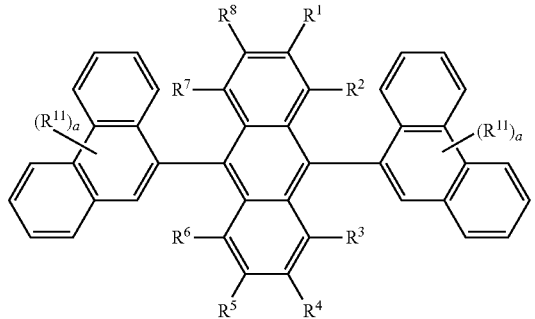

(7-1)

wherein,

R¹ to R⁸ are as defined above;

R¹¹ is selected from a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxy group, a halogen atom, a cyano group, a nitro group, and a hydroxyl group;

a is an integer of 0 to 9; and when a is an integer of 2 or more, R¹¹'s may be the same or different as long as two phenanthrenyl groups each optionally having a substituent are the same.

In the anthracene compound represented by formula (7-2), each of Ar¹¹ and Ar¹² of formula (7) is a 2-naphthyl group optionally having a substituent:

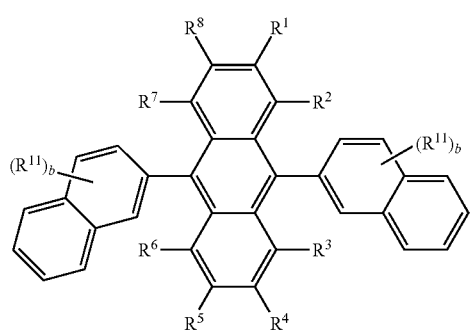

(7-2)

wherein,

R¹ to R⁸ and R¹¹ are as defined above;

b is an integer of 1 to 7; and when b is an integer of 2 or more, R¹¹'s may be the same or different as long as two 2-naphthyl groups each optionally having a substituent are the same.

In the anthracene compound represented by formula (7-3), each of Ar¹¹ and Ar¹² of formula (7) is a 1-naphthyl group optionally having a substituent:

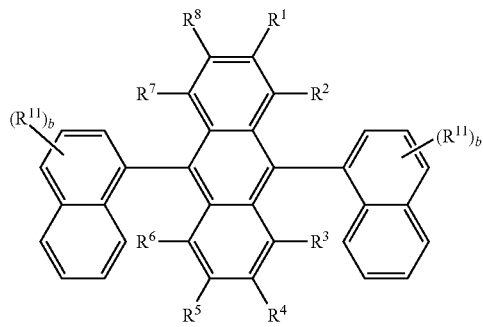

(7-3)

wherein,

R¹ to R⁸, R¹¹, and b are as defined above, and when b is an integer of 2 or more, R¹¹'s may be the same or different as long as two 1-naphthyl groups each optionally having a substituent are the same.

In the anthracene compound wherein Ar¹¹ and Ar¹² of formula (7) are different fused aryl groups each optionally having a substituent, each of Ar¹¹ and Ar¹² is preferably any of a substituted or unsubstituted 9-phenanthrenyl group, a substituted or unsubstituted 1-naphthyl group, and a substituted or unsubstituted 2-naphthyl group.

For example, Ar¹¹ is a 1-naphthyl group and Ar¹² is a 2-naphthyl group; Ar¹¹ is a 1-naphthyl group and Ar¹² is a 9-phenanthryl group; or Ar¹¹ is a 2-naphthyl group and Ar¹² is a 9-phenanthryl group.

Anthracene Compound (B)

The anthracene compound (B) is a compound, wherein one of Ar¹¹ and Ar¹² of formula (7) is a substituted or unsubstituted phenyl group and the other is a substituted or unsubstituted fused aryl group having 10 to 50 ring carbon atoms. Examples thereof include an anthracene compound represented by formula (7-4) or (7-5).

In the anthracene compound represented by formula (7-4), Ar¹¹ of formula (7) is a substituted or unsubstituted 1-naphthyl group and Ar¹² is a substituted or unsubstituted phenyl group:

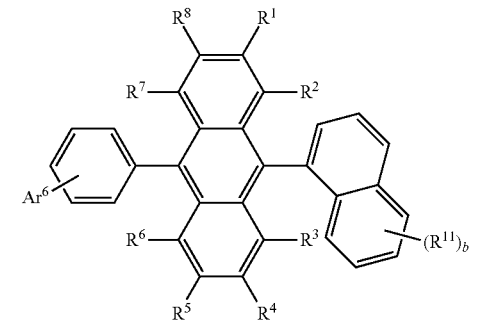

(7-4)

wherein,

R¹ to R⁸, R¹¹, and b are as defined above;

Ar⁶ is a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 ring carbon atoms, a substituted or unsubstituted aralkyl group having 7 to 50 carbon atoms, a substituted or unsubstituted heterocyclic group having 5 to 50 ring atoms, a 9,9-dimethylfluorene-1-yl group, a 9,9-dimethylfluorene-2-yl group, a 9,9-dimethylfluorene-3-yl group, a 9,9-dimethylfluorene-4-yl group, a dibenzofuran-1-yl group, a dibenzofuran-2-yl group, a dibenzofuran-3-yl group, or a dibenzofuran-4-yl group;

alternatively, $Ar^6$ may form a ring, such as a substituted or unsubstituted fluorenyl group and a substituted or unsubstituted dibenzofuranyl group, together with the benzene ring to which $Ar^6$ is bonded; and when b is an integer of two or more, $R^{11}$'s may be the same or different.

In the anthracene compound represented by formula (7-5), $Ar^{11}$ of formula (7) is a substituted or unsubstituted 2-naphthyl group and $Ar^{12}$ is a substituted or unsubstituted phenyl group:

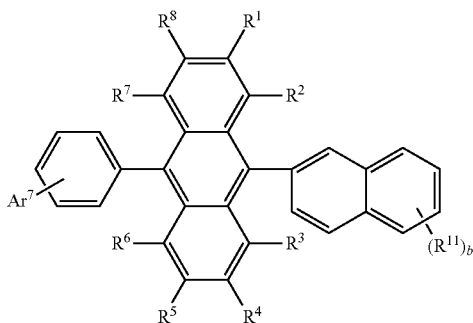

(7-5)

wherein, $R^1$ to $R^8$, $R^{11}$, b are as defined above;

$Ar^7$ is a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 ring carbon atoms, a substituted or unsubstituted aralkyl group having 7 to 50 carbon atoms, a dibenzofuran-1-yl group, a dibenzofuran-2-yl group, a dibenzofuran-3-yl group, or a dibenzofuran-4-yl group;

alternatively, $Ar^7$ may form a ring, such as a substituted or unsubstituted fluorenyl group and a substituted or unsubstituted dibenzofuranyl group, together with the benzene ring to which $Ar^7$ is bonded; and when b is an integer of two or more, $R^{11}$'s may be the same or different.

Anthracene Compound (C)

The anthracene compound (C) is represented by formula (7-6) and preferably represented by any of formulae (7-6-1), (7-6-2), and (7-6-3):

wherein, $R^1$ to $R^8$, and $Ar^6$ are as defined above;

$Ar^5$ is a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 ring carbon atoms, a substituted or unsubstituted aralkyl group having 7 to 50 carbon atoms, or a substituted or unsubstituted heterocyclic group having 5 to 50 ring atoms; and $Ar^5$ and $Ar^6$ are selected independently;

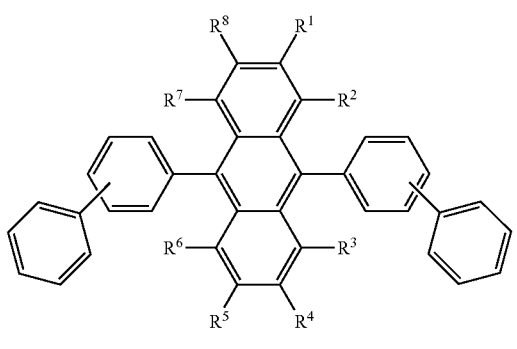

wherein $R^1$ to $R^8$ are as defined above;

wherein, $R^1$ to $R^8$ are as defined above; and $Ar^8$ is a substituted or unsubstituted fused aryl group having 10 to 20 ring carbon atoms;

wherein, $R^1$ to $R^8$ are as defined in formula (7); and each of $Ar^{5a}$ and $Ar^{6a}$ is independently a substituted or unsubstituted fused aryl group having 10 to 20 ring carbon atoms.

The groups referred to by the symbols in formulae (7), (7-1) to (7-6), and (7-6-1) to (7-6-3) are described below.

Examples of the substituted or unsubstituted aryl group having 6 to 50 ring carbon atoms for $R^1$ to $R^8$, $R^{11}$, $Ar^5$ to $Ar^7$, $Ar^{11}$, and $Ar^{12}$ include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 6-chrysenyl group, a 1-benzo[c]phenanthryl group, a 2-benzo[c]phenanthryl group, a 3-benzo[c]phenanthryl group, a 4-benzo[c]phenanthryl group, a 5-benzo[c]phenanthryl group, a 6-benzo[c]phenanthryl group, a 1-benzo[g]chrysenyl group, a 2-benzo[g]chrysenyl group, a 3-benzo[g]chrysenyl group, a 4-benzo[g]chrysenyl group, a 5-benzo[g]chrysenyl group, a 6-benzo[g]chrysenyl group, a 7-benzo[g]chrysenyl group, a 8-benzo[g]chrysenyl group, a 9-benzo[g]chrysenyl group, a 10-benzo[g]chrysenyl group, a 11-benzo[g]chrysenyl group, a 12-benzo[g]chrysenyl group, a 13-benzo[g]chrysenyl group, a 14-benzo[g]chrysenyl group, a 1-triphenyl group, a 2-triphenyl group, a 2-fluorenyl group, a 9,9-dimethylfluorene-2-yl group, a 9,9-diphenylfluorene-2-yl group, a benzofluorenyl group, a dibenzofluorenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-a 2-naphthyl group, a 4-methyl-a 1-naphthyl group, a 4-methyl-1-anthryl group, a 4'-methylbiphenylyl group, and a 4"-t-butyl-p-terphenyl-4-yl group. Preferred are an unsubstituted phenyl group, a substituted phenyl group, a substituted or unsubstituted aryl group having 10 to 14 ring carbon atoms (for example, a 1-naphthyl group, a 2-naphthyl group, and a 9-phenanthryl group), a substituted or unsubstituted fluorenyl group (a 2-fluorenyl group), and a substituted or unsubstituted pyrenyl group (a 1-pyrenyl group, a 2-pyrenyl group, a 4-pyrenyl group).

Examples of the substituted or unsubstituted fused aryl group having 10 to 20 ring carbon atoms for $Ar^{5a}$, $Ar^{8a}$, and $Ar^8$ include a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, and a 2-fluorenyl group. Particularly preferred are a 1-naphthyl group, a 2-naphthyl group, a 9-phenanthryl group, and a fluorenyl group (a 2-fluorenyl group).

Examples of the substituted or unsubstituted heterocyclic group having 5 to 50 ring atoms for $R^1$ to $R^8$, $R^{11}$, $Ar^5$ to $Ar^7$, $Ar^{11}$, and $Ar^{12}$ include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 1-dibenzofuranyl group, a 2-dibenzofuranyl group, a 3-dibenzofuranyl group, a 4-dibenzofuranyl group, a benzonaphthofuranyl group, a 1-dibenzothiophenyl group, a 2-dibenzothiophenyl group, a 3-dibenzothiophenyl group, a 4-dibenzothiophenyl group, a benzonaphthothiophenyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a benzocarbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group. Preferred are a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-carbazolyl group, a 2-carbazolyl group, a 3-carbazolyl group, a 4-carbazolyl group, a 9-carbazolyl group, a benzonaphthofuranyl group, a benzonaphthothiophenyl group, and a benzocarbazolyl group.

Examples of the substituted or unsubstituted alkyl group having 1 to 50 carbon atoms for $R^1$ to $R^8$, $R^{11}$, and $Ar^5$ to $Ar^7$ include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group. Preferred are a methyl group, an ethyl group, a propyl group, an isopropyl group, a n-butyl group, a s-butyl group, an isobutyl group, and a t-butyl group.

Examples of the substituted or unsubstituted cycloalkyl group having 3 to 50 ring carbon atoms for $R^1$ to $R^8$, $R^{11}$, and $Ar^5$ to $Ar^7$ include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group, with a cyclopentyl group and a cyclohexyl group being preferred.

The substituted or unsubstituted alkoxy group having 1 to 50 carbon atoms for $R^1$ to $R^8$ and $R^{11}$ is represented by —OZ, wherein Z is selected from the substituted or unsubstituted alkyl group having 1 to 50 carbon atoms described above with respect to $R^1$ to $R^8$.

Examples of the substituted or unsubstituted aralkyl group having 7 to 50 carbon atoms (the aryl portion has 6 to 49 carbon atoms and the alkyl portion has 1 to 44 carbon atoms) for $R^1$ to $R^8$, $R^{11}$, and $Ar^5$ to $Ar^7$ include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, a 1-hydroxy-2-phenylisopropyl group, and a 1-chloro-2-phenylisopropyl group.

The substituted or unsubstituted aryloxy group or arylthio group each having 6 to 50 ring carbon atoms for $R^1$ to $R^8$ and $R^{11}$ are respectively represented by —OY and —SY, wherein Y is selected from the substituted or unsubstituted aryl group having 6 to 50 ring carbon atoms mentioned above with respect to $R^1$ to $R^8$.

The substituted or unsubstituted alkoxycarbonyl group having 2 to 50 carbon atoms (the alkyl portion has 1 to 49 carbon atoms) for $R^1$ to $R^8$ and $R^{11}$ is represented by —COOZ, wherein Z is selected from the substituted or unsubstituted alkyl group having 1 to 50 carbon atoms mentioned above with respect to $R^1$ to $R^8$.

Examples of the substituted silyl group, for $R^1$ to $R^8$ and $R^{11}$ include a trimethylsilyl group, a triethylsilyl group, a t-butyldimethylsilyl group, a vinyldimethylsilyl group, a propyldimethylsilyl group, and a triphenylsilyl group.

The halogen atom for $R^1$ to $R^8$ and $R^{11}$ include a fluorine atom, a chlorine atom, a bromine atom, and an iodine atom.

Electron Transporting Layer

The electron transporting layer comprises a highly electron-transporting material (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative;
(3) a macro molecular compound; and
(4) an alkali metal, an alkaline earth metal, a rare earth metal, and compounds of these metals.

Examples of the metal complex include tris(8-quinolinolato)aluminum (III) (Alq), tris(4-methyl-8-quinolinolato) aluminum ($Almq_3$), bis(10-hydroxybenzo[h]quinolinato)beryllium ($BeBq_2$), bis(2-methyl-8-quinolinato)(4-phenylphenolato)aluminum (III) (BAlq), bis(8-quinolinato) zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macro molecular compound include poly[(9,9-dihexylfluorene-2,7-diyl)-co-(pyridine-3,5-diyl)]

(PF-Py), and poly[(9,9-dioctylfluorene-2,7-diyl)-co-(2,2'-bipyridine-6,6'-diyl)] (PF-BPy).

The electron transporting layer may comprise at least one selected from an alkali metal, an alkaline earth metal, a rare earth metal, and compounds of these metals, because the electron transporting properties are further improved.

Examples of the alkali metal include Li, Na, K, and Cs; examples of the alkaline earth metal include Mg, Ca, Sr, and Ba; and examples of the rare earth metal include Yb, Eu, and Ce.

Examples of the compounds of these metals include an oxide, a halide, such as a fluoride, a chloride, and a bromide, and an organic complex.

The above compounds have an electron mobility of $10^{-6}$ cm$^2$/Vs or more. Materials other than those mentioned above are also usable in the electron transporting layer if their electron transporting ability is higher than their hole transporting ability.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The first electron transporting layer of the organic EL device of the invention works as a hole blocking layer. The triplet blocking layer prevents the diffusion of excitons generated in the light emitting layer to adjacent layers and has a function of confining the excitons in the light emitting layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage to reduce the efficiency.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples. It should be noted that the scope of the invention is not limited to the following examples.

Synthesis of Intermediates A to F

Synthesis of Intermediate a

Under nitrogen atmosphere, a mixture of carbazole (1.7 g), 1-bromo-2-iodobenzene (1.5 ml), potassium carbonate (2.8 g), copper iodide (95 mg), and xylene (25 ml) was refluxed. After cooling to ordinary temperature, the reaction product was extracted with ethyl acetate. The extract was dried over anhydrous magnesium sulfate, and then, the solvent was removed under reduced pressure. The residue was passed through a silica gel column by using a hexane solvent, and then, the solvent was removed under reduced pressure. The obtained residue was vacuum-dried to obtain the intermediate a as a white solid (800 mg, 25% yield).

MS: [M+H]$^+$=323

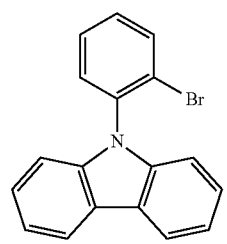

Intermediate a

Synthesis of Intermediate A

Into a solution of the intermediate a (4.19) in purified THF (50 ml), a 2.5 M hexane solution of n-butyllithium (4.8 ml) was added dropwise gradually at −78° C. After stirring at the same temperature for 45 min, 2-bromo-9-fluorenone (2.59 g) was added. After stirring at the same temperature for one hour and further stirring at ordinary temperature for 2 h, the reaction was terminated by adding an aqueous solution of ammonium chloride. After extracting the organic substances with ethyl ether, the extract was dried over anhydrous magnesium sulfate, and then the ethyl ether was removed to obtain a yellow solid. After dispersing the obtained solid in ethanol, the dispersion was stirred. The solid collected by filtration was vacuum-dried to obtain 4.5 g of an intermediate, which was then dispersed in 40 ml of acetic acid. After adding 12 drops of concentrated sulfuric acid, the dispersion was refluxed for 3 h and then cooled to ordinary temperature. The precipitated solid was collected by filtration, washed with ethanol, and vacuum-dried to obtain the intermediate A (3.98 g, 82% yield).

MS: [M+H]$^+$=484

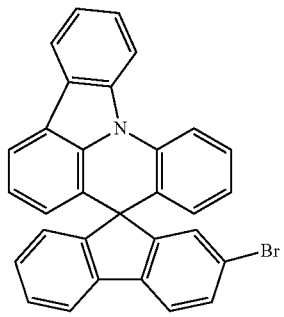

Intermediate A

Synthesis of Intermediate B

A solution of the intermediate a (6.96 g) in purified THF (300 ml) was cooled to −78° C. A 2.5 M hexane solution of n-butyllithium (8.64 ml) was gradually added dropwise. After stirring at the same temperature for 30 min, 4-bromo-9-fluorenone (6.08 g) was added. After stirring at the same temperature for 40 min and further stirring at ordinary temperature for 3 h, the reaction was terminated by adding an aqueous solution of ammonium chloride. After extracting the organic substances with ethyl ether, the extract was dried over anhydrous magnesium sulfate, and then the ethyl ether was removed. The obtained solid was dispersed in ethanol and the dispersion was stirred for one day. The solid collected by filtration was vacuum-dried to obtain an intermediate (10.12 g, 97% yield), which was then dispersed in 10 ml of acetic acid. After adding 10 drops of concentrated sulfuric acid, the dispersion was refluxed for 4 h. The precipitated solid was collected by filtration, washed with ethanol, and vacuum-dried to obtain the intermediate B (9.49 g, 97% yield).

MS: [M+H]$^+$=563

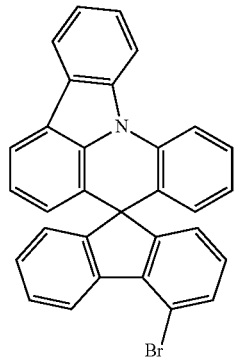

Intermediate B

Synthesis of Intermediate C

The intermediate C was synthesized according to the following synthesis rote.

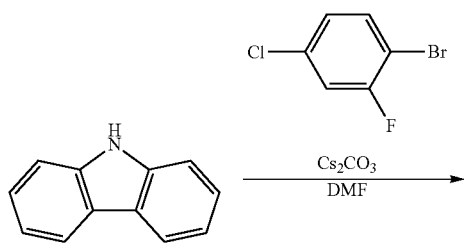

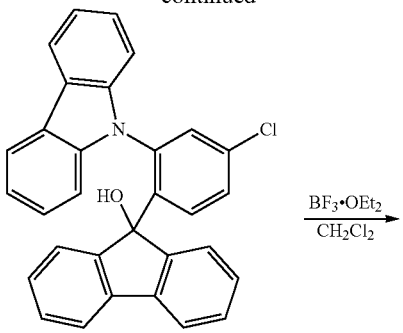

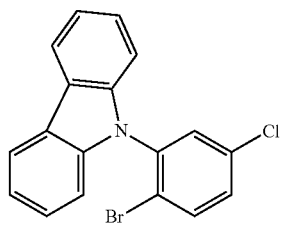

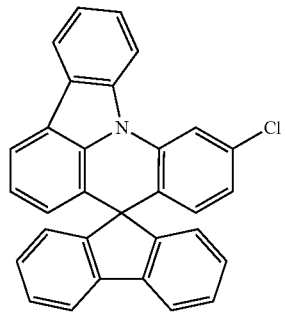

First Step

Under argon atmosphere, a mixture of 9H-carbazole (9.3 g), 1-bromo-4-chloro-2-fluorobenzene (23.3 g), cesium carbonate (36.2 g), and DMF (222 mL) was stirred at 150° C. for 7 h. After adding water at room temperature, the resultant mixture was extracted with ethyl acetate. The organic layer was purified by silica gel column chromatography to obtain 9-(2-bromo-5-chlorophenyl)carbazole as a white solid (11.4 g, 58% yield).

Second and Third Steps

Under argon atmosphere, into a mixture of 9-(2-bromo-5-chlorophenyl)carbazole (11.3 g) and THF (106 mL), a 1.6 M hexane solution of n-butyllithium (25.1 mL) was added dropwise at −78° C. After adding dropwise a solution of fluorenone (6.85 g) in THF (106 mL) at constant temperature, the mixture was stirred for 5 h while raising the temperature gradually. A saturated aqueous solution of ammonium was added dropwise under cooling with ice, and then, the mixture was extracted with ethyl acetate. The obtained organic layer was concentrated to obtain an orange yellow solid, which was used in the next reaction without purification.

In a flask, the obtained orange yellow solid (15.8 g) was dissolved in dichloromethane (463 mL) under heating. After adding boron fluoride ethyl ether complex (3.9 mL) dropwise under cooling with ice, the mixture was stirred at constant temperature for 4 h. The organic layer was extracted and the obtained residue was purified by silica gel column chromatography to obtain a white solid, which was recrystallized from ethyl acetate to obtain the intermediate C (4.9 g, 36% yield (second and third steps)).

Synthesis of Intermediate D

The intermediate D was synthesized according to the following scheme.

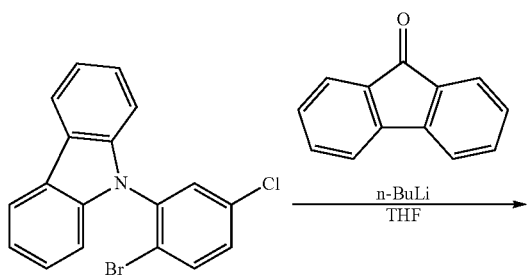

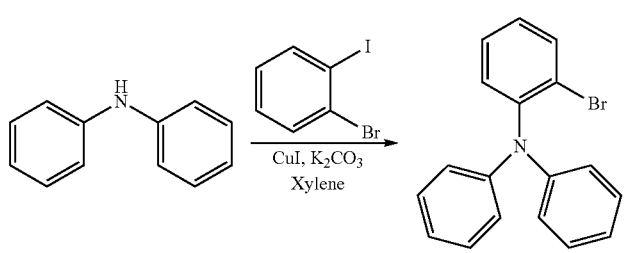

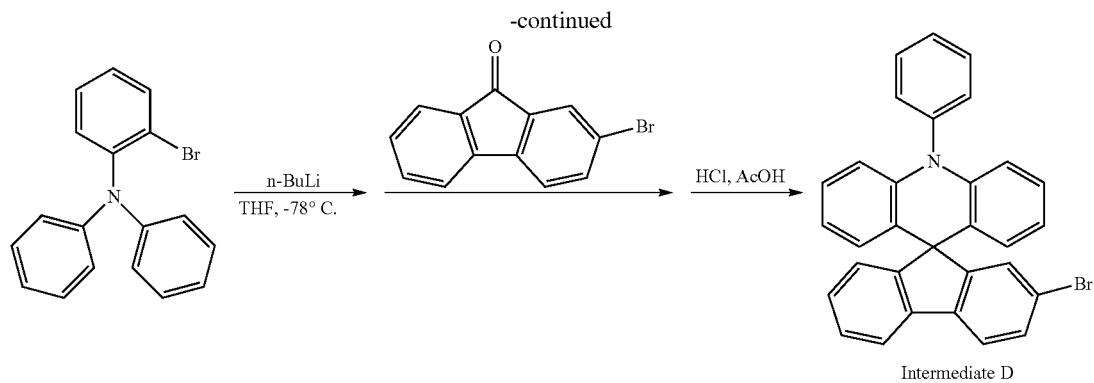

Intermediate D

Synthesis of Intermediate E

The intermediate E was synthesized in the same manner as in the synthesis of the intermediate D except for using 4-bromo-9-fluorenone in place of 2-bromo-9-fluorenone.

Intermediate E

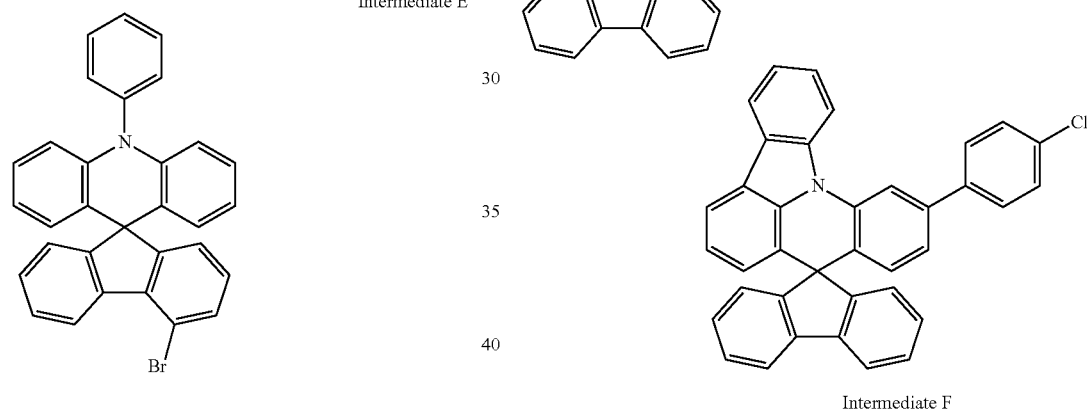

Intermediate F

Synthesis of Intermediate F

The intermediate F was synthesized by using the intermediate C obtained above.

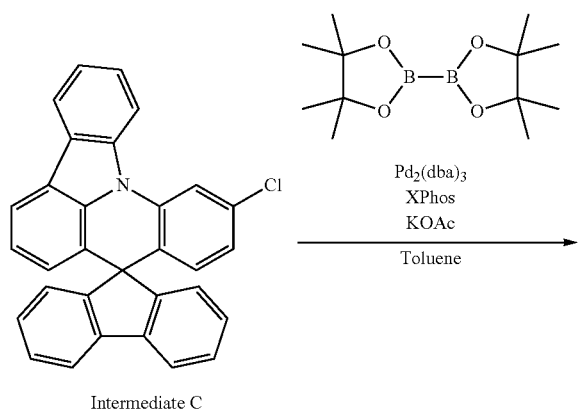

Intermediate C

Under argon atmosphere, a mixture of the intermediate C (7.9 g), bis(pinacolato)diboron (4.25 g), tris(dibenzylideneacetone)dipalladium(0) (824 mg), XPhos (858 mg), potassium acetate (3.53 g), and toluene (200 mL) was stirred at 110° C. for 12 h under heating. After leaving the mixture to stand for cooling, the mixture was extracted with toluene and the extract was purified by silica gel column chromatography to obtain a pinacol ester (7.5 g, 78% yield).

Result of mass spectrometric analysis (molecular weight of pinacol ester)

Calculated: 531.

Found: m/e=531.

Under argon atmosphere, a mixture of the obtained pinacol ester (5.0 g), 1-bromo-4-chlorobenzene (1.8 g), tetrakis(triphenylphosphine)palladium(0) (1.09 g), and a 2 M aqueous solution of sodium carbonate (60 ml) in toluene (100 ml) was stirred at 120° C. for 6 h under heating. After leaving the mixture to stand for cooling, the mixture was extracted with toluene and the extract was purified by silica gel column chromatography to obtain the intermediate F (4.2 g, 87% yield).

Result of mass spectrometric analysis (molecular weight of intermediate F)

Calculated: 515.
Found: m/e=515.

Synthesis Example 1: Synthesis of Compound 1

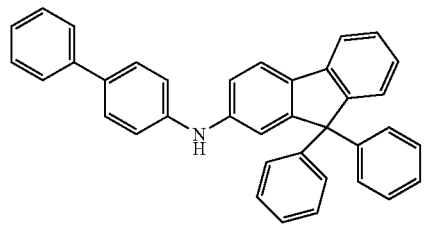

Intermediate 1

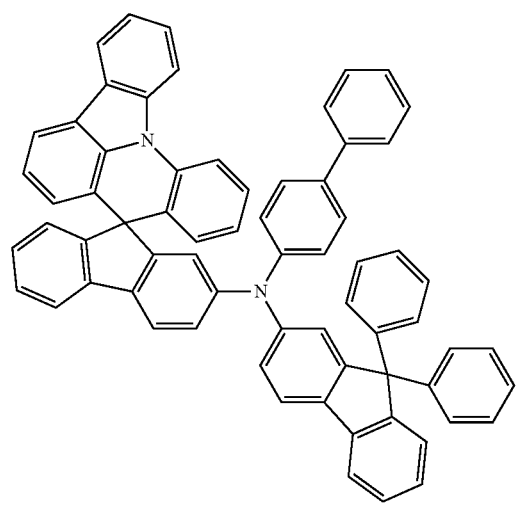

Compound 1

Under argon atmosphere, a mixture of a known intermediate 1 (2.5 g), the intermediate A (2.5 g), tris(dibenzylideneacetone)dipalladium(0) (95 mg), XPhos (194 mg), sodium t-butoxide (1.5 g), toluene (51 mL) was stirred at 110° C. for 6 h under heating. After leaving the mixture to stand for cooling, the precipitated crystal was removed by filtration, the mixture was extracted with toluene, and the extract was purified by silica gel column chromatography to obtain the compound 1 as a white solid (1.5 g, 33% yield).

The result of mass spectrometric analysis was m/e=888 to the molecular weight 888 of the compound 1.

Synthesis Example 2: Synthesis of Compound 2

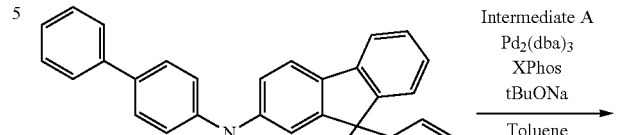

Intermediate 2

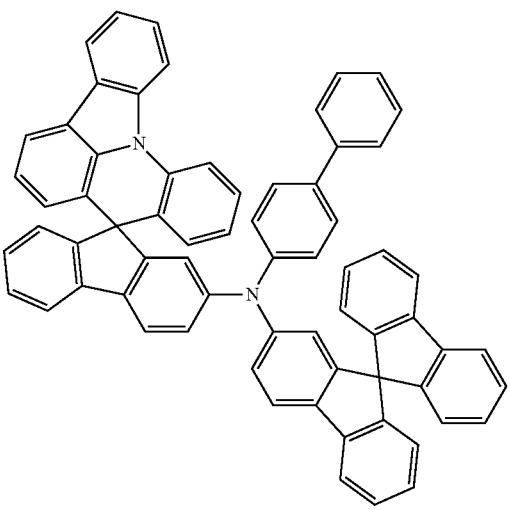

Compound 2

The compound 2 was synthesized in the same manner as in the synthesis of the compound 1 except for using the intermediate 2 in place of the intermediate 1.

The result of mass spectrometric analysis was m/e=886 to the molecular weight 886 of the compound 2.

Synthesis Example 3: Synthesis of Compound 3

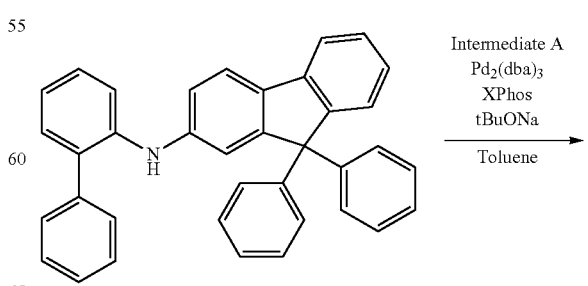

Intermediate 3

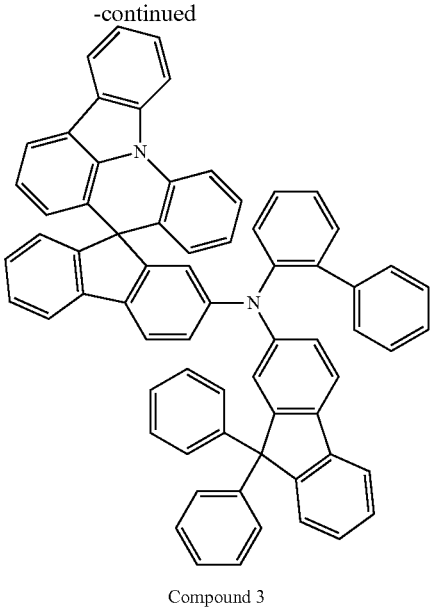

Compound 3

The compound 3 was synthesized in the same manner as in the synthesis of the compound 1 except for using the intermediate 3 in place of the intermediate 1.

The result of mass spectrometric analysis was m/e=888 to the molecular weight 888 of the compound 3.

Synthesis Example 4: Synthesis of Compound 4

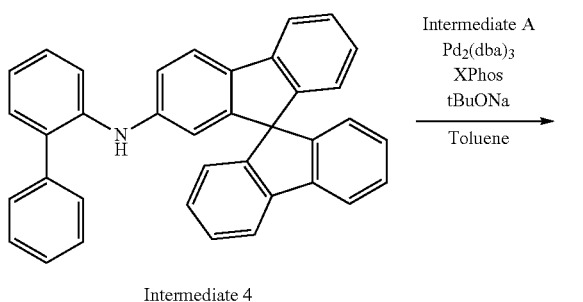

Intermediate 4

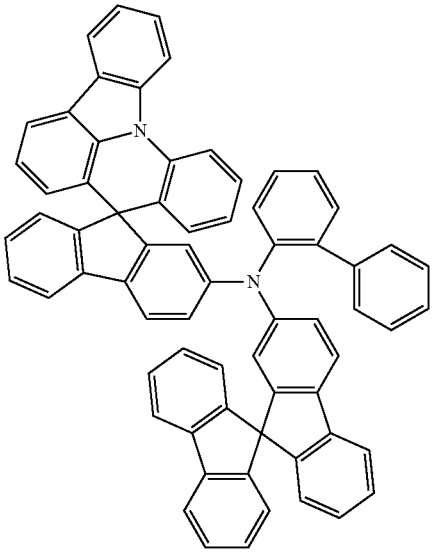

Compound 4

The compound 4 was synthesized in the same manner as in the synthesis of the compound 1 except for using the intermediate 4 in place of the intermediate 1.

The result of mass spectrometric analysis was m/e=886 to the molecular weight 886 of the compound 4.

Synthesis Example 5: Synthesis of Compound 5

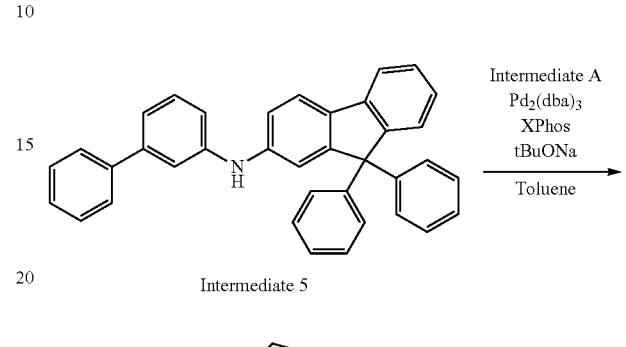

Intermediate 5

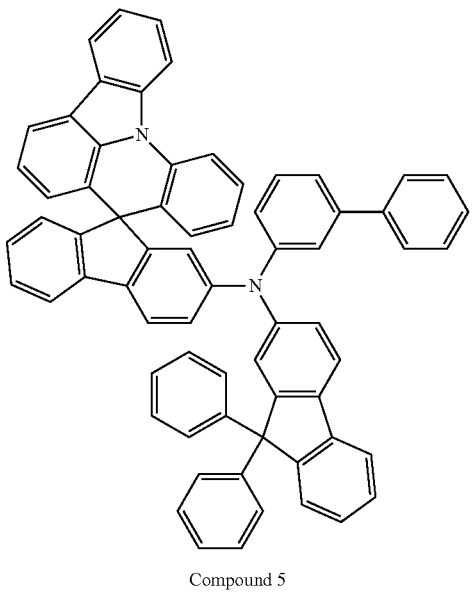

Compound 5

The compound 5 was synthesized in the same manner as in the synthesis of the compound 1 except for using the intermediate 5 in place of the intermediate 1.

The result of mass spectrometric analysis was m/e=888 to the molecular weight 888 of the compound 5.

Synthesis Example 6: Synthesis of Compound 6

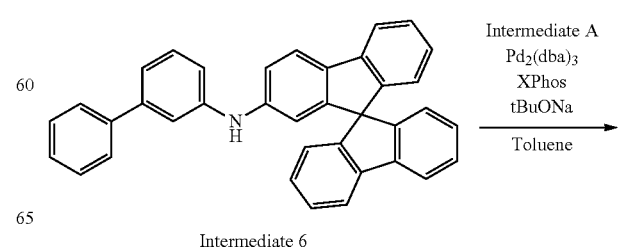

Intermediate 6

-continued

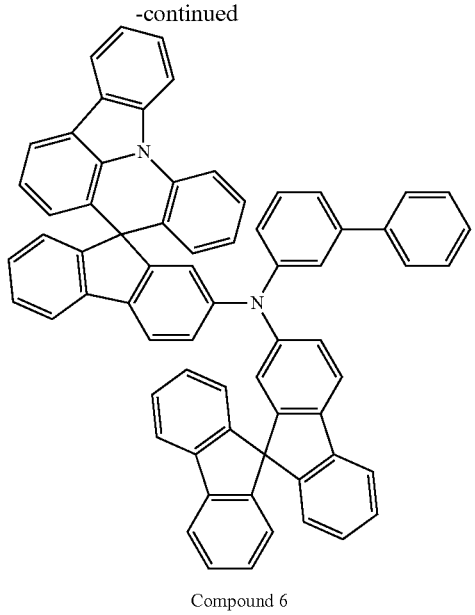

Compound 6

The compound 6 was synthesized in the same manner as in the synthesis of the compound 1 except for using the intermediate 6 in place of the intermediate 1.

The result of mass spectrometric analysis was m/e=886 to the molecular weight 886 of the compound 6.

Synthesis Example 7: Synthesis of Compound 7

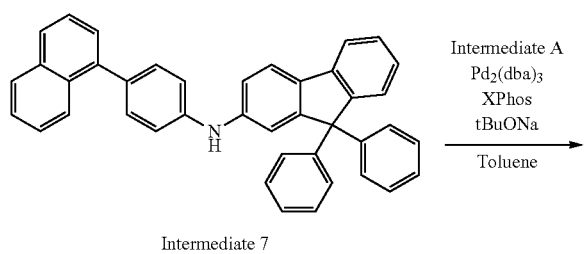

Intermediate 7

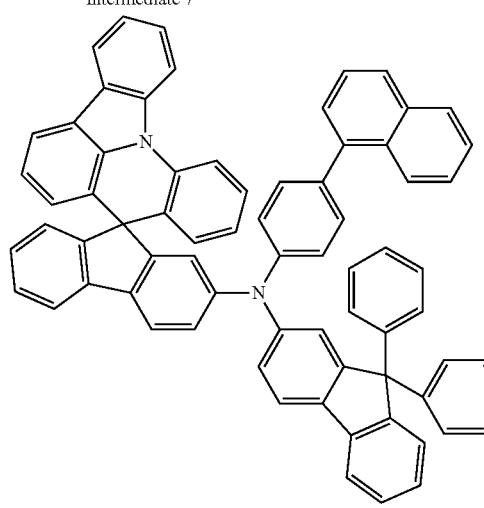

Compound 7

The compound 7 was synthesized in the same manner as in the synthesis of the compound 1 except for using the intermediate 7 in place of the intermediate 1.

The result of mass spectrometric analysis was m/e=938 to the molecular weight 938 of the compound 7.

Synthesis Example 8: Synthesis of Compound 8

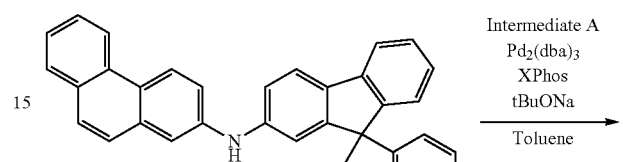

Intermediate 8

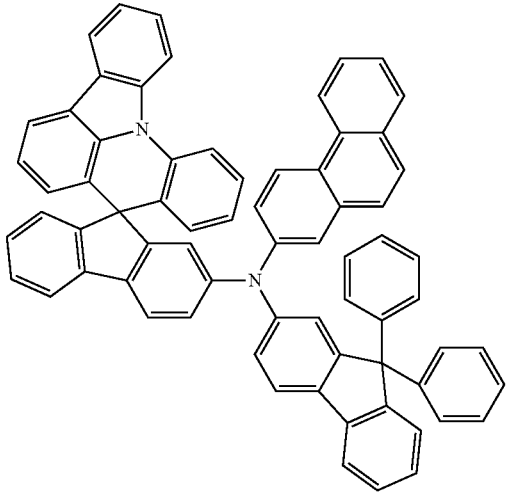

Compound 8

The compound 8 was synthesized in the same manner as in the synthesis of the compound 1 except for using the intermediate 8 in place of the intermediate 1.

The result of mass spectrometric analysis was m/e=912 to the molecular weight 912 of the compound 8.

Synthesis Example 9: Synthesis of Compound 9

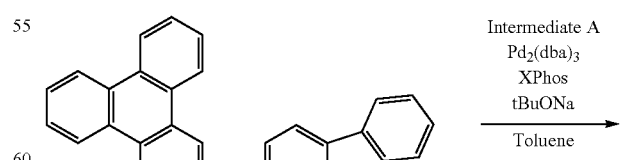

Intermediate 9

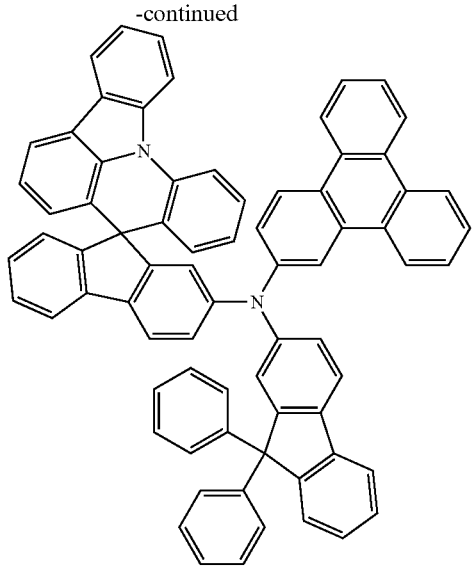

Compound 9

The compound 9 was synthesized in the same manner as in the synthesis of the compound 1 except for using the intermediate 9 in place of the intermediate 1.

The result of mass spectrometric analysis was m/e=962 to the molecular weight 962 of the compound 9.

Synthesis Example 10: Synthesis of Compound 10

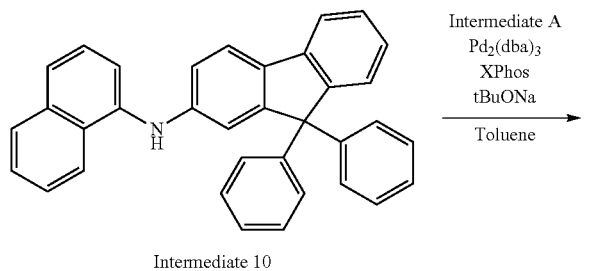

Intermediate 10

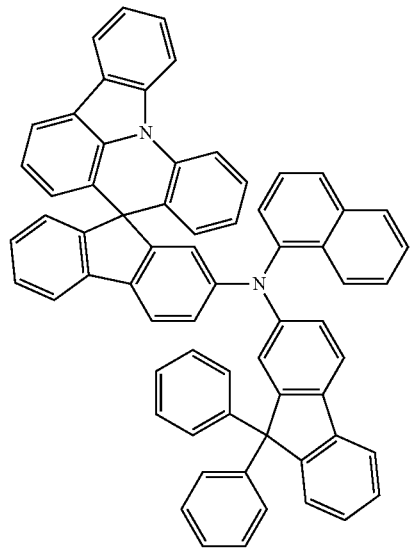

Compound 10

The compound 10 was synthesized in the same manner as in the synthesis of the compound 1 except for using the intermediate 10 in place of the intermediate 1.

The result of mass spectrometric analysis was m/e=862 to the molecular weight 862 of the compound 10.

Synthesis Example 11: Synthesis of Compound 11

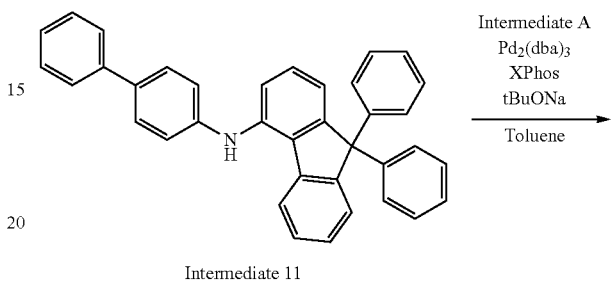

Intermediate 11

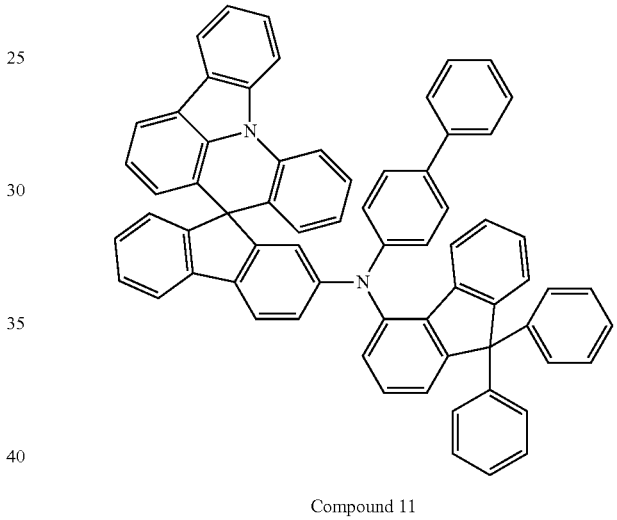

Compound 11

The compound 11 was synthesized in the same manner as in the synthesis of the compound 1 except for using the intermediate 11 in place of the intermediate 1.

The result of mass spectrometric analysis was m/e=888 to the molecular weight 888 of the compound 11.

Synthesis Example 12: Synthesis of Compound 12

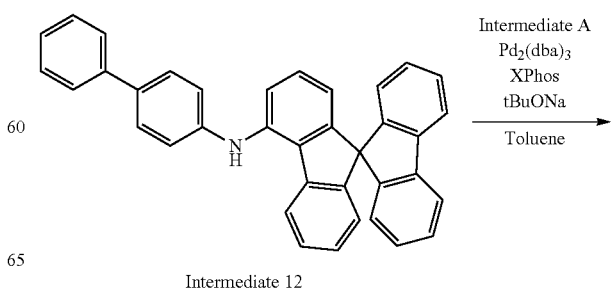

Intermediate 12

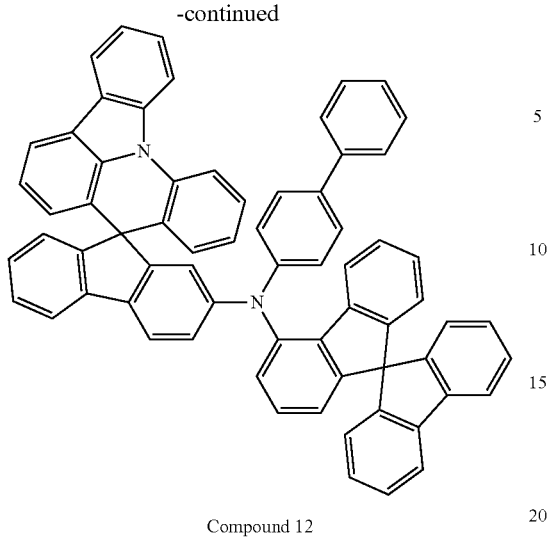
Compound 12
The compound 12 was synthesized in the same manner as in the synthesis of the compound 1 except for using the intermediate 12 in place of the intermediate 1.
The result of mass spectrometric analysis was m/e=886 to the molecular weight 886 of the compound 12.
Synthesis Example 13: Synthesis of Compound 13
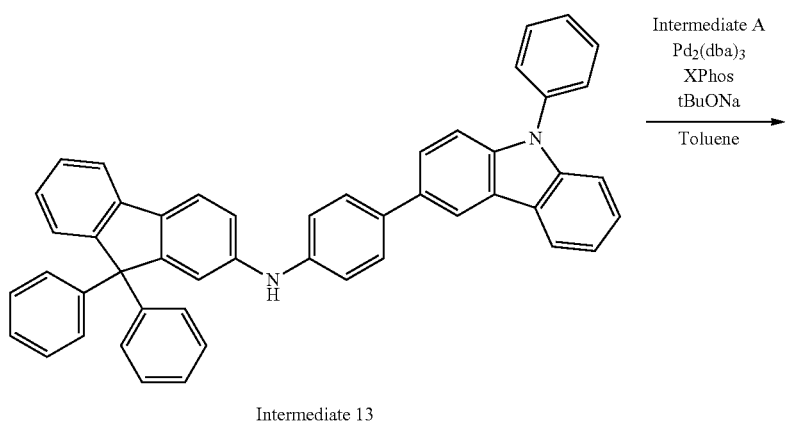
Intermediate 13
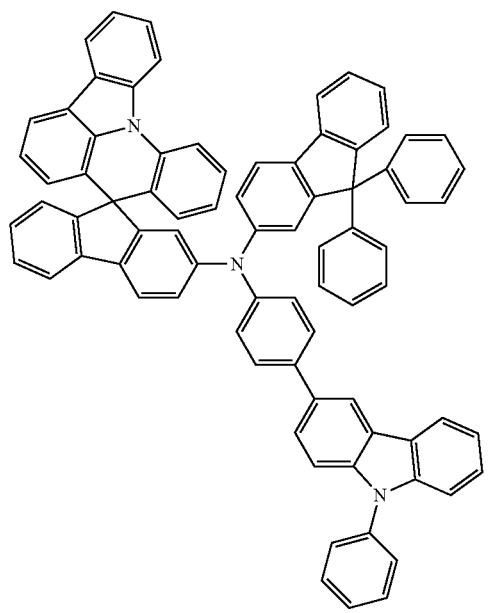
Compound 13

The compound 13 was synthesized in the same manner as in the synthesis of the compound 1 except for using the intermediate 13 in place of the intermediate 1.

The result of mass spectrometric analysis was m/e=1053 to the molecular weight 1053 of the compound 13.

Synthesis Example 14: Synthesis of Compound 14

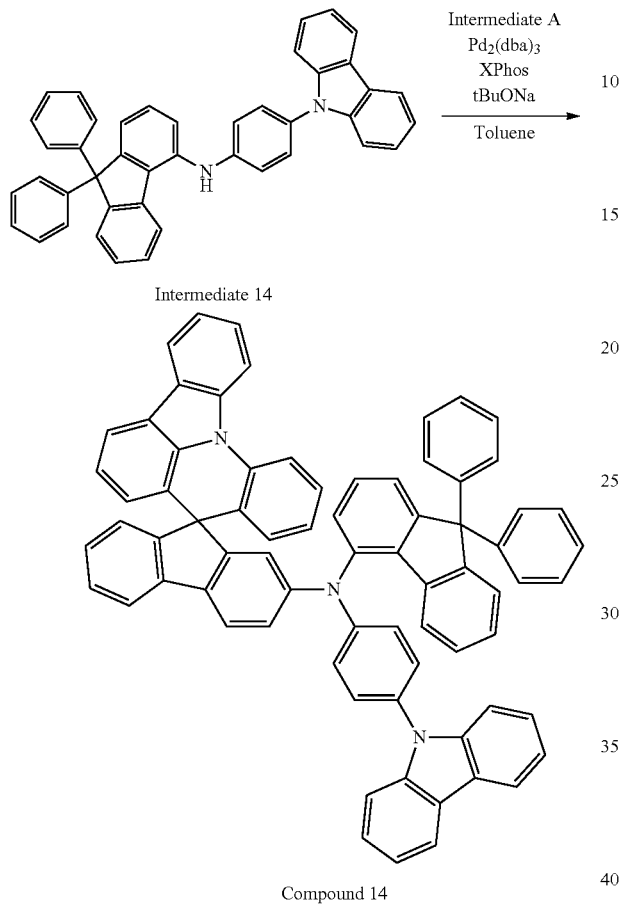

Intermediate 14

Compound 14

The compound 14 was synthesized in the same manner as in the synthesis of the compound 1 except for using the intermediate 14 in place of the intermediate 1.

The result of mass spectrometric analysis was m/e=977 to the molecular weight 977 of the compound 14.

Synthesis Example 15: Synthesis of Compound 15

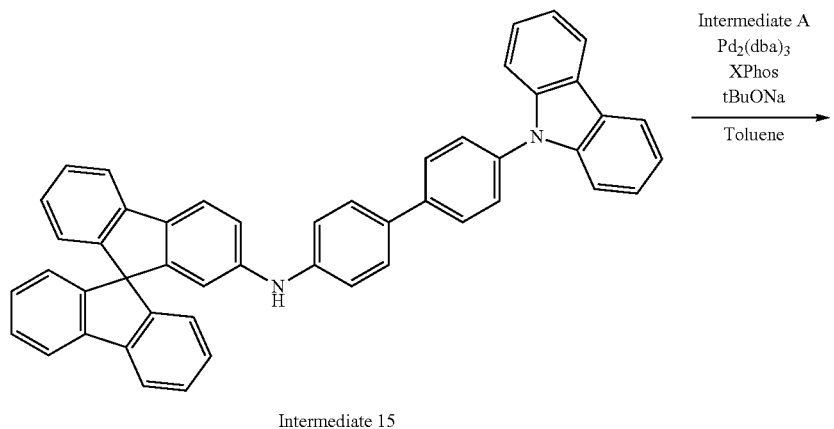

Intermediate 15

-continued
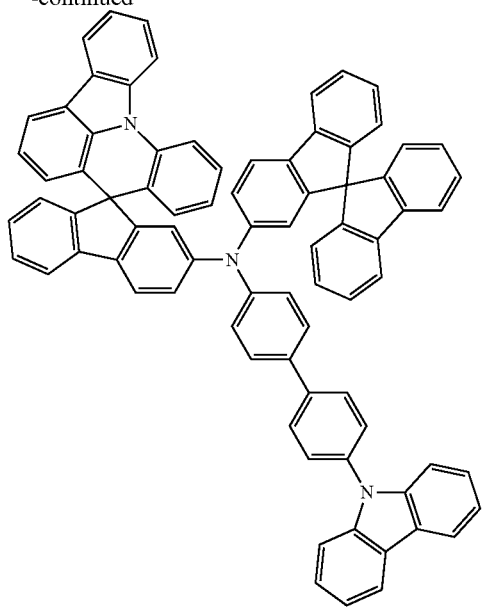
Compound 15
The compound 15 was synthesized in the same manner as in the synthesis of the compound 1 except for using the intermediate 15 in place of the intermediate 1.
The result of mass spectrometric analysis was m/e=1051 to the molecular weight 1051 of the compound 15.
Synthesis Example 16: Synthesis of Compound 16
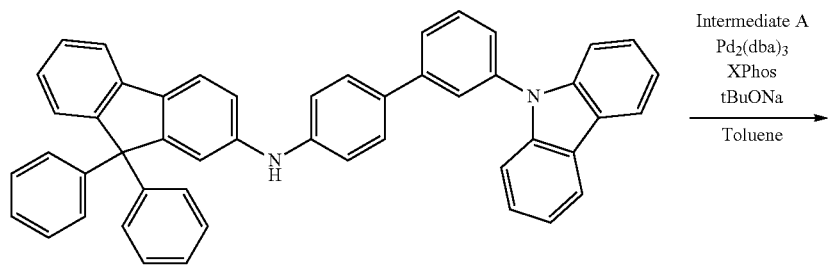
Intermediate 16

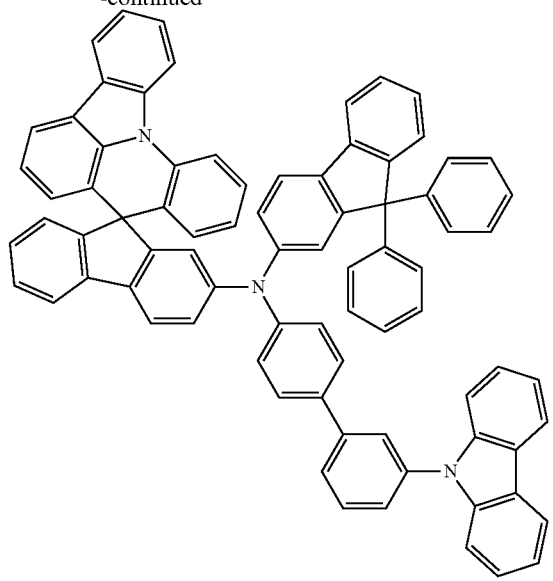

Compound 16

The compound 16 was synthesized in the same manner as in the synthesis of the compound 1 except for using the intermediate 16 in place of the intermediate 1.

The result of mass spectrometric analysis was m/e=1053 to the molecular weight 1053 of the compound 16.

The compound 17 was synthesized in the same manner as in the synthesis of the compound 1 except for using the intermediate 17 in place of the intermediate 1.

The result of mass spectrometric analysis was m/e=978 to the molecular weight 978 of the compound 17.

Synthesis Example 17: Synthesis of Compound 17

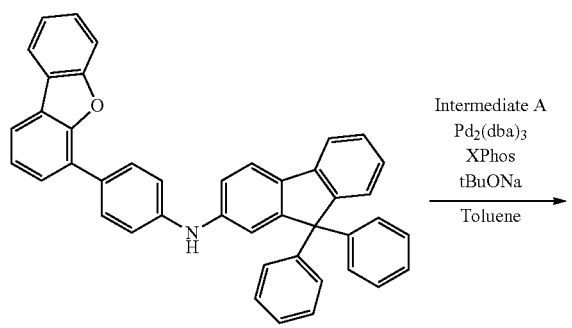

Intermediate 17

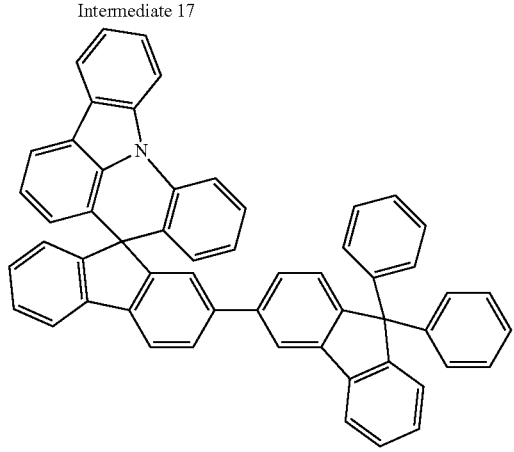

Compound 17

Synthesis Example 18: Synthesis of Compound 18

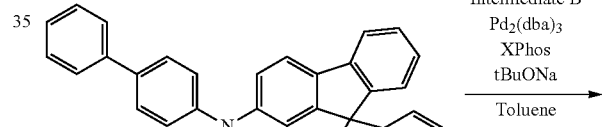

Intermediate 1

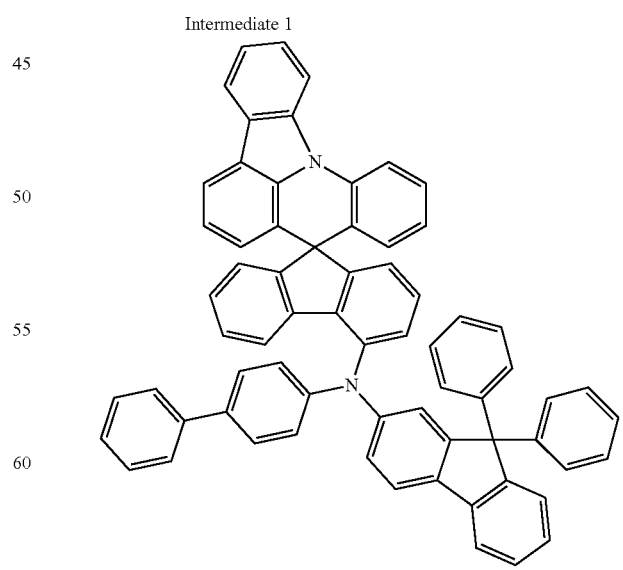

Compound 18

The compound 18 was synthesized in the same manner as in the synthesis of the compound 1 except for using the intermediate B in place of the intermediate A.

The result of mass spectrometric analysis was m/e=888 to the molecular weight 888 of the compound 18.

Synthesis Example 19: Synthesis of Compound 19

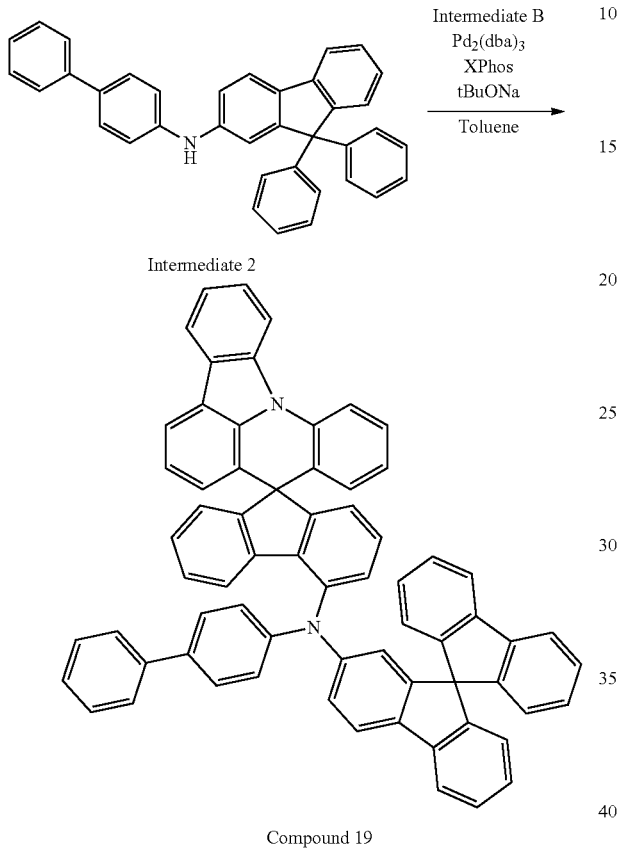

Compound 19

The compound 19 was synthesized in the same manner as in the synthesis of the compound 2 except for using the intermediate B in place of the intermediate A.

The result of mass spectrometric analysis was m/e=886 to the molecular weight 886 of the compound 19.

Synthesis Example 20: Synthesis of Compound 20

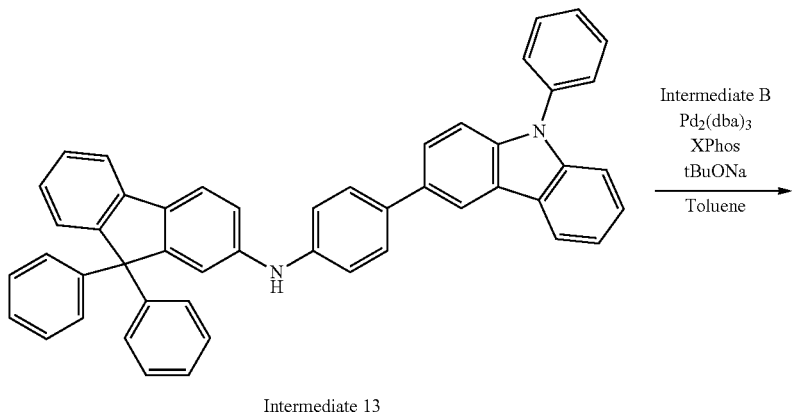

Intermediate 13

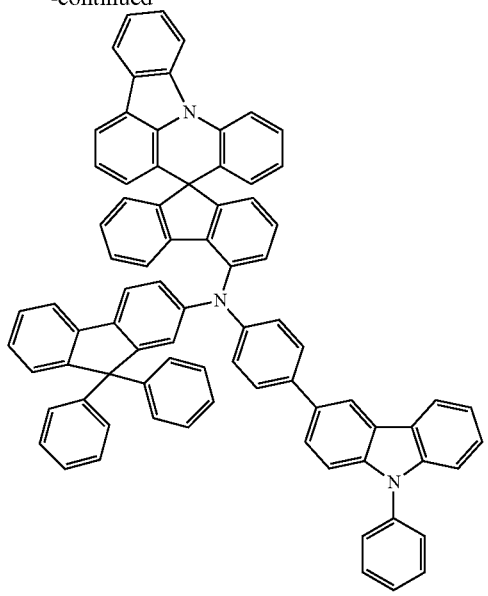

Compound 20

The compound 20 was synthesized in the same manner as in the synthesis of the compound 13 except for using the intermediate B in place of the intermediate A.

The result of mass spectrometric analysis was m/e=1053 to the molecular weight 1053 of the compound 20.

Synthesis Example 21: Synthesis of Compound 21

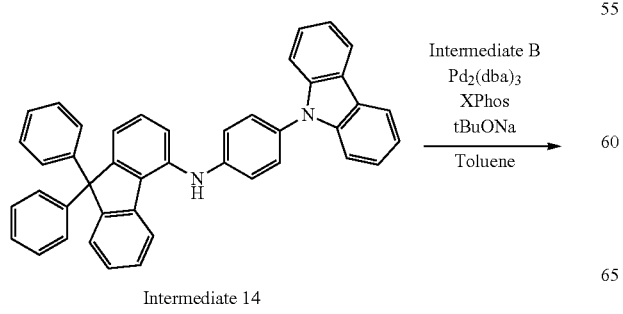

Intermediate 14

Intermediate B
Pd₂(dba)₃
XPhos
tBuONa
Toluene

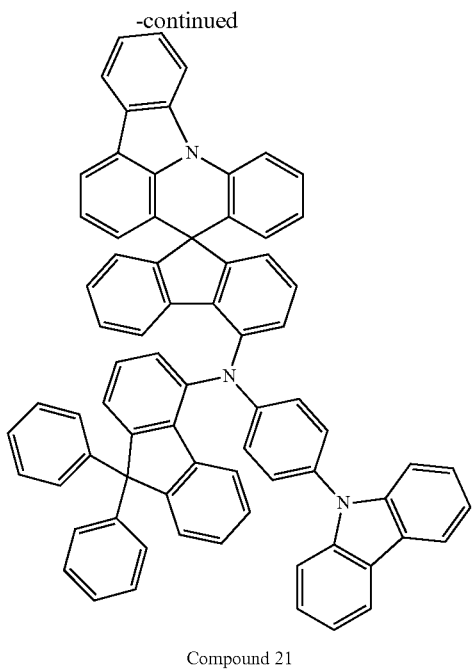

Compound 21

The compound 21 was synthesized in the same manner as in the synthesis of the compound 14 except for using the intermediate B in place of the intermediate A.

The result of mass spectrometric analysis was m/e=977 to the molecular weight 977 of the compound 21.

Synthesis Example 22: Synthesis of Compound 22
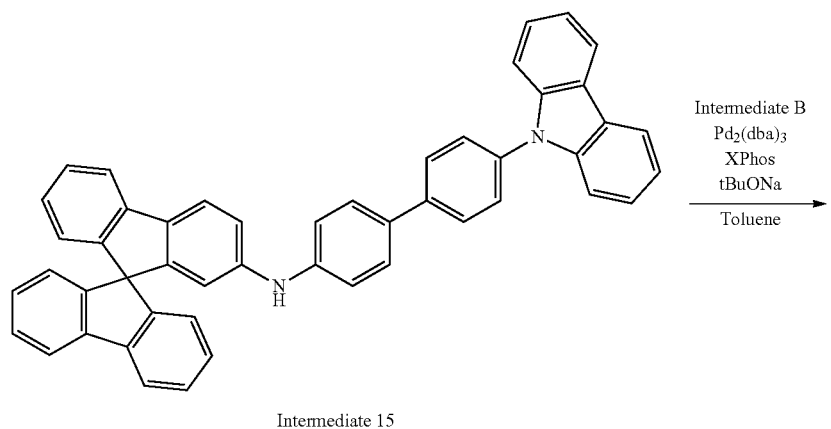
Intermediate 15
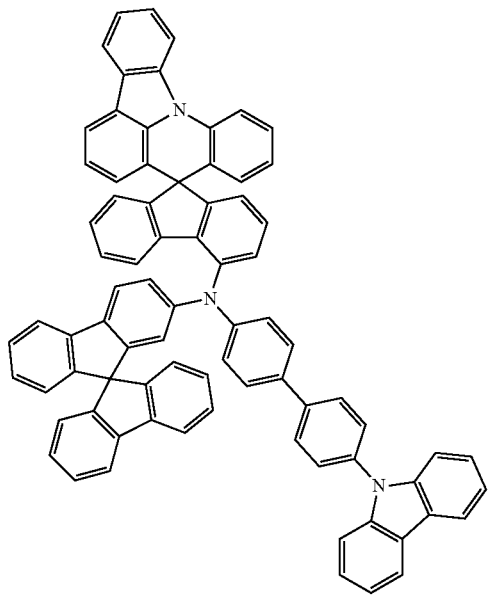
Compound 22
The compound 22 was synthesized in the same manner as in the synthesis of the compound 15 except for using the intermediate B in place of the intermediate A.
The result of mass spectrometric analysis was m/e=1051 to the molecular weight 1051 of the compound 22.

Synthesis Example 23: Synthesis of Compound 23

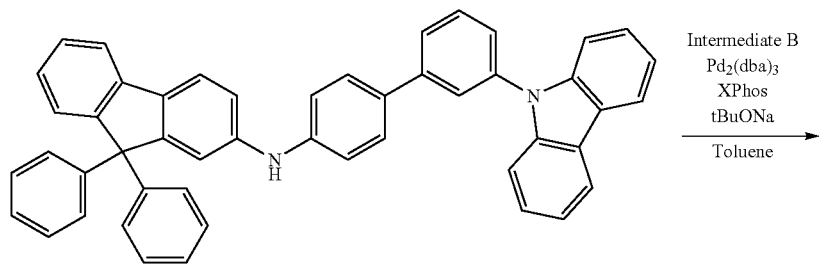

Intermediate 16

Intermediate B
Pd₂(dba)₃
XPhos
tBuONa
Toluene

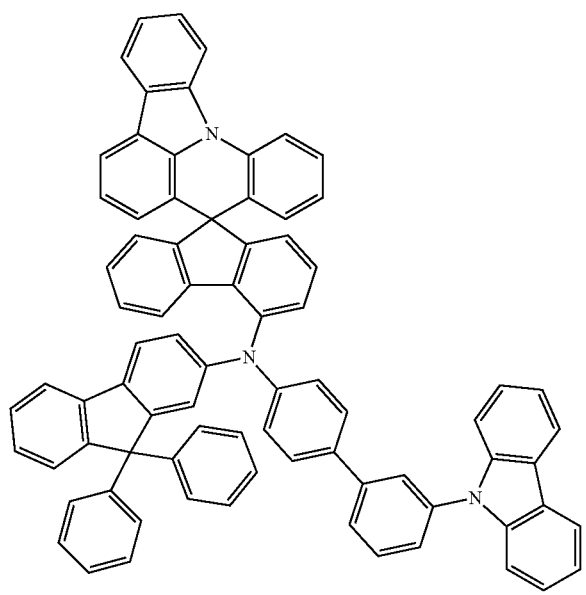

Compound 23

The compound 23 was synthesized in the same manner as in the synthesis of the compound 16 except for using the intermediate B in place of the intermediate A.

The result of mass spectrometric analysis was m/e=1053 to the molecular weight 1053 of the compound 23.

Synthesis Example 24: Synthesis of Compound 24

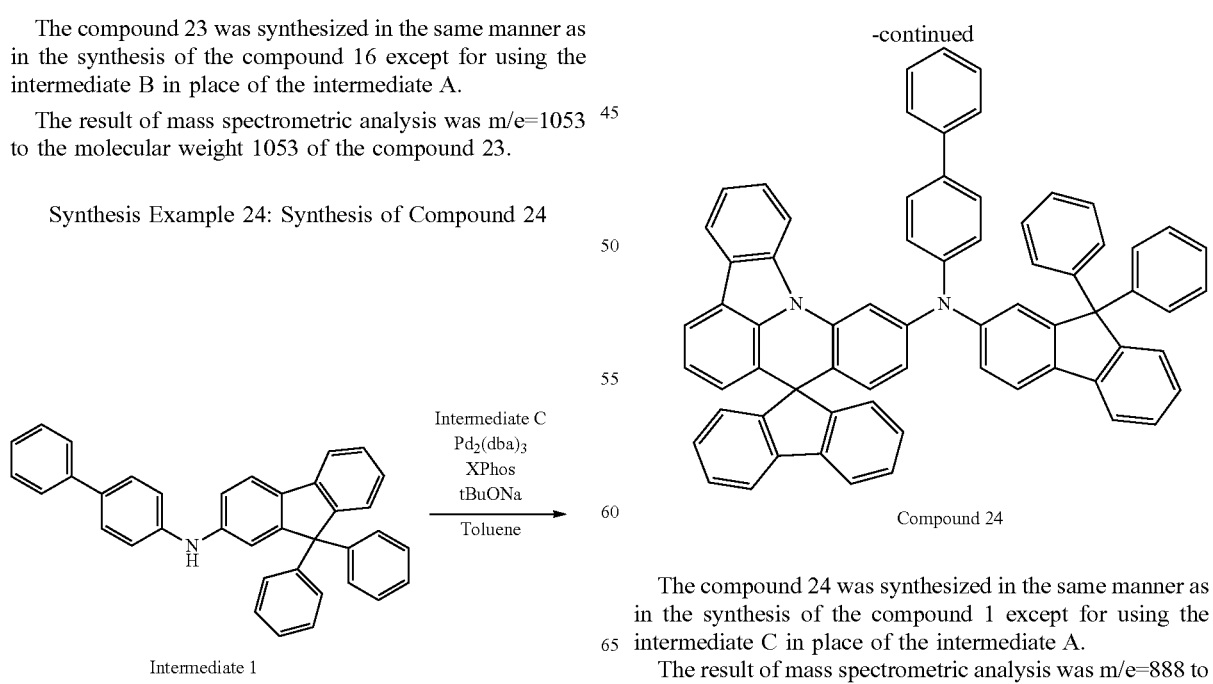

Intermediate 1

Intermediate C
Pd₂(dba)₃
XPhos
tBuONa
Toluene

Compound 24

The compound 24 was synthesized in the same manner as in the synthesis of the compound 1 except for using the intermediate C in place of the intermediate A.

The result of mass spectrometric analysis was m/e=888 to the molecular weight 888 of the compound 24.

Synthesis Example 25: Synthesis of Compound 25

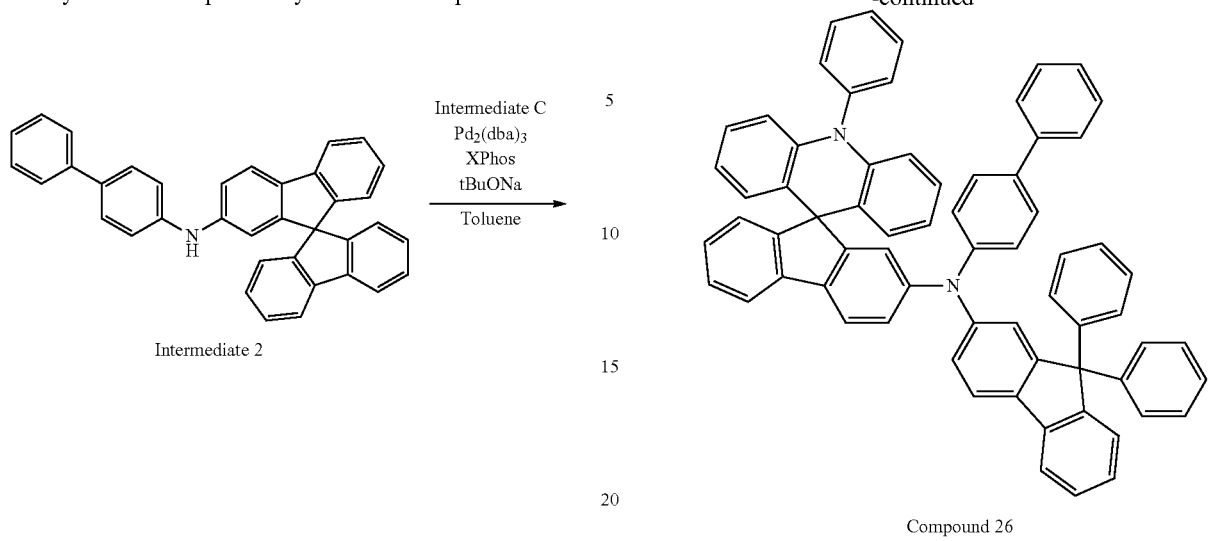

Compound 25

The compound 25 was synthesized in the same manner as in the synthesis of the compound 2 except for using the intermediate C in place of the intermediate A.

The result of mass spectrometric analysis was m/e=886 to the molecular weight 886 of the compound 25.

Synthesis Example 26: Synthesis of Compound 26

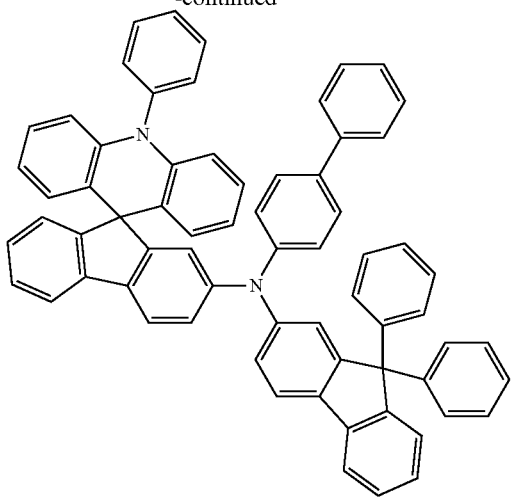

Compound 26

The compound 26 was synthesized in the same manner as in the synthesis of the compound 1 except for using the intermediate D in place of the intermediate A.

The result of mass spectrometric analysis was m/e=890 to the molecular weight 890 of the compound 26.

Synthesis Example 27: Synthesis of Compound 27

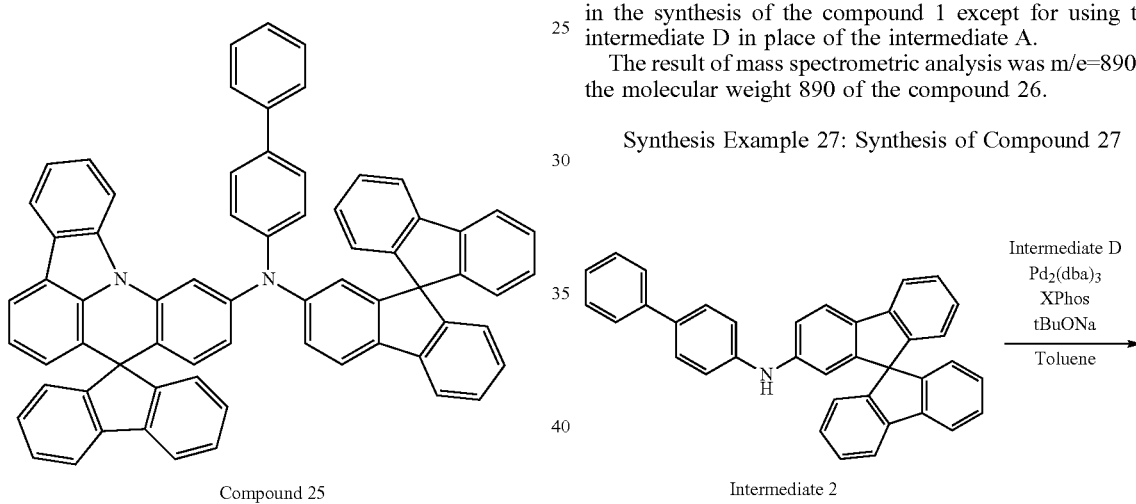

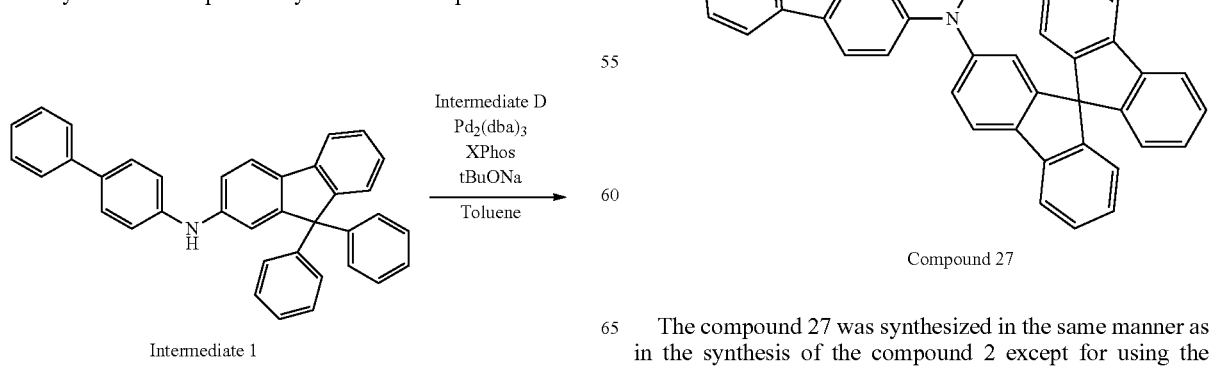

Compound 27

The compound 27 was synthesized in the same manner as in the synthesis of the compound 2 except for using the intermediate D in place of the intermediate A.

The result of mass spectrometric analysis was m/e=888 to the molecular weight 888 of the compound 27.

Synthesis Example 28: Synthesis of Compound 28

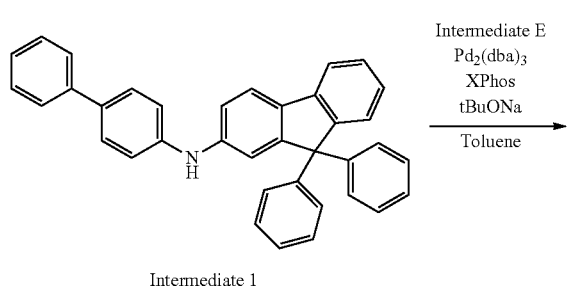

Intermediate 1

Intermediate E
Pd₂(dba)₃
XPhos
tBuONa
Toluene

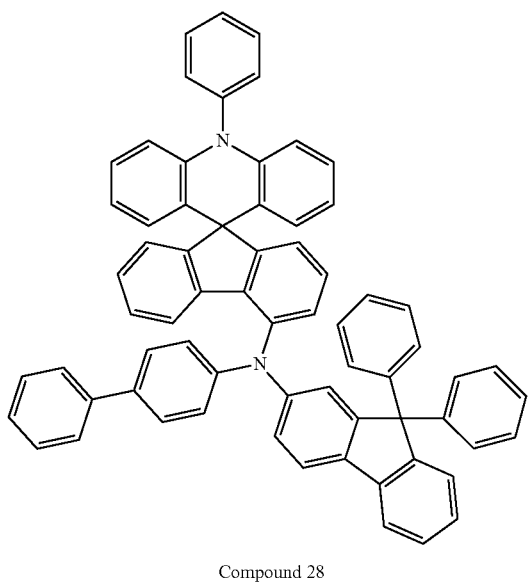

Compound 28

The compound 28 was synthesized in the same manner as in the synthesis of the compound 1 except for using the intermediate E in place of the intermediate A.

The result of mass spectrometric analysis was m/e=890 to the molecular weight 890 of the compound 28.

Synthesis Example 29: Synthesis of Compound 29

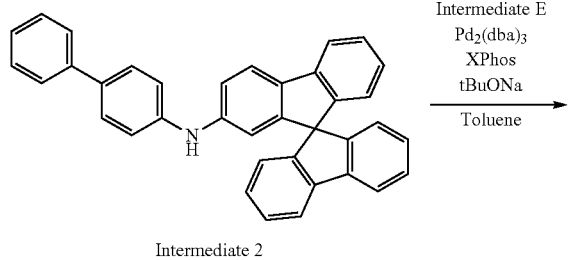

Intermediate 2

Intermediate E
Pd₂(dba)₃
XPhos
tBuONa
Toluene

-continued

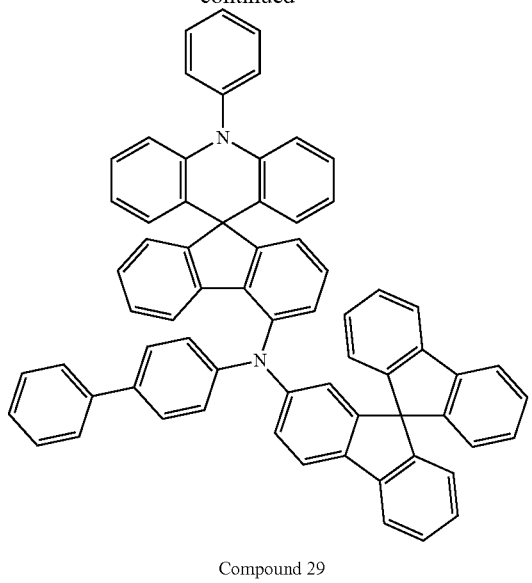

Compound 29

The compound 29 was synthesized in the same manner as in the synthesis of the compound 2 except for using the intermediate E in place of the intermediate A.

The result of mass spectrometric analysis was m/e=888 to the molecular weight 888 of the compound 29.

Synthesis Example 30: Synthesis of Compound 30

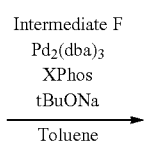

Intermediate 1

Intermediate F
Pd₂(dba)₃
XPhos
tBuONa
Toluene

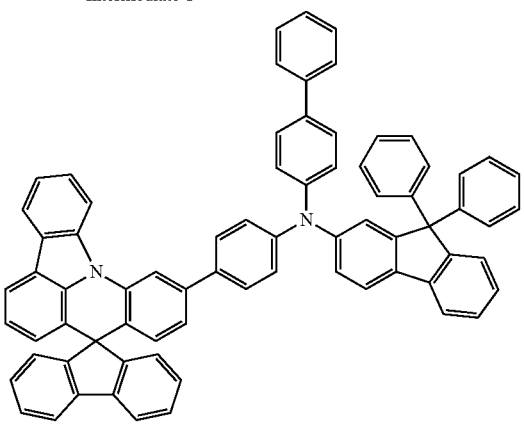

Compound 30

The compound 30 was synthesized in the same manner as in the synthesis of the compound 1 except for using the intermediate F in place of the intermediate A.

The result of mass spectrometric analysis was m/e=964 to the molecular weight 964 of the compound 30.

Synthesis Example 31: Synthesis of Compound 31

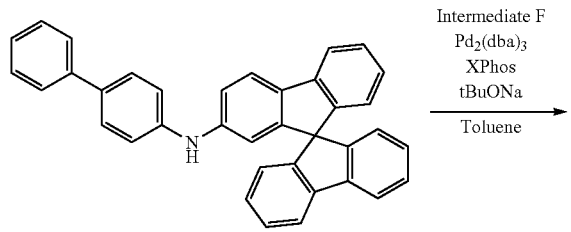

Intermediate 2

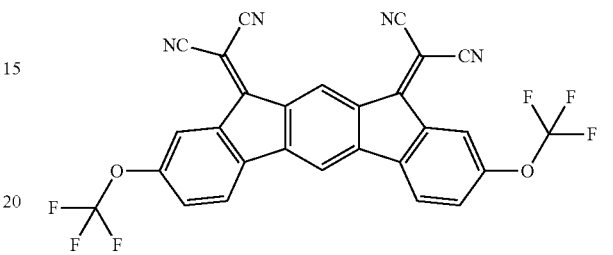

Compound 31

The compound 31 was synthesized in the same manner as in the synthesis of the compound 2 except for using the intermediate F in place of the intermediate A.

The result of mass spectrometric analysis was m/e=962 to the molecular weight 962 of the compound 31.

Example 1

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of ITO was 130 nm.

The cleaned glass substrate having the transparent electrode line was mounted to a substrate holder of a vacuum vapor deposition apparatus. First, the compound HI was vapor-deposited so as to cover the transparent electrode line to form a hole injecting layer with a thickness of 5 nm.

On the hole injecting layer, the compound 1 was vapor-deposited to form a first hole transporting layer with a thickness of 80 nm.

On the first hole transporting layer, the compound HT2 was vapor-deposited to form a second hole transporting layer with a thickness of 10 nm.

On the second hole transporting layer, the compound BH (host material) and the compound BD (dopant material) were vapor co-deposited to form a light emitting layer with a thickness of 25 nm. The ratio of the compound BH and the compound BD in the light emitting layer was 96:4 by mass.

Successively after forming the light emitting layer, the compound ET1 was vapor-deposited to form a first electron transporting layer with a thickness of 10 nm, and then, the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

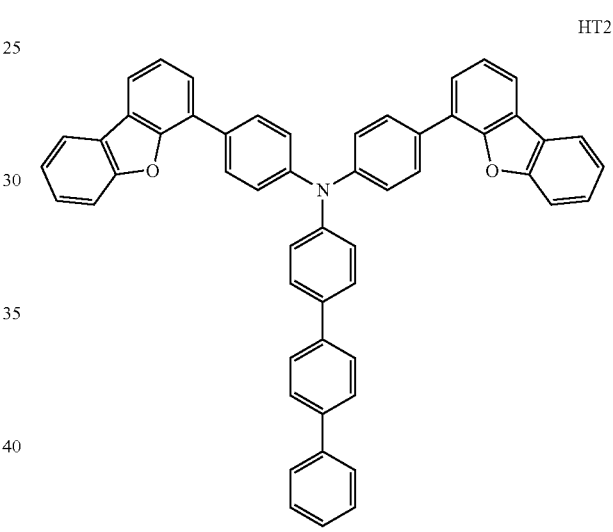

HI

HT2

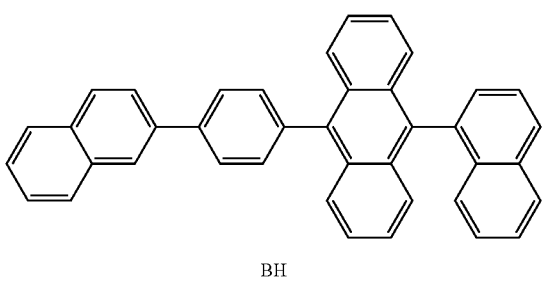

BH

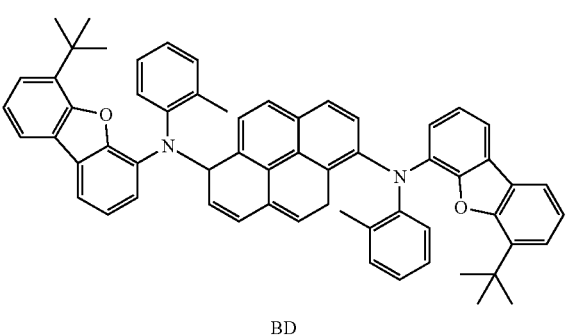

BD

ET1

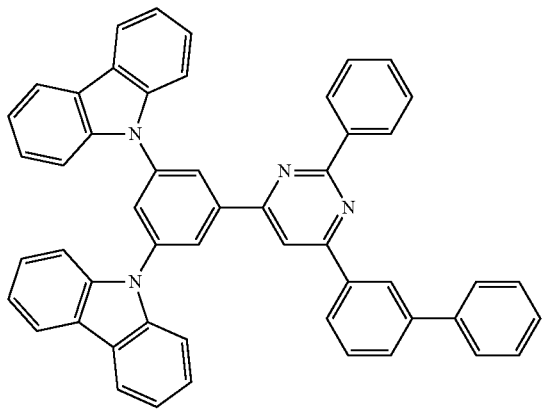

ET2

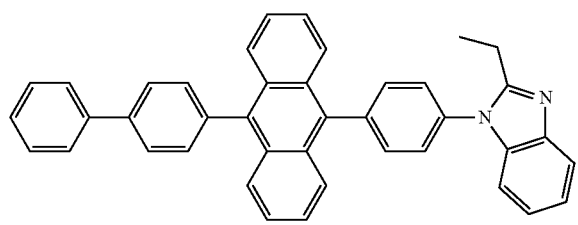

Compound 1

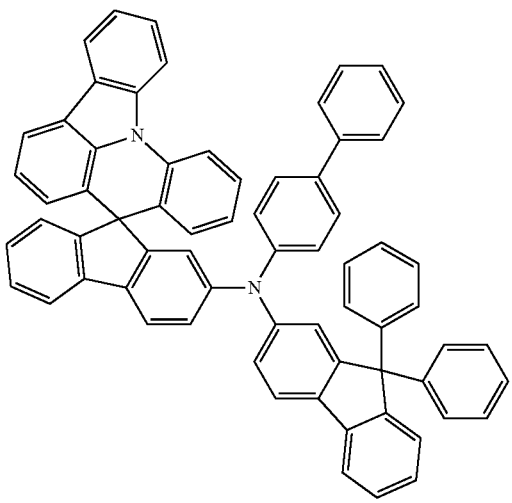

Comparative Example 1

An organic EL device was produced in the same manner as in Example 1 except for forming the first hole transporting layer by using the comparative compound 1 in place of the compound 1.

Comparative compound 1

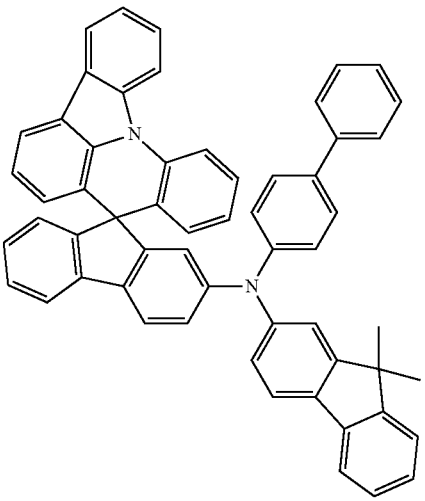

Example 2

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of ITO was 130 nm.

The cleaned glass substrate having the transparent electrode line was mounted to a substrate holder of a vacuum vapor deposition apparatus. First, the compound HI was vapor-deposited so as to cover the transparent electrode line to form a hole injecting layer with a thickness of 5 nm.

On the hole injecting layer, the compound HT1 was vapor-deposited to form a first hole transporting layer with a thickness of 80 nm.

On the first hole transporting layer, the compound 1 was vapor-deposited to form a second hole transporting layer with a thickness of 10 nm.

On the second hole transporting layer, the compound BH (host material) and the compound BD (dopant material) were vapor co-deposited to form a light emitting layer with a thickness of 25 nm. The ratio of the compound BH and the compound BD in the light emitting layer was 96:4 by mass.

Successively after forming the light emitting layer, the compound ET1 was vapor-deposited to form a first electron transporting layer with a thickness of 10 nm, and then, the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

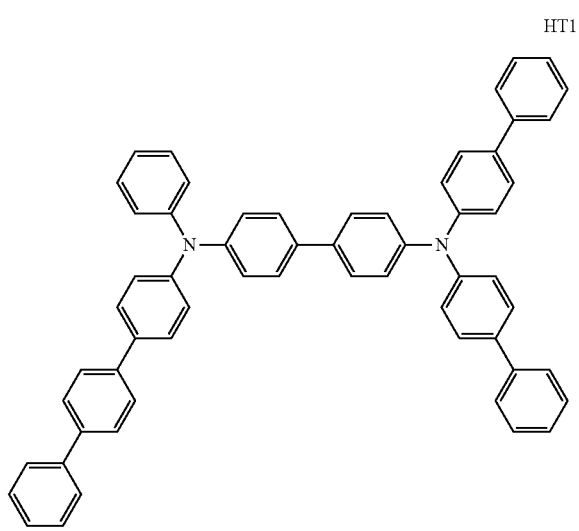 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

Comparative Example 2

An organic EL device was produced in the same manner as in Example 1 except for forming the second hole transporting layer by using the comparative compound 1 in place of the compound 1.

Evaluation of EL Device Performance

Each organic EL device thus produced was operated at a constant direct current to measure the driving voltage at a current density of 10 mA/cm² and a luminance and emission spectrum using a luminance meter. Using the obtained results, the external quantum efficiency (EQE (%)) was determined.

The results are shown in Table 1.

TABLE 1

|  | First hole transporting layer | Second hole transporting layer | EQE (%) |
|---|---|---|---|
| Example 1 | Compound 1 | HT2 | 6.5 |
| Comparative example 1 | Comparative compound 1 | HT2 | 5.9 |
| Example 2 | HT1 | Compound 1 | 7.4 |
| Comparative example 2 | HT1 | Comparative compound 1 | 6.5 |

REFERENCE SIGNS LIST

1: Organic EL device
2: Substrate
3: Anode
4: Cathode
5: Anode-side organic layer (second hole transporting layer)
6: Anode-side organic layer (first hole transporting layer)
7: Light emitting layer
8: Cathode-side organic layer (electron transporting layer)
10: Emission unit

The invention claimed is:

1. An organic electroluminescence device, comprising a cathode, an anode and an organic layer between the cathode and the anode,
wherein the organic layer comprises a light emitting layer, and a hole transporting region between the anode and the light emitting layer,
the hole transporting region comprises a first hole transporting layer and a second hole transporting layer from the anode toward the light emitting layer in this order, and
the first hole transporting layer comprises a compound represented by the following formula (1):

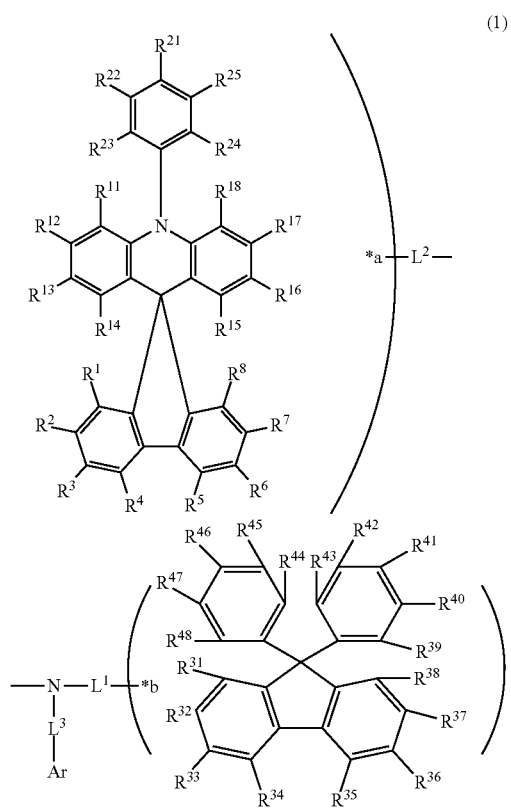

wherein one selected from $R^1$ to $R^8$, $R^{11}$ to $R^{18}$, and $R^{21}$ to $R^{25}$ is a single bond bonded to *a;
each of $R^1$ to $R^8$, $R^{11}$ to $R^{18}$, and $R^{21}$ to $R^{25}$ which is not the single bond bonded to *a is a hydrogen atom or a substituent;
$R^{11}$ and $R^{23}$, or $R^{18}$ and $R^{24}$ may be bonded to each other to form a single bond;
one selected from $R^{31}$ to $R^{48}$ is a single bond bonded to *b;
each of $R^{31}$ to $R^{38}$ and $R^{39}$ to $R^{48}$ which is not the single bond bonded to *b is a hydrogen atom or a substituent;
$R^{43}$ and $R^{44}$ may be bonded to each other to form a single bond;
adjacent two selected from $R^{31}$ to $R^{34}$ may be bonded to each other to form a ring structure;
adjacent two selected from $R^{35}$ to $R^{38}$ may be bonded to each other to form a ring structure;
adjacent two selected from $R^{39}$ to $R^{43}$ may be bonded to each other to form a ring structure;
adjacent two selected from $R^{44}$ to $R^{48}$ may be bonded to each other to form a ring structure;
each of $L^1$, $L^2$, and $L^3$ is independently a single bond or a substituted or unsubstituted arylene group having 6 to 30 ring carbon atoms; and
Ar is a substituted or unsubstituted aryl group having 6 to 30 ring carbon atoms or a substituted or unsubstituted heteroaryl group having 5 to 30 ring atoms, wherein the substituted or unsubstituted aryl group having 6 to 30 ring carbon atoms is a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, or a perylenyl group, and the substituted or unsubstituted heteroaryl group having 5 to 30 ring carbon atoms is a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group, a naphthobenzothiophenyl group, a carbazolyl group (a N-carbazolyl group and a C-carbazolyl group), a benzocarbazolyl group (a benzo-N-carbazolyl group and a benzo-C-carbazolyl group), a phenanthridinyl group, an acridinyl group, a phenanthrolinyl group, a phenazinyl group, a phenothiazinyl group, a phenoxazinyl group, or a xanthenyl group.

2. The organic electroluminescence device according to claim 1, wherein the light emitting layer comprises a dopant material, and the dopant material is a fluorescent emitting material or a phosphorescent emitting material.

3. An electronic device comprising the organic electroluminescence device according to claim 1.

4. The organic electroluminescence device according to claim 1, wherein the compound is represented by formula (2):

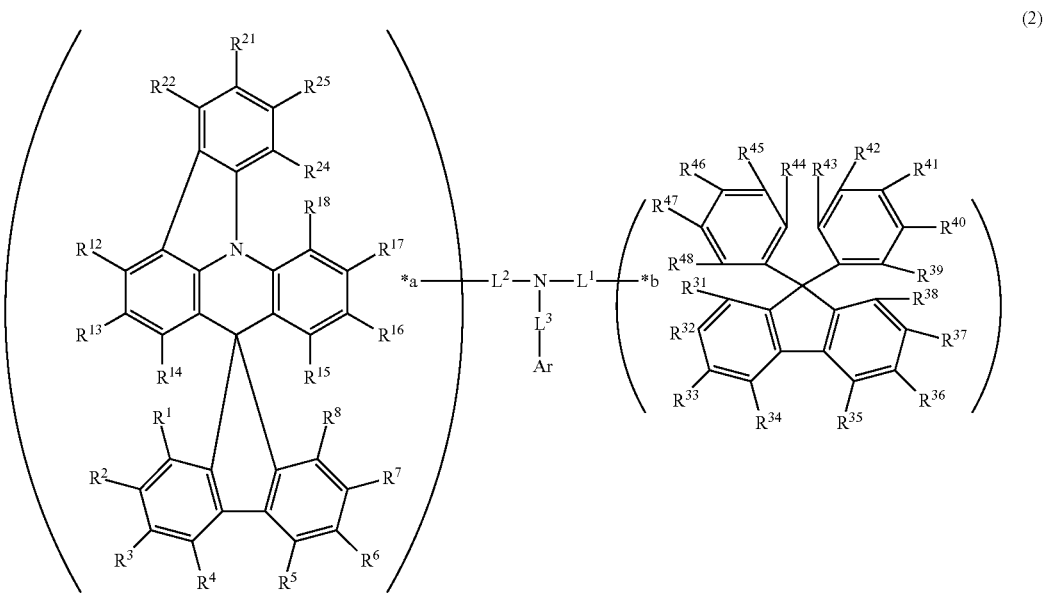

(2)

wherein $R^1$ to $R^8$, $R^{12}$ to $R^{18}$, $R^{21}$ to $R^{22}$, $R^{24}$ to $R^{25}$, $R^{31}$ to $R^{48}$, $L^1$ to $L^3$, and Ar are as defined above.

5. The organic electroluminescence device according to claim 1, wherein the compound is represented by formula (3):

(3)

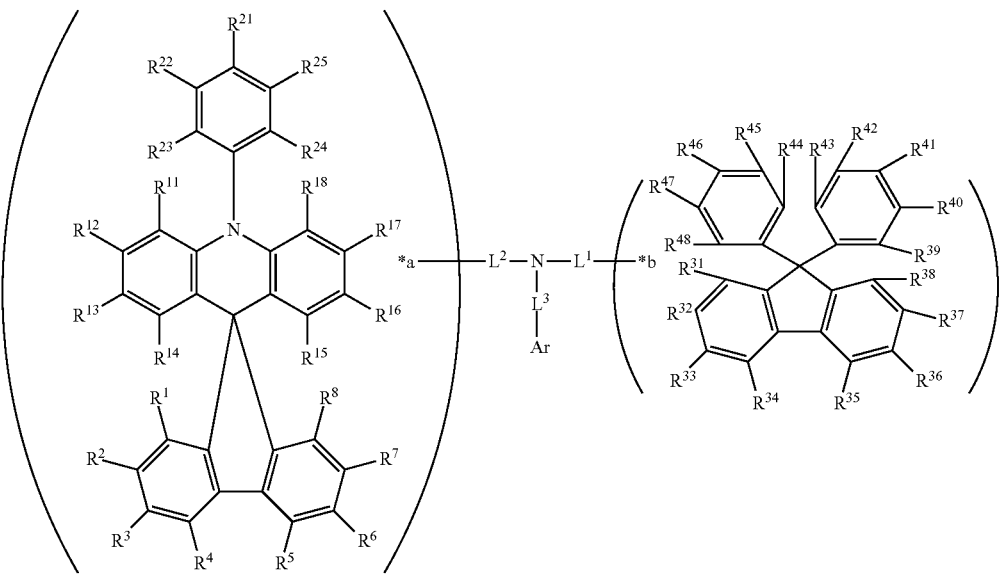

wherein $R^1$ to $R^8$, $R^{12}$ to $R^{18}$, $R^{21}$ to $R^{25}$, $R^{31}$ to $R^{48}$, $L^1$ to $L^3$, and Ar are as defined above, provided that $R^{11}$ and $R^{23}$ are not bonded to each other.

6. The organic electroluminescence device according to claim 1, wherein the compound is represented by formula (4):

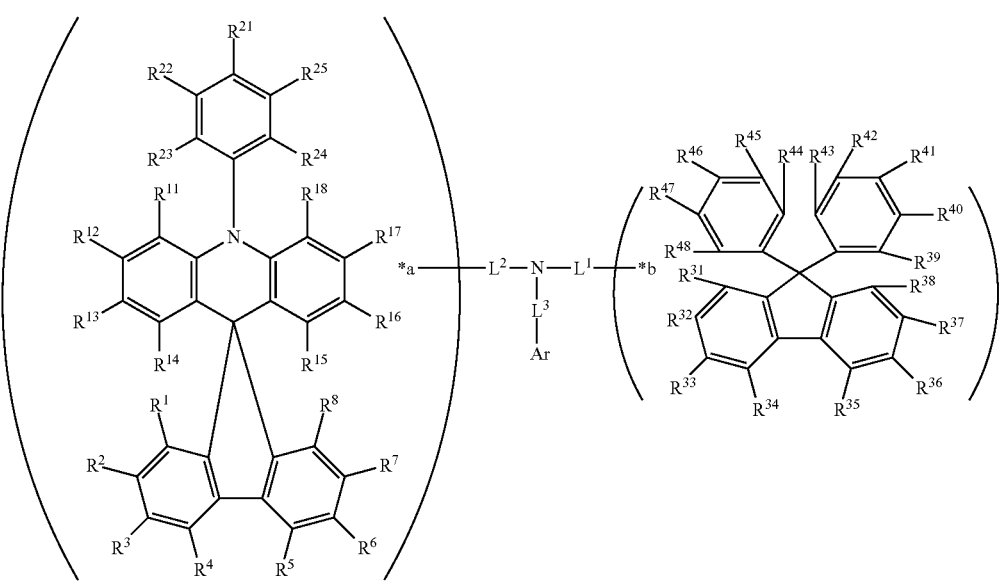

(4)

wherein $R^1$ to $R^8$, $R^{12}$ to $R^{18}$, $R^{21}$ to $R^{25}$, $R^{31}$ to $R^{48}$, $L^1$ to $L^3$, and Ar are as defined above, provided that $R^{18}$ and $R^{24}$ are not bonded to each other.

7. The organic electroluminescence device according to claim 1, wherein $R^2$, $R^4$, $R^5$, or $R^7$ is the single bond bonded to *a.

8. The organic electroluminescence device according to claim 1, wherein the compound is represented by formula (2a):

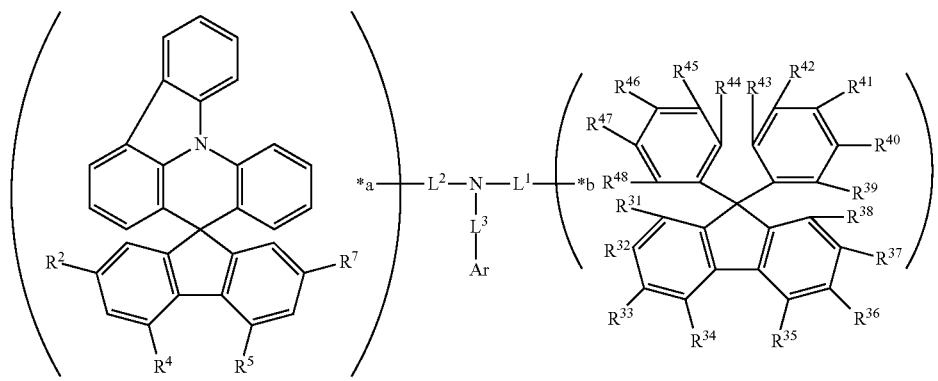

(2a)

wherein $R^2$, $R^4$, $R^5$, $R^7$, $R^{31}$ to $R^{48}$, $L^1$ to $L^3$, and Ar are as defined above, provided that $R^{43}$ and $R^{44}$ are not bonded to each other.

9. The organic electroluminescence device according to claim 1, wherein the compound is represented by formula (3a):

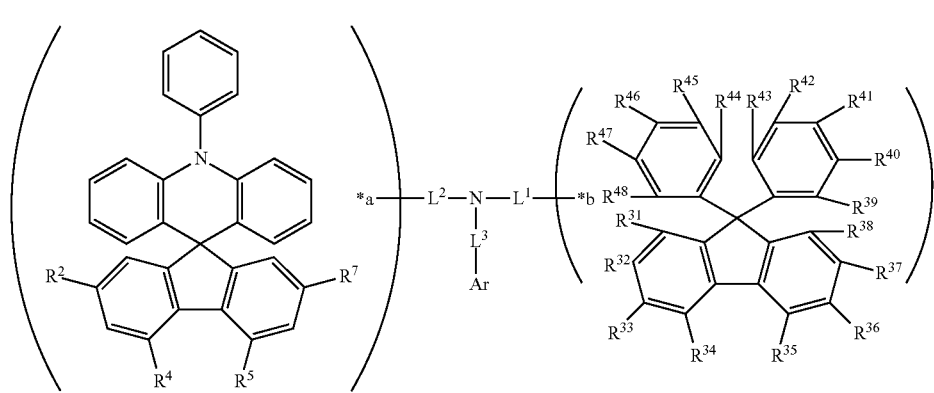

(3a)

wherein, $R^2$, $R^4$, $R^5$, $R^7$, $R^{31}$ to $R^{48}$, $L^1$ to $L^3$, and Ar are as defined above, provided that $R^{43}$ and $R^{44}$ are not bonded to each other.

10. The organic electroluminescence device according to claim 1, wherein the compound is represented by formula (2b):

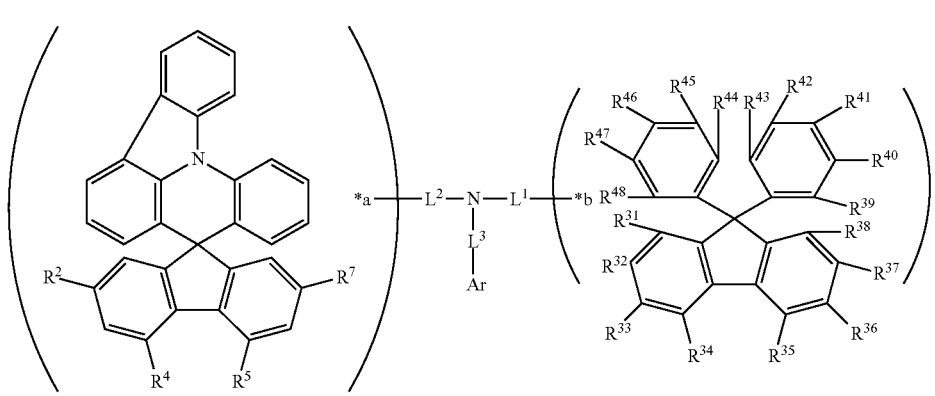

(2b)

wherein $R^2$, $R^4$, $R^5$, $R^7$, to $R^{42}$, $R^{45}$ to $R^{48}$, $L^1$ to $L^3$, and Ar are as defined above.

11. The organic electroluminescence device according to claim 1, wherein the compound is represented by formula (3b):

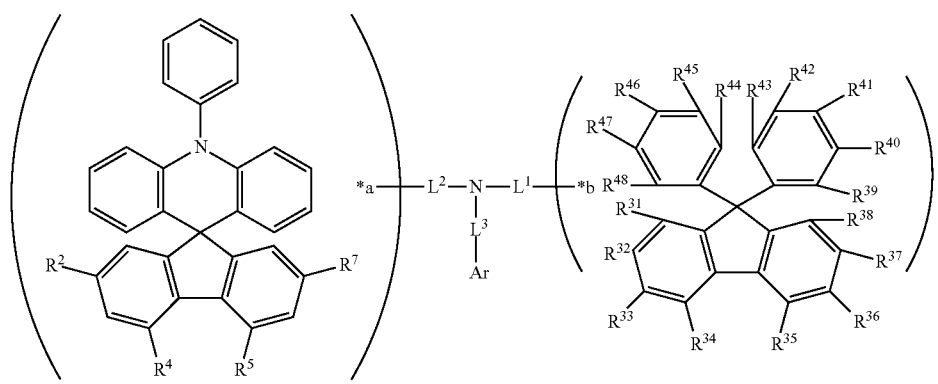

(3b)

wherein $R^2$, $R^4$, $R^5$, $R^7$, $R^{31}$ to $R^{42}$, $R^{45}$ to $R^{48}$, $L^1$ to $L^3$, and Ar are as defined above.

12. The organic electroluminescence device according to claim 1, wherein $R^{32}$, $R^{34}$, $R^{35}$, or $R^{37}$ is the single bond bonded to *b.

13. The organic electroluminescence device according to claim 1, wherein $R^2$, $R^4$, $R^5$, or $R^7$ is the single bond bonded to *a, and $R^{32}$, $R^{34}$, $R^{35}$, or $R^{37}$ is the single bond bonded to *b.

14. The organic electroluminescence device according to claim 1, wherein each of $L^1$, $L^2$, and $L^3$ is independently a phenylene group, a biphenylene group, a terphenylene group, or a naphthylene group.

15. The organic electroluminescence device according to claim 1, wherein $L^1$ and $L^2$ are both single bonds.

16. The organic electroluminescence device according to claim 1, wherein Ar is the substituted or unsubstituted aryl group having 6 to 30 ring carbon atoms.

17. The organic electroluminescence device according to claim 1, wherein Ar is the substituted or unsubstituted heteroaryl group having 5 to 30 ring atoms.

18. The organic electroluminescence device according to claim 1, wherein $L^3$ is the substituted or unsubstituted arylene group having 6 to 30 ring carbon atoms.

19. The organic electroluminescence device according to claim 1, wherein each of the substituent, and the optional substituent which is referred to by "substituted or unsubstituted" is at least one selected from the group consisting of an alkyl group having 1 to 30 carbon atoms; a cycloalkyl group having 3 to 30 ring carbon atoms; an aryl group (inclusive of a non-fused aryl group, a fused aryl group, and an aromatic ring assembly) having 6 to 30 ring carbon atoms; an aralkyl group having 7 to 31 carbon atoms which includes an aryl group having 6 to 30 ring carbon atoms; an alkoxy group having an alkyl group having 1 to 30 carbon atoms; an aryloxy group having an aryl group (inclusive of a non-fused aryl group, a fused aryl group, and an aromatic ring assembly) having 6 to 30 ring carbon atoms; a mono-, di- or tri-substituted silyl group having a substituent selected from an alkyl group having 1 to 30 carbon atoms and an aryl group (inclusive of a non-fused aryl group, a fused aryl group, and an aromatic ring assembly) having 6 to 30 ring carbon atoms; a haloalkyl group having 1 to 30 carbon atoms; a haloalkoxy group having a haloalkyl group having 1 to 30 carbon atoms; a halogen atom; a cyano group; and a nitro group.

20. The organic electroluminescence device according to claim 1, wherein the substituted or unsubstituted aryl group having 6 to 30 ring carbon atoms is a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, or a perylenyl group, and the substituted or unsubstituted heteroaryl group having 5 to 30 ring carbon atoms is a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isohenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a phenanthridinyl group, an acridinyl group, a phenanthrolinyl group, a phenazinyl group, a phenothiazinyl group, a phenoxazinyl group, or a xanthenyl group.

21. The organic electroluminescence device according to claim 1, wherein the substituted or unsubstituted aryl group having 6 to 30 ring carbon atoms is a phenyl group, a biphenylyl group, or a terphenylyl group.

\* \* \* \* \*

UNITED STATES PATENT AND TRADEMARK OFFICE
CERTIFICATE OF CORRECTION

PATENT NO.       : 10,941,144 B2
APPLICATION NO.  : 15/850109
DATED            : March 9, 2021
INVENTOR(S)      : Tasuku Haketa et al.

It is certified that error appears in the above-identified patent and that said Letters Patent is hereby corrected as shown below:

In the Claims

In Column 514, Claim 10, Lines 50-67:

"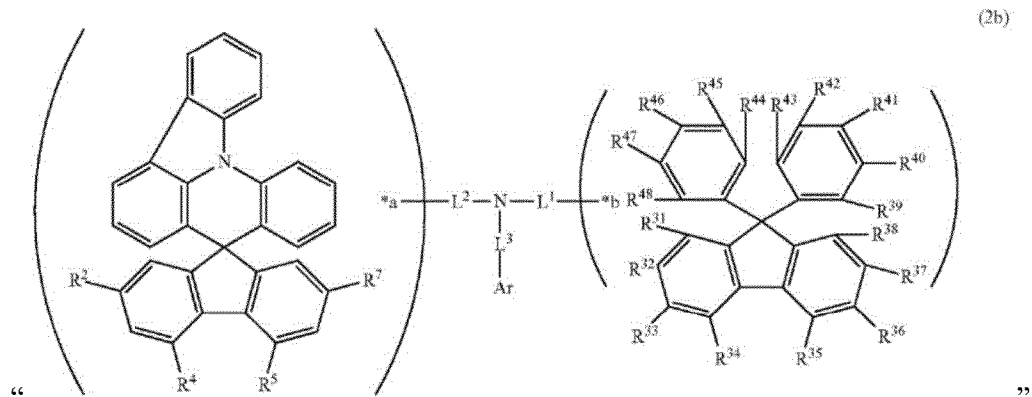"

Should read:

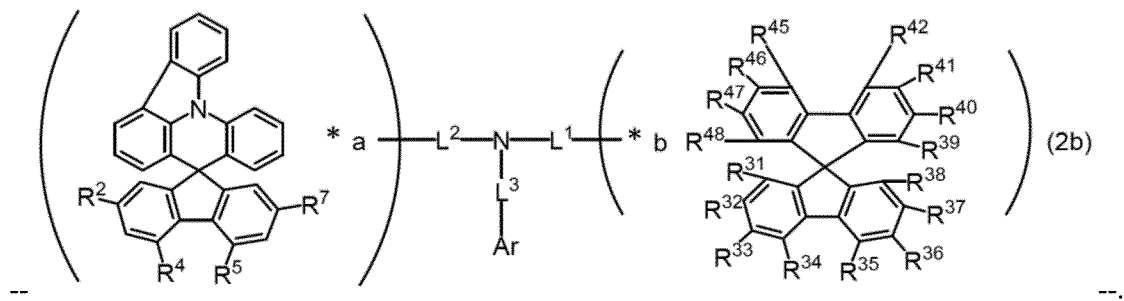

--.

Signed and Sealed this
Eighth Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,941,144 B2

In Column 515, Claim 11, Lines 5-24:

"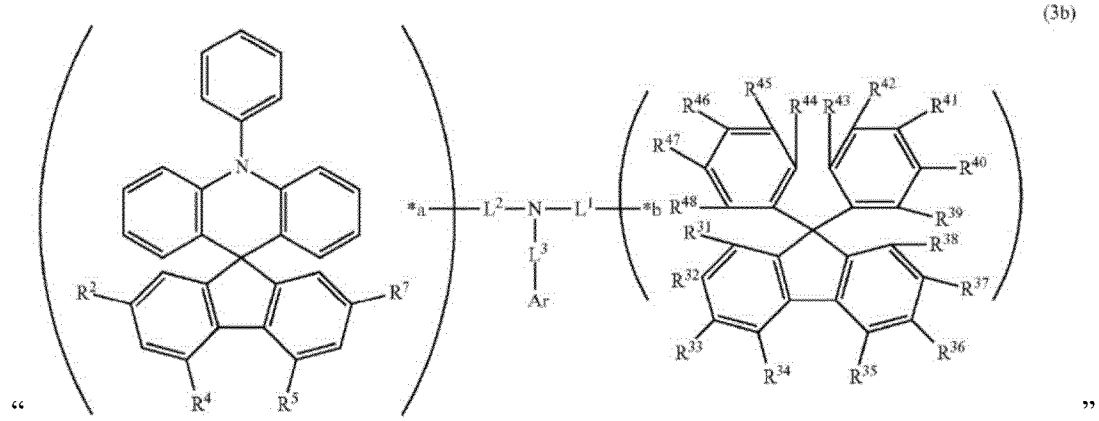"

Should read:

--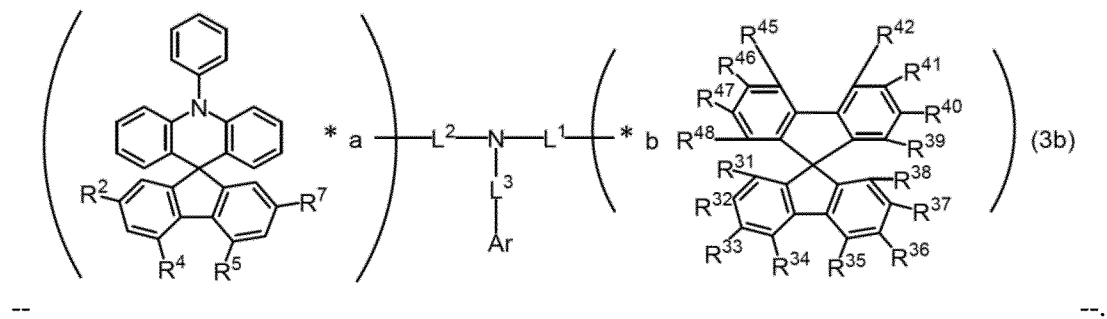--.